US008178097B2

(12) United States Patent
Bloom et al.

(10) Patent No.: US 8,178,097 B2
(45) Date of Patent: May 15, 2012

(54) METHODS OF TREATMENT UTILIZING BINDING PROTEINS OF THE INTERLEUKIN-21 RECEPTOR

(75) Inventors: Laird Bloom, Needham, MA (US); Davinder Gill, Andover, MA (US); Yulia Vugmeyster, North Reading, MA (US); Deborah A. Young, Melrose, MA (US); Margot O'Toole, Newtonville, MA (US); Heath M. Guay, Waltham, MA (US); Karissa K. Adkins, Haverhill, MA (US); Amy Arlene Weaver, North Reading, MA (US); Sadhana Jain, West Roxbury, MA (US); Maya Arai, Brookline, MA (US)

(73) Assignee: Wyeth LLC, Madison, NJ (US)

( * ) Notice: Subject to any disclaimer, the term of this patent is extended or adjusted under 35 U.S.C. 154(b) by 191 days.

(21) Appl. No.: 12/472,237

(22) Filed: May 26, 2009

(65) Prior Publication Data
US 2009/0298081 A1    Dec. 3, 2009

Related U.S. Application Data

(60) Provisional application No. 61/055,543, filed on May 23, 2008, provisional application No. 61/099,476, filed on Sep. 23, 2008.

(51) Int. Cl.
*A61K 39/395* (2006.01)
*C07K 16/28* (2006.01)

(52) U.S. Cl. ............... 424/143.1; 424/130.1; 424/139.1; 530/387.1; 530/388.22; 530/389.1

(58) Field of Classification Search .................. None
See application file for complete search history.

(56) References Cited

U.S. PATENT DOCUMENTS

| | | | | |
|---|---|---|---|---|
| 6,057,128 A | 5/2000 | Donaldson et al. | ........... | 435/69.1 |
| 6,307,024 B1 | 10/2001 | Novak et al. | .................... | 530/351 |
| 6,576,744 B1 | 6/2003 | Presnell et al. | ............... | 530/351 |
| 6,777,539 B2 | 8/2004 | Sprecher et al. | ............... | 530/350 |
| 6,929,932 B2 | 8/2005 | Presnell et al. | ............ | 435/69.52 |
| 7,189,400 B2 | 3/2007 | Carter et al. | ............... | 424/185.1 |
| 7,198,789 B2 | 4/2007 | Carter et al. | ............... | 424/130.1 |
| 7,276,478 B2 | 10/2007 | Sivakumar et al. | ............. | 514/12 |
| 7,314,623 B2 | 1/2008 | Grusby et al. | ............. | 424/185.1 |
| 7,495,085 B2 | 2/2009 | Valge-Archer et al. | .... | 530/387.9 |
| 7,705,123 B2 | 4/2010 | Donaldson et al. | ........... | 530/350 |
| 2004/0009150 A1 | 1/2004 | Nelson et al. | ................ | 424/85.2 |
| 2004/0016010 A1 | 1/2004 | Kasaian et al. | ................ | 800/18 |
| 2006/0024268 A1 | 2/2006 | Kasaian et al. | ................ | 424/85.2 |
| 2006/0039902 A1 | 2/2006 | Young et al. | ................ | 424/133.1 |
| 2006/0159655 A1 | 7/2006 | Collins et al. | ................ | 424/85.2 |
| 2006/0257403 A1 | 11/2006 | Young et al. | ................ | 424/144.1 |
| 2008/0241098 A1 | 10/2008 | Young et al. | ................ | 424/85.2 |

FOREIGN PATENT DOCUMENTS

| | | |
|---|---|---|
| WO | WO 00/53761 | 9/2000 |
| WO | WO 00/69880 | 11/2000 |
| WO | WO 01/85792 A2 | 11/2001 |
| WO | WO 2004/083249 A2 | 9/2004 |
| WO | WO 2004/084835 A2 | 10/2004 |
| WO | WO 2006/135385 A2 | 12/2006 |
| WO | WO 2008/081198 A1 | 7/2008 |

OTHER PUBLICATIONS

Paul, Fundamental Immunology, 3rd Edition, 1993, pp. 292-295, under the heading Fv Structure and Diversity in Three Dimensions.*
Casset et al (Biochemical and Biophysical Research Communications, 307:198-205, 2003.*
Gammon et al, J Am Academy Dermatology, 2011, vol. 65, pp. 717-721.*
Chang et al. Current Rheumatology Reports, 2011, vol. 13, pp. 300-307.*
Yildirim-Toruner et al. The Journal of allergy and clinical immunology, 2011, vol. 127, pp. 303-312.*
Asano et al. (2002), "Antitumor Activity of Interleukin-21 Prepared by Novel Refolding Procedure from Inclusion Bodies Expressed in *Escherichia coli*," *FEBS Lett.* 528:70-6.
Cosman, David (1993) "The Hematopoietin Receptor Superfamily," *Cytokine* 5:95-106.
Kasaian et al. (2002), "IL-21 Limits NK Cell Responses and Promotes Antigen-Specific T Cell Activation: A Mediator of the Transition from Innate to Adaptive Immunity", *Immunity* 16:559-69.
King et al. (2004), "Homeostatic Expansion of T Cells During Immune Insufficiency Generates Autoimmunity," *Cell* 117:265-77.
Leonard and Spolski (2005), "Interleukin-21: A Modulator of Lymphoid Proliferation, Apoptosis and Differentiation," *Nat. Rev. Immunol.* 5:688-98.
Liu et al. (2006), "Autoreactive T Cells Mediate NK Cell Degeneration in Autoimmune Disease," *J. Immunol.* 176:5247-54.
Livak and Schmittgen (2001), "Analysis of Relative Gene Expression Data Using Real-Time Quantitative PCR and the 2(-Delta Delta C(T)) Method," *Methods* 25:402-08.
Ozaki et al. (2000), "Cloning of a Type I Cytokine Receptor Most Related to the IL-2 Receptor β Chain", *Proc. Natl. Acad. Sci. U.S.A.* 97:11439-44.
Ozaki et al. (2004), "Regulation of B Cell Differentiation and Plasma Cell Generation by IL-21, a Novel Inducer of Blimp-1 and Bcl-6", *J. Immunol.* 173:5361-71.
Parrish-Novak et al. (2000), "Interleukin 21 and Its Receptor Are Involved in NK Cell Expansion and Regulation of Lymphocyte Function", *Nature* 408:57-63.

(Continued)

*Primary Examiner* — Bridget E Brunner
*Assistant Examiner* — Fozia Hamud
(74) *Attorney, Agent, or Firm* — Fitzpatrick, Cella, Harper & Scinto

(57) ABSTRACT

The present invention provides binding proteins and antigen-binding fragments thereof, including human antibodies, that specifically bind to the human interleukin-21 receptor (IL-21R), and methods of using them. The binding proteins can act as, e.g., antagonists of IL-21R activity, thereby modulating immune responses in general, and those mediated by IL-21R in particular. The disclosed compositions and methods may be used, e.g., in diagnosing, treating, and/or preventing IL-21R-associated disorders, e.g., inflammatory disorders, autoimmune diseases, allergies, transplant rejection, and other immune system disorders.

23 Claims, 191 Drawing Sheets

OTHER PUBLICATIONS

Shang et al. (2006), "IgE isotype switch and IgE production are enhanced in IL-21-deficient but not IFN-γ-deficient mice in a Th2-biased response," *Cell Immunol.* 241:66-74.

Sivakumar et al. (2004), "Interleukin-21 is a T-helper cytokine that regulates humoral immunity and cell-mediated anti-tumor responses," *Immunology* 112:177-82.

Stebbings et al. (2007), "'Cytokine Storm'" in the Phase I Trial of Monoclonal Antibody TGN1412: Better Understanding the Causes to Improve PreClinical Testing of Immunotherapeutics, *J. Immunol.* 179(5):3325-31.

Suntharalingam et al. (2006), "Cytokine Storm in a Phase 1 Trial of the Anti-CD28 Monoclonal Antibody TGN1412," *N. Engl. J. Med.* 355:1018-28.

Vollmer et al. (2005), "Differential Effects of IL-21 during Initiation and Progression of Autoimmunity against Neuroantigen," *J. Immunol.* 174:2696-2701.

Wing, et al. (1996), "Mechanism of First-Dose Cytokine-Release Syndrome by CAMPATH 1-H: involvement of CD16 (Fc γRIII) and CD11A/CD18 (LFA-1) on NK Cells," *J. Clin. Invest.* 98:2819-26.

Asao et al. (2001), "Cutting Edge: The Common γ-Chain is an Indispensable Subunit of the IL-21 Receptor Complex," *J. Immunol.*, 167:1-5.

Parrish-Novak et al. (2002), "Interleukin-21 and the IL-21 Receptor: Novel Effectors of NK and T Cell Responses" *J. Leukoc. Biol.* 72:856-63.

Muyldermans (2001), "Single Domain Camel Antibodies: Current Status," Rev. Mol. Biotechnol. 74:277-302.

International Preliminary Report on Patentability and Written Opinion of the International Searching Authority, and transmittal, issued in Applicants' corresponding International Patent Application No. PCT/US2009/045188, mailed Dec. 2, 2010, 7 pp.

Communication Pursuant to Rules 161(1) and 162 EPC, issued in Applicants' corresponding EPO Application No. 09751754.4, dated Jan. 28, 2011, 2 pp.

International Preliminary Report on Patentability and Written Opinion of the International Searching Authority, and transmittal, issued in Applicants' related International Patent Application No. PCT/US2009/045182, mailed Dec. 2, 2010, 6 pp.

Communication Pursuant to Rules 161(1) and 162 EPC, issued in Applicants' related EPO Application No. 09751751.0, dated Jan. 28, 2011, 2 pp.

Examination Report, issued in Applicants' related New Zealand Application No. 589330, dated Apr. 11, 2011, 2 pp.

\* cited by examiner

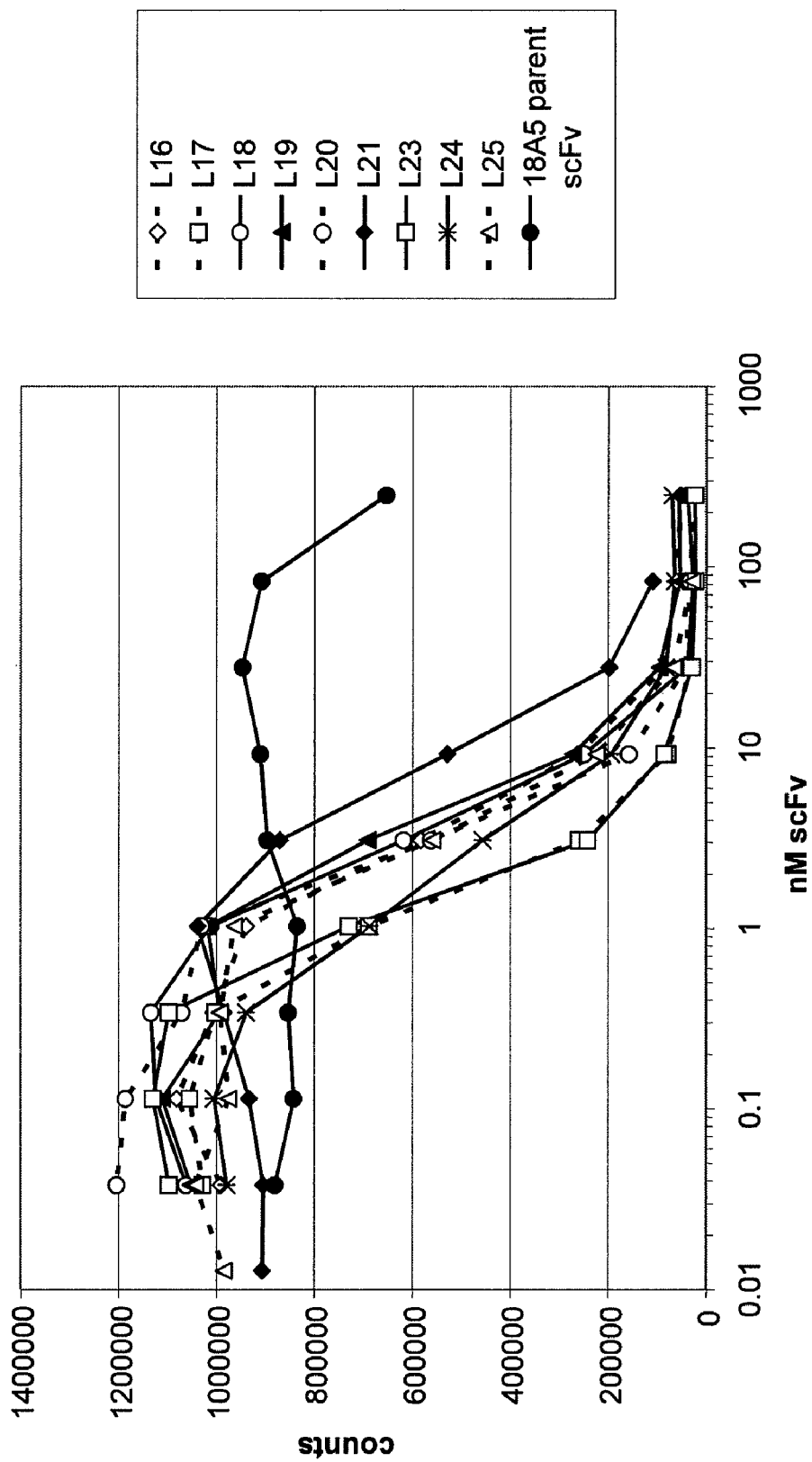

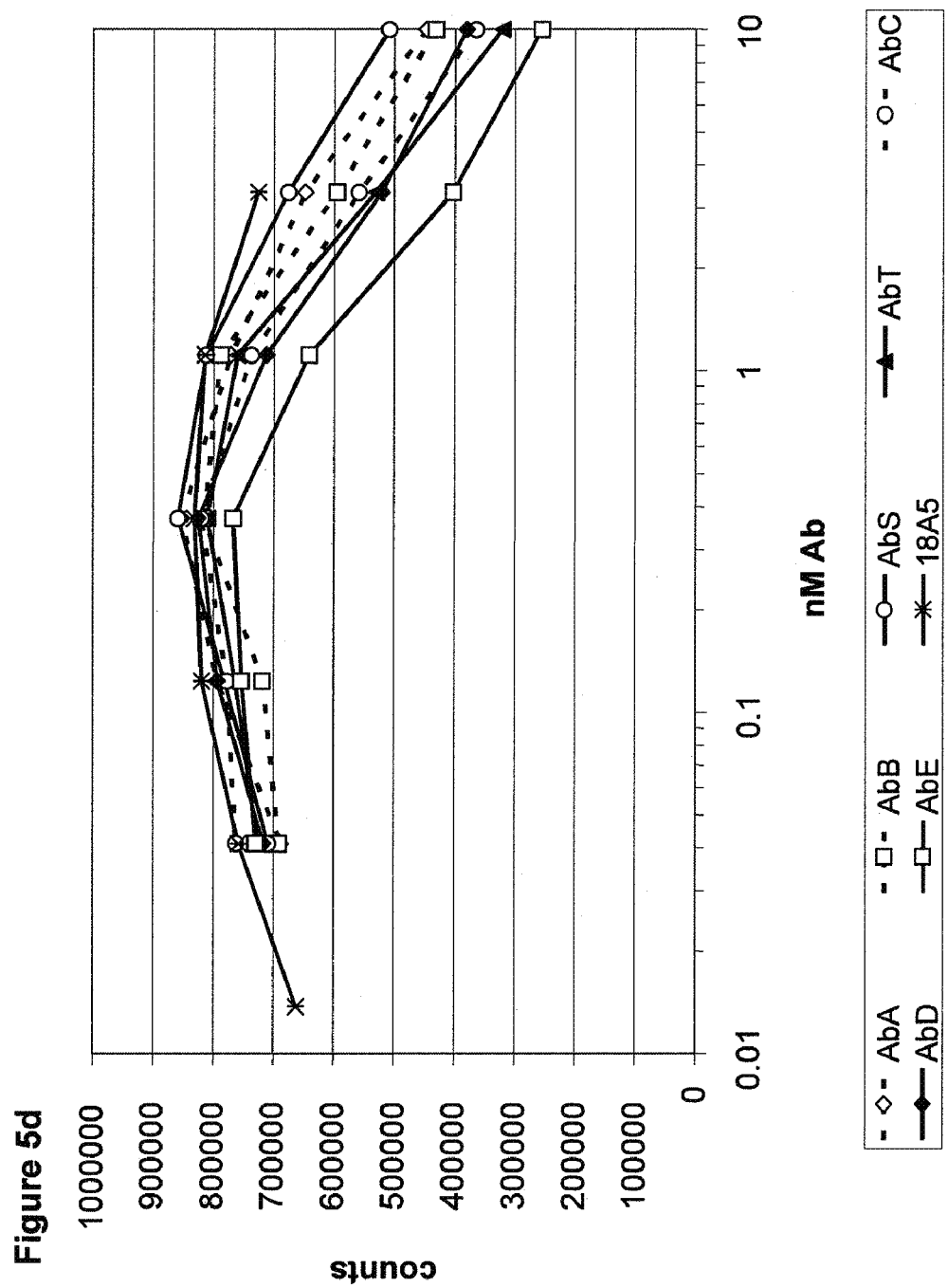

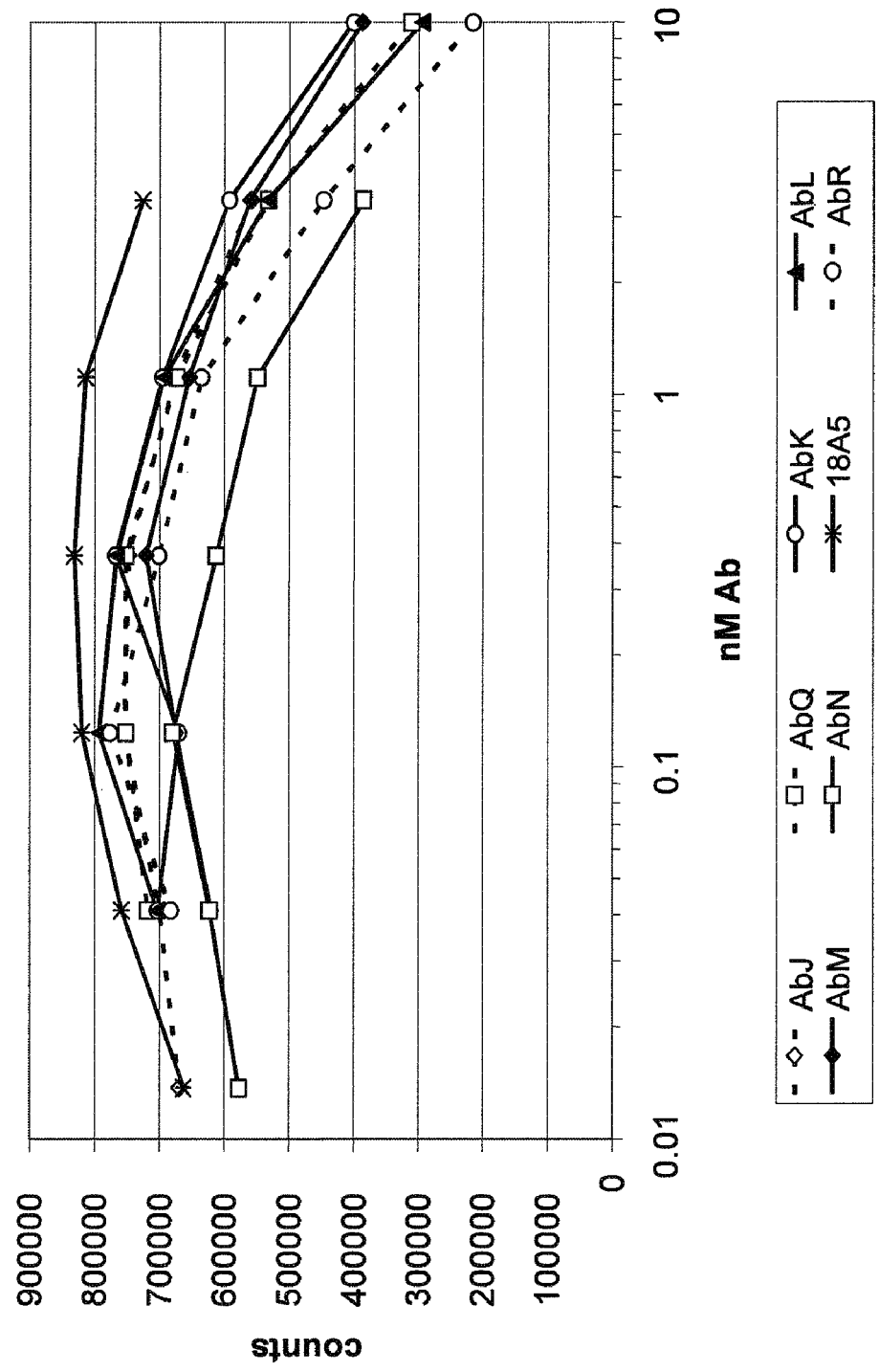

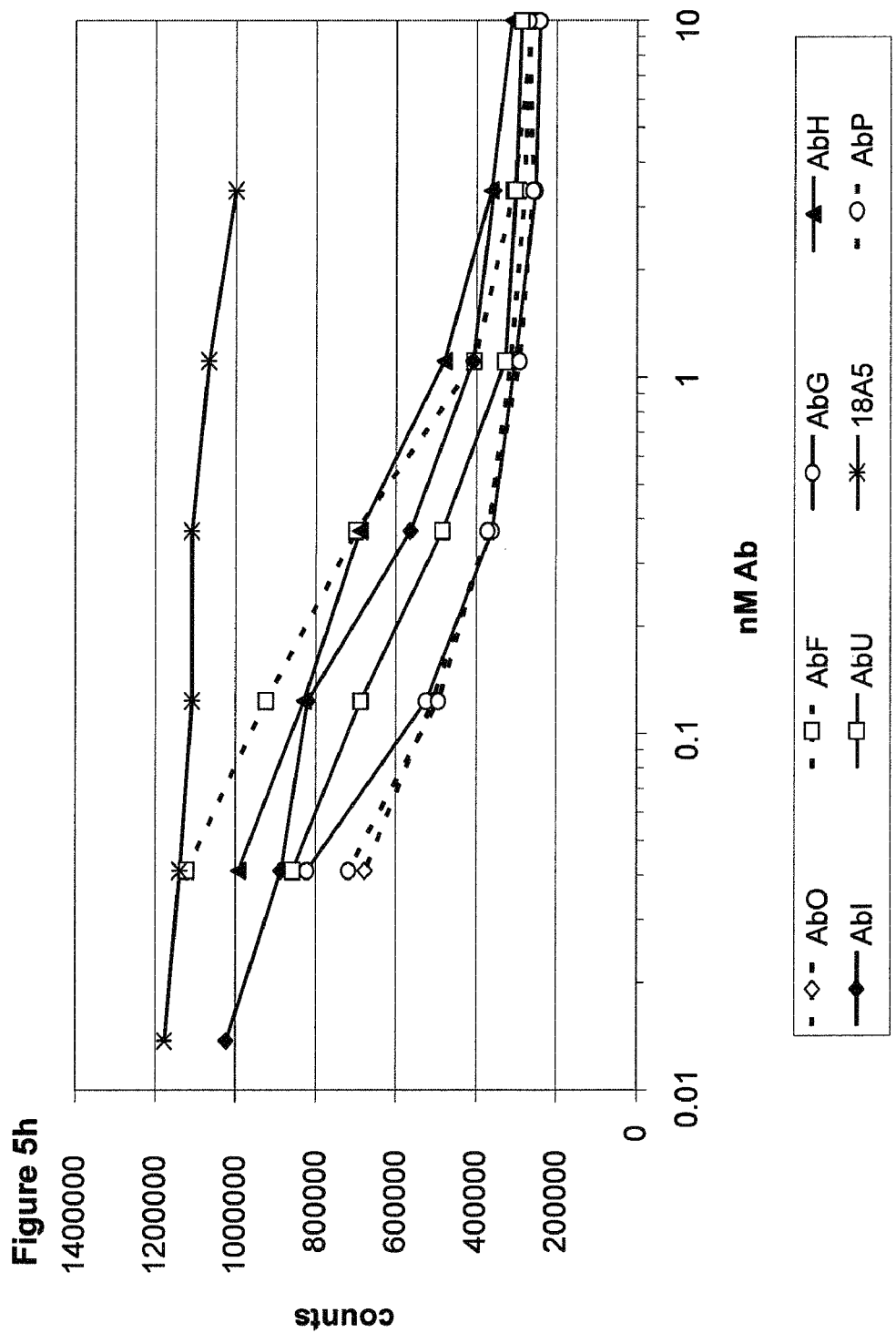

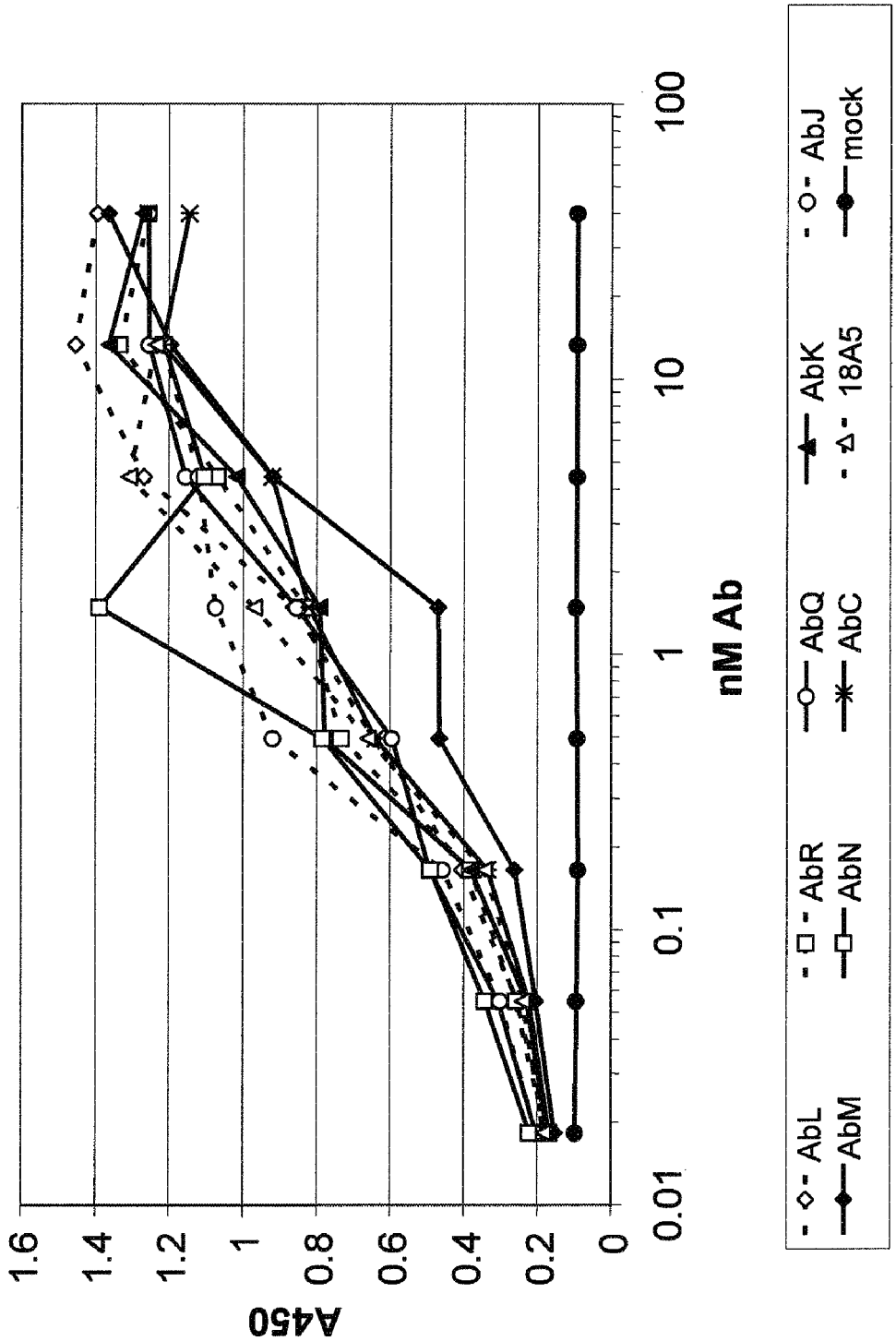

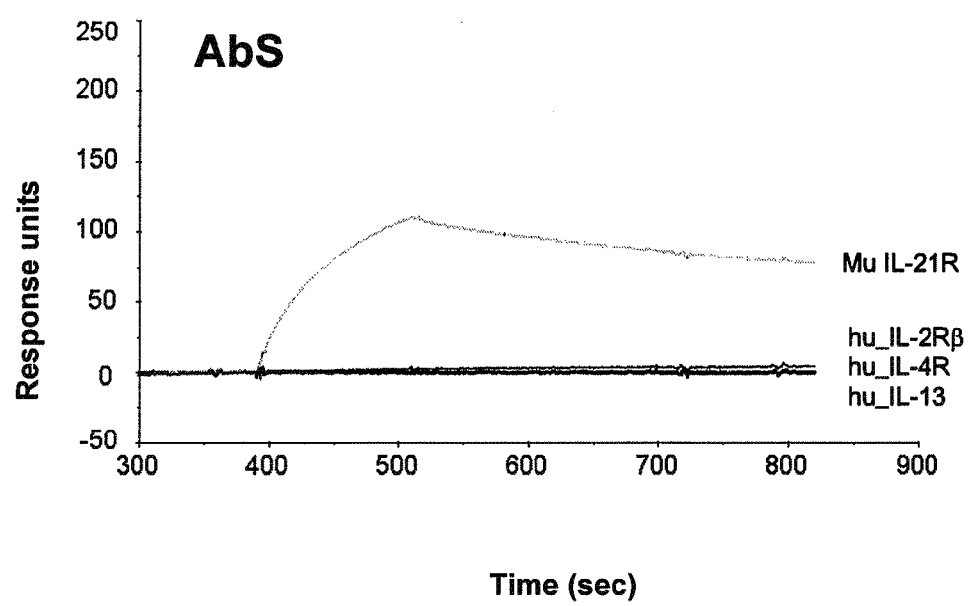

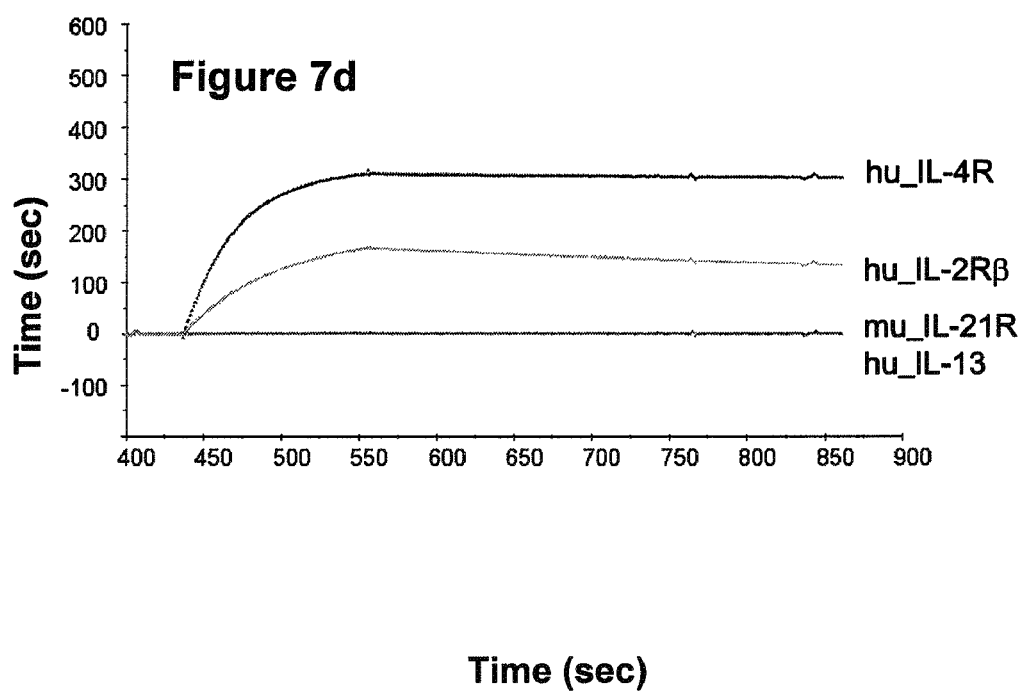

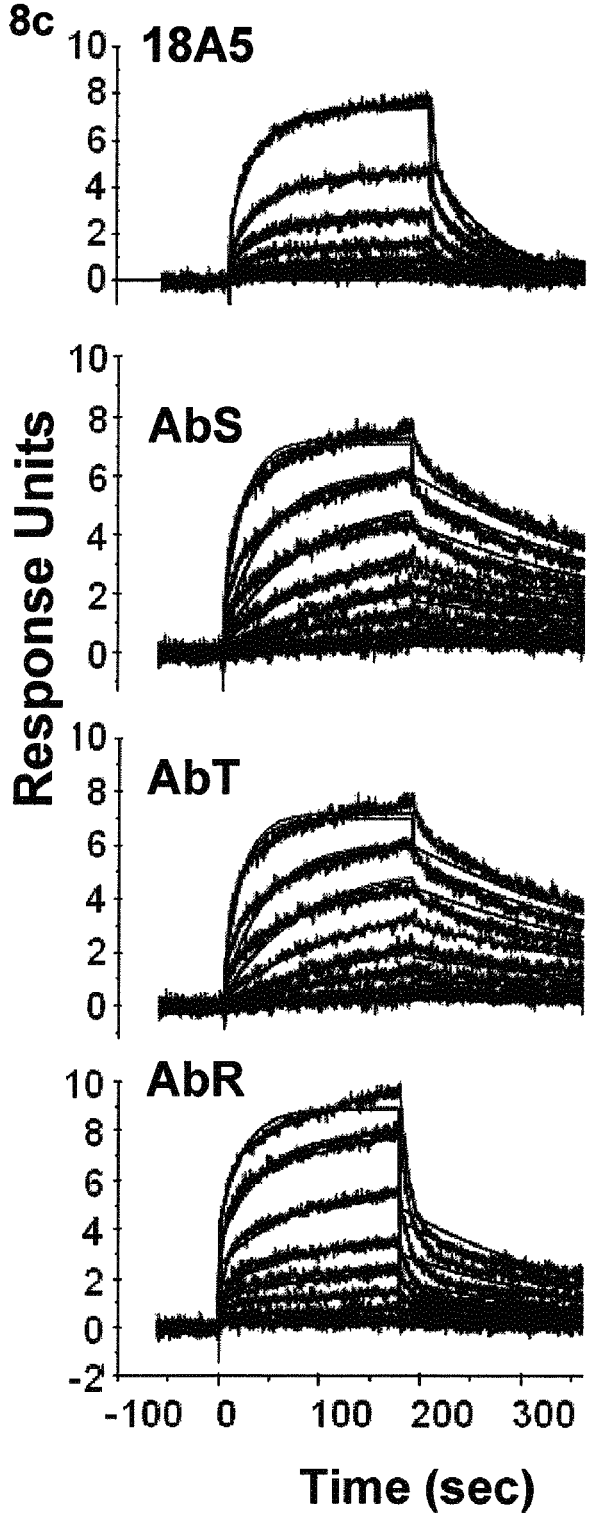

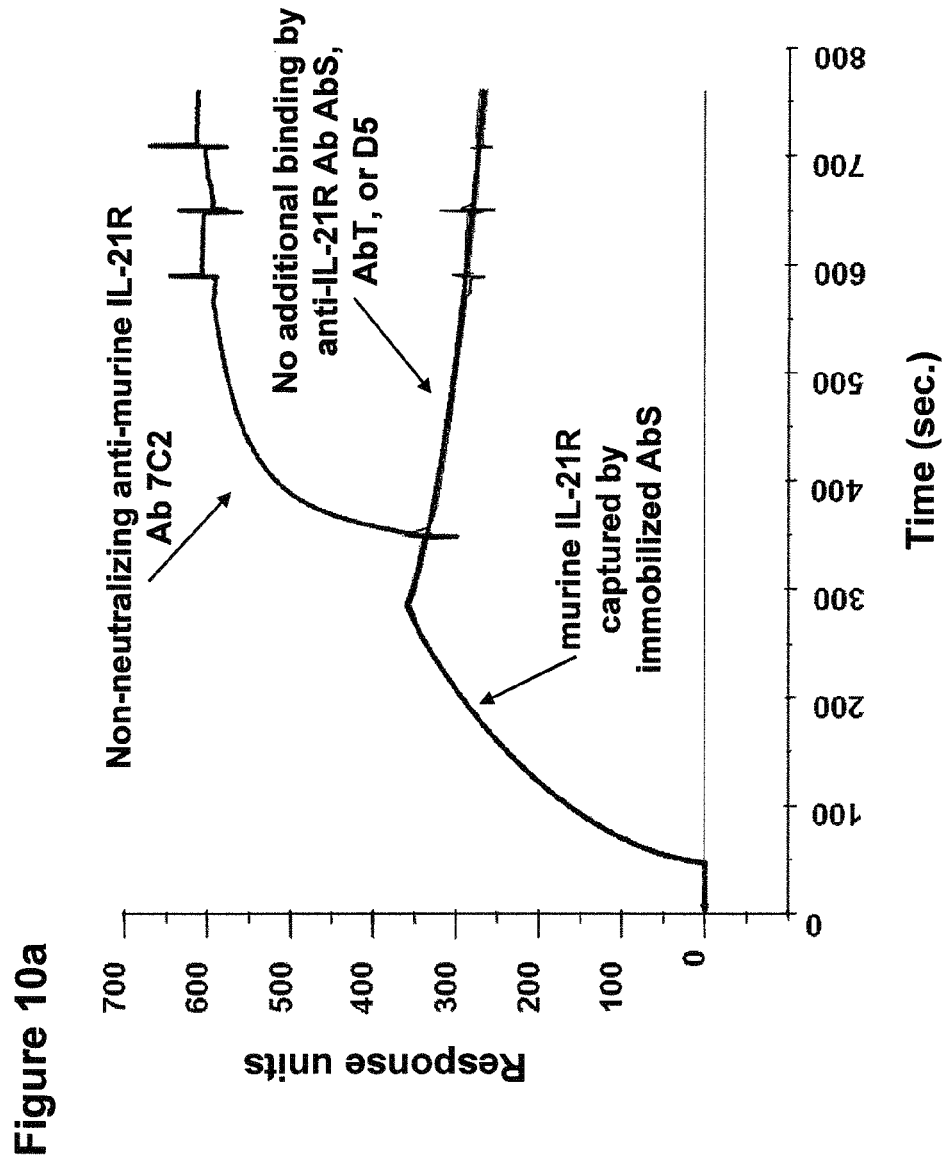

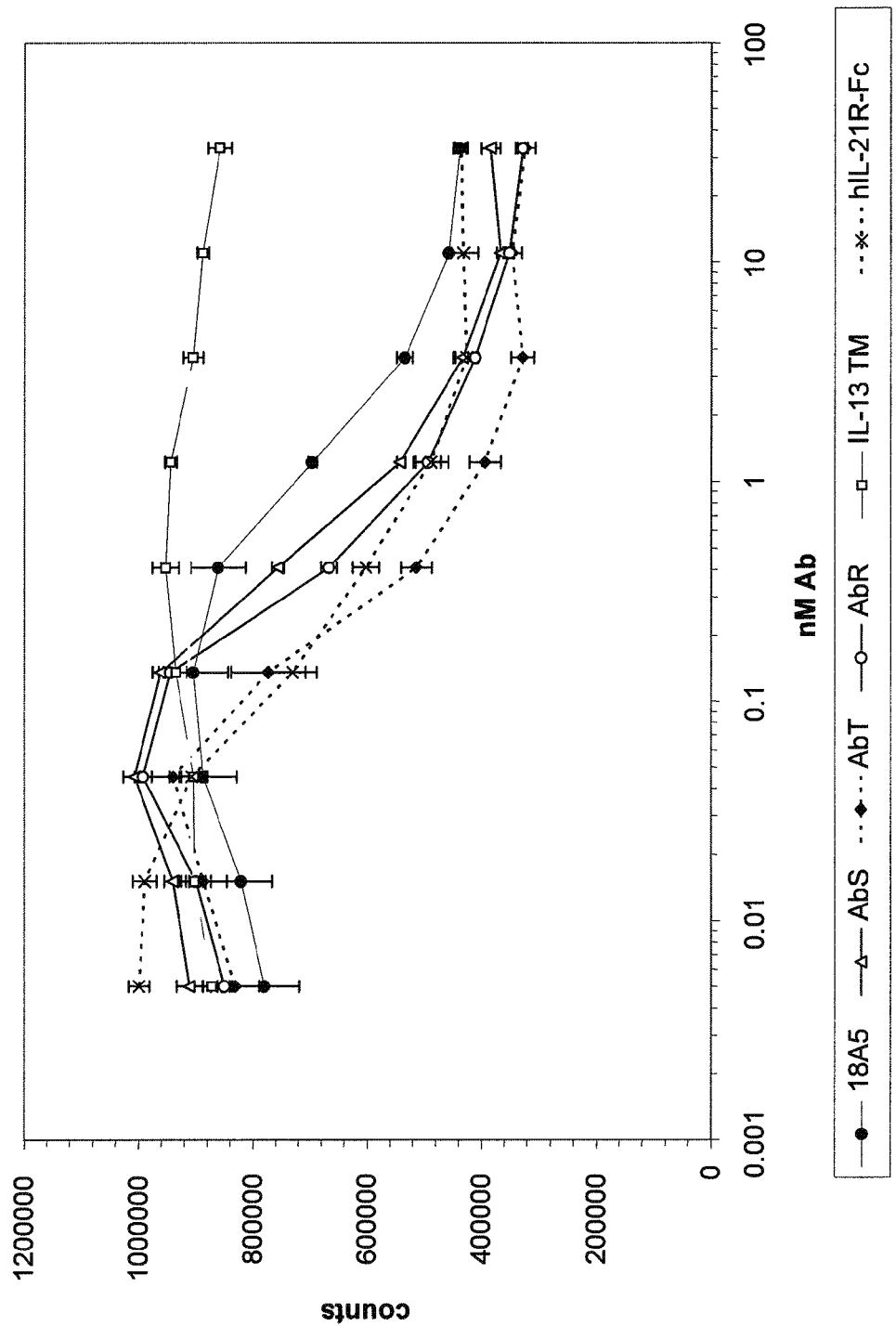

Figure 17a

AbQ:

Heavy chain for AbQ (SEQ ID NO:213), with CDRs H1, H2, and H3 underlined (SEQ ID NOs:163, 164, and 165, respectively). The heavy chain constant region is shown in lower case italics with the double mutation (L234A G237A) shown in bold lowercase underlined text (SEQ ID NO: 197).

QVQLQESGPGLVKPSETLSLTCAVSGYSISS<u>SGYYWG</u>WIRQPPGKGL
EWIG<u>SISHTGNTYYNPPLKSRVTISVDTSKNQFSLKLSSVTAADTA
VYYCAR<u>FMGFGRPEY</u>WGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papea̲lga̲psvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbQ (SEQ ID NO: 214), with CDRs L1, L2, and L3 underlined (SEQ ID NOs:194, 195, and 172, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VARSV
VGNPHVLF</u>GGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:213 is the full-length heavy chain for AbQ:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papealgapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 17b

SEQ ID NO:14 is the V$_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:165 is the CDR H3 portion of the V$_H$ portion of the full-length heavy chain:

FMGFGRPEY

SEQ ID NO:197 is the heavy chain constant region with the double mutation (L234A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapealgapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklrvdksrwqqgnvfscsvmhealhnhytqk
slslspgk*

SEQ ID NO:214 is the full-length light chain for AbQ:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 17c

SEQ ID NO:215 is the V$_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL

SEQ ID NO:194 is the CDR L1 portion of the V$_L$ portion of the full-length light chain:

QGDSLRTYYAS

SEQ ID NO:195 is the CDR L2 portion of the V$_L$ portion of the full-length light chain:

GKHKRPS

SEQ ID NO:172 is the CDR L3 portion of the V$_L$ portion of the full-length light chain:

VARSVVGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 18a

AbR:

Heavy chain for AbR (SEQ ID NO:213), with CDRs H1, H2, and H3 underlined (SEQ ID NOs:163, 164, and 165, respectively). The heavy chain constant region is shown in lower case italics with the double mutation (L234A G237A) shown in bold lowercase underlined text (SEQ ID NO: 197).

QVQLQESGPGLVKPSETLSLTCAVSGYSIS<u>SGYYWG</u>WIRQPPGKGL
EWIGS<u>ISHTGNTYYNPPLKS</u>RVTISVDTSKNQFSLKLSSVTAADTA
VYYCAR<u>FMGFGRPEYWGQ</u>GTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbR (SEQ. ID NO:216), with CDRs L1, L2, and L3 underlined (SEQ. ID NOs:194, 195, and 187, respectively). The constant lambda light chain sequence is indicated by lower-case italics (SEQ. ID. NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VTRSV</u>
<u>KGNPHV</u>LFGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:213 is the full-length heavy chain for AbR:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papealgapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 18b

SEQ ID NO:14 is the $V_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the $V_H$ portion of the full-length heavy chain:

SGYYWG

SEQ ID NO:164 is the CDR H2 portion of the $V_H$ portion of the full-length heavy chain:

SISHTGNTYYNPPLKS

SEQ ID NO:165 is the CDR H3 portion of the $V_H$ portion of the full-length heavy chain:

FMGFGRPEY

SEQ ID NO:197 is the heavy chain constant region with the double mutation (L234A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapealgapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:216 is the full-length light chain for AbR:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 18c

SEQ ID NO:217 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:187 is the CDR L3 portion of the $V_L$ portion of the full-length light chain:

VTRSVKGNPHVL

SEQ ID NO:198 is the lambda light chain constant region

*gqpkaapsvtlfppsseelqankatlvclisdfypgavtvawkads
spvkagvetttpskqsnnkyaassylsltpeqwkshrsyscqvthe
gstvektvaptecs*

Figure 19a

AbW:

Heavy chain for AbW (SEQ ID NO:218), with CDRs H1, H2, and H3 underlined (SEQ ID NOs:163, 164, and 165, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIGS<u>ISHTGNTYYNPPLKS</u>RVTISVDTSKNQFSLKLSSVTAADTA
VYYCAR<u>FMGFGRPEY</u>WGQGTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbW (SEQ ID NO:216), with CDRs L1, L2, and L3 underlined (SEQ ID NOs:194, 195, and 187, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IYGKHKRPSGIPDRFSGSSSGNTASLTITGAQAEDEADYYC<u>VTRSV</u>
<u>KGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:218 is the full-length heavy chain for AbW:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 19b

SEQ ID NO:14 is the V$_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:165 is the CDR H3 portion of the V$_H$ portion of the full-length heavy chain:

FMGFGRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:216 is the full-length light chain for AbW:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 19c

SEQ ID NO:217 is V_L portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSV
KGNPHVLFGGGTQLTVL

SEQ ID NO:194 is the CDR L1 portion of the V_L portion of the full-length light chain:

QGDSLRTYYAS

SEQ ID NO:195 is the CDR L2 portion of the V_L portion of the full-length light chain:

GKHKRPS

SEQ ID NO:187 is the CDR L3 portion of the V_L portion of the full-length light chain:

VTRSVKGNPHVL

SEQ ID NO:198 is the lambda light chain constant region gqpkaapsvtlfppsseelqankatlvclisdfypgavtvawkads
spvkagvetttpskqsnnkyaassylsltpeqwkshrsyscqvthe
gstvektvaptecs

Figure 20a

AbS:

Heavy chain for AbS (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>GYYWG</u>WIRQPPGKGL
EWIGS<u>ISHTGNTYYNPPLKSRVTISVDTSKNQFSLKLSSVTAADTA</u>
VYYCAR<u>GGGISRPEYWGQ</u>GTLVTVSS*astkgpsvfplapssksts g*
*gtaalgclvkdyfpepvtvswnsgaltsgvhtfpavlqssglysls*
*svvtvpssslgtqtyicnvnhkpsntkvdkkvepkscdkthtcppc*
*pape*aaga*psvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbS (SEQ ID NO:220), with CDRs L1, L2, and L3 underlined (SEQ ID NOs:194, 195, and 176, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>MSRSI</u>
<u>WGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:219 is the full-length heavy chain for AbS:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapssksts g*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 20b

SEQ ID NO:6 is the V$_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS

SEQ ID NO:163 is the CDR H1 portion of the V$_H$ portion of the full-length heavy chain:

SGYYWG

SEQ ID NO:164 is the CDR H2 portion of the V$_H$ portion of the full-length heavy chain:

SISHTGNTYYNPPLKS

SEQ ID NO:169 is the CDR H3 portion of the V$_H$ portion of the full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklrvdksrwqqgnvfscsvmhealhnhytqk
slslspgk*

SEQ ID NO:220 is the full-length light chain for AbS:

SSELTQDPAVSVALGQTVRITCQGDSLRTYYASWYQQKPGQAPVLV
IYGKHKRPSGIPDRFSGSSSGNTASLTITGAQAEDEADYYCMSRSI
WGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 20c

SEQ ID NO:221 is the V$_L$ portion of the full-length light chain:

SSELTQDPAVSVALGQTVRITCQGDSLRTYYASWYQQKPGQAPVLV
IYGKHKRPSGIPDRFGSSSGNTASLTITGAQAEDEADYYCMSRSI
WGNPHVLFGGGTQLTVL

SEQ ID NO:194 is the CDR L1 portion of the V$_L$ portion of the full-length light chain:

QGDSLRTYYAS

SEQ ID NO:195 is the CDR L2 portion of the V$_L$ portion of the full-length light chain:

GKHKRPS

SEQ ID NO:176 is the CDR L3 portion of the V$_L$ portion of the full-length light chain:

MSRSIWGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 21a

AbT:

Heavy chain for AbT (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIG<u>SISHTGNTYYNPPLKS</u>RVTISVDTSKNQFSLKLSSVTAADTA
VYYCAR<u>GGGISRPEYWGQGTLVTVSS</u>*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbT (SEQ ID NO:222), with CDRs L1, L2, and L3 underlined (SEQ ID NOs:194, 195, and 178, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VARSN
KGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:219 is the full-length heavy chain for AbT:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapsskstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 21b

SEQ ID NO:6 is the V$_H$ portion of full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS

SEQ ID NO:163 is the CDR H1 portion of the V$_H$ portion of full-length heavy chain:

SGYYWG

SEQ ID NO:164 is the CDR H2 portion of the V$_H$ portion of full-length heavy chain:

SISHTGNTYYNPPLKS

SEQ ID NO:169 is the CDR H3 portion of the V$_H$ portion of full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpsslgtqtyicnvnhkpsnt
kvdkkvepkscdkthtcppcpapeaagapsvflfppkpdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklt vdksrwqqgnvfscsvmhealhnhytqk
slslspgk*

SEQ ID NO:222 is the full-length light chain for AbT:

SSELTQDPAVSVALGQTVRITCQGDSLRTYYASWYQQKPGQAPVLV
IYGKHKRPSGIPDRFSGSSSGNTASLTITGAQAEDEADYYCVARSN
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 21c

SEQ ID NO:223 is the V$_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSN
KGNPHVLFGGGTQLTVL

SEQ ID NO:194 is the CDR L1 portion of the V$_L$ portion of the full-length light chain:

QGDSLRTYYAS

SEQ ID NO:195 is the CDR L2 portion of the V$_L$ portion of the full-length light chain:

GKHKRPS

SEQ ID NO:178 is the CDR L3 portion of the V$_L$ portion of the full-length light chain:

VARSNKGNPHVL

SEQ ID NO:198 is the lambda light chain constant region:

*gqpkaapsvtlfppsseelqankatlvclisdfypgavtvawkads
spvkagvetttpskqsnnkyaassylsltpeqwkshrsyscqvthe
gstvektvaptecs*

Figure 22a

AbO:

Heavy chain for AbO (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIG<u>SISHTGNTYYNPPLKSRVTISVDTSKNQFSLKLSSVTAADTA
VYYCAR<u>GGGISRPEYW</u>GQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Light chain for AbO (SEQ ID NO:224), with CDRs L1, L2, and L3 underlined (SEQ ID NOs:194, 195, and 185, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VTRSA
KGNPHVL</u>FGGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:219 is the full-length heavy chain for AbO:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 22b

SEQ ID NO:6 is the V<sub>H</sub> portion of full-length heavy chain:

QVQLQESGPGLVKPSETLSLTCAVSGYSISS<u>SGYYWG</u>WIRQPPGKGL
EWIGSISHTGNTYYNPPLKSRVTISVDTSKNQFSLKLSSVTAADTA
VYYCAR<u>GGGISRPEY</u>WGQGTLVTVSS

SEQ ID NO:163 is the CDR H1 portion of the V<sub>H</sub> portion of full-length heavy chain:

SGYYWG

SEQ ID NO:164 is the CDR H2 portion of the V<sub>H</sub> portion of full-length heavy chain:

SISHTGNTYYNPPLKS

SEQ ID NO:169 is the CDR H3 portion of the V<sub>H</sub> portion of full-length heavy chain:

GGGISRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:224 is the full-length light chain for AbO:

SSELTQDPAVSVALGQTVRITCQGDSLRTYYASWYQQKPGQAPVLV
IYGKHKRPSGIPDRFGSSSGNTASLTITGAQAEDEADYYCVTRSA
KGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 22c

SEQ ID NO:225 is the V$_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVTRSA
KGNPHVLFGGGTQLTVL

SEQ ID NO:194 is the CDR L1 portion of the V$_L$ portion of the full-length light chain:

QGDSLRTYYAS

SEQ ID NO:195 is the CDR L2 portion of the V$_L$ portion of the full-length light chain:

GKHKRPS

SEQ ID NO:185 is the CDR L3 portion of the V$_L$ portion of the full-length light chain:

VTRSAKGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 23a

AbP:

Heavy chain for AbP (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>SGYYWG</u>WIRQPPGKGL
EWIGS<u>ISHTGNTYYNPPLKSRVTISVDTSKNQFSLKLSSVTAADTA</u>
VYYCAR<u>GGGISRPEYWGQGTLVTVSS</u>*astkgpsvfplapsskstsg*
*gtaalgclvkdyfpepvtvswnsgaltsgvhtfpavlqssglysls*
*svvtvpsslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbP (SEQ ID NO:226), with CDRs L1, L2, and L3 underlined (SEQ ID NOs:194, 195, and 189, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VSRSA</u>
<u>KGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:219 is the full-length heavy chain for AbP:

QVQLQESGPGLVKPSETLSLTCAVSGYSISS<u>SGYYWG</u>WIRQPPGKGL
EWIGS<u>ISHTGNTYYNPPLKSRVTISVDTSKNQFSLKLSSVTAADTA</u>
VYYCAR<u>GGGISRPEYWGQGTLVTVSS</u>*astkgpsvfplapsskstsg*
*gtaalgclvkdyfpepvtvswnsgaltsgvhtfpavlqssglysls*
*svvtvpsslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 23b

SEQ ID NO:6 is the V<sub>H</sub> portion of full-length heavy chain:

```
QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS
```

SEQ ID NO:163 is the CDR H1 portion of the V<sub>H</sub> portion of full-length heavy chain:

```
SGYYWG
```

SEQ ID NO:164 is the CDR H2 portion of the V<sub>H</sub> portion of full-length heavy chain:

```
SISHTGNTYYNPPLKS
```

SEQ ID NO:169 is the CDR H3 portion of the V<sub>H</sub> portion of full-length heavy chain:

```
GGGISRPEY
```

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpssslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklt vdksrwqqgnvfscsvmhealhnhytqk
slslspgk*

SEQ ID NO:226 is the full-length light chain for AbP:

```
SSELTQDPAVSVALGQTVRITCQGDSLRTYYASWYQQKPGQAPVLV
IYGKHKRPSGIPDRFSGSSSGNTASLTITGAQAEDEADYYCVSRSA
KGNPHVLFGGGTQLTVL
```
*gqpkaapsvtlfppsseelqankatlvcl
isdfypgavtvawkadsspvkagvetttpskqsnnkyaassylslt
peqwkshrsyscqvthegstvektvaptecs*

Figure 23c

SEQ ID NO:227 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVSRSA
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:189 is the CDR L3 portion of the $V_L$ portion of the full-length light chain:

VSRSAKGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 24a

AbU:

Heavy chain for AbU (SEQ ID NO:219), with CDRs H1, H2, and H3 underlined (SEQ ID NOs:163, 164, and 169, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSIS<u>SGYYWG</u>WIRQPPGKGL
EWIG<u>SISHTGNTYYNPPLKS</u>RVTISVDTSKNQFSLKLSSVTAADTA
VYYCAR<u>GGGISRPEY</u>WGQGTLVTVSS*astkgpsvfplapssкstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Light chain for AbU (SEQ ID NO:228), with CDRs L1, L2, and L3 underlined (SEQ ID NOs:194, 195, and 193, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>TTRSN
KGNPHVL</u>FGGGTQLTVL*gqpkaapsvtlfppsseelqankatlvcl*
*isdfypgavtvawkadsspvkagvetttpskqsnnkyaassylslt*
*peqwkshrsyscqvthegstvektvaptecs*

SEQ ID NO:219 is the full-length heavy chain for AbU:

QVQLQESGPGLVKPSETLSLTCAVSGYSIS<u>SGYYWG</u>WIRQPPGKGL
EWIG<u>SISHTGNTYYNPPLKS</u>RVTISVDTSKNQFSLKLSSVTAADTA
VYYCAR<u>GGGISRPEY</u>WGQGTLVTVSS*astkgpsvfplapssкstsg*
*gtaalgclvkdyfpepvtvswnsgaltsgvhtfpavlqssglysls*
*svvtvpssslgtqtyicnvnhkpsntkvdkkvepkscdkthtcppc*
*papeaagapsvflfppkpkdtlmisrtpevtcvvvdvshedpevkf*
*nwyvdgvevhnaktkpreeqynstyrvvsvltvlhqdwlngkeykc*
*kvsnkalpapiektiskakgqprepqvytlppsreemtknqvsltc*
*lvkgfypsdiavewesngqpennykttppvldsdgsfflyskltvd*
*ksrwqqgnvfscsvmhealhnhytqkslslspgk*

Figure 24b

SEQ ID NO:6 is the V<sub>H</sub> portion of full-length heavy chain:

```
QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARGGGISRPEYWGQGTLVTVSS
```

SEQ ID NO:163 is the CDR H1 portion of the V<sub>H</sub> portion of full-length heavy chain:

```
SGYYWG
```

SEQ ID NO:164 is the CDR H2 portion of the V<sub>H</sub> portion of full-length heavy chain:

```
SISHTGNTYYNPPLKS
```

SEQ ID NO:169 is the CDR H3 portion of the V<sub>H</sub> portion of full-length heavy chain:

```
GGGISRPEY
```

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpsslgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflysklktvdksrwqqgnvfscsvmhealhnhytqk
slslspgk*

SEQ ID NO:228 is the full-length light chain for AbU:

```
SSELTQDPAVSVALGQTVRITCQGDSLRTYYASWYQQKPGQAPVLV
IYGKHKRPSGIPDRFSGSSSGNTASLTITGAQAEDEADYYCTTRSN
KGNPHVLFGGGTQLTVL
```
*gqpkaapsvtlfppsseelqankatlvcl
isdfypgavtvawkadsspvkagvetttpskqsnnkyaassylslt
peqwkshrsyscqvthegstvektvaptecs*

Figure 24c

SEQ ID NO:229 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCTTRSN
KGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:193 is the CDR L3 portion of the $V_L$ portion of the full-length light chain:

TTRSNKGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

Figure 25a

AbV:

Heavy chain for AbV (SEQ ID NO:218), with CDRs H1, H2, and H3 underlined (SEQ ID NOs:163, 164, and 165, respectively). The heavy chain constant region is shown in lower case italics with the triple mutation (L234A L235A G237A) shown in bold lowercase underlined text (SEQ ID NO:196).

QVQLQESGPGLVKPSETLSLTCAVSGYSISS<u>SGYYWG</u>WIRQPPGKGL
EWIGS<u>ISHTGNTYYNPPLKSRVTISVDTSKNQFSLKLSSVTAADTA
VYYCAR<u>FMGFGRPEY</u>WGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgkk*

Light chain for AbV (SEQ ID NO:214), with CDRs L1, L2, and L3 underlined (SEQ ID NOs:194, 195, and 172, respectively). The constant lambda light chain sequence is indicated by lower-case italics (SEQ ID NO:198).

SSELTQDPAVSVALGQTVRITC<u>QGDSLRTYYAS</u>WYQQKPGQAPVLV
IY<u>GKHKRPS</u>GIPDRFSGSSSGNTASLTITGAQAEDEADYYC<u>VARSV
VGNPHVLF</u>GGGTQLTVL*gqpkaapsvtlfppsseelqankatlvcl
isdfypgavtvawkadsspvkagvetttpskqsnnkyaassylslt
peqwkshrsyscqvthegstvektvaptecs*

SEQ ID NO:218 is the full-length heavy chain for AbV:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS*astkgpsvfplapsskstsg
gtaalgclvkdyfpepvtvswnsgaltsgvhtfpavlqssglysls
svvtvpssslgtqtyicnvnhkpsntkvdkkvepkscdkthtcppc
papeaagapsvflfppkpkdtlmisrtpevtcvvvdvshedpevkf
nwyvdgvevhnaktkpreeqynstyrvvsvltvlhqdwlngkeykc
kvsnkalpapiektiskakgqprepqvytlppsreemtknqvsltc
lvkgfypsdiavewesngqpennykttppvldsdgsfflyskltvd
ksrwqqgnvfscsvmhealhnhytqkslslspgk*

Figure 25b

SEQ ID NO:14 is the $V_H$ portion of the full-length heavy chain:

QVQLQESGPGLVKPSETLSLTCAVSGYSISSGYYWGWIRQPPGKGL
EWIGSISHTGNTYYNPPLKSRVTISVDTSKNQFSLKLSSVTAADTA
VYYCARFMGFGRPEYWGQGTLVTVSS

SEQ ID NO:163 is the CDR H1 portion of the $V_H$ portion of the full-length heavy chain:

SGYYWG

SEQ ID NO:164 is the CDR H2 portion of the $V_H$ portion of the full-length heavy chain:

SISHTGNTYYNPPLKS

SEQ ID NO:165 is the CDR H3 portion of the $V_H$ portion of the full-length heavy chain:

FMGFGRPEY

SEQ ID NO:196 is the heavy chain constant region with the triple mutation (L234A L235A G237A) shown in bold lowercase underlined text:

*astkgpsvfplapsskstsggtaalgclvkdyfpepvtvswnsgal
tsgvhtfpavlqssglyslssvvtvpsssIgtqtyicnvnhkpsnt
kvdkkvepkscdkthtcppcpapeaagapsvflfppkpkdtlmisr
tpevtcvvvdvshedpevkfnwyvdgvevhnaktkpreeqynstyr
vvsvltvlhqdwlngkeykckvsnkalpapiektiskakgqprepq
vytlppsreemtknqvsltclvkgfypsdiavewesngqpennykt
tppvldsdgsfflyskltvdksrwqqgnvfscsvmhealhnhytqk
slslspgk*

SEQ ID NO:214 is the full-length light chain for AbV:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL*gqpkaapsvtlfppsseelqankatlvcl
isdfypgavtvawkadsspvkagvetttpskqsnnkyaassylslt
peqwkshrsyscqvthegstvektvaptecs*

Figure 25c

SEQ ID NO:215 is the $V_L$ portion of the full-length light chain:

SSELTQDPAVSVALGQTVRITCQGDSLRTYYASWYQQKPGQAPVLV
IYGKHKRPSGIPDRFSGSSSGNTASLTITGAQAEDEADYYCVARSV
VGNPHVLFGGGTQLTVL

SEQ ID NO:194 is the CDR L1 portion of the $V_L$ portion of the full-length light chain:

QGDSLRTYYAS

SEQ ID NO:195 is the CDR L2 portion of the $V_L$ portion of the full-length light chain:

GKHKRPS

SEQ ID NO:172 is the CDR L3 portion of the $V_L$ portion of the full-length light chain:

VARSVVGNPHVL

SEQ ID NO:198 is the lambda light chain constant region:

gqpkaapsvtlfppsseelqankatlvclisdfypgavtvawkads
spvkagvetttpskqsnnkyaassylsltpeqwkshrsyscqvthe
gstvektvaptecs

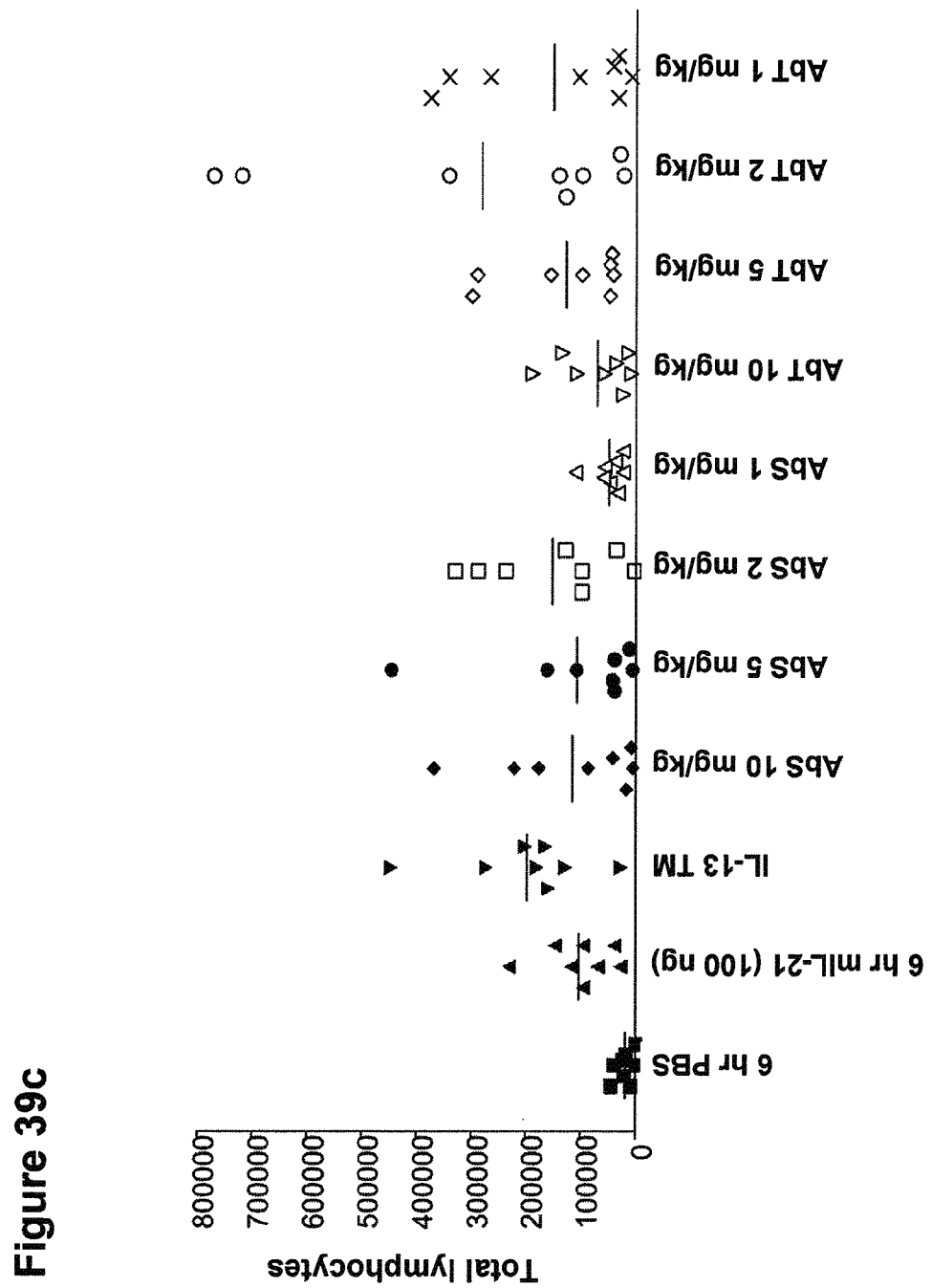

Figure 54

| 18S | GAPDH | GUSB | PGK1 | ZNF592 | IFNG | IL10 | IL12A | IL1B | IL21R | IL2RA | IL6 | IL8 | PRF1 | STAT3 | TBX21 | TNF |
|---|---|---|---|---|---|---|---|---|---|---|---|---|---|---|---|---|
| | | | | | CCL3 | CD19 | CXCL10 | CXCL11 | GNLY | GZMB | ICAM1 | | | | | |

Endo Controls: 18S, GAPDH, GUSB, PGK1, ZNF592

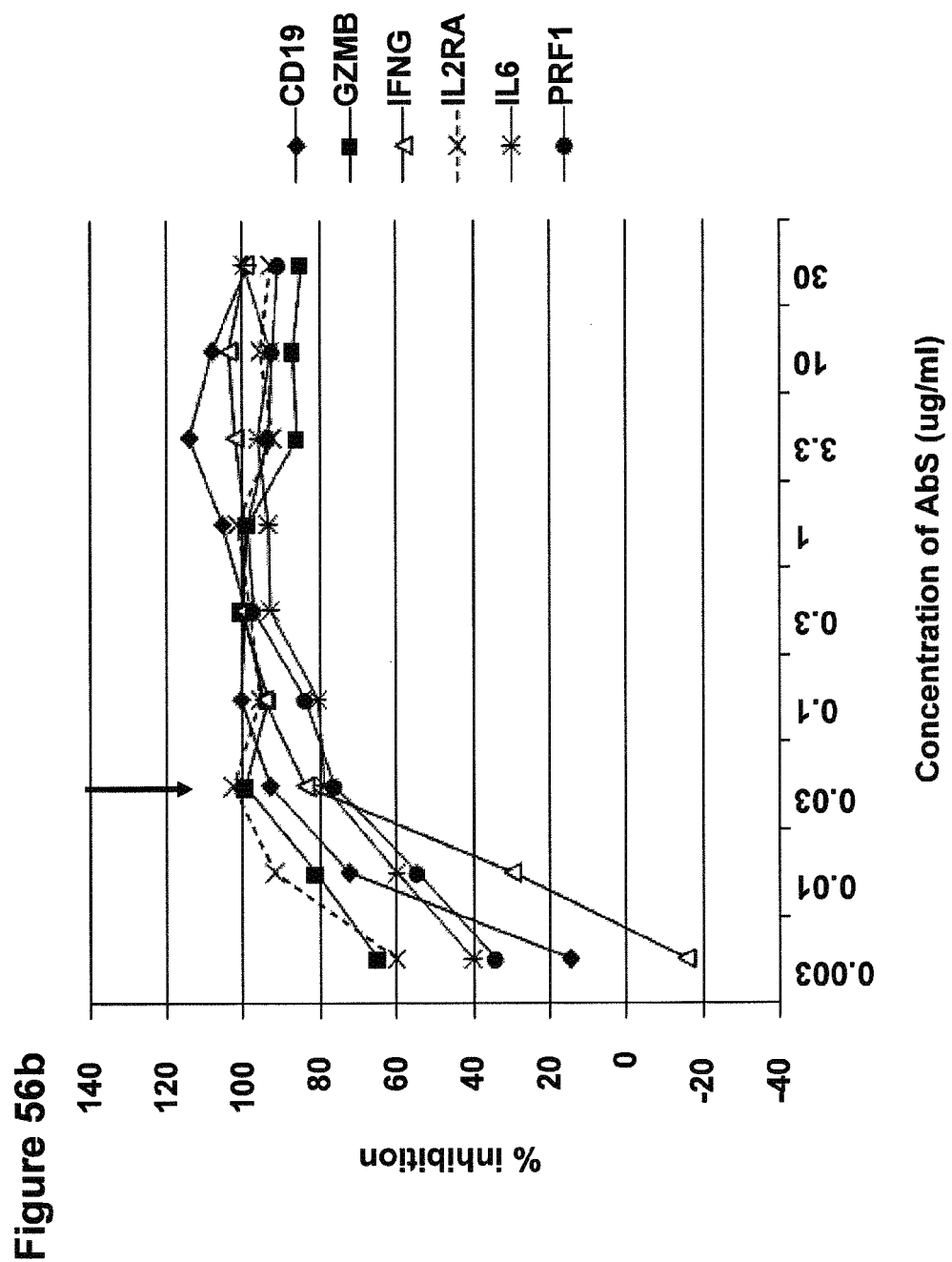

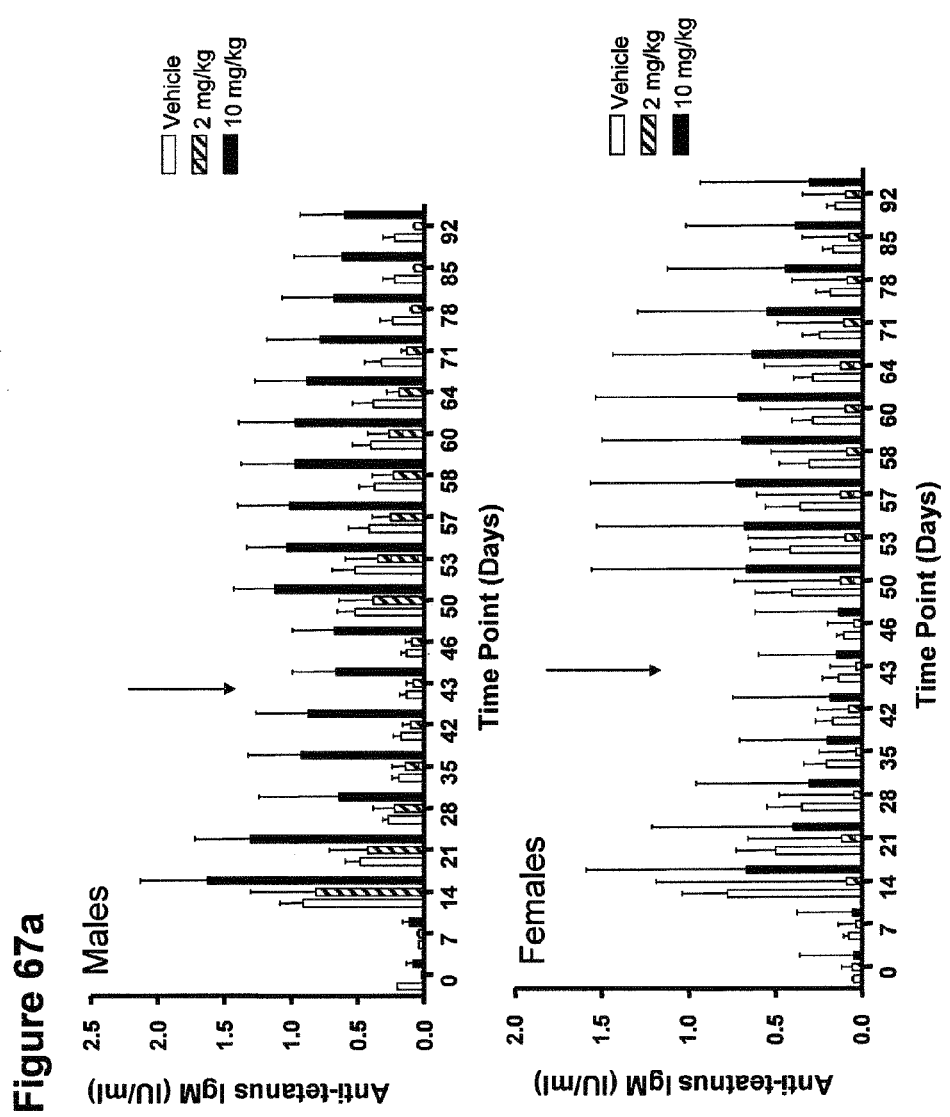

SEQUENCE LISTING

<160> NUMBER OF SEQ ID NOS: 248

<210> SEQ ID NO 1
<211> LENGTH: 2665
<212> TYPE: DNA
<213> ORGANISM: Homo sapiens
<220> FEATURE:
<221> NAME/KEY: CDS
<222> LOCATION: (236)..(1849)

<400> SEQUENCE: 1

```
gtcgactgga ggcccagctg cccgtcatca gagtgacagg tcttatgaca gcctgattgg      60
tgactcgggc tgggtgtgga ttctcacccc aggcctctgc ctgctttctc agaccctcat     120
ctgtcacccc cacgctgaac ccagctgcca cccccagaag cccatcagac tgcccccagc     180
acacggaatg gatttctgag aaagaagccg aaacagaagg cccgtgggag tcagc atg     238
                                                                     Met
                                                                      1 ccg cgt ggc tgg gcc gcc ccc ttg ctc ctg ctg ctg ctc cag gga ggc      286
Pro Arg Gly Trp Ala Ala Pro Leu Leu Leu Leu Leu Leu Gln Gly Gly
         5                  10                  15 tgg ggc tgc ccc gac ctc gtc tgc tac acc gat tac ctc cag acg gtc      334
Trp Gly Cys Pro Asp Leu Val Cys Tyr Thr Asp Tyr Leu Gln Thr Val
    20                  25                  30
```

```
atc tgc atc ctg gaa atg tgg aac ctc cac ccc agc acg ctc acc ctt      382
Ile Cys Ile Leu Glu Met Trp Asn Leu His Pro Ser Thr Leu Thr Leu
 35              40                  45 acc tgg caa gac cag tat gaa gag ctg aag gac gag gcc acc tcc tgc      430
Thr Trp Gln Asp Gln Tyr Glu Glu Leu Lys Asp Glu Ala Thr Ser Cys
 50              55                  60                  65 agc ctc cac agg tcg gcc cac aat gcc acg cat gcc acc tac acc tgc      478
Ser Leu His Arg Ser Ala His Asn Ala Thr His Ala Thr Tyr Thr Cys
                 70                  75                  80 cac atg gat gta ttc cac ttc atg gcc gac gac att ttc agt gtc aac      526
His Met Asp Val Phe His Phe Met Ala Asp Asp Ile Phe Ser Val Asn
                     85                  90                  95 atc aca gac cag tct ggc aac tac tcc cag gag tgt ggc agc ttt ctc      574
Ile Thr Asp Gln Ser Gly Asn Tyr Ser Gln Glu Cys Gly Ser Phe Leu
            100                 105                 110 ctg gct gag agc atc aag ccg gct ccc cct ttc aac gtg act gtg acc      622
Leu Ala Glu Ser Ile Lys Pro Ala Pro Pro Phe Asn Val Thr Val Thr
            115                 120                 125 ttc tca gga cag tat aat atc tcc tgg cgc tca gat tac gaa gac cct      670
Phe Ser Gly Gln Tyr Asn Ile Ser Trp Arg Ser Asp Tyr Glu Asp Pro
130                 135                 140                 145 gcc ttc tac atg ctg aag ggc aag ctt cag tat gag ctg cag tac agg      718
Ala Phe Tyr Met Leu Lys Gly Lys Leu Gln Tyr Glu Leu Gln Tyr Arg
                150                 155                 160 aac cgg gga gac ccc tgg gct gtg agt ccg agg aga aag ctg atc tca      766
Asn Arg Gly Asp Pro Trp Ala Val Ser Pro Arg Arg Lys Leu Ile Ser
                    165                 170                 175 gtg gac tca aga agt gtc tcc ctc ctc ccc ctg gag ttc cgc aaa gac      814
Val Asp Ser Arg Ser Val Ser Leu Leu Pro Leu Glu Phe Arg Lys Asp
            180                 185                 190 tcg agc tat gag ctg cag gtg cgg gca ggg ccc atg cct ggc tcc tcc      862
Ser Ser Tyr Glu Leu Gln Val Arg Ala Gly Pro Met Pro Gly Ser Ser
            195                 200                 205 tac cag ggg acc tgg agt gaa tgg agt gac ccg gtc atc ttt cag acc      910
Tyr Gln Gly Thr Trp Ser Glu Trp Ser Asp Pro Val Ile Phe Gln Thr
210                 215                 220                 225 cag tca gag gag tta aag gaa ggc tgg aac cct cac ctg ctg ctt ctc      958
Gln Ser Glu Glu Leu Lys Glu Gly Trp Asn Pro His Leu Leu Leu Leu
                230                 235                 240 ctc ctg ctt gtc ata gtc ttc att cct gcc ttc tgg agc ctg aag acc     1006
Leu Leu Leu Val Ile Val Phe Ile Pro Ala Phe Trp Ser Leu Lys Thr
            245                 250                 255 cat cca ttg tgg agg cta tgg aag aag ata tgg gcc gtc ccc agc cct     1054
His Pro Leu Trp Arg Leu Trp Lys Lys Ile Trp Ala Val Pro Ser Pro
            260                 265                 270 gag cgg ttc ttc atg ccc ctg tac aag ggc tgc agc gga gac ttc aag     1102
Glu Arg Phe Phe Met Pro Leu Tyr Lys Gly Cys Ser Gly Asp Phe Lys
            275                 280                 285 aaa tgg gtg ggt gca ccc ttc act ggc tcc agc ctg gag ctg gga ccc     1150
Lys Trp Val Gly Ala Pro Phe Thr Gly Ser Ser Leu Glu Leu Gly Pro
290                 295                 300                 305 tgg agc cca gag gtg ccc tcc acc ctg gag gtg tac agc tgc cac cca     1198
Trp Ser Pro Glu Val Pro Ser Thr Leu Glu Val Tyr Ser Cys His Pro
                310                 315                 320 cca cgg agc ccg gcc aag agg ctg cag ctc acg gag cta caa gaa cca     1246
Pro Arg Ser Pro Ala Lys Arg Leu Gln Leu Thr Glu Leu Gln Glu Pro
                325                 330                 335 gca gag ctg gtg gag tct gac ggt gtg ccc aag ccc agc ttc tgg ccg     1294
Ala Glu Leu Val Glu Ser Asp Gly Val Pro Lys Pro Ser Phe Trp Pro
340                 345                 350
```

| | | |
|---|---|---|
| aca gcc cag aac tcg ggg ggc tca gct tac agt gag gag agg gat cgg<br>Thr Ala Gln Asn Ser Gly Gly Ser Ala Tyr Ser Glu Glu Arg Asp Arg<br>355                                  360                             365 | | 1342 |
| cca tac ggc ctg gtg tcc att gac aca gtg act gtg cta gat gca gag<br>Pro Tyr Gly Leu Val Ser Ile Asp Thr Val Thr Val Leu Asp Ala Glu<br>370                                  375                          380                        385 | | 1390 |
| ggg cca tgc acc tgg ccc tgc agc tgt gag gat gac ggc tac cca gcc<br>Gly Pro Cys Thr Trp Pro Cys Ser Cys Glu Asp Asp Gly Tyr Pro Ala<br>                        390                                395                              400 | | 1438 |
| ctg gac ctg gat gct ggc ctg gag ccc agc cca ggc cta gag gac cca<br>Leu Asp Leu Asp Ala Gly Leu Glu Pro Ser Pro Gly Leu Glu Asp Pro<br>405                                  410                                415 | | 1486 |
| ctc ttg gat gca ggg acc aca gtc ctg tcc tgt ggc tgt gtc tca gct<br>Leu Leu Asp Ala Gly Thr Thr Val Leu Ser Cys Gly Cys Val Ser Ala<br>                      420                                425                              430 | | 1534 |
| ggc agc cct ggg cta gga ggg ccc ctg gga agc ctc ctg gac aga cta<br>Gly Ser Pro Gly Leu Gly Gly Pro Leu Gly Ser Leu Leu Asp Arg Leu<br>435                                  440                                445 | | 1582 |
| aag cca ccc ctt gca gat ggg gag gac tgg gct ggg gga ctg ccc tgg<br>Lys Pro Pro Leu Ala Asp Gly Glu Asp Trp Ala Gly Gly Leu Pro Trp<br>450                                  455                                460                        465 | | 1630 |
| ggt ggc cgg tca cct gga ggg gtc tca gag agt gag gcg ggc tca ccc<br>Gly Gly Arg Ser Pro Gly Gly Val Ser Glu Ser Glu Ala Gly Ser Pro<br>                      470                                475                              480 | | 1678 |
| ctg gcc ggc ctg gat atg gac acg ttt gac agt ggc ttt gtg ggc tct<br>Leu Ala Gly Leu Asp Met Asp Thr Phe Asp Ser Gly Phe Val Gly Ser<br>485                                  490                                495 | | 1726 |
| gac tgc agc agc cct gtg gag tgt gac ttc acc agc ccc ggg gac gaa<br>Asp Cys Ser Ser Pro Val Glu Cys Asp Phe Thr Ser Pro Gly Asp Glu<br>                      500                                505                              510 | | 1774 |
| gga ccc ccc cgg agc tac ctc cgc cag tgg gtg gtc att cct ccg cca<br>Gly Pro Pro Arg Ser Tyr Leu Arg Gln Trp Val Val Ile Pro Pro Pro<br>515                                  520                                525 | | 1822 |
| ctt tcg agc cct gga ccc cag gcc agc taatgaggct gactggatgt<br>Leu Ser Ser Pro Gly Pro Gln Ala Ser<br>530                                  535 | | 1869 |
| ccagagctgg ccaggccact gggccctgag ccagagacaa ggtcacctgg gctgtgatgt | | 1929 |
| gaagacacct gcagcctttg gtctcctgga tgggcctttg agcctgatgt ttacagtgtc | | 1989 |
| tgtgtgtgtg tgtgcatatg tgtgtgtgtg catatgcatg tgtgtgtgtg tgtgtgtctt | | 2049 |
| aggtgcgcag tggcatgtcc acgtgtgtgt gtgattgcac gtgcctgtgg gcctgggata | | 2109 |
| atgcccatgg tactccatgc attcacctgc cctgtgcatg tctggactca cggagctcac | | 2169 |
| ccatgtgcac aagtgtgcac agtaaacgtg tttgtggtca acagatgaca acagccgtcc | | 2229 |
| tccctcctag ggtcttgtgt tgcaagttgg tccacagcat ctccggggct ttgtgggatc | | 2289 |
| agggcattgc ctgtgactga ggcggagccc agccctccag cgtctgcctc caggagctgc | | 2349 |
| aagaagtcca tatttgttcct tatcacctgc aacaggaag cgaaagggga tggagtgagc | | 2409 |
| ccatggtgac ctcgggaatg gcaattttt gggcggcccc tggacgaagg tctgaatccc | | 2469 |
| gactctgata ccttctggct gtgctacctg agccaagtcg cctcccctct ctgggctaga | | 2529 |
| gtttccttat ccagacagtg gggaaggcat gacacacctg ggggaaattg gcgatgtcac | | 2589 |
| ccgtgtacgg tacgcagccc agagcagacc ctcaataaac gtcagcttcc ttcaaaaaaa | | 2649 |
| aaaaaaaaaa tctaga | | 2665 |

<210> SEQ ID NO 2
<211> LENGTH: 538
<212> TYPE: PRT

<213> ORGANISM: Homo sapiens

<400> SEQUENCE: 2

```
Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Ile Phe Ser Val
                85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
                180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
            370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
```

```
                405                 410                 415
Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Ile Pro Pro
        515                 520                 525

Pro Leu Ser Ser Pro Gly Pro Gln Ala Ser
    530                 535
```

<210> SEQ ID NO 3
<211> LENGTH: 2628
<212> TYPE: DNA
<213> ORGANISM: Mus musculus
<220> FEATURE:
<221> NAME/KEY: CDS
<222> LOCATION: (407)..(1993)

<400> SEQUENCE: 3

```
gtcgacgcgg cggtaccagc tgtctgccca cttctcctgt ggtgtgcctc acggtcactt      60
gcttgtctga ccgcaagtct gcccatccct ggggcagcca actggcctca gcccgtgccc     120
caggcgtgcc ctgtctctgt ctggctgccc cagccctact gtcttcctct gtgtaggctc     180
tgcccagatg cccggctggt cctcagcctc aggactatct cagcagtgac tcccctgatt     240
ctggacttgc acctgactga actcctgccc acctcaaacc ttcacctccc accaccacca     300
ctccgagtcc cgctgtgact cccacgccca ggagaccacc caagtgcccc agcctaaaga     360
atggctttct gagaaagacc ctgaaggagt aggtctggga cacagc atg ccc cgg        415
                                                 Met Pro Arg
                                                   1 ggc cca gtg gct gcc tta ctc ctg ctg att ctc cat gga gct tgg agc       463
Gly Pro Val Ala Ala Leu Leu Leu Leu Ile Leu His Gly Ala Trp Ser
        5                  10                  15 tgc ctg gac ctc act tgc tac act gac tac ctc tgg acc atc acc tgt       511
Cys Leu Asp Leu Thr Cys Tyr Thr Asp Tyr Leu Trp Thr Ile Thr Cys
20                  25                  30                  35 gtc ctg gag aca cgg agc ccc aac ccc agc ata ctc agt ctc acc tgg       559
Val Leu Glu Thr Arg Ser Pro Asn Pro Ser Ile Leu Ser Leu Thr Trp
                40                  45                  50 caa gat gaa tat gag gaa ctt cag gac caa gag acc ttc tgc agc cta       607
Gln Asp Glu Tyr Glu Glu Leu Gln Asp Gln Glu Thr Phe Cys Ser Leu
            55                  60                  65 cac agg tct ggc cac aac acc aca cat ata tgg tac acg tgc cat atg       655
His Arg Ser Gly His Asn Thr Thr His Ile Trp Tyr Thr Cys His Met
        70                  75                  80 cgc ttg tct caa ttc ctg tcc gat gaa gtt ttc att gtc aat gtg acg       703
Arg Leu Ser Gln Phe Leu Ser Asp Glu Val Phe Ile Val Asn Val Thr
    85                  90                  95 gac cag tct ggc aac aac tcc caa gag tgt ggc agc ttt gtc ctg gct       751
Asp Gln Ser Gly Asn Asn Ser Gln Glu Cys Gly Ser Phe Val Leu Ala
100                 105                 110                 115
```

| | | |
|---|---|---|
| gag agc atc aaa cca gct ccc ccc ttg aac gtg act gtg gcc ttc tca<br>Glu Ser Ile Lys Pro Ala Pro Pro Leu Asn Val Thr Val Ala Phe Ser<br>120 125 130 | | 799 |
| gga cgc tat gat atc tcc tgg gac tca gct tat gac gaa ccc tcc aac<br>Gly Arg Tyr Asp Ile Ser Trp Asp Ser Ala Tyr Asp Glu Pro Ser Asn<br>135 140 145 | | 847 |
| tac gtg ctg agg ggc aag cta caa tat gag ctg cag tat cgg aac ctc<br>Tyr Val Leu Arg Gly Lys Leu Gln Tyr Glu Leu Gln Tyr Arg Asn Leu<br>150 155 160 | | 895 |
| aga gac ccc tat gct gtg agg ccg gtg acc aag ctg atc tca gtg gac<br>Arg Asp Pro Tyr Ala Val Arg Pro Val Thr Lys Leu Ile Ser Val Asp<br>165 170 175 | | 943 |
| tca aga aac gtc tct ctt ctc cct gaa gag ttc cac aaa gat tct agc<br>Ser Arg Asn Val Ser Leu Leu Pro Glu Glu Phe His Lys Asp Ser Ser<br>180 185 190 195 | | 991 |
| tac cag ctg cag gtg cgg gca gcg cct cag cca ggc act tca ttc agg<br>Tyr Gln Leu Gln Val Arg Ala Ala Pro Gln Pro Gly Thr Ser Phe Arg<br>200 205 210 | | 1039 |
| ggg acc tgg agt gag tgg agt gac ccc gtc atc ttt cag acc cag gct<br>Gly Thr Trp Ser Glu Trp Ser Asp Pro Val Ile Phe Gln Thr Gln Ala<br>215 220 225 | | 1087 |
| ggg gag ccc gag gca ggc tgg gac cct cac atg ctg ctc ctg gct<br>Gly Glu Pro Glu Ala Gly Trp Asp Pro His Met Leu Leu Leu Ala<br>230 235 240 | | 1135 |
| gtc ttg atc att gtc ctg gtt ttc atg ggt ctg aag atc cac ctg cct<br>Val Leu Ile Ile Val Leu Val Phe Met Gly Leu Lys Ile His Leu Pro<br>245 250 255 | | 1183 |
| tgg agg cta tgg aaa aag ata tgg gca cca gtg ccc acc cct gag agt<br>Trp Arg Leu Trp Lys Lys Ile Trp Ala Pro Val Pro Thr Pro Glu Ser<br>260 265 270 275 | | 1231 |
| ttc ttc cag ccc ctg tac agg gag cac agc ggg aac ttc aag aaa tgg<br>Phe Phe Gln Pro Leu Tyr Arg Glu His Ser Gly Asn Phe Lys Lys Trp<br>280 285 290 | | 1279 |
| gtt aat acc cct ttc acg gcc tcc agc ata gag ttg gtg cca cag agt<br>Val Asn Thr Pro Phe Thr Ala Ser Ser Ile Glu Leu Val Pro Gln Ser<br>295 300 305 | | 1327 |
| tcc aca aca aca tca gcc tta cat ctg tca ttg tat cca gcc aag gag<br>Ser Thr Thr Thr Ser Ala Leu His Leu Ser Leu Tyr Pro Ala Lys Glu<br>310 315 320 | | 1375 |
| aag aag ttc ccg ggg ctg ccg ggt ctg gaa gag caa ctg gag tgt gat<br>Lys Lys Phe Pro Gly Leu Pro Gly Leu Glu Glu Gln Leu Glu Cys Asp<br>325 330 335 | | 1423 |
| gga atg tct gag cct ggt cac tgg tgc ata atc ccc ttg gca gct ggc<br>Gly Met Ser Glu Pro Gly His Trp Cys Ile Ile Pro Leu Ala Ala Gly<br>340 345 350 355 | | 1471 |
| caa gcg gtc tca gcc tac agt gag gag aga gac cgg cca tat ggt ctg<br>Gln Ala Val Ser Ala Tyr Ser Glu Glu Arg Asp Arg Pro Tyr Gly Leu<br>360 365 370 | | 1519 |
| gtg tcc att gac aca gtg act gtg gga gat gca gag ggc ctg tgt gtc<br>Val Ser Ile Asp Thr Val Thr Val Gly Asp Ala Glu Gly Leu Cys Val<br>375 380 385 | | 1567 |
| tgg ccc tgt agc tgt gag gat gat ggc tat cca gcc atg aac ctg gat<br>Trp Pro Cys Ser Cys Glu Asp Asp Gly Tyr Pro Ala Met Asn Leu Asp<br>390 395 400 | | 1615 |
| gct ggc cga gag tct ggc cct aat tca gag gat ctg ctc ttg gtc aca<br>Ala Gly Arg Glu Ser Gly Pro Asn Ser Glu Asp Leu Leu Leu Val Thr<br>405 410 415 | | 1663 |
| gac cct gct ttt ctg tct tgc ggc tgt gtc tca ggt agt ggt ctc agg<br>Asp Pro Ala Phe Leu Ser Cys Gly Cys Val Ser Gly Ser Gly Leu Arg<br>420 425 430 435 | | 1711 |

-continued

```
ctt gga ggc tcc cca ggc agc cta ctg gac agg ttg agg ctg tca ttt     1759
Leu Gly Gly Ser Pro Gly Ser Leu Leu Asp Arg Leu Arg Leu Ser Phe
            440                 445                 450 gca aag gaa ggg gac tgg aca gca gac cca acc tgg aga act ggg tcc     1807
Ala Lys Glu Gly Asp Trp Thr Ala Asp Pro Thr Trp Arg Thr Gly Ser
        455                 460                 465 cca gga ggg ggc tct gag agt gaa gca ggt tcc ccc cct ggt ctg gac     1855
Pro Gly Gly Gly Ser Glu Ser Glu Ala Gly Ser Pro Pro Gly Leu Asp
    470                 475                 480 atg gac aca ttt gac agt ggc ttt gca ggt tca gac tgt ggc agc ccc     1903
Met Asp Thr Phe Asp Ser Gly Phe Ala Gly Ser Asp Cys Gly Ser Pro
485                 490                 495 gtg gag act gat gaa gga ccc cct cga agc tat ctc cgc cag tgg gtg     1951
Val Glu Thr Asp Glu Gly Pro Pro Arg Ser Tyr Leu Arg Gln Trp Val
500                 505                 510                 515 gtc agg acc cct cca cct gtg gac agt gga gcc cag agc agc                 1993
Val Arg Thr Pro Pro Pro Val Asp Ser Gly Ala Gln Ser Ser
                520                 525 tagcatataa taaccagcta tagtgagaag aggcctctga gcctggcatt tacagtgtga     2053
acatgtaggg gtgtgtgtgt gtgtgtgtgt gtgtgtgtgt gtgtgtgtgt gtgtgtgtgt     2113
gtgtgtgtgt cttgggttgt gtgttagcac atccatgttg ggatttggtc tgttgctatg     2173
tattgtaatg ctaaattctc tacccaaagt tctaggccta cgagtgaatt ctcatgttta     2233
caaacttgct gtgtaaacct tgttccttaa tttaatacca ttggttaaat aaaattggct     2293
gcaaccaatt actggaggga ttagaggtag ggggcttttg agttacctgt ttggagatgg     2353
agaaggagag aggagagacc aagaggagaa ggaggaagga gaggagagga gaggagagga     2413
gaggagagga gaggagagga gaggagagga gaggagaggc tgccgtgagg ggagagggac     2473
catgagcctg tggccaggag aaacagcaag tatctggggt acactggtga ggaggtggcc     2533
aggccagcag ttagaagagt agattagggg tgacctccag tatttgtcaa agccaattaa     2593 ataacaaaa aaaaaaaaaa agcggccgct ctaga                                2628
```

<210> SEQ ID NO 4
<211> LENGTH: 529
<212> TYPE: PRT
<213> ORGANISM: Mus musculus

<400> SEQUENCE: 4

```
Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
```

```
                130                 135                 140
Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
            165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
            195                 200                 205

Ser Phe Arg Gly Thr Trp Ser Glu Trp Ser Asp Pro Val Ile Phe Gln
210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
            245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
            275                 280                 285

Lys Lys Trp Val Asn Thr Pro Phe Thr Ala Ser Ser Ile Glu Leu Val
290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
            325                 330                 335

Glu Cys Asp Gly Met Ser Glu Pro Gly His Trp Cys Ile Ile Pro Leu
            340                 345                 350

Ala Ala Gly Gln Ala Val Ser Ala Tyr Ser Glu Glu Arg Asp Arg Pro
            355                 360                 365

Tyr Gly Leu Val Ser Ile Asp Thr Val Thr Val Gly Asp Ala Glu Gly
            370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
            405                 410                 415

Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
            435                 440                 445

Leu Ser Phe Ala Lys Glu Gly Asp Trp Thr Ala Asp Pro Thr Trp Arg
450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
            485                 490                 495

Gly Ser Pro Val Glu Thr Asp Glu Gly Pro Pro Arg Ser Tyr Leu Arg
            500                 505                 510

Gln Trp Val Val Arg Thr Pro Pro Val Asp Ser Gly Ala Gln Ser
            515                 520                 525

Ser

<210> SEQ ID NO 5
<211> LENGTH: 354
<212> TYPE: DNA
```

<213> ORGANISM: Homo sapiens

<400> SEQUENCE: 5

| | |
|---|---:|
| caggtgcagc tgcaggagtc gggcccagga ctggtgaaga cttcggagac cctgtccctc | 60 |
| acctgcgctg tctctggtta ctccatcagc agtggttact actggggctg gatccggcag | 120 |
| cccccaggga aggggttgga gtggattggg agtatctctc atactgggaa cacctactac | 180 |
| aacccgcccc tcaagagtcg cgtcaccata tcagtagaca cgtccaagaa ccagttctcc | 240 |
| ctgaaactga gctctgtgac cgccgcagac acggccgtgt attactgtgc gcgaggtggg | 300 |
| ggaattagca ggccggagta ctggggcaaa ggcaccctgg tcaccgtctc gagt | 354 |

<210> SEQ ID NO 6
<211> LENGTH: 118
<212> TYPE: PRT
<213> ORGANISM: Homo sapiens

<400> SEQUENCE: 6

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser
        115

<210> SEQ ID NO 7
<211> LENGTH: 354
<212> TYPE: DNA
<213> ORGANISM: Homo sapiens

<400> SEQUENCE: 7

| | |
|---|---:|
| caggtgcagc tgcaggagtc tggccctggc ctggtgaagc cttccgagac cctgtctctg | 60 |
| acctgtgccg tgtccggcta ctccatctcc tccggctact actggggctg gatcagacag | 120 |
| cctcctggca agggcctgga gtggatcggc tccatctctc acaccggcaa cacctactac | 180 |
| aaccccctc tgaagtccag agtgaccatc tccgtggaca cctccaagaa ccagttctcc | 240 |
| ctgaagctgt cctctgtgac cgctgccgat accgccgtgt actactgtgc cagaggcggc | 300 |
| ggaatctcca gacctgagta ctggggccag ggcaccctgg tgaccgtgtc ctct | 354 |

<210> SEQ ID NO 8
<211> LENGTH: 118
<212> TYPE: PRT
<213> ORGANISM: Homo sapiens

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly

|   |   |   |   | 20  |   |   |   |   | 25  |   |   |   |   | 30  |   |   |
|---|---|---|---|---|---|---|---|---|---|---|---|---|---|---|---|---|

Tyr Tyr Trp Gly Trp Ile Arg Gln Pro Pro Gly Lys Gly Leu Glu Trp
          35                  40                  45

Ile Gly Ser Ile Ser His Thr Gly Asn Thr Tyr Tyr Asn Pro Pro Leu
50                     55                  60

Lys Ser Arg Val Thr Ile Ser Val Asp Thr Ser Lys Asn Gln Phe Ser
65                     70                  75                  80

Leu Lys Leu Ser Ser Val Thr Ala Ala Asp Thr Ala Val Tyr Tyr Cys
          85                  90                  95

Ala Arg Gly Gly Gly Ile Ser Arg Pro Glu Tyr Trp Gly Gln Gly Thr
          100                105              110

Leu Val Thr Val Ser Ser
        115

<210> SEQ ID NO 9
<211> LENGTH: 327
<212> TYPE: DNA
<213> ORGANISM: Homo sapiens

<400> SEQUENCE: 9

```
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcagggat cccagaccgc     180
ttctctggct ccacctcagg agacacagct tccttgacca tcactggggc tcaggcggaa     240
gacgaggctg actattactg taactcccgg gactccagtg caaccccca tgttctgttc     300
ggcggaggga cccagctcac cgttttta                                        327
```

<210> SEQ ID NO 10
<211> LENGTH: 109
<212> TYPE: PRT
<213> ORGANISM: Homo sapiens

<400> SEQUENCE: 10

Ser Ser Glu Leu Thr Gln Asp Pro Pro Val Ser Val Ala Leu Gly Gln
1                  5                  10                  15

Thr Val Thr Leu Thr Cys Gln Gly Asp Ser Leu Arg Thr Tyr Tyr Ala
          20                25                30

Ser Trp Tyr Gln Gln Lys Ser Gly Gln Ala Pro Ile Leu Leu Leu Tyr
          35                40                45

Gly Lys His Lys Arg Pro Ser Gly Ile Pro Asp Arg Phe Ser Gly Ser
          50                55                60

Thr Ser Gly Asp Thr Ala Ser Leu Thr Ile Thr Gly Ala Gln Ala Glu
65                     70                  75                  80

Asp Glu Ala Asp Tyr Tyr Cys Asn Ser Arg Asp Ser Ser Gly Asn Pro
          85                  90                  95

His Val Leu Phe Gly Gly Gly Thr Gln Leu Thr Val Leu
          100                105

<210> SEQ ID NO 11
<211> LENGTH: 327
<212> TYPE: DNA
<213> ORGANISM: Homo sapiens

<400> SEQUENCE: 11

```
tcctctgagc tgacccagga tcctgctgtg tctgtggccc tgggccagac cgtcaggatc      60
acctgccagg gcgatagcct gagaacctac tacgcctcct ggtatcagca gaagcctgga     120
```

```
caggcccctg tgctggtgat ctacggcaag cacaagaggc catccggcat ccctgacaga      180
ttctccggct cctcctctgg caataccgcc tccctgacca tcaccggcgc tcaggccgag      240
gacgaggccg actactactg taactcccgg gactcttccg caacccctca cgtgctgttt      300
ggcggcggaa cccagctgac cgtgcta                                         327
```

```
<210> SEQ ID NO 12
<211> LENGTH: 109
<212> TYPE: PRT
<213> ORGANISM: Homo sapiens

<400> SEQUENCE: 12

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

His Val Leu Phe Gly Gly Gly Thr Gln Leu Thr Val Leu
            100                 105
```

```
<210> SEQ ID NO 13
<211> LENGTH: 354
<212> TYPE: DNA
<213> ORGANISM: artificial
<220> FEATURE:
<223> OTHER INFORMATION: H3 VH

<400> SEQUENCE: 13
caggtgcagc tgcaggagtc gggcccagga ctggtgaaga cttcggagac cctgtccctc      60
acctgcgctg tctctggtta ctccatcagc agtggttact actggggctg atccggcag      120 cccccaggga aggggttgga gtggattggg agtatctctc atactgggaa cacctactac      180
aacccgcccc tcaagagtcg cgtcaccata tcagtagaca cgtccaagaa ccagttctcc      240
ctgaaactga gctctgtgac cgccgcagac acggccgtgt attactgtgc gcgattcatg      300
gggttcggcc gcccggagta ctggggcaaa ggcaccctgg tcaccgtctc gagt            354
```

```
<210> SEQ ID NO 14
<211> LENGTH: 118
<212> TYPE: PRT
<213> ORGANISM: artificial
<220> FEATURE:
<223> OTHER INFORMATION: H3 VH

<400> SEQUENCE: 14

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
```

```
            50                  55                  60
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Phe Met Gly Phe Gly Arg Pro Glu Tyr Trp Gly Lys Gly Thr
            100                 105                 110

Leu Val Thr Val Ser Ser
        115

<210> SEQ ID NO 15
<211> LENGTH: 354
<212> TYPE: DNA
<213> ORGANISM: artificial
<220> FEATURE:
<223> OTHER INFORMATION: H4 VH

<400> SEQUENCE: 15
caggtgcagc tgcaggagtc gggcccagga ctggtgaaga cttcggagac cctgtccctc     60
acctgcgctg tctctggtta ctccatcagc agtggttact actggggctg gatccggcag    120
cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgatggctc    300
gggttcggcc gccggagta ctggggcaaa ggcaccctgg tcaccgtctc gagt           354
```



```
ctgaaactga gctctgtgac cgccgcagac acggccgtgt attactgtgc gcgatggctc    300
gggttcggcc gccggagta ctggggcaaa ggcaccctgg tcaccgtctc gagt           354

<210> SEQ ID NO 16
<211> LENGTH: 118
<212> TYPE: PRT
<213> ORGANISM: artificial
<220> FEATURE:
<223> OTHER INFORMATION: H4 VH

<400> SEQUENCE: 16

Gln Val Gln Leu Gln Glu Ser Gly Pro Gly Leu Val Lys Thr Ser Glu
  1               5                  10                  15

Thr Leu Ser Leu Thr Cys Ala Val Ser Gly Tyr Ser Ile Ser Ser Gly
                 20                  25                  30

Tyr Tyr Trp Gly Trp Ile Arg Gln Pro Pro Gly Lys Gly Leu Glu Trp
             35                  40                  45

Ile Gly Ser Ile Ser His Thr Gly Asn Thr Tyr Tyr Asn Pro Pro Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Trp Leu Gly Phe Gly Arg Pro Glu Tyr Trp Gly Lys Gly Thr
            100                 105                 110

Leu Val Thr Val Ser Ser
        115

<210> SEQ ID NO 17
<211> LENGTH: 354
<212> TYPE: DNA
<213> ORGANISM: artificial
<220> FEATURE:
<223> OTHER INFORMATION: H5 VH

<400> SEQUENCE: 17
```

```
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgattcttg   300
ggcttcggcc ggccggagta ctggggcaaa ggcaccctgg tcaccgtctc gagt         354
```

<210> SEQ ID NO 18
<211> LENGTH: 118
<212> TYPE: PRT
<213> ORGANISM: artificial
<220> FEATURE:
<223> OTHER INFORMATION: H5 VH

<400> SEQUENCE: 18

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Leu Gly Phe Gly Arg Pro Glu Tyr Trp Gly Lys Gly Thr
            100                 105                 110

Leu Val Thr Val Ser Ser
        115
```

<210> SEQ ID NO 19
<211> LENGTH: 354
<212> TYPE: DNA
<213> ORGANISM: artificial
<220> FEATURE:
<223> OTHER INFORMATION: H6 VH

<400> SEQUENCE: 19

```
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgattcttc   300
ggcttcggcc gcccggagta ctggggcaaa ggcaccctgg tcaccgtctc gagt         354
```

<210> SEQ ID NO 20
<211> LENGTH: 118
<212> TYPE: PRT
<213> ORGANISM: artificial
<220> FEATURE:
<223> OTHER INFORMATION: H6 VH

<400> SEQUENCE: 20

```
Gln Val Gln Leu Gln Glu Ser Gly Pro Gly Leu Val Lys Thr Ser Glu
1               5                   10                  15
```

```
Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
             35                  40                  45

Ile Gly Ser Ile Ser His Thr Gly Asn Thr Tyr Tyr Asn Pro Pro Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Phe Phe Gly Phe Gly Arg Pro Glu Tyr Trp Gly Lys Gly Thr
            100                 105                 110

Leu Val Thr Val Ser Ser
            115

<210> SEQ ID NO 21
<211> LENGTH: 327
<212> TYPE: DNA
<213> ORGANISM: artificial
<220> FEATURE:
<223> OTHER INFORMATION: L1 VL

<400> SEQUENCE: 21
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcagggat cccagaccgc    180
ttctctggct ccacctcagg agacacagct tccttgacca tcactggggc tcaggcggaa    240
gacgaggctg actattactg tgcgtcccgg tcggtgagcg caaccccca tgttctgttc     300 ggcggaggga cccagctcac cgtttta                                        327

<210> SEQ ID NO 22
<211> LENGTH: 109
<212> TYPE: PRT
<213> ORGANISM: artificial
<220> FEATURE:
<223> OTHER INFORMATION: L1 VL

<400> SEQUENCE: 22

Ser Ser Glu Leu Thr Gln Asp Pro Pro Val Ser Val Ala Leu Gly Gln
  1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
             35                  40                  45

Gly Lys His Lys Arg Pro Ser Gly Ile Pro Asp Arg Phe Ser Gly Ser
 50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ala Ser Arg Ser Val Ser Gly Asn Pro
                 85                  90                  95

His Val Leu Phe Gly Gly Gly Thr Gln Leu Thr Val Leu
            100                 105

<210> SEQ ID NO 23
<211> LENGTH: 327
<212> TYPE: DNA
<213> ORGANISM: artificial
```

<220> FEATURE:
<223> OTHER INFORMATION: L2 VL

<400> SEQUENCE: 23

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactgggc tcaggcggaa    240
gacgaggctg actattactg tgtcgcccgg tcggtggtgg gcaaccccca tgttctgttc   300
ggcggaggga cccagctcac cgttttta                                      327
```

<210> SEQ ID NO 24
<211> LENGTH: 109
<212> TYPE: PRT
<213> ORGANISM: artificial
<220> FEATURE:
<223> OTHER INFORMATION: L2 VL

<400> SEQUENCE: 24

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
                85                  90                  95

His Val Leu Phe Gly Gly Gly Thr Gln Leu Thr Val Leu
            100                 105

<210> SEQ ID NO 25
<211> LENGTH: 327
<212> TYPE: DNA
<213> ORGANISM: artificial
<220> FEATURE:
<223> OTHER INFORMATION: L3 VL

<400> SEQUENCE: 25

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactgggc tcaggcggaa    240
gacgaggctg actattactg tgtcagcagg cggtggtgg gcaaccccca tgttctgttc    300
ggcggaggga cccagctcac cgttttta                                      327
```

<210> SEQ ID NO 26
<211> LENGTH: 109
<212> TYPE: PRT
<213> ORGANISM: artificial
<220> FEATURE:
<223> OTHER INFORMATION: L3 VL

<400> SEQUENCE: 26

```
Ser Ser Glu Leu Thr Gln Asp Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65              70                  75                  80

Asp Glu Ala Asp Tyr Tyr Cys Val Ser Arg Ala Val Val Gly Asn Pro
                85                  90                  95

His Val Leu Phe Gly Gly Gly Thr Gln Leu Thr Val Leu
            100                 105
```

<210> SEQ ID NO 27
<211> LENGTH: 327
<212> TYPE: DNA
<213> ORGANISM: Artificial
<220> FEATURE:
<223> OTHER INFORMATION: L4 VL

<400> SEQUENCE: 27

```
tcttctgagc tgactcagga ccctcctgtg tctgtggcct tgggacagac agtcacgctc      60
acatgccaag agacagcct cagaacctat tatgcaagct ggtaccagca gaagtcagga     120
caggcccta tacttctcct ctatggtaaa cacaaacggc cctcaggat cccagaccgc     180
ttctctggct ccacctcagg agacacagct tccttgacca tcactggggc tcaggcggaa     240
gacgaggctg actattactg tagcacccgc agcagcaagg caaccccca tgttctgttc     300
ggcggaggga cccagctcac cgttttta                                       327
```

<210> SEQ ID NO 28
<211> LENGTH: 109
<212> TYPE: PRT
<213> ORGANISM: artificial
<220> FEATURE:
<223> OTHER INFORMATION: L4 VL

<400> SEQUENCE: 28

```
Ser Ser Glu Leu Thr Gln Asp Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65              70                  75                  80

Asp Glu Ala Asp Tyr Tyr Cys Ser Thr Arg Ser Ser Lys Gly Asn Pro
                85                  90                  95

His Val Leu Phe Gly Gly Gly Thr Gln Leu Thr Val Leu
            100                 105
```

<210> SEQ ID NO 29
<211> LENGTH: 327
<212> TYPE: DNA
<213> ORGANISM: artificial
<220> FEATURE:

<223> OTHER INFORMATION: L5 VL

<400> SEQUENCE: 29

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tgccagcagg tcctccaagg caaccccca tgttctgttc    300
ggcggaggga cccagctcac cgtttta                                      327
```

<210> SEQ ID NO 30
<211> LENGTH: 109
<212> TYPE: PRT
<213> ORGANISM: artificial
<220> FEATURE:
<223> OTHER INFORMATION: L5 VL

<400> SEQUENCE: 30

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ala Ser Arg Ser Ser Lys Gly Asn Pro
                85                  90                  95

His Val Leu Phe Gly Gly Gly Thr Gln Leu Thr Val Leu
            100                 105

<210> SEQ ID NO 31
<211> LENGTH: 327
<212> TYPE: DNA
<213> ORGANISM: artificial
<220> FEATURE:
<223> OTHER INFORMATION: L6 VL

<400> SEQUENCE: 31

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tatgcaggag agcatctggg caaccccca tgttctgttc    300
ggcggaggga cccagctcac cgtttta                                      327
```

<210> SEQ ID NO 32
<211> LENGTH: 109
<212> TYPE: PRT
<213> ORGANISM: artificial
<220> FEATURE:
<223> OTHER INFORMATION: L6 VL

<400> SEQUENCE: 32

Ser Ser Glu Leu Thr Gln Asp Pro Pro Val Ser Val Ala Leu Gly Gln

```
                   1               5                  10                 15
Thr Val Thr Leu Thr Cys Gln Gly Asp Ser Leu Arg Thr Tyr Tyr Ala
                    20                 25                 30

Ser Trp Tyr Gln Gln Lys Ser Gly Gln Ala Pro Ile Leu Leu Leu Tyr
            35                 40                     45

Gly Lys His Lys Arg Pro Ser Gly Ile Pro Asp Arg Phe Ser Gly Ser
        50                 55                 60

Thr Ser Gly Asp Thr Ala Ser Leu Thr Ile Thr Gly Ala Gln Ala Glu
65                  70                 75                 80

Asp Glu Ala Asp Tyr Tyr Cys Met Ser Arg Ser Ile Trp Gly Asn Pro
                    85                 90                 95

His Val Leu Phe Gly Gly Gly Thr Gln Leu Thr Val Leu
                100                 105
```

<210> SEQ ID NO 33
<211> LENGTH: 327
<212> TYPE: DNA
<213> ORGANISM: artificial
<220> FEATURE:
<223> OTHER INFORMATION: L8 VL

<400> SEQUENCE: 33

```
tcttctgagc tgactcagga ccctcctgtg tctgtggcct tgggacagac agtcacgctc     60
acatgccaag gagacagcct cagaacctat tatgcaagct ggtaccagca gaagtcagga   120
caggccccta tacttctcct ctatggtaaa cacaaacggc cctcaggat  cccagaccgc   180
ttctctggct ccacctcagg agacacagct tccttgacca tcactggggc tcaggcggaa   240
gacgaggctg actattactg taccacgcgc tccacccagg caacccccca tgttctgttc   300
ggcggaggga cccagctcac cgtttta                                       327
```

<210> SEQ ID NO 34
<211> LENGTH: 109
<212> TYPE: PRT
<213> ORGANISM: artificial
<220> FEATURE:
<223> OTHER INFORMATION: L8 VL

<400> SEQUENCE: 34

```
Ser Ser Glu Leu Thr Gln Asp Pro Pro Val Ser Val Ala Leu Gly Gln
1               5                  10                 15

Thr Val Thr Leu Thr Cys Gln Gly Asp Ser Leu Arg Thr Tyr Tyr Ala
                    20                 25                 30

Ser Trp Tyr Gln Gln Lys Ser Gly Gln Ala Pro Ile Leu Leu Leu Tyr
            35                 40                     45

Gly Lys His Lys Arg Pro Ser Gly Ile Pro Asp Arg Phe Ser Gly Ser
        50                 55                 60

Thr Ser Gly Asp Thr Ala Ser Leu Thr Ile Thr Gly Ala Gln Ala Glu
65                  70                 75                 80

Asp Glu Ala Asp Tyr Tyr Cys Thr Thr Arg Ser Thr Gln Gly Asn Pro
                    85                 90                 95

His Val Leu Phe Gly Gly Gly Thr Gln Leu Thr Val Leu
                100                 105
```

<210> SEQ ID NO 35
<211> LENGTH: 327
<212> TYPE: DNA
<213> ORGANISM: artificial
<220> FEATURE:
<223> OTHER INFORMATION: L9 VL

<400> SEQUENCE: 35

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tgtcgccagg tccaacaagg gcaaccccca tgttctgttc   300
ggcggaggga cccagctcac cgtttta                                      327
```

<210> SEQ ID NO 36
<211> LENGTH: 109
<212> TYPE: PRT
<213> ORGANISM: artificial
<220> FEATURE:
<223> OTHER INFORMATION: L9 VL

<400> SEQUENCE: 36

```
Ser Ser Glu Leu Thr Gln Asp Pro Pro Val Ser Val Ala Leu Gly Gln
1               5                   10                  15
Thr Val Thr Leu Thr Cys Gln Gly Asp Ser Leu Arg Thr Tyr Tyr Ala
                20                  25                  30
Ser Trp Tyr Gln Gln Lys Ser Gly Gln Ala Pro Ile Leu Leu Leu Tyr
            35                  40                  45
Gly Lys His Lys Arg Pro Ser Gly Ile Pro Asp Arg Phe Ser Gly Ser
        50                  55                  60
Thr Ser Gly Asp Thr Ala Ser Leu Thr Ile Thr Gly Ala Gln Ala Glu
65                  70                  75                  80
Asp Glu Ala Asp Tyr Tyr Cys Val Ala Arg Ser Asn Lys Gly Asn Pro
                85                  90                  95
His Val Leu Phe Gly Gly Gly Thr Gln Leu Thr Val Leu
            100                 105
```

<210> SEQ ID NO 37
<211> LENGTH: 327
<212> TYPE: DNA
<213> ORGANISM: artificial
<220> FEATURE:
<223> OTHER INFORMATION: L10 VL

<400> SEQUENCE: 37

```
tcttctgagc tgactcagga ccctcctgtg tctgtggcct tgggacagac agtcacgctc    60
acatgccaag gagacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tatcagccgg tcgatctacg gcaaccccca tgttctgttc   300
ggcggaggga cccagctcac cgtttta                                      327
```

<210> SEQ ID NO 38
<211> LENGTH: 109
<212> TYPE: PRT
<213> ORGANISM: artificial
<220> FEATURE:
<223> OTHER INFORMATION: L10 VL

<400> SEQUENCE: 38

```
Ser Ser Glu Leu Thr Gln Asp Pro Pro Val Ser Val Ala Leu Gly Gln
1               5                   10                  15
```

```
Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ile Ser Arg Ser Ile Tyr Gly Asn Pro
                85                  90                  95

His Val Leu Phe Gly Gly Gly Thr Gln Leu Thr Val Leu
            100                 105
```

<210> SEQ ID NO 39
<211> LENGTH: 327
<212> TYPE: DNA
<213> ORGANISM: artificial
<220> FEATURE:
<223> OTHER INFORMATION: L11 VL

<400> SEQUENCE: 39

```
tcttctgagc tgactcagga ccctcctgtg tctgtggcct tgggacagac agtcacgctc    60
acatgccaag agacagcct cagaacctat tatgcaagct ggtaccagca aaagtcagga   120
caggccccta tacttctcct ctatggtaaa cacaaacggc cctcagggat cccagaccgc   180
ttctctggct ccacctcagg agacacagct tccttgacca tcactgggc tcaggcggaa   240
gacgaggctg actattactg ttcctcccgc tcccgccacg gcaaccccca tgttctgttc   300
ggcggaggga cccagctcac cgtttta                                       327
```

<210> SEQ ID NO 40
<211> LENGTH: 109
<212> TYPE: PRT
<213> ORGANISM: artificial
<220> FEATURE:
<223> OTHER INFORMATION: L11 VL

<400> SEQUENCE: 40

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
            35                  40                  45

Gly Lys His Lys Arg Pro Ser Gly Ile Pro Asp Arg Phe Ser Gly Ser
        50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ser Ser Arg Ser Arg His Gly Asn Pro
                85                  90                  95

His Val Leu Phe Gly Gly Gly Thr Gln Leu Thr Val Leu
            100                 105
```

<210> SEQ ID NO 41
<211> LENGTH: 327
<212> TYPE: DNA
<213> ORGANISM: artificial
<220> FEATURE:
<223> OTHER INFORMATION: L12 VL -continued

<400> SEQUENCE: 41

```
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcaggat cccagaccgc     180 ttctctggct ccacctcagg agacacagct tccttgacca tcactggggc tcaggcggaa     240
gacgaggctg actattactg tgtcgcgagg gggacgaggg gcaaccccca tgttctgttc     300
ggcggaggga cccagctcac cgttttta                                       327
```

<210> SEQ ID NO 42
<211> LENGTH: 109
<212> TYPE: PRT
<213> ORGANISM: artificial
<220> FEATURE:
<223> OTHER INFORMATION: L12 VL

<400> SEQUENCE: 42

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Ala Arg Gly Thr Arg Gly Asn Pro
                85                  90                  95

His Val Leu Phe Gly Gly Gly Thr Gln Leu Thr Val Leu
            100                 105

<210> SEQ ID NO 43
<211> LENGTH: 327
<212> TYPE: DNA
<213> ORGANISM: artificial
<220> FEATURE:
<223> OTHER INFORMATION: L13 VL

<400> SEQUENCE: 43

```
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta tacttctcct ctatggtaaa cacaaacggc cctcaggat cccagaccgc     180 ttctctggct ccacctcagg agacacagct tccttgacca tcactggggc tcaggcggaa     240
gacgaggctg actattactg tgtcacccgc aaccgctacg gcaaccccca tgttctgttc     300
ggcggaggga cccagctcac cgttttta                                       327
```

<210> SEQ ID NO 44
<211> LENGTH: 109
<212> TYPE: PRT
<213> ORGANISM: artificial
<220> FEATURE:
<223> OTHER INFORMATION: L13 VL

<400> SEQUENCE: 44

Ser Ser Glu Leu Thr Gln Asp Pro Pro Val Ser Val Ala Leu Gly Gln
1               5                   10                  15

```
Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Thr Arg Asn Arg Tyr Gly Asn Pro
                85                  90                  95

His Val Leu Phe Gly Gly Gly Thr Gln Leu Thr Val Leu
            100                 105
```

<210> SEQ ID NO 45
<211> LENGTH: 327
<212> TYPE: DNA
<213> ORGANISM: artificial
<220> FEATURE:
<223> OTHER INFORMATION: L14 VL

<400> SEQUENCE: 45

```
tcttctgagc tgactcagga ccctcctgtg tctgtggcct tgggacagac agtcacgctc    60
acatgccaag agacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tatggcgagg tcgaggaagg gcaaccccca tgttctgttc   300
ggcggaggga cccagctcac cgttttta                                      327
```

<210> SEQ ID NO 46
<211> LENGTH: 109
<212> TYPE: PRT
<213> ORGANISM: artificial
<220> FEATURE:
<223> OTHER INFORMATION: L14 VL

<400> SEQUENCE: 46

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Met Ala Arg Ser Arg Lys Gly Asn Pro
                85                  90                  95

His Val Leu Phe Gly Gly Gly Thr Gln Leu Thr Val Leu
            100                 105
```

<210> SEQ ID NO 47
<211> LENGTH: 327
<212> TYPE: DNA
<213> ORGANISM: artificial
<220> FEATURE:
<223> OTHER INFORMATION: L15 VL

<400> SEQUENCE: 47

```
tcttctgagc tgactcagga cccctcctgtg tctgtggcct tgggacagac agtcacgctc      60
acatgccaag agacagcct cagaacctat tatgcaagct ggtaccagca gaagtcagga       120
caggccccta cttctctcct ctatggtaaa cacaaacggc cctcagggat cccagaccgc      180
ttctctggct ccacctcagg agacacagct tccttgacca tcactggggc tcaggcggaa      240
gacgaggctg actattactg ttccacccgc gccatccacg gcaaccccca tgttctgttc      300
ggcggaggga cccagctcac cgtttta                                          327
```

```
<210> SEQ ID NO 48
<211> LENGTH: 109
<212> TYPE: PRT
<213> ORGANISM: artificial
<220> FEATURE:
<223> OTHER INFORMATION: L15 VL

<400> SEQUENCE: 48

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ser Thr Arg Ala Ile His Gly Asn Pro
                85                  90                  95

His Val Leu Phe Gly Gly Gly Thr Gln Leu Thr Val Leu
            100                 105
```

```
<210> SEQ ID NO 49
<211> LENGTH: 327
<212> TYPE: DNA
<213> ORGANISM: artificial
<220> FEATURE:
<223> OTHER INFORMATION: L16 VL

<400> SEQUENCE: 49
tcttctgagc tgactcagga cccctcctgtg tctgtggcct tgggacagac agtcacgctc      60
acatgccaag agacagcct cagaacctat tatgcaagct ggtaccagca gaagtcagga       120
caggccccta cttctctcct ctatggtaaa cacaaacggc cctcagggat cccagaccgc      180
ttctctggct ccacctcagg agacacagct tccttgacca tcactggggc tcaggcggaa      240
gacgaggctg actattactg tgtgacgagg agcgcgaagg gcaaccccca tgttctgttc      300
ggcggaggga cccagctcac cgtttta                                          327
```

```
<210> SEQ ID NO 50
<211> LENGTH: 109
<212> TYPE: PRT
<213> ORGANISM: artificial
<220> FEATURE:
<223> OTHER INFORMATION: L16 VL

<400> SEQUENCE: 50

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
```

Ser Trp Tyr Gln Gln Lys Ser Gly Gln Ala Pro Ile Leu Leu Leu Tyr
          35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Thr Arg Ser Ala Lys Gly Asn Pro
                85                  90                  95

His Val Leu Phe Gly Gly Gly Thr Gln Leu Thr Val Leu
            100                 105

<210> SEQ ID NO 51
<211> LENGTH: 327
<212> TYPE: DNA
<213> ORGANISM: artificial
<220> FEATURE:
<223> OTHER INFORMATION: L17 VL

<400> SEQUENCE: 51

```
tcttctgagc tgactcagga ccctcctgtg tctgtggcct tgggacagac agtcacgctc      60
acatgccaag agacagcct cagaacctat tatgcaagct ggtaccagca gaagtcagga      120
caggccccta tacttctcct ctatggtaaa cacaaacggc cctcaggat ccccgaccgc      180
ttctctggct ccacctcagg agacacagct ccttgacca tcactggggc tcaggcggaa      240
gacgaggctg actattactg tagcacgagg tcgaggaagg gcaaccccca tgttctgttc      300
ggcggaggga cccagctcac cgtttta                                         327
```

<210> SEQ ID NO 52
<211> LENGTH: 109
<212> TYPE: PRT
<213> ORGANISM: artificial
<220> FEATURE:
<223> OTHER INFORMATION: L17 VL

<400> SEQUENCE: 52

Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
          35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ser Thr Arg Ser Arg Lys Gly Asn Pro
                85                  90                  95

His Val Leu Phe Gly Gly Gly Thr Gln Leu Thr Val Leu
            100                 105

<210> SEQ ID NO 53
<211> LENGTH: 327
<212> TYPE: DNA
<213> ORGANISM: artificial
<220> FEATURE:
<223> OTHER INFORMATION: L18 VL

<400> SEQUENCE: 53

```
tcttctgagc tgactcagga ccctcctgtg tctgtggcct tgggacagac agtcacgctc    60
acatgccaag agacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tgtcacgagg agcgtgaagg gcaaccccca tgttctgttc   300
ggcggaggga cccagctcac cgtttta                                       327
```

<210> SEQ ID NO 54
<211> LENGTH: 109
<212> TYPE: PRT
<213> ORGANISM: artificial
<220> FEATURE:
<223> OTHER INFORMATION: L18 VL

<400> SEQUENCE: 54

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Val Thr Arg Ser Val Lys Gly Asn Pro
                85                  90                  95

His Val Leu Phe Gly Gly Gly Thr Gln Leu Thr Val Leu
            100                 105
```

<210> SEQ ID NO 55
<211> LENGTH: 327
<212> TYPE: DNA
<213> ORGANISM: artificial
<220> FEATURE:
<223> OTHER INFORMATION: L19 VL

<400> SEQUENCE: 55

```
tcttctgagc tgactcagga ccctcctgtg tctgtggcct tgggacagac agtcacgctc    60
acatgccaag agacagcct cagaacctat tatgcaagct ggtaccagca gaagtcagga   120
caggccccta tacttctcct ctatggtaaa cacaaacggc cctcagggat cccagaccgc   180
ttctctggct ccacctcagg agacacagct tccttgacca tcactggggc tcaggcggaa   240
gacgaggctg actattactg tgtcgcgcgg gcggtgaggg gcaaccccca tgttctgttc   300
ggcggaggga cccagctcac cgtttta                                       327
```

<210> SEQ ID NO 56
<211> LENGTH: 109
<212> TYPE: PRT
<213> ORGANISM: artificial
<220> FEATURE:
<223> OTHER INFORMATION: L19 VL

<400> SEQUENCE: 56

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30
```

```
Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Ala Arg Ala Val Arg Gly Asn Pro
                 85                  90                  95

His Val Leu Phe Gly Gly Gly Thr Gln Leu Thr Val Leu
                100                 105

<210> SEQ ID NO 57
<211> LENGTH: 327
<212> TYPE: DNA
<213> ORGANISM: artificial
<220> FEATURE:
<223> OTHER INFORMATION: L20 VL

<400> SEQUENCE: 57
tcttctgagc tgactcagga ccctcctgtg tctgtggcct tgggacagac agtcacgctc    60
acatgccaag agacagcct cagaacctat tatgcaagct ggtaccagca gaagtcagga   120
caggccccta acttctcct ctatggtaaa cacaaacggc cctcaggat cccagaccgc    180 ttctctggct ccacctcagg agacacagct ccttgacca tcactggggc tcaggcggaa   240
gacgaggctg actattactg tgtctcccgc agcgcgaagg gcaacccca tgttctgttc    300 ggcggaggga cccagctcac cgttta                                        327

<210> SEQ ID NO 58
<211> LENGTH: 109
<212> TYPE: PRT
<213> ORGANISM: artificial
<220> FEATURE:
<223> OTHER INFORMATION: L20 VL

<400> SEQUENCE: 58

Ser Ser Glu Leu Thr Gln Asp Pro Pro Val Ser Val Ala Leu Gly Gln
  1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
         35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Val Ser Arg Ser Ala Lys Gly Asn Pro
                 85                  90                  95

His Val Leu Phe Gly Gly Gly Thr Gln Leu Thr Val Leu
                100                 105

<210> SEQ ID NO 59
<211> LENGTH: 327
<212> TYPE: DNA
<213> ORGANISM: artificial
<220> FEATURE:
<223> OTHER INFORMATION: L21 VL

<400> SEQUENCE: 59
tcttctgagc tgactcagga ccctcctgtg tctgtggcct tgggacagac agtcacgctc    60
```

```
acatgccaag gagacagcct cagaacctat tatgcaagct ggtaccagca gaagtcagga    120
caggccccta tacttctcct ctatggtaaa cacaaacggc cctcagggat cccagaccgc    180
ttctctggct ccacctcagg agacacagct tccttgacca tcactggggc tcaggcggaa    240
gacgaggctg actattactg tgccacccgg gcggtccggg caaccccca tgttctgttc     300 ggcggaggga cccagctcac cgttttta                                       327
```

<210> SEQ ID NO 60
<211> LENGTH: 109
<212> TYPE: PRT
<213> ORGANISM: artificial
<220> FEATURE:
<223> OTHER INFORMATION: L21 VL

<400> SEQUENCE: 60

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30

Ser Trp Tyr Gln Gln Lys Ser Gly Gln Ala Pro Ile Leu Leu Leu Tyr
        35                  40                  45

Gly Lys His Lys Arg Pro Ser Gly Ile Pro Asp Arg Phe Ser Gly Ser
    50                  55                  60

Thr Ser Gly Asp Thr Ala Ser Leu Thr Ile Thr Gly Ala Gln Ala Glu
65                  70                  75                  80

Asp Glu Ala Asp Tyr Tyr Cys Ala Thr Arg Ala Val Arg Gly Asn Pro
                85                  90                  95

His Val Leu Phe Gly Gly Gly Thr Gln Leu Thr Val Leu
            100                 105
```

<210> SEQ ID NO 61
<211> LENGTH: 327
<212> TYPE: DNA
<213> ORGANISM: artificial
<220> FEATURE:
<223> OTHER INFORMATION: L23 VL

<400> SEQUENCE: 61

```
tcttctgagc tgactcagga ccctcctgtg tctgtggcct tgggacagac agtcacgctc    60
acatgccaag gagacagcct cagaacctat tatgcaagct ggtaccagca gaagtcagga    120
caggccccta tacttctcct ctatggtaaa cacaaacggc cctcagggat cccagaccgc    180
ttctctggct ccacctcagg agacacagct tccttgacca tcactggggc tcaggcggaa    240
gacgaggctg actattactg ttcggcgcgg tcggtgaggg caaccccca tgttctgttc     300 ggcggaggga cccagctcac cgttttta                                       327
```

<210> SEQ ID NO 62
<211> LENGTH: 109
<212> TYPE: PRT
<213> ORGANISM: artificial
<220> FEATURE:
<223> OTHER INFORMATION: L23 VL

<400> SEQUENCE: 62

```
Ser Ser Glu Leu Thr Gln Asp Pro Pro Val Ser Val Ala Leu Gly Gln
1               5                   10                  15

Thr Val Thr Leu Thr Cys Gln Gly Asp Ser Leu Arg Thr Tyr Tyr Ala
            20                  25                  30
```

Ser Trp Tyr Gln Gln Lys Ser Gly Gln Ala Pro Ile Leu Leu Leu Tyr
          35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ser Ala Arg Ser Val Arg Gly Asn Pro
                 85                  90                  95

His Val Leu Phe Gly Gly Gly Thr Gln Leu Thr Val Leu
            100                 105

<210> SEQ ID NO 63
<211> LENGTH: 327
<212> TYPE: DNA
<213> ORGANISM: artificial
<220> FEATURE:
<223> OTHER INFORMATION: L24 VL

<400> SEQUENCE: 63
tcttctgagc tgactcagga ccctcctgtg tctgtggcct tgggacagac agtcacgctc      60
acatgccaag agacagcct cagaacctat tatgcaagct ggtaccagca gaagtcagga     120
caggccccta acttctcct ctatggtaaa cacaaacggc cctcagggat cccagaccgc     180
ttctctggct ccacctcagg agacacagct tccttgacca tcactgggc tcaggcggaa     240 gacgaggctg actattactg tatcgccagg agcaacaagg gcaaccccca tgttctgttc     300
ggcggaggga cccagctcac cgtttta                                        327

<210> SEQ ID NO 64
<211> LENGTH: 109
<212> TYPE: PRT
<213> ORGANISM: artificial
<220> FEATURE:
<223> OTHER INFORMATION: L24 VL

<400> SEQUENCE: 64

Ser Ser Glu Leu Thr Gln Asp Pro Pro Val Ser Val Ala Leu Gly Gln
 1               5                  10                  15

Thr Val Thr Leu Thr Cys Gln Gly Asp Ser Leu Arg Thr Tyr Tyr Ala
             20                  25                  30

Ser Trp Tyr Gln Gln Lys Ser Gly Gln Ala Pro Ile Leu Leu Leu Tyr
          35                  40                  45

Gly Lys His Lys Arg Pro Ser Gly Ile Pro Asp Arg Phe Ser Gly Ser
     50                  55                  60

Thr Ser Gly Asp Thr Ala Ser Leu Thr Ile Thr Gly Ala Gln Ala Glu
 65                  70                  75                  80

Asp Glu Ala Asp Tyr Tyr Cys Ile Ala Arg Ser Asn Lys Gly Asn Pro
                 85                  90                  95

His Val Leu Phe Gly Gly Gly Thr Gln Leu Thr Val Leu
            100                 105

<210> SEQ ID NO 65
<211> LENGTH: 327
<212> TYPE: DNA
<213> ORGANISM: artificial
<220> FEATURE:
<223> OTHER INFORMATION: L25 VL

<400> SEQUENCE: 65
tcttctgagc tgactcagga ccctcctgtg tctgtggcct tgggacagac agtcacgctc      60

| | |
|---|---|
| acatgccaag agacagcct cagaacctat tatgcaagct ggtaccagca gaagtcagga | 120 |
| caggccccta tacttctcct ctatggtaaa cacaaacggc cctcaggat cccagaccgc | 180 |
| ttctctggct ccacctcagg agacacagct tccttgacca tcactggggc tcaggcggaa | 240 |
| gacgaggctg actattactg tacgacgcgg agcaacaagg caacccccca tgttctgttc | 300 |
| ggcggaggga cccagctcac cgttttta | 327 |

<210> SEQ ID NO 66
<211> LENGTH: 109
<212> TYPE: PRT
<213> ORGANISM: artificial
<220> FEATURE:
<223> OTHER INFORMATION: L25 VL

<400> SEQUENCE: 66

```
Ser Ser Glu Leu Thr Gln Asp Pro Pro Val Ser Val Ala Leu Gly Gln
1               5                   10                  15
Thr Val Thr Leu Thr Cys Gln Gly Asp Ser Leu Arg Thr Tyr Tyr Ala
            20                  25                  30
Ser Trp Tyr Gln Gln Lys Ser Gly Gln Ala Pro Ile Leu Leu Leu Tyr
        35                  40                  45
Gly Lys His Lys Arg Pro Ser Gly Ile Pro Asp Arg Phe Ser Gly Ser
    50                  55                  60
Thr Ser Gly Asp Thr Ala Ser Leu Thr Ile Thr Gly Ala Gln Ala Glu
65                  70                  75                  80
Asp Glu Ala Asp Tyr Tyr Cys Thr Thr Arg Ser Asn Lys Gly Asn Pro
                85                  90                  95
His Val Leu Phe Gly Gly Gly Thr Gln Leu Thr Val Leu
            100                 105
```

<210> SEQ ID NO 67
<211> LENGTH: 1401
<212> TYPE: DNA
<213> ORGANISM: artificial
<220> FEATURE:
<223> OTHER INFORMATION: VH4 heavy chain

<400> SEQUENCE: 67

| | |
|---|---|
| atgggatgga gctgtatcat cctcttcttg gtagcaacag ctacaggcgc gcactctcag | 60 |
| gtgcagctgc aggagtctgg ccctggcctg gtgaagcctt ccgagaccct gtctctgacc | 120 |
| tgtgccgtgt ccggctactc catctcctcc ggctactact ggggctggat cagacagcct | 180 |
| cctggcaagg gcctggagtg gatcggctcc atctctcaca ccggcaacac ctactacaac | 240 |
| cccctctga gtccagagt gaccatctcc gtggacacct ccaagaacca gttctccctg | 300 |
| aagctgtcct ctgtgaccgc tgccgatacc gccgtgtact actgtgccag atggctcggg | 360 |
| ttcggccgcc cggagtactg gggcaaaggc accctggtga ccgtgtcctc tgcctccacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga agttgagcc caaatcttgt | 720 |
| gacaaaactc acacatgccc accgtgccca gcacctgaag ccgcggggc accgtcagtc | 780 |
| ttcctcttcc cccaaaaacc caaggacacc ctcatgatct cccggacccc tgaggtcaca | 840 |
| tgcgtggtgg tggacgtgag ccacgaagac cctgaggtca agttcaactg gtacgtggac | 900 |

```
ggcgtggagg tgcataatgc aagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                              1401
```

<210> SEQ ID NO 68
<211> LENGTH: 467
<212> TYPE: PRT
<213> ORGANISM: artificial
<220> FEATURE:
<223> OTHER INFORMATION: VH4 heavy chain

<400> SEQUENCE: 68

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Trp Leu Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Glu Glu Met Thr Lys Asn Gln Val Ser
370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 69
<211> LENGTH: 1401
<212> TYPE: DNA
<213> ORGANISM: artificial
<220> FEATURE:
<223> OTHER INFORMATION: VH5 heavy chain

<400> SEQUENCE: 69
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240
ccccctctga agtccagagt gaccatctcc gtggacacct ccaagaacca gttctccctg     300
aagctgtcct ctgtgaccgc tgccgatacc gccgtgtact actgtgccag attcttgggc     360
ttcggccggc cggagtactg gggcaaaggc accctggtga ccgtgtcctc tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt      720 gacaaaactc acacatgccc accgtgccca gcacctgaag ccgcggggc accgtcagtc      780 ttcctcttcc cccaaaaacc caaggacacc ctcatgatct cccggacccc tgaggtcaca      840
tgcgtggtgg tggacgtgag ccacgaagac cctgaggtca agttcaactg gtacgtggac      900
ggcgtggagg tgcataatgc caagacaaag ccgcgggagg agcagtacaa cagcacgtac      960
```

-continued

```
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
ggtcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca agagcaggtg gcagcagggg    1320
aacgtcttct catgctccgt gatgcatgag gctctgcaca accactacac gcagaagagc    1380
ctctccctgt ccccgggtaa a                                              1401
```

<210> SEQ ID NO 70
<211> LENGTH: 467
<212> TYPE: PRT
<213> ORGANISM: artificial
<220> FEATURE:
<223> OTHER INFORMATION: VH5 heavy chain

<400> SEQUENCE: 70

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Leu Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 71
<211> LENGTH: 1401
<212> TYPE: DNA
<213> ORGANISM: artificial
<220> FEATURE:
<223> OTHER INFORMATION: VH6 heavy chain

<400> SEQUENCE: 71
atgggatgga gctgtatcat cctcttcttg gtagcaacag ctacaggcgc gcactctcag     60
gtgcagctgc aggagtctgg ccctggcctg gtgaagcctt ccgagaccct gtctctgacc    120
tgtgccgtgt ccggctactc catctcctcc ggctactact ggggctggat cagacagcct    180
cctggcaagg gcctggagtg gatcggctcc atctctcaca ccggcaacac ctactacaac    240
ccccctctga gtccagagt gaccatctcc gtggacacct ccaagaacca gttctccctg     300
aagctgtcct ctgtgaccgc tgccgatacc gccgtgtact actgtgccag attcttcggc    360
ttcggccgcc cggagtactg gggcaaaggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaag ccgcggggc accgtcagtc    780 ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
```

```
tgcaaggtct ccaacaaagc cctcccagcc cccatcgaga aaaccatctc caaagccaaa      1080
ggtcagcccc gagaaccaca ggtgtacacc ctgcccccat cccgggagga gatgaccaag      1140
aaccaggtca gcctgacctg cctggtcaaa ggcttctatc ccagcgacat cgccgtggag      1200
tgggagagca atgggcagcc ggagaacaac tacaagacca cgcctcccgt gctggactcc      1260
gacggctcct tcttcctcta tagcaagctc accgtggaca agagcaggtg gcagcagggg      1320
aacgtcttct catgctccgt gatgcatgag gctctgcaca accactacac gcagaagagc      1380 ctctcccctgt ccccgggtaa a                                               1401
```

<210> SEQ ID NO 72
<211> LENGTH: 467
<212> TYPE: PRT
<213> ORGANISM: artificial
<220> FEATURE:
<223> OTHER INFORMATION: VH6 heavy chain

<400> SEQUENCE: 72

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Phe Gly Phe Gly Arg Pro Glu Tyr Trp Gly
        115                 120                 125

Lys Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 73
<211> LENGTH: 702
<212> TYPE: DNA
<213> ORGANISM: artificial
<220> FEATURE:
<223> OTHER INFORMATION: VL3 light chain

<400> SEQUENCE: 73
atgggatgga gctgtatcat cctcttcttg gtagcaacag ctacaggcgc gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cagcagggcg gtggtgggca accccatgt tctgttcggc     360 ggagggaccc agctcaccgt tttaggtcag cccaaggctg ccccctcggt cactctgttc     420 ccgcccctcct ctgaggagct tcaagccaac aaggccacac tggtgtgtct cataagtgac     480
ttctaccggg gagccgtgac agtggcctgg aaggcagata gcagccccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702

<210> SEQ ID NO 74
<211> LENGTH: 234
<212> TYPE: PRT
<213> ORGANISM: artificial
<220> FEATURE:
<223> OTHER INFORMATION: VL3 light chain

<400> SEQUENCE: 74

Met Gly Trp Ser Cys Ile Ile Leu Phe Leu Val Ala Thr Ala Thr Gly

```
              1               5                  10                  15
Ala His Ser Ser Ser Glu Leu Thr Gln Asp Pro Ala Val Ser Val Ala
                  20                  25                  30

Leu Gly Gln Thr Val Arg Ile Thr Cys Gln Gly Asp Ser Leu Arg Thr
              35                  40                  45

Tyr Tyr Ala Ser Trp Tyr Gln Gln Lys Pro Gly Gln Ala Pro Val Leu
          50                  55                  60

Val Ile Tyr Gly Lys His Lys Arg Pro Ser Gly Ile Pro Asp Arg Phe
 65                  70                  75                  80

Ser Gly Ser Ser Ser Gly Asn Thr Ala Ser Leu Thr Ile Thr Gly Ala
                  85                  90                  95

Gln Ala Glu Asp Glu Ala Asp Tyr Tyr Cys Val Ser Arg Ala Val Val
              100                 105                 110

Gly Asn Pro His Val Leu Phe Gly Gly Thr Gln Leu Thr Val Leu
              115                 120                 125

Gly Gln Pro Lys Ala Ala Pro Ser Val Thr Leu Phe Pro Pro Ser Ser
          130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
              165                 170                 175

Val Lys Ala Gly Val Glu Thr Thr Thr Pro Ser Lys Gln Ser Asn Asn
              180                 185                 190

Lys Tyr Ala Ala Ser Ser Tyr Leu Ser Leu Thr Pro Glu Gln Trp Lys
              195                 200                 205

Ser His Arg Ser Tyr Ser Cys Gln Val Thr His Glu Gly Ser Thr Val
          210                 215                 220

Glu Lys Thr Val Ala Pro Thr Glu Cys Ser
225                 230
```

<210> SEQ ID NO 75
<211> LENGTH: 702
<212> TYPE: DNA
<213> ORGANISM: artificial
<220> FEATURE:
<223> OTHER INFORMATION: VL11 light chain

<400> SEQUENCE: 75

```
atgggatgga gctgtatcat cctcttcttg gtagcaacag ctacaggcgc gcactcttcc      60
tctgagctga cccaggatcc tgctgtgtct gtggccctgg ccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgttc ctcccgctcc cgccacggca accccatgt tctgttcggc     360
ggagggaccc agctcaccgt tttaggtcag cccaaggctg cccctcggt cactctgttc     420
ccgcccctcct ctgaggagct tcaagccaac aaggccacac tggtgtgtct cataagtgac     480
ttctacccgg agccgtgac agtggcctgg aaggcagata gcagcccgt caaggcggga     540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702
```

<210> SEQ ID NO 76

<211> LENGTH: 234
<212> TYPE: PRT
<213> ORGANISM: artificial
<220> FEATURE:
<223> OTHER INFORMATION: VL11 light chain

<400> SEQUENCE: 76

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
                35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ser Ser Arg Ser Arg His
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 77
<211> LENGTH: 702
<212> TYPE: DNA
<213> ORGANISM: artificial
<220> FEATURE:
<223> OTHER INFORMATION: VL13 light chain

<400> SEQUENCE: 77

```
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctgggctca ggcggaagac      300
gaggctgact attactgtgt cacccgcaac cgctacggca accccatgt tctgttcggc      360
ggagggaccc agctcaccgt tttaggtcag cccaaggctg ccccctcggt cactctgttc     420
ccgccctcct ctgaggagct tcaagccaac aaggccacac tggtgtgtct cataagtgac     480
ttctacccgg gagccgtgac agtggcctgg aaggcagata gcagccccgt caaggcggga     540
```

```
gtggagacca ccacaccctc caaacaaagc aacaacaagt acgcggccag cagctatctg    600
agcctgacgc ctgagcagtg aagtccac agaagctaca gctgccaggt cacgcatgaa     660
gggagcaccg tggagaagac agtggcccct acagaatgtt ca                      702
```

<210> SEQ ID NO 78
<211> LENGTH: 234
<212> TYPE: PRT
<213> ORGANISM: artificial
<220> FEATURE:
<223> OTHER INFORMATION: VL13 light chain

<400> SEQUENCE: 78

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Asn Arg Tyr
                100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

<210> SEQ ID NO 79
<211> LENGTH: 702
<212> TYPE: DNA
<213> ORGANISM: artificial
<220> FEATURE:
<223> OTHER INFORMATION: VL14 light chain

<400> SEQUENCE: 79

```
atgggatgga gctgtatcat cctcttcttg gtagcaacag ctacaggcgc gcactcttcc    60
tctgagctga cccaggatcc tgctgtgtct gtggccctgg ccagaccgt caggatcacc    120 tgccagggcg atagcctgag aacctactac gcctcctggt atcagcagaa gcctggacag    180
gcccctgtgc tggtgatcta cggcaagcac aagaggccat ccggcatccc tgacagattc    240
```

```
tccggctcct cctctggcaa taccgcctcc ctgaccatca ctggggctca ggcggaagac    300
gaggctgact attactgtat ggcgaggtcg aggaagggca accccatgt tctgttcggc    360 ggagggaccc agctcaccgt tttaggtcag cccaaggctg ccccctcggt cactctgttc    420 ccgcccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc tgagcagtg gaagtcccac agaagctaca gctgccaggt cacgcatgaa    660
gggagcaccg tggagaagac agtggcccct acagaatgtt ca                      702
```

<210> SEQ ID NO 80
<211> LENGTH: 234
<212> TYPE: PRT
<213> ORGANISM: artificial
<220> FEATURE:
<223> OTHER INFORMATION: VL14 light chain

<400> SEQUENCE: 80

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Met Ala Arg Ser Arg Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 81
<211> LENGTH: 702
<212> TYPE: DNA
<213> ORGANISM: artificial
<220> FEATURE:
<223> OTHER INFORMATION: VL17 light chain

<400> SEQUENCE: 81

-continued

```
atgggatgga gctgtatcat cctcttcttg gtagcaacag ctacaggcgc gcactcttcc      60
tctgagctga cccaggatcc tgctgtgtct gtggccctgg ccagaccag aatcctgacc     120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctgggctca ggcggaagac     300 gaggctgact attactgtag cacgaggtcg aggaagggca accccatgt tctgttcggc     360 ggagggaccc agctcaccgt tttaggtcag cccaaggctg ccccctcggt cactctgttc    420
ccgccctcct ctgaggagct tcaagccaac aaggccacac tggtgtgtct cataagtgac    480
ttctacccgg agccgtgac agtggcctgg aaggcagata gcagcccgt caaggcggga     540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca                       702
```

<210> SEQ ID NO 82
<211> LENGTH: 234
<212> TYPE: PRT
<213> ORGANISM: artificial
<220> FEATURE:
<223> OTHER INFORMATION: VL17 light chain

<400> SEQUENCE: 82

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Arg Ile Leu Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ser Thr Arg Ser Arg Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

<210> SEQ ID NO 83
<211> LENGTH: 702
<212> TYPE: DNA
<213> ORGANISM: artificial
<220> FEATURE:
<223> OTHER INFORMATION: VL23 light chain

<400> SEQUENCE: 83

```
atgggatgga gctgtatcat cctcttcttg gtagcaacag ctacaggcgc gcactcttcc     60
tctgagctga cccaggatcc tgctgtgtct gtggccctgg ccagaccgt caggatcacc    120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgttc ggcgcggtcg gtgaggggca ccccccatgt tctgttcggc    360
ggagggaccc agctcaccgt tttaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca                       702
```

<210> SEQ ID NO 84
<211> LENGTH: 234
<212> TYPE: PRT
<213> ORGANISM: artificial
<220> FEATURE:
<223> OTHER INFORMATION: VL23 light chain

<400> SEQUENCE: 84

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ser Ala Arg Ser Val Arg
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190
```

```
Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

<210> SEQ ID NO 85
<211> LENGTH: 702
<212> TYPE: DNA
<213> ORGANISM: artificial
<220> FEATURE:
<223> OTHER INFORMATION: VL24 light chain

<400> SEQUENCE: 85

```
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtat cgccaggagc aacaagggca accccatgt tctgttcggc     360 ggagggaccc agctcaccgt tttaggtcag cccaaggctg cccctcggt cactctgttc     420 ccgccctcct ctgaggagct tcaagccaac aaggccacac tggtgtgtct cataagtgac     480
ttctacccgg agccgtgac agtggcctgg aaggcagata gcagcccgt caaggcggga     540 gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggccccct acagaatgtt ca                      702
```

<210> SEQ ID NO 86
<211> LENGTH: 234
<212> TYPE: PRT
<213> ORGANISM: artificial
<220> FEATURE:
<223> OTHER INFORMATION: VL24 light chain

<400> SEQUENCE: 86

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Ile Ala Arg Ser Asn Lys
            100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
    130                 135                 140
```

-continued

```
Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
            165                 170                 175

Val Lys Ala Gly Val Glu Thr Thr Thr Pro Ser Lys Gln Ser Asn Asn
        180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

<210> SEQ ID NO 87
<211> LENGTH: 1401
<212> TYPE: DNA
<213> ORGANISM: artificial
<220> FEATURE:
<223> OTHER INFORMATION: VHPTM heavy chain with signal sequence

<400> SEQUENCE: 87

```
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240
cccccctctga agtccagagt gaccatctcc gtggacacct ccaagaacca gttctccctg     300
aagctgtcct ctgtgaccgc tgccgatacc gccgtgtact actgtgccag aggcggcgga     360
atctccagac tgagtactg ggaccagggc accctggtga ccgtgtcctc tgcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaag ccgcggggggc accgtcagtc     780
ttcctcttcc cccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaccatctc caaagccaaa    1080
ggtcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca gagcaggtg gcagcagggg    1320
aacgtcttct catgctccgt gatgcatgag gctctgcaca accactacac gcagaagagc    1380
ctctccctgt ccccgggtaa a                                              1401
```

<210> SEQ ID NO 88
<211> LENGTH: 467
<212> TYPE: PRT

```
<213> ORGANISM: artificial
<220> FEATURE:
<223> OTHER INFORMATION: VHPTM heavy chain with signal sequence

<400> SEQUENCE: 88

Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400
```

```
Trp Ser Asn Gly Gln Pro Glu Asn Tyr Lys Thr Thr Pro Pro
        405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 89
<211> LENGTH: 1401
<212> TYPE: DNA
<213> ORGANISM: artificial
<220> FEATURE:
<223> OTHER INFORMATION: VHPDM heavy chain with signal sequence

<400> SEQUENCE: 89
atgggatgga gctgtatcat cctcttcttg gtagcaacag ctacaggcgc gcactctcag     60
gtgcagctgc aggagtctgg ccctggcctg gtgaagcctt ccgagaccct gtctctgacc    120
tgtgccgtgt ccggctactc catctcctcc ggctactact ggggctggat cagacagcct    180
cctggcaagg gcctggagtg gatcggctcc atctctcaca ccggcaacac ctactacaac    240 cccctctga gtccagagt gaccatctcc gtggacacct ccaagaacca gttctccctg    300
```

```
aagctgtcct ctgtgaccgc tgccgatacc gccgtgtact actgtgccag aggcggcgga    360
atctccagac tgagtactg gggccagggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaag ccctggggggc accgtcagtc    780 ttcctcttcc cccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc ccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ccccgggtaa a                                             1401

<210> SEQ ID NO 90
<211> LENGTH: 467
<212> TYPE: PRT
<213> ORGANISM: artificial
<220> FEATURE:
```

<223> OTHER INFORMATION: VHPDM heavy chain with signal sequence

<400> SEQUENCE: 90

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
```

```
                   405                 410                 415
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 91
<211> LENGTH: 1401
<212> TYPE: DNA
<213> ORGANISM: artificial
<220> FEATURE:
<223> OTHER INFORMATION: VH3TM heavy chain with signal sequence

<400> SEQUENCE: 91
atgggatgga gctgtatcat cctcttcttg gtagcaacag ctacaggcgc gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240 cccctctga agtccagagt gaccatctcc gtggacacct ccaagaacca gttctccctg     300
aagctgtcct ctgtgaccgc tgccgatacc gccgtgtact actgtgccag attcatgggg     360
ttcggccgcc ggagtactg gggccagggc accctggtga ccgtgtcctc tgcctccacc     420
aagggcccat cggtcttccc cctggcaccc tcctccaaga gcacctctgg ggcacagcg     480 gccctgggct gcctggtcaa ggactacttc cccgaaccgg tgacggtgtc gtggaactca     540 ggcgcctga ccagcggcgt gcacaccttc cggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720 gacaaaactc acacatgccc accgtgccca gcacctgaag ccgcggggc accgtcagtc     780 ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
ggtcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta tagcaagctc accgtggaca gagcaggtg gcagcagggg    1320 aacgtcttct catgctccgt gatgcatgag gctctgcaca accactacac gcagaagagc    1380
ctctccctgt ccccgggtaa a                                             1401

<210> SEQ ID NO 92
<211> LENGTH: 467
<212> TYPE: PRT
<213> ORGANISM: artificial
<220> FEATURE:
<223> OTHER INFORMATION: VH3DM heavy chain with signal sequence
```

<400> SEQUENCE: 92

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Met Gly Phe Gly Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 93
<211> LENGTH: 1401
<212> TYPE: DNA
<213> ORGANISM: artificial
<220> FEATURE:
<223> OTHER INFORMATION: VH3DM heavy chain with signal sequence

<400> SEQUENCE: 93

| | | |
|---|---|---|
| atgggatgga gctgtatcat cctcttcttg gtagcaacag ctacaggcgc gcactctcag | 60 |
| gtgcagctgc aggagtctgg ccctggcctg gtgaagcctt ccgagaccct gtctctgacc | 120 |
| tgtgccgtgt ccggctactc catctcctcc ggctactact ggggctggat cagacagcct | 180 |
| cctggcaagg gcctggagtg gatcggctcc atctctcaca ccggcaacac ctactacaac | 240 |
| cccctctga agtccagagt gaccatctcc gtggacacct ccaagaacca gttctccctg | 300 |
| aagctgtcct ctgtgaccgc tgccgatacc gccgtgtact actgtgccag attcatgggg | 360 |
| ttcggccgcc cggagtactg gggccagggc accctggtga ccgtgtcctc tgcctccacc | 420 |
| aagggcccat cggtcttccc cctggcaccc tcctccaaga gcacctctgg gggcacagcg | 480 |
| gccctgggct gcctggtcaa ggactacttc cccgaaccgg tgacggtgtc gtggaactca | 540 |
| ggcgccctga ccagcggcgt gcacaccttc ccggctgtcc tacagtcctc aggactctac | 600 |
| tccctcagca gcgtggtgac cgtgccctcc agcagcttgg gcacccagac ctacatctgc | 660 |
| aacgtgaatc acaagcccag caacaccaag gtggacaaga agttgagcc caaatcttgt | 720 |
| gacaaaactc acacatgccc accgtgccca gcacctgaag ccctggggc accgtcagtc | 780 |
| ttcctcttcc ccccaaaacc caaggacacc ctcatgatct cccggacccc tgaggtcaca | 840 |
| tgcgtggtgg tggacgtgag ccacgaagac cctgaggtca agttcaactg gtacgtggac | 900 |
| ggcgtggagg tgcataatgc caagacaaag ccgcgggagg agcagtacaa cagcacgtac | 960 |
| cgtgtggtca gcgtcctcac cgtcctgcac caggactggc tgaatggcaa ggagtacaag | 1020 |
| tgcaaggtct ccaacaaagc cctcccagcc cccatcgaga aaaccatctc caaagccaaa | 1080 |
| ggtcagcccc gagaaccaca ggtgtacacc ctgcccccat cccgggagga gatgaccaag | 1140 |
| aaccaggtca gcctgacctg cctggtcaaa ggcttctatc ccagcgacat cgccgtggag | 1200 |
| tgggagagca atgggcagcc ggagaacaac tacaagacca cgcctcccgt gctggactcc | 1260 |
| gacggctcct tcttcctcta tagcaagctc accgtggaca gagcaggtg gcagcagggg | 1320 |
| aacgtcttct catgctccgt gatgcatgag gctctgcaca accactacac gcagaagagc | 1380 |
| ctctccctgt ccccgggtaa a | 1401 |

<210> SEQ ID NO 94
<211> LENGTH: 467
<212> TYPE: PRT
<213> ORGANISM: artificial
<220> FEATURE:
<223> OTHER INFORMATION: VH3TM heavy chain with signal sequence

<400> SEQUENCE: 94

```
Met Gly Trp Ser Cys Ile Ile Leu Phe Leu Val Ala Thr Ala Thr Gly
1               5                   10                  15

Ala His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
            35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Phe Met Gly Phe Gly Arg Pro Glu Tyr Trp Gly
            115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
            245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430
```

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
        450                 455                 460

Pro Gly Lys
465

<210> SEQ ID NO 95
<211> LENGTH: 702
<212> TYPE: DNA
<213> ORGANISM: artificial
<220> FEATURE:
<223> OTHER INFORMATION: VL2 light chain with signal sequence

<400> SEQUENCE: 95
atgggatgga gctgtatcat cctcttcttg gtagcaacag ctacaggcgc gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cgcccggtcg gtggtgggca accccatgt tctgttcggc     360 ggagggaccc agctcaccgt tttaggtcag cccaaggctg cccctcggt cactctgttc     420 ccgccctcct ctgaggagct tcaagccaac aaggccacac tggtgtgtct cataagtgac     480
ttctacccgg gagccgtgac agtggcctgg aaggcagata gcagcccgt caaggcggga     540 gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702

<210> SEQ ID NO 96
<211> LENGTH: 234
<212> TYPE: PRT
<213> ORGANISM: artificial
<220> FEATURE:
<223> OTHER INFORMATION: VL2 light chain with signal sequence

<400> SEQUENCE: 96

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ala Arg Ser Val Val
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
            165                 170                 175

Val Lys Ala Gly Val Glu Thr Thr Thr Pro Ser Lys Gln Ser Asn Asn
        180                 185                 190

Lys Tyr Ala Ala Ser Ser Tyr Leu Ser Leu Thr Pro Glu Gln Trp Lys
    195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 97
<211> LENGTH: 702
<212> TYPE: DNA
<213> ORGANISM: artificial
<220> FEATURE:
<223> OTHER INFORMATION: VL6 light chain with signal sequence

<400> SEQUENCE: 97
atgggatgga gctgtatcat cctcttcttg gtagcaacag ctacaggcgc gcactcttcc      60
tctgagctga cccaggatcc tgctgtgtct gtggccctgg ccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctgggctca ggcggaagac      300
gaggctgact attactgtat gagcaggagc atctggggca ccccccatgt tctgttcggc     360
ggagggaccc agctcaccgt tttaggtcag cccaaggctg cccctcggt cactctgttc      420
ccgccctcct ctgaggagct tcaagccaac aaggccacac tggtgtgtct cataagtgac     480
ttctacccgg gagccgtgac agtggcctgg aaggcagata gcagccccgt caaggcggga     540
gtggagacca ccacccctc caaacaaagc aacaacaagt acgcggccag cagctatctg      600
agcctgacgc ctgagcagtg gaagtcccac agaagctaca gctgccaggt cacgcatgaa     660
gggagcaccg tggagaagac agtggcccct acagaatgtt ca                        702

<210> SEQ ID NO 98
<211> LENGTH: 234
<212> TYPE: PRT
<213> ORGANISM: artificial
<220> FEATURE:
<223> OTHER INFORMATION: VL6 light chain with signal sequence

<400> SEQUENCE: 98

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
            85                  90                  95

Gln Ala Glu Asp Glu Ala Asp Tyr Tyr Cys Met Ser Arg Ser Ile Trp
                100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Pro Ser Lys Gln Ser Asn Asn
            180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
            210                 215                 220

Glu Lys Thr Val Ala Pro Thr Glu Cys Ser
225                 230

<210> SEQ ID NO 99
<211> LENGTH: 702
<212> TYPE: DNA
<213> ORGANISM: artificial
<220> FEATURE:
<223> OTHER INFORMATION: VL9 light chain with signal sequence

<400> SEQUENCE: 99
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctgggctca ggcggaagac     300
gaggctgact attactgtgt cgccaggtcc aacaagggca accccatgt tctgttcggc     360
ggagggaccc agctcaccgt tttaggtcag cccaaggctg cccctcggt cactctgttc     420
ccgccctcct ctgaggagct tcaagccaac aaggccacac tggtgtgtct cataagtgac     480
ttctacccgg agccgtgac agtggcctgg aaggcagata gcagcccgt caaggcggga     540
gtggagacca ccacccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                       702

<210> SEQ ID NO 100
<211> LENGTH: 234
<212> TYPE: PRT
<213> ORGANISM: artificial
<220> FEATURE:
<223> OTHER INFORMATION: VL9 light chain with signal sequence

<400> SEQUENCE: 100

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
 50                  55                  60

Val Ile Tyr Gly Lys His Lys Arg Pro Ser Gly Ile Pro Asp Arg Phe
 65                  70                  75                  80

Ser Gly Ser Ser Ser Gly Asn Thr Ala Ser Leu Thr Ile Thr Gly Ala
                 85                  90                  95

Gln Ala Glu Asp Glu Ala Asp Tyr Tyr Cys Val Ala Arg Ser Asn Lys
            100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 101
<211> LENGTH: 702
<212> TYPE: DNA
<213> ORGANISM: artificial
<220> FEATURE:
<223> OTHER INFORMATION: VL16 light chain with signal sequence

<400> SEQUENCE: 101
atgggatgga gctgtatcat cctcttcttg gtagcaacag ctacaggcgc gcactcttcc    60
tctgagctga cccaggatcc tgctgtgtct gtggccctgg gccagaccgt caggatcacc   120
tgccagggcg atagcctgag aacctactac gcctcctggt atcagcagaa gcctggacag   180
gcccctgtgc tggtgatcta cggcaagcac aagaggccat ccggcatccc tgacagattc   240
tccggctcct cctctggcaa taccgcctcc ctgaccatca ctggggctca ggcggaagac   300
gaggctgact attactgtgt gacgaggagc gcgaagggca accccatgt tctgttcggc   360 ggagggaccc agctcaccgt tttaggtcag cccaaggctg cccctcggt cactctgttc   420 ccgcccctcct ctgaggagct tcaagccaac aaggccacac tggtgtgtct cataagtgac   480
ttctacccgg agccgtgac agtggcctgg aaggcagata gcagcccgt caaggcggga   540 gtggagacca ccacaccctc caaacaaagc aacaacaagt acgcggccag cagctatctg   600
agcctgacgc ctgagcagtg gaagtccac agaagctaca gctgccaggt cacgcatgaa   660
gggagcaccg tggagaagac agtggcccct acagaatgtt ca                      702

<210> SEQ ID NO 102
<211> LENGTH: 234
<212> TYPE: PRT
<213> ORGANISM: artificial
<220> FEATURE:
<223> OTHER INFORMATION: VL16 light chain with signal sequence

<400> SEQUENCE: 102

```
Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Ala Lys
                100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230
```

<210> SEQ ID NO 103
<211> LENGTH: 702
<212> TYPE: DNA
<213> ORGANISM: artificial
<220> FEATURE:
<223> OTHER INFORMATION: VL18 light chain with signal sequence

<400> SEQUENCE: 103

```
atgggatgga gctgtatcat cctcttcttg gtagcaacag ctacaggcgc gcactcttcc      60
tctgagctga cccaggatcc tgctgtgtct gtggccctgg gccagaccgt caggatcacc     120
tgccagggcg atagcctgag aacctactac gcctcctggt atcagcagaa gcctggacag     180
gcccctgtgc tggtgatcta cggcaagcac aagaggccat ccggcatccc tgacagattc     240
tccggctcct cctctggcaa taccgcctcc ctgaccatca ctggggctca ggcggaagac     300
gaggctgact attactgtgt cacgaggagc gtgaagggca cccccatgt tctgttcggc      360
ggagggaccc agctcaccgt tttaggtcag cccaaggctg cccctcggt cactctgttc       420
ccgccctcct ctgaggagct tcaagccaac aaggccacac tggtgtgtct cataagtgac     480
ttctacccgg agccgtgac agtggcctgg aaggcagata gcagcccgt caaggcggga       540
gtggagacca ccacaccctc caaacaaagc aacaacaagt acgcggccag cagctatctg     600
agcctgacgc ctgagcagtg gaagtcccac agaagctaca gctgccaggt cacgcatgaa     660
gggagcaccg tggagaagac agtggcccct acagaatgtt ca                        702
```

<210> SEQ ID NO 104
<211> LENGTH: 234
<212> TYPE: PRT
<213> ORGANISM: artificial
<220> FEATURE:
<223> OTHER INFORMATION: VL18 light chain with signal sequence

<400> SEQUENCE: 104

Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Val Lys
            100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 105
<211> LENGTH: 702
<212> TYPE: DNA
<213> ORGANISM: artificial
<220> FEATURE:
<223> OTHER INFORMATION: VL20 light chain with signal sequence

<400> SEQUENCE: 105
atgggatgga gctgtatcat cctcttcttg gtagcaacag ctacaggcgc gcactcttcc    60
tctgagctga cccaggatcc tgctgtgtct gtggccctgg gccagaccgt caggatcacc   120
tgccagggcg atagcctgag aacctactac gcctcctggt atcagcagaa gcctggacag   180
gcccctgtgc tggtgatcta cggcaagcac aagaggccat ccggcatccc tgacagattc   240
tccggctcct cctctggcaa taccgcctcc ctgaccatca ctggggctca ggcggaagac   300
gaggctgact attactgtgt ctcccgcagc gcgaagggca accccatgt tctgttcggc   360 ggagggaccc agctcaccgt tttaggtcag cccaaggctg ccccctcggt cactctgttc   420 ccgcccctcct ctgaggagct tcaagccaac aaggccacac tggtgtgtct cataagtgac   480

```
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca                      702
```

```
<210> SEQ ID NO 106
<211> LENGTH: 234
<212> TYPE: PRT
<213> ORGANISM: artificial
<220> FEATURE:
<223> OTHER INFORMATION: VL20 light chain with signal sequence

<400> SEQUENCE: 106
```

Met Gly Trp Ser Cys Ile Ile Leu Phe Leu Val Ala Thr Ala Thr Gly
1               5                   10                  15

Ala His Ser Ser Ser Glu Leu Thr Gln Asp Pro Ala Val Ser Val Ala
                20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Ser Arg Ser Ala Lys
                100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

```
<210> SEQ ID NO 107
<211> LENGTH: 702
<212> TYPE: DNA
<213> ORGANISM: artificial
<220> FEATURE:
<223> OTHER INFORMATION: VL25 light chain with signal sequence

<400> SEQUENCE: 107
```

```
atgggatgga gctgtatcat cctcttcttg gtagcaacag ctacaggcgc gcactcttcc    60
tctgagctga cccaggatcc tgctgtgtct gtggccctgg gccagaccgt caggatcacc    120
tgccagggcg atagcctgag aacctactac gcctcctggt atcagcagaa gcctggacag    180
```

```
gccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgtac gacgcggagc aacaagggca ccccatgt tctgttcggc     360 ggagggaccc agctcaccgt tttaggtcag cccaaggctg cccctcggt cactctgttc     420 ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca                      702
```

```
<210> SEQ ID NO 108
<211> LENGTH: 234
<212> TYPE: PRT
<213> ORGANISM: artificial
<220> FEATURE:
<223> OTHER INFORMATION: VL25 light chain with signal sequence

<400> SEQUENCE: 108
```

```
Met Gly Trp Ser Cys Ile Ile Leu Phe Leu Val Ala Thr Ala Thr Gly
1               5                   10                  15

Ala His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
        35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Thr Thr Arg Ser Asn Lys
            100                 105                 110

Gly Asn Pro His Val Leu Phe Gly Gly Gly Thr Gln Leu Thr Val Leu
        115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

```
<210> SEQ ID NO 109
<211> LENGTH: 732
<212> TYPE: DNA
<213> ORGANISM: artificial
<220> FEATURE:
<223> OTHER INFORMATION: H3 scFV
```

<400> SEQUENCE: 109

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgattcatg     300
gggttcggcc gccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtaact cccgggactc cagtggcaac ccccatgttc tgttcggcgg agggacccag     720
ctcaccgttt ta                                                         732
```

<210> SEQ ID NO 110
<211> LENGTH: 244
<212> TYPE: PRT
<213> ORGANISM: artificial
<220> FEATURE:
<223> OTHER INFORMATION: H3 scFV

<400> SEQUENCE: 110

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220
```

Arg Asp Ser Ser Gly Asn Pro His Val Leu Phe Gly Gly Thr Gln
225                 230                 235                 240

Leu Thr Val Leu

<210> SEQ ID NO 111
<211> LENGTH: 732
<212> TYPE: DNA
<213> ORGANISM: artificial
<220> FEATURE:
<223> OTHER INFORMATION: H4 scFV

<400> SEQUENCE: 111
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgatggctc   300
gggttcggcc gccggagta ctggggcaaa ggcaccctgg tcaccgtctc gagtggaggc   360
ggcggttcag gcggaggtgg ctctggcggt ggcggaagtg cactttcttc tgagctgact   420 caggacccctc ctgtgtctgt ggccttggga cagacagtca cgctcacatg ccaaggagac   480
agcctcagaa cctattatgc aagctggtac cagcagaagt caggacaggc ccctatactt   540
ctcctctatg gtaaacacaa acggccctca gggatcccag accgcttctc tggctccacc   600
tcaggagaca cagcttcctt gaccatcact ggggctcagg cggaagacga ggctgactat   660
tactgtaact cccgggactc cagtggcaac cccatgttc tgttcggcgg agggacccag   720
ctcaccgttt ta                                                        732

<210> SEQ ID NO 112
<211> LENGTH: 244
<212> TYPE: PRT
<213> ORGANISM: artificial
<220> FEATURE:
<223> OTHER INFORMATION: H4 scFV

<400> SEQUENCE: 112

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Leu Gly Phe Gly Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp 145                 150                 155                 160
Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
            195                 200                 205

Ile Thr Gly Ala Gln Ala Glu Asp Glu Ala Asp Tyr Tyr Cys Asn Ser
            210                 215                 220

Arg Asp Ser Ser Gly Asn Pro His Val Leu Phe Gly Gly Gly Thr Gln
225                 230                 235                 240

Leu Thr Val Leu

<210> SEQ ID NO 113
<211> LENGTH: 732
<212> TYPE: DNA
<213> ORGANISM: artificial
<220> FEATURE:
<223> OTHER INFORMATION: H5 scFV

<400> SEQUENCE: 113
caggtgcagc tgcaggagtc gggcccagga ctggtgaaga cttcggagac cctgtccctc     60
acctgcgctg tctctggtta ctccatcagc agtggttact actggggctg gatccggcag    120
ccccccaggga aggggttgga gtggatt

```
Leu Lys Leu Ser Ser Val Thr Ala Ala Asp Thr Ala Val Tyr Tyr Cys
            85                  90                  95

Ala Arg Phe Leu Gly Phe Gly Arg Pro Glu Tyr Trp Gly Lys Gly Thr
        100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Asn Ser
    210                 215                 220

Arg Asp Ser Ser Gly Asn Pro His Val Leu Phe Gly Gly Gly Thr Gln
225                 230                 235                 240

Leu Thr Val Leu

<210> SEQ ID NO 115
<211> LENGTH: 732
<212> TYPE: DNA
<213> ORGANISM: artificial
<220> FEATURE:
<223> OTHER INFORMATION: H6 scFv

<400> SEQUENCE: 115
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactggaa cacctactac      180 aacccgcccc tcaagagtcg cgtcaccata tcagtagaca cgtccaagaa ccagttctcc     240
ctgaaactga gctctgtgac cgccgcagac acggccgtgt attactgtgc gcgattcttc     300
ggcttcggcc gccggagta ctggggcaaa ggcaccctgg tcaccgtctc gagtggaggc      360
ggcggttcag gcggaggtgg ctctggcggt ggcggaagtg cactttcttc tgagctgact     420
caggacccct ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtaact cccgggactc cagtggcaac cccatgttc tgttcggcgg agggacccag      720
ctcaccgttt ta                                                         732

<210> SEQ ID NO 116
<211> LENGTH: 244
<212> TYPE: PRT
<213> ORGANISM: artificial
<220> FEATURE:
<223> OTHER INFORMATION: H6 scFv

<400> SEQUENCE: 116

Gln Val Gln Leu Gln Glu Ser Gly Pro Gly Leu Val Lys Thr Ser Glu
1               5                   10                  15
```

```
Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Phe Phe Gly Phe Gly Arg Pro Glu Tyr Trp Gly Lys Gly Thr
            100                 105                 110

Leu Val Thr Val Ser Ser Gly Gly Gly Ser Gly Gly Gly Gly Ser
            115                 120                 125

Gly Gly Gly Gly Ser Ala Leu Ser Ser Glu Leu Thr Gln Asp Pro Pro
            130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
            195                 200                 205

Ile Thr Gly Ala Gln Ala Glu Asp Glu Ala Asp Tyr Tyr Cys Asn Ser
 210                 215                 220

Arg Asp Ser Ser Gly Asn Pro His Val Leu Phe Gly Gly Gly Thr Gln
225                 230                 235                 240

Leu Thr Val Leu

<210> SEQ ID NO 117
<211> LENGTH: 732
<212> TYPE: DNA
<213> ORGANISM: artificial
<220> FEATURE:
<223> OTHER INFORMATION: L1 scFv

<400> SEQUENCE: 117
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgcgt cccggtcggt gagcggcaac cccatgttc tgttcggcgg agggacccag      720
ctcaccgttt ta                                                         732
```

<210> SEQ ID NO 118
<211> LENGTH: 244
<212> TYPE: PRT
<213> ORGANISM: artificial
<220> FEATURE:
<223> OTHER INFORMATION: L1 scFv

<400> SEQUENCE: 118

```
Gln Val Gln Leu Gln Glu Ser Gly Pro Gly Leu Val Lys Thr Ser Glu
1               5                   10                  15
Thr Leu Ser Leu Thr Cys Ala Val Ser Gly Tyr Ser Ile Ser Ser Gly
            20                  25                  30
Tyr Tyr Trp Gly Trp Ile Arg Gln Pro Pro Gly Lys Gly Leu Glu Trp
        35                  40                  45
Ile Gly Ser Ile Ser His Thr Gly Asn Thr Tyr Tyr Asn Pro Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Gly Gly Ile Ser Arg Pro Glu Tyr Trp Gly Lys Gly Thr
            100                 105                 110
Leu Val Thr Val Ser Ser Gly Gly Gly Ser Gly Gly Gly Gly Ser
        115                 120                 125
Gly Gly Gly Gly Ser Ala Leu Ser Ser Glu Leu Thr Gln Asp Pro Pro
    130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
            180                 185                 190
Pro Asp Arg Phe Ser Gly Ser Thr Ser Gly Asp Thr Ala Ser Leu Thr
        195                 200                 205
Ile Thr Gly Ala Gln Ala Glu Asp Glu Ala Asp Tyr Tyr Cys Ala Ser
    210                 215                 220
Arg Ser Val Ser Gly Asn Pro His Val Leu Phe Gly Gly Gly Thr Gln
225                 230                 235                 240
Leu Thr Val Leu
```

<210> SEQ ID NO 119
<211> LENGTH: 732
<212> TYPE: DNA
<213> ORGANISM: artificial
<220> FEATURE:
<223> OTHER INFORMATION: L2 scFv

<400> SEQUENCE: 119

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc     360
```

```
ggcggttcag gcggaggtgg ctctggcggt ggcggaagtg cactttcttc tgagctgact    420
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtgtcg cccggtcggt ggtgggcaac cccatgttc tgttcggcgg agggacccag    720
ctcaccgttt ta                                                         732
```

<210> SEQ ID NO 120
<211> LENGTH: 244
<212> TYPE: PRT
<213> ORGANISM: artificial
<220> FEATURE:
<223> OTHER INFORMATION: L2 scFv

<400> SEQUENCE: 120

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Ser Val Val Gly Asn Pro His Val Leu Phe Gly Gly Gly Thr Gln
225                 230                 235                 240

Leu Thr Val Leu

<210> SEQ ID NO 121
<211> LENGTH: 732
<212> TYPE: DNA
<213> ORGANISM: artificial
<220> FEATURE:
<223> OTHER INFORMATION: L3 scFV

<400> SEQUENCE: 121

```
caggtgcagc tgcaggagtc gggcccagga ctggtgaaga cttcggagac cctgtccctc    60
acctgcgctg tctctggtta ctccatcagc agtggttact actggggctg gatccggcag   120
cccccaggga aggggttgga gtggattggg agtatctctc atactgggaa cacctactac   180
aacccgcccc tcaagagtcg cgtcaccata tcagtagaca cgtccaagaa ccagttctcc   240
ctgaaactga gctctgtgac cgccgcagac acggccgtgt attactgtgc gcgaggtggg   300
ggaattagca ggccggagta ctgggcaaa ggcaccctgg tcaccgtctc gagtggaggc   360
ggcggttcag gcgaggtgg ctctggcggt ggcggaagtg cactttcttc tgagctgact   420
caggaccctc ctgtgtctgt ggccttggga cagacagtca cgctcacatg ccaaggagac   480
agcctcagaa cctattatgc aagctggtac cagcagaagt caggacaggc ccctatactt   540
ctcctctatg gtaaacacaa acggccctca gggatcccag accgcttctc tggctccacc   600
tcaggagaca cagcttcctt gaccatcact ggggctcagg cggaagacga ggctgactat   660
tactgtgtca gcagggcggt ggtgggcaac ccccatgttc tgttcggcgg agggacccag   720
ctcaccgttt ta                                                       732
```

<210> SEQ ID NO 122
<211> LENGTH: 244
<212> TYPE: PRT
<213> ORGANISM: artificial
<220> FEATURE:
<223> OTHER INFORMATION: L3 scFv

<400> SEQUENCE: 122

```
Gln Val Gln Leu Gln Glu Ser Gly Pro Gly Leu Val Lys Thr Ser Glu
1               5                  10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Ser Gly Asp Thr Ala Ser Leu Thr
        195                 200                 205

Ile Thr Gly Ala Gln Ala Glu Asp Glu Ala Asp Tyr Tyr Cys Val Ser
    210                 215                 220

Arg Ala Val Val Gly Asn Pro His Val Leu Phe Gly Gly Gly Thr Gln
```

```
225                 230                 235                 240
Leu Thr Val Leu

<210> SEQ ID NO 123
<211> LENGTH: 732
<212> TYPE: DNA
<213> ORGANISM: artificial
<220> FEATURE:
<223> OTHER INFORMATION: L4 scFv

<400> SEQUENCE: 123
caggtgcagc tgcaggagtc gggcccagga ctggtgaaga cttcggagac cctgtccctc       60
acctgcgctg tctctggtta ctccatcagc agtggttact actggggctg gatccggcag      120
cccccaggga aggggttgga gtggattggg agtatctctc atactgggaa cacctactac      180
aacccgcccc tcaagagtcg cgtcaccata tcagtagaca cgtccaagaa ccagttctcc      240
ctgaaactga gctctgtgac cgccgcagac acggccgtgt attactgtgc gcgaggtggg      300
ggaattagca ggccggagta ctggggcaaa ggcaccctgg tcaccgtctc gagtggaggc      360
ggcggttcag gcggaggtgg ctctggcggt ggcggaagtg cactttcttc tgagctgact      420
caggaccctc ctgtgtctgt ggccttggga cagacagtca cgctcacatg ccaaggagac      480
agcctcagaa cctattatgc aagctggtac agcagaagt caggacaggc ccctatactt      540
ctcctctatg gtaaacacaa acggccctca gggatcccag accgcttctc tggctccacc      600
tcaggagaca cagcttcctt gaccatcact ggggctcagg cggaagacga ggctgactat      660
tactgtagca cccgcagcag caagggcaac cccatgttc tgttcggcgg agggaccag       720 ctcaccgttt ta                                                          732

<210> SEQ ID NO 124
<211> LENGTH: 244
<212> TYPE: PRT
<213> ORGANISM: artificial
<220> FEATURE:
<223> OTHER INFORMATION: L4 scFv

<400> SEQUENCE: 124

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Ser His Thr Gly Asn Thr Tyr Tyr Asn Pro Pro Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160
```

Ser Leu Arg Thr Tyr Tyr Ala Ser Trp Tyr Gln Gln Lys Ser Gly Gln
            165                 170                 175

Ala Pro Ile Leu Leu Tyr Gly Lys His Lys Arg Pro Ser Gly Ile
        180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Thr
        210                 215                 220

Arg Ser Ser Lys Gly Asn Pro His Val Leu Phe Gly Gly Gly Thr Gln
225                 230                 235                 240

Leu Thr Val Leu

<210> SEQ ID NO 125
<211> LENGTH: 732
<212> TYPE: DNA
<213> ORGANISM: artificial
<220> FEATURE:
<223> OTHER INFORMATION: L5 scFv

<400> SEQUENCE: 125
caggtgcagc tgcaggagtc gggcccagga ctggtgaaga cttcggagac cctgtccctc        60
acctgcgctg tctctggtta ctccatcagc agtggttact actggggctg atccggcag       120 cccccaggga aggggttgga gtggattggg agtatctctc atactgggaa cacctactac       180
aacccgcccc tcaagagtcg cgtcaccata tcagtagaca cgtccaagaa ccagttctcc       240
ctgaaactga gctctgtgac cgccgcagac acggccgtgt attactgtgc gcgaggtggg       300
ggaattagca ggccggagta ctggggcaaa ggcaccctgg tcaccgtctc gagtggaggc       360
ggcggttcag gcggaggtgg ctctggcggt ggcggaagtg cactttcttc tgagctgact       420 caggacccte ctgtgtctgt ggccttggga cagacagtca cgctcacatg ccaaggagac       480
agcctcagaa cctattatgc aagctggtac cagcagaagt caggacaggc ccctatactt       540
ctcctctatg gtaaacacaa acggccctca gggatcccag accgcttctc tggctccacc       600
tcaggagaca cagcttcctt gaccatcact ggggctcagg cggaagacga ggctgactat       660
tactgtgcca gcaggtcctc aagggcaac ccccatgttc tgttcggcgg agggacccag       720
ctcaccgttt ta                                                          732

<210> SEQ ID NO 126
<211> LENGTH: 244
<212> TYPE: PRT
<213> ORGANISM: artificial
<220> FEATURE:
<223> OTHER INFORMATION: L5 scFv

<400> SEQUENCE: 126

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

```
Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ala Ser
    210                 215                 220

Arg Ser Ser Lys Gly Asn Pro His Val Leu Phe Gly Gly Gly Thr Gln
225                 230                 235                 240

Leu Thr Val Leu

<210> SEQ ID NO 127
<211> LENGTH: 732
<212> TYPE: DNA
<213> ORGANISM: artificial
<220> FEATURE:
<223> OTHER INFORMATION: L6 scFv

<400> SEQUENCE: 127
caggtgcagc tgcaggagtc gggcccagga ctggtgaaga cttcggagac cctgtccctc      60
acctgcgctg tctctggtta ctccatcagc agtggttact actggggctg gatccggcag     120
ccccagggaa aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtatga gcaggagcat ctggggcaac cccatgttc tgttcggcgg agggacccag     720
ctcaccgttt ta                                                         732

<210> SEQ ID NO 128
<211> LENGTH: 244
<212> TYPE: PRT
<213> ORGANISM: artificial
<220> FEATURE:
<223> OTHER INFORMATION: L6 scFv

<400> SEQUENCE: 128

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
```

```
                 20                  25                  30
Tyr Tyr Trp Gly Trp Ile Arg Gln Pro Pro Gly Lys Gly Leu Glu Trp
             35                  40                  45
Ile Gly Ser Ile Ser His Thr Gly Asn Thr Tyr Tyr Asn Pro Pro Leu
 50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Gly Gly Gly Ile Ser Arg Pro Glu Tyr Trp Gly Lys Gly Thr
                100                 105                 110
Leu Val Thr Val Ser Ser Gly Gly Gly Gly Ser Gly Gly Gly Gly Ser
                115                 120                 125
Gly Gly Gly Gly Ser Ala Leu Ser Ser Glu Leu Thr Gln Asp Pro Pro
            130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
            180                 185                 190
Pro Asp Arg Phe Ser Gly Ser Thr Ser Gly Asp Thr Ala Ser Leu Thr
            195                 200                 205
Ile Thr Gly Ala Gln Ala Glu Asp Glu Ala Asp Tyr Tyr Cys Met Ser
        210                 215                 220
Arg Ser Ile Trp Gly Asn Pro His Val Leu Phe Gly Gly Gly Thr Gln
225                 230                 235                 240
Leu Thr Val Leu

<210> SEQ ID NO 129
<211> LENGTH: 732
<212> TYPE: DNA
<213> ORGANISM: artificial
<220> FEATURE:
<223> OTHER INFORMATION: L8 scFv

<400> SEQUENCE: 129
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420 caggacccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtacca cgcgctccac ccagggcaac ccccatgttc tgttcggcgg agggacccag     720
ctcaccgttt ta                                                         732
```

<210> SEQ ID NO 130
<211> LENGTH: 244
<212> TYPE: PRT
<213> ORGANISM: artificial
<220> FEATURE:
<223> OTHER INFORMATION: L8 scFv

<400> SEQUENCE: 130

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Thr Thr
    210                 215                 220

Arg Ser Thr Gln Gly Asn Pro His Val Leu Phe Gly Gly Gly Thr Gln
225                 230                 235                 240

Leu Thr Val Leu

<210> SEQ ID NO 131
<211> LENGTH: 732
<212> TYPE: DNA
<213> ORGANISM: artificial
<220> FEATURE:
<223> OTHER INFORMATION: L9 scFv

<400> SEQUENCE: 131
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420

```
caggaccctc ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtgtcg ccaggtccaa caagggcaac ccccatgttc tgttcggcgg agggacccag    720
ctcaccgttt ta                                                         732
```

<210> SEQ ID NO 132
<211> LENGTH: 244
<212> TYPE: PRT
<213> ORGANISM: artificial
<220> FEATURE:
<223> OTHER INFORMATION: L9 scFv

<400> SEQUENCE: 132

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Ser Asn Lys Gly Asn Pro His Val Leu Phe Gly Gly Gly Thr Gln
225                 230                 235                 240

Leu Thr Val Leu
```

<210> SEQ ID NO 133
<211> LENGTH: 732
<212> TYPE: DNA
<213> ORGANISM: artificial
<220> FEATURE:
<223> OTHER INFORMATION: L10 scFv

<400> SEQUENCE: 133

```
caggtgcagc tgcaggagtc gggcccagga ctggtgaaga cttcggagac cctgtccctc    60
```

-continued

```
acctgcgctg tctctggtta ctccatcagc agtggttact actggggctg gatccggcag      120
cccccaggga aggggttgga gtggattggg agtatctctc atactgggaa cacctactac      180
aacccgcccc tcaagagtcg cgtcaccata tcagtagaca cgtccaagaa ccagttctcc      240
ctgaaactga gctctgtgac cgccgcagac acggccgtgt attactgtgc gcgaggtggg      300
ggaattagca ggccggagta ctggggcaaa ggcaccctgg tcaccgtctc gagtggaggc      360
ggcggttcag gcggaggtgg ctctggcggt ggcggaagtg cactttcttc tgagctgact      420 caggacccte ctgtgtctgt ggccttggga cagacagtca cgctcacatg ccaaggagac      480
agcctcagaa cctattatgc aagctggtac cagcagaagt caggacaggc ccctatactt      540
ctcctctatg gtaaacacaa acggccctca gggatcccag accgcttctc tggctccacc      600
tcaggagaca cagcttcctt gaccatcact ggggctcagg cggaagacga ggctgactat      660
tactgtatca gccggtcgat ctacggcaac ccccatgttc tgttcggcgg agggacccag      720
ctcaccgttt ta                                                          732
```

<210> SEQ ID NO 134
<211> LENGTH: 244
<212> TYPE: PRT
<213> ORGANISM: artificial
<220> FEATURE:
<223> OTHER INFORMATION: L10 scFv

<400> SEQUENCE: 134

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ile Ser
    210                 215                 220

Arg Ser Ile Tyr Gly Asn Pro His Val Leu Phe Gly Gly Gly Thr Gln
225                 230                 235                 240
```

Leu Thr Val Leu

<210> SEQ ID NO 135
<211> LENGTH: 732
<212> TYPE: DNA
<213> ORGANISM: artificial
<220> FEATURE:
<223> OTHER INFORMATION: L11 scFv

<400> SEQUENCE: 135

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgttcct cccgctcccg ccacggcaac ccccatgttc tgttcggcgg agggacccag     720
ctcaccgttt ta                                                         732
```

<210> SEQ ID NO 136
<211> LENGTH: 244
<212> TYPE: PRT
<213> ORGANISM: artificial
<220> FEATURE:
<223> OTHER INFORMATION: L11 scFv

<400> SEQUENCE: 136

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175
```

```
Ala Pro Ile Leu Leu Leu Tyr Gly Lys His Lys Arg Pro Ser Gly Ile
                180                 185                 190

Pro Asp Arg Phe Ser Gly Ser Thr Ser Gly Asp Thr Ala Ser Leu Thr
            195                 200                 205

Ile Thr Gly Ala Gln Ala Glu Asp Glu Ala Asp Tyr Tyr Cys Ser Ser
        210                 215                 220

Arg Ser Arg His Gly Asn Pro His Val Leu Phe Gly Gly Gly Thr Gln
225                 230                 235                 240

Leu Thr Val Leu

<210> SEQ ID NO 137
<211> LENGTH: 732
<212> TYPE: DNA
<213> ORGANISM: artificial
<220> FEATURE:
<223> OTHER INFORMATION: L12 scFv

<400> SEQUENCE: 137
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggacccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtcg cgaggggggac gaggggcaac ccccatgttc tgttcggcgg agggacccag     720
ctcaccgttt ta                                                        732

<210> SEQ ID NO 138
<211> LENGTH: 244
<212> TYPE: PRT
<213> ORGANISM: artificial
<220> FEATURE:
<223> OTHER INFORMATION: L12 scFv

<400> SEQUENCE: 138

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
```

100                 105                 110
Leu Val Thr Val Ser Ser Gly Gly Gly Ser Gly Gly Gly Ser
        115                 120                 125

Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ala
    210                 215                 220

Arg Gly Thr Arg Gly Asn Pro His Val Leu Phe Gly Gly Gly Thr Gln
225                 230                 235                 240

Leu Thr Val Leu

<210> SEQ ID NO 139
<211> LENGTH: 732
<212> TYPE: DNA
<213> ORGANISM: artificial
<220> FEATURE:
<223> OTHER INFORMATION: L13 scFv

<400> SEQUENCE: 139
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc cctatacttt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtca cccgcaaccg ctacggcaac cccatgttc tgttcggcgg agggaccag      720
ctcaccgttt ta                                                       732

<210> SEQ ID NO 140
<211> LENGTH: 244
<212> TYPE: PRT
<213> ORGANISM: artificial
<220> FEATURE:
<223> OTHER INFORMATION: L13 scFv

<400> SEQUENCE: 140

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

-continued

```
Tyr Tyr Trp Gly Trp Ile Arg Gln Pro Pro Gly Lys Gly Leu Glu Trp
         35                  40                  45
Ile Gly Ser Ile Ser His Thr Gly Asn Thr Tyr Tyr Asn Pro Pro Leu
 50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Gly Gly Gly Ile Ser Arg Pro Glu Tyr Trp Gly Lys Gly Thr
                100                 105                 110
Leu Val Thr Val Ser Ser Gly Gly Gly Ser Gly Gly Gly Gly Ser
                115                 120                 125
Gly Gly Gly Gly Ser Ala Leu Ser Ser Glu Leu Thr Gln Asp Pro Pro
        130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
                180                 185                 190
Pro Asp Arg Phe Ser Gly Ser Thr Ser Gly Asp Thr Ala Ser Leu Thr
                195                 200                 205
Ile Thr Gly Ala Gln Ala Glu Asp Glu Ala Asp Tyr Tyr Cys Val Thr
        210                 215                 220
Arg Asn Arg Tyr Gly Asn Pro His Val Leu Phe Gly Gly Gly Thr Gln
225                 230                 235                 240
Leu Thr Val Leu
```

<210> SEQ ID NO 141
<211> LENGTH: 732
<212> TYPE: DNA
<213> ORGANISM: artificial
<220> FEATURE:
<223> OTHER INFORMATION: L14 scFv

<400> SEQUENCE: 141

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctgggcaaa ggcaccctgg tcaccgtctc gagtggaggc      360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtatgg cgaggtcgag gaagggcaac cccatgttc tgttcggcgg agggacccag      720
ctcaccgttt ta                                                         732
```

<210> SEQ ID NO 142
<211> LENGTH: 244

```
<212> TYPE: PRT
<213> ORGANISM: artificial
<220> FEATURE:
<223> OTHER INFORMATION: L14 scFv

<400> SEQUENCE: 142

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Met Ala
    210                 215                 220

Arg Ser Arg Lys Gly Asn Pro His Val Leu Phe Gly Gly Gly Thr Gln
225                 230                 235                 240

Leu Thr Val Leu

<210> SEQ ID NO 143
<211> LENGTH: 732
<212> TYPE: DNA
<213> ORGANISM: artificial
<220> FEATURE:
<223> OTHER INFORMATION: L15 scFv

<400> SEQUENCE: 143
caggtgcagc tgcaggagtc gggcccagga ctggtgaaga cttcggagac cctgtccctc      60
acctgcgctg tctctggtta ctccatcagc agtggttact actggggctg gatccggcag     120
ccccagggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
```

```
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgttcca cccgcgccat ccacggcaac cccatgttc tgttcggcgg agggacccag     720
ctcaccgttt ta                                                         732
```

<210> SEQ ID NO 144
<211> LENGTH: 244
<212> TYPE: PRT
<213> ORGANISM: artificial
<220> FEATURE:
<223> OTHER INFORMATION: L15 scFv

<400> SEQUENCE: 144

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Thr
    210                 215                 220

Arg Ala Ile His Gly Asn Pro His Val Leu Phe Gly Gly Gly Thr Gln
225                 230                 235                 240

Leu Thr Val Leu
```

<210> SEQ ID NO 145
<211> LENGTH: 732
<212> TYPE: DNA
<213> ORGANISM: artificial
<220> FEATURE:
<223> OTHER INFORMATION: L16 scFv

<400> SEQUENCE: 145

```
caggtgcagc tgcaggagtc gggcccagga ctggtgaaga cttcggagac cctgtccctc     60
acctgcgctg tctctggtta ctccatcagc agtggttact actggggctg gatccggcag    120
```

```
cccccaggga aggggttgga gtggattggg agtatctctc atactgggaa cacctactac      180
aacccgcccc tcaagagtcg cgtcaccata tcagtagaca cgtccaagaa ccagttctcc      240
ctgaaactga gctctgtgac cgccgcagac acggccgtgt attactgtgc gcgaggtggg      300
ggaattagca ggccggagta ctgggcaaa ggcaccctgg tcaccgtctc gagtggaggc       360
ggcggttcag gcggaggtgg ctctggcggt ggcggaagtg cactttcttc tgagctgact      420
caggaccctc ctgtgtctgt ggccttggga cagacagtca cgctcacatg ccaaggagac      480
agcctcagaa cctattatgc aagctggtac cagcagaagt caggacaggc cctatactt       540 ctcctctatg gtaaacacaa acggccctca gggatcccag accgcttctc tggctccacc      600
tcaggagaca cagcttcctt gaccatcact ggggctcagg cggaagacga ggctgactat      660
tactgtgtga cgaggagcgc gaagggcaac cccatgttc tgttcggcgg agggacccag       720
ctcaccgttt ta                                                          732
```

<210> SEQ ID NO 146
<211> LENGTH: 244
<212> TYPE: PRT
<213> ORGANISM: artificial
<220> FEATURE:
<223> OTHER INFORMATION: L16 scFv

<400> SEQUENCE: 146

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Thr
    210                 215                 220

Arg Ser Ala Lys Gly Asn Pro His Val Leu Phe Gly Gly Thr Gln
225                 230                 235                 240

Leu Thr Val Leu
```

<210> SEQ ID NO 147
<211> LENGTH: 732
<212> TYPE: DNA
<213> ORGANISM: artificial
<220> FEATURE:
<223> OTHER INFORMATION: L17 scFv

<400> SEQUENCE: 147

```
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcgaggtgg ctctggcggt ggcggaagtg cactttcttc tgagctgact      420
caggacccte ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtagca cgaggtcgag gaagggcaac cccatgttc tgttcggcgg agggacccag      720
ctcaccgttt ta                                                         732
```

<210> SEQ ID NO 148
<211> LENGTH: 244
<212> TYPE: PRT
<213> ORGANISM: artificial
<220> FEATURE:
<223> OTHER INFORMATION: L17 scFv

<400> SEQUENCE: 148

```
Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
```

180                 185                 190
Pro Asp Arg Phe Ser Gly Ser Thr Gly Asp Thr Ala Ser Leu Thr
        195                 200                 205

Ile Thr Gly Ala Gln Ala Glu Asp Glu Ala Asp Tyr Tyr Cys Ser Thr
        210                 215                 220

Arg Ser Arg Lys Gly Asn Pro His Val Leu Phe Gly Gly Gly Thr Gln
225                 230                 235                 240

Leu Thr Val Leu

<210> SEQ ID NO 149
<211> LENGTH: 732
<212> TYPE: DNA
<213> ORGANISM: artificial
<220> FEATURE:
<223> OTHER INFORMATION: L18 scFv

<400> SEQUENCE: 149
caggtgcagc tgcaggagtc gggcccagga ctggtgaaga cttcggagac cctgtccctc     60
acctgcgctg tctctggtta ctccatcagc agtggttact actggggctg atccggcag    120 cccccaggga aggggttgga gtggattggg agtatctctc atactgggaa cacctactac    180
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcgagagtgg ctctggcggt ggcggaagtg cactttcttc tgagctgact    420 caggacccto ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgtgtca cgaggagcgt gaagggcaac cccatgttc tgttcggcgg agggacccag    720
ctcaccgttt ta                                                        732

<210> SEQ ID NO 150
<211> LENGTH: 244
<212> TYPE: PRT
<213> ORGANISM: artificial
<220> FEATURE:
<223> OTHER INFORMATION: L18 scFv

<400> SEQUENCE: 150

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

```
Leu Val Thr Val Ser Ser Gly Gly Gly Gly Ser
        115                 120                 125
Gly Gly Gly Gly Ser Ala Leu Ser Ser Glu Leu Thr Gln Asp Pro Pro
        130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
                180                 185                 190
Pro Asp Arg Phe Ser Gly Ser Thr Ser Gly Asp Thr Ala Ser Leu Thr
                195                 200                 205
Ile Thr Gly Ala Gln Ala Glu Asp Glu Ala Asp Tyr Tyr Cys Val Thr
        210                 215                 220
Arg Ser Val Lys Gly Asn Pro His Val Leu Phe Gly Gly Thr Gln
225                 230                 235                 240

Leu Thr Val Leu

<210> SEQ ID NO 151
<211> LENGTH: 732
<212> TYPE: DNA
<213> ORGANISM: artificial
<220> FEATURE:
<223> OTHER INFORMATION: L19 scFv

<400> SEQUENCE: 151
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtcg cgcgggcggt gaggggcaac cccatgttc tgttcggcgg agggacccag     720
ctcaccgttt ta                                                         732

<210> SEQ ID NO 152
<211> LENGTH: 244
<212> TYPE: PRT
<213> ORGANISM: artificial
<220> FEATURE:
<223> OTHER INFORMATION: L19 scFv

<400> SEQUENCE: 152

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45
```

```
Ile Gly Ser Ile Ser His Thr Gly Asn Thr Tyr Tyr Asn Pro Pro Leu
         50                  55                  60
Lys Ser Arg Val Thr Ile Ser Val Asp Thr Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Gly Gly Ile Ser Arg Pro Glu Tyr Trp Gly Lys Gly Thr
                100                 105                 110
Leu Val Thr Val Ser Ser Gly Gly Gly Gly Ser Gly Gly Gly Gly Ser
                115                 120                 125
Gly Gly Gly Ser Ala Leu Ser Ser Glu Leu Thr Gln Asp Pro Pro
        130                 135                 140
Val Ser Val Ala Leu Gly Gln Thr Val Thr Leu Thr Cys Gln Gly Asp
145                 150                 155                 160
Ser Leu Arg Thr Tyr Tyr Ala Ser Trp Tyr Gln Gln Lys Ser Gly Gln
                165                 170                 175
Ala Pro Ile Leu Leu Leu Tyr Gly Lys His Lys Arg Pro Ser Gly Ile
                180                 185                 190
Pro Asp Arg Phe Ser Gly Ser Thr Ser Gly Asp Thr Ala Ser Leu Thr
                195                 200                 205
Ile Thr Gly Ala Gln Ala Glu Asp Glu Ala Asp Tyr Tyr Cys Val Ala
        210                 215                 220
Arg Ala Val Arg Gly Asn Pro His Val Leu Phe Gly Gly Gly Thr Gln
225                 230                 235                 240
Leu Thr Val Leu

<210> SEQ ID NO 153
<211> LENGTH: 732
<212> TYPE: DNA
<213> ORGANISM: artificial
<220> FEATURE:
<223> OTHER INFORMATION: L20 scFv

<400> SEQUENCE: 153
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtgtct cccgcagcgc gaagggcaac ccccatgttc tgttcggcgg agggacccag     720
ctcaccgttt ta                                                         732

<210> SEQ ID NO 154
<211> LENGTH: 244
<212> TYPE: PRT
<213> ORGANISM: artificial
```

<220> FEATURE:
<223> OTHER INFORMATION: L20 scFv

<400> SEQUENCE: 154

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Val Ser
    210                 215                 220

Arg Ser Ala Lys Gly Asn Pro His Val Leu Phe Gly Gly Gly Thr Gln
225                 230                 235                 240

Leu Thr Val Leu

<210> SEQ ID NO 155
<211> LENGTH: 732
<212> TYPE: DNA
<213> ORGANISM: artificial
<220> FEATURE:
<223> OTHER INFORMATION: L21 scFv

<400> SEQUENCE: 155
caggtgcagc tgcaggagtc gggcccagga ctggtgaaga cttcggagac cctgtccctc      60
acctgcgctg tctctggtta ctccatcagc agtggttact actggggctg atccggcag     120 cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540

```
ctcctctatg gtaaacacaa acggccctca gggatcccag accgcttctc tggctccacc    600
tcaggagaca cagcttcctt gaccatcact ggggctcagg cggaagacga ggctgactat    660
tactgtgcca cccgggcggt ccggggcaac ccccatgttc tgttcggcgg agggacccag    720
ctcaccgttt ta                                                        732
```

<210> SEQ ID NO 156
<211> LENGTH: 244
<212> TYPE: PRT
<213> ORGANISM: artificial
<220> FEATURE:
<223> OTHER INFORMATION: L21 scFv

<400> SEQUENCE: 156

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Ser His Thr Gly Asn Thr Tyr Tyr Asn Pro Pro Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ala Thr
    210                 215                 220

Arg Ala Val Arg Gly Asn Pro His Val Leu Phe Gly Gly Gly Thr Gln
225                 230                 235                 240

Leu Thr Val Leu

<210> SEQ ID NO 157
<211> LENGTH: 732
<212> TYPE: DNA
<213> ORGANISM: artificial
<220> FEATURE:
<223> OTHER INFORMATION: L23 scFv

<400> SEQUENCE: 157

```
caggtgcagc tgcaggagtc gggcccagga ctggtgaaga cttcggagac cctgtccctc     60
acctgcgctg tctctggtta ctccatcagc agtggttact actggggctg gatccggcag    120
cccccaggga aggggttgga gtggattggg agtatctctc atactgggaa cacctactac    180
```

```
aacccgcccc tcaagagtcg cgtcaccata tcagtagaca cgtccaagaa ccagttctcc    240
ctgaaactga gctctgtgac cgccgcagac acggccgtgt attactgtgc gcgaggtggg    300
ggaattagca ggccggagta ctggggcaaa ggcaccctgg tcaccgtctc gagtggaggc    360
ggcggttcag gcggaggtgg ctctggcggt ggcggaagtg cactttcttc tgagctgact    420 caggacccte ctgtgtctgt ggccttggga cagacagtca cgctcacatg ccaaggagac    480
agcctcagaa cctattatgc aagctggtac cagcagaagt caggacaggc ccctatactt    540
ctcctctatg gtaaacacaa acggccctca gggatcccag accgcttctc tggctccacc    600
tcaggagaca cagcttcctt gaccatcact ggggctcagg cggaagacga ggctgactat    660
tactgttcgg cgcggtcggt gaggggcaac ccccatgttc tgttcggcgg agggacccag    720
ctcaccgttt ta                                                        732
```

<210> SEQ ID NO 158
<211> LENGTH: 244
<212> TYPE: PRT
<213> ORGANISM: artificial
<220> FEATURE:
<223> OTHER INFORMATION: L23 scFv

<400> SEQUENCE: 158

```
Gln Val Gln Leu Gln Glu Ser Gly Pro Gly Leu Val Lys Thr Ser Glu
 1               5                  10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
        195                 200                 205

Ile Thr Gly Ala Gln Ala Glu Asp Glu Ala Asp Tyr Tyr Cys Ser Ala
    210                 215                 220

Arg Ser Val Arg Gly Asn Pro His Val Leu Phe Gly Gly Gly Thr Gln
225                 230                 235                 240

Leu Thr Val Leu
```

<210> SEQ ID NO 159

```
<211> LENGTH: 732
<212> TYPE: DNA
<213> ORGANISM: artificial
<220> FEATURE:
<223> OTHER INFORMATION: L24 scFv

<400> SEQUENCE: 159
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtatcg ccaggagcaa caagggcaac cccatgttct gttcggcgg agggacccag      720
ctcaccgttt ta                                                          732

<210> SEQ ID NO 160
<211> LENGTH: 244
<212> TYPE: PRT
<213> ORGANISM: artificial
<220> FEATURE:
<223> OTHER INFORMATION: L24 scFv

<400> SEQUENCE: 160

Gln Val Gln Leu Gln Glu Ser Gly Pro Gly Leu Val Lys Thr Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Lys Gly Thr
            100                 105                 110

Leu Val Thr Val Ser Ser Gly Gly Gly Ser Gly Gly Gly Gly Ser
        115                 120                 125

Gly Gly Gly Gly Ser Ala Leu Ser Ser Glu Leu Thr Gln Asp Pro Pro
    130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190
```

```
Pro Asp Arg Phe Ser Gly Ser Thr Ser Gly Asp Thr Ala Ser Leu Thr
        195                 200                 205
Ile Thr Gly Ala Gln Ala Glu Asp Glu Ala Asp Tyr Tyr Cys Ile Ala
    210                 215                 220
Arg Ser Asn Lys Gly Asn Pro His Val Leu Phe Gly Gly Gly Thr Gln
225                 230                 235                 240
Leu Thr Val Leu

<210> SEQ ID NO 161
<211> LENGTH: 732
<212> TYPE: DNA
<213> ORGANISM: artificial
<220> FEATURE:
<223> OTHER INFORMATION: L25 scFv

<400> SEQUENCE: 161
caggtgcagc tgcaggagtc gggcccagga ctggtgaaga cttcggagac cctgtccctc      60
acctgcgctg tctctggtta ctccatcagc agtggttact actggggctg gatccggcag     120
cccccaggga aggggttgga gtggattggg agtatctctc atactgggaa cacctactac     180
aacccgcccc tcaagagtcg cgtcaccata tcagtagaca cgtccaagaa ccagttctcc     240
ctgaaactga gctctgtgac cgccgcagac acggccgtgt attactgtgc gcgaggtggg     300
ggaattagca ggccggagta ctggggcaaa ggcaccctgg tcaccgtctc gagtggaggc     360
ggcggttcag gcggaggtgg ctctggcggt ggcggaagtg cactttcttc tgagctgact     420
caggaccctc ctgtgtctgt ggccttggga cagacagtca cgctcacatg ccaaggagac     480
agcctcagaa cctattatgc aagctggtac cagcagaagt caggacaggc ccctatactt     540
ctcctctatg gtaaacacaa acggccctca gggatcccag accgcttctc tggctccacc     600
tcaggagaca cagcttcctt gaccatcact ggggctcagg cggaagacga ggctgactat     660
tactgtacga cgcggagcaa caagggcaac cccatgttc tgttcggcgg agggacccag      720
ctcaccgttt ta                                                         732

<210> SEQ ID NO 162
<211> LENGTH: 244
<212> TYPE: PRT
<213> ORGANISM: artificial
<220> FEATURE:
<223> OTHER INFORMATION: L25 scFv

<400> SEQUENCE: 162

Gln Val Gln Leu Gln Glu Ser Gly Pro Gly Leu Val Lys Thr Ser Glu
1               5                   10                  15
Thr Leu Ser Leu Thr Cys Ala Val Ser Gly Tyr Ser Ile Ser Ser Gly
            20                  25                  30
Tyr Tyr Trp Gly Trp Ile Arg Gln Pro Pro Gly Lys Gly Leu Glu Trp
        35                  40                  45
Ile Gly Ser Ile Ser His Thr Gly Asn Thr Tyr Tyr Asn Pro Pro Leu
    50                  55                  60
Lys Ser Arg Val Thr Ile Ser Val Asp Thr Ser Lys Asn Gln Phe Ser
65                  70                  75                  80
Leu Lys Leu Ser Ser Val Thr Ala Ala Asp Thr Ala Val Tyr Tyr Cys
                85                  90                  95
Ala Arg Gly Gly Gly Ile Ser Arg Pro Glu Tyr Trp Gly Lys Gly Thr
            100                 105                 110
Leu Val Thr Val Ser Ser Gly Gly Gly Gly Ser Gly Gly Gly Gly Ser
        115                 120                 125
```

```
Gly Gly Gly Gly Ser Ala Leu Ser Ser Glu Leu Thr Gln Asp Pro Pro
            130                 135                 140

Val Ser Val Ala Leu Gly Gln Thr Val Thr Leu Thr Cys Gln Gly Asp
145                 150                 155                 160

Ser Leu Arg Thr Tyr Tyr Ala Ser Trp Tyr Gln Gln Lys Ser Gly Gln
                165                 170                 175

Ala Pro Ile Leu Leu Leu Tyr Gly Lys His Lys Arg Pro Ser Gly Ile
            180                 185                 190

Pro Asp Arg Phe Ser Gly Ser Thr Ser Gly Asp Thr Ala Ser Leu Thr
            195                 200                 205

Ile Thr Gly Ala Gln Ala Glu Asp Glu Ala Asp Tyr Tyr Cys Thr Thr
    210                 215                 220

Arg Ser Asn Lys Gly Asn Pro His Val Leu Phe Gly Gly Thr Gln
225                 230                 235                 240

Leu Thr Val Leu
```

<210> SEQ ID NO 163
<211> LENGTH: 6
<212> TYPE: PRT
<213> ORGANISM: Homo sapiens

<400> SEQUENCE: 163

```
Ser Gly Tyr Tyr Trp Gly
1               5
```

<210> SEQ ID NO 164
<211> LENGTH: 16
<212> TYPE: PRT
<213> ORGANISM: Homo sapiens

<400> SEQUENCE: 164

```
Ser Ile Ser His Thr Gly Asn Thr Tyr Tyr Asn Pro Pro Leu Lys Ser
1               5                   10                  15
```

<210> SEQ ID NO 165
<211> LENGTH: 9
<212> TYPE: PRT
<213> ORGANISM: artificial
<220> FEATURE:
<223> OTHER INFORMATION: H3 heavy chain CDR3

<400> SEQUENCE: 165

```
Phe Met Gly Phe Gly Arg Pro Glu Tyr
1               5
```

<210> SEQ ID NO 166
<211> LENGTH: 9
<212> TYPE: PRT
<213> ORGANISM: artificial
<220> FEATURE:
<223> OTHER INFORMATION: H4 heavy chain CDR3

<400> SEQUENCE: 166

```
Trp Leu Gly Phe Gly Arg Pro Glu Tyr
1               5
```

<210> SEQ ID NO 167
<211> LENGTH: 9
<212> TYPE: PRT
<213> ORGANISM: artificial
<220> FEATURE:
<223> OTHER INFORMATION: H5 heavy chain CDR3

```
<400> SEQUENCE: 167

Phe Leu Gly Phe Gly Arg Pro Glu Tyr
1               5

<210> SEQ ID NO 168
<211> LENGTH: 9
<212> TYPE: PRT
<213> ORGANISM: artificial
<220> FEATURE:
<223> OTHER INFORMATION: H6 heavy chain CDR3

<400> SEQUENCE: 168

Phe Phe Gly Phe Gly Arg Pro Glu Tyr
1               5

<210> SEQ ID NO 169
<211> LENGTH: 9
<212> TYPE: PRT
<213> ORGANISM: Homo sapiens

<400> SEQUENCE: 169

Gly Gly Gly Ile Ser Arg Pro Glu Tyr
1               5

<210> SEQ ID NO 170
<211> LENGTH: 12
<212> TYPE: PRT
<213> ORGANISM: Homo sapiens

<400> SEQUENCE: 170

Asn Ser Arg Asp Ser Ser Gly Asn Pro His Val Leu
1               5                   10

<210> SEQ ID NO 171
<211> LENGTH: 12
<212> TYPE: PRT
<213> ORGANISM: artificial
<220> FEATURE:
<223> OTHER INFORMATION: L1 light chain CDR3

<400> SEQUENCE: 171

Ala Ser Arg Ser Val Ser Gly Asn Pro His Val Leu
1               5                   10

<210> SEQ ID NO 172
<211> LENGTH: 12
<212> TYPE: PRT
<213> ORGANISM: artificial
<220> FEATURE:
<223> OTHER INFORMATION: L2 light chain CDR3

<400> SEQUENCE: 172

Val Ala Arg Ser Val Val Gly Asn Pro His Val Leu
1               5                   10

<210> SEQ ID NO 173
<211> LENGTH: 12
<212> TYPE: PRT
<213> ORGANISM: artificial
<220> FEATURE:
<223> OTHER INFORMATION: L3 light chain CDR3

<400> SEQUENCE: 173

Val Ser Arg Ala Val Val Gly Asn Pro His Val Leu
1               5                   10
```

```
<210> SEQ ID NO 174
<211> LENGTH: 12
<212> TYPE: PRT
<213> ORGANISM: artificial
<220> FEATURE:
<223> OTHER INFORMATION: L4 light chain CDR3

<400> SEQUENCE: 174

Ser Thr Arg Ser Ser Lys Gly Asn Pro His Val Leu
1               5                   10

<210> SEQ ID NO 175
<211> LENGTH: 12
<212> TYPE: PRT
<213> ORGANISM: artificial
<220> FEATURE:
<223> OTHER INFORMATION: L5 light chain CDR3

<400> SEQUENCE: 175

Ala Ser Arg Ser Ser Lys Gly Asn Pro His Val Leu
1               5                   10

<210> SEQ ID NO 176
<211> LENGTH: 12
<212> TYPE: PRT
<213> ORGANISM: artificial
<220> FEATURE:
<223> OTHER INFORMATION: L6 light chain CDR3

<400> SEQUENCE: 176

Met Ser Arg Ser Ile Trp Gly Asn Pro His Val Leu
1               5                   10

<210> SEQ ID NO 177
<211> LENGTH: 12
<212> TYPE: PRT
<213> ORGANISM: artificial
<220> FEATURE:
<223> OTHER INFORMATION: L8 light chain CDR3

<400> SEQUENCE: 177

Thr Thr Arg Ser Thr Gln Gly Asn Pro His Val Leu
1               5                   10

<210> SEQ ID NO 178
<211> LENGTH: 12
<212> TYPE: PRT
<213> ORGANISM: artificial
<220> FEATURE:
<223> OTHER INFORMATION: L9 light chain CDR3

<400> SEQUENCE: 178

Val Ala Arg Ser Asn Lys Gly Asn Pro His Val Leu
1               5                   10

<210> SEQ ID NO 179
<211> LENGTH: 12
<212> TYPE: PRT
<213> ORGANISM: artificial
<220> FEATURE:
<223> OTHER INFORMATION: L10 light chain CDR3

<400> SEQUENCE: 179

Ile Ser Arg Ser Ile Tyr Gly Asn Pro His Val Leu
1               5                   10

<210> SEQ ID NO 180
<211> LENGTH: 12
```

```
<212> TYPE: PRT
<213> ORGANISM: artificial
<220> FEATURE:
<223> OTHER INFORMATION: L11 light chain CDR3

<400> SEQUENCE: 180

Ser Ser Arg Ser Arg His Gly Asn Pro His Val Leu
1               5                   10

<210> SEQ ID NO 181
<211> LENGTH: 12
<212> TYPE: PRT
<213> ORGANISM: artificial
<220> FEATURE:
<223> OTHER INFORMATION: L12 light chain CDR3

<400> SEQUENCE: 181

Val Ala Arg Gly Thr Arg Gly Asn Pro His Val Leu
1               5                   10

<210> SEQ ID NO 182
<211> LENGTH: 12
<212> TYPE: PRT
<213> ORGANISM: artificial
<220> FEATURE:
<223> OTHER INFORMATION: L13 light chain CDR3

<400> SEQUENCE: 182

Val Thr Arg Asn Arg Tyr Gly Asn Pro His Val Leu
1               5                   10

<210> SEQ ID NO 183
<211> LENGTH: 12
<212> TYPE: PRT
<213> ORGANISM: artificial
<220> FEATURE:
<223> OTHER INFORMATION: L14 light chain CDR3

<400> SEQUENCE: 183

Met Ala Arg Ser Arg Lys Gly Asn Pro His Val Leu
1               5                   10

<210> SEQ ID NO 184
<211> LENGTH: 12
<212> TYPE: PRT
<213> ORGANISM: artificial
<220> FEATURE:
<223> OTHER INFORMATION: L15 light chain CDR3

<400> SEQUENCE: 184

Ser Thr Arg Ala Ile His Gly Asn Pro His Val Leu
1               5                   10

<210> SEQ ID NO 185
<211> LENGTH: 12
<212> TYPE: PRT
<213> ORGANISM: artificial
<220> FEATURE:
<223> OTHER INFORMATION: L16 light chain CDR3

<400> SEQUENCE: 185

Val Thr Arg Ser Ala Lys Gly Asn Pro His Val Leu
1               5                   10

<210> SEQ ID NO 186
<211> LENGTH: 12
<212> TYPE: PRT
<213> ORGANISM: artificial
```

```
<220> FEATURE:
<223> OTHER INFORMATION: L17 light chain CDR3

<400> SEQUENCE: 186

Ser Thr Arg Ser Arg Lys Gly Asn Pro His Val Leu
1               5                   10

<210> SEQ ID NO 187
<211> LENGTH: 12
<212> TYPE: PRT
<213> ORGANISM: artificial
<220> FEATURE:
<223> OTHER INFORMATION: L18 light chain CDR3

<400> SEQUENCE: 187

Val Thr Arg Ser Val Lys Gly Asn Pro His Val Leu
1               5                   10

<210> SEQ ID NO 188
<211> LENGTH: 12
<212> TYPE: PRT
<213> ORGANISM: artificial
<220> FEATURE:
<223> OTHER INFORMATION: L19 light chain CDR3

<400> SEQUENCE: 188

Val Ala Arg Ala Val Arg Gly Asn Pro His Val Leu
1               5                   10

<210> SEQ ID NO 189
<211> LENGTH: 12
<212> TYPE: PRT
<213> ORGANISM: artificial
<220> FEATURE:
<223> OTHER INFORMATION: L20 light chain CDR3

<400> SEQUENCE: 189

Val Ser Arg Ser Ala Lys Gly Asn Pro His Val Leu
1               5                   10

<210> SEQ ID NO 190
<211> LENGTH: 12
<212> TYPE: PRT
<213> ORGANISM: artificial
<220> FEATURE:
<223> OTHER INFORMATION: L21 light chain CDR3

<400> SEQUENCE: 190

Ala Thr Arg Ala Val Arg Gly Asn Pro His Val Leu
1               5                   10

<210> SEQ ID NO 191
<211> LENGTH: 12
<212> TYPE: PRT
<213> ORGANISM: artificial
<220> FEATURE:
<223> OTHER INFORMATION: L23 light chain CDR3

<400> SEQUENCE: 191

Ser Ala Arg Ser Val Arg Gly Asn Pro His Val Leu
1               5                   10

<210> SEQ ID NO 192
<211> LENGTH: 12
<212> TYPE: PRT
<213> ORGANISM: artificial
<220> FEATURE:
<223> OTHER INFORMATION: L24 light chain CDR3
```

<400> SEQUENCE: 192

Ile Ala Arg Ser Asn Lys Gly Asn Pro His Val Leu
1               5                   10

<210> SEQ ID NO 193
<211> LENGTH: 12
<212> TYPE: PRT
<213> ORGANISM: artificial
<220> FEATURE:
<223> OTHER INFORMATION: L25 light chain CDR3

<400> SEQUENCE: 193

Thr Thr Arg Ser Asn Lys Gly Asn Pro His Val Leu
1               5                   10

<210> SEQ ID NO 194
<211> LENGTH: 11
<212> TYPE: PRT
<213> ORGANISM: Homo sapiens

<400> SEQUENCE: 194

Gln Gly Asp Ser Leu Arg Thr Tyr Tyr Ala Ser
1               5                   10

<210> SEQ ID NO 195
<211> LENGTH: 7
<212> TYPE: PRT
<213> ORGANISM: Homo sapiens

<400> SEQUENCE: 195

Gly Lys His Lys Arg Pro Ser
1               5

<210> SEQ ID NO 196
<211> LENGTH: 330
<212> TYPE: PRT
<213> ORGANISM: artificial
<220> FEATURE:
<223> OTHER INFORMATION: human IgG constant region TM

<400> SEQUENCE: 196

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 197
<211> LENGTH: 330
<212> TYPE: PRT
<213> ORGANISM: artificial
<220> FEATURE:
<223> OTHER INFORMATION: human IgG constant region DM

<400> SEQUENCE: 197

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Leu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 198
<211> LENGTH: 106
<212> TYPE: PRT
<213> ORGANISM: Homo sapiens

<400> SEQUENCE: 198

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 199
<211> LENGTH: 100
<212> TYPE: DNA
<213> ORGANISM: Homo sapiens

<400> SEQUENCE: 199
gctctgtgac cgccgcagac acggccgtgt attactgtgc gcgaggtggg ggaattagca      60
ggccggagta ctggggcaaa ggcaccctgg tcaccgtctc                            100

<210> SEQ ID NO 200
<211> LENGTH: 34
<212> TYPE: PRT
<213> ORGANISM: Homo sapiens

<400> SEQUENCE: 200

Ser Ser Val Thr Ala Ala Asp Thr Ala Val Tyr Tyr Cys Ala Arg Gly
1               5                   10                  15

Gly Gly Ile Ser Arg Pro Glu Tyr Trp Gly Lys Gly Thr Leu Val Thr

```
              20                  25                  30
Val Ser

<210> SEQ ID NO 201
<211> LENGTH: 60
<212> TYPE: DNA
<213> ORGANISM: artificial
<220> FEATURE:
<223> OTHER INFORMATION: H3B1 VH library
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 201
cacataatga cacgcgctnn snnsnnsnns nnsnnsggcc tcatgacccc gtttccgtgg      60

<210> SEQ ID NO 202
<211> LENGTH: 20
<212> TYPE: PRT
<213> ORGANISM: artificial
<220> FEATURE:
<223> OTHER INFORMATION: H3B1 VH library

<400> SEQUENCE: 202

Val Tyr Tyr Cys Ala Arg Gly Gly Ile Ser Arg Pro Glu Tyr Trp
1               5                  10                  15

Gly Lys Gly Thr
            20

<210> SEQ ID NO 203
<211> LENGTH: 56
<212> TYPE: DNA
<213> ORGANISM: artificial
<220> FEATURE:
<223> OTHER INFORMATION: H3B2 VH library
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
```

```
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 203
gacacgcgct ccaccccctn nsnnsnnsnn snnsnnsacc ccgtttccgt gggacc      56

<210> SEQ ID NO 204
<211> LENGTH: 18
<212> TYPE: PRT
<213> ORGANISM: artificial
<220> FEATURE:
<223> OTHER INFORMATION: H3B2 VH library

<400> SEQUENCE: 204

Cys Ala Arg Gly Gly Gly Ile Ser Arg Pro Glu Tyr Trp Gly Lys Gly
1               5                   10                  15

Thr Leu

<210> SEQ ID NO 205
<211> LENGTH: 85
<212> TYPE: DNA
<213> ORGANISM: Homo sapiens

<400> SEQUENCE: 205
ggctgactat tactgtaact cccgggactc cagtggcaac ccccatgttc tgttcggcgg   60
agggacccag ctcaccgttt taagt                                        85

<210> SEQ ID NO 206
<211> LENGTH: 28
<212> TYPE: PRT
<213> ORGANISM: Homo sapiens

<400> SEQUENCE: 206

Ala Asp Tyr Tyr Cys Asn Ser Arg Asp Ser Ser Gly Asn Pro His Val
1               5                   10                  15

Leu Phe Gly Gly Gly Thr Gln Leu Thr Val Leu Ser
            20                  25

<210> SEQ ID NO 207
<211> LENGTH: 55
<212> TYPE: DNA
<213> ORGANISM: artificial
<220> FEATURE:
<223> OTHER INFORMATION: L3B1 VL library
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
```

```
<220> FEATURE:
<221> NAME/KEY: misc_feature
<222> LOCATION: (32)..(33)
<223> OTHER INFORMATION: n is a, c, g, or t

<400> SEQUENCE: 207
ccgactgata atgacannsn nsnnsnnsnn snnsccgttg ggggtacaag acaag          55

<210> SEQ ID NO 208
<211> LENGTH: 18
<212> TYPE: PRT
<213> ORGANISM: artificial
<220> FEATURE:
<223> OTHER INFORMATION: L3B1 VL library

<400> SEQUENCE: 208

Ala Asp Tyr Tyr Cys Asn Ser Arg Asp Ser Ser Gly Asn Pro His Val
1               5                   10                  15

Leu Phe

<210> SEQ ID NO 209
<211> LENGTH: 59
<212> TYPE: DNA
<213> ORGANISM: artificial
<220> FEATURE:
<223> OTHER INFORMATION: L3B2 VL library
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 209
gacattgagg gccctgaggt cannsnnsnn snnsnnsnns aagccgcctc cctgggtcg     59

<210> SEQ ID NO 210
<211> LENGTH: 19
<212> TYPE: PRT
<213> ORGANISM: artificial
<220> FEATURE:
<223> OTHER INFORMATION: L3B2 VL library

<400> SEQUENCE: 210

Cys Asn Ser Arg Asp Ser Ser Gly Asn Pro His Val Leu Phe Gly Gly
1               5                   10                  15

Gly Thr Gln

<210> SEQ ID NO 211
<211> LENGTH: 617
<212> TYPE: DNA
<213> ORGANISM: Homo sapiens
```

```
<220> FEATURE:
<221> NAME/KEY: CDS
<222> LOCATION: (47)..(532)

<400> SEQUENCE: 211
gctgaagtga aaacgagacc aaggtctagc tctactgttg gtactt atg aga tcc         55
                                                Met Arg Ser
                                                  1 agt cct ggc aac atg gag agg att gtc atc tgt ctg atg gtc atc ttc       103
Ser Pro Gly Asn Met Glu Arg Ile Val Ile Cys Leu Met Val Ile Phe
  5              10                  15 ttg ggg aca ctg gtc cac aaa tca agc tcc caa ggt caa gat cgc cac       151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat       199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta       247
Tyr Val Asn Asp Leu Val Pro Glu Phe Leu Pro Ala Pro Glu Asp Val
             55                  60                  65 gag aca aac tgt gag tgg tca gct ttt tcc tgc ttt cag aag gcc caa       295
Glu Thr Asn Cys Glu Trp Ser Ala Phe Ser Cys Phe Gln Lys Ala Gln
         70                  75                  80 cta aag tca gca aat aca gga aac aat gaa agg ata atc aat gta tca       343
Leu Lys Ser Ala Asn Thr Gly Asn Asn Glu Arg Ile Ile Asn Val Ser
 85                  90                  95 att aaa aag ctg aag agg aaa cca cct tcc aca aat gca ggg aga aga       391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa       439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctt ctc caa aag atg       487
Pro Pro Lys Glu Phe Leu Glu Arg Phe Lys Ser Leu Leu Gln Lys Met
            135                 140                 145 att cat cag cat ctg tcc tct aga aca cac gga agt gaa gat tcc           532
Ile His Gln His Leu Ser Ser Arg Thr His Gly Ser Glu Asp Ser
        150                 155                 160 tgaggatcta acttgcagtt ggacactatg ttacatactc taatatagta gtgaaagtca    592
tttctttgta ttccaagtgg aggag                                          617

<210> SEQ ID NO 212
<211> LENGTH: 162
<212> TYPE: PRT
<213> ORGANISM: Homo sapiens

<400> SEQUENCE: 212

Met Arg Ser Ser Pro Gly Asn Met Glu Arg Ile Val Ile Cys Leu Met
  1               5                  10                  15

Val Ile Phe Leu Gly Thr Leu Val His Lys Ser Ser Ser Gln Gly Gln
             20                  25                  30

Asp Arg His Met Ile Arg Met Arg Gln Leu Ile Asp Ile Val Asp Gln
         35                  40                  45

Leu Lys Asn Tyr Val Asn Asp Leu Val Pro Glu Phe Leu Pro Ala Pro
     50                  55                  60

Glu Asp Val Glu Thr Asn Cys Glu Trp Ser Ala Phe Ser Cys Phe Gln
 65                  70                  75                  80

Lys Ala Gln Leu Lys Ser Ala Asn Thr Gly Asn Asn Glu Arg Ile Ile
                 85                  90                  95
```

Asn Val Ser Ile Lys Lys Leu Lys Arg Lys Pro Ser Thr Asn Ala
                100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
130                 135                 140

Gln Lys Met Ile His Gln His Leu Ser Ser Arg Thr His Gly Ser Glu
145                 150                 155                 160

Asp Ser

<210> SEQ ID NO 213
<211> LENGTH: 448
<212> TYPE: PRT
<213> ORGANISM: artificial
<220> FEATURE:
<223> OTHER INFORMATION: VH3DM heavy chain

<400> SEQUENCE: 213

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Leu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

```
Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 214
<211> LENGTH: 215
<212> TYPE: PRT
<213> ORGANISM: artificial
<220> FEATURE:
<223> OTHER INFORMATION: VL2 light chain

<400> SEQUENCE: 214

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 215
<211> LENGTH: 109
<212> TYPE: PRT
<213> ORGANISM: artificial
<220> FEATURE:
<223> OTHER INFORMATION: variable region of VL2 light chain

<400> SEQUENCE: 215

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ala Arg Ser Val Val Gly Asn Pro
                85                  90                  95

His Val Leu Phe Gly Gly Gly Thr Gln Leu Thr Val Leu
            100                 105

<210> SEQ ID NO 216
<211> LENGTH: 215
<212> TYPE: PRT
<213> ORGANISM: artificial
<220> FEATURE:
<223> OTHER INFORMATION: VL18 light chain

<400> SEQUENCE: 216

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Val Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

```
Val Ala Pro Thr Glu Cys Ser
    210             215
```

<210> SEQ ID NO 217
<211> LENGTH: 109
<212> TYPE: PRT
<213> ORGANISM: artificial
<220> FEATURE:
<223> OTHER INFORMATION: variable region of VL18 light chain

<400> SEQUENCE: 217

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Val Lys Gly Asn Pro
                85                  90                  95

His Val Leu Phe Gly Gly Gly Thr Gln Leu Thr Val Leu
            100                 105
```

<210> SEQ ID NO 218
<211> LENGTH: 448
<212> TYPE: PRT
<213> ORGANISM: artificial
<220> FEATURE:
<223> OTHER INFORMATION: VH3TM heavy chain

<400> SEQUENCE: 218

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Met Gly Phe Gly Arg Pro Glu Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

-continued

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 219
<211> LENGTH: 448
<212> TYPE: PRT
<213> ORGANISM: artificial
<220> FEATURE:
<223> OTHER INFORMATION: VHPTM heavy chain

<400> SEQUENCE: 219

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Ser His Thr Gly Asn Thr Tyr Tyr Asn Pro Pro Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Gly Ile Ser Arg Pro Glu Tyr Trp Gly Gln Gly Thr
            100                 105                 110

Leu Val Thr Val Ser Ser Ala Ser Thr Lys Gly Pro Ser Val Phe Pro

```
                  115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 220
<211> LENGTH: 215
<212> TYPE: PRT
<213> ORGANISM: artificial
<220> FEATURE:
<223> OTHER INFORMATION: VL6 light chain

<400> SEQUENCE: 220

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45
```

Gly Lys His Lys Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Met Ser Arg Ser Ile Trp Gly Asn Pro
                 85                  90                  95

His Val Leu Phe Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
            130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
            210                 215

<210> SEQ ID NO 221
<211> LENGTH: 109
<212> TYPE: PRT
<213> ORGANISM: artificial
<220> FEATURE:
<223> OTHER INFORMATION: variable region of VL6 light chain

<400> SEQUENCE: 221

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
 65                 70                  75                  80

Asp Glu Ala Asp Tyr Tyr Cys Met Ser Arg Ser Ile Trp Gly Asn Pro
                85                  90                  95

His Val Leu Phe Gly Gly Thr Gln Leu Thr Val Leu
            100                 105

<210> SEQ ID NO 222
<211> LENGTH: 215
<212> TYPE: PRT
<213> ORGANISM: artificial
<220> FEATURE:
<223> OTHER INFORMATION: VL9 light chain

<400> SEQUENCE: 222

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

-continued

```
Ser Trp Tyr Gln Gln Lys Pro Gly Gln Ala Pro Val Leu Val Ile Tyr
         35                  40                  45

Gly Lys His Lys Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Val Ala Arg Ser Asn Lys Gly Asn Pro
                 85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 223
<211> LENGTH: 109
<212> TYPE: PRT
<213> ORGANISM: artificial
<220> FEATURE:
<223> OTHER INFORMATION: variable region of VL9 light chain

<400> SEQUENCE: 223

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
         35                  40                  45

Gly Lys His Lys Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Val Ala Arg Ser Asn Lys Gly Asn Pro
                 85                  90                  95

His Val Leu Phe Gly Gly Gly Thr Gln Leu Thr Val Leu
            100                 105

<210> SEQ ID NO 224
<211> LENGTH: 215
<212> TYPE: PRT
<213> ORGANISM: artificial
<220> FEATURE:
<223> OTHER INFORMATION: VL16 light chain

<400> SEQUENCE: 224

Ser Ser Glu Leu Thr Gln Asp Pro Ala Val Ser Val Ala Leu Gly Gln
1               5                   10                  15
```

```
Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Ala Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 225
<211> LENGTH: 109
<212> TYPE: PRT
<213> ORGANISM: artificial
<220> FEATURE:
<223> OTHER INFORMATION: variable region of VL16 light chain

<400> SEQUENCE: 225

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Thr Arg Ser Ala Lys Gly Asn Pro
                85                  90                  95

His Val Leu Phe Gly Gly Gly Thr Gln Leu Thr Val Leu
            100                 105

<210> SEQ ID NO 226
<211> LENGTH: 215
<212> TYPE: PRT
<213> ORGANISM: artificial
<220> FEATURE:
<223> OTHER INFORMATION: VL20 light chain

<400> SEQUENCE: 226
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ser Arg Ser Ala Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
            130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
            195                 200                 205

Val Ala Pro Thr Glu Cys Ser
            210                 215

<210> SEQ ID NO 227
<211> LENGTH: 109
<212> TYPE: PRT
<213> ORGANISM: artificial
<220> FEATURE:
<223> OTHER INFORMATION: variable region of VL20 light chain

<400> SEQUENCE: 227

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
            35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Val Ser Arg Ser Ala Lys Gly Asn Pro
                85                  90                  95

His Val Leu Phe Gly Gly Gly Thr Gln Leu Thr Val Leu
            100                 105

<210> SEQ ID NO 228
<211> LENGTH: 215
<212> TYPE: PRT
<213> ORGANISM: artificial
<220> FEATURE:
```

<223> OTHER INFORMATION: VL25 light chain

<400> SEQUENCE: 228

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Thr Thr Arg Ser Asn Lys Gly Asn Pro
                85                  90                  95

His Val Leu Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 229
<211> LENGTH: 109
<212> TYPE: PRT
<213> ORGANISM: artificial
<220> FEATURE:
<223> OTHER INFORMATION: variable region of VL25 light chain

<400> SEQUENCE: 229

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Lys Pro Gly Gln Ala Pro Val Leu Val Ile Tyr
        35                  40                  45

Gly Lys His Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Thr Thr Arg Ser Asn Lys Gly Asn Pro
                85                  90                  95

His Val Leu Phe Gly Gly Gly Thr Gln Leu Thr Val Leu
            100                 105

<210> SEQ ID NO 230
<211> LENGTH: 34

```
<212> TYPE: DNA
<213> ORGANISM: Artificial Sequence
<220> FEATURE:
<223> OTHER INFORMATION: Primer BssHII_II_VH_F

<400> SEQUENCE: 230
gcttggcgcg cactctcagg tgcagctgca ggag                                34

<210> SEQ ID NO 231
<211> LENGTH: 21
<212> TYPE: DNA
<213> ORGANISM: Artificial Sequence
<220> FEATURE:
<223> OTHER INFORMATION: Primer GVH_R_for_BssHII

<400> SEQUENCE: 231
tcagggagaa ctggttcttg g                                              21

<210> SEQ ID NO 232
<211> LENGTH: 21
<212> TYPE: DNA
<213> ORGANISM: Artificial Sequence
<220> FEATURE:
<223> OTHER INFORMATION: Primer G_VH_F_for_SalI

<400> SEQUENCE: 232
tccaagaacc agttctccct g                                              21

<210> SEQ ID NO 233
<211> LENGTH: 45
<212> TYPE: DNA
<213> ORGANISM: Artificial Sequence
<220> FEATURE:
<223> OTHER INFORMATION: Primer scFv_SalI_VH_R

<400> SEQUENCE: 233
gcgacgtcga caggactcac cactcgagac ggtgaccagg gtgcc                    45

<210> SEQ ID NO 234
<211> LENGTH: 32
<212> TYPE: DNA
<213> ORGANISM: Artificial Sequence
<220> FEATURE:
<223> OTHER INFORMATION: Primer Sal_VH_R_RJ

<400> SEQUENCE: 234
gcgacgtcga caggactcac cactcgagac gg                                  32

<210> SEQ ID NO 235
<211> LENGTH: 34
<212> TYPE: DNA
<213> ORGANISM: Artificial Sequence
<220> FEATURE:
<223> OTHER INFORMATION: Primer BssHII_II_VL_F

<400> SEQUENCE: 235
gcttggcgcg cactcttcct ctgagctgac ccag                                34

<210> SEQ ID NO 236
<211> LENGTH: 22
<212> TYPE: DNA
<213> ORGANISM: Artificial Sequence
<220> FEATURE:
<223> OTHER INFORMATION: Primer scFv_VL_R_for_BssHII

<400> SEQUENCE: 236
gcctgagccc cagtgatggt ca                                             22
```

<210> SEQ ID NO 237
<211> LENGTH: 20
<212> TYPE: DNA
<213> ORGANISM: Artificial Sequence
<220> FEATURE:
<223> OTHER INFORMATION: Primer GVL_F_for_XbaI

<400> SEQUENCE: 237
accgcctccc tgaccatcac                                                  20

<210> SEQ ID NO 238
<211> LENGTH: 50
<212> TYPE: DNA
<213> ORGANISM: Artificial Sequence
<220> FEATURE:
<223> OTHER INFORMATION: Primer scFv_XbaI_VL_R

<400> SEQUENCE: 238
gcgccgtcta gagttattct actcacctaa aacggtgagc tgggtccctc                 50

<210> SEQ ID NO 239
<211> LENGTH: 1401
<212> TYPE: DNA
<213> ORGANISM: artificial
<220> FEATURE:
<223> OTHER INFORMATION: VHPTM heavy chain with signal sequence

<400> SEQUENCE: 239
atgggatgga gctgtatcat cctcttcttg gtggcaacag ctacaggcgt gcactctcag      60
gtgcagctgc aggagtctgg ccctggcctg gtgaagcctt ccgagaccct gtctctgacc     120
tgtgccgtgt ccggctactc catctcctcc ggctactact ggggctggat cagacagcct     180
cctggcaagg gcctggagtg gatcggctcc atctctcaca ccggcaacac ctactacaac     240
ccccctctga gtccagagt gaccatctcc gtggacacct ccaagaacca gttctccctg      300
aagctgtcct ctgtgaccgc tgccgatacc gccgtgtact actgtgccag aggcggcgga    360
atctccagac tgagtactg gggccagggc accctggtga ccgtgtcctc tgcctccacc      420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga agttgagcc caaatcttgt     720
gacaaaactc acacatgccc accgtgccca gcacctgaag ccgcggggc accgtcagtc      780
ttcctcttcc cccaaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccgcgggagg agcagtacaa cagcacgtac     960
cgtgtggtca gcgtcctcac cgtcctgcac caggactggc tgaatggcaa ggagtacaag    1020
tgcaaggtct ccaacaaagc cctcccagcc cccatcgaga aaaccatctc caaagccaaa    1080
ggtcagcccc gagaaccaca ggtgtacacc ctgcccccat cccgggagga tgaccaag       1140
aaccaggtca gcctgacctg cctggtcaaa ggcttctatc cagcgacat cgccgtggag     1200
tgggagagca atgggcagcc ggagaacaac tacaagacca cgcctcccgt gctggactcc    1260
gacggctcct tcttcctcta tagcaagctc accgtggaca gagcaggtg gcagcagggg     1320
aacgtcttct catgctccgt gatgcatgag gctctgcaca accactacac gcagaagagc    1380
ctctccctgt ccccgggtaa a        1401

<210> SEQ ID NO 240
<211> LENGTH: 467
<212> TYPE: PRT
<213> ORGANISM: artificial
<220> FEATURE:
<223> OTHER INFORMATION: VHPTM heavy chain with signal sequence

<400> SEQUENCE: 240

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Ala Val Ser Gly Tyr Ser Ile
        35                  40                  45

Ser Ser Gly Tyr Tyr Trp Gly Trp Ile Arg Gln Pro Pro Gly Lys Gly
    50                  55                  60

Leu Glu Trp Ile Gly Ser Ile Ser His Thr Gly Asn Thr Tyr Tyr Asn
65                  70                  75                  80

Pro Pro Leu Lys Ser Arg Val Thr Ile Ser Val Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Arg Gly Gly Gly Ile Ser Arg Pro Glu Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Ala Ala Gly
                245                 250                 255

Ala Pro Ser Val Phe Leu Phe Pro Pro Lys Pro Lys Asp Thr Leu Met
            260                 265                 270

Ile Ser Arg Thr Pro Glu Val Thr Cys Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val

```
                355                 360                 365
Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
        450                 455                 460

Pro Gly Lys
465

<210> SEQ ID NO 241
<211> LENGTH: 1401
<212> TYPE: DNA
<213> ORGANISM: artificial
<220> FEATURE:
<223> OTHER INFORMATION: VH3TM heavy chain with signal sequence

<400> SEQUENCE: 241
atgggatgga gctgtatcat cctcttcttg gtggcaacag ctacaggcgt gcactctcag     60
gtgcagctgc aggagtctgg ccctggcctg gtgaagcctt ccgagaccct gtctctgacc    120
tgtgccgtgt ccggctactc catctcctcc ggctactact ggggctggat cagacagcct    180
cctggcaagg gcctggagtg gatcggctcc atctctcaca ccggcaacac ctactacaac    240
ccccctctga agtccagagt gaccatctcc gtggacacct ccaagaacca gttctccctg    300
aagctgtcct ctgtgaccgc tgccgatacc gccgtgtact actgtgccag attcatgggg    360
ttcggccgcc cggagtactg ggggccaggggc accctggtga ccgtgtcctc tgcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt    720 gacaaaactc acacatgccc accgtgccca gcacctgaag ccgcggggc accgtcagtc    780 ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggtcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca gagcaggtg gcagcagggg   1320 aacgtcttct catgctccgt gatgcatgag gctctgcaca accactacac gcagaagagc   1380
ctctccctgt ccccgggtaa a                                             1401
```

<210> SEQ ID NO 242
<211> LENGTH: 467
<212> TYPE: PRT
<213> ORGANISM: artificial
<220> FEATURE:
<223> OTHER INFORMATION: VH3TM heavy chain with signal sequence

<400> SEQUENCE: 242

| | | | | | | | | | | | | | | | |
|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly |
| 1 | | | | 5 | | | | | 10 | | | | | 15 | |
| Val | His | Ser | Gln | Val | Gln | Leu | Gln | Glu | Ser | Gly | Pro | Gly | Leu | Val | Lys |
| | | | 20 | | | | | 25 | | | | | 30 | | |
| Pro | Ser | Glu | Thr | Leu | Ser | Leu | Thr | Cys | Ala | Val | Ser | Gly | Tyr | Ser | Ile |
| | | | | 35 | | | | | 40 | | | | | 45 | |
| Ser | Ser | Gly | Tyr | Tyr | Trp | Gly | Trp | Ile | Arg | Gln | Pro | Pro | Gly | Lys | Gly |
| | 50 | | | | | 55 | | | | | 60 | | | | |
| Leu | Glu | Trp | Ile | Gly | Ser | Ile | Ser | His | Thr | Gly | Asn | Thr | Tyr | Tyr | Asn |
| 65 | | | | | 70 | | | | | 75 | | | | | 80 |
| Pro | Pro | Leu | Lys | Ser | Arg | Val | Thr | Ile | Ser | Val | Asp | Thr | Ser | Lys | Asn |
| | | | | 85 | | | | | 90 | | | | | 95 | |
| Gln | Phe | Ser | Leu | Lys | Leu | Ser | Ser | Val | Thr | Ala | Ala | Asp | Thr | Ala | Val |
| | | | 100 | | | | | 105 | | | | | 110 | | |
| Tyr | Tyr | Cys | Ala | Arg | Phe | Met | Gly | Phe | Gly | Arg | Pro | Glu | Tyr | Trp | Gly |
| | | | | 115 | | | | | 120 | | | | | 125 | |
| Gln | Gly | Thr | Leu | Val | Thr | Val | Ser | Ser | Ala | Ser | Thr | Lys | Gly | Pro | Ser |
| | 130 | | | | | 135 | | | | | 140 | | | | |
| Val | Phe | Pro | Leu | Ala | Pro | Ser | Ser | Lys | Ser | Thr | Ser | Gly | Gly | Thr | Ala |
| 145 | | | | | 150 | | | | | 155 | | | | | 160 |
| Ala | Leu | Gly | Cys | Leu | Val | Lys | Asp | Tyr | Phe | Pro | Glu | Pro | Val | Thr | Val |
| | | | | 165 | | | | | 170 | | | | | 175 | |
| Ser | Trp | Asn | Ser | Gly | Ala | Leu | Thr | Ser | Gly | Val | His | Thr | Phe | Pro | Ala |
| | | | 180 | | | | | 185 | | | | | 190 | | |
| Val | Leu | Gln | Ser | Ser | Gly | Leu | Tyr | Ser | Leu | Ser | Ser | Val | Val | Thr | Val |
| | | | | 195 | | | | | 200 | | | | | 205 | |
| Pro | Ser | Ser | Ser | Leu | Gly | Thr | Gln | Thr | Tyr | Ile | Cys | Asn | Val | Asn | His |
| | 210 | | | | | 215 | | | | | 220 | | | | |
| Lys | Pro | Ser | Asn | Thr | Lys | Val | Asp | Lys | Val | Glu | Pro | Lys | Ser | Cys |
| 225 | | | | | 230 | | | | | 235 | | | | | 240 |
| Asp | Lys | Thr | His | Thr | Cys | Pro | Pro | Cys | Pro | Ala | Pro | Glu | Ala | Ala | Gly |
| | | | | 245 | | | | | 250 | | | | | 255 | |
| Ala | Pro | Ser | Val | Phe | Leu | Phe | Pro | Pro | Lys | Pro | Lys | Asp | Thr | Leu | Met |
| | | | 260 | | | | | 265 | | | | | 270 | | |
| Ile | Ser | Arg | Thr | Pro | Glu | Val | Thr | Cys | Val | Val | Val | Asp | Val | Ser | His |
| | | | 275 | | | | | 280 | | | | | 285 | | |
| Glu | Asp | Pro | Glu | Val | Lys | Phe | Asn | Trp | Tyr | Val | Asp | Gly | Val | Glu | Val |
| | | 290 | | | | | 295 | | | | | 300 | | | |
| His | Asn | Ala | Lys | Thr | Lys | Pro | Arg | Glu | Glu | Gln | Tyr | Asn | Ser | Thr | Tyr |
| 305 | | | | | 310 | | | | | 315 | | | | | 320 |
| Arg | Val | Val | Ser | Val | Leu | Thr | Val | Leu | His | Gln | Asp | Trp | Leu | Asn | Gly |
| | | | | 325 | | | | | 330 | | | | | 335 | |
| Lys | Glu | Tyr | Lys | Cys | Lys | Val | Ser | Asn | Lys | Ala | Leu | Pro | Ala | Pro | Ile |
| | | | 340 | | | | | 345 | | | | | 350 | | |
| Glu | Lys | Thr | Ile | Ser | Lys | Ala | Lys | Gly | Gln | Pro | Arg | Glu | Pro | Gln | Val |
| | | | | 355 | | | | | 360 | | | | | 365 | |

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 243
<211> LENGTH: 703
<212> TYPE: DNA
<213> ORGANISM: artificial
<220> FEATURE:
<223> OTHER INFORMATION: VL2 light chain with signal sequence

<400> SEQUENCE: 243
atgggatgga gctgtatcat cctcttcttg gtggcaacag ctacaggcgt gcactcttcc      60
tctgagctga cccaggatcc tgctgtgtct gtggccctgg ccagaccgt caggatcacc     120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgtgt cgcccggtcg gtggtgggca ccccatgt tctgttcggc     360 ggagggaccc agctcaccgt tttaggtcag cccaaggctg ccccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtccac agaagctaca gctgccaggt cacgcatgaa    660
gggagcaccg tggagaagac agtggcccct acagaatgtt cat                      703

<210> SEQ ID NO 244
<211> LENGTH: 234
<212> TYPE: PRT
<213> ORGANISM: artificial
<220> FEATURE:
<223> OTHER INFORMATION: VL2 light chain with signal sequence

<400> SEQUENCE: 244

Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
        50                  55                  60

Val Ile Tyr Gly Lys His Lys Arg Pro Ser Gly Ile Pro Asp Arg Phe
65                  70                  75                  80

```
Ser Gly Ser Ser Ser Gly Asn Thr Ala Ser Leu Thr Ile Thr Gly Ala
            85                  90                  95

Gln Ala Glu Asp Glu Ala Asp Tyr Tyr Cys Val Ala Arg Ser Val Val
        100                 105                 110

Gly Asn Pro His Val Leu Phe Gly Gly Thr Gln Leu Thr Val Leu
        115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230

<210> SEQ ID NO 245
<211> LENGTH: 703
<212> TYPE: DNA
<213> ORGANISM: artificial
<220> FEATURE:
<223> OTHER INFORMATION: VL18 light chain with signal sequence

<400> SEQUENCE: 245
atgggatgga gctgtatcat cctcttcttg gtggcaacag ctacaggcgt gcactcttcc     60
tctgagctga cccaggatcc tgctgtgtct gtggccctgg ccagaccgt caggatcacc    120 tgccagggcg atagcctgag aacctactac gcctcctggt atcagcagaa gcctggacag    180
gcccctgtgc tggtgatcta cggcaagcac aagaggccat ccggcatccc tgacagattc    240
tccggctcct cctctggcaa taccgcctcc ctgaccatca ctggggctca ggcggaagac    300
gaggctgact attactgtgt cacgaggagc gtgaagggca ccccatgt tctgttcggc    360 ggagggaccc agctcaccgt tttaggtcag cccaaggctg cccctcggt cactctgttc    420 ccgccctcct ctgaggagct tcaagccaac aaggccacac tggtgtgtct cataagtgac    480
ttctacccgg gagccgtgac agtggcctgg aaggcagata gcagcccgt caaggcggga    540 gtggagacca ccacaccctc caaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggccct acagaatgtt cat                       703

<210> SEQ ID NO 246
<211> LENGTH: 234
<212> TYPE: PRT
<213> ORGANISM: artificial
<220> FEATURE:
<223> OTHER INFORMATION: VL18 light chain with signal sequence

<400> SEQUENCE: 246

Met Gly Trp Ser Cys Ile Ile Leu Phe Leu Val Ala Thr Ala Thr Gly
1               5                   10                  15

Val His Ser Ser Glu Leu Thr Gln Asp Pro Ala Val Ser Val Ala
            20                  25                  30
```

-continued

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
 50                  55                  60

Val Ile Tyr Gly Lys His Lys Arg Pro Ser Gly Ile Pro Asp Arg Phe
 65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Val Thr Arg Ser Val Lys
            100                 105                 110

Gly Asn Pro His Val Leu Phe Gly Gly Gly Thr Gln Leu Thr Val Leu
            115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
210                 215                 220

Glu Lys Thr Val Ala Pro Thr Glu Cys Ser
225                 230

<210> SEQ ID NO 247
<211> LENGTH: 703
<212> TYPE: DNA
<213> ORGANISM: artificial
<220> FEATURE:
<223> OTHER INFORMATION: VL25 light chain with signal sequence

<400> SEQUENCE: 247
atgggatgga gctgtatcat cctcttcttg gtggcaacag ctacaggcgt gcactcttcc       60
tctgagctga cccaggatcc tgctgtgtct gtggccctgg ccagaccgt caggatcacc      120 tgccagggcg atagcctgag aacctactac gcctcctggt atcagcagaa gcctggacag      180
gcccctgtgc tggtgatcta cggcaagcac aagaggccat ccggcatccc tgacagattc      240
tccggctcct cctctggcaa taccgcctcc ctgaccatca ctgggctca gcggaagac      300 gaggctgact attactgtac gacgcggagc aacaagggca accccatgt tctgttcggc      360 ggagggaccc agctcaccgt tttaggtcag cccaaggctg ccccctcggt cactctgttc      420
ccgccctcct ctgaggagct tcaagccaac aaggccacac tggtgtgtct cataagtgac      480
ttctacccgg gagccgtgac agtggcctgg aaggcagata gcagcccgt caaggcggga      540 gtggagacca ccacccctc caaacaaagc aacaacaagt acgcggccag cagctatctg      600
agcctgacgc tgagcagtg gaagtcccac agaagctaca gctgccaggt cacgcatgaa      660
gggagcaccg tggagaagac agtggcccct acagaatgtt cat                       703

<210> SEQ ID NO 248
<211> LENGTH: 234
<212> TYPE: PRT
<213> ORGANISM: artificial
<220> FEATURE:
<223> OTHER INFORMATION: VL25 light chain with signal sequence -continued

```
<400> SEQUENCE: 248

Met Gly Trp Ser Cys Ile Ile Leu Phe Leu Val Ala Thr Ala Thr Gly
1               5                   10                  15

Val His Ser Ser Ser Glu Leu Thr Gln Asp Pro Ala Val Ser Val Ala
            20                  25                  30

Leu Gly Gln Thr Val Arg Ile Thr Cys Gln Gly Asp Ser Leu Arg Thr
            35                  40                  45

Tyr Tyr Ala Ser Trp Tyr Gln Gln Lys Pro Gly Gln Ala Pro Val Leu
    50                  55                  60

Val Ile Tyr Gly Lys His Lys Arg Pro Ser Gly Ile Pro Asp Arg Phe
65                  70                  75                  80

Ser Gly Ser Ser Ser Gly Asn Thr Ala Ser Leu Thr Ile Thr Gly Ala
            85                  90                  95

Gln Ala Glu Asp Glu Ala Asp Tyr Tyr Cys Thr Thr Arg Ser Asn Lys
                100                 105                 110

Gly Asn Pro His Val Leu Phe Gly Gly Thr Gln Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230
```

METHODS OF TREATMENT UTILIZING BINDING PROTEINS OF THE INTERLEUKIN-21 RECEPTOR

RELATED APPLICATIONS

This application claims the benefit of priority from U.S. Provisional Patent Application No. 61/055,543, filed May 23, 2008, and U.S. Provisional Patent Application No. 61/099,476, filed Sep. 23, 2008, the contents of which are hereby incorporated by reference herein in their entireties.

BACKGROUND OF THE INVENTION

1. Field of the Invention

The present invention relates to binding proteins and antigen-binding fragments thereof that bind interleukin-21 receptor (IL-21R), in particular, human IL-21R, and their use in regulating IL-21R-associated activities, e.g., IL-21 effects on the levels of expression of IL-21 responsive genes. The binding proteins disclosed herein are useful in treating and/or diagnosing IL-21R-associated disorders, e.g., inflammatory disorders, autoimmune diseases, allergies, transplant rejection, hyperproliferative disorders of the blood, and other immune system disorders. The invention further provides methods for determining pharmacodynamic and pharmacokinetic properties of the antibodies of the invention.

2. Related Background Art

Antigens initiate immune responses and activate the two largest populations of lymphocytes: T cells and B cells. After encountering antigen, T cells proliferate and differentiate into effector cells, while B cells proliferate and differentiate into antibody-secreting plasma cells. These effector cells secrete and/or respond to cytokines, which are small proteins (less than about 30 kDa) secreted by lymphocytes and other cell types.

Human IL-21 is a cytokine that shows sequence homology to IL-2, IL-4 and IL-15 (Parrish-Novak et al. (2000) *Nature* 408:57-63). Despite low sequence homology among interleukin cytokines, cytokines share a common fold into a "four-helix-bundle" structure that is representative of the family. Most cytokines bind either class I or class II cytokine receptors. Class II cytokine receptors include the receptors for IL-10 and the interferons, whereas class I cytokine receptors include the receptors for IL-2 through IL-7, IL-9, IL-11, IL-12, IL-13, and IL-15, as well as hematopoietic growth factors, leptin, and growth hormone (Cosman (1993) *Cytokine* 5:95-106).

Human IL-21R is a class I cytokine receptor. The nucleotide and amino acid sequences encoding human IL-21 and its receptor (IL-21R) are described in International Application Publication Nos. WO 00/053761 and WO 01/085792; Parrish-Novak et al. (2000) supra; and Ozaki et al. (2000) *Proc. Natl. Acad. Sci. USA* 97:11439-44. IL-21R has the highest sequence homology to the IL-2 receptor β chain and the IL-4 receptor α chain (Ozaki et al. (2000) supra). Upon ligand binding, IL-21R associates with the common gamma cytokine receptor chain (γc) that is shared by receptor complexes for IL-2, IL-3, IL-4, IL-7, IL-9, IL-13 and IL-15 (Ozaki et al. (2000) supra; Asao et al. (2001) *J. Immunol.* 167:1-5).

IL-21R is expressed in lymphoid tissues, particularly on T cells, B cells, natural killer (NK) cells, dendritic cells (DC) and macrophages (Parrish-Novak et al. (2000) supra), which allows these cells to respond to IL-21 (Leonard and Spolski (2005) *Nat. Rev. Immunol.* 5:688-98). The widespread lymphoid distribution of IL-21R indicates that IL-21 plays an important role in immune regulation. In vitro studies have shown that IL-21 significantly modulates the function of B cells, $CD4^+$ and $CD8^+$ T cells, and NK cells (Parrish-Novak et al. (2000) supra; Kasaian et al. (2002) *Immunity* 16:559-69). Recent evidence suggests that IL-21-mediated signaling can have antitumor activity (Sivakumar et al. (2004) *Immunology* 112:177-82), and that IL-21 can prevent antigen-induced asthma in mice (Shang et al. (2006) *Cell. Immunol.* 241:66-74).

In autoimmunity, disruption of the IL-21 gene and injection of recombinant IL-21 have been shown to modulate the progression of experimental autoimmune myasthenia gravis (EAMG) and experimental autoimmune encephalomyelitis (EAE), respectively (King et al. (2004) *Cell* 117:265-77; Ozaki et al. (2004) *J. Immunol.* 173:5361-71; Vollmer et al. (2005) *J. Immunol.* 174:2696-2701; Liu et al. (2006) *J. Immunol.* 176:5247-54). In these experimental systems, it has been suggested that the manipulation of IL-21-mediated signaling directly altered the function of $CD8^+$ cells, B cells, T helper cells, and NK cells.

Thus, the present invention provides novel therapeutic agents for treating, e.g., autoimmune diseases that act by blocking the IL-21 signaling pathway, i.e., anti-IL-21R antibodies. In order for a therapeutic agent, such as an anti-IL-21R antibody, to be effective in vivo, a minimum serum concentration of the anti-IL-21R antibody necessary to modulate IL-21 responses should be determined; thus a method that allows accurate determination of such minimum serum concentration is required.

SUMMARY OF THE INVENTION

The present invention describes the isolation and characterization of binding proteins, for example, human antibodies and fragments thereof, that specifically bind to the human and murine IL-21R. The binding proteins described herein are derived from antibody 18A5, which is disclosed in U.S. Pat. No. 7,495,085, the entirety of which is hereby incorporated by reference herein. The binding proteins of the present invention have a much greater degree of affinity to human and/or murine IL-21R than does the parental 18A5 antibody.

The invention provides, at least in part, IL-21R binding agents (such as binding proteins and antigen-binding fragments thereof) that bind to IL-21R, in particular, human IL-21R, with high affinity and specificity. The binding proteins, and antigen-binding fragments thereof, of the present invention are also referred to herein as "anti-IL-21R binding proteins" and "fragments thereof," respectively. In one embodiment, the binding protein or fragment thereof reduces, inhibits, or antagonizes IL-21R activity. Such binding proteins can be used to regulate immune responses or IL-21R-associated disorders by antagonizing IL-21R activity. In other embodiments, the anti-IL-21R binding protein can be used diagnostically, or as a targeting binding protein to deliver a therapeutic or cytotoxic agent to an IL-21R-expressing cell. Thus, the anti-IL-21R binding proteins of the invention are useful in diagnosing and treating IL-21R-associated disorders, e.g., inflammatory disorders, autoimmune diseases, allergies, transplant rejection, hyperproliferative disorders of the blood, and other immune system disorders, as described more fully herein.

Accordingly, in one aspect, the binding proteins of the invention feature an isolated binding protein (e.g., an isolated antibody) or antigen-binding fragment thereof that binds to IL-21R, in particular, human IL-21R. In certain embodiments, the anti-IL-21R binding protein (e.g., antibody) can have one or more of the following characteristics: (1) it is a monoclonal or single specificity binding protein; (2) it is a human binding protein; (3) it is an in vitro-generated binding protein; (4) it is an in vivo-generated (for example, a transgenic mouse system) binding protein; (5) it inhibits the binding of IL-21 to IL-21R; (6) it is an IgG1; (7) it binds to human IL-21R with an association constant of at least about $10^5$ $M^{-1}s^{-1}$; (8) it binds to murine IL-21R with an association constant of at least about $5 \times 10^4 M^{-1}s^{-1}$; (9) it binds to human IL-21R with a dissociation constant of about $10^{-3}$ $s^{-1}$ or less; (10) it binds to murine IL-21R with a dissociation constant of about $10^{-2}$ $s^{-1}$ or less; (11) it inhibits human IL-21R-mediated proliferation of human IL-21R-expressing BaF3 cells with an $IC_{50}$ of about 1.75 nM or less; (12) it inhibits murine IL-21R-mediated proliferation of murine IL-21R-expressing BaF3 cells with an $IC_{50}$ of about 0.5 nM or less; (13) it inhibits human IL-21R-mediated proliferation of human IL-21R-expressing TF1 cells with an $IC_{50}$ of about 14.0 nM or less; (14) it inhibits IL-21-mediated proliferation of human primary B cells with an $IC_{50}$ of about 1.9 nM or less; (15) it inhibits IL-21-mediated proliferation of human primary CD4$^+$ T cells with an $IC_{50}$ of about 1.5 nM or less; (16) it inhibits IL-21-mediated proliferation of murine primary CD4$^+$ T cells with an $IC_{50}$ of about 5.0 nM or less; (17) it has a mean total body clearance of about 0.1-7.5 ml/hr/kg following, e.g., intravenous (i.v.) administration to animals, e.g., mammals, e.g., humans, nonhuman primates, rodents; (18) it has a mean elimination half-life of about 20-700 hr following, e.g., i.v., subcutaneous (s.c.), or intraperitoneal (i.p.) administration to animals, e.g., mammals, e.g., humans, nonhuman primates, rodents; (19) it has a mean steady-state volume of distribution of about 40-1500 ml/kg in animals, e.g., mammals, e.g., humans, nonhuman primates, rodents; (20) it has a bioavailability of about 35-100% following, e.g., s.c. administration to animals, e.g., mammals, e.g., humans, nonhuman primates, rodents; (21) it has a mean dose-normalized AUC of about 200-10,000 μg*hr/ml (per 1 mg/kg dosage) following, e.g., i.v., s.c., or i.p. administration to animals, e.g., mammals, e.g., humans, nonhuman primates, rodents; (22) it has a mean dose-normalized Cmax (maximum serum concentration) of about 0.5-30 μg/ml following, e.g., i.v., s.c., or i.p. administration to animals, e.g., mammals, e.g., humans, nonhuman primates, rodents; and (23) it modulates expression of IL-21 responsive cytokines or IL-21 responsive genes.

Nonlimiting illustrative embodiments of the binding proteins of the invention (the term "binding proteins" also includes and refers to antigen-binding fragments thereof, as appropriate) are referred to herein as AbA-AbZ, and correlation of these terms with terms used in U.S. Provisional Patent Application No. 61/055,543 is presented in Table 2A. Other illustrative embodiments of the binding proteins of the present invention, i.e., scFv, are referred to herein as H3-H6, L1-L6, L8-L21, and L23-L25, as detailed in Table 2B.

In one embodiment, the binding proteins of the invention are antibodies. In further embodiments, the antibodies are polyclonal, monoclonal, monospecific, polyspecific, nonspecific, humanized, human, single-chain, chimeric, synthetic, recombinant, hybrid, mutated, grafted, in vitro-generated and/or multispecific (e.g., bispecific antibodies formed from at least two intact antibodies).

One embodiment of the invention is a method of treating or preventing an IL-21R-associated disorder in a subject, comprising administering to the subject a binding protein or antigen-binding fragment thereof that specifically binds to human IL-21R in an amount sufficient to inhibit or reduce immune cell activity in the subject thereby treating or preventing the disorder, wherein the binding protein or antigen-binding fragment thereof comprises at least one amino acid sequence that is at least about 95% identical to an amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

In embodiments of the invention, the binding protein or antigen-binding fragment can be, e.g., an antibody, an scFv, a $V_H$, a $V_L$, and/or a CDR.

Another embodiment of the invention is a method of treating or preventing an IL-21R-associated disorder in a subject, comprising administering to the subject a binding protein or antigen-binding fragment thereof that specifically binds to human IL-21R in an amount sufficient to inhibit or reduce immune cell activity in the subject thereby treating or preventing the disorder, wherein the binding protein or antigen-binding fragment thereof comprises at least one amino acid sequence encoded by a nucleotide sequence that is at least about 95% identical to a nucleotide sequence(s) selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247.

In one embodiment of the invention, the binding protein or antigen-binding fragment comprises at least one amino acid sequence selected from the group consisting of SEQ ID NOs: 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

Another embodiment of the invention is a method of treating or preventing an IL-21R-associated disorder in a subject, comprising administering to the subject a binding protein or antigen-binding fragment thereof that specifically binds to human IL-21R in an amount sufficient to inhibit or reduce immune cell activity in the subject thereby treating or preventing the disorder, wherein the binding protein or antigen-binding fragment thereof comprises at least one amino acid sequence that is at least about 95% identical to an amino acid sequence(s) selected from the group consisting of SEQ ID NOs:6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162-195, 213-229, 240, 242, 244, 246, and 248, and wherein, if the binding protein or antigen-binding fragment comprises at least one amino acid sequence that is at least about 95% identical to the sequence(s) selected from the group consisting of SEQ ID NOs:6, 8, 10, 12, 163, 164, 169, 170, 194, and 195, then the binding protein or antigen-binding fragment must also comprise at least one amino acid sequence that is at least about 95% identical to the amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

Another embodiment of the invention is a method of treating or preventing an IL-21R-associated disorder in a subject, comprising administering to the subject a binding protein or antigen-binding fragment thereof that specifically binds to human IL-21R in an amount sufficient to inhibit or reduce immune cell activity in the subject thereby treating or preventing the disorder, wherein the binding protein or antigen-binding fragment thereof comprises at least one amino acid sequence encoded by a nucleotide sequence that is at least about 95% identical to a nucleotide sequence(s) selected from the group consisting of SEQ ID NOs:5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247, and wherein, if the binding protein or antigen-binding fragment comprises at least one amino acid sequence encoded by a nucleotide sequence that is at least about 95% identical to the sequence(s) selected from the group consisting of SEQ ID NOs:5, 7, 9, and 11, then the binding protein or antigen-binding fragment must also comprise at least one amino acid sequence encoded by a nucleotide sequence that is at least about 95% identical to the nucleotide sequence(s) selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247.

In one embodiment of the invention, the binding protein or antigen-binding fragment comprises at least one amino acid sequence selected from the group consisting of SEQ ID NOs: 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162-195, 213-229, 240, 242, 244, 246, and 248, wherein, if the binding protein or antigen-binding fragment comprises at least one amino acid sequence that is at least about 95% identical to the sequence(s) selected from the group consisting of SEQ ID NOs:6, 8, 10, 12, 163, 164, 169, 170, 194, and 195, then the binding protein or antigen-binding fragment must also comprise at least one amino acid sequence that is at least about 95% identical to the amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248.

A further embodiment of the invention is a method of treating or preventing an IL-21R-associated disorder in a subject, comprising administering to the subject a binding protein or antigen-binding fragment thereof that specifically binds to IL-21R, wherein the binding protein or antigen-binding fragment thereof comprises a light chain and a heavy chain, and wherein the heavy chain comprises at least one amino acid sequence selected from the group consisting of SEQ ID NOs:14, 16, 18, 20, 68, 70, 72, 88, 90, 92, 94, 213, 218, 219, 240, and 242. In one embodiment, the binding protein or antigen-binding fragment comprises a $V_L$ domain and a $V_H$ domain, and the $V_H$ domain comprises at least one sequence selected from the group consisting of SEQ ID NOs: 14, 16, 18, and 20.

Another embodiment of the invention is a method of treating or preventing an IL-21R-associated disorder in a subject, comprising administering to the subject a binding protein or antigen-binding fragment thereof that specifically binds to IL-21R, wherein the binding protein or antigen-binding fragment thereof comprises a light chain and a heavy chain, and wherein the light chain comprises at least one amino acid sequence selected from the group consisting of SEQ ID NOs: 22, 24, 26, 28, 30, 32, 34, 36, 38, 40, 42, 44, 46, 48, 50, 52, 54, 56, 58, 60, 62, 64, 66, 74, 76, 78, 80, 82, 84, 86, 96, 98, 100, 102, 104, 106, 108, 214-217, 220-229, 244, 246, and 248. In one embodiment, the binding protein or antigen-binding fragment comprises a $V_L$ domain and a $V_H$ domain, and the $V_L$ domain comprises at least one sequence selected from the group consisting of SEQ ID NOs:22, 24, 26, 28, 30, 32, 34, 36, 38, 40, 42, 44, 46, 48, 50, 52, 54, 56, 58, 60, 62, 64, 66, 215, 217, 221, 223, 225, 227, and 229.

In another embodiment of the methods of the invention, the heavy chain comprises an amino acid sequence selected from the group consisting of SEQ ID NOs:88, 90, 92, 94, 213, 218, 219, 240, and 242, and the light chain comprises an amino acid sequence selected from the group consisting of SEQ ID NOs:96, 98, 100, 102, 104, 106, 108, 214, 216, 220, 222, 224, 226, 228, 244, 246, and 248.

One embodiment of the invention is a method of treating or preventing an IL-21R-associated disorder in a subject, comprising administering to the subject a binding protein or antigen-binding fragment thereof that specifically binds to a human IL-21R epitope that is recognized by a binding protein selected from the group consisting of AbA-AbW, H3-H6, L1-L6, L8-L21, and L23-L25, wherein the binding protein or antigen-binding fragment competitively inhibits the binding of a binding protein selected from the group consisting of AbA-AbW, H3-H6, L1-L6, L8-L21, and L23-L25 to human IL-21R, in an amount sufficient to inhibit or reduce immune cell activity in the subject thereby treating or preventing the disorder. In another embodiment, the binding protein or antigen-binding fragment thereof comprises a heavy chain, a light chain, or an $F_v$ fragment comprising an amino acid sequence selected from the group consisting of SEQ ID NOs: 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. In yet another embodiment, the binding protein or antigen-binding fragment thereof comprises a heavy chain, a light chain, or an $F_v$ fragment comprising an amino acid sequence encoded by a nucleotide sequence selected from the group consisting of SEQ ID NOs:13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 239, 241, 243, 245, and 247. In still another embodiment, the binding protein specifically binds to an IL-21R epitope that is recognized by AbO, AbP, AbQ, AbR, AbS, AbT, AbU, AbV, and/or AbW, and the binding protein competitively inhibits the binding of AbO, AbP, AbQ, AbR, AbS, AbT, AbU, AbV, and/or AbW to human IL-21R.

In one embodiment of the methods of the invention, the IL-21R-associated disorder is selected from the group consisting of autoimmune disorders, inflammatory conditions, allergies, transplant rejections, and hyperproliferative disorders of the blood. In another embodiment, the IL-21R-associated disorder is selected from the group consisting of immune disorders, hyperproliferative disorders of the blood, transplant rejection, graft-versus-host disease, allergy (including atopic allergy), diabetes mellitus, arthritic disorders (including rheumatoid arthritis, juvenile rheumatoid arthritis, osteoarthritis, psoriatic arthritis, ankylosing spondylitis), spondyloarthropathy, multiple sclerosis, encephalomyelitis, myasthenia gravis, systemic lupus erythematosus (SLE), cutaneous lupus erythematosus, autoimmune thyroiditis, dermatitis (including atopic dermatitis, eczematous dermatitis), psoriasis, Sjögren's syndrome, IBD (including Crohn's disease, ulcerative colitis), asthma (including intrinsic asthma, allergic asthma), scleroderma and vasculitis. In a further embodiment, the IL-21R-associated disorder is selected from the group consisting of multiple sclerosis, systemic lupus erythematosus, psoriasis, transplant rejection, rheumatoid arthritis, and other arthritic disorders.

In one embodiment of the methods of the invention, the binding protein or antigen-binding fragment thereof has an association constant for human IL-21R of at least $10^5 M^{-1}s^{-1}$. In another embodiment, the binding protein or antigen-binding fragment thereof inhibits IL-21-mediated BAF3 cell proliferation with an $IC_{50}$ of about 1.75 nM or less, wherein the BAF3 cells comprise a human IL-21 receptor. In another embodiment, the binding protein or antigen-binding fragment thereof inhibits IL-21-mediated proliferation of TF1 cells with an $IC_{50}$ of about 14 nM or less, wherein the TF1 cells comprise a human IL-21 receptor. In still another embodiment, the binding protein or antigen-binding fragment thereof inhibits IL-21-mediated proliferation of primary human B cells with an $IC_{50}$ of about 1.9 nM or less, wherein the B cells comprise a human IL-21R. In yet another embodiment, the binding protein or antigen-binding fragment thereof inhibits IL-21-mediated proliferation of primary human $CD4^+$ cells with an $IC_{50}$ of about 1.5 nM or less, wherein the $CD4^+$ cells comprise a human IL-21R. In further embodiments of the invention, other ranges and values for these parameters, and for other pharmacokinetic and pharmacodynamic parameters, are provided herein.

In one embodiment, the invention provides a method of determining whether an anti-IL-21R antibody is a therapeutic anti-IL-21R antibody comprising the steps of: contacting a first blood sample from a subject with an IL-21 ligand; determining a level of expression of at least one IL-21-responsive gene in the first blood sample contacted with the IL-21 ligand; contacting a second blood sample from the subject with the IL-21 ligand in the presence of an anti-IL-21R antibody; determining the level of expression of the at least one IL-21-responsive gene in the second blood sample contacted with the IL-21 ligand in the presence of the anti-IL-21R antibody; and comparing the levels of expression of the at least one IL-21-responsive gene determined above, wherein a change in the level of expression of the at least one IL-21-responsive gene indicates that the anti-IL-21R antibody is a therapeutic antibody. In another embodiment of the invention, the subject is a mammal, e.g., a monkey or a human. In another embodiment, the at least one IL-21-responsive gene is selected from the group consisting of TNF, IFNγ, IL-6, IL-8, IL-10, CD19, STAT3, TBX21, CSF1, GZMB, PRF1, IL-2Rα, and IL-21R. In a further embodiment, the at least one IL-21-responsive gene is IL-2Rα.

In one embodiment, the invention provides a method of determining the pharmacodynamic activity of an anti-IL-21R antibody comprising detecting a modulation in a level of expression of at least one IL-21-responsive gene in a blood sample of a subject. In a further embodiment, detecting the modulation in the level of expression of the at least one IL-21-responsive gene comprises the steps of: administering the anti-IL-21R antibody to the subject, wherein the subject is treated with the anti-IL-21R antibody; contacting a blood sample from the subject treated with the anti-IL-21R antibody with an IL-21 ligand; determining the level of expression of the at least one IL-21-responsive gene in the blood sample from the subject treated with the anti-IL-21R antibody and contacted with the IL-21 ligand; and comparing the level of expression of the at least one IL-21-responsive gene determined above with the level of expression of the at least one IL-21 responsive gene in a different blood sample contacted with the IL-21 ligand, wherein the different blood sample is from a subject not treated with the anti-IL-21R antibody. In another embodiment of the invention, the subject is a mammal, e.g., a monkey or a human. In another embodiment, the at least one IL-21-responsive gene is selected from the group consisting of TNF, IFNγ, IL-6, IL-8, IL-10, CD19, STAT3, TBX21, CSF1, GZMB, PRF1, IL-2Rα, and IL-21R. In a further embodiment, the at least one IL-21-responsive gene is selected from the group consisting of CD19, GZMB, PRF1, IL-2Rα, IFNγ, and IL-6. In another further embodiment, the at least one IL-21-responsive gene is IL-2Rα.

In one embodiment, the invention provides a method of decreasing, inhibiting, or reducing an acute phase response in a subject, comprising administering to the subject a binding protein or antigen-binding fragment thereof that specifically binds to human IL-21R in an amount sufficient to decrease, inhibit or reduce the acute phase response in the subject, wherein the binding protein or antigen-binding fragment thereof comprises at least one amino acid sequence that is at least about 95% identical to an amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. In a further embodiment, the binding protein or antigen-binding fragment thereof is administered locally.

One embodiment of the invention is a method of increasing the efficacy of a vaccine formulation used to immunize a subject, comprising administering to the subject a therapeutically effective amount of a binding protein or antigen-binding fragment thereof that specifically binds to human IL-21R, wherein the binding protein or antigen-binding fragment thereof comprises at least one amino acid sequence that is at least about 95% identical to an amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. In some embodiments, the binding protein or antigen-binding fragment thereof is administered before, during and/or after immunization.

Another embodiment of the invention provides a method for detecting the presence of IL-21R in a sample in vitro, comprising (a) contacting a sample with a binding protein or antigen-binding fragment thereof that specifically binds to human IL-21R, and (b) detecting formation of a complex between the binding protein or antigen-binding fragment thereof and the sample, wherein a significant difference in the formation of the complex in the sample relative to in a control or reference sample or level is indicative of the presence of IL-21R in the sample, and wherein the binding protein or antigen-binding fragment thereof comprises at least one amino acid sequence that is at least about 95% identical to an amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. In a further embodiment, the sample is serum, plasma, or tissue.

Yet another embodiment of the invention provides a method for detecting the presence of IL-21R in vivo, comprising (a) administering a binding protein or antigen-binding fragment thereof that specifically binds to human IL-21R to a subject under conditions that allow for binding of the binding protein or antigen-binding fragment thereof to IL-21R, and (b) detecting formation of a complex between the binding protein or antigen-binding fragment thereof and IL-21R, wherein a significant difference in the formation of the complex in the subject relative to a control or reference sample or level of formation of the complex is indicative of the presence of IL-21R, and wherein the binding protein or antigen-binding fragment thereof comprises at least one amino acid sequence that is at least about 95% identical to the amino acid sequence(s) selected from the group consisting of SEQ ID NOs:14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 165-168, 171-193, 213-229, 240, 242, 244, 246, and 248. In some embodiments, the binding protein or antigen-binding fragment thereof is directly or indirectly labeled with a detectable substance to facilitate detection of bound or unbound antibody. In further embodiments, the detectable substance is an enzyme, a prosthetic group, a fluorescent material, a luminescent material, or a radioactive material.

In some embodiments, the invention provides methods further comprising administering to the subject another therapeutic agent chosen from the group consisting of a cytokine inhibitor, a growth factor inhibitor, an immunosuppressant, an anti-inflammatory agent, a metabolic inhibitor, an enzyme inhibitor, a cytotoxic agent, and a cytostatic agent. In further embodiments, the therapeutic agent is chosen from the group consisting of a TNF antagonist, an IL-12 antagonist, an IL-15 antagonist, an IL-17 antagonist, an IL-18 antagonist, an IL-19 antagonist, an IL-20 antagonist, an IL-21 antagonist, an IL-23 antagonist, a T cell-depleting agent, a B cell-depleting agent, methotrexate, leflunomide, sirolimus (rapamycin) or an analog thereof, a cox2 inhibitor, a cPLA2 inhibitor, an NSAID, and a p38 inhibitor. As in other methods of the invention, in some embodiments the subject is a mammal, e.g., a human.

Another embodiment of the invention provides a method for measuring, determining, and/or assessing the levels of production of anti-product antibodies, e.g., anti-product antibodies to anti-IL-21R binding proteins and antigen-binding fragments thereof.

Additional aspects of the disclosure will be set forth in part in the description, and in part will be obvious from the description, or may be learned by practicing the invention. The invention is set forth and particularly pointed out in the claims, and the disclosure should not be construed as limiting the scope of the claims. The following detailed description includes exemplary representations of various embodiments of the invention, which are not restrictive of the invention as claimed. The accompanying figures constitute a part of this specification and, together with the description, serve only to illustrate embodiments and not limit the invention.

BRIEF DESCRIPTION OF THE DRAWINGS

FIG. 7(a-c) depicts the binding specificity of particular anti-IL-21R antibodies (FIG. 7a, AbS; FIG. 7d shows that human IL-2Rβ and human soluble IL-4R are captured by specific anti-IL-2Rβ and anti-IL-4R antibodies, respectively (control).

FIG. 9 depicts the binding of anti-IL-21R antibodies to human and cynomolgus monkey IL-21R. Human anti-IL-21R antibodies AbS and AbT were captured on anti-human IgG immobilized on a BIACORE™ chip. Varying concentrations of human and cynomolgus monkey IL-21R-His/FLAG were allowed to flow over the chip, and binding and dissociation were monitored.

FIG. 12 depicts the neutralization of IL-21-dependent proliferation of human primary B cells. The indicated antibodies were added to primary human B cells along with anti-CD40 antibodies and human IL-21. Incorporation of $^3$H-thymidine was measured after three days.

FIG. 17(a-c) depicts amino acid sequences for AbQ, including $V_H$ and $V_L$ domains, CDRs (H1, H2, H3, L1, L2, and L3), and constant regions.

FIG. 18(a-c) depicts amino acid sequences for AbR, including $V_H$ and $V_L$ domains, CDRs (H1, H2, H3, L1, L2, and L3), and constant regions.

FIG. 19(a-c) depicts amino acid sequences for AbW, including $V_H$ and $V_L$ domains, CDRs (H1, H2, H3, L1, L2, and L3), and constant regions.

FIG. 20(a-c) depicts amino acid sequences for AbS, including $V_H$ and $V_L$ domains, CDRs (H1, H2, H3, L1, L2, and L3), and constant regions.

FIG. 21(a-c) depicts amino acid sequences for AbT, including $V_H$ and $V_L$ domains, CDRs (H1, H2, H3, L1, L2, and L3), and constant regions.

FIG. 22(a-c) depicts amino acid sequences for AbO, including $V_H$ and $V_L$ domains, CDRs (H1, H2, H3, L1, L2, and L3), and constant regions.

FIG. 23(a-c) depicts amino acid sequences for AbP including $V_H$ and $V_L$ domains, CDRs (H1, H2, H3, L1, L2, and L3), and constant regions.

FIG. 24(a-c) depicts amino acid sequences for AbU, including $V_H$ and $V_L$ domains, CDRs (H1, H2, H3, L1, L2, and L3), and constant regions.

FIG. 25(a-c) depicts amino acid sequences for AbV, including $V_H$ and $V_L$ domains, CDRs (H1, H2, H3, L1, L2, and L3), and constant regions.

FIG. 30 depicts NP-specific primary antibody response in animals treated with anti-IL-21R antibodies.

FIG. 31 depicts anti-double-stranded DNA (anti-dsDNA) antibodies in MRL-Fas$^{lpr}$ mice treated with anti-IL-21R antibodies. Twelve-week-old male MRL-Fas$^{lpr}$ mice were treated with either saline (control) or the indicated triple-mutant antibodies (10 mg/kg i.p., 3×/week); an anti-human IL-13 human IgG1 A234 A235 A237 triple-mutant antibody with no reactivity to murine IL-21 (IL-13 TM) was used as an isotype control. Serum collected biweekly was tested by ELISA for the presence of anti-dsDNA. In FIGS. 31a and 31c-g, asterisks indicate a significant difference as compared to both the saline and IL-13 controls (p<0.01). In FIG. 31b, the asterisk indicates a significant difference as compared to the other three groups (p<0.01). The dashed line in FIGS. 31b-g indicates the level of detection.

FIG. 38 depicts development of anti-dsDNA antibodies in MRL-Fas$^{lpr}$ mice treated with anti-IL-21R antibodies.

FIG. 39 depicts cellular infiltration into the dorsal air pouch in mice or rats treated with anti-IL-21R antibodies. FIGS. 39a-e: three days after injection of 3 ml of air under the dorsal skin of BALB/C mice to create an air pouch, pouches were reinflated. Two days later, either saline (control) or the indicated triple-mutant antibodies were injected i.p. One hundred ng of murine IL-21 was injected into the air pouch 24 hr after antibody injection. Six hours later, the pouches were washed out with 3 ml of PBS, and total cell counts (FIG. 39a), monocytes (FIG. 39b), lymphocytes (FIG. 39c), and neutrophils (FIG. 39d) were determined. FIG. 39e depicts total cell counts in a replicate of the experiment shown in FIGS. 39a-d. FIG. 39f depicts cellular infiltration following administration of either 20 μg mIL-21 for 6 hr or 1 μg mIL-21 for 20 hr, in the presence or absence of AbS or control antibody. FIGS. 39g-h depict cellular infiltration into rat air pouches in replicate experiments in which 20 μg mIL-21 was administered for 6 hr in the presence of 1, 3, or 10 μg/kg AbS or a control antibody. In the experiment shown in FIG. 39i, rats were treated for 6 hr with 20 μg mIL-21 and 1 mg/kg antibody (either AbS or isotype control), singly or in combination, as well as a combination of 20 μg mIL-21 and 10 mg/kg antibody. In FIG. 39j, 10, 20, or 40 μg mIL-21 were tested in combination with either 1 or 10 mg/kg AbS.

FIG. 40 depicts the concentration-time profiles of AbS in CD-1 mice after a single intravenous or subcutaneous administration. Concentrations below the limit of quantitation were treated as zero for the calculation of mean and standard deviation. N=4-8 for each data point.

FIG. 44 depicts the concentration-time profiles of AbS and AbT after a single administration to mice.

FIG. 50 depicts the biodistribution of $^{125}$I-AbS in IL-21R knockout and wild-type C57BL/6 (control) mice after a single 2.5 mg/kg intravenous dose.

FIG. 51 depicts the biodistribution of $^{125}$I-AbS in MRL-Fas$^{lpr}$ mice after a single 2.5 mg/kg i.p. dose.

FIG. 54 depicts the genes included on custom TLDA (Taqman® Low Density Array) for assay; Endogenous (Endo) controls are indicated.

FIGS. 56b-c depict percent inhibition (Y-axes) of IL-21 response of the same genes after treatment with different concentrations of either AbS or control IgG1 TM (X-axes).

FIG. 59 shows correlation of antibody serum concentrations (second Y-axis), pharmacodynamic (PD) activity ("RQ"; first Y-axis), and anti-product antibody response (indicated by "A"), including neutralizing anti-product antibody response (indicated by "AN"), following single 10 mg/kg i.v. administration of anti-IL-21R antibody AbS to male cynomolgus monkeys, as measured at various times pre- and post-dose administration (X-axis; Time (days)).

FIG. 60 shows correlations similar to those in FIG. 59 for AbT (single 10 mg/kg i.v. administration).

62a) or 10 mg/kg (FIG. 62b) to tetanus-toxoid challenged male and female cynomolgus monkeys.

Figure 63A:
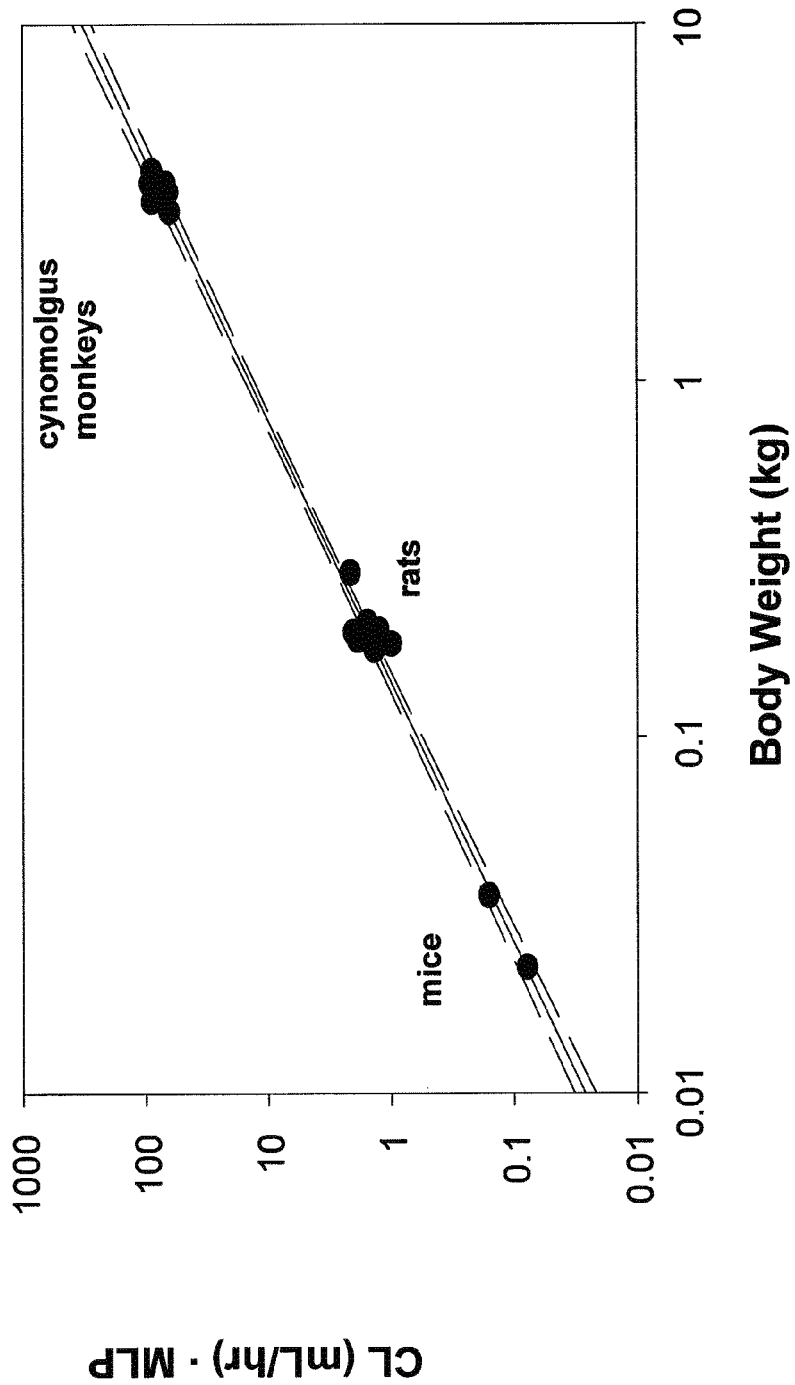
Figure 63B:
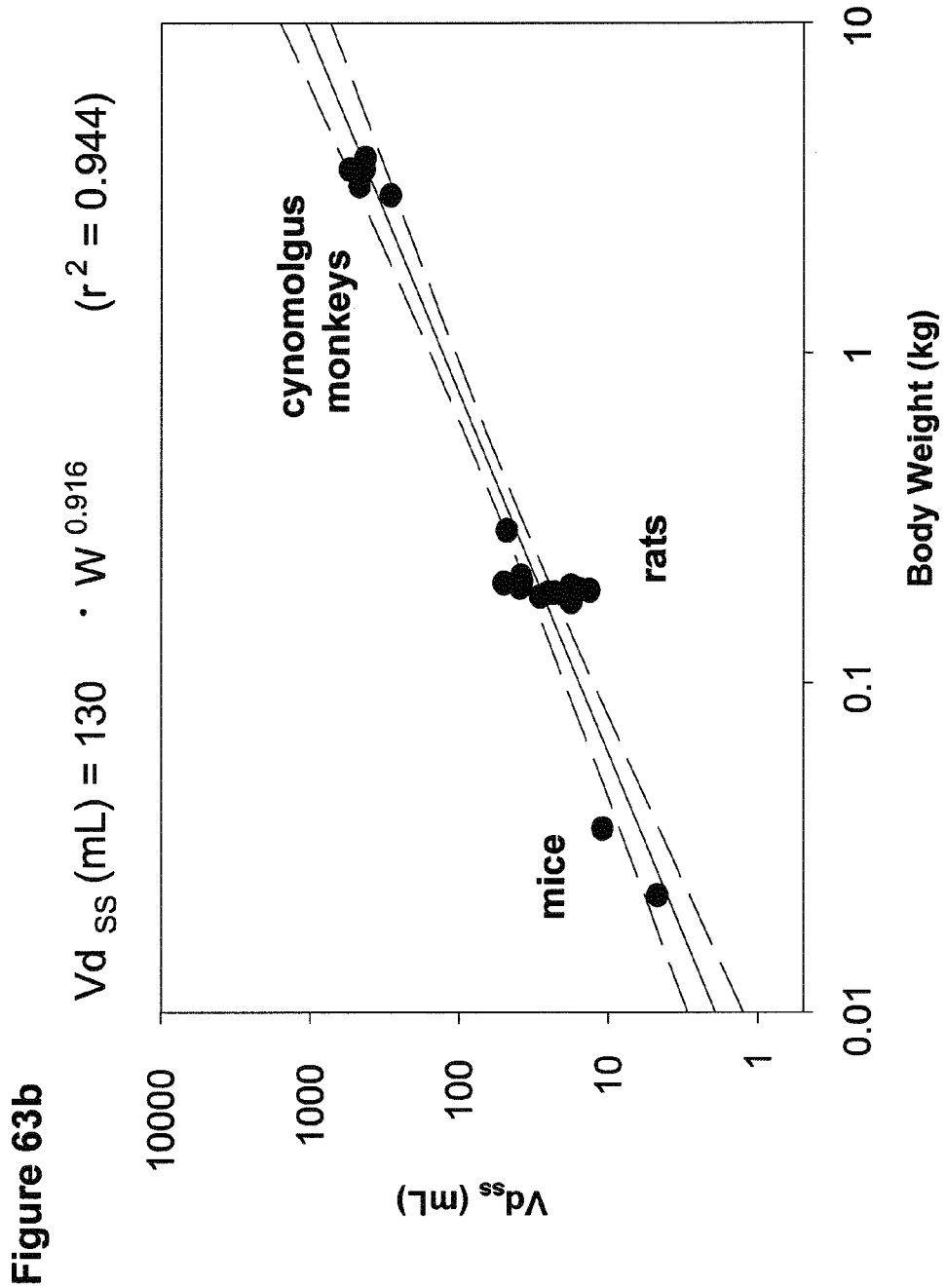

FIG. 63 depicts allometric scaling of AbS PK parameters after i.v. administration. Body weight (W); maximum span potential (in years; MLP). FIG. 63a represents CL•MLP (Y-axis) plotted against body weight (X-axis); FIG. 63b represents volume of distribution (Y-axis) plotted against body weight (X-axis). Solid lines represent fitted curves based on a linear regression using data from mice, rats, and cynomolgus monkeys. Dotted lines represent 95% confidence intervals.

Figure 64A:
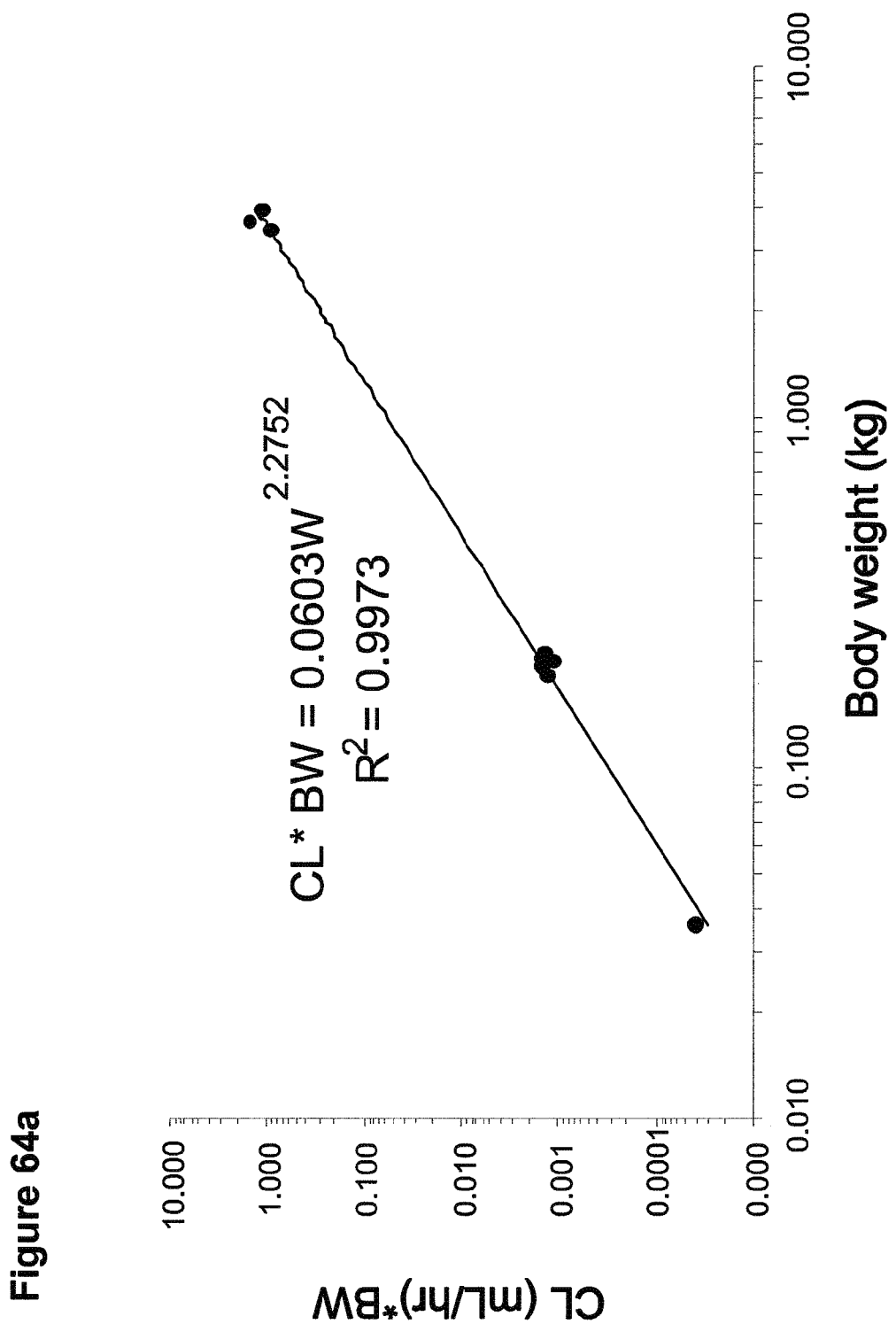
Figure 64B:
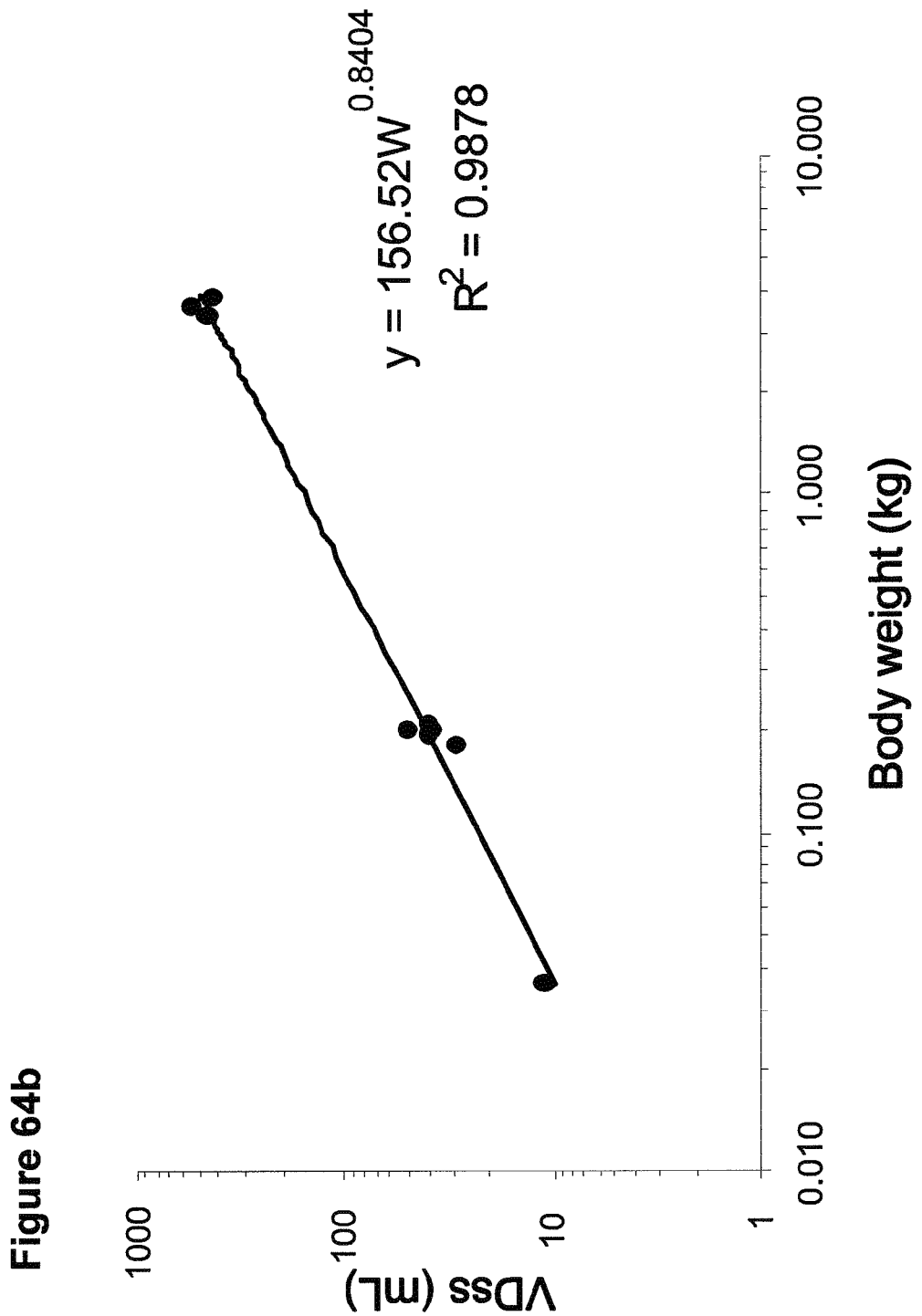

FIG. 64 represents allometric scaling of AbT PK parameters after i.v. administration. Body weight (W); brain weight ("BW"). FIG. 64a represents CL*BW (Y-axis) plotted against body weight (X-axis); FIG. 64b represents volume of distribution (Y-axis) plotted against body weight (X-axis).

Figure 65A:
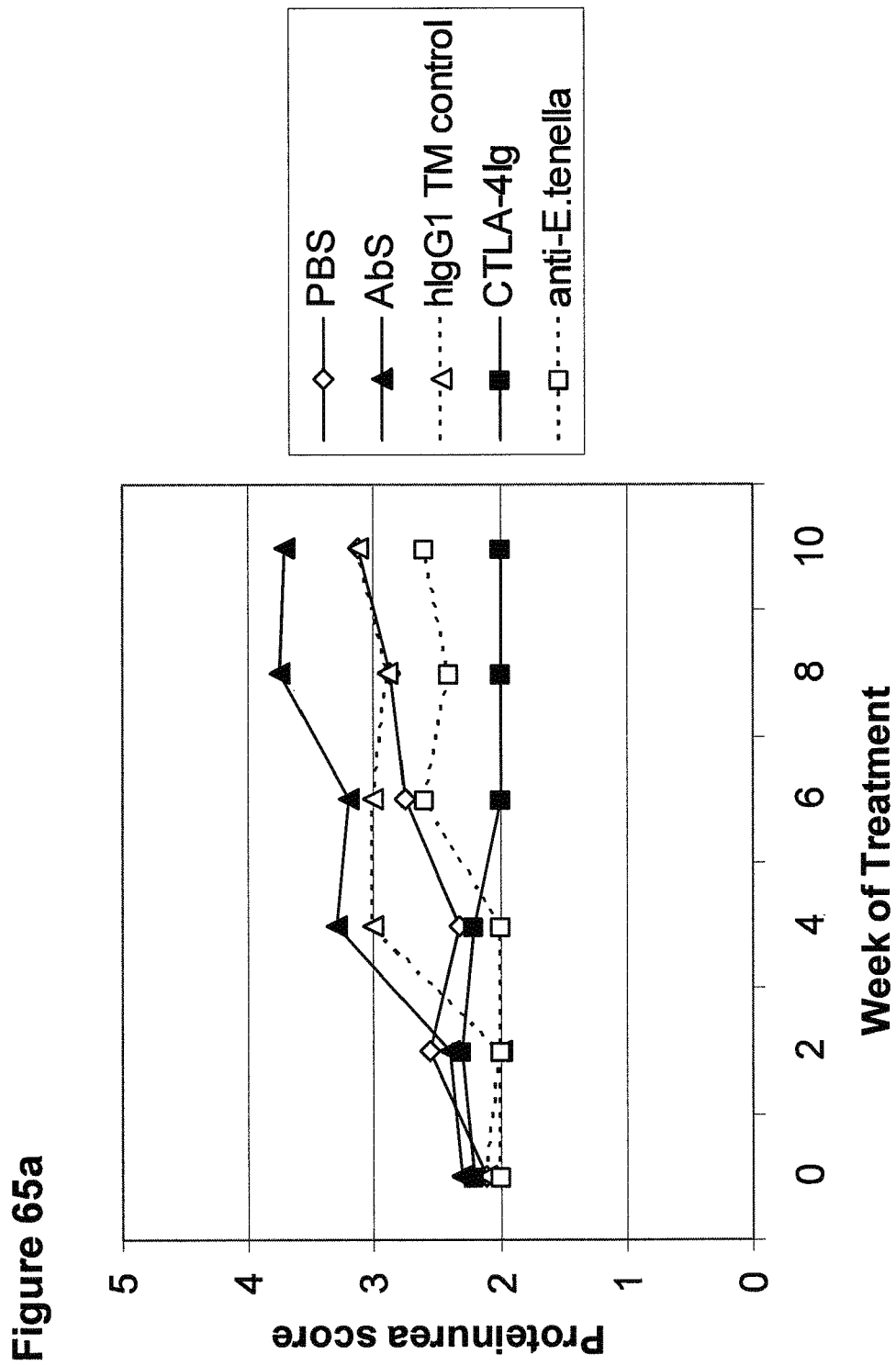
Figure 65B:
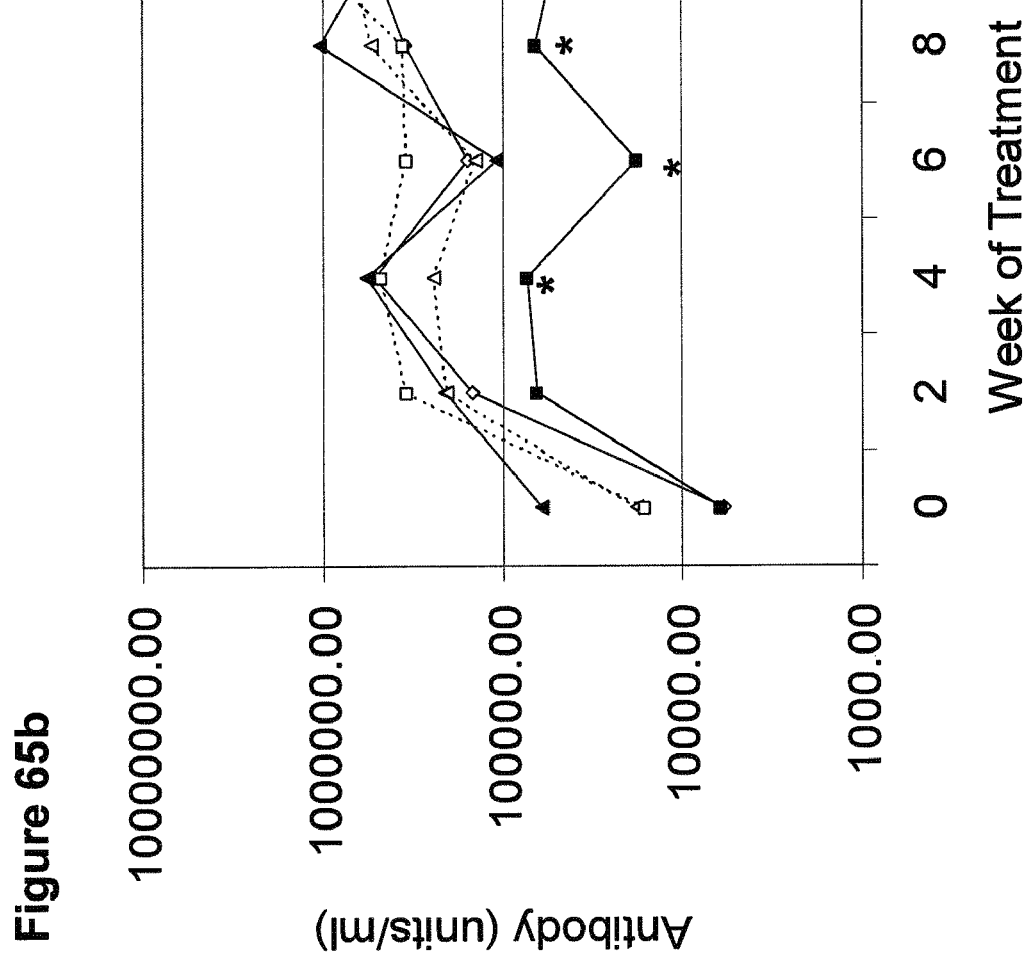

FIG. 65(a-b) depicts the effects of AbS on the development of proteinuria (FIG. 65a) and anti-dsDNA IgG serum antibody titers (FIG. 65b) in NZBWF1/J mice. Female 26-week old NZBWF1/J mice were administered 400 µg of either saline, anti-E. tenalla antibody, mCTLA-4Ig, hIgGTm antibody or AbS antibody 3×/week for 10 weeks. Urine protein levels and anti-dsDNA IgG serum antibody titers were measured at the beginning of the study, and every two weeks thereafter for 10 weeks. Animals treated with CTLA4-Ig showed significant reductions in anti-dsDNA titers (asterisks; p<0.05) at weeks 4-10.

Figure 66A:
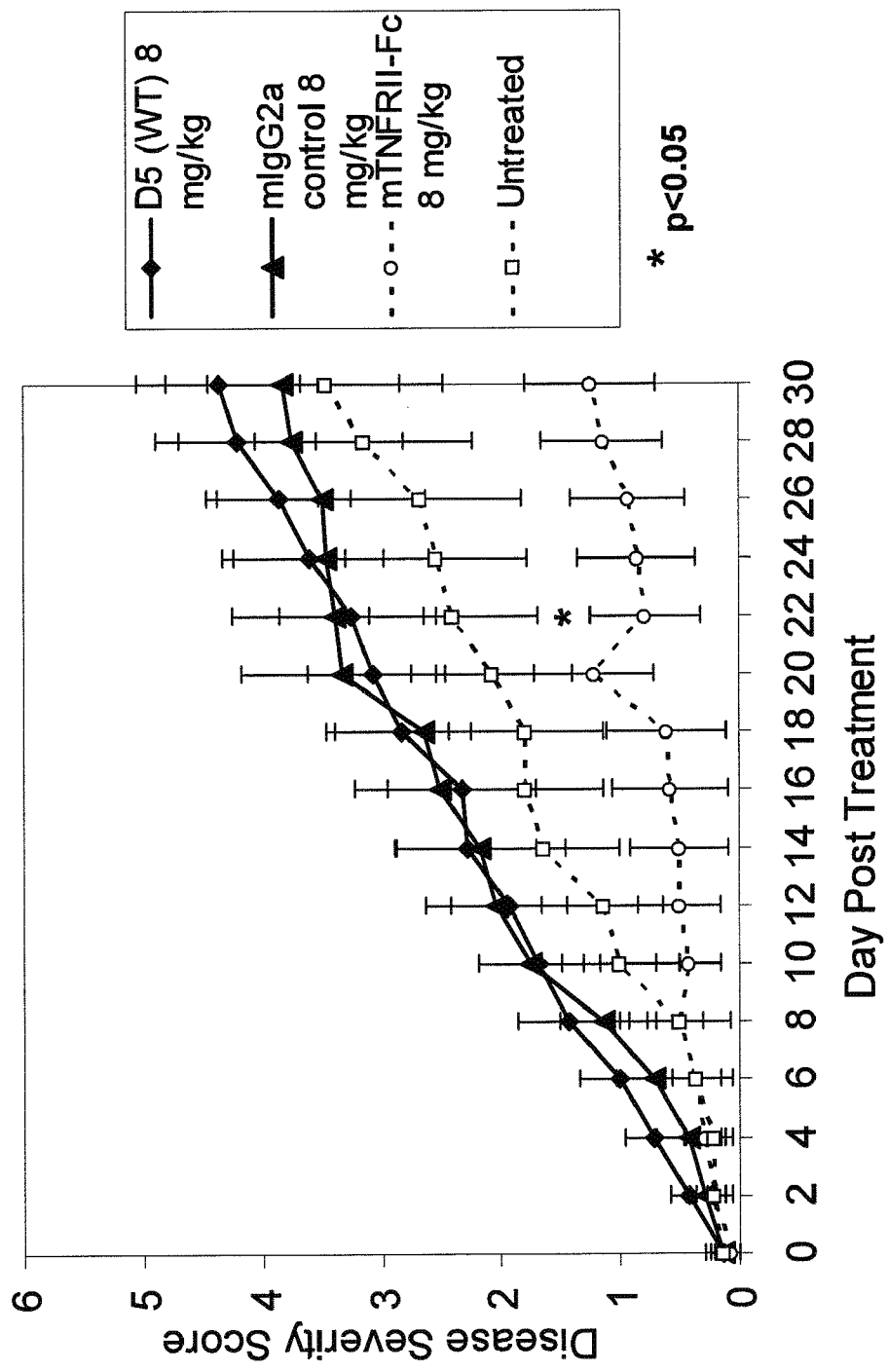
Figure 66B:
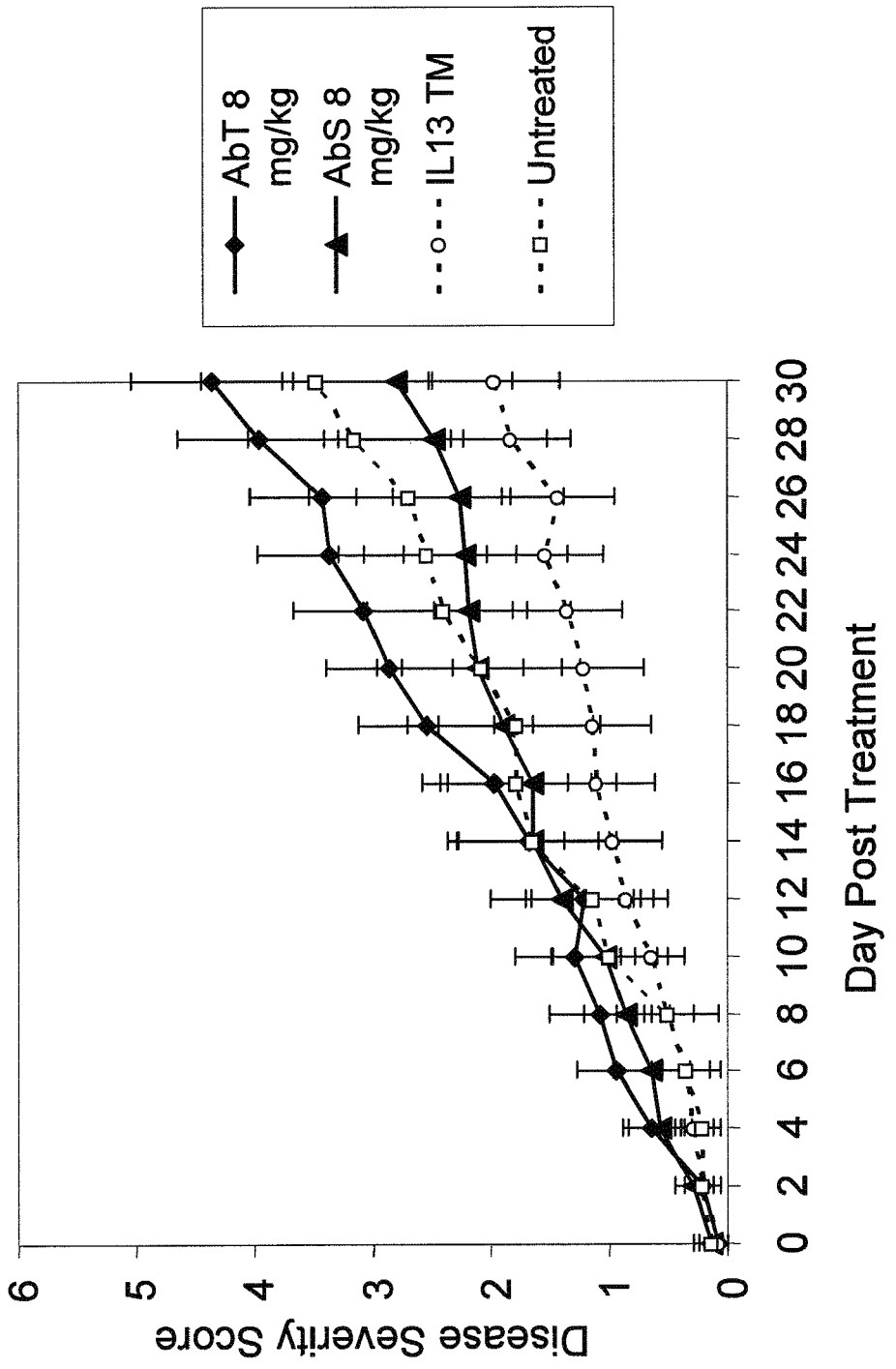
Figure 66C:
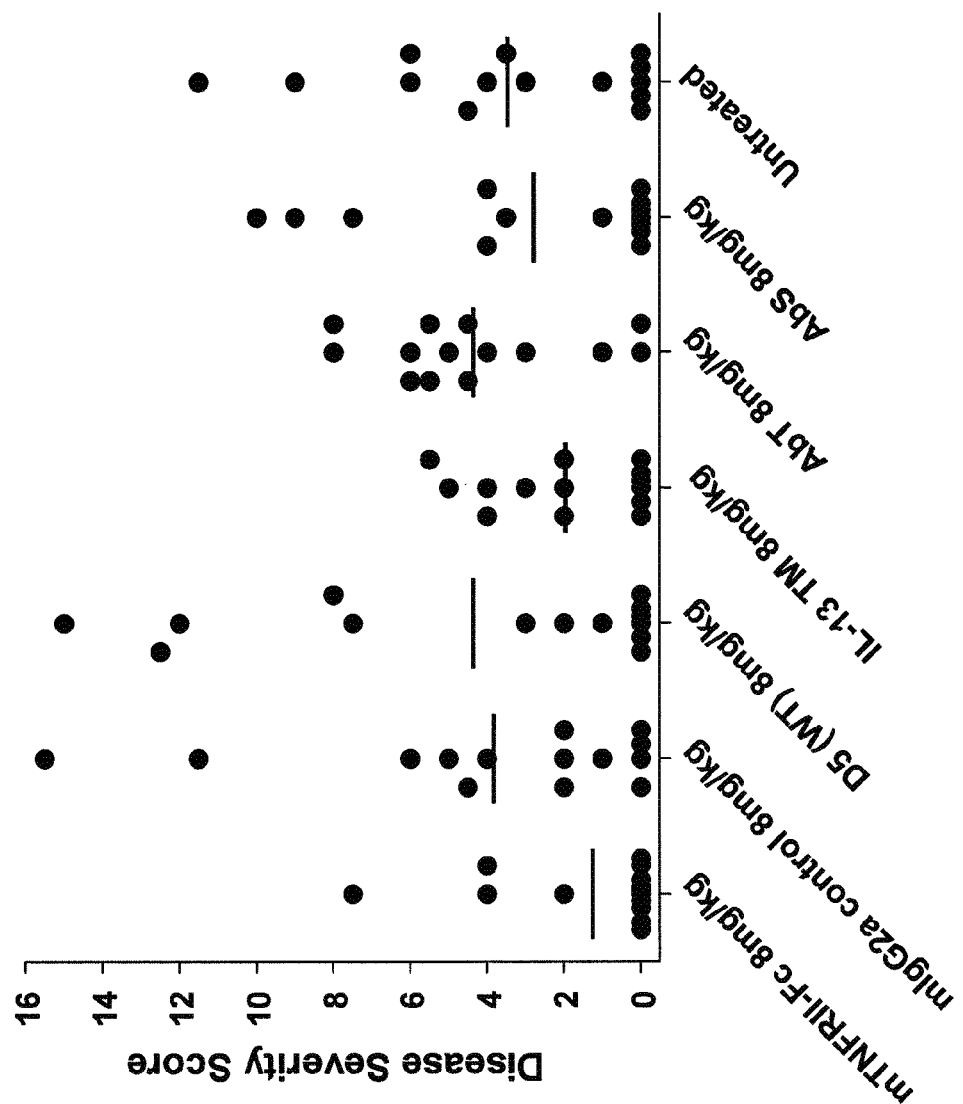

FIG. 66 depicts the effects of anti-IL-21R neutralization on disease outcome in a semi-therapeutic CIA mouse model of rheumatoid arthritis. Female DBA/1 mice were immunized and boosted with bovine collagen type II; when 10% of the animals in the study exhibited paw swelling, mice were dosed 3×/week for 30 days with 8 mg/kg of either murine IgG2a isotype control antibody, anti-mouse IL-21R antibody D5 (murine IgG2a antibody), mTNFRII-Fc (positive control, murine IgG2a isotype) (FIG. 66a); or anti-IL-13TM antibody (human IgG1 isotype control antibody), AbT, or AbS (FIG. 66b). Individual animal scores on day 30 of the study are depicted in FIG. 66c.

Figure 67B:
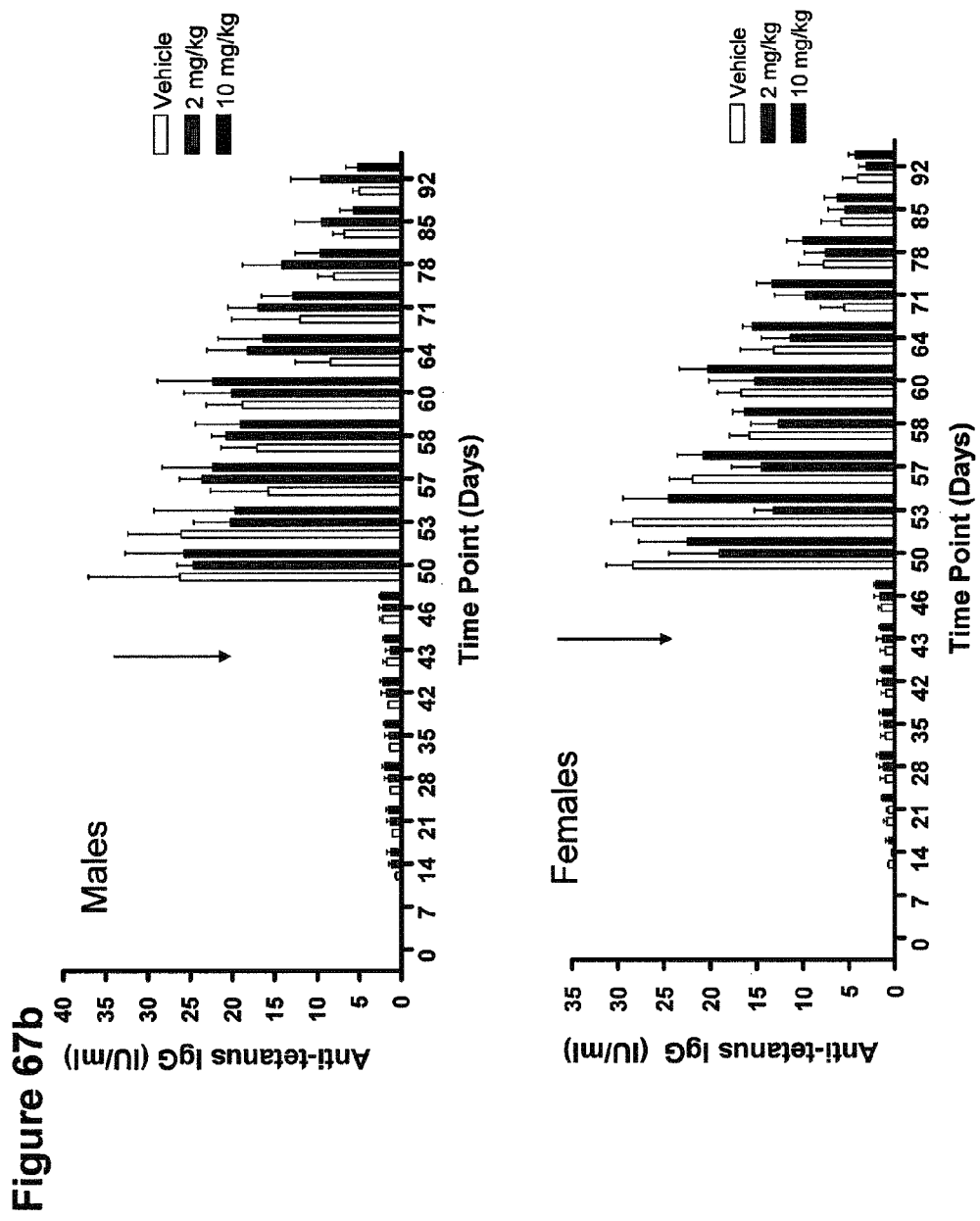

FIG. 67 depicts the development of amnestic tetanus-specific IgM and IgG serum antibody responses to tetanus toxoid in cynomolgus monkeys in the presence of AbS. Nine male and nine female cynomolgus monkeys were immunized with tetanus toxoid and rested for 43 days. After 43 days, male and female monkeys were randomly assigned into groups of three, and treated with either saline (vehicle), 2 mg/kg AbS, or 10 mg/kg AbS 1×/week for 3 weeks. Twenty-four hr after the first dose of either vehicle or AbS (arrows), monkeys were immunized a second time with tetanus toxoid. Monkeys were routinely bled throughout the course of the study, and examined for tetanus-specific IgM (FIG. 67a) and IgG (FIG. 67b) serum antibody titers.

DETAILED DESCRIPTION OF THE INVENTION

The binding proteins of the present invention were initially derived from parental antibody 18A5, but differ from 18A5 in the amino acid sequences of portions of the heavy chain and/or light chain complementarity determining region 3 (CDR3). Additionally, the present binding proteins show improved potency in binding to and neutralizing both human and murine IL-21R as compared to 18A5 in the equivalent format (e.g., scFv or IgG). High-potency neutralization of IL-21R from both species (human and mouse) by a single binding protein has not previously been reported. The present binding proteins having a greater neutralization potency than their parental antibody may translate into higher efficacy as compared to agents previously described. In addition, the amino acid sequence of the $V_H$ and $V_L$ framework regions has been altered to match sequences encoded by human genomic sequence, thereby reducing the potential for human anti-human antibody responses in patients treated with the present binding proteins.

DEFINITIONS

In order that the present invention may be more readily understood, certain terms are first defined. Additional definitions are set forth throughout the detailed description and elsewhere in the specification.

The term "binding protein" as used herein includes any naturally occurring, recombinant, synthetic, or genetically engineered protein, or a combination thereof, that binds an antigen, target protein, or peptide, or a fragment(s) thereof. Binding proteins of the invention can include antibodies, or be derived from at least one antibody fragment. The binding proteins can include naturally occurring proteins and/or proteins that are synthetically engineered. Binding proteins of the invention can bind to an antigen or a fragment thereof to form a complex and elicit a biological response (e.g., agonize or antagonize a particular biological activity). Binding proteins can include isolated antibody fragments, "Fv" fragments consisting of the variable regions of the heavy and light chains of an antibody, recombinant single-chain polypeptide molecules in which light and heavy chain variable regions are connected by a peptide linker ("scFv proteins"), and minimal recognition units consisting of the amino acid residues that mimic the hypervariable region. Binding protein fragments can also include functional fragments of an antibody, such as, for example, Fab, Fab', F(ab')$_2$, Fc, Fd, Fd', Fv, and a single variable domain of an antibody (dAb). The binding proteins can be double or single chain, and can comprise a single binding domain or multiple binding domains.

Binding proteins can also include binding domain-immunoglobulin fusion proteins, including a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain other than CH1, for example, the CH2 and CH3 regions of IgG and IgA, or the CH3 and CH4 regions of IgE (see, e.g., Ledbetter et al., U.S. Patent Publication 2005/0136049, for a more complete description). The binding domain-immunoglobulin fusion protein can further include a region that includes a native or engineered immunoglobulin heavy chain CH2 constant region polypeptide (or CH3 in the case of a construct derived in whole or in part from IgE) that is fused or otherwise connected to the hinge region polypeptide, and a native or engineered immunoglobulin heavy chain CH3 constant region polypeptide (or CH4 in the case of a construct derived in whole or in part from IgE) that is fused or otherwise connected to the CH2 constant region polypeptide (or CH3 in the case of a construct derived in whole or in part from IgE). Typically, such binding domain-immunoglobulin fusion proteins are capable of at least one immunological activity selected from the group consisting of antibody-dependent cell-mediated cytotoxicity, complement fixation, and/or binding to a target, for example, a target antigen. The binding proteins of the invention can be derived from any species including, but not limited to mouse, rat, human, camel, llama, fish, shark, goat, rabbit, chicken, and bovine.

The term "antibody" as used herein refers to an immunoglobulin that is reactive to a designated protein or peptide or fragment thereof. Suitable antibodies include, but are not limited to, human antibodies, primatized antibodies, chimeric antibodies, monoclonal antibodies, monospecific antibodies, polyclonal antibodies, polyspecific antibodies, nonspecific antibodies, bispecific antibodies, multispecific antibodies, humanized antibodies, synthetic antibodies, recombinant antibodies, hybrid antibodies, mutated antibodies, grafted conjugated antibodies (i.e., antibodies conjugated or fused to other proteins, radiolabels, cytotoxins), and in vitro-generated antibodies. The antibody can be from any class of antibodies including, but not limited to, IgG, IgA, IgM, IgD, and IgE, and from any subclass (e.g., IgG1, IgG2, IgG3, and IgG4) of antibodies. The antibody can have a heavy chain constant region chosen from, e.g., IgG1, IgG2, IgG3, or IgG4. The antibody can also have a light chain chosen from, e.g., kappa (κ) or lambda (λ). The antibodies of the invention can be derived from any species including, but not limited to mouse, rat, human, camel, llama, fish, shark, goat, rabbit, chicken, and bovine. Constant regions of the antibodies can be altered, e.g., mutated, to modify the properties of the antibody (e.g., to increase or decrease one or more of: Fc receptor binding, antibody glycosylation, the number of cysteine residues, effector cell function, or complement function). Typically, the antibody specifically binds to a predetermined antigen, e.g., an antigen associated with a disorder, e.g., an inflammatory, immune, autoimmune, neurodegenerative, metabolic, and/or malignant disorder.

The term "single domain binding protein" as used herein includes any single domain binding scaffold that binds to an antigen, protein, or polypeptide. Single domain binding proteins can include any natural, recombinant, synthetic, or genetically engineered protein scaffold, or a combination thereof, that binds an antigen or fragment thereof to form a complex and elicit a biological response (e.g., agonize or antagonize a particular biological activity). Single domain binding proteins may be derived from naturally occurring proteins or antibodies, or they can be synthetically engineered or produced by recombinant technology. Single domain binding proteins may be any in the art or any future single domain binding proteins, and may be derived from any species including, but not limited to mouse, human, camel, llama, fish, shark, goat, rabbit, chicken, and bovine. In some embodiments of the invention, a single domain binding protein scaffold can be derived from a variable region of the immunoglobulin found in fish, such as, for example, that which is derived from the immunoglobulin isotype known as Novel Antigen Receptor (NAR) found in the serum of shark. Methods of producing single domain binding scaffolds derived from a variable region of NAR ("IgNARs") are described in International Application Publication No. WO 03/014161 and Streltsov (2005) *Protein Sci.* 14(11):2901-09.

In other embodiments, a single domain binding protein is a naturally occurring single domain binding protein, which has been described in the art as a heavy chain antibody devoid of light chains. Such single domain binding proteins are disclosed in, e.g., International Application Publication No. WO 94/004678. For clarity reasons, a variable domain binding protein that is derived from a heavy chain antibody naturally devoid of light chain is known herein as a VHH or "nanobody" to distinguish it from the conventional $V_H$ of four-chain immunoglobulins. Such a VHH molecule can be derived from antibodies raised in Camelidae species, for example in camel, llama, dromedary, alpaca, and guanaco. Other families besides Camelidae may also be used to produce heavy chain binding proteins naturally devoid of light chains. VHH molecules are approximately ten times smaller than traditional IgG molecules. They are single polypeptides and are very stable, resisting extreme pH and temperature conditions. Moreover, they are resistant to the action of proteases, which is not the case for conventional antibodies. Furthermore, in vitro expression of VHHs can produce high-yield, properly folded functional VHHs. In addition, binding proteins generated in Camelids can recognize epitopes other than those recognized by antibodies generated in vitro via antibody libraries or via immunization of mammals other than Camelids (see, e.g., International Application Publication Nos. WO 97/049805 and WO 94/004678, both hereby incorporated by reference herein).

The terms "antigen-binding domain" and "antigen-binding fragment" refer to a part of a binding protein that comprises amino acids responsible for the specific binding between the binding protein and an antigen. The part of the antigen that is specifically recognized and bound by the binding protein is referred to as the "epitope." An antigen-binding domain may comprise a light chain variable region ($V_L$) and a heavy chain variable region ($V_H$) of an antibody; however, it does not have to comprise both. Fd fragments, for example, have two $V_H$ regions and often retain antigen-binding function of the intact antigen-binding domain. Examples of antigen-binding fragments of a binding protein include, but are not limited to: (1) a Fab fragment, a monovalent fragment having $V_L$, $V_H$, $C_L$ and $C_H1$ domains; (2) a F(ab')$_2$ fragment, a bivalent fragment having two Fab fragments linked by a disulfide bridge at the hinge region; (3) an Fd fragment, having two $V_H$ and one $C_H1$ domains; (4) an Fv fragment, having the $V_L$ and $V_H$ domains of a single arm of an antibody; (5) a dAb fragment (see, e.g., Ward et al. (1989) *Nature* 341:544-46), having a $V_H$ domain; (6) an isolated CDR; and (7) a single chain variable fragment (scFv). Although the two domains of an Fv fragment, $V_L$ and $V_H$ are coded for by separate genes, they can be joined, using recombinant methods, by a synthetic linker that enables them to be made as a single protein chain in which the $V_L$ and $V_H$ regions pair to form monovalent molecules (known as scFv) (see, e.g., Bird et al. (1988) *Science* 242:423-26; Huston et al. (1988) *Proc. Natl. Acad. Sci. USA* 85:5879-83). These binding domain fragments can be obtained using conventional techniques known to those with skill in the art, and the fragments are evaluated for function in the same manner as are intact binding proteins such as, for example, antibodies.

The term "neutralizing" refers to a binding protein or antigen-binding fragment thereof (for example, an antibody) that reduces or blocks the activity of a signaling pathway or an antigen, e.g., IL-21/IL-21R signaling pathway or IL-21R antigen. "An anti-product antibody," as used herein, refers to an antibody formed in response to exogenous protein, e.g., an anti-IL-21R antibody. "A neutralizing anti-product antibody," as used herein, refers to an anti-product antibody that blocks the in vivo activity of the exogenously introduced protein, e.g., an anti-IL-21R antibody. In some embodiments of the invention, a neutralizing anti-product antibody diminishes in vivo activity of an IL-21R antibody, e.g., in vivo pharmacodynamic (PD) activity of an IL-21R antibody (such as the ability of an anti-IL-21R antibody to modulate expression of IL-21-responsive cytokines or genes).

The term "effective amount" refers to a dosage or amount that is sufficient to regulate IL-21R activity to ameliorate or lessen the severity of clinical symptoms or achieve a desired biological outcome, e.g., decreased T cell and/or B cell activity, suppression of autoimmunity, suppression of transplant rejection.

The term "human binding protein" includes binding proteins having variable and constant regions corresponding substantially to human germline immunoglobulin sequences known in the art, including, for example, those described by Kabat et al. (5th ed. 1991) *Sequences of Proteins of Immuno-*

*logical Interest*, U.S. Department of Health and Human Services, NIH Publication No. 91-3242. The human antibodies of the invention may include amino acid residues not encoded by human germline immunoglobulin sequences (e.g., mutations introduced by random or site-specific mutagenesis in vitro or by somatic mutation in vivo), for example, in the CDRs, and in particular, CDR3. The human antibody can have at least one, two, three, four, five, or more positions replaced with an amino acid residue that is not encoded by the human germline immunoglobulin sequence.

The phrases "inhibit," "antagonize," "block," or "neutralize" IL-21R activity and its cognates refer to a reduction, inhibition, or otherwise diminution of at least one activity of IL-21R due to binding an anti-IL-21R antibody, wherein the reduction is relative to the activity of IL-21R in the absence of the same antibody. The IL-21R activity can be measured using any technique known in the art. Inhibition or antagonism does not necessarily indicate a total elimination of the IL-21R biological activity. A reduction in activity may be about 10%, 20%, 30%, 40%, 50%, 60%, 70%, 80%, 90%, 95%, or more.

The terms "interleukin-21 receptor" or "IL-21R" or the like refer to a class I cytokine family receptor, also known as MU-1 (see, e.g., U.S. patent application Ser. No. 09/569,384 and U.S. Application Publication Nos. 2004/0265960; 2006/0159655; 2006/0024268; and 2008/0241098), NILR or zalpha11 (see, e.g., International Application Publication No. WO 01/085792; Parrish-Novak et al. (2000) supra; Ozaki et al. (2000) supra), that binds to an IL-21 ligand. IL-21R is homologous to the shared β chain of the IL-2 and IL-15 receptors, and IL-4α (Ozaki et al. (2000) supra). Upon ligand binding, IL-21R is capable of interacting with a common gamma cytokine receptor chain (γc) and inducing the phosphorylation of STAT1 and STAT3 (Asao et al. (2001) supra) or STAT5 (Ozaki et al. (2000) supra). IL-21R shows widespread lymphoid tissue distribution. The terms "interleukin-21 receptor" or "IL-21R" or the like also refer to a polypeptide (preferably of mammalian origin, e.g., murine or human IL-21R) or, as context requires, a polynucleotide encoding such a polypeptide, that is capable of interacting with IL-21 (preferably IL-21 of mammalian origin, e.g., murine or human IL-21) and has at least one of the following features: (1) an amino acid sequence of a naturally occurring mammalian IL-21R polypeptide or a fragment thereof, e.g., an amino acid sequence set forth in SEQ ID NO:2 (human—corresponding to GENBANK® (U.S. Dept. of Health and Human Services, Bethesda, Md.) Accession No. NP_068570) or SEQ ID NO:4 (murine—corresponding to GENBANK® Acc. No. NP_068687), or a fragment thereof; (2) an amino acid sequence substantially homologous to, e.g., at least 85%, 90%, 95%, 98%, or 99% homologous to, an amino acid sequence set forth in SEQ ID NO:2 or SEQ ID NO:4, or a fragment thereof; (3) an amino acid sequence that is encoded by a naturally occurring mammalian IL-21R nucleotide sequence or fragment thereof (e.g., SEQ ID NO:1 (human—which comprises an open reading frame corresponding to the open reading frame of GENBANK® Accession No. NM_021798) or SEQ ID NO:3 (murine—which comprises an open reading frame corresponding to the open reading frame of GENBANK® Acc. No. NM_021887), or a fragment thereof); (4) an amino acid sequence encoded by a nucleotide sequence that is substantially homologous to, e.g., at least 85%, 90%, 95%, 98%, or 99% homologous to, a nucleotide sequence set forth in SEQ ID NO:1 or SEQ ID NO:3 or a fragment thereof; (5) an amino acid sequence encoded by a nucleotide sequence degenerate to a naturally occurring IL-21R nucleotide sequence or a fragment thereof, e.g., SEQ ID NO:1 or SEQ ID NO:3, or a fragment thereof; or (6) a nucleotide sequence that hybridizes to one of the foregoing nucleotide sequences under stringent conditions, e.g., highly stringent conditions. In addition, other nonhuman and nonmammalian IL-21Rs are contemplated as useful in the disclosed methods.

The term "interleukin-21" or "IL-21" refers to a cytokine that shows sequence homology to IL-2, IL-4 and IL-15 (Parrish-Novak et al. (2000) supra), and binds to an IL-21R. Such cytokines share a common fold into a "four-helix-bundle" structure that is representative of the family. IL-21 is expressed primarily in activated $CD4^+$ T cells, and has been reported to have effects on NK, B and T cells (Parrish-Novak et al. (2000) supra; Kasaian et al. (2002) supra). Upon IL-21 binding to IL-21R, activation of IL-21R leads to, e.g., STAT5 or STAT3 signaling (Ozaki et al. (2000) supra). The term "interleukin-21" or "IL-21" also refers to a polypeptide (preferably of mammalian origin, e.g., murine or human IL-21), or as context requires, a polynucleotide encoding such a polypeptide, that is capable of interacting with IL-21R (preferably of mammalian origin, e.g., murine or human IL-21R) and has at least one of the following features: (1) an amino acid sequence of a naturally occurring mammalian IL-21 or a fragment thereof, e.g., an amino acid sequence set forth in SEQ ID NO:212 (human), or a fragment thereof; (2) an amino acid sequence substantially homologous to, e.g., at least 85%, 90%, 95%, 98%, or 99% homologous to, an amino acid sequence set forth in SEQ ID NO:212, or a fragment thereof; (3) an amino acid sequence that is encoded by a naturally occurring mammalian IL-21 nucleotide sequence or a fragment thereof (e.g., SEQ ID NO:211 (human), or a fragment thereof); (4) an amino acid sequence encoded by a nucleotide sequence that is substantially homologous to, e.g., at least 85%, 90%, 95%, 98%, or 99% homologous to, a nucleotide sequence set forth in SEQ ID NO:211 or a fragment thereof; (5) an amino acid sequence encoded by a nucleotide sequence degenerate to a naturally occurring IL-21 nucleotide sequence or a fragment thereof; or (6) a nucleotide sequence that hybridizes to one of the foregoing nucleotide sequences under stringent conditions, e.g., highly stringent conditions.

The terms "IL-21R activity" and the like (e.g., "activity of IL-21R," "IL-21/IL-21R activity") refer to at least one cellular process initiated or interrupted as a result of IL-21R binding. IL-21R activities include, but are not limited to: (1) interacting with, e.g., binding to, a ligand, e.g., an IL-21 polypeptide; (2) associating with or activating signal transduction (also called "signaling," which refers to the intracellular cascade occurring in response to a particular stimuli) and signal transduction molecules (e.g., gamma chain (γc) and JAK1), and/or stimulating the phosphorylation and/or activation of STAT proteins, e.g., STAT5 and/or STAT3; (3) modulating the proliferation, differentiation, effector cell function, cytolytic activity, cytokine secretion, and/or survival of immune cells, e.g., T cells, NK cells, B cells, macrophages, regulatory T cells (Tregs) and megakaryocytes; and (4) modulating expression of IL-21-responsive genes or cytokines, e.g., modulating IL-21 effects on the level of expression of, e.g., TNF, IFNγ, IL-6, IL-8, IL-10, CD19, STAT3, ICAM-1, TBX21, CSF1, GZMB, PRF1, IL-2Rα, IL-21R, etc.

As used herein, "in vitro-generated antibody" refers to an antibody where all or part of the variable region (e.g., at least one CDR) is generated in a nonimmune cell selection (e.g., an in vitro phage display, protein chip, or any other method in which candidate sequences can be tested for their ability to bind to an antigen).

The term "isolated" refers to a molecule that is substantially free of its natural environment. For instance, an isolated protein is substantially free of cellular material or other proteins from the cell or tissue source from which it was derived. The term also refers to preparations where the isolated protein is sufficiently pure for pharmaceutical compositions, or is at least 70-80% (w/w) pure, at least 80-90% (w/w) pure, at least 90-95% (w/w) pure, or at least 95%, 96%, 97%, 98%, 99%, or 100% (w/w) pure.

The phrase "percent identical" or "percent identity" refers to the similarity between at least two different sequences. This percent identity can be determined by standard alignment algorithms, for example, the Basic Local Alignment Search Tool (BLAST) described by Altshul et al. ((1990) *J. Mol. Biol.* 215:403-10); the algorithm of Needleman et al. ((1970) *J. Mol. Biol.* 48:444-53); or the algorithm of Meyers et al. ((1988) *Comput. Appl. Biosci.* 4:11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) *CABIOS* 4:11-17), which has been incorporated into the ALIGN program (version 2.0), using a PAM120 weight residue table, a gap length penalty of 12, and a gap penalty of 4. The percent identity is usually calculated by comparing sequences of similar length.

The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, or other methods (see, e.g., U.S. Pat. No. 5,565,332). A repertoire may include only one sequence or may include a plurality of sequences, including ones in a genetically diverse collection.

The terms "specific binding," "specifically binds," and the like refer to two molecules forming a complex that is relatively stable under physiologic conditions. Specific binding is characterized by a high affinity and a low-to-moderate capacity as distinguished from nonspecific binding, which usually has a low affinity with a moderate-to-high capacity. Typically, binding is considered specific when the association constant Ka is higher than about $10^6$ $M^{-1}s^{-1}$. If necessary, nonspecific binding can be reduced without substantially affecting specific binding by varying the binding conditions. The appropriate binding conditions, such as concentration of binding protein, ionic strength of the solution, temperature, time allowed for binding, concentration of a blocking agent (e.g., serum albumin or milk casein), etc., can be improved by a skilled artisan using routine techniques. Illustrative conditions are set forth herein, but other conditions known to the person of ordinary skill in the art fall within the scope of this invention.

As used herein, the terms "stringent," "stringency," and the like describe conditions for hybridization and washing. The isolated polynucleotides of the present invention can be used as hybridization probes and primers to identify and isolate nucleic acids having sequences identical to or similar to those encoding the disclosed polynucleotides. Therefore, polynucleotides isolated in this fashion may be used to produce binding proteins against IL-21R or to identify cells expressing such binding proteins. Hybridization methods for identifying and isolating nucleic acids include polymerase chain reaction (PCR), Southern hybridizations, in situ hybridization and Northern hybridization, and are well known to those skilled in the art.

Hybridization reactions can be performed under conditions of different stringencies. The stringency of a hybridization reaction includes the difficulty with which any two nucleic acid molecules will hybridize to one another and the conditions under which they will remain hybridized. Preferably, each hybridizing polynucleotide hybridizes to its corresponding polynucleotide under reduced stringency conditions, more preferably stringent conditions, and most preferably highly stringent conditions. Stringent conditions are known to those skilled in the art and can be found in, e.g., *Current Protocols in Molecular Biology*, John Wiley & Sons, N.Y. (1989) 6.3.1-6.3.6. Both aqueous and nonaqueous methods are described in this reference, and either can be used. One example of stringent hybridization conditions is hybridization in 6× sodium chloride/sodium citrate (SSC) at about 45° C., followed by at least one wash in 0.2×SSC/0.1% SDS at 50° C. Stringent hybridization conditions are also accomplished with wash(es) in, e.g., 0.2×SSC/0.1% SDS at 55° C., 60° C., or 65° C. Highly stringent conditions include, e.g., hybridization in 0.5M sodium phosphate/7% SDS at 65° C., followed by at least one wash at 0.2×SSC/1% SDS at 65° C. Further examples of stringency conditions are shown in Table 1 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 1

Hybridization Conditions

| Condition | Hybrid | Hybrid Length (bp)[1] | Hybridization Temperature and Buffer[2] | Wash Temperature and Buffer[2] |
|---|---|---|---|---|
| A | DNA:DNA | >50 | 65° C.; 1X SSC -or- 42° C.; 1X SSC, 50% formamide | 65° C.; 0.3X SSC |
| B | DNA:DNA | <50 | $T_B$*; 1X SSC | $T_B$*; 1X SSC |
| C | DNA:RNA | >50 | 67° C.; 1X SSC -or- 45° C.; 1X SSC, 50% formamide | 67° C.; 0.3X SSC |
| D | DNA:RNA | <50 | $T_D$*; 1X SSC | $T_D$*; 1X SSC |
| E | RNA:RNA | >50 | 70° C.; 1X SSC -or- 50° C.; 1X SSC, 50% formamide | 70° C.; 0.3X SSC |
| F | RNA:RNA | <50 | $T_F$*; 1X SSC | $T_F$*; 1X SSC |
| G | DNA:DNA | >50 | 65° C.; 4X SSC -or- 42° C.; 4X SSC, 50% formamide | 65° C.; 1X SSC |
| H | DNA:DNA | <50 | $T_H$*; 4X SSC | $T_H$*; 4X SSC |
| I | DNA:RNA | >50 | 67° C.; 4X SSC -or- 45° C.; 4X SSC, 50% formamide | 67° C.; 1X SSC |
| J | DNA:RNA | <50 | $T_J$*; 4X SSC | $T_J$*; 4X SSC |
| K | RNA:RNA | >50 | 70° C.; 4X SSC -or- 50° C.; 4X SSC, 50% formamide | 67° C.; 1X SSC |
| L | RNA:RNA | <50 | $T_L$*; 2X SSC | $T_L$*; 2X SSC |
| M | DNA:DNA | >50 | 50° C.; 4X SSC -or- 40° C.; 6X SSC, 50% formamide | 50° C.; 2X SSC |
| N | DNA:DNA | <50 | $T_N$*; 6X SSC | $T_N$*; 6X SSC |
| O | DNA:RNA | >50 | 55° C.; 4X SSC -or- 42° C.; 6X SSC, 50% formamide | 55° C.; 2X SSC |

TABLE 1-continued

Hybridization Conditions

| Condition | Hybrid | Hybrid Length (bp)[1] | Hybridization Temperature and Buffer[2] | Wash Temperature and Buffer[2] |
|---|---|---|---|---|
| P | DNA:RNA | <50 | $T_P$*; 6X SSC | $T_P$*; 6X SSC |
| Q | RNA:RNA | >50 | 60° C.; 4X SSC -or- 45° C.; 6X SSC, 50% formamide | 60° C.; 2X SSC |
| R | RNA:RNA | <50 | $T_R$*; 4X SSC | $T_R$*; 4X SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1xSSPE is 0.15M NaCl, 10 mM $NaH_2PO_4$, and 1.25 mM EDTA, pH 7.4) can be substituted for SSC (1xSSC is 0.15M NaCl and 15 mM sodium citrate) in the hybridization and wash buffers; washes are performed for 15 min after hybridization is complete.
$T_B$*-$T_R$* The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}Na^+$) + 0.41(% G + C) − (600/N), where N is the number of bases in the hybrid, and $Na^+$ is the concentration of sodium ions in the hybridization buffer ($Na^+$ for 1X SSC = 0.165 M).
Additional examples of stringency conditions for polynucleotide hybridization are provided in Sambrook et al. (1989) Molecular Cloning: A Laboratory Manual, Chs. 9 & 11, Cold Spring Harbor Laboratory Press, Cold Spring Harbor, NY, and Ausubel et al. eds. (1995) Current Protocols in Molecular Biology Sects. 2.10 & 6.3-6.4 John Wiley & Sons, Inc., herein incorporated by reference.

The isolated polynucleotides of the present invention may be used as hybridization probes and primers to identify and isolate DNAs having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least about 90% sequence identity (more preferably, at least about 95% identity; most preferably, at least about 99% identity) with the disclosed polynucleotides. The isolated polynucleotides of the present invention may also be used as hybridization probes and primers to identify and isolate DNAs having sequences encoding polypeptides homologous to the disclosed polynucleotides. These homologs are polynucleotides and polypeptides isolated from a different species than that of the disclosed polypeptides and polynucleotides, or within the same species, but with significant sequence similarity to the disclosed polynucleotides and polypeptides. Preferably, polynucleotide homologs have at least about 50% sequence identity (more preferably, at least about 75% identity; most preferably, at least about 90% identity) with the disclosed polynucleotides, whereas polypeptide homologs have at least about 30% sequence identity (more preferably, at least about 45% identity; most preferably, at least about 60% identity) with the disclosed binding proteins/polypeptides. Preferably, homologs of the disclosed polynucleotides and polypeptides are those isolated from mammalian species. The isolated polynucleotides of the present invention may additionally be used as hybridization probes and primers to identify cells and tissues that express the binding proteins of the present invention and the conditions under which they are expressed.

The phrases "substantially as set out," "substantially identical," and "substantially homologous" mean that the relevant amino acid or nucleotide sequence (e.g., CDR(s), $V_H$, or $V_L$ domain(s)) will be identical to or have insubstantial differences (e.g., through conserved amino acid substitutions) in comparison to the sequences which are set out. Insubstantial differences include minor amino acid changes, such as one or two substitutions in a five amino acid sequence of a specified region. In the case of antibodies, the second antibody has the same specificity and has at least about 50% of the affinity of the first antibody.

Sequences substantially identical or homologous to the sequences disclosed herein are also part of this application. In some embodiments, the sequence identity can be about 85%, 90%, 95%, 96%, 97%, 98%, 99%, or higher. Alternatively, substantial identity or homology exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

The term "therapeutic agent" or the like is a substance that treats or assists in treating a medical disorder or symptoms thereof. Therapeutic agents may include, but are not limited to, substances that modulate immune cells or immune responses in a manner that complements the use of anti-IL-21R binding proteins. In one embodiment of the invention, a therapeutic agent is a therapeutic antibody, e.g., an anti-IL-21R antibody. In another embodiment of the invention, a therapeutic agent is a therapeutic binding protein, e.g., an anti-IL-21R nanobody. Nonlimiting examples and uses of therapeutic agents are described herein.

As used herein, a "therapeutically effective amount" of an anti-IL-21R binding protein (e.g., an antibody) refers to an amount of the binding protein that is effective, upon single or multiple dose administration to a subject (such as a human patient) for treating, preventing, curing, delaying, reducing the severity of, and/or ameliorating at least one symptom of a disorder or a recurring disorder, or prolonging the survival of the subject beyond that expected in the absence of such treatment. In one embodiment, a therapeutically effective amount may be an amount of an anti-IL-21R binding protein that is sufficient to modulate expression of at least one IL-21-responsive cytokine or gene.

The term "treatment" refers to a therapeutic or preventative measure. The treatment may be administered to a subject having a medical disorder or who ultimately may acquire the disorder, in order to prevent, cure, delay, reduce the severity of, and/or ameliorate one or more symptoms of a disorder or a recurring disorder, or in order to prolong the survival of a subject beyond that expected in the absence of such treatment.

Anti-IL-21R Binding Proteins

The disclosure of the present application provides novel anti-IL-21R binding proteins that comprise novel antigen-binding fragments. Numerous methods known to those skilled in the art are available for obtaining binding proteins or antigen-binding fragments thereof. For example, anti-IL-21R binding proteins that comprise antibodies can be produced using recombinant DNA methods (see, e.g., U.S. Pat. No. 4,816,567). Monoclonal antibodies may also be produced by generation of hybridomas in accordance with known methods (see, e.g., Kohler and Milstein (1975) *Nature* 256:495-99). Hybridomas formed in this manner are then screened using standard methods, such as enzyme-linked immunosorbent assays (ELISA) and surface plasmon resonance (BIACORE™) analysis, to identify one or more hybridomas that produce an antibody that specifically binds with a particular antigen. Any form of the specified antigen may be used as the immunogen, e.g., recombinant antigen, naturally occurring forms, any variants or fragments thereof, and antigenic peptides thereof.

One exemplary method of making binding proteins that comprise antibodies includes screening protein expression libraries, e.g., phage or ribosome display libraries. Phage display is described, for example, in U.S. Pat. No. 5,223,409; Smith (1985) *Science* 228:1315-17; Clackson et al. (1991) *Nature* 352:624-28; Marks et al. (1991) *J. Mol. Biol.* 222:581-97; and International Application Publication Nos. WO 92/018619; WO 91/017271; WO 92/020791; WO 92/015679; WO 93/001288; WO 92/001047; WO 92/009690; and WO 90/002809.

In addition to the use of display libraries, the specified antigen can be used to immunize a nonhuman animal, e.g., a cynomolgus monkey, a chicken, or a rodent (e.g., a mouse, hamster, or rat). In one embodiment, the nonhuman animal includes at least a part of a human immunoglobulin gene. For example, it is possible to engineer mouse strains deficient in mouse antibody production with large fragments of the human Ig loci. Using the hybridoma technology, antigen-specific monoclonal binding proteins, such as antibodies, derived from the genes with the desired specificity may be produced and selected (see, e.g., XENOMOUSE™ (Amgen, Inc., Thousand Oaks, Calif.); Green et al. (1994) *Nat. Genet.* 7:13-21; U.S. Pat. No. 7,064,244; and International Application Publication Nos. WO 96/034096 and WO 96/033735).

In one embodiment of the invention, the binding proteins is a monoclonal antibody that is obtained from a nonhuman animal, and then modified (e.g., humanized, deimmunized, or chimeric) using recombinant DNA techniques known in the art. A variety of approaches for making chimeric antibodies have been described (see, e.g., Morrison et al. (1985) *Proc. Natl. Acad. Sci. USA* 81(21):6851-55; Takeda et al. (1985) *Nature* 314(6010):452-54; U.S. Pat. Nos. 4,816,567 and 4,816,397; European Application Publication Nos. EP 0 171 496 and EP 0 173 494; and United Kingdom Patent No. GB 2 177 096). Humanized binding proteins may also be produced, for example, using transgenic mice that express human heavy and light chain genes, but are incapable of expressing the endogenous mouse immunoglobulin heavy and light chain genes. Winter (U.S. Pat. No. 5,225,539) describes an exemplary CDR-grafting method that may be used to prepare the humanized binding proteins described herein. All of the CDRs of a particular human binding protein may be replaced with at least a portion of a nonhuman CDR, or only some of the CDRs may be replaced with nonhuman CDRs. It is only necessary to replace the number of CDRs required for binding of the humanized binding protein to a predetermined antigen.

Humanized binding proteins or fragments thereof can be generated by replacing sequences of the Fv variable domain that are not directly involved in antigen binding with equivalent sequences from human Fv variable domains. Exemplary methods for generating humanized binding proteins or fragments thereof are provided by, e.g., Morrison (1985) *Science* 229:1202-07; Oi et al. (1986) *BioTechniques* 4:214; and U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized binding protein is improved by the introduction of conservative substitutions, consensus sequence substitutions, germline substitutions and/or backmutations. Such altered immunoglobulin molecules can be made by any of several techniques known in the art, (see, e.g., Teng et al. (1983) *Proc. Natl. Acad. Sci. USA* 80:7308-73; Kozbor et al. (1983) *Immunol. Today* 4:7279; Olsson et al. (1982) *Meth. Enzymol.* 92:3-16); International Application Publication No. WO 92/006193; and European Patent No. EP 0 239 400).

A binding protein or fragment thereof may also be modified by specific deletion of human T cell epitopes or "deimmunization" by the methods disclosed in, e.g., International Application Publication Nos. WO 98/052976 and WO 00/034317. Briefly, the heavy and light chain variable domains of a binding protein (such as, for example, a binding protein derived from an antibody) can be analyzed for peptides that bind to MHC Class II; these peptides represent potential T cell epitopes (as defined in, e.g., International Application Publication Nos. WO 98/052976 and WO 00/034317). For detection of potential T cell epitopes, a computer modeling approach termed "peptide threading" can be applied, and in addition a database of human MHC class II binding peptides can be searched for motifs present in the $V_H$ and $V_L$ sequences, as described in International Application Publication Nos. WO 98/052976 and WO 00/034317. These motifs bind to any of the 18 major MHC Class II DR allotypes and thus, constitute potential T cell epitopes. Potential T cell epitopes detected can be eliminated by substituting small numbers of amino acid residues in the variable domains or by single amino acid substitutions. Typically, conservative substitutions are made. Often, but not exclusively, an amino acid common to a position in human germline antibody sequences may be used. Human germline sequences are disclosed in, e.g., Tomlinson et al. (1992) *J. Mol. Biol.* 227:776-98; Cook et al. (1995) *Immunol. Today* 16(5):237-42; Chothia et al. (1992) *J. Mol. Biol.* 227:799-817; and Tomlinson et al. (1995) *EMBO J.* 14:4628-38. The V BASE directory provides a comprehensive directory of human immunoglobulin variable region sequences (compiled by Tomlinson et al., MRC Centre for Protein Engineering, Cambridge, UK). These sequences can be used as a source of human sequence, e.g., for framework regions and CDRs. Consensus human framework regions can also be used, as described in, e.g., U.S. Pat. No. 6,300,064.

In certain embodiments, a binding protein can contain an altered immunoglobulin constant or Fc region. For example, binding proteins produced in accordance with the teachings herein may bind more strongly or with more specificity to effector molecules such as complement and/or Fc receptors, which can control several immune functions of the binding protein such as effector cell activity, lysis, complement-mediated activity, binding protein clearance, and binding protein half-life. Typical Fc receptors that bind to an Fc region of a binding protein (e.g., an IgG antibody) include, but are not limited to, receptors of the FcγRI, FcγRII, and FcRn subclasses, including allelic variants and alternatively spliced forms of these receptors. Fc receptors are reviewed in, e.g., Ravetch and Kinet (1991) *Annu. Rev. Immunol.* 9:457-92; Capel et al. (1994) *Immunomethods* 4:25-34; and de Haas et al. (1995) *J. Lab. Clin. Med.* 126:330-41. For additional binding protein/antibody production techniques, see, e.g., *Antibodies: A Laboratory Manual* (1988) Harlow et al. eds., Cold Spring Harbor Laboratory. The present invention is not necessarily limited to any particular source, method of production, or other special characteristic of a binding protein or an antibody.

Binding proteins comprising antibodies (immunoglobulins) are typically tetrameric glycosylated proteins composed of two light (L) chains of approximately 25 kDa each and two heavy (H) chains of approximately 50 kDa each. Two types of light chains, termed lambda (λ) and kappa (κ), may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2. Each light chain includes an N-terminal variable (V) domain ($V_L$) and a constant (C) domain ($C_L$). Each heavy chain includes an N-terminal V domain ($V_H$), three or four C domains ($C_H$s), and a hinge region. The $C_H$ domain most proximal to $V_H$ is designated as $C_H1$. The $V_H$ and $V_L$ domains consist of four regions of relatively conserved sequences called framework regions (FR1, FR2, FR3, and FR4) that form a scaffold for three regions of hypervariable sequences, called CDRs. The CDRs contain most of the residues responsible for specific interactions of the antibody with the antigen. CDRs are referred to as CDR1, CDR2, and CDR3. CDR constituents on the heavy chain are referred to as H1, H2, and H3 (also referred to herein as CDR H1, CDR H2, and CDR H3, respectively), while CDR constituents on the light chain are referred to as L1, L2, and L3 (also referred to herein as CDR L1, CDR L2, and CDR L3, respectively).

CDR3 is typically the greatest source of molecular diversity within the antigen-binding site. CDR H3, for example, can be as short as two amino acid residues or greater than 26 amino acids. The subunit structures and three-dimensional configurations of different classes of immunoglobulins are well known in the art. For a review of antibody structure, see, e.g., Harlow et al. (1988) supra. One of skill in the art will recognize that each subunit structure, e.g., a $C_H$, $V_H$, $C_L$, $V_L$, CDR, and/or FR structure, comprises active fragments, e.g., the portion of the $V_H$, $V_L$, or CDR subunit that binds to the antigen, i.e., the antigen-binding fragment, or, e.g., the portion of the $C_H$ subunit that binds to and/or activates, e.g., an Fc receptor and/or complement. The CDRs typically refer to the Kabat CDRs (as described in Kabat et al. (1991) supra). Another standard for characterizing the antigen-binding site is to refer to the hypervariable loops as described in, e.g., Chothia et al. (1992) supra and Tomlinson et al. (1995) supra. Still another standard is the "AbM" definition used by Oxford Molecular's AbM antibody modeling software (see, generally, e.g., *Protein Sequence and Structure Analysis of Antibody Variable Domains* in: *Antibody Engineering* (2001) Duebel and Kontermann eds., Springer-Verlag, Heidelberg). Embodiments described with respect to Kabat CDRs can alternatively be implemented using similar described relationships with respect to Chothia hypervariable loops or to the AbM-defined loops.

The Fab fragment consists of $V_H$-$C_H1$ and $V_L$-$C_L$ domains covalently linked by a disulfide bond between the constant regions. The $F_v$ fragment is smaller and consists of $V_H$ and $V_L$ domains noncovalently linked. To overcome the tendency of noncovalently linked domains to dissociate, an scFv can be constructed. The scFv contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide, for example, may be used as a linker, but other linkers are known in the art.

The sequence of antibody genes after assembly and somatic mutation is highly varied, and these varied genes are estimated to encode $10^{10}$ different antibody molecules (*Immunoglobulin Genes* (2nd ed. 1995) Jonio et al. eds., Academic Press, San Diego, Calif.).

In certain embodiments of the invention, the binding protein is a single domain binding protein. Single domain binding proteins include binding proteins wherein the CDRs are part of a single domain polypeptide. Examples include, but are not limited to, heavy chain binding proteins, binding proteins that are naturally devoid of light chains, single domain binding proteins derived from conventional four-chain antibodies, engineered binding proteins, and single domain protein scaffolds other than those derived from antibodies. Single domain binding proteins include any known in the art, as well as any future-determined or -learned single domain binding proteins.

Single domain binding proteins may be derived from any species including, but not limited to, mouse, human, camel, llama, fish, shark, goat, rabbit, chicken, and bovine. In one aspect of the invention, the single domain binding protein can be derived from a variable region of the immunoglobulin found in fish, such as, for example, that which is derived from the immunoglobulin isotype known as Novel Antigen Receptor (NAR) found in the serum of shark. Methods of producing single domain binding proteins derived from a variable region of NAR (IgNARs) are described in, e.g., International Application Publication No. WO 03/014161 and Streltsov (2005) *Protein Sci.* 14:2901-09. Single domain binding proteins also include naturally occurring single domain binding proteins known in the art as heavy chain antibodies devoid of light chains. This variable domain derived from a heavy chain antibody naturally devoid of a light chain is known herein as a VHH, or a nanobody, to distinguish it from the conventional $V_H$ of four-chain immunoglobulins. Such a VHH molecule can be derived from antibodies raised in Camelidae species, for example, in camel, llama, dromedary, alpaca, and guanaco, and is sometimes called a camelid or camelized variable domain (see, e.g., Muyldermans (2001) *J. Biotechnol.* 74(4): 277-302, incorporated herein by reference). Other species besides those in the family Camelidae may also produce heavy chain binding proteins naturally devoid of light chains. VHH molecules are about ten times smaller than IgG molecules. They are single polypeptides and are very stable, resisting extreme pH and temperature conditions. Moreover, they are resistant to the actions of proteases, which is not the case for conventional antibodies. Furthermore, in vitro expression of VHHs can produce high-yield, properly folded functional VHHs. In addition, binding proteins generated in camelids will recognize epitopes other than those recognized by antibodies generated in vitro via antibody libraries or via immunization of mammals other than camelids (see, e.g., International Application Publication Nos. WO 97/049805 and WO 94/004678, which are incorporated herein by reference).

A "bispecific" or "bifunctional" binding protein is an artificial hybrid binding protein having two different heavy/light chain pairs and two different binding sites. Bispecific binding proteins can be produced by a variety of methods including fusion of hybridomas or linking of Fab' fragments (see, e.g., Songsivilai and Lachmann (1990) *Clin. Exp. Immunol.* 79:315-21; Kostelny et al. (1992) *J. Immunol.* 148:1547-53). In one embodiment, the bispecific binding protein comprises a first binding domain polypeptide, such as a Fab' fragment, linked via an immunoglobulin constant region to a second binding domain polypeptide.

Another binding protein according to the invention can comprise, for example, a binding domain-immunoglobulin fusion protein that includes a binding domain polypeptide that is fused or otherwise connected to an immunoglobulin hinge or hinge-acting region polypeptide, which in turn is fused or otherwise connected to a region comprising one or more native or engineered constant regions from an immunoglobulin heavy chain, other than $C_H1$, for example, the $C_H2$ and $C_H3$ regions of IgG and IgA1 or the $C_H3$ and $C_H4$ regions of IgE (see, e.g., U.S. Application Publication No. 2005/0136049, which is incorporated by reference herein, for a more complete description). The binding domain-immunoglobulin fusion protein can further include a region that includes a native or engineered immunoglobulin heavy chain $C_H2$ constant region polypeptide (or $C_H3$ in the case of a construct derived in whole or in part from IgE) that is fused or otherwise connected to the hinge region polypeptide and a native or engineered immunoglobulin heavy chain $C_H3$ constant region polypeptide (or $C_H4$ in the case of a construct derived in whole or in part from IgE) that is fused or otherwise connected to the $C_H2$ constant region polypeptide (or $C_H3$ in the case of a construct derived in whole or in part from IgE). Typically, such binding domain-immunoglobulin fusion proteins are capable of at least one immunological activity selected from the group consisting of antibody-dependent cell-mediated cytotoxicity (ADCC), complement fixation, and/or binding to a target, for example, a target antigen, such as human IL-21R.

Binding proteins of the invention can also comprise peptide mimetics. Peptide mimetics are peptide-containing molecules that mimic elements of protein secondary structure (see, for example, Johnson et al. *Peptide Turn Mimetics in Biotechnology and Pharmacy* (1993), Pezzuto et al. eds., Chapman and Hall, New York, incorporated by reference herein in its entirety). The underlying rationale behind the use of peptide mimetics is that the peptide backbone of proteins exists chiefly to orient amino acid side chains in such a way as to facilitate molecular interactions, such as those between antibody and antigen. A peptide mimetic is expected to permit molecular interactions similar to the natural molecule. These principles may be used to engineer second generation molecules having many of the natural properties of the targeting peptides disclosed herein, but with altered and potentially improved characteristics.

Other embodiments of binding proteins useful for practicing the invention include fusion proteins. These molecules generally have all or a substantial portion of a targeting peptide, for example, IL-21R or an anti IL-21R antibody, linked at the N- or C-terminus, to all or a portion of a second polypeptide or protein. For example, fusion proteins may employ leader (or signal) sequences from other species to permit the recombinant expression of a protein in a heterologous host. For example, amino acid sequences, or nucleic acid sequences encoding amino acid sequences, of the binding proteins and antigen-binding fragments thereof of the present invention comprising leader (or signal) sequence may be selected from SEQ ID NOs:87-109 and 239-248. Another useful fusion includes the addition of an immunologically active domain, such as a binding protein epitope, to facilitate purification of the fusion protein. Inclusion of a cleavage site at or near the fusion junction will facilitate removal of the extraneous polypeptide after purification. Other useful fusions include the linking of functional domains, such as active sites from enzymes, glycosylation domains, cellular targeting signals, or transmembrane regions. Examples of proteins or peptides that may be incorporated into a fusion protein include, but are not limited to, cytostatic proteins, cytocidal proteins, pro-apoptosis agents, anti-angiogenic agents, hormones, cytokines, growth factors, peptide drugs, antibodies, Fab fragments of antibodies, antigens, receptor proteins, enzymes, lectins, MHC proteins, cell adhesion proteins, and binding proteins. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

In one embodiment, the targeting peptide, for example, IL-21R, is fused with an immunoglobulin heavy chain constant region, such as an Fc fragment, which contains two constant region domains and a hinge region, but lacks the variable region (see, e.g., U.S. Pat. Nos. 6,018,026 and 5,750, 375, incorporated by reference herein). The Fc region may be a naturally occurring Fc region, or may be altered to improve certain qualities, e.g., therapeutic qualities, circulation time, reduced aggregation. Peptides and proteins fused to an Fc region typically exhibit a greater half-life in vivo than the unfused counterpart does. In addition, a fusion to an Fc region permits dimerization/multimerization of the fusion polypeptide.

One aspect of the present invention comprises binding proteins and antigen-binding fragments thereof that bind IL-21R. The disclosure provides novel CDRs that have been derived from human immunoglobulin gene libraries. The protein structure that is generally used to carry a CDR is an antibody heavy or light chain or a portion thereof, wherein the CDR is localized to a region associated with a naturally occurring CDR. The structures and locations of variable domains may be determined as described in Kabat et al. ((1991) supra).

Illustrative embodiments of the binding proteins (and antigen-binding fragments thereof) of the invention are identified as AbA-AbU, H3-H6, L1-L6, L8-L21, and L23-L25. DNA and amino acid sequences of the nonlimiting illustrative embodiments of the anti-IL-21R binding proteins of the invention are set forth in SEQ ID NOs:5-195, 213-229, and 239-248. DNA and amino acid sequences of some illustrative embodiments of the anti-IL-21R binding proteins of the invention, including their scFv fragments, $V_H$ and $V_L$ domains, and CDRs, as well as their present codes and previous designations, are set forth in FIGS. 17-25, and Tables 2A and 2B.

TABLE 2A

Correlation of Present Antibody Codes and Previous Designations

| Present Code | Previous Designation |
|---|---|
| AbA | VHP/VL2 |
| AbB | VHP/VL3 |
| AbC | VHP/VL11 |
| AbD | VHP/VL13 |
| AbE | VHP/VL14 |
| AbF | VHP/VL17 |
| AbG | VHP/VL18 |
| AbH | VHP/VL19 |
| AbI | VHP/VL24 |
| AbJ | VH3/VLP |
| AbK | VH3/VL3 |
| AbL | VH3/VL13 |
| AbM | VH6/VL13 |
| AbN | VH6/VL24 |
| AbO | VHP/VL16; VHPTM/VL16 |
| AbP | VHP/VL20; VHPTM/VL20 |
| AbQ | VH3/VL2; VH3DM/VL2 |
| AbR | VH3/VL18; VH3DM/VL18 |
| AbS | VHP/VL6; VHPTM/VL6; VL6 |
| AbT | VHP/VL9; VHPTM/VL9; VL9 |
| AbU | VHP/VL25; VHPTM/VL25 |
| AbV | VH3TM/VL2 |
| AbW | VH3TM/VL18 |
| AbX | VHPDM/VL9 |
| AbY | VHPg4/VL9 |
| AbZ | VHPWT/VL9 |

TABLE 2B

Amino Acid and Nucleotide Sequences of $V_H$ and $V_L$ Domains, scFv, and CDRs of Illustrative Binding Proteins of the Invention

| REGION | TYPE | H3 SEQ ID | H4 SEQ ID | H5 SEQ ID | H6 SEQ ID | L1 SEQ ID |
|---|---|---|---|---|---|---|
| $V_H$ | AA | NO: 14 | NO: 16 | NO: 18 | NO: 20 | NO: 6 |
| $V_L$ | AA | NO: 10 | NO: 10 | NO: 10 | NO: 10 | NO: 22 |
| scFv | AA | NO: 110 | NO: 112 | NO: 114 | NO: 116 | NO: 118 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 165 | NO: 166 | NO: 167 | NO: 168 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 170 | NO: 170 | NO: 170 | NO: 170 | NO: 171 |
| $V_H$ | DNA | NO: 13 | NO: 15 | NO: 17 | NO: 19 | NO: 5 |
| $V_L$ | DNA | NO: 9 | NO: 9 | NO: 9 | NO: 9 | NO: 21 |
| scFv | DNA | NO: 109 | NO: 111 | NO: 113 | NO: 115 | NO: 117 |

| REGION | TYPE | L2 SEQ ID | L3 SEQ ID | L4 SEQ ID | L5 SEQ ID | L6 SEQ ID |
|---|---|---|---|---|---|---|
| $V_H$ | AA | NO: 6 | NO: 6 | NO: 6 | NO: 6 | NO: 6 |
| $V_L$ | AA | NO: 24 | NO: 26 | NO: 28 | NO: 30 | NO: 32 |
| scFv | AA | NO: 120 | NO: 122 | NO: 124 | NO: 126 | NO: 128 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 172 | NO: 173 | NO: 174 | NO: 175 | NO: 176 |
| $V_H$ | DNA | NO: 5 | NO: 5 | NO: 5 | NO: 5 | NO: 5 |
| $V_L$ | DNA | NO: 23 | NO: 25 | NO: 27 | NO: 29 | NO: 31 |
| scFv | DNA | NO: 119 | NO: 121 | NO: 123 | NO: 125 | NO: 127 |

| REGION | TYPE | L8 SEQ ID | L9 SEQ ID | L10 SEQ ID | L11 SEQ ID | L12 SEQ ID |
|---|---|---|---|---|---|---|
| $V_H$ | AA | NO: 6 | NO: 6 | NO6 | NO: 6 | NO: 6 |
| $V_L$ | AA | NO: 34 | NO: 36 | NO: 38 | NO: 40 | NO: 42 |
| scFv | AA | NO: 130 | NO: 132 | NO: 134 | NO: 136 | NO: 138 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 177 | NO: 178 | NO: 179 | NO: 180 | NO: 181 |
| $V_H$ | DNA | NO: 5 | NO: 5 | NO: 5 | NO: 5 | NO: 5 |
| $V_L$ | DNA | NO: 33 | NO: 35 | NO: 37 | NO: 39 | NO: 41 |
| scFv | DNA | NO: 129 | NO: 131 | NO: 133 | NO: 135 | NO: 137 |

| REGION | TYPE | L13 SEQ ID | L14 SEQ ID | L15 SEQ ID | L16 SEQ ID | L17 SEQ ID |
|---|---|---|---|---|---|---|
| $V_H$ | AA | NO: 6 | NO: 6 | NO: 6 | NO: 6 | NO: 6 |
| $V_L$ | AA | NO: 44 | NO: 46 | NO: 48 | NO: 50 | NO: 52 |
| scFv | AA | NO: 140 | NO: 142 | NO: 144 | NO: 146 | NO: 148 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 182 | NO: 183 | NO: 184 | NO: 185 | NO: 186 |
| $V_H$ | DNA | NO: 5 | NO: 5 | NO: 5 | NO: 5 | NO: 5 |
| $V_L$ | DNA | NO: 43 | NO: 45 | NO: 47 | NO: 49 | NO: 51 |
| scFv | DNA | NO: 139 | NO: 141 | NO: 143 | NO: 145 | NO: 147 |

| REGION | TYPE | L18 SEQ ID | L19 SEQ ID | L20 SEQ ID | L21 SEQ ID | L23 SEQ ID |
|---|---|---|---|---|---|---|
| $V_H$ | AA | NO: 6 | NO: 6 | NO: 6 | NO: 6 | NO: 6 |
| $V_L$ | AA | NO: 54 | NO: 56 | NO: 58 | NO: 60 | NO: 62 |
| scFv | AA | NO: 150 | NO: 152 | NO: 154 | NO: 156 | NO: 158 |
| CDR H1 | AA | NO: 163 | NO: 163 | NO: 163 | NO: 163 | NO: 163 |
| CDR H2 | AA | NO: 164 | NO: 164 | NO: 164 | NO: 164 | NO: 164 |
| CDR H3 | AA | NO: 169 | NO: 169 | NO: 169 | NO: 169 | NO: 169 |
| CDR L1 | AA | NO: 194 | NO: 194 | NO: 194 | NO: 194 | NO: 194 |
| CDR L2 | AA | NO: 195 | NO: 195 | NO: 195 | NO: 195 | NO: 195 |
| CDR L3 | AA | NO: 187 | NO: 188 | NO: 189 | NO: 190 | NO: 191 |
| $V_H$ | DNA | NO: 5 | NO: 5 | NO: 5 | NO: 5 | NO: 5 |
| $V_L$ | DNA | NO: 53 | NO: 55 | NO: 57 | NO: 59 | NO: 61 |
| scFv | DNA | NO: 149 | NO: 151 | NO: 153 | NO: 155 | NO: 157 |

TABLE 2B-continued

Amino Acid and Nucleotide Sequences of V$_H$ and V$_L$ Domains, scFv, and CDRs of Illustrative Binding Proteins of the Invention

| REGION | TYPE | L24 SEQ ID | L25 SEQ ID |
|---|---|---|---|
| V$_H$ | AA | NO: 6 | NO: 6 |
| V$_L$ | AA | NO: 64 | NO: 66 |
| scFv | AA | NO: 160 | NO: 162 |
| CDR H1 | AA | NO: 163 | NO: 163 |
| CDR H2 | AA | NO: 164 | NO: 164 |
| CDR H3 | AA | NO: 169 | NO: 169 |
| CDR L1 | AA | NO: 194 | NO: 194 |
| CDR L2 | AA | NO: 195 | NO: 195 |
| CDR L3 | AA | NO: 192 | NO: 193 |
| V$_H$ | DNA | NO: 5 | NO: 5 |
| V$_L$ | DNA | NO: 63 | NO: 65 |
| scFv | DNA | NO: 159 | NO: 161 |

Anti-IL-21R binding proteins of the present invention may comprise antibody constant regions or parts thereof. For example, a V$_L$ domain may be attached at its C-terminal end to a light chain constant domain like Cκ or Cλ. Similarly, a V$_H$ domain, or portion thereof, may be attached to all or part of a heavy chain like IgA, IgD, IgE, IgG, and IgM, and any isotype subclass. Constant regions are known in the art (see, e.g., Kabat et al. (1991) supra). Therefore, binding proteins within the scope of this invention include V$_H$ and V$_L$ domains, or portions thereof, combined with constant regions known in the art.

Certain embodiments comprise a V$_H$ domain, a V$_L$ domain, or a combination thereof, of the Fv fragment from AbA-AbZ, H3-H6, L1-L6, L8-L21, and/or L23-L25. Further embodiments comprise one, two, three, four, five or six CDRs from the V$_H$ and V$_L$ domains. Binding proteins whose CDR sequence(s) are the same as, or similar to (i.e., differ insubstantially from), one or more CDR sequence(s) present within the sequences set forth in SEQ ID NOs:5-195, 213-229, and 239-248 are encompassed within the scope of the invention.

In certain embodiments, the V$_H$ and/or V$_L$ domains may be germlined, i.e., the FR of these domains are mutated using conventional molecular biology techniques to match those produced by the germline cells. In other embodiments, the FR sequences remain diverged from the consensus germline sequences.

In one embodiment, mutagenesis is used to make a binding protein more similar to one or more germline sequences. This may be desirable when mutations are introduced into the FR of a binding protein (e.g., an antibody) through somatic mutagenesis or through error prone PCR. Germline sequences for the V$_H$ and V$_L$ domains can be identified by performing amino acid and nucleic acid sequence alignments against the VBASE database (MRC Center for Protein Engineering, UK). VBASE is a comprehensive directory of all human germline variable region sequences compiled from over a thousand published sequences, including those in the current releases of the GENBANK® and EMBL data libraries. In some embodiments, the FRs of scFvs are mutated in conformity with the closest matches in the VBASE database and the CDR portions are kept intact.

In certain embodiments, binding proteins of the invention specifically react with an epitope that is the same as the epitope recognized by AbA-AbZ, H3-H6, L1-L6, L8-L21, or L23-L25, such that they competitively inhibit the binding of AbA-AbZ, H3-H6, L1-L6, L8-L21, or L23-L25 to human IL-21R. Such binding proteins can be determined in competitive binding assays. In one embodiment, the association constant (K$_A$) of these binding proteins for human IL-21R is at least $10^5$ M$^{-1}$s$^{-1}$. The binding affinity may be determined using techniques known in the art, such as ELISA, biosensor technology (such as biospecific interaction analysis) or other techniques, including those described in this application.

It is contemplated that binding proteins of the invention may bind other proteins, such as, for example, recombinant proteins comprising all or a portion of IL-21R.

One of ordinary skill in the art will recognize that the disclosed binding proteins may be used to detect, measure, and/or inhibit proteins that differ somewhat from IL-21R. For example, these proteins may be homologs of IL-21R. Anti-IL-21R binding proteins are expected to bind proteins that comprise a sequence that is at least about 60%, 70%, 80%, 90%, 95%, or more identical to any sequence of at least 100, 80, 60, 40, or 20 contiguous amino acids in the sequence set forth SEQ ID NOs:2 or 4.

In addition to sequence homology analyses, epitope mapping (see, e.g., *Epitope Mapping Protocols* (1996) Morris ed., Humana Press), and secondary and tertiary structure analyses can be carried out to identify specific 3D structures assumed by the presently disclosed binding proteins and their complexes with antigens. Such methods include, but are not limited to, x-ray crystallography (Engstom (1974) *Biochem. Exp. Biol.* 11:7-13) and computer modeling of virtual representations of the present binding proteins (Fletterick et al. (1986) *Computer Graphics and Molecular Modeling, in Current Communications in Molecular Biology*, Cold Spring Harbor Laboratory, Cold Spring Harbor, N.Y.).

The disclosure provides a method for obtaining anti-IL-21R binding proteins. The method comprises creating binding proteins with V$_H$ and/or V$_L$ sequence(s) that are altered from those sequences disclosed herein. Such binding proteins may be derived by a skilled artisan using techniques known in the art. For example, amino acid substitutions, deletions, or additions can be introduced in FR and/or CDR regions. FR changes are usually designed to improve the stability and immunogenicity of the binding protein, while CDR changes are typically designed to increase a binding protein's affinity for its antigen. The changes that increase affinity may be tested by altering one or more CDR sequences and measuring the affinity of the binding protein for its target (see, e.g., *Antibody Engineering* (2nd ed. 1995) Borrebaeck ed., Oxford University Press).

Binding proteins whose CDR sequences differ insubstantially from those set forth in or included within the sequences of SEQ ID NOs:5-195, 213-229, and 239-248 are encompassed within the scope of this invention. Typically, such an insubstantial difference(s) involves substitution of an amino acid with an amino acid having similar charge, hydrophobicity, or stereochemical characteristics. More drastic substitutions in FR regions, in contrast to CDR regions, may also be made as long as they do not adversely affect (e.g., reduce affinity by more than 50% as compared to the unsubstituted binding protein) the binding properties of the binding protein. Substitutions may also be made to germline the binding protein or stabilize its antigen-binding site.

Conservative modifications will produce molecules having functional and chemical characteristics similar to those of the molecule from which such modifications are made. In contrast, substantial modifications in the functional and/or chemical characteristics of the molecules may be accomplished by selecting substitutions in the amino acid sequence that differ significantly in their effect on maintaining (1) the structure of the molecular backbone in the area of the substitution, for example, as a sheet or helical conformation, (2) the charge or hydrophobicity of the molecule at the target site, and/or (3) the size of the molecule.

For example, a "conservative amino acid substitution" may involve a substitution of a native amino acid residue with a normative residue such that there is little or no effect on the polarity or charge of the amino acid residue at that position (see, e.g., MacLennan et al. (1998) Acta Physiol. Scand. Suppl. 643:55-67; Sasaki et al. (1998) Adv. Biophys. 35:1-24).

Desired amino acid substitutions (whether conservative or nonconservative) can be determined by those skilled in the art at the time such substitutions are desired. For example, amino acid substitutions can be used to identify important residues of the molecule sequence, or to increase or decrease the affinity of the molecules described herein. Exemplary amino acid substitutions include, but are not limited to, those set forth in Table 3.

TABLE 3

Exemplary Amino Acid Substitutions

| Original Residues | Exemplary Substitutions | More Conservative Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-diamino-butyric acid, Gln, Asn | Arg |
| Met (M) | Leu, Phe, Ile | Leu |
| Phe (F) | Leu, Val, Ile, Ala, Tyr | Leu |
| Pro (P) | Ala, Gly | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

In certain embodiments, conservative amino acid substitutions also encompass nonnaturally occurring amino acid residues that are typically incorporated by chemical peptide synthesis rather than by synthesis in biological systems.

In one embodiment, the method for making a variant $V_H$ domain comprises adding, deleting, or substituting at least one amino acid in the disclosed $V_H$ domains, or combining the disclosed $V_H$ domains with at least one $V_L$ domain, and testing the variant $V_H$ domain for IL-21R binding or modulation of IL-21R/IL-21 activity.

An analogous method for making a variant $V_L$ domain comprises adding, deleting, or substituting at least one amino acid in the disclosed $V_L$ domains, or combining the disclosed $V_L$ domains with at least one $V_H$ domain, and testing the variant $V_L$ domain for IL-21R binding or modulation of IL-21R activity.

In some alternative embodiments, the anti-IL-21R binding proteins can be linked to a protein (e.g., albumin) by chemical cross-linking or recombinant methods. The disclosed binding proteins may also be linked to a variety of nonproteinaceous polymers (e.g., polyethylene glycol, polypropylene glycol, or polyoxyalkylenes) in manners set forth in U.S. Pat. Nos. 4,640,835; 4,496,689; 4,301,144; 4,670,417; 4,791,192; and 4,179,337. The binding proteins can be chemically modified by covalent conjugation to a polymer, for example, to increase their half-life in blood circulation. Exemplary polymers and attachment methods are shown in U.S. Pat. Nos. 4,766,106; 4,179,337; 4,495,285; and 4,609,546.

The disclosed binding proteins can be modified to alter their glycosylation; that is, at least one carbohydrate moiety can be deleted or added to the binding protein. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the binding protein, e.g., antibody (see, e.g., International Application Publication No. WO 87/05330 and Aplin et al. (1981) CRC Crit. Rev. Biochem. 22:259-306). Removal of carbohydrate moieties can also be accomplished chemically or enzymatically (see, e.g., Hakimuddin et al. (1987) Arch. Biochem. Biophys. 259:52; Edge et al. (1981) Anal. Biochem. 118:131; and Thotakura et al. (1987) Meth. Enzymol. 138:350). Modification of carbohydrate structures may be preferable as amino acid changes in the Fc domain may enhance immunogenicity of a pharmaceutical composition (see, e.g., International Application Publication No. WO 2008/052030). For immunoglobulin molecules it has been demonstrated that attachment of N-linked carbohydrate to Asn-297 of the CH2 domain is critical for ADCC activity. Its removal enzymatically or through mutation of the N-linked consensus site results in little to no ADCC activity. In glycoproteins, carbohydrates may attach to the amide nitrogen atom in the side chain of an asparagine in a tripeptide motif Asn-X-Thr/Ser. This type of glycosylation, termed N-linked glycosylation, commences in the endoplasmic reticulum (ER) with the addition of multiple monosaccharides to a dolichol phosphate to form a 14-residue branched carbohydrate complex. This carbohydrate complex is then transferred to the protein by the oligosaccharyltransferase (OST) complex. Before the glycoprotein leaves the lumen of the ER, three glucose molecules are removed from the 14-residue oligosaccharide. The enzymes ER glucosidase I, ER glucosidase II and ER mannosidase are involved in ER processing. Subsequently, the polypeptides are transported to the Golgi complex, where the N-linked sugar chains are modified in many different ways. In the cis and medial compartments of the Golgi complex, the original 14-saccharide N-linked complex may be trimmed through removal of mannose (Man) residues and elongated through addition of N-acetylglucosamine (GlcNac) and/or fucose (Fuc) residues. The various forms of N-linked carbohydrates generally have in common a pentasaccharide core consisting of three mannose and two N-acetylglucosamine residues. Finally, in the trans Golgi, other GlcNac residues can be added, followed by galactose (Gal) and a terminal sialic acid (Sial). Carbohydrate processing in the Golgi complex is called "terminal glycosylation" to distinguish it from "core glycosylation," which takes place in the ER. The final complex carbohydrate units can take on many forms and structures, some of which have two, three or four branches (termed biantennary, triantennary or tetraantennary). A number of enzymes are involved in Golgi processing, including Golgi mannosidases IA, IB and IC, GlcNAc-transferase I, Golgi mannosidase II, GlcNAc-transferase II, galactosyl transferase and sialyl transferase.

Methods for altering the constant region of a binding protein (such as, for example, the constant region of an antibody) are known in the art. Binding proteins with altered function (e.g., altered affinity for an effector ligand such as FcR on a cell or the C1 component of complement) can be produced by replacing at least one amino acid residue in the constant portion with a different residue (see, e.g., European Application Publication No. EP 0 388 151 and U.S. Pat. Nos. 5,624,821 and 5,648,260). Similar types of alterations could be described that, if applied to a murine or other species of binding protein, would reduce or eliminate similar functions.

For example, it is possible to alter the affinity of an Fc region of a binding protein (e.g., an IgG, such as a human IgG) for FcR (e.g., Fc gamma R1) or C1q. The affinity may be altered by replacing at least one specified residue with at least one residue having an appropriate functionality on its side chain, or by introducing a charged functional group, such as glutamate or aspartate, or perhaps an aromatic nonpolar residue such as phenylalanine, tyrosine, tryptophan or alanine (see, e.g., U.S. Pat. No. 5,624,821).

For example, replacing residue 297 (asparagine) with alanine in the IgG constant region significantly inhibits recruitment of effector cells, while only slightly reducing (about three-fold weaker) affinity for C1q (see, e.g., U.S. Pat. No. 5,624,821). The numbering of the residues in the heavy chain is that of the EU index (see Kabat et al. (1991) supra). This alteration destroys the glycosylation site, and it is believed that the presence of carbohydrate is required for Fc receptor binding. Any other substitution at this site that destroys the glycosylation site is believed to cause a similar decrease in lytic activity. Other amino acid substitutions, e.g., changing any one of residues 318 (Glu), 320 (Lys) and 322 (Lys), to Ala, are also known to abolish C1q binding to the Fc region of IgG antibodies (see, e.g., U.S. Pat. No. 5,624,821).

Modified binding proteins can be produced which have a reduced interaction with an Fc receptor. For example, it has been shown that in human IgG$_3$, which binds to the human Fc gamma R1 receptor, changing Leu 235 to Glu destroys its interaction with the receptor. Mutations on adjacent or close sites in the hinge link region of a binding protein (e.g., replacing residues 234, 235 and 237 with Ala) can also be used to affect binding protein affinity for the Fc gamma R1 receptor. The numbering of the residues in the heavy chain is based on the EU index (see Kabat et al. (1991) supra). Thus, in some embodiments of the invention, the Fc region of the binding proteins of the invention contains at least one constant region mutation, such as, for example, changing Leu to Ala at position 234 (L234A), changing Leu to Ala at position 235 (L235A), and/or changing Gly to Ala at position 237 (G237A). In one embodiment, the Fc region of the binding protein contains two constant region mutations, L234A and G237A (i.e., "double-mutant" or "DM"). In another embodiment, the Fc region of the binding protein contains three constant region mutations, L234A, L235A, and G237A (i.e., "triple-mutant" or "TM"). For example, a human IgG constant region triple-mutant is set forth in SEQ ID NO:196.

Additional methods for altering the lytic activity of a binding protein, for example, by altering at least one amino acid in the N-terminal region of the CH2 domain, are described in International Application Publication No. WO 94/029351 and U.S. Pat. No. 5,624,821.

The binding proteins of the invention can be tagged with a detectable or functional label. These labels include radiolabels (e.g., $^{131}$I and $^{99}$Tc), enzymatic labels (e.g., horseradish peroxidase and alkaline phosphatase), and other chemical moieties (e.g., biotin).

The invention may also feature an isolated binding protein or antigen-binding fragment thereof that binds to IL-21R, in particular, human IL-21R. In certain embodiments, the anti-IL-21R binding protein may have at least one of the following characteristics: (1) it is a monoclonal or single specificity binding protein; (2) it is a human binding protein; (3) it is an in vitro generated binding protein; (4) it is an in vivo generated binding protein (e.g., transgenic mouse system); (5) it inhibits the binding of IL-21 to IL-21R; (6) it is an IgG1; (7) it binds to human IL-21R with an association constant of at least about $10^5$ M$^{-1}$s$^{-1}$; (8) it binds to murine IL-21R with an association constant of at least about $5 \times 10^4$ M$^{-1}$s$^{-1}$; (9) it binds to human IL-21R with a dissociation constant of about $10^{-3}$ (1/s) or less; (10) it binds to murine IL-21R with a dissociation constant of about $10^{-2}$ (1/s) or less; (11) it inhibits human IL-21R-mediated proliferation of human IL-21R-expressing BaF3 cells with an IC$_{50}$ of about 1.75 nM or less; (12) it inhibits murine IL-21R-mediated proliferation of murine IL-21R-expressing BaF3 cells with an IC$_{50}$ of about 0.5 nM or less; (13) it inhibits human IL-21R-mediated proliferation of human IL-21R-expressing TF1 cells with an IC$_{50}$ of about 14.0 nM or less; (14) it inhibits IL-21-mediated proliferation of human primary B cells with an IC$_{50}$ of about 1.9 nM or less; (15) it inhibits IL-21-mediated proliferation of human primary CD4$^+$ T cells with an IC$_{50}$ of about 1.5 nM or less; (16) it inhibits IL-21-mediated proliferation of murine primary CD4$^+$ T cells with an IC$_{50}$ of about 5.0 nM or less; (17) it has a mean total body clearance of about 0.1-7.5 ml/hr/kg following, e.g., i.v. administration to animals, e.g., mammals, e.g., humans, nonhuman primates, rodents; (18) it has a mean elimination half-life of about 20-700 hr following, e.g., i.v., s.c., or i.p. administration to animals, e.g., mammals, e.g., humans, nonhuman primates, rodents; (19) it has a mean steady-state volume of distribution of about 40-1500 ml/kg in animals, e.g., mammals, e.g., humans, nonhuman primates, rodents; (20) it has a bioavailability of about 35-100% following, e.g., s.c. administration to animals, e.g., mammals, e.g., humans, nonhuman primates, rodents; (21) it has a mean dose-normalized AUC of about 200-10,000 μg*hr/mL (per 1 mg/kg dosage) following, e.g., i.v., s.c., or i.p. administration to animals, e.g., mammals, e.g., humans, nonhuman primates, rodents; (22) it has a mean dose-normalized Cmax (maximum serum concentration) of about 0.5-30 μg/ml following, e.g., i.v., s.c., or i.p. administration to animals, e.g., mammals, e.g., humans, nonhuman primates, rodents; and (23) it modulates expression of IL-21 responsive cytokines or IL-21 responsive genes.

One of skill in the art will appreciate that the modifications described above are not exhaustive, and that many other modifications will be obvious to a skilled artisan in light of the teachings of the present disclosure.

Nucleic Acids, Cloning and Expression Systems

The disclosure provides isolated nucleic acids encoding the disclosed binding proteins. The nucleic acids may comprise DNA or RNA, and they may be synthetic (completely or partially) or recombinant (completely or partially). Reference to a nucleotide sequence as set out herein encompasses a DNA molecule with the specified sequence, and encompasses an RNA molecule with the specified sequence in which U is substituted for T.

Also contemplated are nucleic acids that comprise a coding sequence for one, two, or three CDRs, a $V_H$ domain, a $V_L$ domain, or combinations thereof, as disclosed herein, or a sequence substantially identical thereto (e.g., a sequence at least 50%, 60%, 70%, 80%, 85%, 90%, 95%, 96%, 97%, 98%, 99% or higher identical thereto, or which is capable of hybridizing under stringent conditions to the sequences).

In one embodiment, the isolated nucleic acids have nucleotide sequences encoding heavy chain and light chain variable regions of an anti-IL-21R binding protein comprising at least one CDR chosen from the amino acid sequences of SEQ ID NOs:163-195, or a sequence encoding a CDR which differs by one or two or three or four amino acids from the sequences described herein.

The nucleic acid can encode only the light chain or the heavy chain variable region, or can encode a binding protein light or heavy chain constant region, operatively linked to the corresponding variable region. In one embodiment, the light chain variable region is linked to a constant region chosen from a kappa or a lambda constant region. The light chain constant region may also be a human kappa or lambda type. In another embodiment, the heavy chain variable region is linked to a heavy chain constant region of a binding protein isotype chosen from IgG (e.g., IgG1, IgG2, IgG3, and IgG4), IgM, IgA1, IgA2, IgD, and IgE. The heavy chain constant region may be an IgG (e.g., an IgG1) isotype.

The nucleic acid compositions of the present invention, while often in the native sequence (of cDNA or genomic DNA or mixtures thereof), except for modified restriction sites and the like, can be mutated in accordance with standard techniques to provide gene sequences. For coding sequences, these mutations, may affect amino acid sequences as desired. In particular, nucleotide sequences substantially identical to or derived from native V, D, J, constant, switches and other such sequences described herein are contemplated (where "derived" indicates that a sequence is identical to or modified from another sequence).

In one embodiment, the nucleic acid differs (e.g., differs by substitution, insertion, or deletion) from that of the sequences provided (e.g., by at least one but less than 10, 20, 30, or 40 nucleotides; at least one but less than 1%, 5%, 10% or 20% of the nucleotides in the subject nucleic acid). If necessary for this analysis the sequences should be aligned for maximum homology. "Looped" out sequences from deletions or insertions, or mismatches, are considered differences. The difference may be at a nucleotide(s) encoding a nonessential residue(s), or the difference may be a conservative substitution(s).

The disclosure also provides nucleic acid constructs in the form of plasmids, vectors, and transcription or expression cassettes, which comprise at least one nucleic acid as described herein.

The disclosure further provides a host cell that comprises at least one nucleic acid construct described herein.

Also provided is a method of making an encoded protein(s) from a nucleic acid(s) comprising the sequence(s) described herein. The method comprises culturing host cells under appropriate conditions so they express the protein from the nucleic acid. Following expression and production, the $V_H$ or $V_L$ domain, or specific binding member, may be isolated and/or purified using any suitable technique, and then used as appropriate. The method can also include the steps of fusing a nucleic acid encoding an scFv with nucleic acids encoding an Fc portion of a binding protein, and expressing the fused nucleic acid in a cell. The method can also include a step of germlining.

Antigen-binding fragments, $V_H$ and/or $V_L$ domains, and encoding nucleic acid molecules and vectors may be isolated and/or purified from their natural environment, in substantially pure or homogenous form, or, in the case of nucleic acids, free or substantially free of nucleic acids or genes of origin other than the sequence encoding a polypeptide with the require function.

Systems for cloning and expressing polypeptides in a variety of host cells are known in the art. Cells suitable for producing binding proteins are described in, for example, Fernandez et al. (1999) *Gene Expression Systems*, Academic Press. In brief, suitable host cells include mammalian cells, insect cells, plant cells, yeast cells, or prokaryotic cells, e.g., *E. coli*. Mammalian cells available in the art for heterologous polypeptide expression include lymphocytic cell lines (e.g., NSO), HEK293 cells, Chinese hamster ovary (CHO) cells, COS cells, HeLa cells, baby hamster kidney cells, oocyte cells, and cells from a transgenic animal, e.g., mammary epithelial cells. In other embodiments, the nucleic acids encoding the binding proteins of the invention are placed under the control of a tissue-specific promoter (e.g., a mammary-specific promoter) and the binding proteins are produced in transgenic animals. For example, the binding proteins are secreted into the milk of the transgenic animal, such as a transgenic cow, pig, horse, sheep, goat, or rodent.

Suitable vectors may be chosen or constructed to contain appropriate regulatory sequences, including promoter sequences, terminator sequences, polyadenylation sequences, enhancer sequences, marker genes, and other sequences. The vectors may also contain a plasmid or viral backbone. For details, see, e.g., Sambrook et al. *Molecular Cloning: A Laboratory Manual* (2nd ed. 1989), Cold Spring Harbor Laboratory Press. Many established techniques used with vectors, including the manipulation, preparation, mutagenesis, sequencing, and transfection of DNA, are described, e.g., in *Current Protocols in Molecular Biology* (2nd ed. 1992) Ausubel et al. eds., John Wiley & Sons.

A further aspect of the disclosure provides a method of introducing the nucleic acid into a host cell. For eukaryotic cells, suitable transfection techniques may include calcium phosphate, DEAE-Dextran, electroporation, liposome-mediated transfection, and transduction using a retrovirus or other virus(es), e.g., vaccinia or baculovirus. For bacterial cells, suitable techniques may include calcium chloride transformation, electroporation, and transfection using bacteriophage. DNA introduction may be followed by a selection method (e.g., drug resistance) to select cells that contain the nucleic acid.

Uses of Anti-IL-21R Binding Proteins

Anti-IL-21R binding proteins that act as antagonists to IL-21R (e.g., binding proteins, or antigen-binding fragments thereof, of the present invention) can be used to regulate at least one IL-21R-mediated immune response, such as one or more of cell proliferation, cytokine expression or secretion, chemokine secretion, and cytolytic activity, of T cells, B cells, NK cells, macrophages, or synovial cells. Accordingly, the binding proteins of the invention can be used to inhibit the activity (e.g., proliferation, differentiation, and/or survival) of an immune or hematopoietic cell (e.g., a cell of myeloid, lymphoid, or erythroid lineage, or precursor cells thereof), and, thus, can be used to treat a variety of immune disorders and hyperproliferative disorders of the blood. Examples of IL-21R-associated disorders/immune disorders that can be treated include, but are not limited to, transplant rejection, graft-versus-host disease (GVHD), allergies (for example, atopic allergy), and autoimmune diseases. Autoimmune diseases include, but are not limited to, diabetes mellitus, arthritic disorders (including rheumatoid arthritis, juvenile rheumatoid arthritis, osteoarthritis, psoriatic arthritis, and ankylosing spondylitis), spondyloarthropathy, multiple sclerosis, encephalomyelitis, myasthenia gravis, systemic lupus erythematosus (SLE), cutaneous lupus erythematosus, autoimmune thyroiditis, dermatitis (including atopic dermatitis and eczematous dermatitis), psoriasis, Sjögren's syndrome, IBD (including Crohn's disease and ulcerative colitis), asthma (including intrinsic asthma and allergic asthma), scleroderma and vasculitis. The binding proteins, or antigen-binding fragments thereof, of the present invention can be used in methods to treat or prevent IL-21R-associated disorders/immune disorders in subjects, e.g., in humans.

Multiple sclerosis is a central nervous system disease that is characterized by inflammation and loss of myelin sheaths (the fatty material that insulates nerves and is needed for proper nerve function). Inflammation that results from an immune response that is dependent on IL-21/IL-21R can be treated with the binding proteins and compositions of this invention. In the experimental autoimmune encephalitis (EAE) mouse model for multiple sclerosis (see, e.g., Tuohy et al. (1988) *J. Immunol.* 141:1126-30; Sobel et al. (1984) *J. Immunol.* 132:2393-401; and Traugott (1989) *Cell Immunol.* 119:114-29), treatment of mice with injections of an IL-21R antibody prior to (and continuously after) induction of EAE profoundly delayed the onset of the disease. The binding proteins, or antigen-binding fragments thereof, of the present invention can be used in methods to treat or prevent multiple sclerosis in subjects, e.g., in humans.

Arthritis is a disease characterized by inflammation in the joints. Rheumatoid arthritis (RA) is the most frequent form of arthritis, involving inflammation of connective tissue and the synovial membrane, a membrane that lines the joint. The inflamed synovial membrane often infiltrates the joint and damages joint cartilage and bone. Studies show that treatment of synovial cells and macrophages with IL-21 induces these cells to secrete cytokines and chemokines associated with inflammation. In the collagen-induced arthritis (CIA) mouse model for rheumatoid arthritis (see, e.g., Courtenay et al. (1980) *Nature* 283:666-28; and Williams et al. (1995) *Immunol.* 84:433-39), treatment of mice with IL-21 subsequent to CIA induction (and continuously) exacerbates the disease. Increased secretion of inflammatory cytokines and chemokines, and more importantly, increased levels of disease resulting from immune responses that are dependent on IL-21, may be treated with the binding proteins of the invention. Similarly, the binding proteins, or antigen-binding fragments thereof, of the present invention can be used in methods to treat or prevent RA or other arthritic diseases in subjects, e.g., in humans.

Transplant rejection is the immunological phenomenon where tissues from a donor are specifically "attacked" by immune cells of the host. The principle "attacking" cells are T cells, whose T cell receptors recognize the donor's MHC molecules as "foreign." This recognition activates the T cell, which proliferates and secretes a variety of cytokines and cytolytic proteins that ultimately destroy the transplant. T cells in a mixed lymphocyte reaction (MLR), an in vitro assay of transplant rejection, proliferate more strongly when supplemented with IL-21. MLR and transplantation models have been described in *Current Protocols in Immunology* (2nd ed. 1994) Coligan et al. eds., John Wiley & Sons (see also Kasaian et al. (2002) supra; Fulmer et al. (1963) *Am. J. Anat.* 113:273-85; and Lenschow et al. (1992) *Science* 257: 789-92). The binding proteins, or antigen-binding fragments thereof, of the present invention can be used in methods to reduce or prevent the MLR and/or to treat or prevent transplant rejection and related diseases (e.g., GVHD) that are dependent on IL-21 in subjects, e.g., in humans.

Systemic lupus erythematosus (SLE) is an autoimmune disease characterized by the presence of autoantibodies, including antibodies to DNA, nuclear antigens, and ribonucleoproteins. These autoantibodies are associated with tissue and organ damage. The cause of SLE is unknown, but the occurrence of autoantibodies suggests inadequate inhibition of autoreactive T cells or B cells. The binding proteins, or antigen-binding fragments thereof, of the present invention can be used in methods to inhibit the IL-21-mediated activities of autoreactive T cells and B cells and/or to treat or prevent SLE or related diseases in subjects, e.g., in humans or in MRL-Fas$^{lpr}$ mice (a mouse model for SLE) (*Immunologic Defects in Laboratory Animals* (1981) Gershwin et al. eds., Plenum Press).

The binding proteins, or antigen-binding fragments thereof, of the present invention also can be used in methods to treat or prevent hyperproliferative disorders of the blood that are associated with aberrant activity of IL-21-responsive cells and IL-21R-responsive cells in subjects, e.g., in humans. Examples of such cells include neoplastic cells of hematopoietic origin, e.g., cells arising from myeloid, lymphoid or erythroid lineages, or precursor cells thereof. Examples of such neoplastic disorders include leukemic cancers and tumors of the blood, bone marrow (e.g., myeloma), and lymph tissue (e.g., lymphomas). In certain embodiments, the present invention is directed to the treatment of various leukemic cancers including, but not limited to, acute promyeloid leukemia (APML), acute myelogenous leukemia (AML) and chronic myelogenous leukemia (CML) (reviewed in Vaickus (1991) *Crit. Rev. Oncol./Hemotol.* 11:267-97). Examples of lymphoid malignancies that may be treated by the present methods include, but are not limited to, acute lymphoblastic leukemia (ALL, which includes B-lineage ALL and T-lineage ALL), chronic lymphocytic leukemia (CLL), prolymphocytic leukemia (PLL), hairy cell leukemia (HCL), and Waldenstrom's macroglobulinemia (WM). Additional forms of malignant lymphomas that can be treated by the present invention include, but are not limited to, non-Hodgkin's lymphoma, peripheral T cell lymphomas, adult T cell leukemia/ lymphoma (ATL), cutaneous T cell lymphoma (CTCL), large granular lymphocytic leukemia (LGL), Hodgkin's lymphoma, and variants thereof.

In another aspect, the invention features a method of decreasing, inhibiting or reducing an acute phase response in a subject. An acute phase response is a response to inflammation, including the modulation of levels of acute phase proteins (e.g., C-reactive protein and serum albumin). The method includes administering to the subject an anti-IL-21R binding protein or antigen-binding fragment thereof as described herein, in an amount sufficient to decrease, inhibit or reduce the acute phase response in the subject. In one embodiment, the subject is a mammal, e.g., a human suffering from an IL-21R-associated disorder as described herein, including, e.g., respiratory disorders, inflammatory disorders and autoimmune disorders.

Combination Therapy

In one embodiment, a pharmaceutical composition comprising at least one anti-IL-21R binding protein or antigen-binding fragment thereof and at least one therapeutic agent is administered in combination therapy. The therapy is useful for treating pathological conditions or disorders, such as immune and inflammatory disorders. The term "in combination" in this context means that the binding protein composition and the therapeutic agent are given substantially contemporaneously, either simultaneously or sequentially. If given sequentially, at the onset of administration of the second compound, the first of the two compounds may still be detectable at effective concentrations at the site of treatment.

For example, the combination therapy can include at least one anti-IL-21R binding protein, such as, for example, an anti-IL-21R antibody, coformulated with, and/or coadministered with, at least one additional therapeutic agent. The additional agents may include at least one cytokine inhibitor, growth factor inhibitor, immunosuppressant, anti-inflammatory agent, metabolic inhibitor, enzyme inhibitor, cytotoxic agent, and/or cytostatic agent, as described in more detail below. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-21/IL-21R pathway, and thus are expected to enhance and/or synergize with the effects of the anti-IL-21R binding proteins.

Therapeutic agents used in combination with anti-IL-21R binding proteins may be those agents that interfere at different stages in the autoimmune and subsequent inflammatory response. In one embodiment, at least one anti-IL-21R binding protein described herein may be coformulated with, and/or coadministered with, at least one cytokine and/or growth factor antagonist. The antagonists may include soluble receptors, peptide inhibitors, small molecules, ligand fusions, antibodies (that bind cytokines or growth factors, or their receptors or other cell surface molecules), and "anti-inflammatory cytokines" and agonists thereof.

Examples of the agents that can be used in combination with the anti-IL-21R binding proteins described herein, include, but are not limited to, antagonists of at least one interleukin (e.g., IL-1, IL-2, IL-6, IL-7, IL-8, IL-12, IL-13, IL-15, IL-16, IL-17, IL-18, and IL-22), cytokine (e.g., TNF-α, LT, EMAP-II, and GM-CSF), or growth factor (e.g., FGF and PDGF). The agents may also include, but are not limited to, antagonists of at least one receptor for an interleukin, cytokine, or growth factor. Anti-IL-21R binding proteins can also be combined with inhibitors (e.g., antibodies) to cell surface molecules such as CD2, CD3, CD4, CD8, CD25, CD28, CD30, CD40, CD45, CD69, CD80 (B7.1), CD86 (B7.2), CD90, or their ligands (e.g., CD154 (gp39, CD40L)), or LFA-1/ICAM-1 or VLA-4/VCAM-1 (see Yusuf-Makagiansar et al. (2002) *Med. Res. Rev.* 22(2):146-67)). Antagonists that can be used in combination with anti-IL-21R binding proteins described herein may include antagonists of IL-1, IL-12, TNF-α, IL-15, IL-17, IL-18, IL-22, and their receptors.

Examples of IL-12 antagonists include antibodies that bind IL-12 (see, e.g., International Application Publication No. WO 00/056772); IL-12 receptor inhibitors (e.g., antibodies to the IL-12 receptor), and soluble IL-12 receptor and fragments thereof. Examples of IL-15 antagonists include antibodies against IL-15 or its receptor, soluble fragments of the IL-15 receptor, and IL-15-binding proteins. Examples of IL-18 antagonists include antibodies to IL-18, soluble fragments of the IL-18 receptor, and IL-18 binding proteins (IL-18BP, Mallet et al. (2001) *Circ. Res.* 28). Examples of IL-1 antagonists include Interleukin-1-Converting Enzyme (ICE) inhibitors (such as Vx740), IL-1 antagonists (e.g., IL-IRA (anakinra, Amgen)), sIL-IRII (Immunex), and anti-IL-1 receptor antibodies.

Examples of TNF antagonists include antibodies to TNF (e.g., human TNF-α), such as D2E7 (human anti-TNF-α antibody, U.S. Pat. No. 6,258,562, HUMIRA™, BASF, Parsippany, N.J.), CDP-571/CDP-870/BAY-10-3356 (humanized anti-TNF-α antibodies, Celltech/Pharmacia), cA2 (chimeric anti-TNF-α antibody, REMICADE™, Centocor), and anti-TNF antibody fragments (e.g., CPD870). Other examples include soluble TNF receptor (e.g., human p55 or p75) fragments and derivatives, such as p55 kdTNFR-IgG (55 kD TNF receptor-IgG fusion protein, LENERCEPT™) and 75 kdTNFR-IgG (75 kD TNF receptor-IgG fusion protein, ENBREL™, Immunex; see, e.g., *Arthritis Rheumatism* (1994) 37:S295 and *J. Invest. Med.* (1996) 44:235A). Further examples include enzyme antagonists (e.g., TNF-α converting enzyme inhibitors (TACE) such as alpha-sulfonyl hydroxamic acid derivative (WO 01/055112) or N-hydroxyformamide inhibitor (GW 3333, -005, or -022)) and TNF-bp/s-TNFR (soluble TNF binding protein; see, e.g., *Arthritis Rheumatism* (1996) 39(9):S284 and *Am. J. Physiol. Heart Circ. Physiol.* (1995) 268:37-42).

In other embodiments, the anti-IL-21R binding proteins described herein can be administered in combination with at least one of the following: IL-13 antagonists, such as soluble IL-13 receptors and/or anti-IL-13 antibodies; and IL-2 antagonists, such as IL-2 fusion proteins (e.g., DAB 486-IL-2 and/or DAB 389-IL-2, Seragen (see, e.g., *Arthritis Rheumatism* (1993) 36:1223)) and anti-IL-2R antibodies (e.g., anti-Tac (humanized antibody, Protein Design Labs (see *Cancer Res.* (1990) 50(5): 1495-502))). Another combination includes anti-IL-21R binding proteins in combination with nondepleting anti-CD4 inhibitors such as IDEC-CE9.1/SB 210396 (anti-CD4 antibody, IDEC/SmithKline). Yet other combinations include anti-IL-21R binding proteins with CD80 (B7.1) and CD86 (B7.2) costimulatory pathway antagonists (such as antibodies, soluble receptors, or antagonistic ligands), P-selectin glycoprotein ligand (PSGL), and/or anti-inflammatory cytokines and agonists thereof (e.g., antibodies). The anti-inflammatory cytokines may include IL-4 (DNAX/Schering, Palo Alto, Calif.), IL-10 (SCH 52000, recombinant IL-10, DNAX/Schering), IL-13, and TGF.

In other embodiments, at least one anti-IL-21R binding protein can be coformulated with, and/or coadministered with, at least one anti-inflammatory drug, immunosuppressant, metabolic inhibitor, and enzymatic inhibitor. Nonlimiting examples of the drugs or inhibitors that can be used in combination with the IL-21R binding proteins described herein, include, but are not limited to, at least one of: nonsteroidal anti-inflammatory drugs (NSAID) (such as ibuprofen, tenidap (see, e.g., *Arthritis Rheumatism* (1996) 39(9):S280), naproxen (see, e.g., *NeuroReport* (1996) 7:1209-13), meloxicam, piroxicam, diclofenac, and indomethacin); sulfasalazine (see, e.g., *Arthritis Rheumatism* (1996) 39(9):S281)); corticosteroids (such as prednisolone); cytokine suppressive anti-inflammatory drugs (CSAID); and inhibitors of nucleotide biosynthesis (such as an inhibitor of purine biosynthesis (e.g., a folate antagonist such as methotrexate) and an inhibitor of pyrimidine biosynthesis (e.g., a dihydroorotate dehydrogenase (DHODH) inhibitor such as leflunomide (see, e.g., *Arthritis Rheumatism* (1996) 39(9):S131 and *Inflammation Research* (1996) 45:103-7)).

Examples of additional inhibitors include at least one of: corticosteroids (oral, inhaled and local injection); immunosuppressants (such as cyclosporin and tacrolimus (FK-506)); mTOR inhibitors (such as sirolimus (rapamycin) or a rapamycin derivative (e.g., an ester rapamycin derivative such as CCI-779 (see Elit (2002) *Current Opinion Investig. Drugs* 3(8):1249-53 and Huang et al. (2002) *Current Opinion Inves-*

*tig. Drugs* 3(2):295-304))); agents which interfere with the signaling of proinflammatory cytokines such as TNF-α and IL-1 (e.g., IRAK, NIK, IKK, p38, or a MAP kinase inhibitor); cox2 inhibitors (e.g., celecoxib and variants thereof (MK-966); see, e.g., *Arthritis Rheumatism* (1996) 39(9):S81); phosphodiesterase inhibitors (such as R973401; see, e.g., *Arthritis Rheumatism* (1996) 39(9):S282); phospholipase inhibitors (e.g., an inhibitor of cytosolic phospholipase 2 (cPLA2) such as trifluoromethyl ketone analogs; see U.S. Pat. No. 6,350,892); inhibitors of vascular endothelial cell growth factor (VEGF); inhibitors of the VEGF receptor; and inhibitors of angiogenesis.

The anti-IL-21R binding proteins disclosed herein can be used in combination with other therapeutic agents to treat specific immune disorders as discussed in further detail below.

Nonlimiting examples of agents for treating arthritic disorders (e.g., rheumatoid arthritis, inflammatory arthritis, rheumatoid arthritis, juvenile rheumatoid arthritis, osteoarthritis and psoriatic arthritis), with which an anti-IL-21R binding protein can be combined include at least one of the following: TNF antagonists (such as anti-TNF antibodies); soluble fragments of TNF receptors (e.g., human p55 and p75) and derivatives thereof (such as p55 kdTNFR-IgG (55 kD TNF receptor-IgG fusion protein, LENERCEPT™) and 75 kdTNFR-IgG (75 kD TNF receptor-IgG fusion protein, ENBREL™)); TNF enzyme antagonists (such as TACE inhibitors); antagonists of IL-12, IL-15, IL-17, IL-18, and IL-22; T cell- and B cell-depleting agents (such as anti-CD4 or anti-CD22 antibodies); small molecule inhibitors (such as methotrexate and leflunomide); sirolimus (rapamycin) and analogs thereof (e.g., CCI-779); cox2 and cPLA2 inhibitors; NSAIDs; p38, TPL-2, Mk-2, and NFκB inhibitors; RAGE or soluble RAGE; P-selectin or PSGL-1 inhibitors (such as antibodies thereto and small molecule inhibitors); estrogen receptor beta (ERB) agonists; and ERB-NFκB antagonists. Therapeutic agents that can be coadministered and/or coformulated with at least one IL-21/IL-21R antagonist may include at least one of: a soluble fragment of a TNF receptor (e.g., human p55 or p75) such as 75 kdTNFR-IgG (75 kD TNF receptor-IgG fusion protein, ENBREL™); methotrexate; leflunomide; and sirolimus (rapamycin) or an analog thereof (e.g., CCI-779).

Nonlimiting examples of agents for treating multiple sclerosis with which an anti-IL-21R binding protein can be combined include interferon-β (for example, IFNβ-1a and IFNβ-1b), copaxone, corticosteroids, IL-1 inhibitors, TNF inhibitors, antibodies to CD40 ligand, antibodies to CD80, and IL-12 antagonists.

Nonlimiting examples of agents for treating inflammatory bowel disease or Crohn's disease with which an anti-IL-21R binding protein can be combined include at least one of the following: budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13, and/or TGFβ or agonists thereof (e.g., agonistic antibodies); IL-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In other embodiments, an anti-IL-21R binding protein can be used in combination with at least one antibody directed at other targets involved in regulating immune responses, e.g., transplant rejection or GVHD. Nonlimiting examples of agents for treating immune responses with which an IL-21/IL-21R antagonist can be combined include the following antibodies against cell surface molecules (e.g., CD25 (IL-2 receptor α), CD11a (LFA-1), CD54 (ICAM-1), CD4, CD45, CD28/CTLA4, CD80 (B7-1), CD86 (B7-2), or combinations thereof). In another embodiment, an anti-IL-21R binding protein is used in combination with at least one general immunosuppressive agent, such as cyclosporin A or FK506.

Another aspect of the present invention relates to kits for carrying out the combined administration of anti-IL-21R binding proteins with other therapeutic agents. In one embodiment, the kit comprises at least one anti-IL-21R binding protein formulated in a pharmaceutical carrier, and at least one therapeutic agent, formulated as appropriate in one or more separate pharmaceutical preparations.

Diagnostic Uses

The binding proteins of the invention may also be used to detect the presence of IL-21R in biological samples. By correlating the presence or level of these proteins with a medical condition, one of skill in the art can diagnose the associated medical condition. For example, stimulated T cells increase their expression of IL-21R, and an unusually high concentration of IL-21R expressing T cells in joints may indicate joint inflammation and possible arthritis. Illustrative medical conditions that may be diagnosed by the binding proteins of this invention include, but are not limited to, multiple sclerosis, rheumatoid arthritis, and transplant rejection.

Binding protein-based detection methods, such as those commonly used for antibodies, are well known in the art, and include ELISA, radioimmunoassays, immunoblots, Western blots, flow cytometry, immunofluorescence, immunoprecipitation, and other related techniques. The binding proteins may be provided in a diagnostic kit that incorporates at least one of these procedures to detect IL-21R. The kit may contain other components, packaging, instructions, reagents, and/or other material to aid the detection of the protein and use of the kit.

Binding proteins may be modified with detectable markers, including ligand groups (e.g., biotin), fluorophores, chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

Binding proteins can also be functionally linked (e.g., by chemical coupling, genetic fusion, noncovalent association, or otherwise) to at least one other molecular entity, such as another binding protein (e.g., a bispecific or a multispecific binding protein), toxins, radioisotopes, cytotoxic or cytostatic agents, among others. Other permutations and possibilities are apparent to those of ordinary skill in the art, and they are considered equivalents within the scope of this invention.

Pharmaceutical Compositions and Methods of Administration

Certain embodiments of the invention include compositions comprising the disclosed binding proteins. The compositions may be suitable for pharmaceutical use and administration to patients. The compositions comprise a binding protein of the present invention and a pharmaceutical excipient. As used herein, "pharmaceutical excipient" includes solvents, dispersion media, coatings, antibacterial and antifungal agents, isotonic and absorption delaying agents, etc., that are compatible with pharmaceutical administration. Use of these agents for pharmaceutically active substances is well known in the art. The compositions may also contain other active compounds providing supplemental, additional, or enhanced therapeutic functions. The pharmaceutical compositions may also be included in a container, pack, or dispenser, together with instructions for administration.

A pharmaceutical composition of the invention is formulated to be compatible with its intended route of administration. Methods to accomplish the administration are known to those of ordinary skill in the art. Pharmaceutical compositions may be topically or orally administered, or capable of transmission across mucous membranes. Examples of administration of a pharmaceutical composition include oral ingestion or inhalation. Administration may also be intravenous, intraperitoneal, intramuscular, intracavity, subcutaneous, cutaneous, or transdermal.

Solutions or suspensions used for intradermal or subcutaneous application typically include at least one of the following components: a sterile diluent such as water, saline solution, fixed oils, polyethylene glycol, glycerine, propylene glycol, or other synthetic solvent; antibacterial agents such as benzyl alcohol or methyl parabens; antioxidants such as ascorbic acid or sodium bisulfite; chelating agents such as ethylenediaminetetraacetic acid (EDTA); buffers such as acetate, citrate, or phosphate; and tonicity agents such as sodium chloride or dextrose. The pH can be adjusted with acids or bases by methods known in the art. Such preparations may be enclosed in ampoules, disposable syringes, or multiple dose vials.

Solutions or suspensions used for intravenous administration include a carrier such as physiological saline, bacteriostatic water, CREMOPHOR EL® (BASF Corp., Ludwigshafen, Germany), ethanol, or polyol. In all cases, the composition must be sterile and fluid for easy syringability. Proper fluidity can often be obtained using lecithin or surfactants. The composition must also be stable under the conditions of manufacture and storage. Prevention of microorganisms can be achieved with antibacterial and antifungal agents, e.g., parabens, chlorobutanol, phenol, ascorbic acid, thimerosal, etc. In many cases, isotonic agents (sugar), polyalcohols (e.g., mannitol and sorbitol), or sodium chloride may be included in the composition. Prolonged absorption of the composition can be accomplished by adding an agent that delays absorption, e.g., aluminum monostearate or gelatin.

Oral compositions include an inert diluent or edible carrier. For the purpose of oral administration, the binding proteins can be incorporated with excipients and placed, e.g., in tablets, troches, capsules, or gelatin. Pharmaceutically compatible binding agents or adjuvant materials can be included in the composition. The compositions may contain (1) a binder such as microcrystalline cellulose, gum tragacanth or gelatin; (2) an excipient such as starch or lactose, (3) a disintegrating agent such as alginic acid, Primogel, or corn starch; (4) a lubricant such as magnesium stearate; (5) a glidant such as colloidal silicon dioxide; and/or (6) a sweetening or flavoring agent.

The composition may also be administered by a transmucosal or transdermal route. For example, binding proteins that comprise an Fc portion (for example, an antibody) may be capable of crossing mucous membranes in the intestine, mouth, or lungs (via Fc receptors). Transmucosal administration can be accomplished by lozenges, nasal sprays, inhalers, or suppositories. Transdermal administration can be accomplished with a composition containing ointments, salves, gels, or creams known in the art. For transmucosal or transdermal administration, penetrants appropriate to the barrier to be permeated are used. For administration by inhalation, the binding proteins may be delivered in an aerosol spray from a pressured container or dispenser, which contains a propellant (e.g., liquid or gas), or a nebulizer.

In certain embodiments, the binding proteins of this invention are prepared with carriers to protect the binding proteins against rapid elimination from the body. Biodegradable polymers (e.g., ethylene vinyl acetate, polyanhydrides, polyglycolic acid, collagen, polyorthoesters, and polylactic acid) are often used. Methods for the preparation of such formulations are known by those skilled in the art. Liposomal suspensions can be used as pharmaceutically acceptable carriers also. The liposomes can be prepared according to established methods known in the art (see, e.g., U.S. Pat. No. 4,522,811).

The binding proteins or binding protein compositions of the invention are administered in therapeutically effective amounts as described. Therapeutically effective amounts may vary with the subject's age, condition, sex, and severity of medical condition. Appropriate dosages can be determined by a physician based upon clinical indications. The binding proteins or compositions may be given as a bolus dose to maximize the circulating levels of binding proteins for the greatest length of time. Continuous infusion may also be used.

As used herein, the term "subject" is intended to include human and nonhuman animals. Subjects may include a human patient having a disorder characterized by cells that express IL-21R, e.g., a cancer cell or an immune cell. The term "nonhuman animals" of the invention includes all vertebrates, such as nonhuman primates, sheep, dogs, cows, chickens, amphibians, reptiles, etc.

Examples of dosage ranges that can be administered to a subject can be chosen from: 1 µg/kg to 20 mg/kg, 1 µg/kg to 10 mg/kg, 1 µg/kg to 1 mg/kg, 10 µg/kg to 1 mg/kg, 10 µg/kg to 100 µg/kg, 100 µg/kg to 1 mg/kg, 250 µg/kg to 2 mg/kg, 250 µg/kg to 1 mg/kg, 500 µg/kg to 2 mg/kg, 500 µg/kg to 1 mg/kg, 1 mg/kg to 2 mg/kg, 1 mg/kg to 5 mg/kg, 5 mg/kg to 10 mg/kg, 10 mg/kg to 20 mg/kg, 15 mg/kg to 20 mg/kg, 10 mg/kg to 25 mg/kg, 15 mg/kg to 25 mg/kg, 20 mg/kg to 25 mg/kg, and 20 mg/kg to 30 mg/kg (or higher). These dosages may be administered daily, weekly, biweekly, monthly, or less frequently, for example, biannually, depending on dosage, method of administration, disorder or symptom(s) to be treated, and individual subject characteristics.

In certain circumstances, it may be advantageous to formulate compositions in dosage unit form for ease of administration and uniformity of dosage. Dosage unit form as used herein refers to physically discrete units suited for the patient. Each dosage unit contains a predetermined quantity of binding protein calculated to produce a therapeutic effect in association with the carrier. The dosage unit depends on the characteristics of the binding protein and the particular therapeutic effect to be achieved.

Toxicity and therapeutic efficacy of the composition can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Binding proteins that exhibit large therapeutic indices may be less toxic and/or more therapeutically effective.

The data obtained from the cell culture assays and animal studies can be used to formulate a dosage range in humans. The dosage of these compounds may lie within the range of circulating binding protein concentrations in the blood, which includes an $ED_{50}$ with little or no toxicity. The dosage may vary within this range depending upon the dosage composition form employed and the route of administration. For any binding protein used in the present invention, the therapeutically effective dose can be estimated initially using cell culture assays. A dose may be formulated in animal models to achieve a circulating plasma concentration range that includes the $IC_{50}$ (i.e., the concentration of binding protein that achieves a half-maximal inhibition of symptoms). The effects of any particular dosage can be monitored by a suitable bioassay. Examples of suitable bioassays include DNA replication assays, transcription-based assays, gene expression assays, IL-21/IL-21R binding assays, and other immunological assays.

In one embodiment of the invention, a dose may be formulated in an ex vivo whole blood cell assay. In such embodiment, a suitable bioassay for determining and monitoring a particular dosage includes a method of determining a minimum serum concentration of an anti-IL-21R binding protein necessary to inhibit or reduce IL-21R activity, such as modulation of expression of IL-21-responsive genes. In one embodiment of the invention, the IL-21-responsive gene is selected from the following nonlimiting list: TNF, IFNγ, IL-6, IL-8, IL-10, CD19, STAT3, TBX21, CSF1, GZMB, PRF1, IL-2Rα, and IL-21R. In a preferred embodiment, the IL-21-responsive gene is selected from CD19, GZMB, IFNγ, IL-2Rα, IL6, and PRF-1. In a most preferred embodiment, the IL-21-responsive gene is IL-2Rα. Thus, the method of determining a minimum serum concentration of an anti-IL-21R antibody necessary to inhibit or reduce IL-21R activity may include determining a level of expression of more than one IL-21-responsive gene, e.g., two, three, four, five, or six IL-21-responsive genes.

The entire contents of all references, patent applications, and patents cited throughout this application are hereby incorporated by reference herein.

EXAMPLES

The invention will be further illustrated in the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art.

Example 1

Generation of Binding Proteins by Phage Display

The scFv parental clone 18A5, described in U.S. Pat. No. 7,495,085 (incorporated by reference herein), was obtained from the CS human scFv library by standard phage display methods, using BaF3 cells expressing human IL-21R as a target in rounds 1 and 3 and biotinylated IL-21R-Fc fusion protein as a target in round 2.

Example 2

Library Construction

Phage display libraries were based upon the parental 18A5 scFv, using a pCANTAB6 vector in which the scFv was fused at its 3' end to the intact gene III. Various CDR3 sequences were derived using techniques well known in the art.

Two overlapping blocks of six consecutive codons were randomized in the CDR3 of the $V_H$ and the $V_L$, producing a total of four libraries: H3B1, H3B2, L3B1, and L3B2. The following identify nucleotide and amino acid sequences, respectively: IL-21R: 18A5 $V_H$CDR3 [SEQ ID NOs:199 and 200]; H3B1 (library size $1.40 \times 10^9$) [SEQ ID NOs:201 and 202]; H3B2 (library size $1.00 \times 10^9$) [SEQ ID NOs:203 and 204]; IL-21R: 18A5 $V_L$CDR3 [SEQ ID NOs:205 and 206]; L3B1 (library size $9.00 \times 10^9$) [SEQ ID NOs:207 and 208]; L3B2 (library size $6.40 \times 10^9$) [SEQ ID NOs:209 and 210].

Example 3

Phage Selection

All derivatives of 18A5 were isolated from the scFv libraries above by selection of phage able to bind in solution phase to biotinylated human IL-21R extracellular domain His-Flag fusion proteins ("biotin-hIL-21R-H/F") and biotinylated murine IL-21R extracellular domain His-Flag fusion proteins ("biotin-mIL-21R-H/F"); all procedures and techniques related to selection are well known to one of skill in the art. A total of twenty-seven anti-IL-21R scFv were isolated by phage selection procedures.

Example 4

Library Screening

Resulting binding proteins in scFv format were chosen based on their ability to compete with parental 18A5 in human IgG1 format for binding to biotin-hIL-21R-H/F and biotin-mIL-21R-H/F, to prevent the hIL-21-dependent proliferation of genetically engineered cell lines expressing human IL-21R and the mIL-21-dependent proliferation of genetically engineered cell lines expressing murine IL-21R.

Example 4.1

Preparation of Crude Periplasmic Material ("Peri-Preps") for Use in Screening Assays Depending on the growth conditions used, scFv can be expressed in solution in the bacterial periplasmic space. To induce release of scFv into the periplasm, 96-deep-well plates containing 990 μl 2×TY media with 0.1% glucose/100 μg/ml ampicillin were inoculated from thawed glycerol stocks (one clone per well) using the QPix2 Colony picker (Genetix, New Milton, England) and grown at 37° C. (999 rpm) for about 4 hr. Cultures were induced with IPTG at a final concentration of 0.02 mM and grown overnight at 30° C. (999 rpm). The contents of the bacterial periplasm (peri-preps) were released by osmotic shock. Briefly, plates were centrifuged and pellets were resuspended in 150 μl TES periplasmic buffer (50 mM Tris/HCl (pH 8.0)/1 mM EDTA (pH 8.0)/20% Sucrose), followed by the addition of 150 μl 1:5 TES:water, and incubated on ice for 30 min. Plates were centrifuged and the scFv-containing supernatant was harvested.

Example 4.2

Epitope Competition Assay for Library Screening

Those scFv able to compete with the parental 18A5 antibody for binding to human or murine IL-21R were identified from selected phage by a homogeneous time-resolved fluorescence (HTRF®) assay. Purified parental 18A5 antibody was covalently modified with cryptate, a derivative of europium, according to the instructions in an HTRF® Cryptate Labeling Kit (Cisbio, Bedford, Mass.). Peri-preps of scFv were prepared as described above and diluted to 0.25% in PBS/0.4 M potassium fluoride/0.1% BSA (HTRF® buffer); then 10 μl of the mixture was transferred to the wells of black 384-shallow-well plates (Nunc, Rochester, N.Y.). Five μl of cryptate-conjugated 18A5 antibody was then added to each well, followed by 5 μl of a mixture of a 1:800 dilution of streptavidin-XL665 conjugate (Cisbio) and either 4.8 nM biotin-hIL-21R-H/F or 40 nM biotin-mIL-21R-H/F. The mixture was incubated for 2 hr at RT, and time-resolved fluorescence measurements were made (340 nm excitation, 615 nm and 665 nm emission). Competition with 18A5 antibody was indicated by a reduction in the background-corrected ratio of emission at 665 nm to emission at 615 nm.

A total of 8280 independently isolated scFv were screened in the HTRF® assay using human IL-21R-H/F, and 376 clones able to compete with the parental 18A5 antibody for binding to biotin-hIL-21R-H/F were chosen for further analysis.

Example 5

DNA Sequence Analysis of Library-Derived scFv—PCR Amplification of scFv Regions for Sequencing Analysis The sequences of 287 18A5-derived scFv variants with improved IL-21R binding over that of the parent 18A5 scFv molecule were determined, and the frequencies of amino acids found at each position were determined. Among the $V_H$ clones, only two (1.7%) were derived from a library which mutated the last six amino acids of, e.g., SEQ ID NO: 169 (at the C-terminus of $V_H$ CDR3), while the remainder were derived from a library which mutated the first six amino acids of, e.g., SEQ ID NO:169. Among the $V_L$ clones, only one clone (0.6%) was derived from a library in which the last six amino acids of, e.g., SEQ ID NO:170 (at the C-terminus of $V_L$ CDR3) were mutated, while the majority were derived from alterations in the first six amino acids of, e.g., SEQ ID NO:170 (at the N-terminus of $V_L$ CDR3).

PCR amplification of scFvs was carried out using VENT® DNA Polymerase (New England Biolabs, Ispwich, Mass.) in HN buffer (Epicentre Biotechnologies, Madison, Wis.) according to the manufacturer's instructions. Five μl of a 1:10 dilution of a stationary phase bacterial culture was used as the template for a final reaction volume of 20 μl. The cycling conditions used were a 2-min hot start at 94° C., 30 cycles of denaturation at 94° C. (1 min), primer annealing at 55° C. (2 min) and extension at 72° C. (1 min), followed by a final extension at 72° C. (5 min). PCR products were verified by agarose gel electrophoresis and cleaned up with ExoI/SAP (shrimp alkaline phosphatase) prior to sequencing with the M13rev primer.

The SEQ ID NOs for the CDR3 sequences of twenty-seven scFv are listed in Table 4. These scFv were chosen for further analysis based on assays described in Example 6.

TABLE 4

| CDR3 SEQ ID NOs of Improved 18A5-derived scFv | | |
|---|---|---|
| scFv | Heavy CDR3 | Light CDR3 |
| H3 | 165 | 170 |
| H4 | 166 | 170 |
| H5 | 167 | 170 |
| H6 | 168 | 170 |
| L1 | 169 | 171 |
| L2 | 169 | 172 |
| L3 | 169 | 173 |
| L4 | 169 | 174 |
| L5 | 169 | 175 |
| L6 | 169 | 176 |
| L8 | 169 | 177 |
| L9 | 169 | 178 |
| L10 | 169 | 179 |
| L11 | 169 | 180 |
| L12 | 169 | 181 |
| L13 | 169 | 182 |
| L14 | 169 | 183 |
| L15 | 169 | 184 |
| L16 | 169 | 185 |
| L17 | 169 | 186 |
| L18 | 169 | 187 |
| L19 | 169 | 188 |
| L20 | 169 | 189 |
| L21 | 169 | 190 |
| L23 | 169 | 191 |
| L24 | 169 | 192 |
| L25 | 169 | 193 |

Example 6

Characterization of Library-Derived scFv

Example 6.1

Preparation of Purified scFv for Quantitative Analysis

Individual scFv clones were purified on a small scale by Ni-NTA purification on PHYTIP® columns (PhyNexus, Inc., San Jose, Calif.). Single colonies were grown in 20 ml 2×TY medium with 0.1% glucose/100 μg/ml ampicillin in 50-ml conical tubes to mid-logarithmic phase at 37° C. with shaking at 250 rpm. Expression of scFv was induced with IPTG at a final concentration of 0.02 mM, and cultures were grown overnight at 30° C. Cells were harvested by centrifugation and resuspended in 1 ml TES periplasmic buffer, followed by the addition of 1 ml 1:5 TES:water and incubation on ice for 30 min. Lysates were centrifuged at 3200 rpm for 10 min at 4° C., and supernatants were brought to 2 mM $MgCl_2$. scFv were captured on Ni-NTA PHYTIPs® (PhyNexus) by repeated passage of the supernatant over the PHYTIPs® on a Perkin Elmer (Waltham, Mass.) MINITRAK™ IX liquid handling robot, followed by washing in IMAC wash buffer and elution with 200 mM imidazole, 50 mM Tris, 300 mM NaCl (pH 8.0). The buffer was exchanged to PBS by three cycles of dilution 1:10 into PBS, followed by concentration on a 10,000 molecular weight cutoff filter plate (Millipore MULTISCREEN ULTRACEL 96-well ultrafiltration plate, Millipore, Billerica, Mass.). Samples were quantitated using a Micro BCA™ kit (Thermo Fisher Scientific Inc., Rockford, Ill.) using the manufacturer's bovine serum albumin standard.

Example 6.2

Assays for IL-21-Dependent Proliferation of Cells Overexpressing Human or Murine IL-21R Inhibition assays were performed with 18A5-derived binding proteins (scFv and IgG) to measure their blockade of IL-21-dependent proliferation of cell lines transfected with human or murine IL-21R. BaF3 cells, a murine pre-B cell line, and TF1 cells, a human erythroid cell line, were retrovirally transduced with IL-21R and green fluorescent protein (GFP). Cells were routinely grown in RPMI 1640 with 10% FBS, 2 mM L-glutamine, 100 U/ml penicillin, 100 μg/ml streptomycin, and 0.00036% β-mercaptoethanol. Human IL-21R-BaF3 cell cultures were supplemented with 50 ng/ml of human IL-21; murine IL-21R-BaF3 cell cultures were supplemented with 10 U/ml of IL-3; TF1 cell cultures were supplemented with 50 ng/ml of GM-CSF. Prior to assay, cells were washed 3× in assay medium lacking supplemental growth factors, resuspended in assay medium, and incubated at 37° C./5% $CO_2$ for 6 hr. To prepare assay plates, 5000 cells were added to the central 60 wells of a 96-well flat-bottomed white tissue culture plate (Thermo Scientific, Waltham, Mass.) in a volume of 55 μl/well. Test scFv or IgG samples were prepared by diluting the stock sample in assay medium and diluting serially three-fold. Twenty-five μl of the binding protein samples were added to the cells and incubated for 30 min at 37° C./5% $CO_2$. Twenty μl of assay medium containing 100-400 pg/ml of human or murine IL-21 was added to each well, and the cells were incubated for an additional 48 hr. Proliferation was measured by bringing plates to RT, adding 15 μl/well CELLTITER-GLO®, incubating for 10 min at RT, and measuring luminescence with a Perkin Elmer ENVISION™ plate reader. After purification with PhyNexus IMAC tips, 108 scFv were tested for neutralization of IL-21-dependent proliferation of all three cell lines. All showed neutralization of human IL-21R-BaF3 cells, with $IC_{50}$s lower than or equal to that of the parental 18A5 scFv. A subset showed strong neutralization of proliferation of murine IL-21R-BaF3 cells and human IL-21R-TF1 cells. Data from the 27 most potent clones are shown in FIGS. 1-3, and are summarized in Table 5.

Figure 1A:
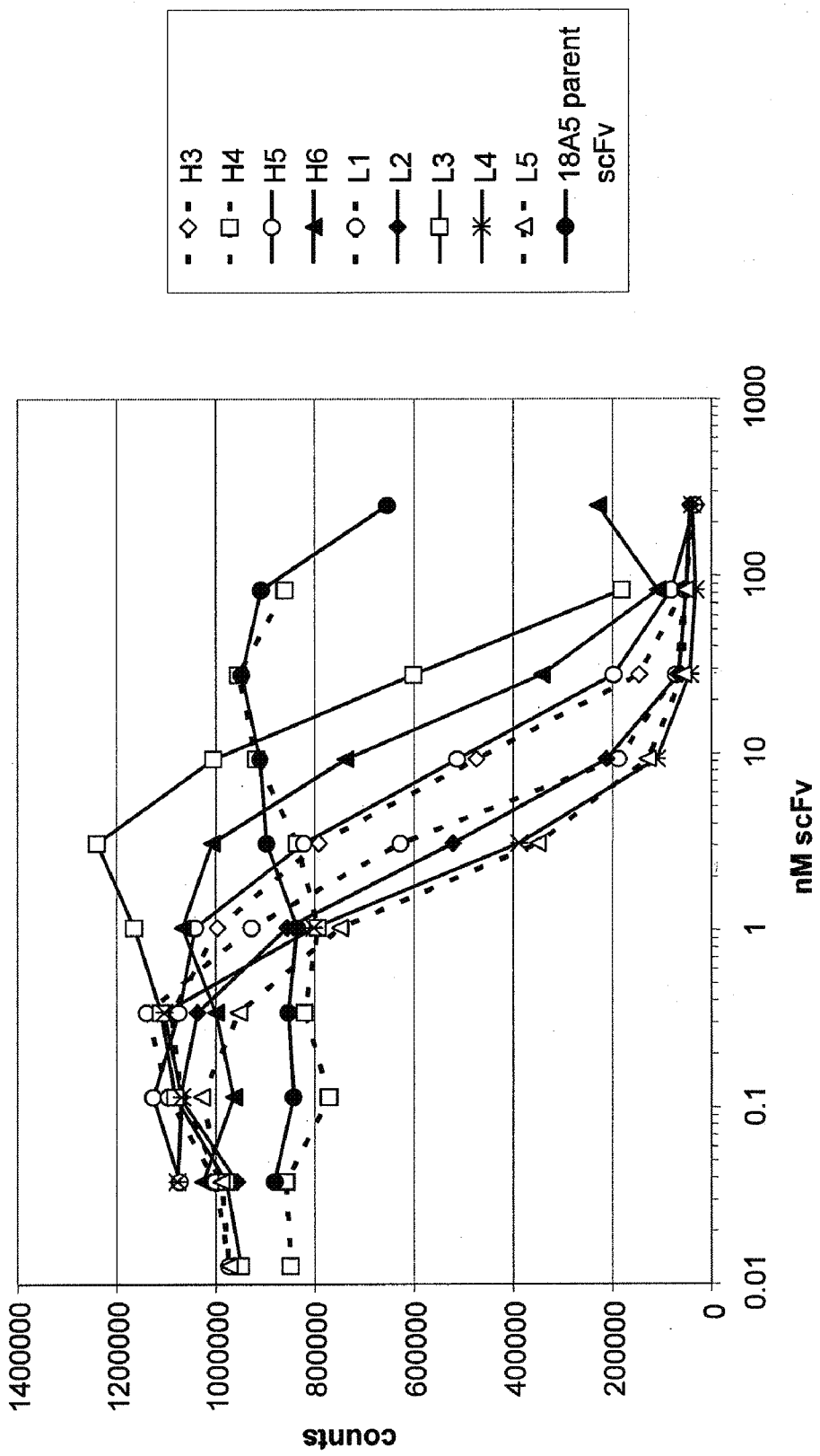
FIG. 1(a-c) depicts the neutralization of proliferation of human IL-21R-BaF3 cells by scFv. Cells were mixed with the indicated scFv and then incubated with 100 pg/ml of human IL-21. Proliferation was measured by CELLTITER-GLO® (Promega Corporation, Madison, Wis.) after 48 hr.
Figure 1B:
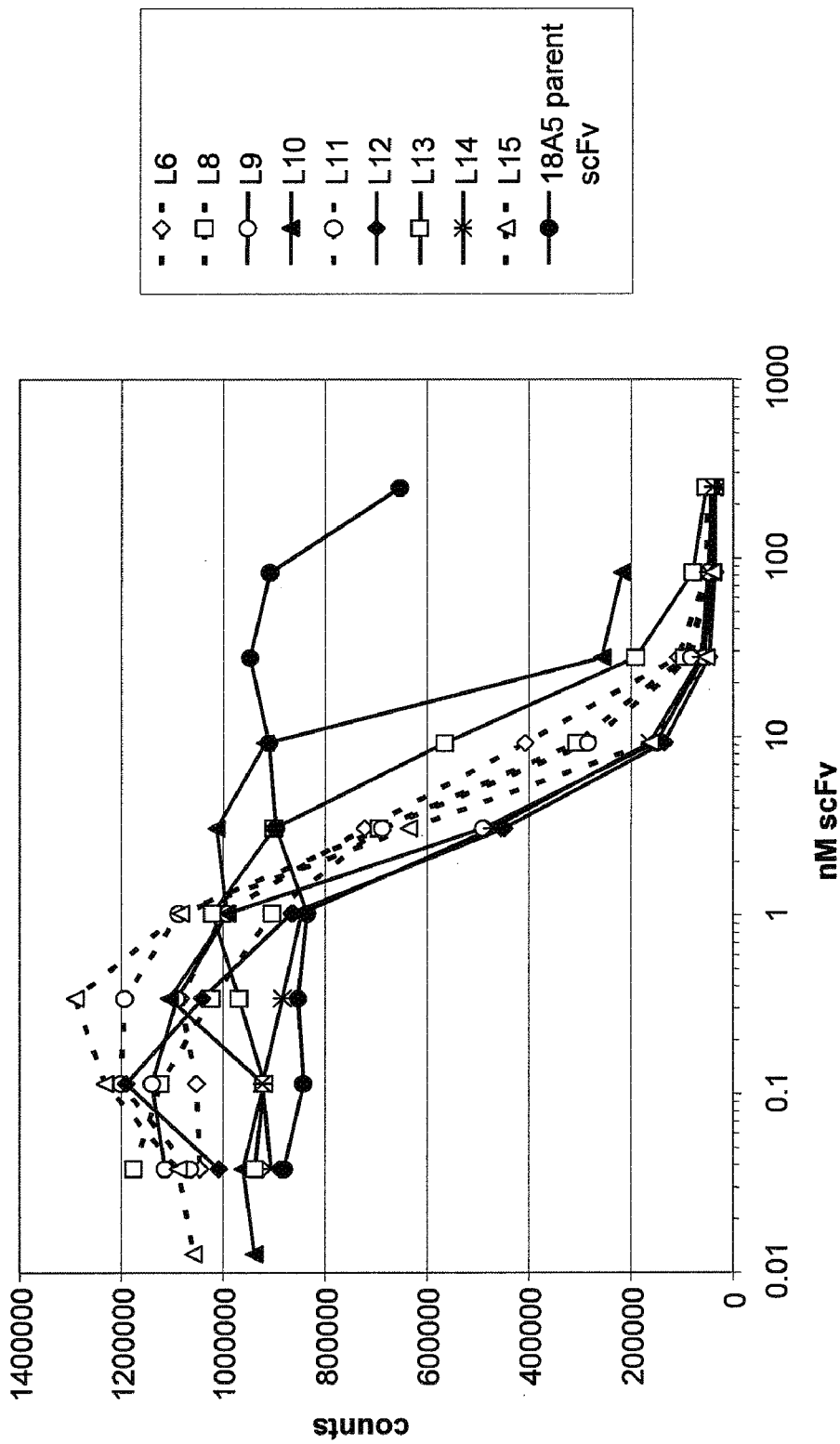
Figure 2A:
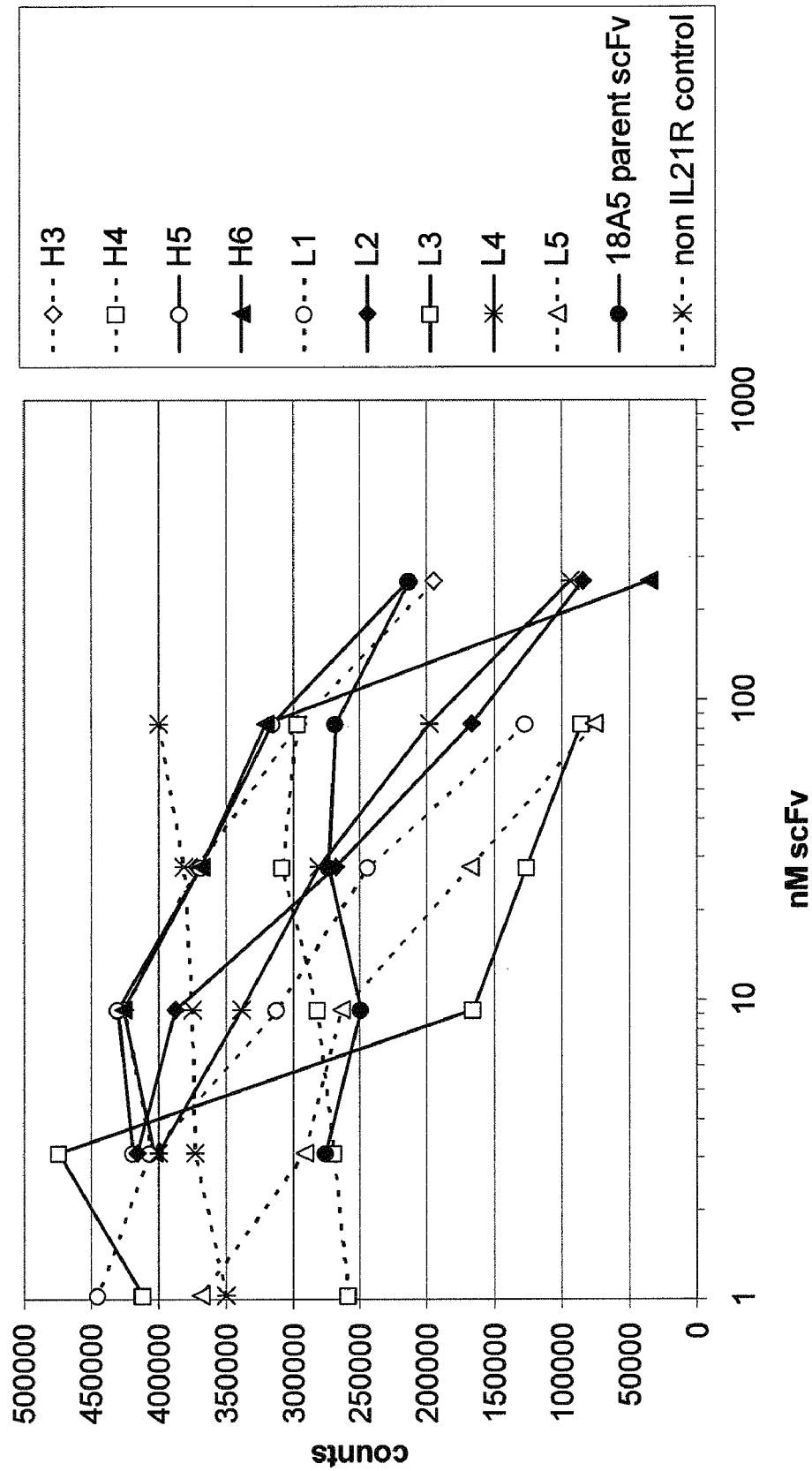
FIG. 2(a-c) depicts the neutralization of proliferation of human IL-21R-TF1 cells by scFv. Cells were mixed with the indicated scFv and then incubated with 100 pg/ml of human IL-21. Proliferation was measured by CELLTITER-GLO® after 48 hr.
Figure 2B:
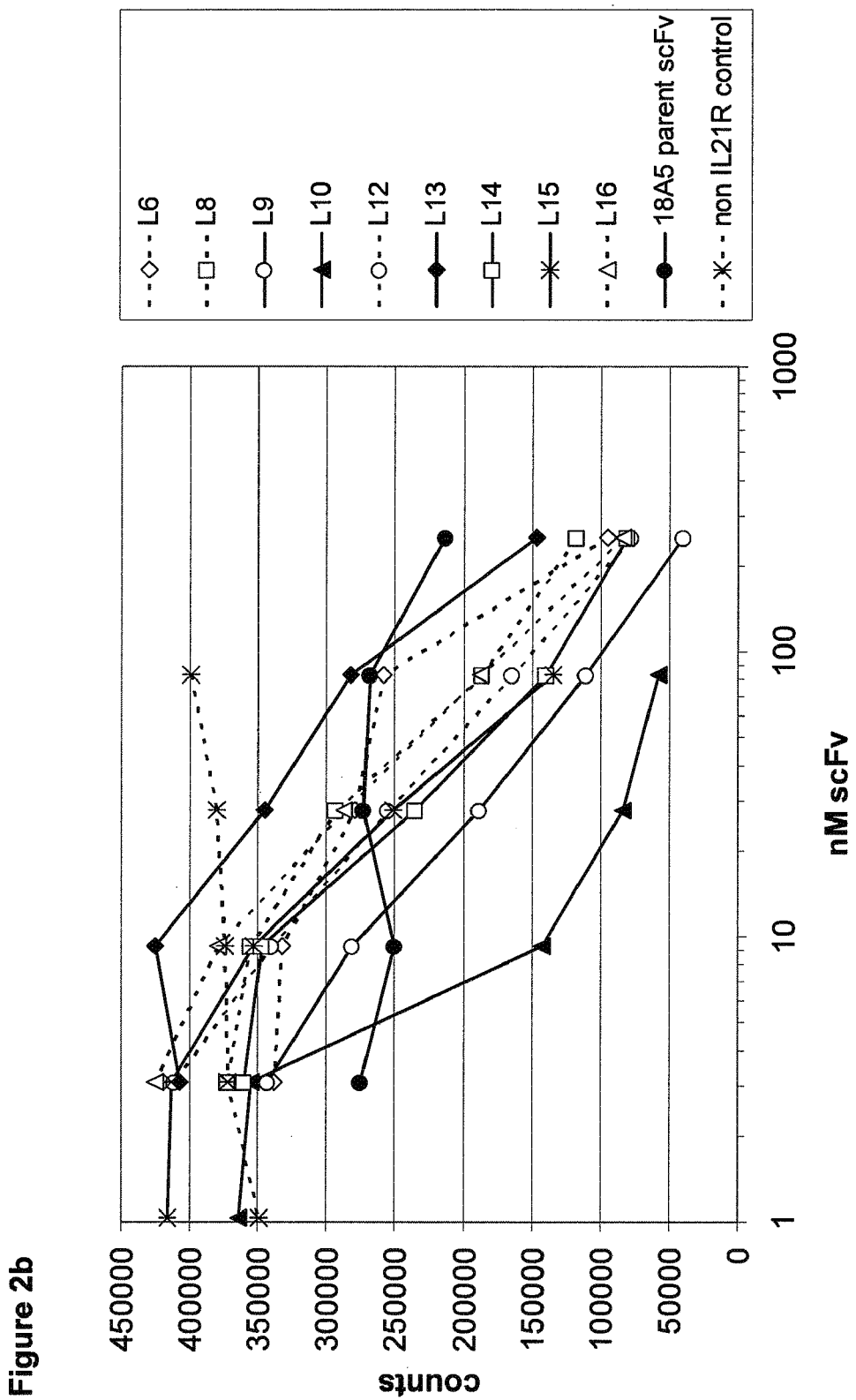
Figure 2C:
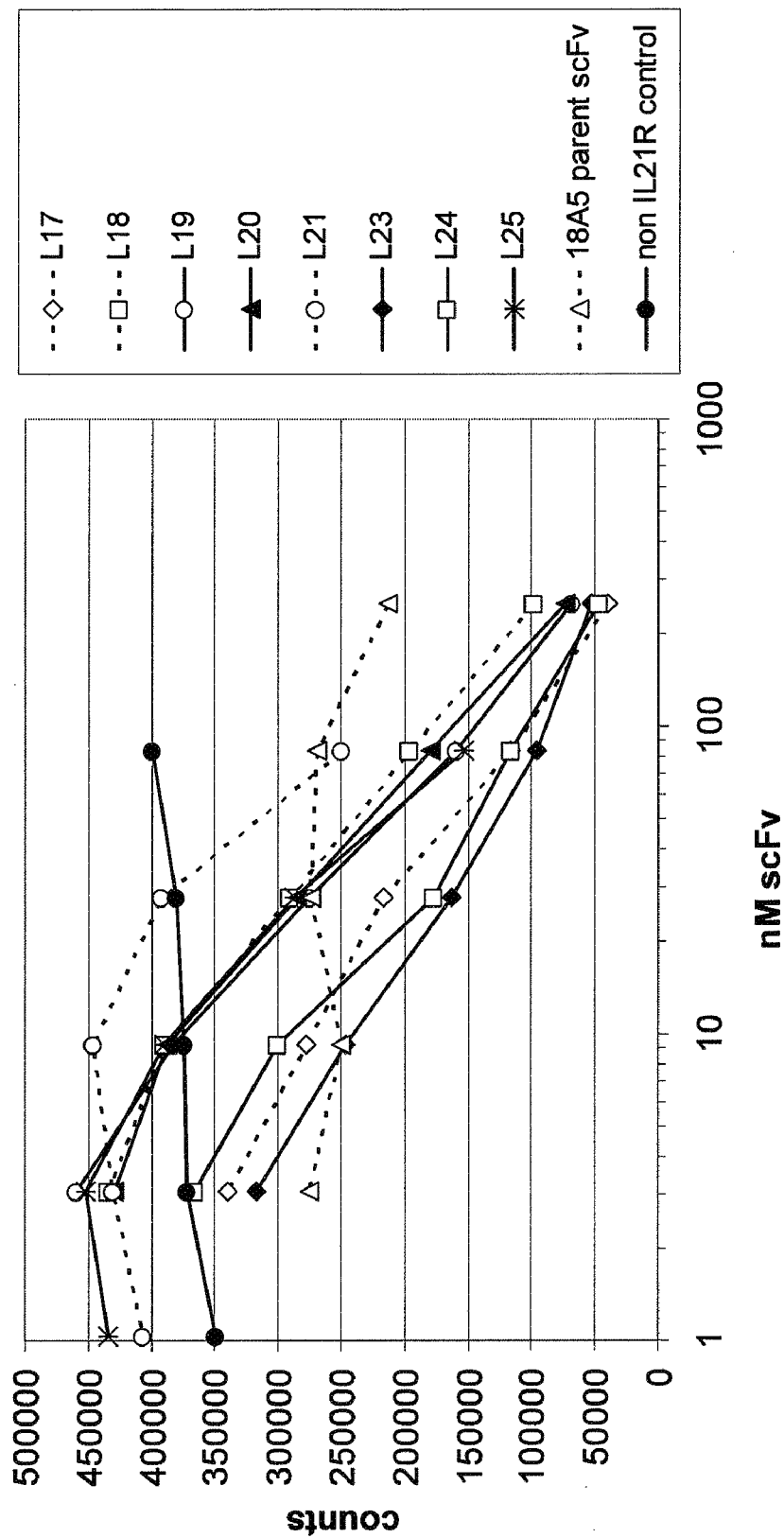
Figure 3A:
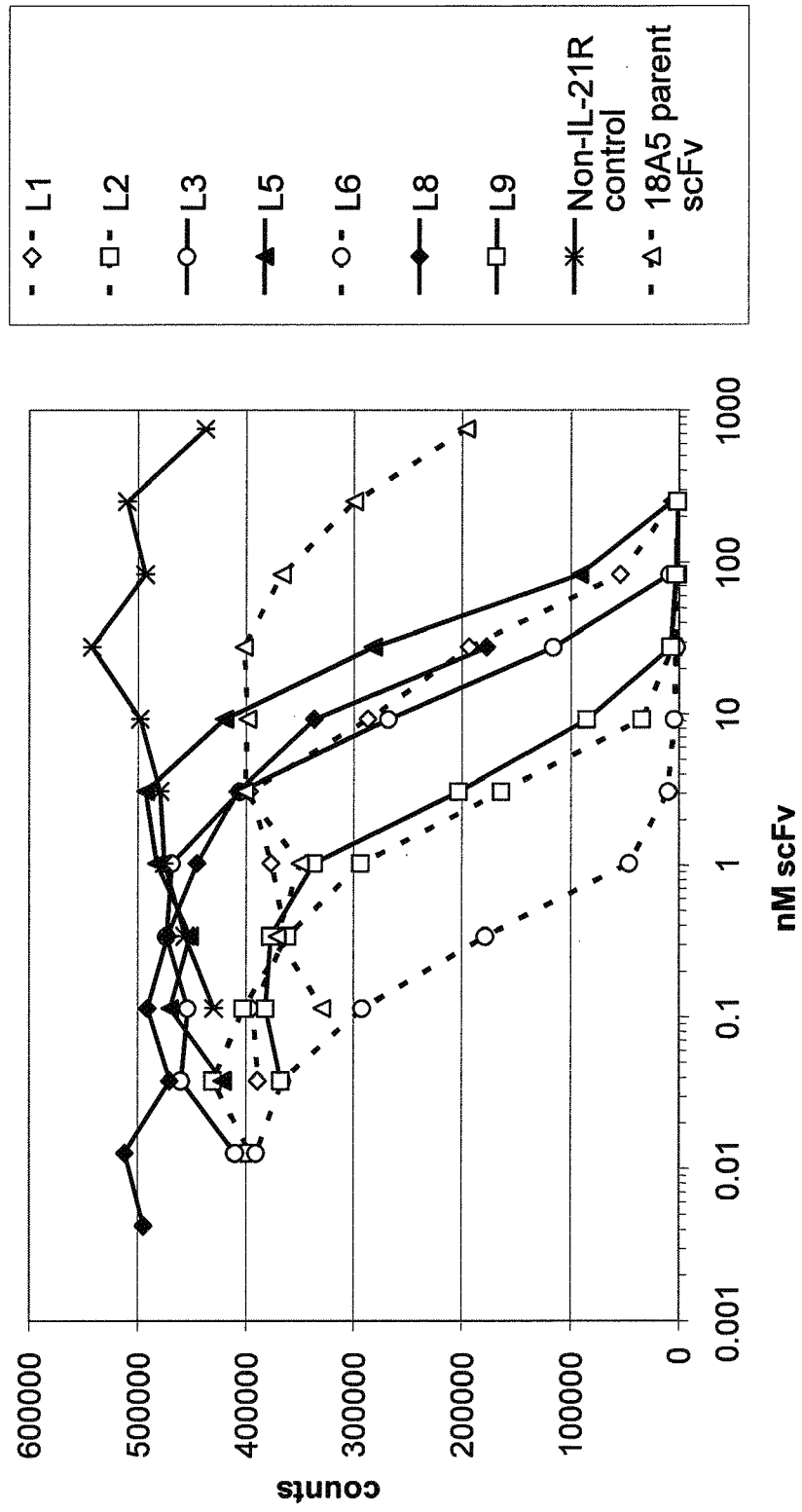
FIG. 3(a-c) depicts the neutralization of proliferation of murine IL-21R-BaF3 cells by scFv. Cells were mixed with the indicated scFv and then incubated with 400 pg/ml of murine IL-21. Proliferation was measured by CELLTITER-GLO® after 48 hr.
Figure 3B:
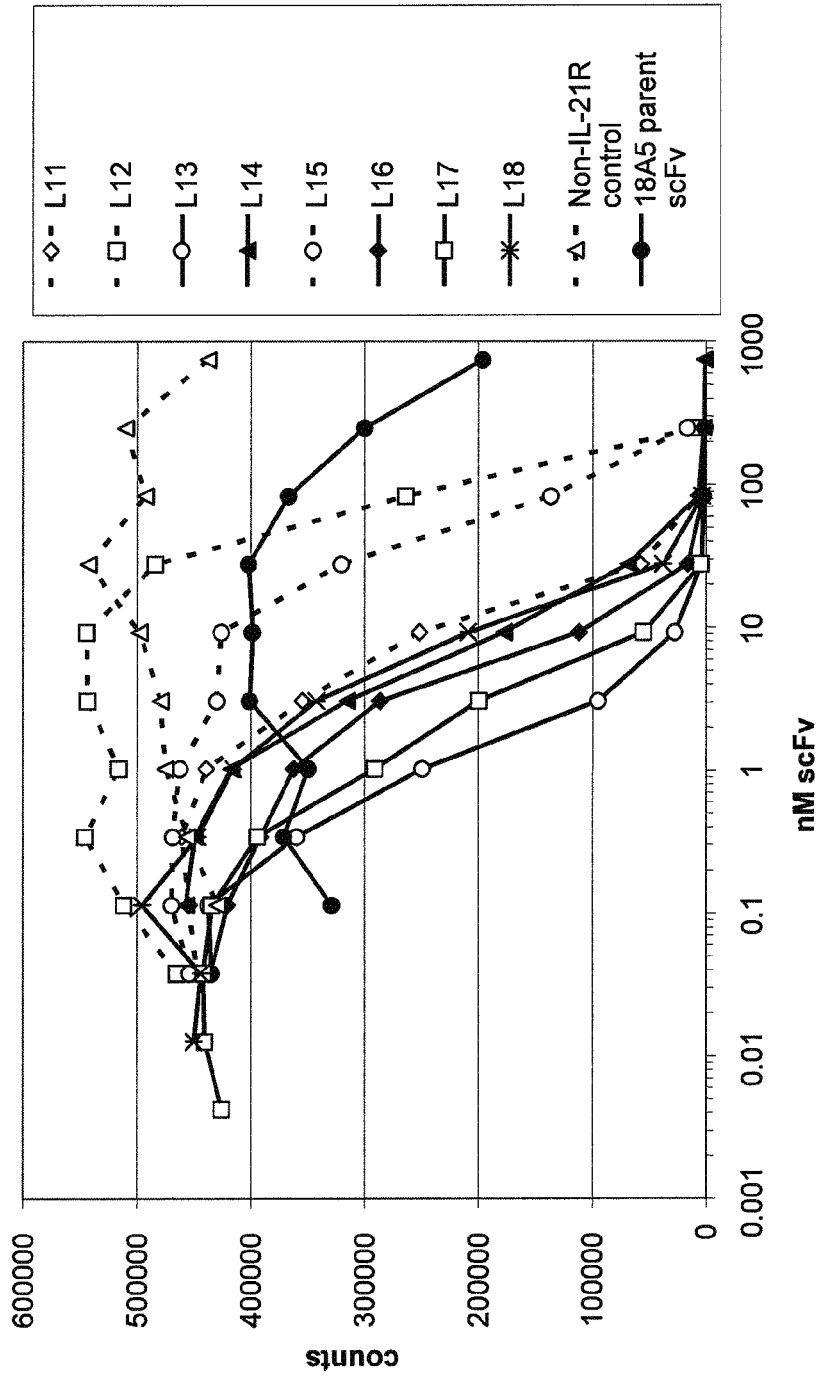
Figure 3C:
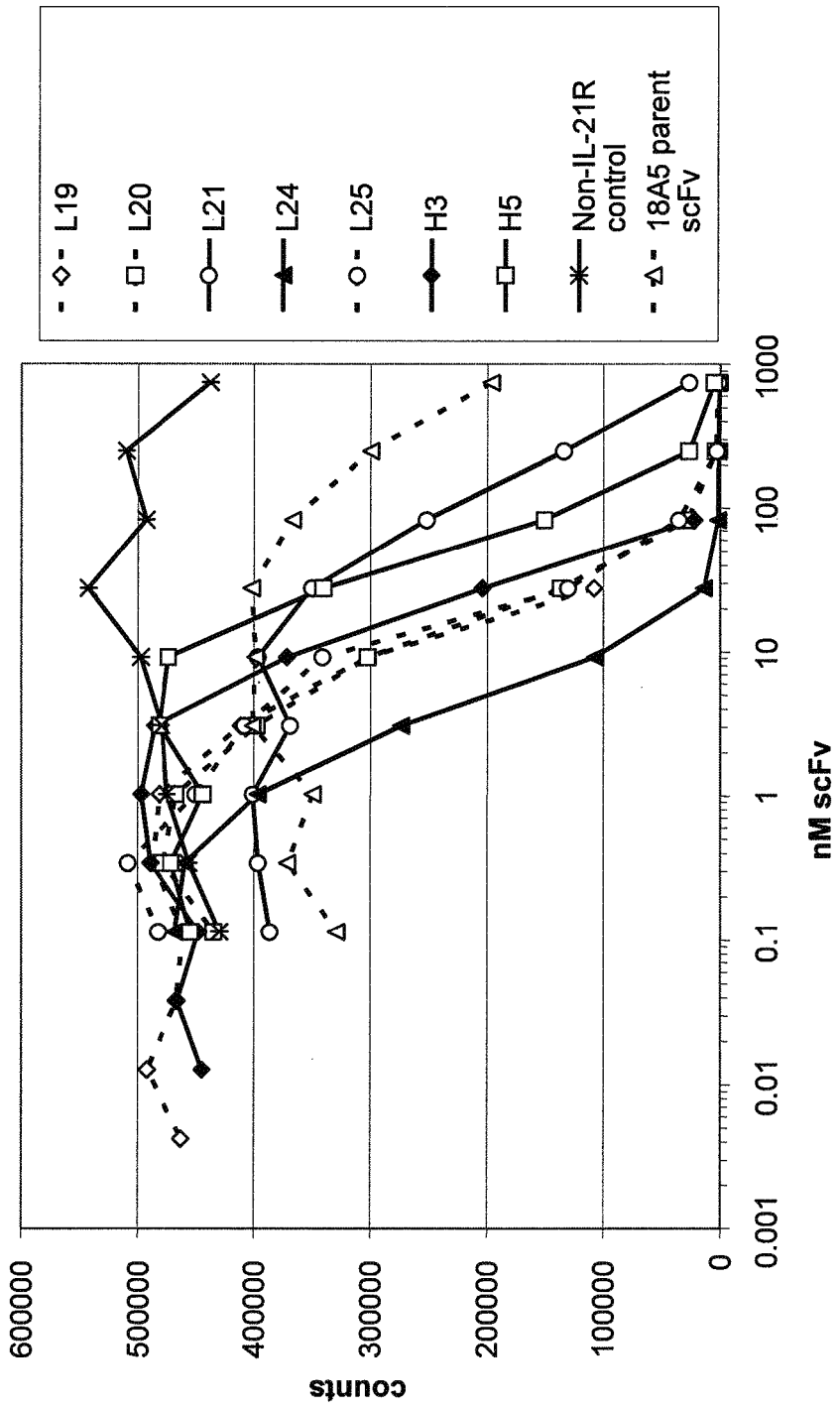

FIGS. 1-3 show the neutralization of proliferation by scFv of human IL-21R-BaF3 cells (FIGS. 1a-c); human IL-21R-TF1 cells (FIGS. 2a-c); and murine IL-21R-BaF3 cells (FIGS. 3a-c). Cells were mixed with the indicated scFv and incubated with 100 pg/ml (FIGS. 1-2) or 400 pg/ml (FIG. 3) of human IL-21.

Example 6.3

Quantitative Epitope Competition Assay

Figure 4A:
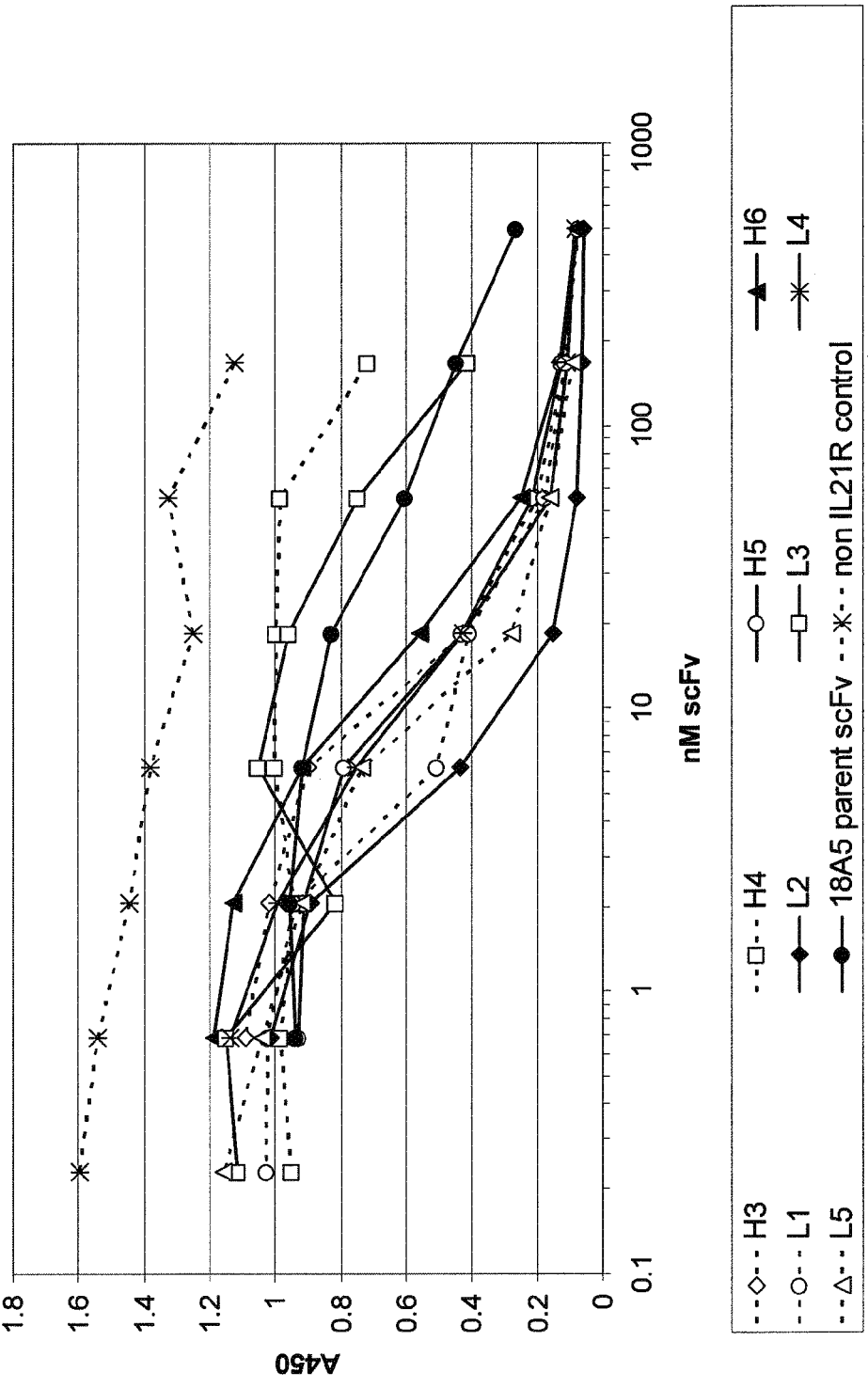
FIG. 4(a-c) depicts scFv competition with parental antibody 18A5 IgG for binding to murine IL-21R. The scFv were mixed with biotinylated-murine IL-21R-H/F, and the mixtures were added to antibody 18A5 immobilized on an ELISA plate. Capture of mIL-21R was detected with HRP-streptavidin, and competition for binding to mIL-21R was indicated by a reduction in the A450 signal.
Figure 4B:
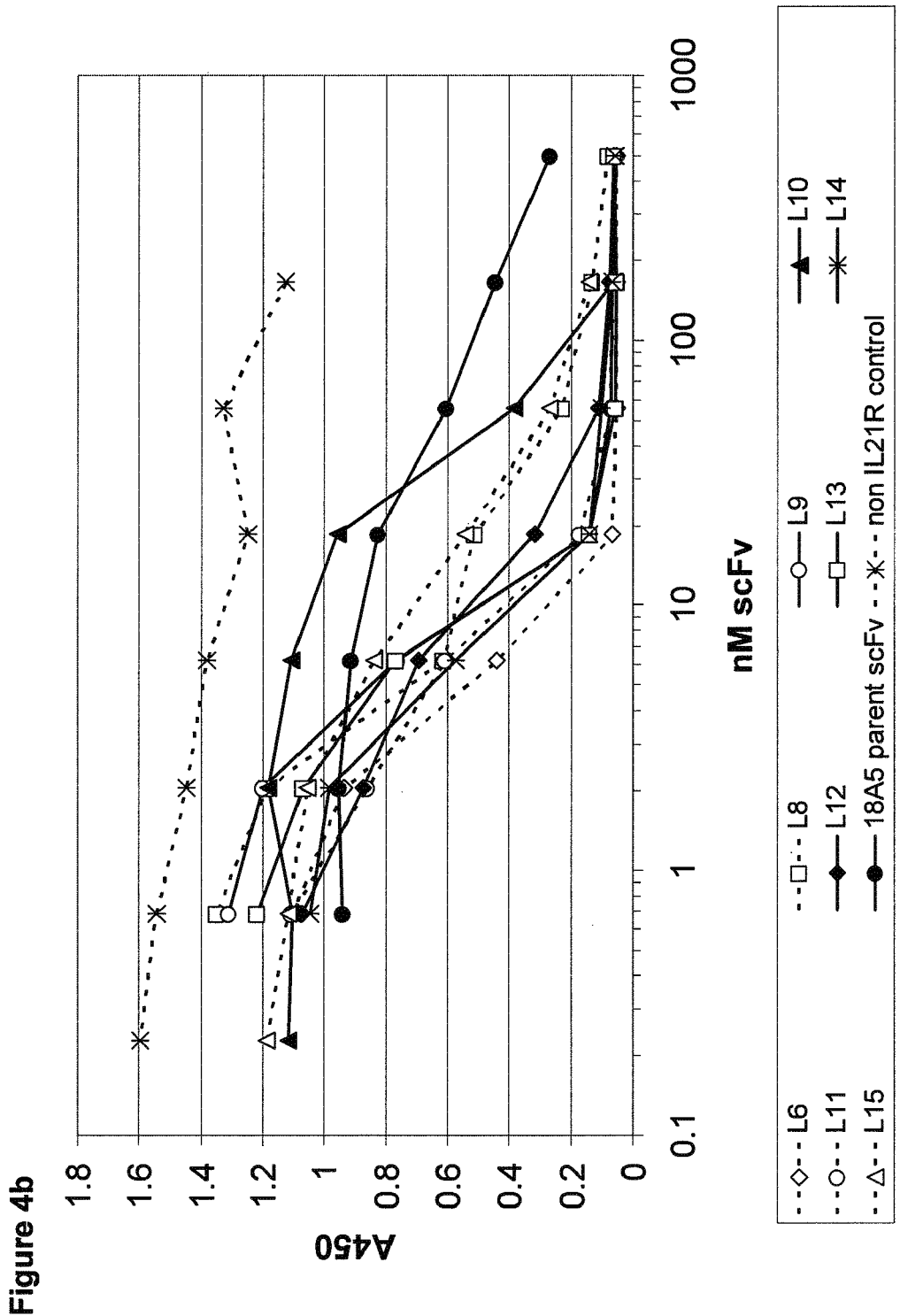
Figure 4C:
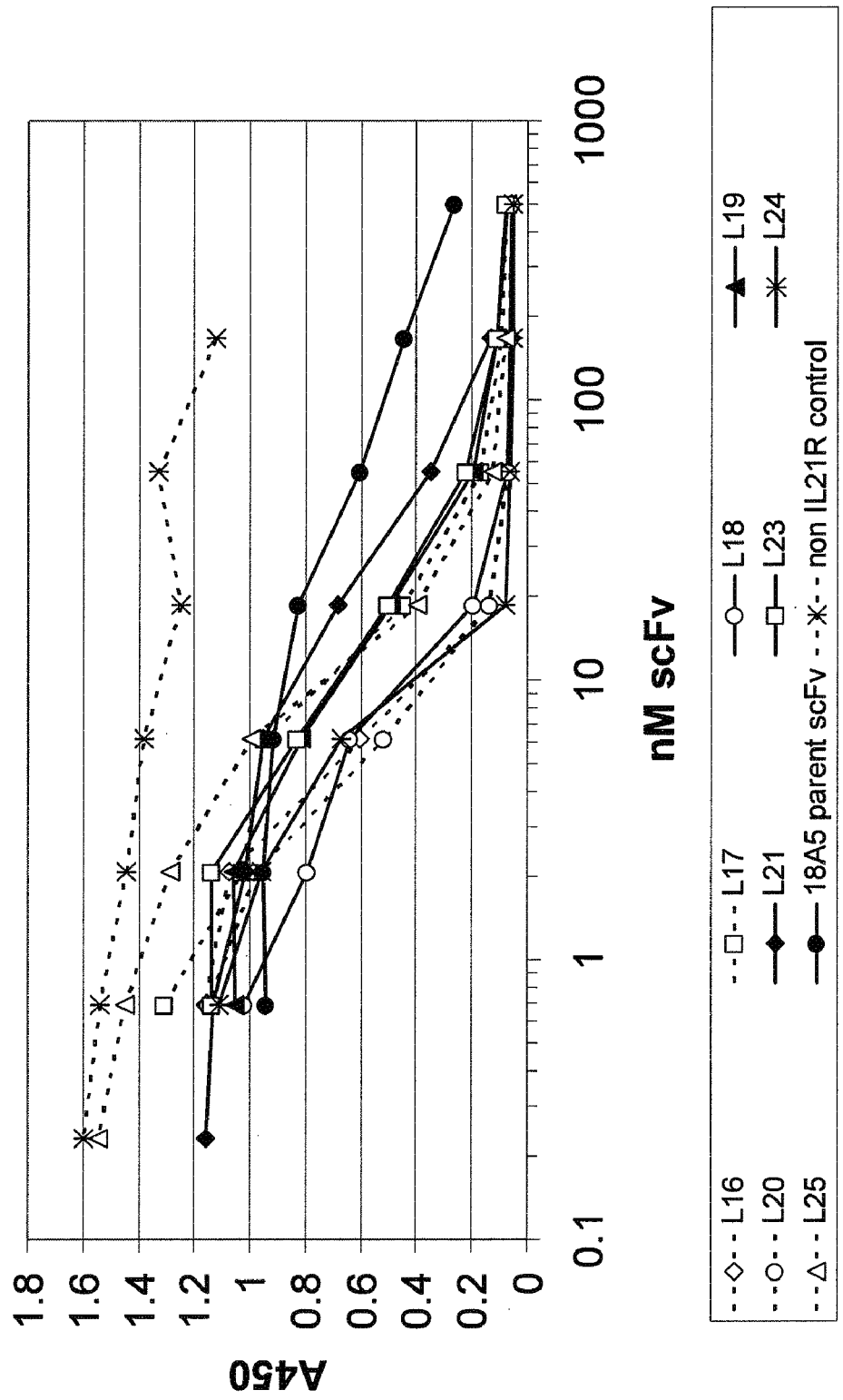

Purified scFv were analyzed quantitatively for their ability to compete with the parental 18A5 antibody for binding to murine IL-21R in an enzyme-linked immunosorbent assay (ELISA). Parental 18A5 antibody was coated overnight at 4° C. on 96-well Nunc MAXISORP® plates at a concentration of 0.75 μg/ml in PBS. Plates were washed 3× using PBS, and then blocked for 3 hr at RT in PBS/1% BSA/0.05% Tween-20. scFv were mixed with 36 nM biotinylated mIL-21R-H/F and incubated for 10 min at RT. Blocked plates were washed 3× with PBS, and 50 μl/well of scFv/IL-21R mixtures were transferred to the appropriate plates and incubated for 1 hr at RT. Plates were washed 5× with PBS prior to the addition of a 1:6000 dilution of horseradish peroxidase-conjugated streptavidin (Southern Biotech, Birmingham, Ala.) secondary antibody to detect bound biotinylated mIL-21R-H/F. Plates were then incubated for 1 hr at RT and washed 7× with PBS. Signal was developed using 3,3',5,5'-tetramethylbenzidine (TMB), the reaction stopped with $H_2SO_4$, and the absorbance read at 450 nm on an ENVISION™ plate reader (Perkin Elmer). 108 scFv purified by PhyNexus IMAC tips were tested in this assay, and most competed with the parental 18A5 antibody for binding to biotinylated murine IL-21R-H/F with $IC_{50}$s lower than that of the parental 18A5 scFv. Epitope competition data for the 27 clones with the highest potencies in cell-based neutralization assays are shown in FIGS. 4a-c and summarized in Table 5.

TABLE 5

Neutralization of Human and Murine IL-21R in Cell-based Assays and Competition with 18A5 Antibody for Murine IL-21R Binding

| | $IC_{50}$ (nM) in Human IL-21R-BaF3 Neutralization Assay | $IC_{50}$ (nM) in Human IL-21R-TF1 Neutralization Assay | $IC_{50}$ (nM) in Murine IL-21R-BaF3 Neutralization Assay | $IC_{50}$ (nM) in Murine IL-21R Epitope Competition ELISA |
|---|---|---|---|---|
| H3 | 7.7 | 98.1 | 25.68 | 14 |
| H4 | 3.8 | 9.3 | nd | nd |
| H5 | 7.9 | 178.5 | 53.66 | 17 |
| H6 | 13.8 | 150 (estimated) | nd | 13 |
| L1 | 3.7 | 55 (estimated) | 28.77 | 7 |
| L2 | 3.1 | 37.5 | 2.41 | 5 |
| L3 | 27.6 | 7 (estimated) | 13.78 | 100 |
| L4 | 2.1 | 60 (estimated) | nd | 8 |
| L5 | 2.1 | 20 (estimated) | 38.52 | 7 |
| L6 | 5.9 | 150 (estimated) | 0.29 | 4 |
| L8 | 4.1 | 51.3 | 715.27 | 7 |
| L9 | 2.8 | 27.7 | 3.61 | 7 |
| L10 | 15.1 | 7 | nd | 40 |
| L11 | 4.2 | 38.3 | 10.03 | 6 |
| L12 | 2.6 | 54.9 | 87.77 | 8 |
| L13 | 11.0 | 257.4 | 1.25 | 7 |
| L14 | 3.2 | 33.5 | 6.49 | 6 |
| L15 | 3.3 | 30.3 | 53.49 | 14 |
| L16 | 3.7 | 67.4 | 4.71 | 6 |
| L17 | 1.6 | 60.3 | 2.66 | 12 |
| L18 | 3.7 | 54.4 | 8.34 | 8 |
| L19 | 4.5 | 35.3 | 13.59 | 15 |
| L20 | 3.1 | 57.5 | 15.39 | 5 |
| L21 | 9.4 | 100 (estimated) | 162.27 | 28 |
| L23 | 1.5 | 15.3 | nd | 12 |
| L24 | 2.4 | 18.7 | 3.73 | 6 |
| L25 | 3.7 | 33.1 | 15.55 | 9 |

Example 7

Conversion of Parental 18A5 IgG to Germline Sequence

The following fifteen scFv with modified $V_L$ regions, along with the germlined parental 18A5 $V_L$ (see below), were chosen for conversion to full-length human IgG lambda: L2, L3, L6, L9, L11, L13, L14, L16, L17, L18, L19, L20, L23, L24, and L25. Four scFv with modified $V_H$ regions, H3, H4, H5, and H6, along with the germlined parental 18A5 $V_H$ (see below) were chosen for conversion to full-length human IgG1.

The $V_H$ and $V_L$ amino sequences of the parental 18A5 antibody were modified so that the sequences outside the CDR regions matched the closest human germline sequences: DP67/VH4B+ (VBASE_AA:WAP00CEAZ_1) and JH1/JH4/JH5 in the case of the $V_H$, and DPL16/VL3.1 (VBASE_AA:WAP00CEMI_1) in the case of the $V_L$. Modifications were done by a combination of gene synthesis at GENEART (Regensburg, Germany) and site-directed changes introduced by PCR. In addition, the sequences were codon-optimized for expression in mammalian cells by GENEART using their proprietary methods. An alignment of the parental 18A5 sequences and the germline-corrected 18A5 sequences is shown below:

18A5 Heavy Chain Comparison

Parental 18A5 $V_H$
(SEQ ID NO: 5)

```
CAGGTGCAGCTGCAGGAGTCGGGCCCAGGACTGGTGAAGACTTCGGAGAC
CCTGTCCCTCACCTGCGCTGTCTCTGGTTACTCCATCAGCAGTGGTTACT
ACTGGGGCTGGATCCGGCAGCCCCCAGGGAAGGGGTTGGAGTGGATTGGG
AGTATCTCTCATACTGGGAACACCTACTACAACCCGCCCCTCAAGAGTCG
CGTCACCATATCAGTAGACACGTCCAAGAACCAGTTCTCCCTGAAACTGA
GCTCTGTGACCGCCGCAGACACGGCCGTGTATTACTGTGCGCGAGGTGGG
GGAATTAGCAGGCCGGAGTACTGGGGCAAAGGCACCCTGGTCACCGTCTC
GAGT
```

Germlined 18A5 $V_H$
(SEQ ID NO: 7)

```
CAGGTGCAGCTGCAGGAGTCTGGCCCTGGCCTGGTGAAGCCTTCCGAGAC
CCTGTCTCTGACCTGTGCCGTGTCCGGCTACTCCATCTCCTCCGGCTACT
ACTGGGGCTGGATCAGACAGCCTCCTGGCAAGGGCCTGGAGTGGATCGGC
TCCATCTCTCACACCGGCAACACCTACTACAACCCCCCTCTGAAGTCCAG
AGTGACCATCTCCGTGGACACCTCCAAGAACCAGTTCTCCCTGAAGCTGT
CCTCTGTGACCGCTGCCGATACCGCCGTGTACTACTGTGCCAGAGGCGGC
GGAATCTCCAGACCTGAGTACTGGGGCCAGGGCACCCTGGTGACCGTGTC
CTCT
```

Germlined 18A5 $V_H$ x Parental 18A5 $V_H$

```
  1 CAGGTGCAGCTGCAGGAGTCTGGCCCTGGCCTGGTGAAGCCTTCCGAGAC   50
    ||||||||||||||||||||| ||||| || ||||||||| |||| |||||
  1 CAGGTGCAGCTGCAGGAGTCGGGCCCAGGACTGGTGAAGACTTCGGAGAC   50

51 CCTGTCTCTGACCTGTGCCGTGTCCGGCTACTCCATCTCCTCCGGCTACT  100
    |||||| || ||||| || || || || ||||||||||  |  || ||||
 51 CCTGTCCCTCACCTGCGCTGTCTCTGGTTACTCCATCAGCAGTGGTTACT  100

101 ACTGGGGCTGGATCAGACAGCCTCCTGGCAAGGGCCTGGAGTGGATCGGC  150
    ||||||||||||||| ||||| || || ||||| |||||||||||| ||
101 ACTGGGGCTGGATCCGGCAGCCCCCAGGGAAGGGGTTGGAGTGGATTGGG  150

151 TCCATCTCTCACACCGGCAACACCTACTACAACCCCCCTCTGAAGTCCAG  200
    |||||||| || || |||||||||||||||||||||| || ||  |||  |
151 AGTATCTCTCATACTGGGAACACCTACTACAACCCGCCCCTCAAGAGTCG  200

201 AGTGACCATCTCCGTGGACACCTCCAAGAACCAGTTCTCCCTGAAGCTGT  250
    || |||||| || || ||||| ||||||||||||||||||||||||| |||
201 CGTCACCATATCAGTAGACACGTCCAAGAACCAGTTCTCCCTGAAACTGA  250

251 CCTCTGTGACCGCTGCCGATACCGCCGTGTACTACTGTGCCAGAGGCGGC  300
    |||||||||||| || || |||||||| |||||||| |||| ||
251 GCTCTGTGACCGCCGCAGACACGGCCGTGTATTACTGTGCGCGAGGTGGG  300

301 GGAATCTCCAGACCTGAGTACTGGGGCCAGGGCACCCTGGTGACCGTGTC  350
    ||||| ||| || ||||||||||||| |||||||||| ||||| ||
301 GGAATTAGCAGGCCGGAGTACTGGGGCAAAGGCACCCTGGTCACCGTCTC  350

351 CTCT  354 (SEQ ID NO: 7)
     |
351 GAGT  354 (SEQ ID NO: 5)
```

18A5 Light Chain Comparison

Parental 18A5 V$_L$
(SEQ ID NO: 9)
```
TCTTCTGAGCTGACTCAGGACCCTCCTGTGTCTGTGGCCTTGGGACAGAC
AGTCACGCTCACATGCCAAGGAGACAGCCTCAGAACCTATTATGCAAGCT
GGTACCAGCAGAAGTCAGGACAGGCCCCTATACTTCTCCTCTATGGTAAA
CACAAACGGCCCTCAGGGATCCCAGACCGCTTCTCTGGCTCCACCTCAGG
AGACACAGCTTCCTTGACCATCACTGGGGCTCAGGCGGAAGACGAGGCTG
ACTATTACTGTAACTCCCGGGACTCCAGTGGCAACCCCATGTTCTGTTC
GGCGGAGGGACCCAGCTCACCGTTTTA
```

Germlined 18A5 V$_L$
(SEQ ID NO: 11)
```
TCCTCTGAGCTGACCCAGGATCCTGCTGTGTCTGTGGCCCTGGGCCAGAC
CGTCAGGATCACCTGCCAGGGCGATAGCCTGAGAACCTACTACGCCTCCT
GGTATCAGCAGAAGCCTGGACAGGCCCCTGTGCTGGTGATCTACGGCAAG
CACAAGAGGCCATCCGGCATCCCTGACAGATTCTCCGGCTCCTCCTCTGG
CAATACCGCCTCCCTGACCATCACCGGCGCTCAGGCCGAGGACGAGGCCG
ACTACTACTGTAACTCCCGGGACTCTTCCGGCAACCCTCACGTGCTGTTT
GGCGGCGGAACCCAGCTGACCGTGCTA
```

Parental
LEWIGSISHTGNTYYNPPLKSRVTISVDTSKNQFSLKLSSVTAADTAVYY
CARGGGISRP

Germlined
LEWIGSISHTGNTYYNPPLKSRVTISVDTSKNQFSLKLSSVTAADTAVYY
CARGGGISRP

Parental
EYWGKGTLVTVSS

Germlined
EYWGQGTLVTVSS

Germline-Corrected V$_L$ Sequence (Changes from Parental Sequence are Bold and Underlined):

Parental
(SEQ ID NO: 10)
SSELTQDPPVSVALGQTVTLTCQGDSLRTYYASWYQQKSGQAPIL

Germlined
(SEQ ID NO: 12)
SSELTQDPAVSVALGQTVRITCQGDSLRTYYASWYQQKPGQAPVL

Parental
LLYGKHKRPSGIPDRFSGSTSGDTASLTITGAQAEDEADYYCNSRDSSGN
PHVLFGGGTQ

Germlined

```
Germlined 18A5 V_L x Parental 18A5 V_L

1 TCCTCTGAGCTGACCCAGGATCCTGCTGTGTCTGTGGCCCTGGGCCAGAC  50
    || |||||||||| ||||| ||| |||||||||| |||||| |||||||
  1 TCTTCTGAGCTGACTCAGGACCCTCCTGTGTCTGTGGCCTTGGGACAGAC  50

51 CGTCAGGATCACCTGCCAGGGCGATAGCCTGAGAACCTACTACGCCTCCT 100
    |||| | |||| ||||| ||| ||||||||||||||| || || ||
 51 AGTCACGCTCACATGCCAAGGAGACAGCCTCAGAACCTATTATGCAAGCT 100

101 GGTATCAGCAGAAGCCTGGACAGGCCCCTGTGCTGGTGATCTACGGCAAG 150
    ||||  ||||||||| |||||||||||| || |  ||||  ||| || ||
101 GGTACCAGCAGAAGTCAGGACAGGCCCCTATACTTCTCCTCTATGGTAAA 150

151 CACAAGAGGCCATCCGGCATCCCTGACAGATTCTCCGGCTCCTCCTCTGG 200
    |||||  ||||  || ||  ||||||  ||| ||  ||||| |||| ||
151 CACAAACGGCCCTCAGGGATCCCAGACCGCTTCTCTGGCTCCACCTCAGG 200

201 CAATACCGCCTCCCTGACCATCACCGGCGCTCAGGCCGAGGACGAGGCCG 250
    | || ||||  || |||||||||| ||||||||||  ||||| ||||| |
201 AGACACAGCTTCCTTGACCATCACTGGGGCTCAGGCGGAAGACGAGGCTG 250

251 ACTACTACTGTAACTCCCGGGACTCTTCCGGCAACCCTCACGTGCTGTTT 300
    |||| |||||||||||||||||||| |||||| || || || |||||
251 ACTATTACTGTAACTCCCGGGACTCCAGTGGCAACCCCATGTTCTGTTC 300

301 GGCGGCGGAACCCAGCTGACCGTGCTA 327 (SEQ ID NO: 11)
    ||||| || ||||||||| || || ||
301 GGCGGAGGGACCCAGCTCACCGTTTTA 327 (SEQ ID NO: 9)
```

Germline-corrected V$_H$ Sequence (Changes from Parental Sequence are Bold and Underlined):

Parental
(SEQ ID NO: 6)
QVQLQESGPGLVKTSETLSLTCAVSGYSISSGYYWGWIRQPPGKG

Germlined
(SEQ ID NO: 8)
QVQLQESGPGLVKPSETLSLTCAVSGYSISSGYYWGWIRQPPGKG

VIYGKHKRPSGIPDRFSGSSSGNTASLTITGAQAEDEADYYCNSRDSSGN
PHVLFGGGTQ

Parental
LTVL

Germlines
LTVL

Example 8

Conversion of Library-Derived scFv to IgG

The CDR3 regions of the $V_L$ and $V_H$ domains of improved 18A5 scFv derivatives were amplified by PCR and subcloned into the germline-corrected $V_L$ and $V_H$ frameworks of the parental 18A5 by the following method. A PCR fragment encompassing the 5' portion of the germlined 18A5 $V_H$ gene was generated by amplification of the plasmid pSMED2_OP18A5G_huIgG1 with primers BssHII_II_$V_H$_F (5'-GCTTGGCGCGCACTCTCAGGTGCAGCT-GCAGGAG-3') [SEQ ID NO:230] and G$V_H$_R_for_BssHII (5'-TCAGGGAGAACTGGTTCTTGG-3') [SEQ ID NO:231]. A PCR fragment encompassing the 3' portion of the $V_H$ gene from the improved scFv clone VH3 was amplified with the following primers: G_$V_H$_F_for_SalI (5'-TCCAA-GAACCAGTTCTCCCTG-3') [SEQ ID NO:232] and scFv_SalI_$V_H$_R (5'-GCGACGTCGACAGGACTCAC-CACTCGAGACGGTGACCAGGGTGCC-3') [SEQ ID NO:233]. Fragments were gel-purified, and then the two were mixed and amplified with the outside primer sets BssHI-I_G_$V_H$_F and SalI_$V_H$_R to generate a complete $V_H$ gene fragment. This was digested with BssHII and SalI and ligated into a vector containing the constant regions of human IgG1 with a triple-mutant hinge region. The insert was reamplified with BssHII_II_$V_H$_$V_H$_F and a new primer (Sal_$V_H$_R_RJ (5'-GCGACGTCGACAGGACTCACCACTCGAGACGG-3')) [SEQ ID NO:234] in order to alter the coding sequence of the $V_H$ J segment to conform to the JH1 germline sequence, and ligated into a human IgG1-triple-mutant constant region vector.

The $V_L$ genes from improved scFv were subcloned by a similar method. A PCR fragment encompassing the 5' portion of the 18A5 $V_L$ gene was generated by amplification of the plasmid pSMEN2_OP18A5G_hu Lambda with primers BssHII_II_$V_L$_F (5'-GCTTGGCGCGCACTCTTCCTCT-GAGCTGACCCAG-3') [SEQ ID NO:235] and scFv_$V_L$_R_for_BssHII (5'-GCCTGAGCCCCAGTGATGGTCA-3') [SEQ ID NO:236]. PCR fragments encompassing the 3' portions of the $V_L$ genes from improved scFv clones were amplified with the primers G$V_L$_F_for_XbaI (5'-ACCGCCTC-CCTGACCATCAC-3') [SEQ ID NO:237] and scFv_XbaI_$V_L$_R (5'-GCGCCGTCTAGAGTTATTCTACT-CACCTAAAACGGTGAGCTGGGTCCC TC-3') [SEQ ID NO:238]. Fragments were gel-purified, and then fragments corresponding to the 5' and 3' portions of each gene were mixed and amplified with the outside primer set BssHII_II_$V_L$_F and scFv_XbaI_$V_L$_R to generate complete $V_L$ gene fragments. These were digested with BssHII and XbaI, and ligated into a vector containing the constant regions of the human lambda gene.

Example 9

Characterization of Improved IgG In Vitro

Example 9.1

Transient Small-Scale Expression of Binding Proteins

Clones were tested for function in full IgG format following transient expression in cos-7 cells. Each light chain in the set of sixteen test sequences (germlined parental 18A5$V_L$ and L2, L3, L6, L9, L11, L13, L14, L16, L17, L18, L19, L20, L23, L24 and L25) was paired with each heavy chain in the set of five test sequences (H3, H4, H5, and H6, along with $V_H$_P, the germlined parental 18A5 $V_H$ domain). Each plasmid in the pair (1.4 μg) was combined with the TRANSIT® transfection reagent (Mirus, Madison, Wis.) according to the manufacturer's instructions, and DNA:TRANSIT® reagent complexes were added to monolayers of cos-7 cells growing in Dulbecco's Modified Eagle's medium (DMEM)/10% heat-inactivated fetal bovine serum/penicillin/streptomycin/2 mM L-glutamine in 6-well tissue culture plates. After 24 hr, the medium was changed to a serum-free medium (R1CD1), and was then collected 48 hr later. Binding proteins, now comprising full-length antibodies, were quantitated by anti-human IgG ELISA.

Example 9.2

Activity of Anti-IL-21R IgG in Neutralization of Cell Proliferation

The 80 transiently expressed IgGs in serum-free conditioned medium were tested for activity in IL-21-dependent proliferation assays in three cell lines as described above: (1) human IL-21R-BaF3 cells, (2) murine IL-21R-BaF3 cells, and (3) human IL-21R-TF1 cells. All 80 pairs showed neutralization of proliferation of human IL-21R-expressing BaF3 cells, and all pairs except those involving VH4 showed neutralization of human IL-21R-expressing TF1 cells (data not shown). All 80 pairs also showed neutralization of proliferation of murine IL-21R-expressing BaF3 cells, with the strongest neutralization generally associated with light chains paired with the parental heavy chain and the weakest neutralization generally associated with the VH4 heavy chain (data not shown). Neutralization data from the most potent 21 IgG combinations (AbA-AbU) are shown in FIG. 5, and $IC_{50}$ data are summarized in Table 6.

Figure 5A:
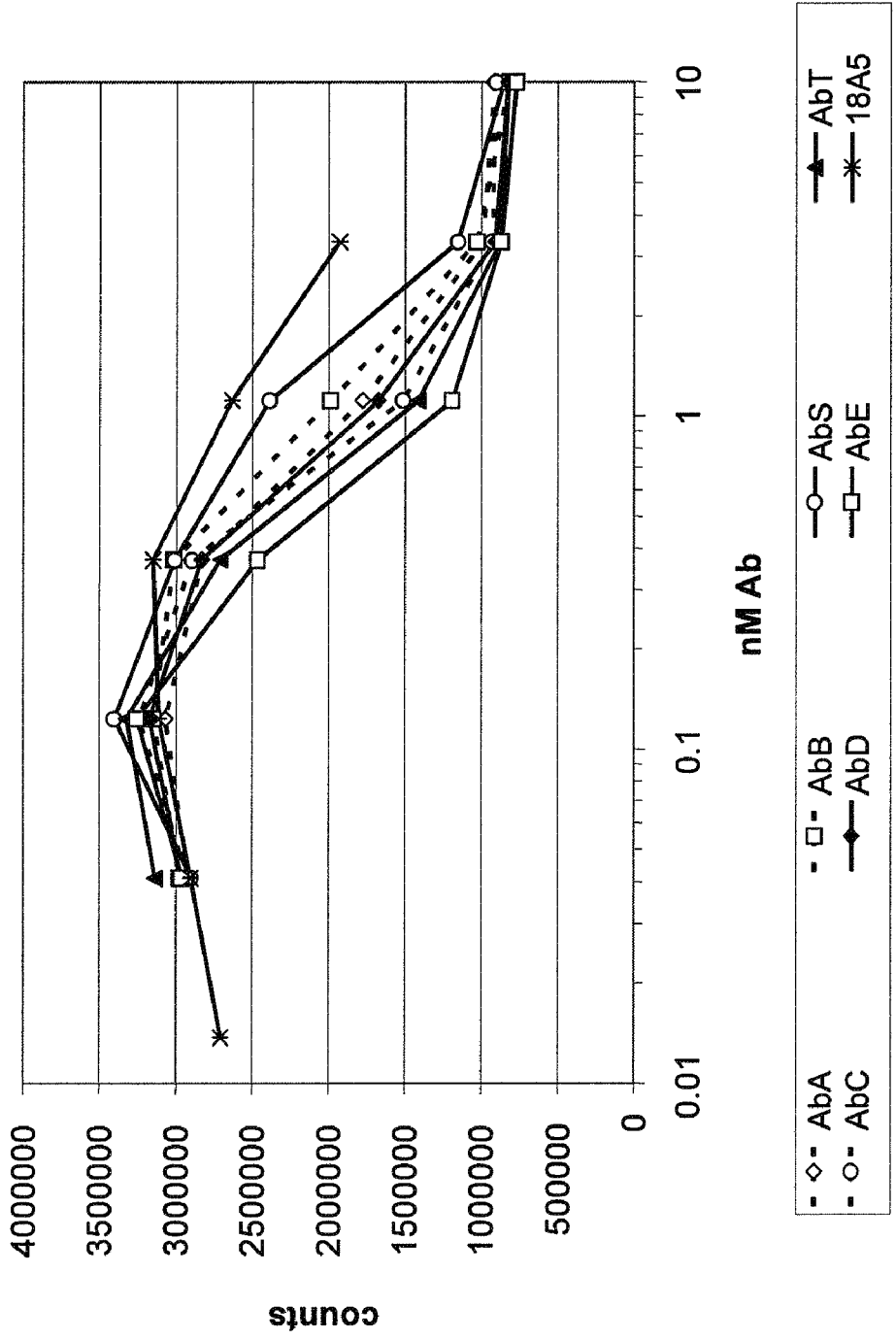
FIG. 5 depicts the neutralization of IL-21-dependent proliferation by 21 heavy chain/light chain pairs. Antibodies, as indicated in the figure, were added to cells. IL-21 was subsequently added, and proliferation measured with CELLTITER-GLO® after 48 hr. Assays were conducted on human IL-21R-BaF3 cells with 100 pg/ml of human IL-21 (FIGS. 5a-c), human IL-21R-TF1 cells with 100 pg/ml of human IL-21 (FIGS. 5d-f), or murine IL-21R-BaF3 cells with 400 pg/ml of murine IL-21 (FIGS. 5g-i).
Figure 5B:
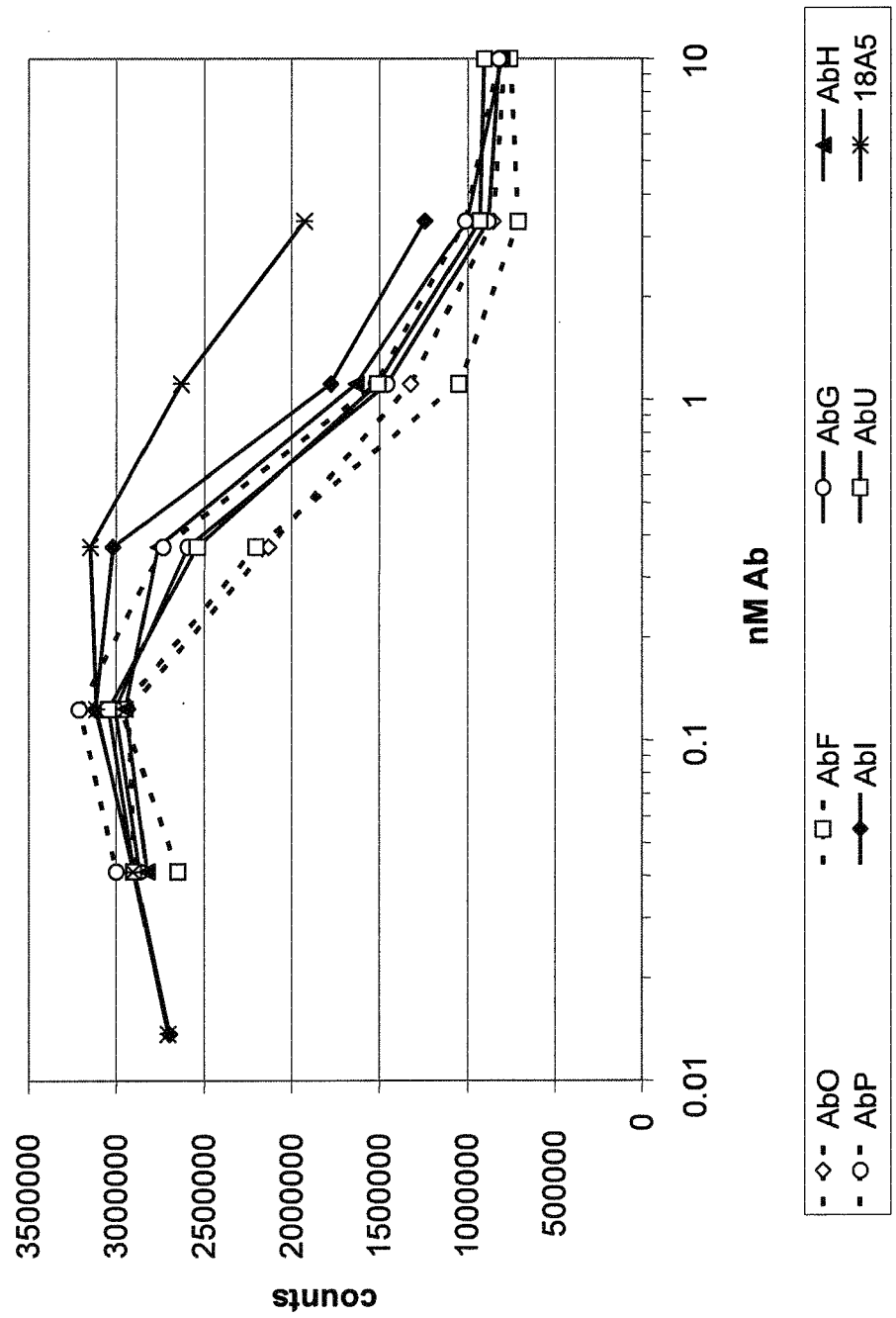
Figure 5C:
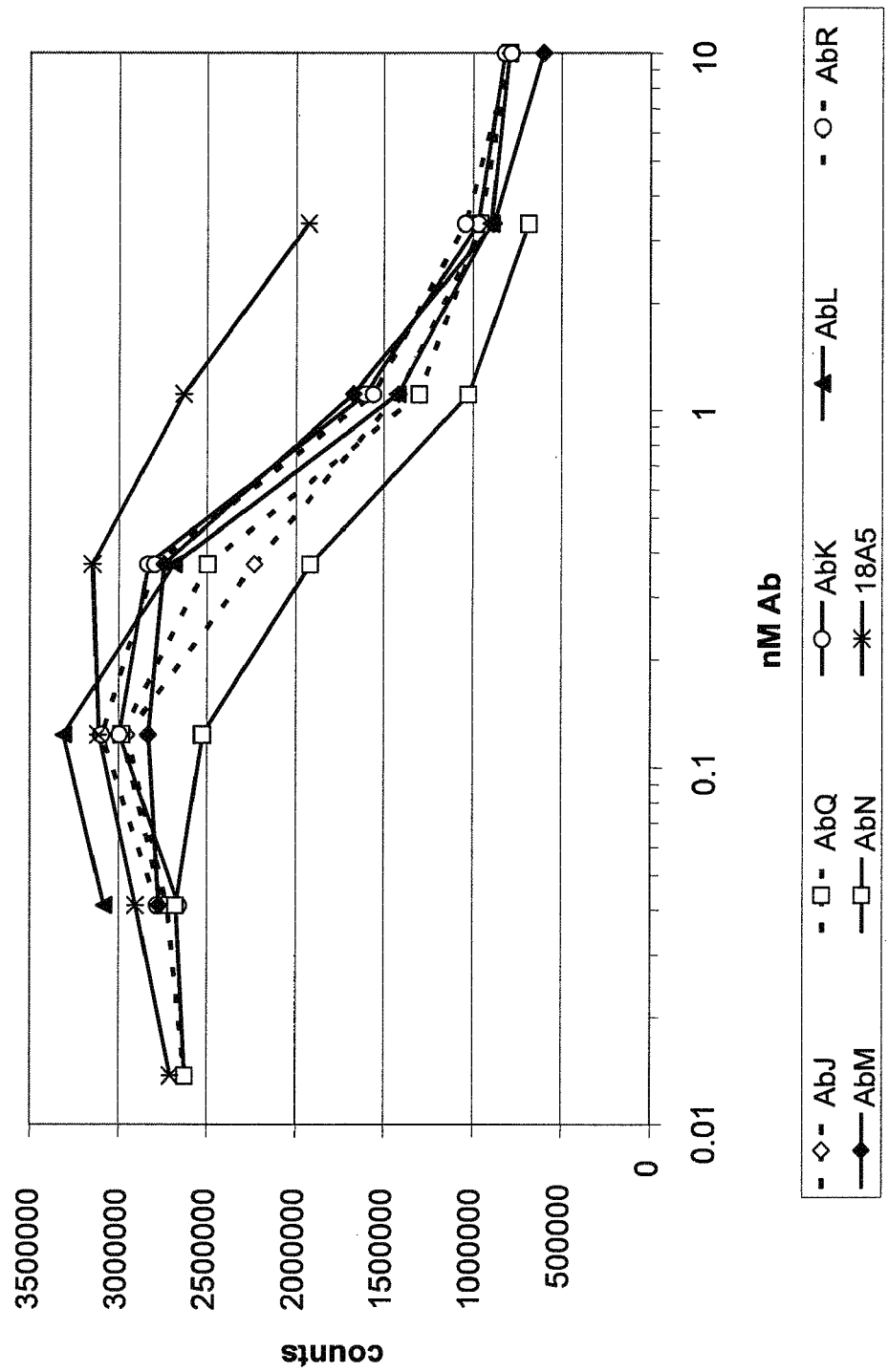
Figure 5E:
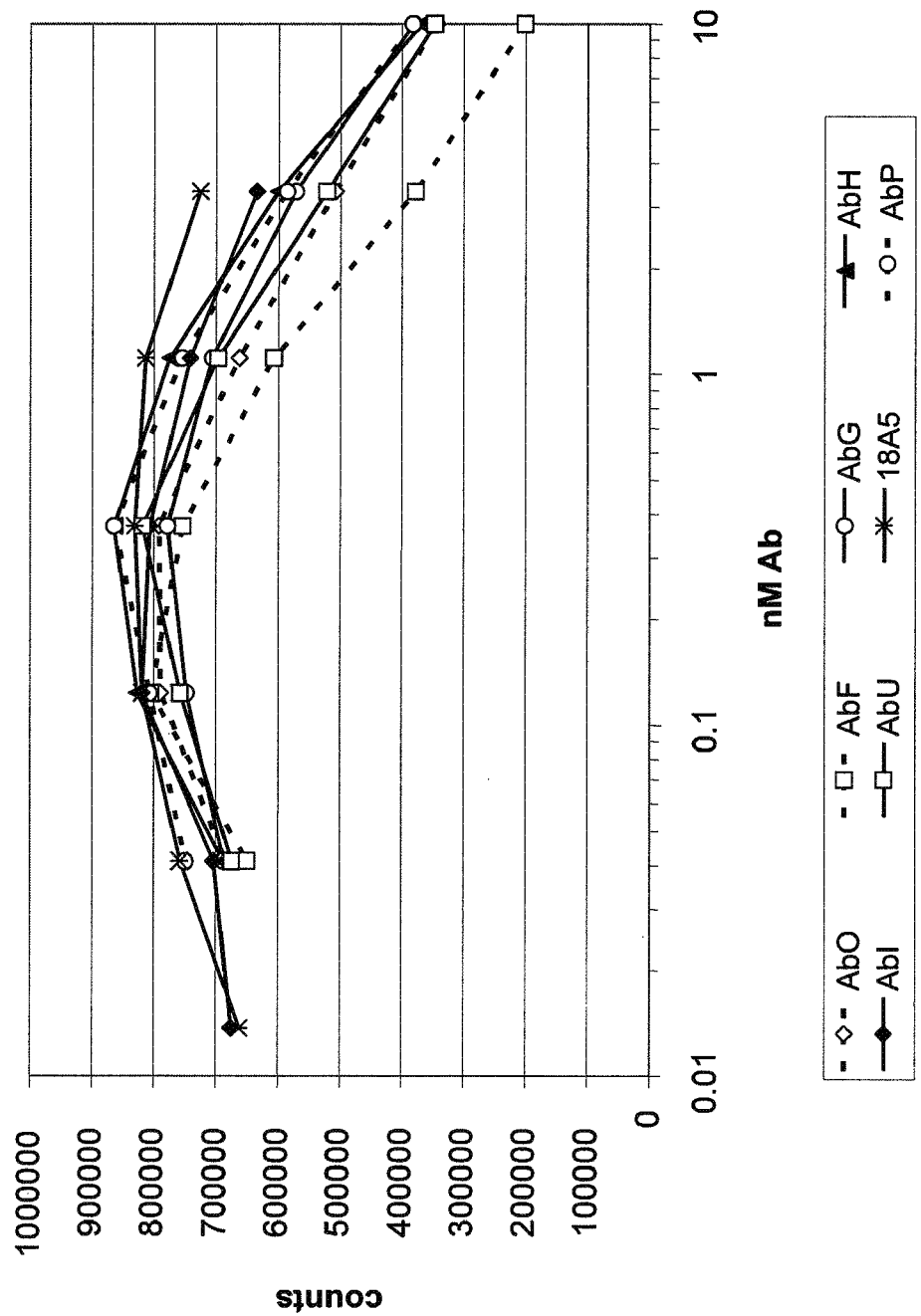
Figure 5G:
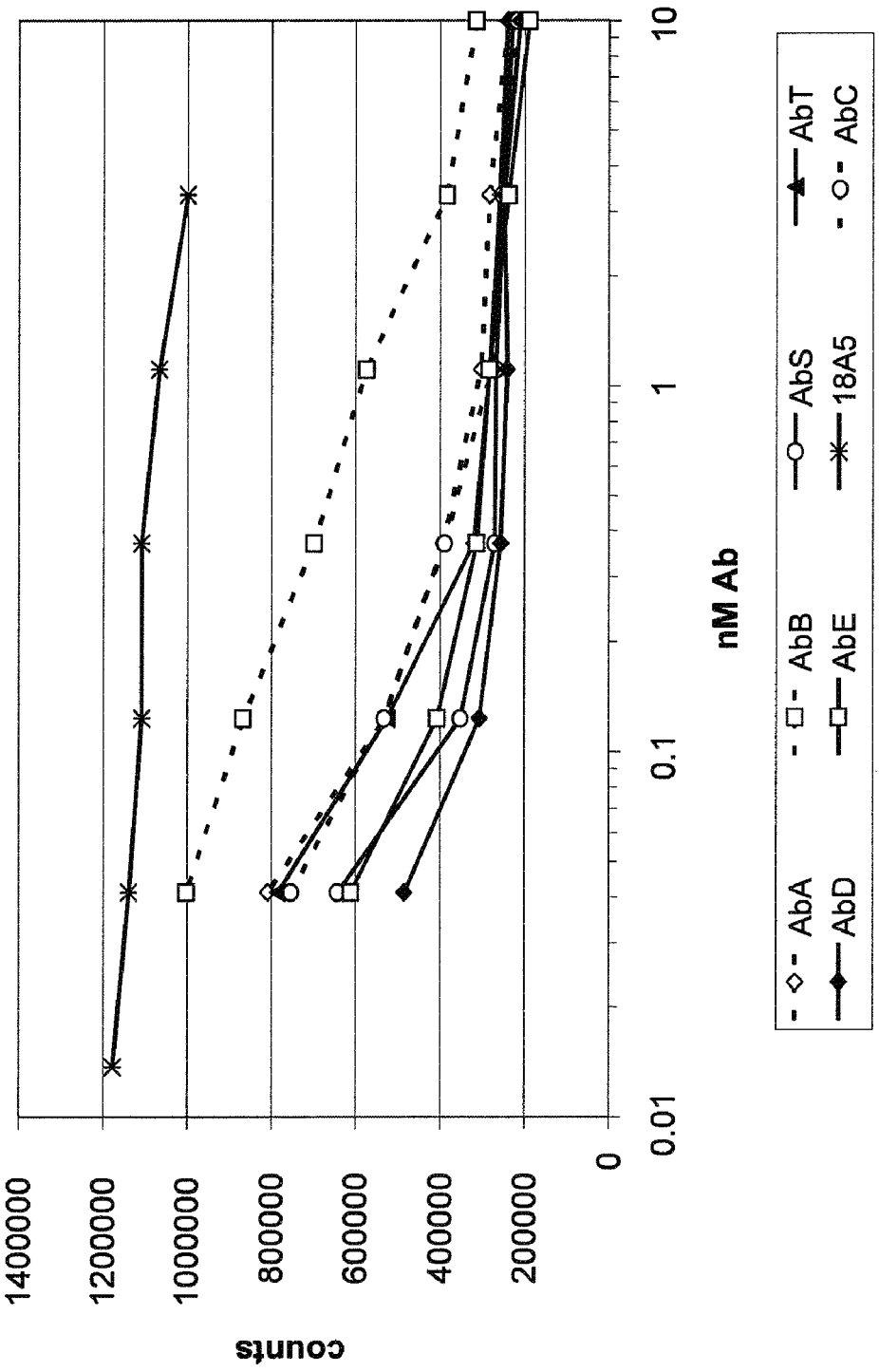
Figure 5I:
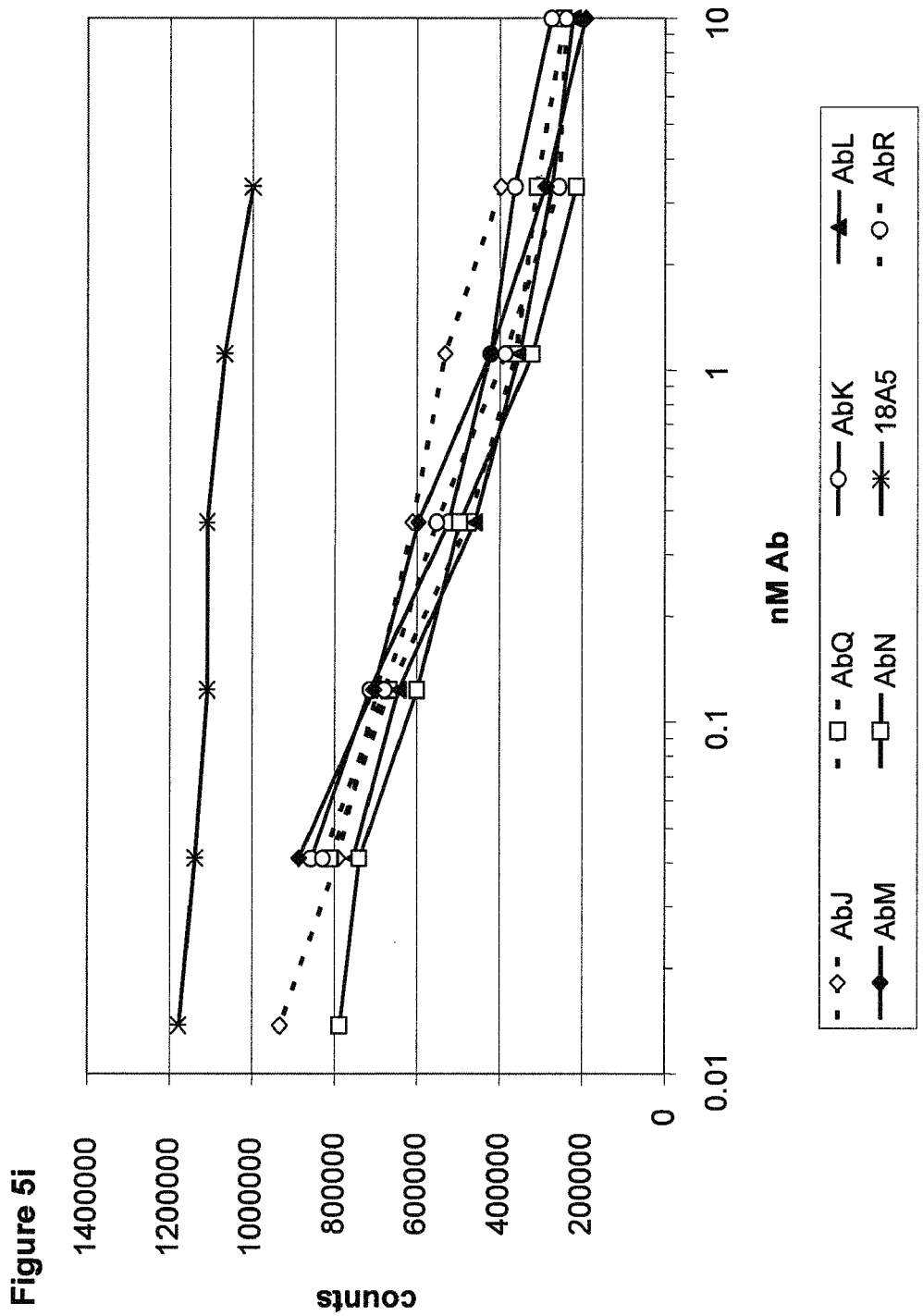
Figure 26A:
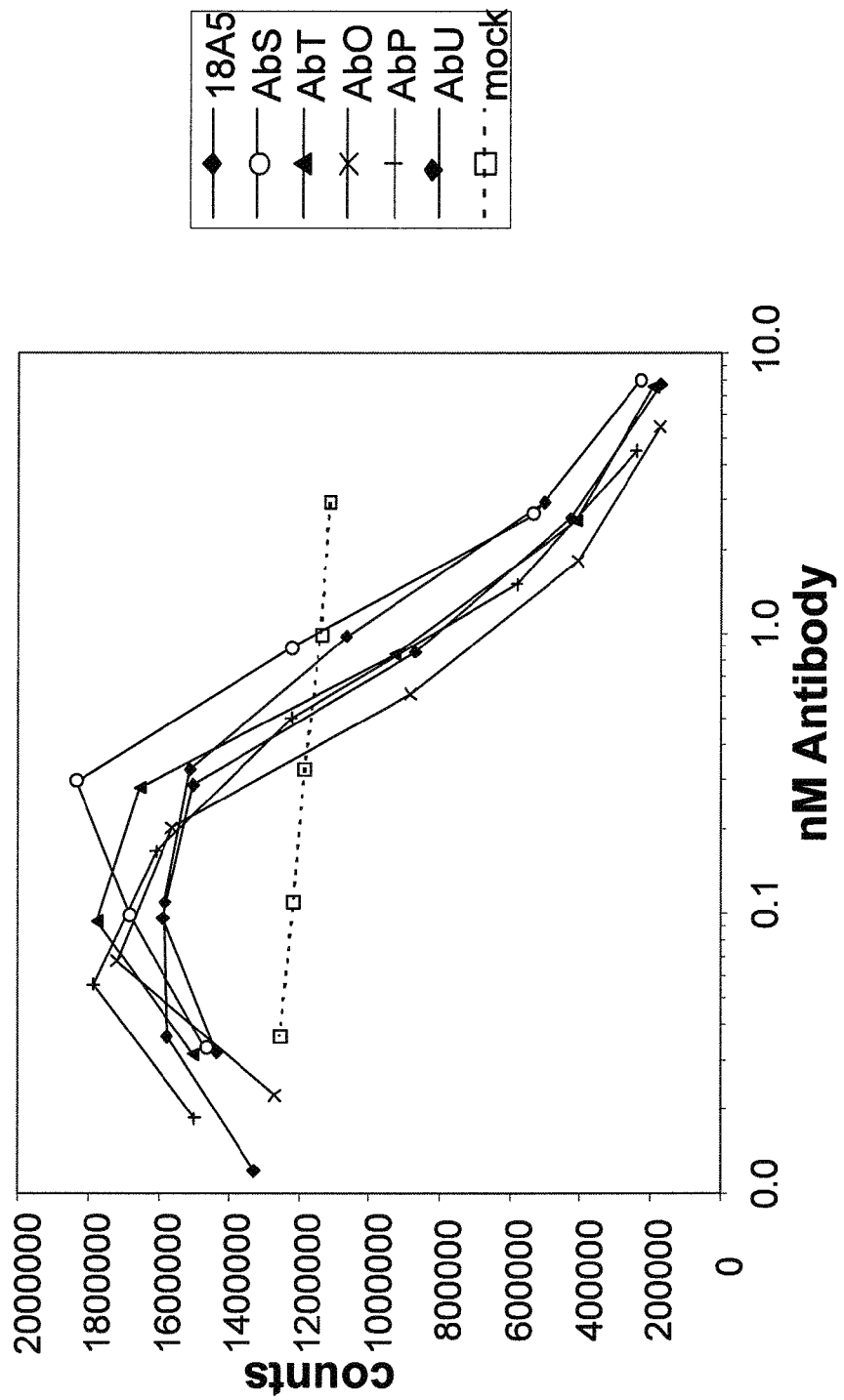
FIGS. 26(a-g) depict results generated from additional studies that were performed similarly to those performed to generate the results shown in FIGS. 5, 11, 12, 13, and 14 (described above).
Figure 26B:
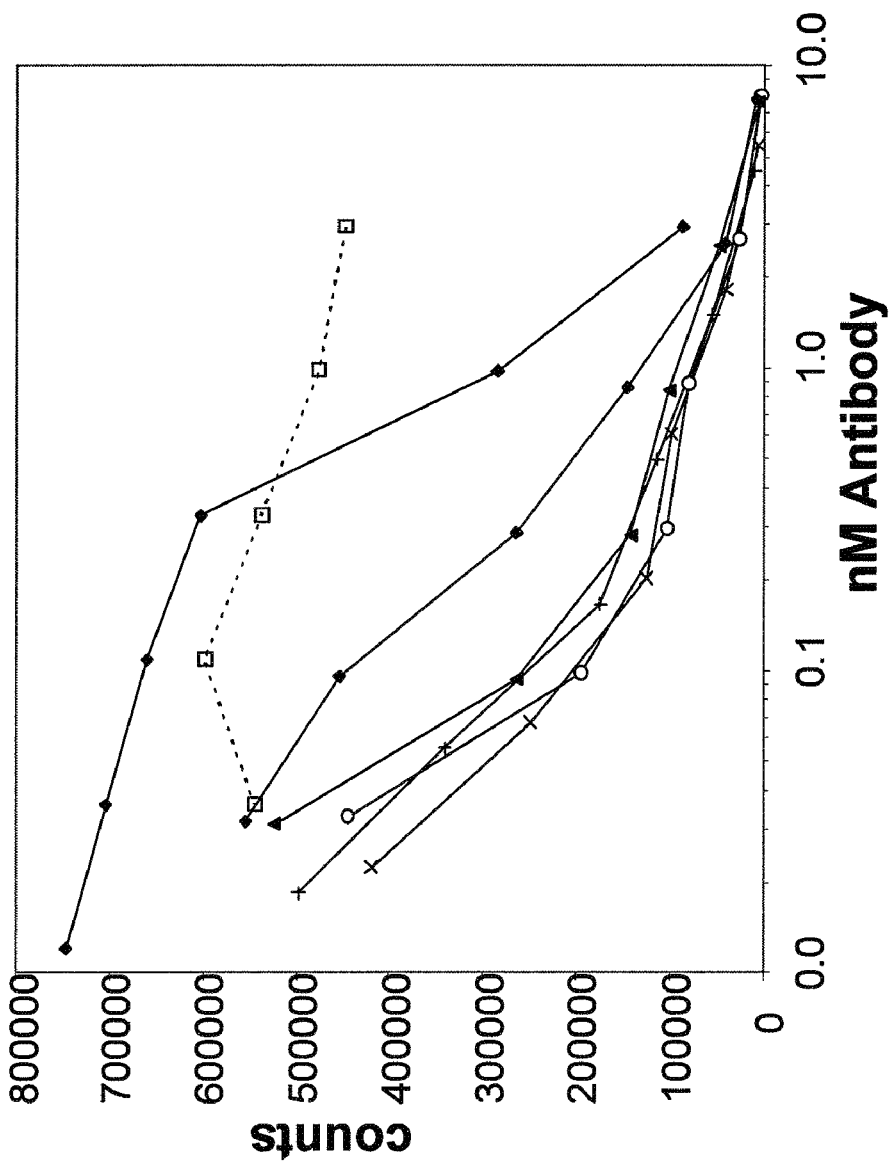
Figure 26C:
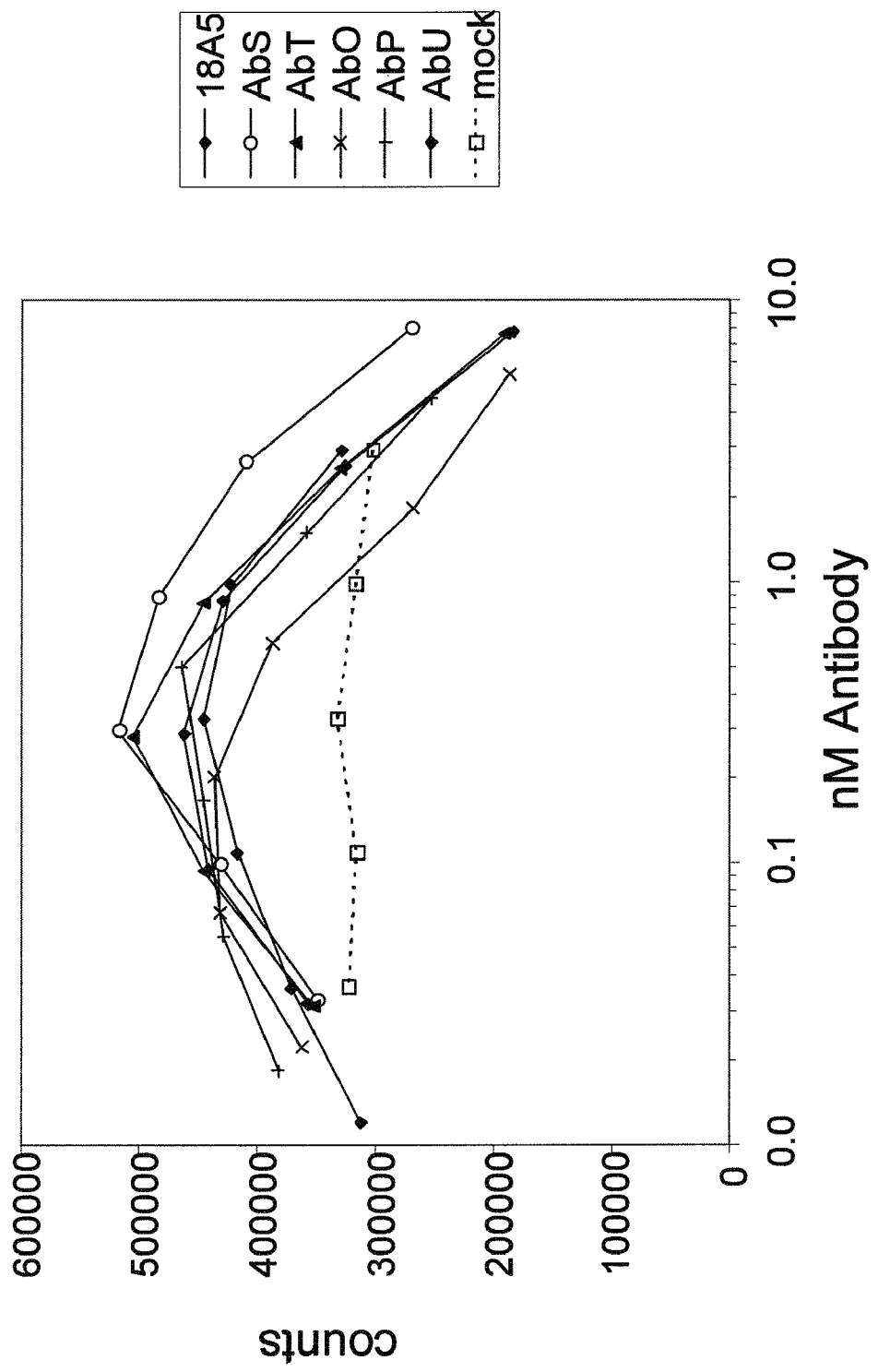

Assays were conducted on human IL-21R-BaF3 cells with 100 pg/ml of human IL-21 (FIGS. 5a-c), human IL-21R-TF1 cells with 100 pg/ml of human IL-21 (FIGS. 5d-f), or murine IL-21R-BaF3 cells with 400 pg/ml of murine IL-21 (FIGS. 5g-i). IL-21 was added to the cells after the indicated antibodies; proliferation was measured with CELLTITER-GLO® after 48 hr. FIGS. 26a-c show additional studies demonstrating similar inhibition in the same three cell lines.

Example 9.3

Anti-IL-21R IgG Binding to Transiently Expressed Rat and Cynomolgus Monkey IL-21R A subset of binding proteins was tested for binding to rat, cynomolgus monkey, human IL-21R, or human IL-2R-γ common subunit expressed transiently on the surfaces of CHO-PA-Dukx cells. Cells were transfected 48 hr prior to the assay. On the day of the assay, cells were washed gently 5× in PBS containing 0.9 mM $CaCl_2$ and 0.45 mM $MgCl_2$ (PBS/CaMg) on an automated plate washer (Titertek, Huntsville, Ala.), and blocked for 1 hr at RT in PBS/CaMg/5% nonfat dry milk. Conditioned media from transiently expressed anti-IL-21R IgGs were serially diluted in blocking buffer and added to the cells in the blocked plates for 1 hr at RT. Cells were washed 5× with PBS/CaMg and then incubated with horseradish peroxidase-conjugated anti-human IgG for 1 hr at RT. Cells were then washed 10× in PBS/CaMg and all of the wash buffer was removed. Cells were incubated with 100 μl TMB until the color reaction reached saturation, stopped with 100 μl of 0.18 M $H_2SO_4$, and read at A450 on a Perkin Elmer ENVISION™ plate reader.

Figure 6B:
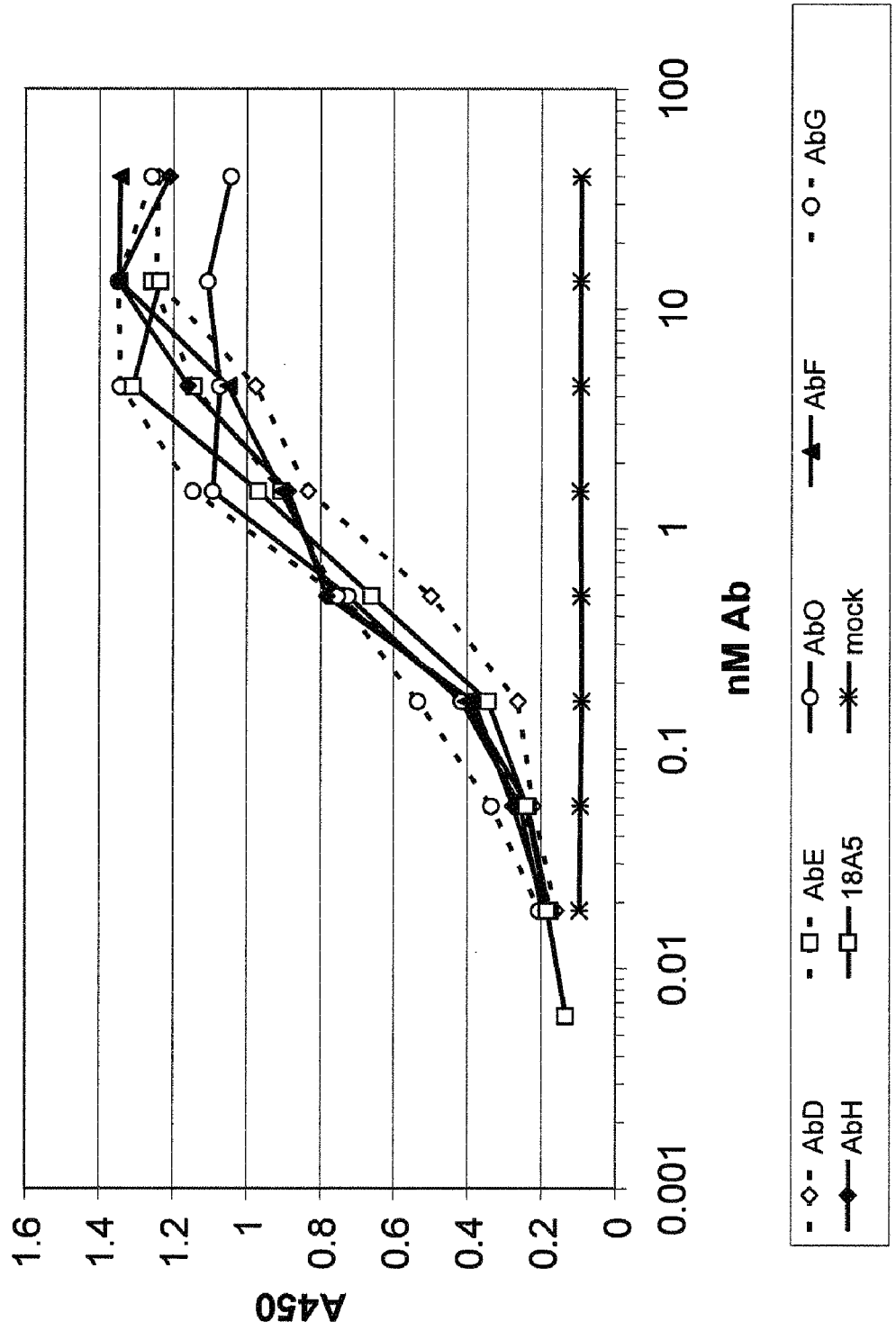
FIG. 6 depicts the binding of 21 anti-IL-21R IgGs to CHO cells transiently expressing human IL-21R (FIGS. 6a-c), rat IL-21R (FIGS. 6d-f), cynomolgus monkey IL-21R (FIGS. 6g-i), and human gamma common chain (FIGS. 6j-l). CHO cells were transiently transfected with IL-21R or the control gamma common chain, and binding was detected with HRP-conjugated anti-human IgG in a cell-based ELISA.
Figure 6C:
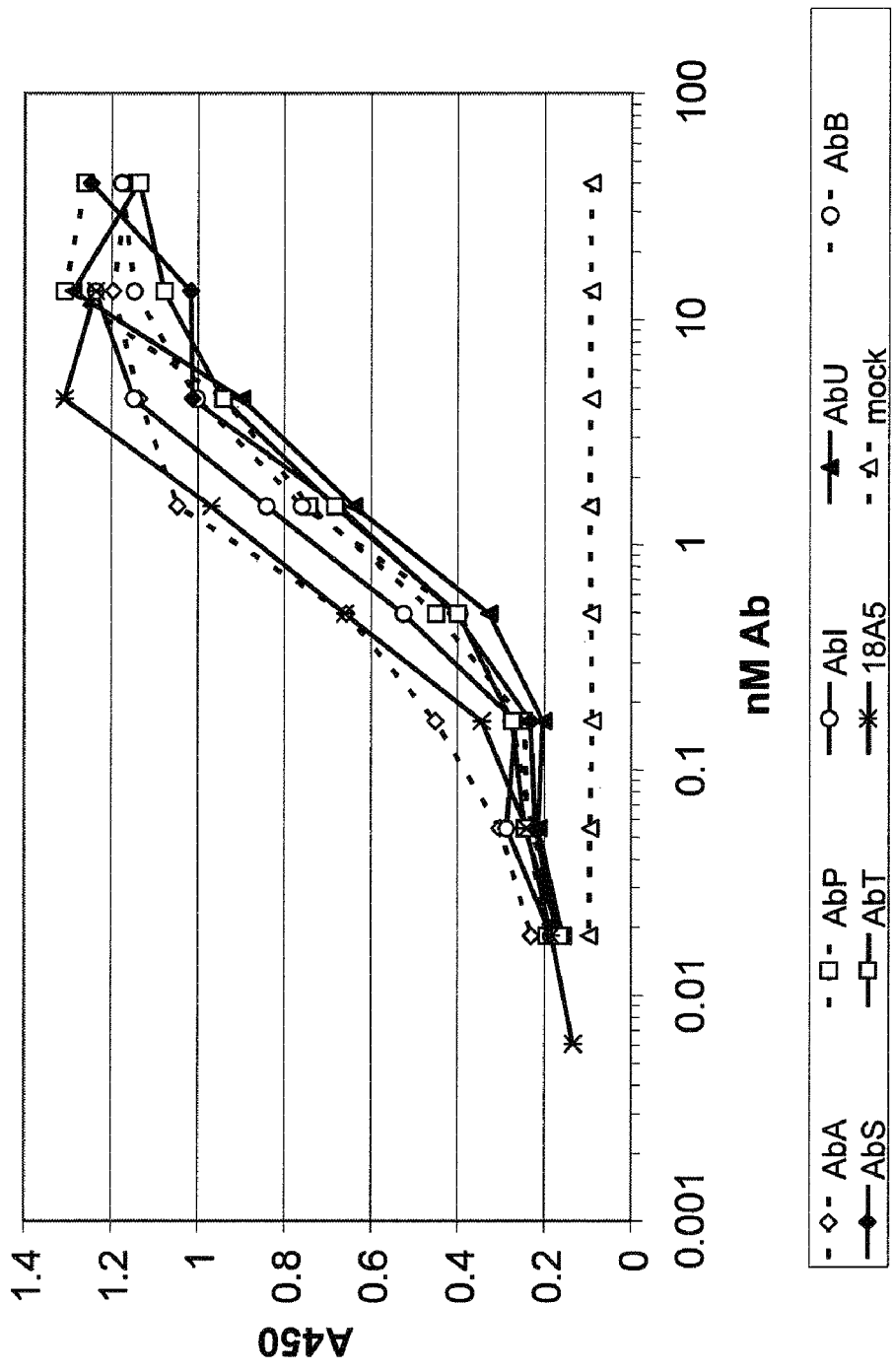
Figure 6D:
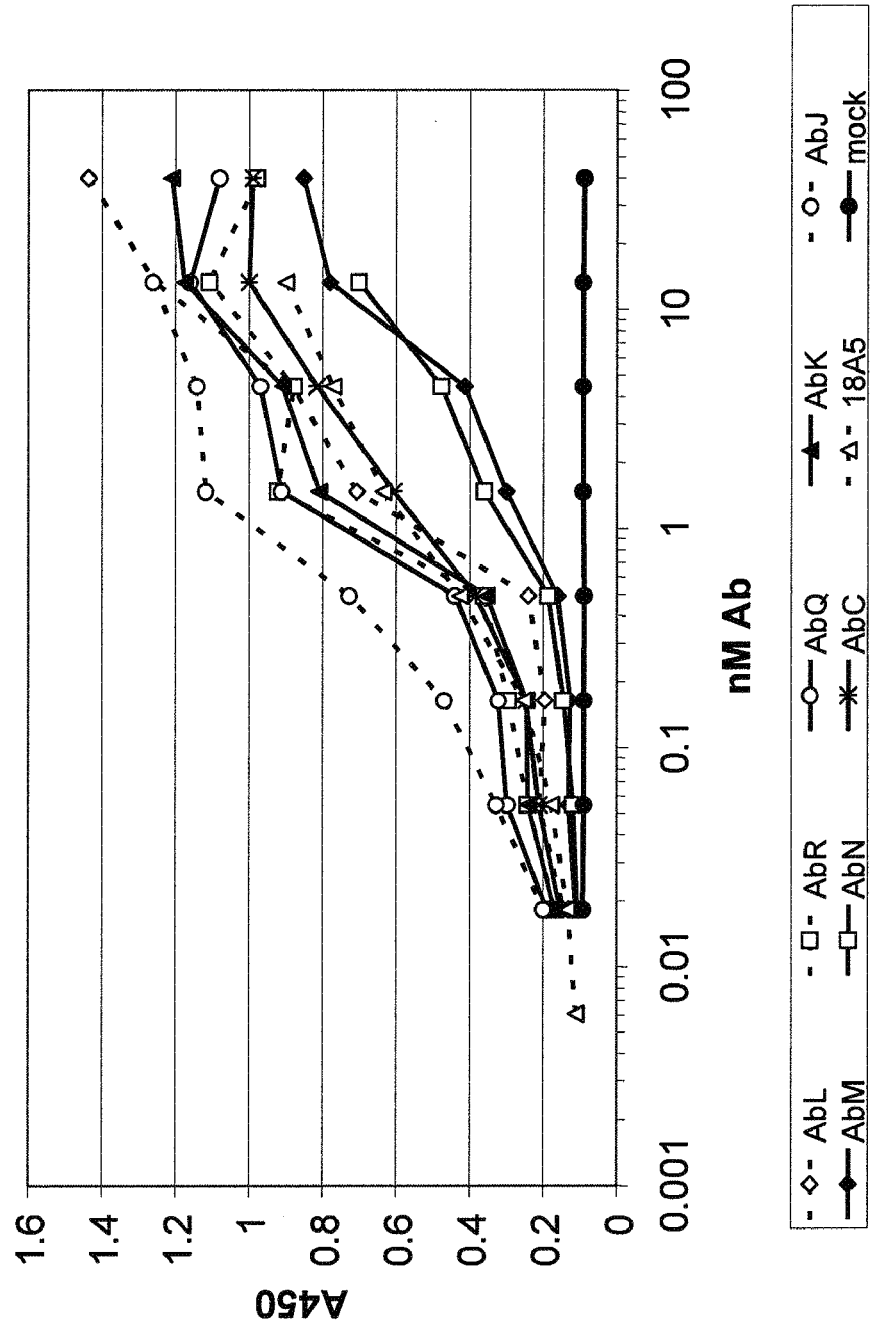
Figure 6E:
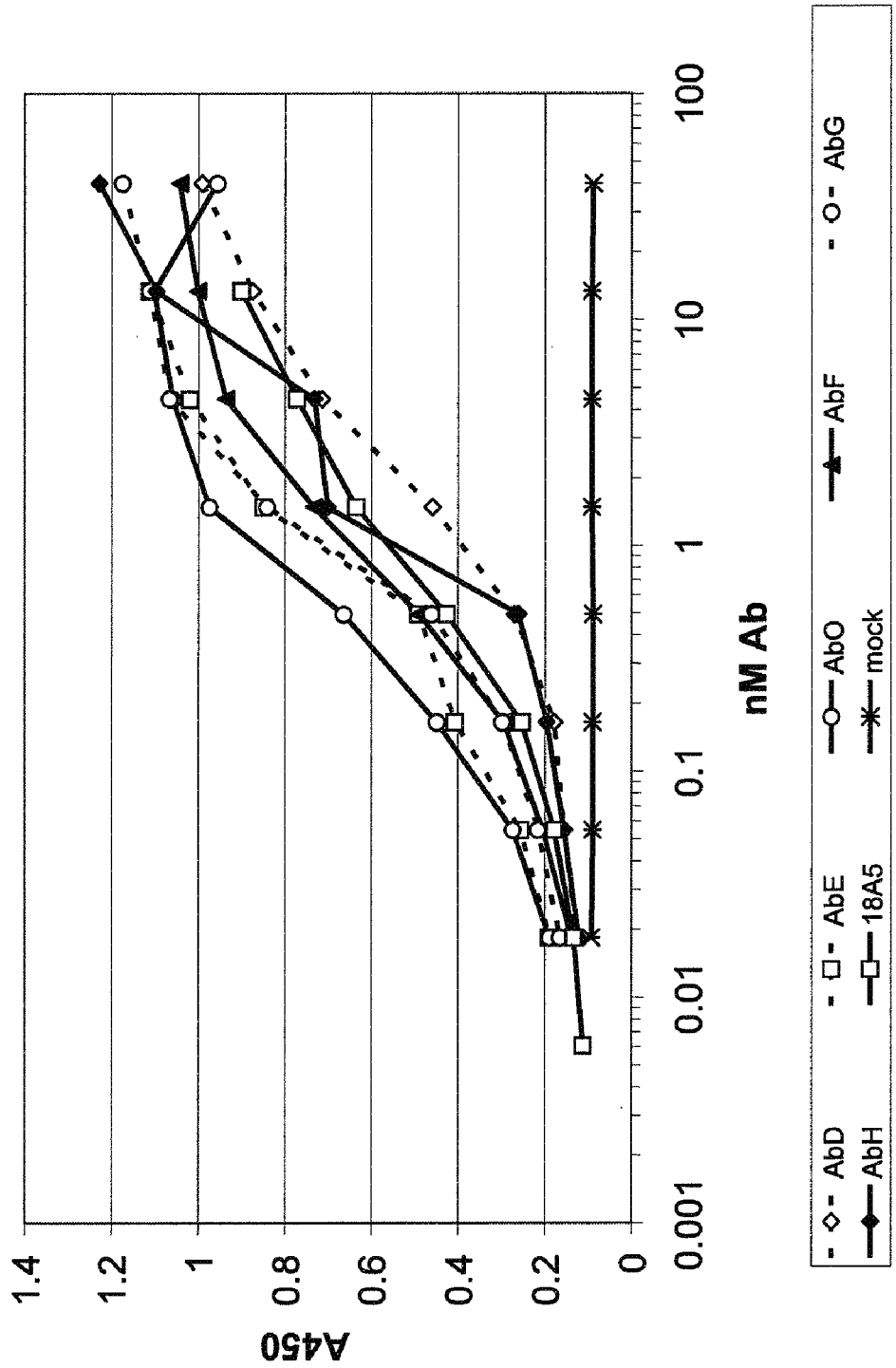
Figure 6F:
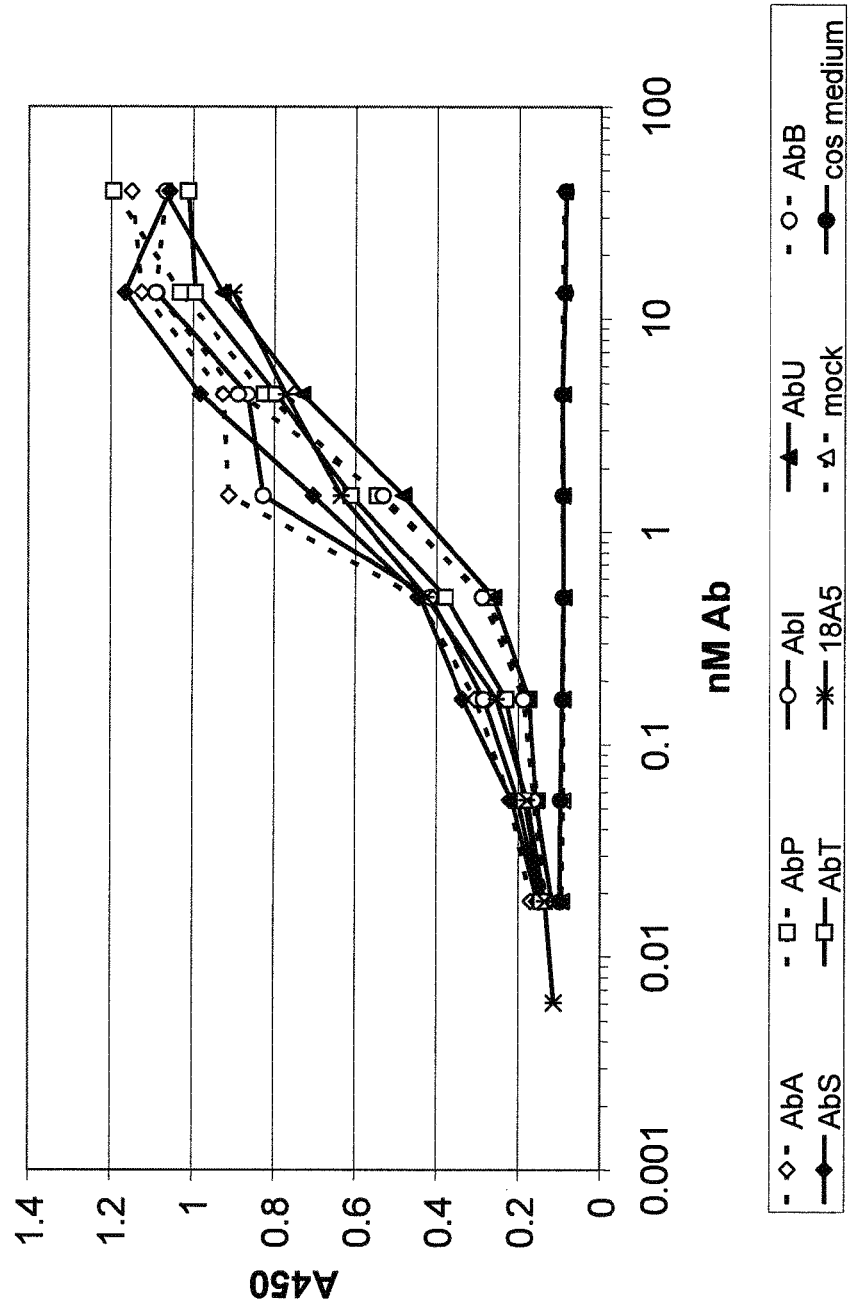
Figure 6G:
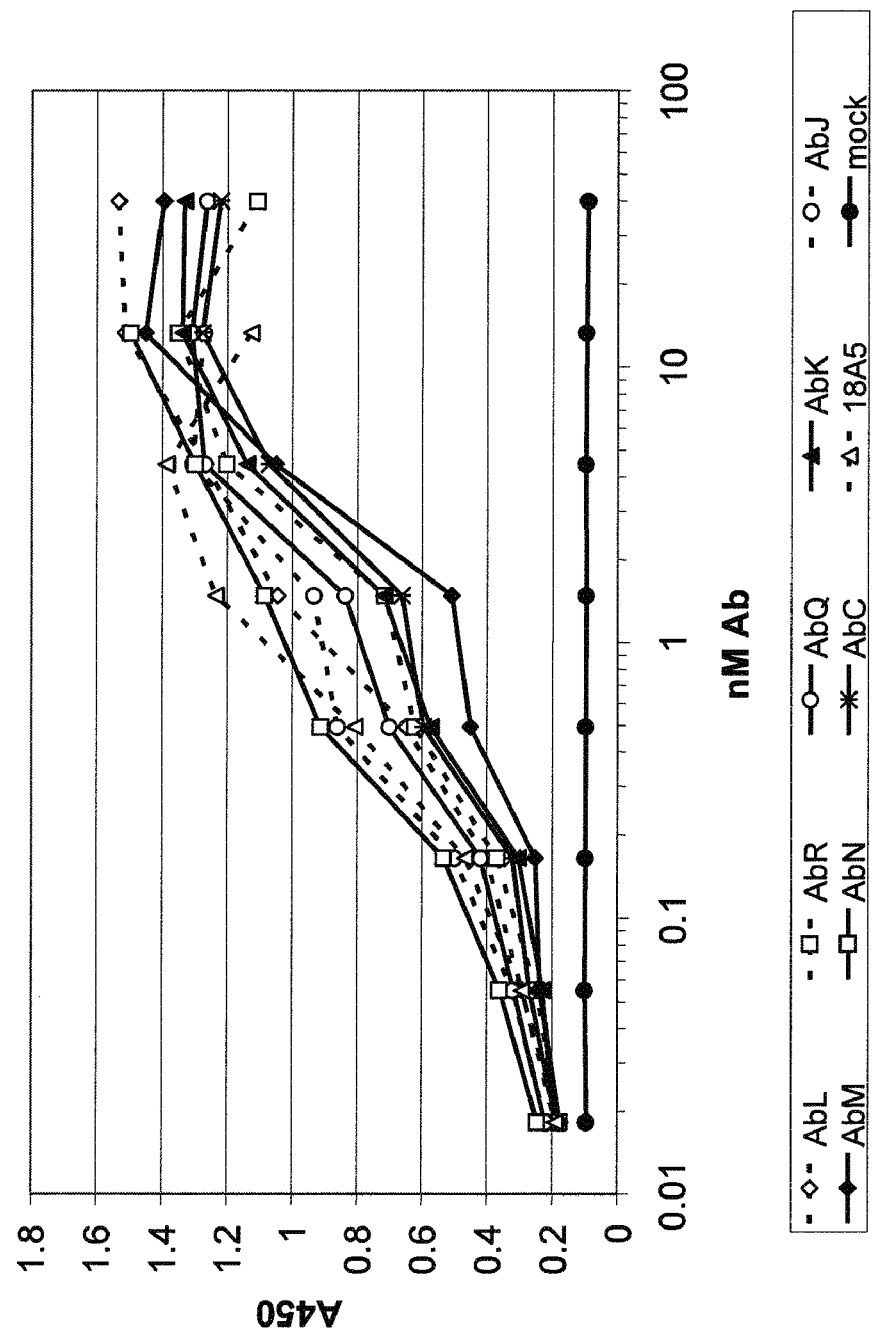
Figure 6H:
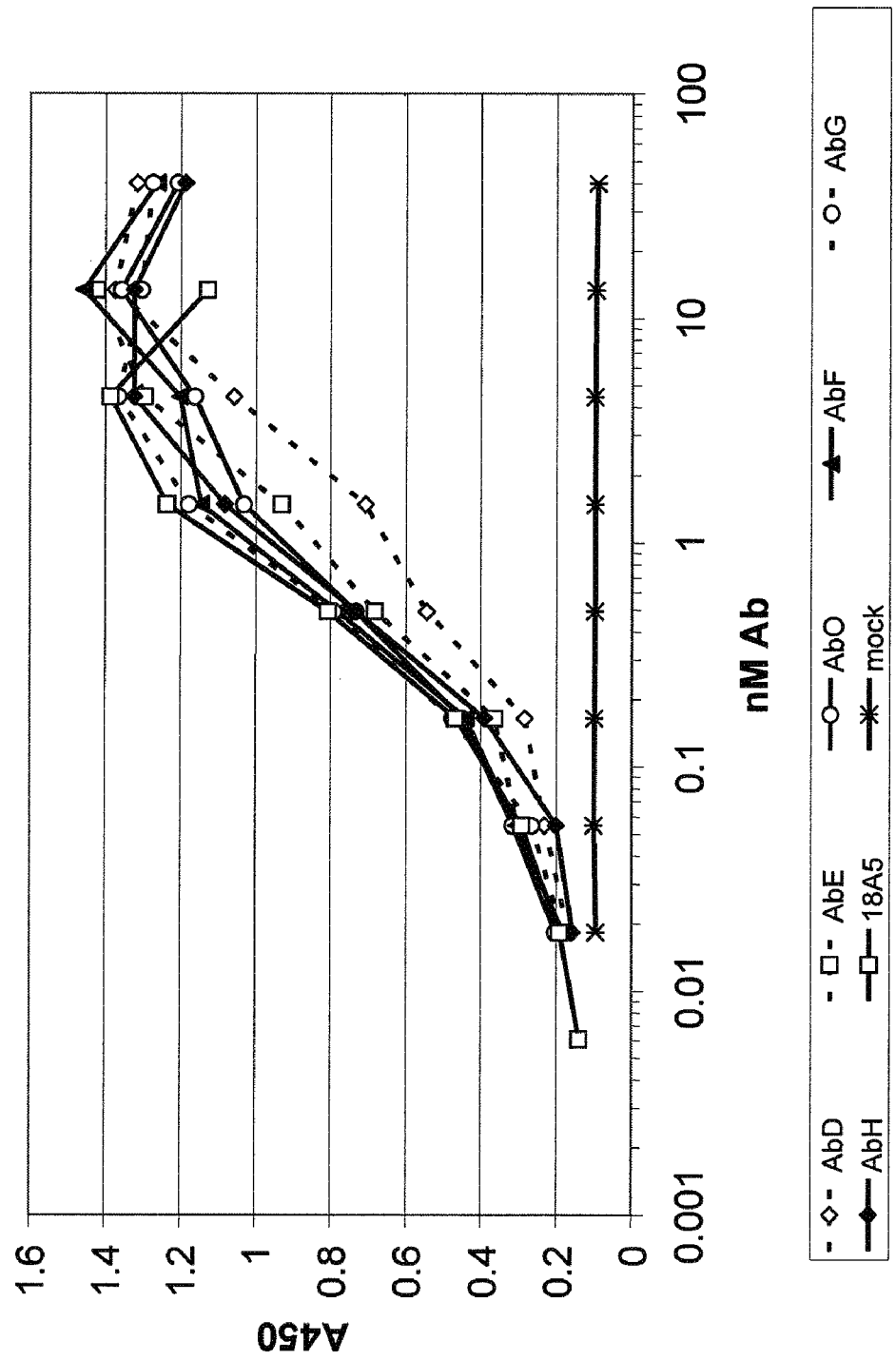
Figure 6I:
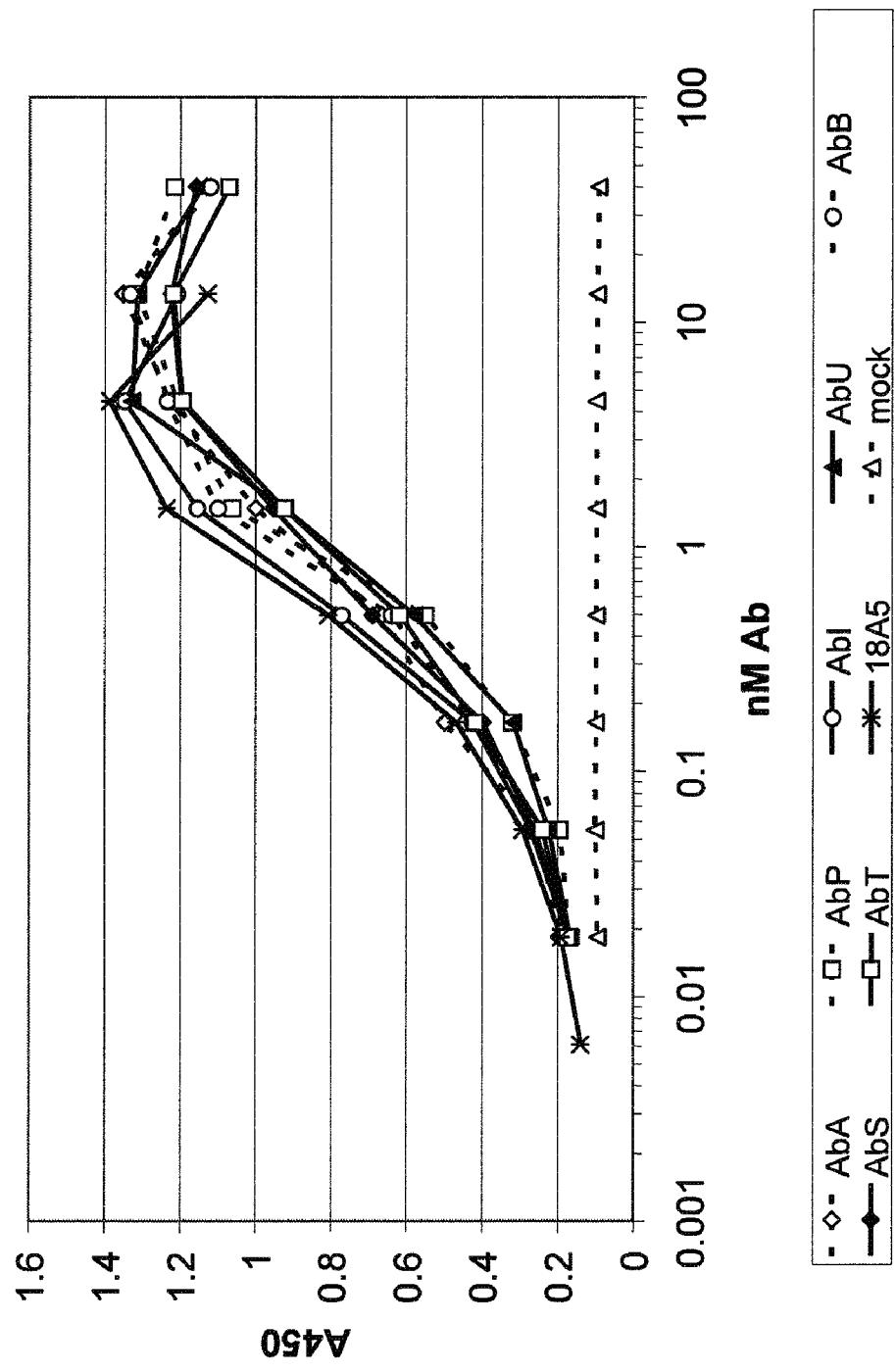
Figure 6J:
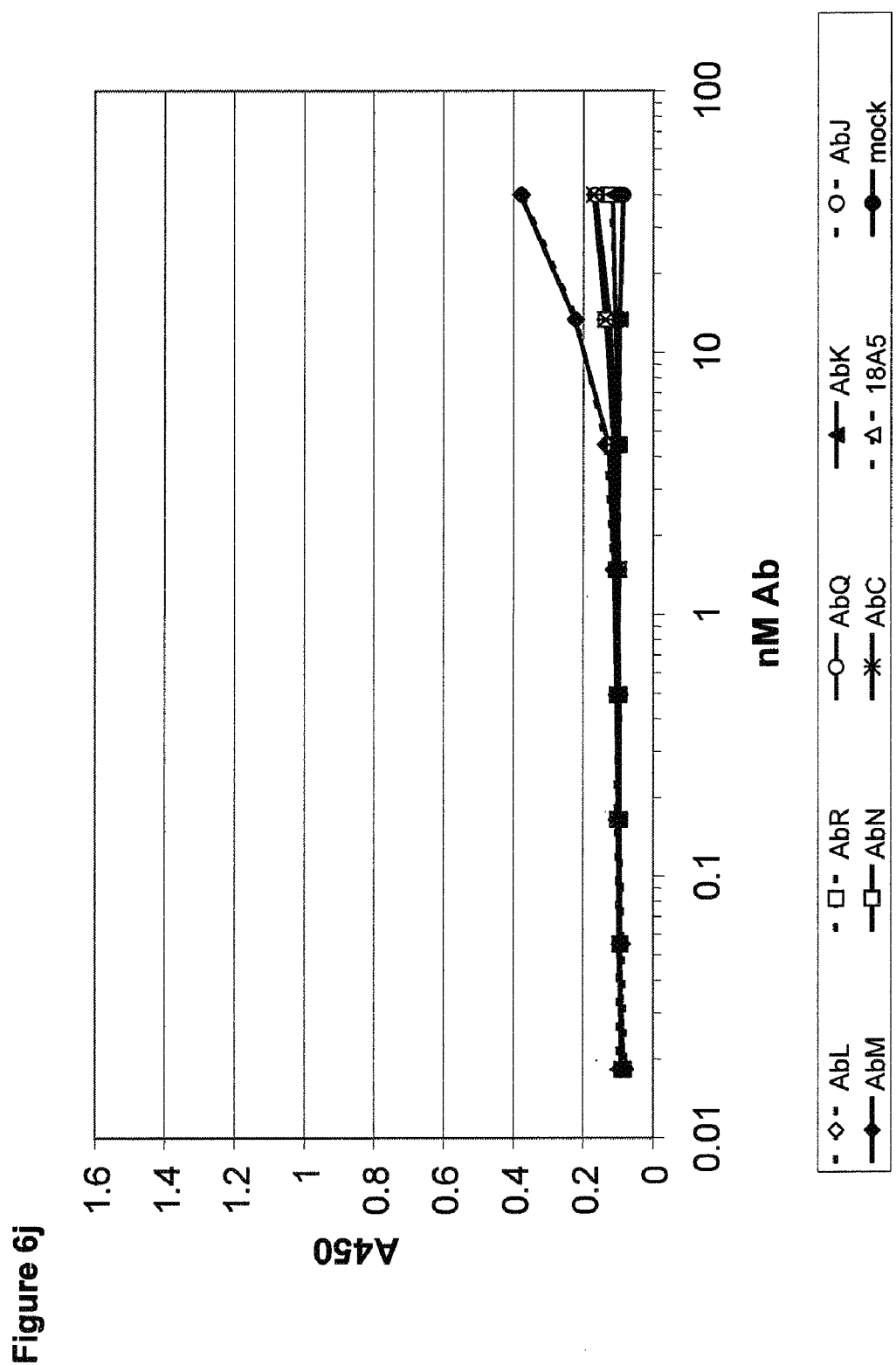
Figure 6K:
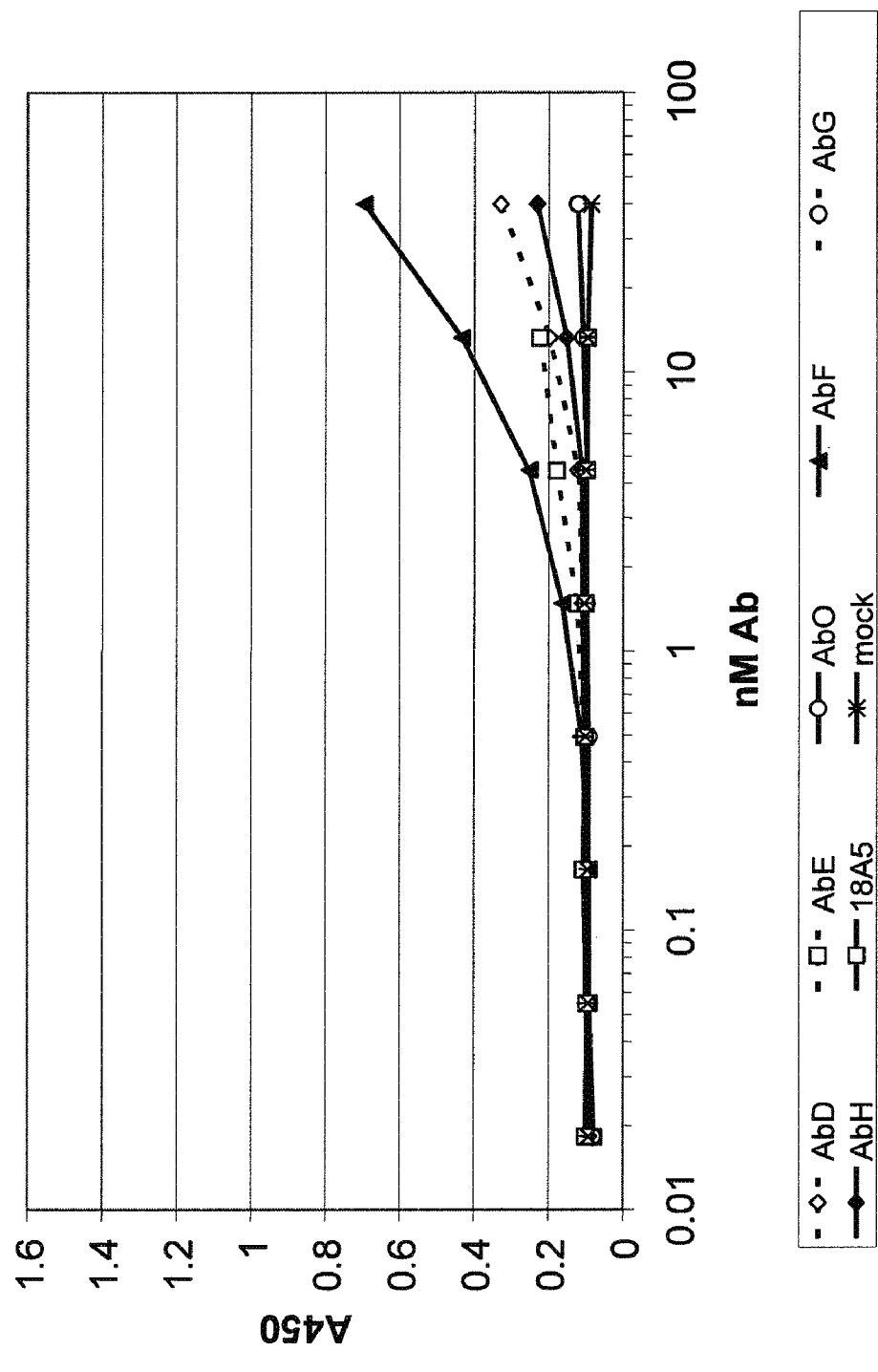
Figure 6I:
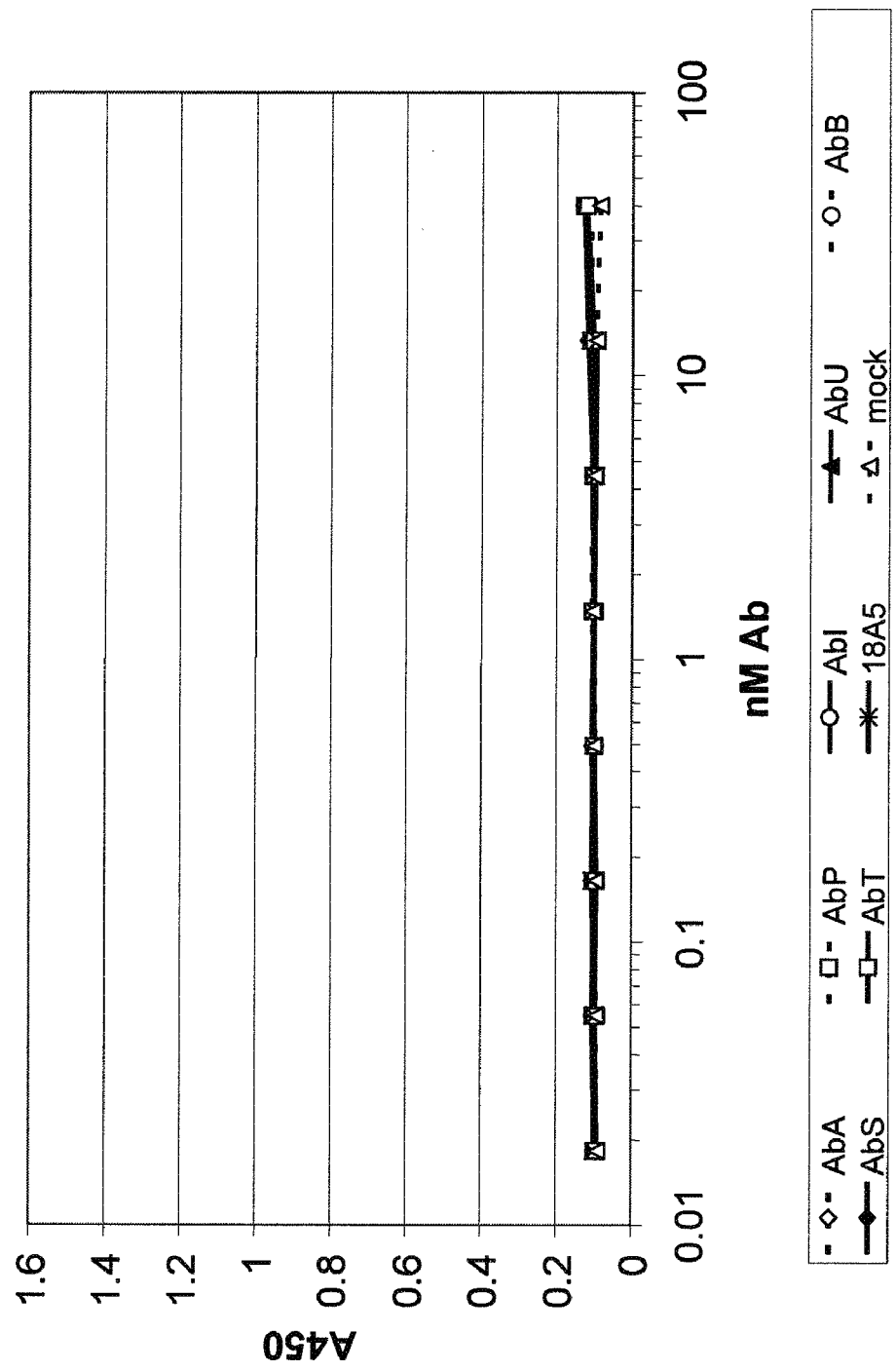

All of the twenty-one IgGs bound to CHO cells transiently expressing human (FIGS. 6a-c), rat (FIGS. 6d-f), or cynomolgus monkey (FIGS. 6g-i) IL-21R. Most showed no binding above background to a control protein (human gamma (γ) common chain) transiently expressed on CHO cells, but a subset of IgGs (AbD, AbE, AbF, AbH, AbL, and AbM) bound above background at 13 nM or greater (FIGS. 6j-1). Data are summarized in Table 6.

human anti-human IL-13 (Wyeth, Cambridge, Mass.)) were diluted in HBS/EP buffer supplemented with 0.2% bovine serum and injected onto all four flow cells of the BIACORE™ chip, capturing 500-700 (RU) of antibody on the species-appropriate capture antibody. Following a 5 sec washing period, 50 nM solutions of a positive control protein (murine IL-21R-H/F), two human proteins related to IL-21R (human IL-2Rβ and human sIL-4R(R&D Systems)), or an unrelated

TABLE 6

Summary of Neutralization of Human and Murine IL-21R Activity in Cell-proliferation Assays and Binding to Human, Rat, and Cynomolgus Monkey IL-21R Expressed on CHO Cells

| Binding Protein | Human IL-21R-BaF3 Proliferation IC$_{50}$ (nM) | Human IL-21R-TF1 Proliferation IC$_{50}$ (nM) | Murine IL-21R-BaF3 Proliferation IC$_{50}$ (nM) | Human IL-21R-Binding (13 nM Ab in Cell ELISA; A450) | Rat IL-21R-Binding (13 nM Ab in Cell ELISA; A450) | Monkey IL-21R-Binding (13 nM Ab in Cell ELISA; A450) | Human γ-Common Binding (13 nM Ab in Cell ELISA; A450) |
|---|---|---|---|---|---|---|---|
| AbA | 0.97 | 3.80 | 0.08 | 1.196 | 1.124 | 1.352 | 0.111 |
| AbB | 1.14 | 3.34 | 0.421 | 1.147 | 1.09 | 1.333 | 0.107 |
| AbC | 0.82 | 3.36 | 0.03 | 1.218 | 0.999 | 1.277 | 0.137 |
| AbD | 0.91 | 2.67 | 0.01 | 1.247 | 0.874 | 1.375 | 0.197 |
| AbE | 0.56 | 2.28 | 0.04 | 1.257 | 1.111 | 1.423 | 0.223 |
| AbF | 0.54 | 2.41 | 0.304 | 1.347 | 1.001 | 1.458 | 0.433 |
| AbG | 0.77 | 3.84 | 0.07 | 1.35 | 1.112 | 1.304 | 0.108 |
| AbH | 0.94 | 3.64 | 0.327 | 1.35 | 1.097 | 1.324 | 0.152 |
| AbI | 1.00 | 3.80 | 0.224 | 1.237 | 1.088 | 1.209 | 0.107 |
| AbJ | 0.65 | 4.60 | 0.4 | 1.217 | 1.261 | 1.273 | 0.126 |
| AbK | 0.98 | 4.00 | 0.079 | 1.364 | 1.175 | 1.338 | 0.108 |
| AbL | 0.68 | 4.25 | 0.227 | 1.454 | 1.257 | 1.514 | 0.219 |
| AbM | 1.08 | 4.22 | 0.125 | 1.197 | 0.78 | 1.45 | 0.224 |
| AbN | 0.50 | 1.59 | 0.435 | 1.214 | 0.702 | 1.497 | 0.136 |
| AbO | 0.52 | 2.91 | 0.065 | 1.107 | 1.101 | 1.358 | 0.108 |
| AbP | 0.75 | 3.48 | 0.03 | 1.308 | 1.03 | 1.313 | 0.112 |
| AbQ | 0.68 | 4.62 | 0.153 | 1.255 | 1.161 | 1.31 | 0.125 |
| AbR | 0.87 | 3.94 | 0.302 | 1.334 | 1.108 | 1.35 | 0.109 |
| AbS | 1.53 | 5.00 | 0.04 | 1.017 | 1.166 | 1.224 | 0.118 |
| AbT | 0.67 | 3.26 | 0.093 | 1.078 | 0.994 | 1.219 | 0.102 |
| AbU | 0.73 | 3.13 | 0.184 | 1.289 | 0.927 | 1.314 | 0.104 |

Example 9.4

BIACORE™ Analysis of Selectivity of Anti-IL-21R IgG Binding to Human IL-21R

The specificity of binding of a subset of transiently expressed anti-IL-21R binding proteins (here antibodies) was tested on a BIACORE™ 2000 surface plasmon resonance instrument. Anti-human-IgG, anti-murine immunoglobulin antibodies, and murine IL-21R-H/F were immobilized onto a research-grade carboxymethyl-dextran chip (CM5) using standard amine coupling. The sensor chip surface was activated with EDC/NHS for 7 min at a flow rate of 20 μl/min. The first flow cell was used as reference surface to correct for bulk refractive index, matrix effects, and nonspecific binding. Capture antibodies (7,150 resonance units (RU) of anti-human-Fc antibody (Invitrogen Corporation, Carlsbad, Calif.) on flow cell 2 and 7,500 RU of anti-murine-Fc antibody on flow cell 3) were diluted to 10 μg/ml in sodium acetate buffer (pH 5.0) and injected over the activated surface. Remaining activated groups were blocked with 1.0 M ethanolamine (pH 8.0). The molecular weights of the anti-human IgG and the anti-murine IgG were both 150 kD, and the molecular weight of the IL-21R monomer was 27 kD.

Conditioned media containing anti-IL-21R antibodies and antibody controls (murine anti-human IL-2Rβ and murine anti-human IL-4R (R&D Systems, Minneapolis, Minn.);

His/FLAG-tagged protein (human IL-13-H/F) were injected over the captured antibodies on the chip. The association and dissociation phases were monitored for 120 and 180 sec, respectively, followed by two 5 μl injections of glycine (pH 1.5) to regenerate a fully active capturing surface. All binding experiments were done at 25° C. in HBS/EP buffer. Blank and buffer effects were subtracted for each sensorgram using double referencing.

Figure 7B:
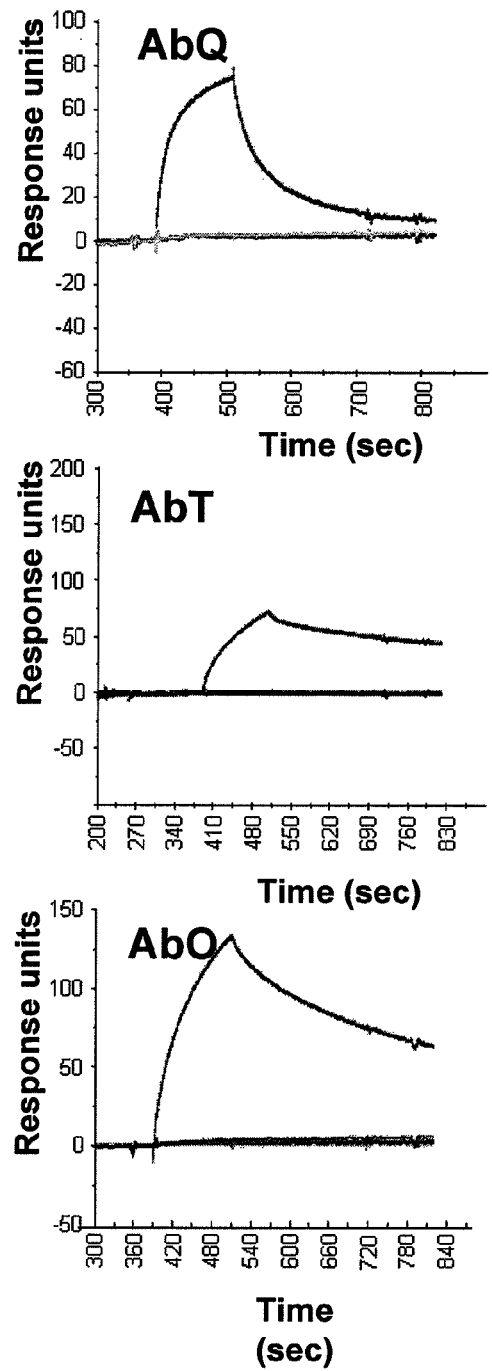
FIG. 7b, AbQ, AbT, AbO.
Figure 7C:
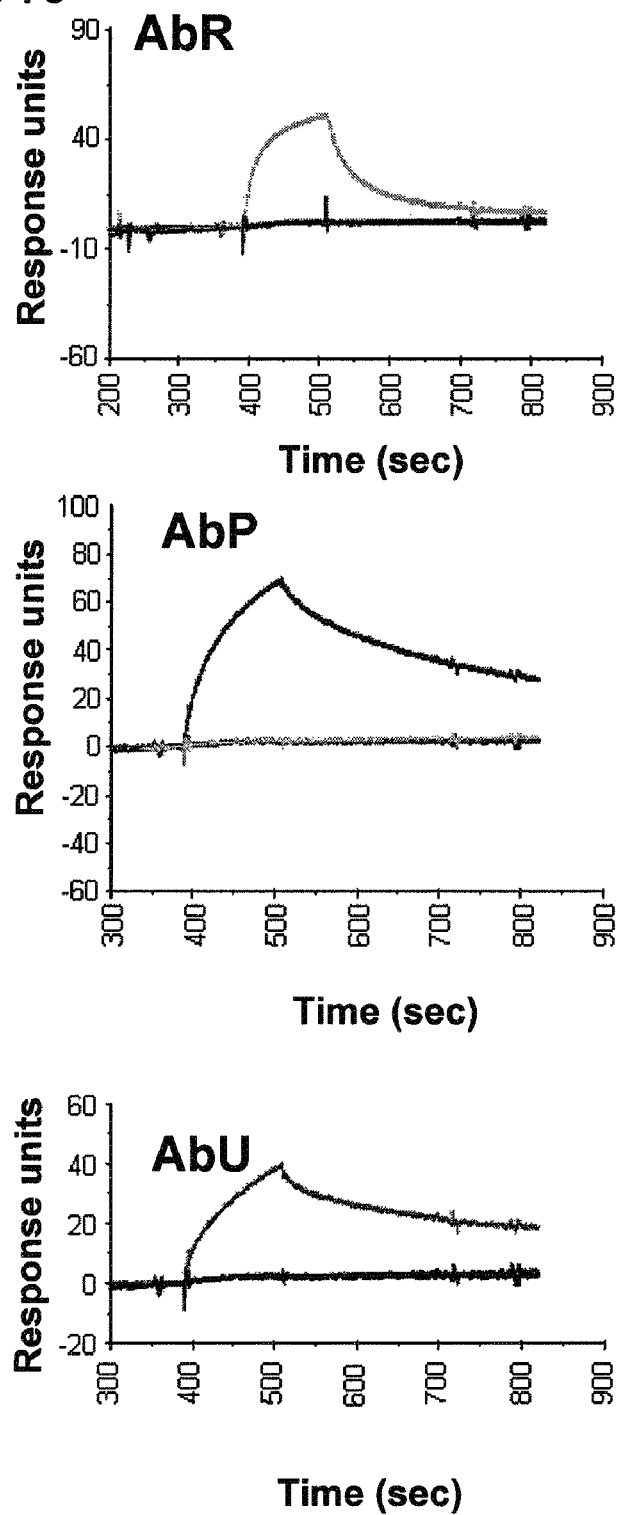
FIG. 7c, AbR, AbP, and AbU), measured by surface plasmon resonance. The anti-IL-21R antibodies were captured on anti-human IgG, and subsequent binding to either murine IL-21R-H/F, human IL-13-H/F, human IL-2Rβ, or human soluble IL-4R was measured in a BIACORE™ instrument (GE Healthcare, Piscataway, N.J.).

All of the anti-IL-21R antibodies tested (18A5 antibody and AbA-AbU) showed clear binding to murine IL-21R, but no binding to the IL-21R-related proteins human IL-2Rβ and human soluble IL-4R, or to the unrelated His/FLAG-tagged protein human IL-13-His/FLAG (FIGS. 7a-c). Controls indicated that IL-2Rβ and human soluble IL-4R could be captured by specific anti-IL-2Rβ and anti-IL-4R antibodies (FIG. 7d).

Example 9.5

Purification of Transiently Expressed Antibodies

Seven antibodies (human IgG1 triple-mutant versions: AbS, AbT, AbO, AbP, and AbU; and double-mutant versions: AbQ and AbR) were transiently expressed in cos-7 cells and purified for further analysis. In addition, three versions of AbT with human IgG tails expected to have different levels of Fc receptor binding (wild-type IgG1, IgG4, and IgG1 double-mutants) were also prepared. The TRANSIT® protocol described above was followed, except that 25 μg of each plasmid was used to transfect cells in each of eight T-175 flasks. Following the first harvest of conditioned medium, fresh R1CD1 was added and then collected after an additional 72 hr. Conditioned media were pooled and filtered on a 0.22 μm filter. Antibodies were loaded onto protein A resin, eluted with 20 mM citric acid/150 mM sodium chloride (pH 2.5), neutralized with Tris (pH 8.5), and dialyzed into PBS.

Example 9.6

BIACORE™ Analysis of Antibody Binding to Human and Murine IL-21R

The kinetics of binding of anti-IL-21R antibodies to human and murine IL-21R-H/F was tested on a BIACORE™ surface plasmon resonance instrument. Anti-human IgG antibodies (Invitrogen Corporation) were immobilized onto a research-grade carboxy-methyl-dextran chip (CM5) using standard amine coupling. The surface was activated with EDC/NHS for 7 min at a flow of 20 μl/min. The first flow cell was used as a reference surface to correct for bulk refractive index, matrix effects, and nonspecific binding. The anti-human-Fc antibody was diluted to 20 μg/ml in 10 mM sodium acetate buffer (pH 5.0), and 2950-3405 resonance units (RU) were captured on each of the four flow cells. Remaining activated groups were blocked with 1.0 M ethanolamine-HCl (pH 8.5).

Figure 8A:
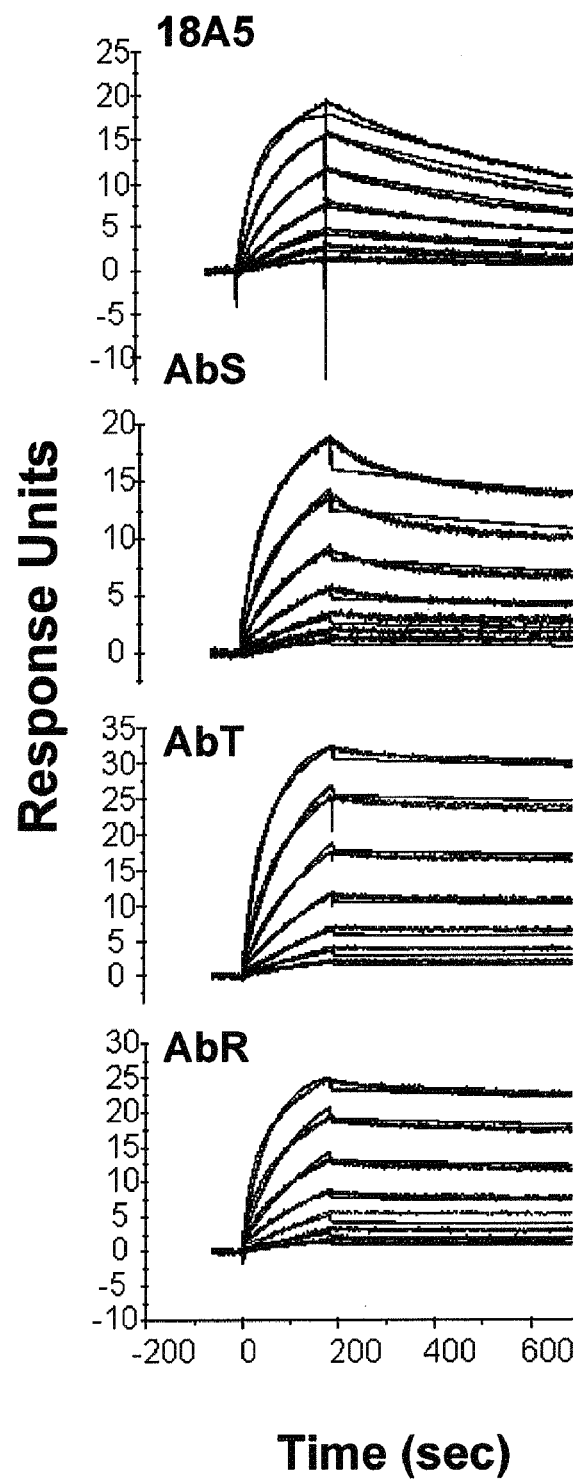
FIG. 8(a-d) depicts the binding of anti-IL-21R antibodies to human and murine IL-21R. The indicated human anti-IL-21R antibodies were captured on anti-human IgG immobilized on a BIACORE™ chip. Varying concentrations of human IL-21R-His/FLAG (FIGS. 8a-b) and murine IL-21R-His/FLAG (FIGS. 8c-d) were allowed to flow over the chip, and binding and dissociation were monitored.
Figure 8B:
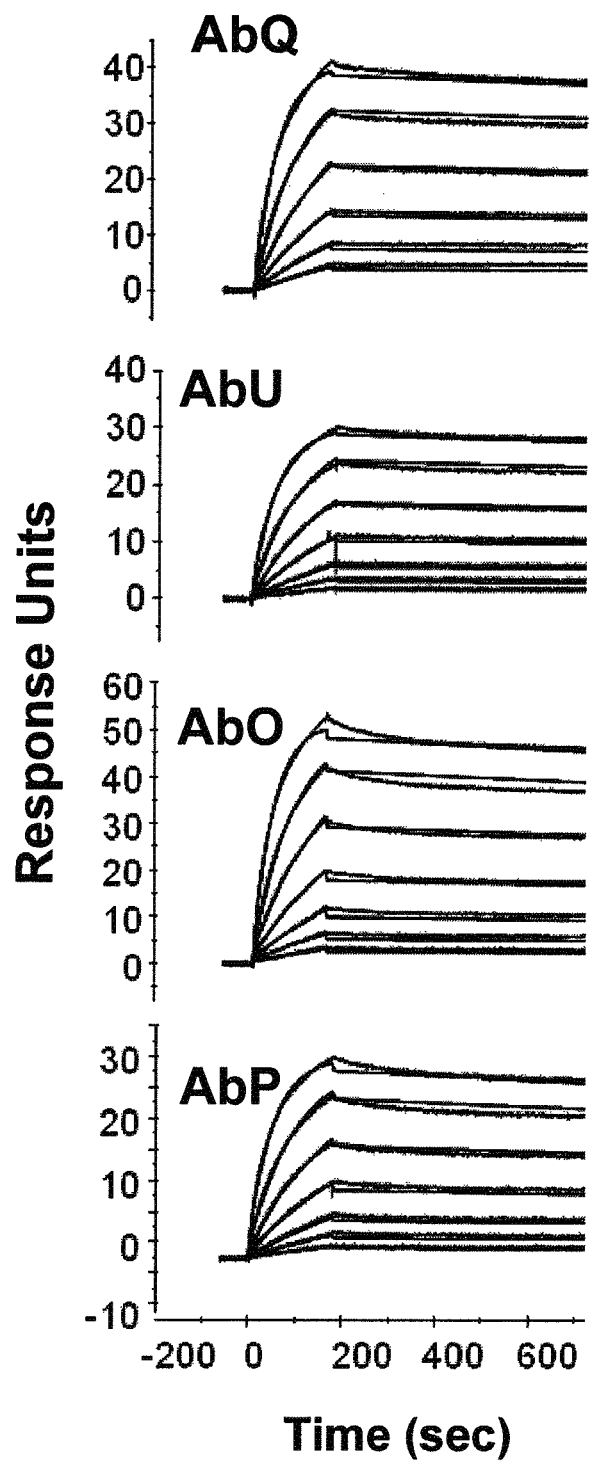
Figure 8D:
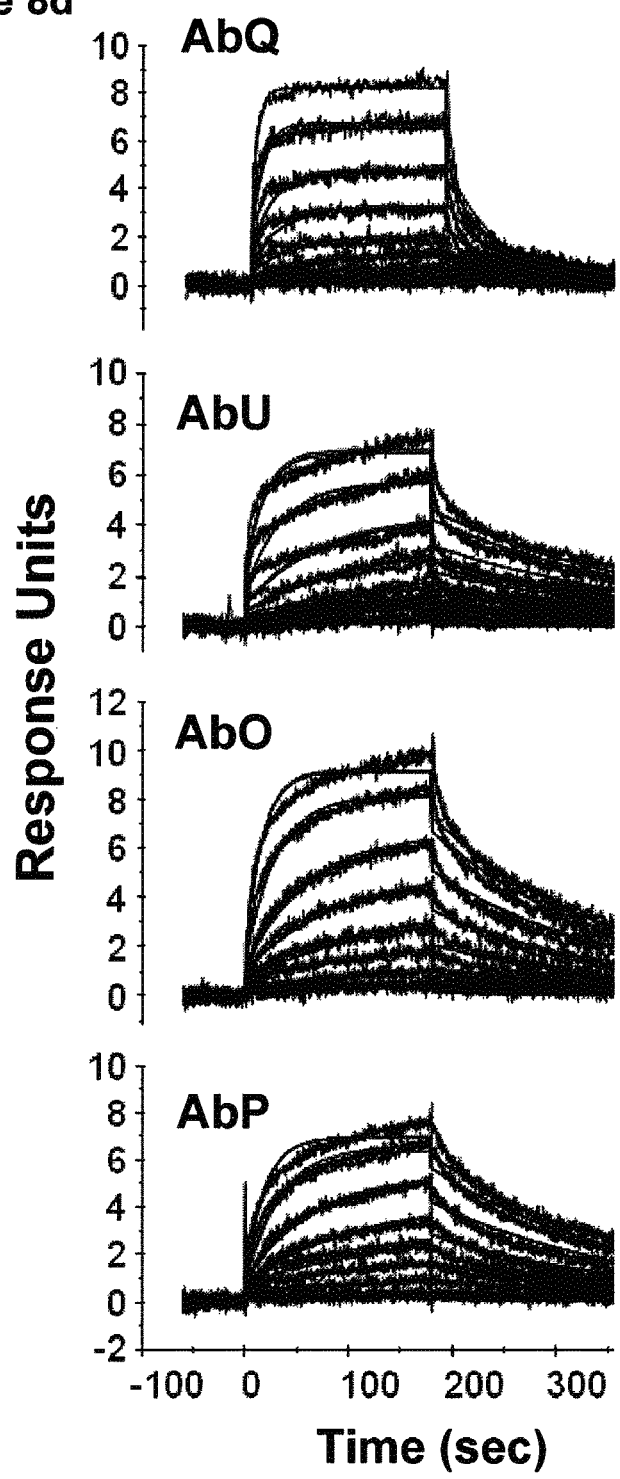
Figure 9A:
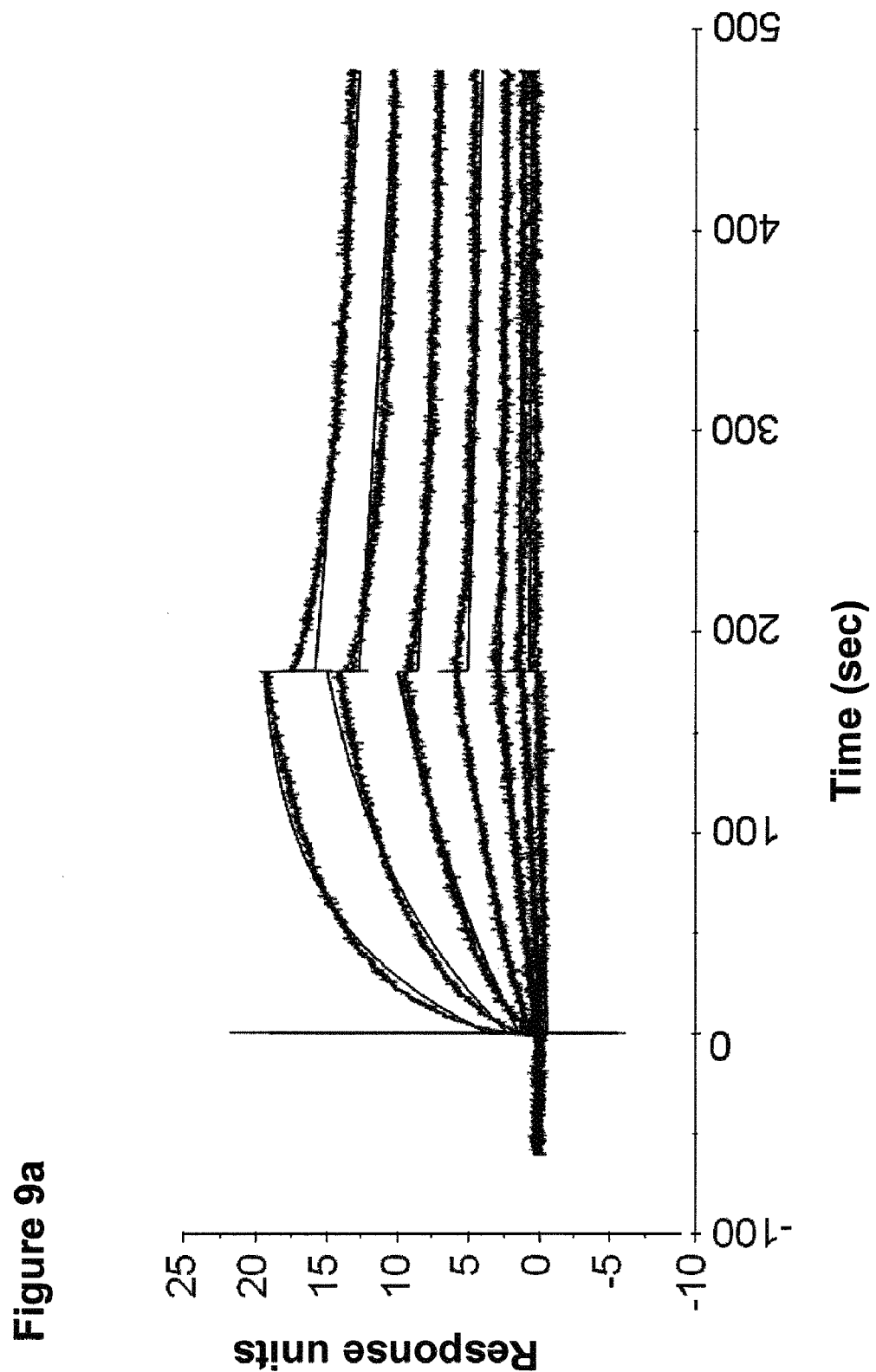
FIG. 9a shows cynomolgus monkey IL-21R-His/FLAG binding to AbS.
Figure 9B:
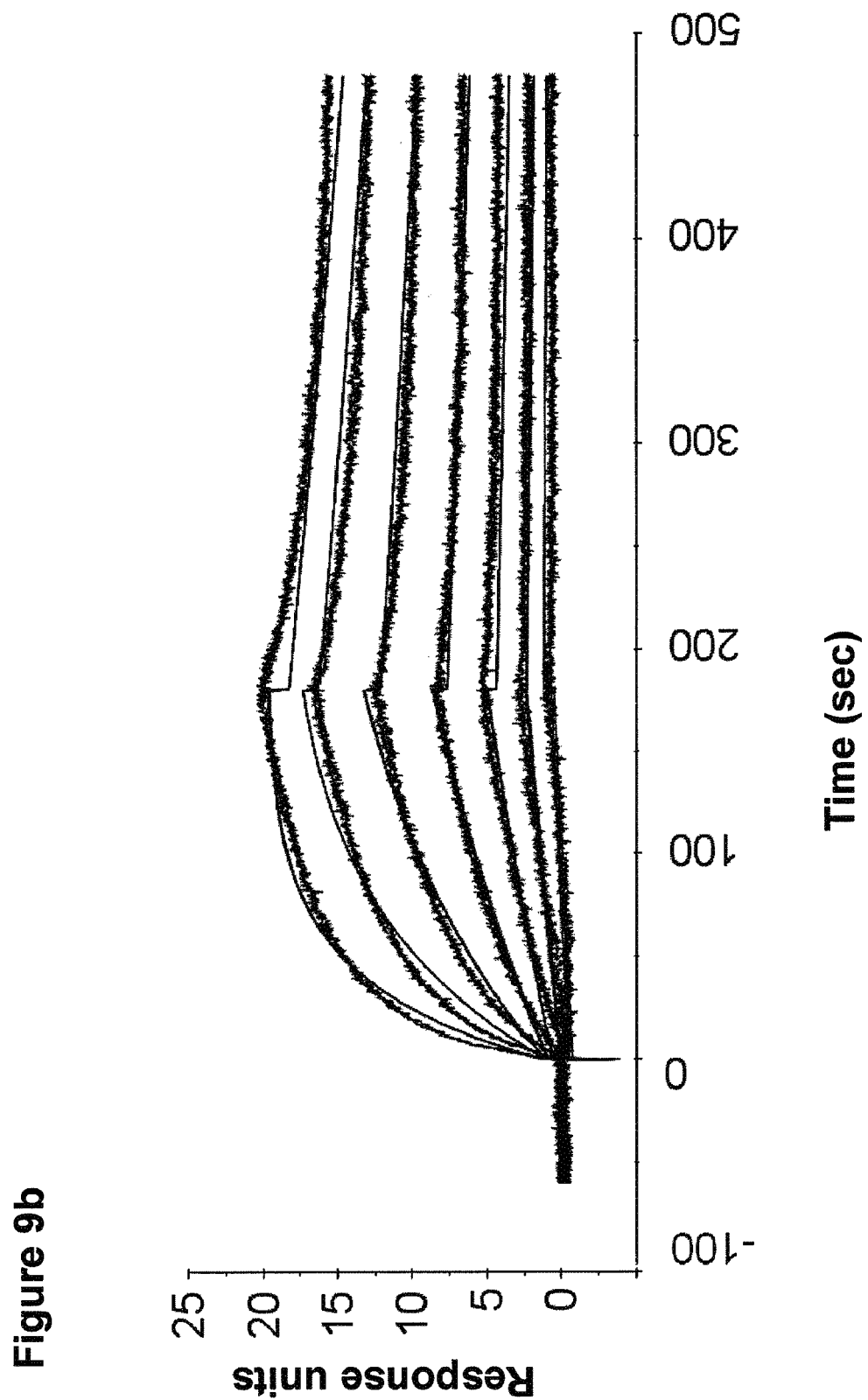
FIG. 9b shows human IL-21R-His/FLAG binding to AbS.
Figure 9C:
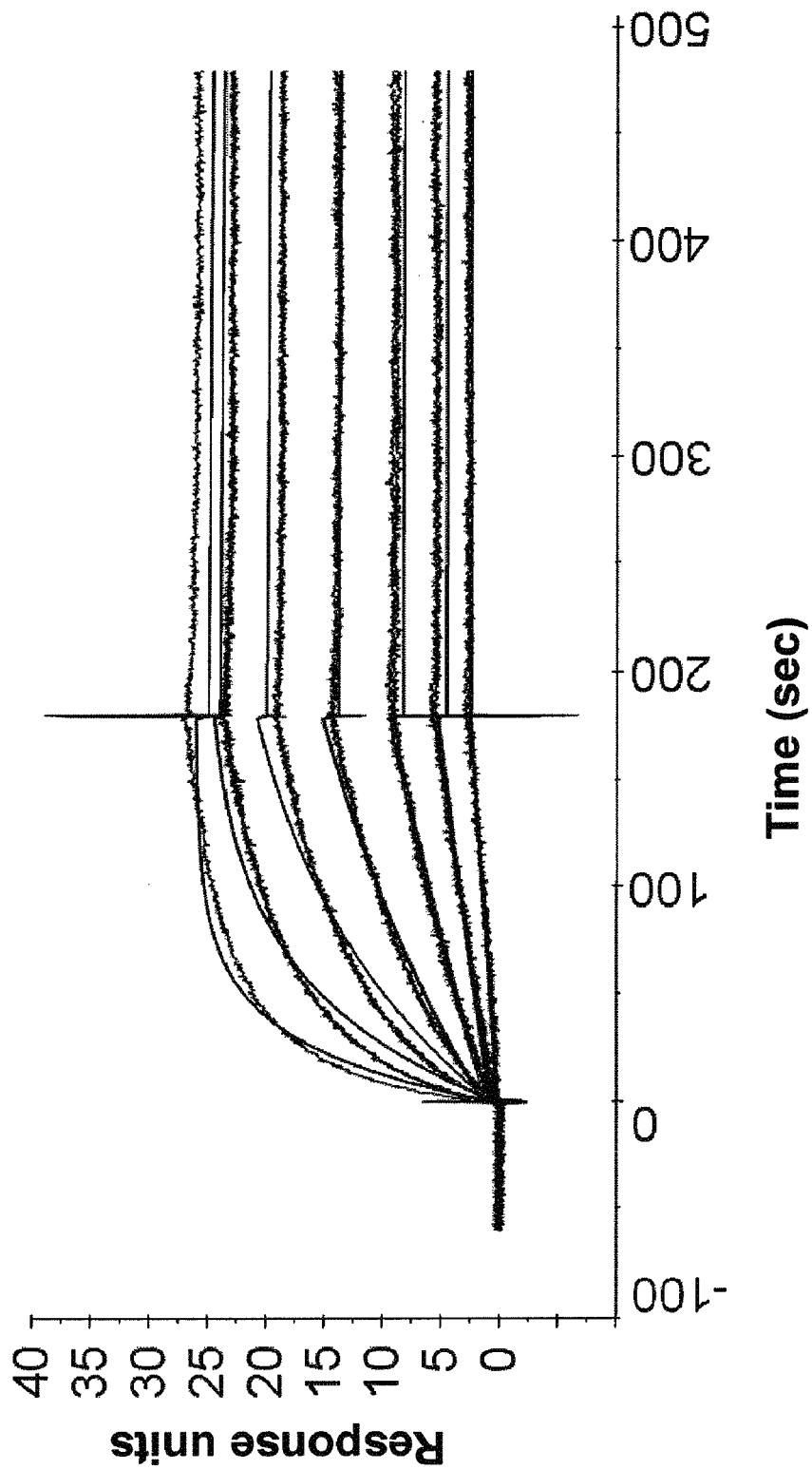
FIG. 9c shows cynomolgus monkey IL-21R-His/FLAG binding to AbT.
Figure 9D:
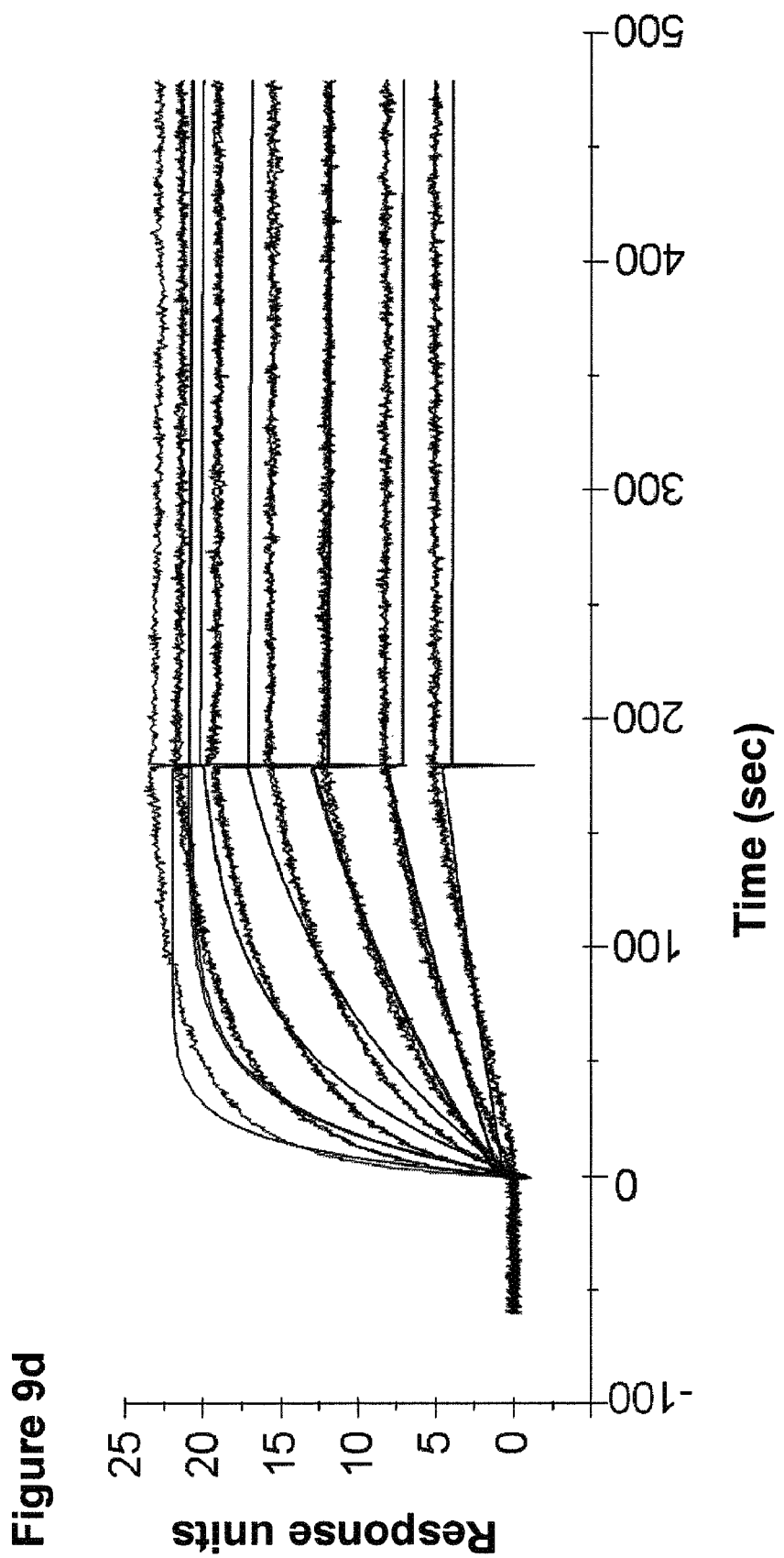
FIG. 9d shows human IL-21R-His/FLAG binding to AbT.

Anti-IL-21R antibodies were diluted to 0.1-0.2 μg/ml in HBS/EP buffer supplemented with 0.2% bovine serum albumin and loaded onto the BIACORE™ chip. Following a brief washing period, solutions of 0-100 nM human IL-21R-H/F or 10-500 nM murine IL-21R-H/F were injected over the chip at a flow rate of 50 μl/min. The association phase was run for 3 min for human and murine IL-21R kinetics, and the dissociation phase was monitored for 15 min for hIL-21R and for 5 min for mIL-21R, followed by two 10 μl injections and one 30 μl injection of glycine (pH 1.5), to regenerate a fully active capturing surface. All binding experiments were done at 25° C. in HBS/EP buffer, and the sample rack was kept at 15° C. Blank and buffer effects were subtracted for each sensorgram using double referencing. Sensorgrams are shown in FIGS. 8a-b (human IL-21R-His/FLAG) and FIGS. 8c-d (murine IL-21R-His/FLAG). Binding kinetic parameters are shown in Table 7A, and additional kinetic data from a replicate experiment are shown in Table 7B.

In addition, AbS and AbT were tested for binding kinetics to cynomolgus monkey IL-21R-His/FLAG by the above-described protocol. Binding profiles to human and cynomolgus monkey IL-21R-H/F were similar for both AbS and AbT (FIG. 9). FIG. 9 shows cynomolgus monkey IL-21R-His/FLAG binding to AbS (9a); and to AbT (9c); and human IL-21R-His/FLAG binding to AbS (9b); and AbT (9d).

TABLE 7A

Kinetic Parameters of Anti-IL-21R Antibody Binding Human and Murine IL-21R-His/FLAG

| | Human IL-21R | | | Murine IL-21R | | |
|---|---|---|---|---|---|---|
| Antibody | ka (1/Ms) | kd (1/s) | KD (M) | ka (1/Ms) | kd (1/s) | KD (M) |
| 18A5 | 2.43E+05 | 1.08E−03 | 4.43E−09 | 2.12E+05 | 1.53E−02 | 7.20E−08 |
| AbO | 2.41E+05 | 1.14E−04 | 4.75E−10 | 1.12E+05 | 5.49E−03 | 4.92E−08 |
| AbP | 1.94E+05 | 1.19E−04 | 6.15E−10 | 9.99E+04 | 5.08E−03 | 5.08E−08 |
| AbQ | 4.39E+05 | 9.34E−05 | 2.13E−10 | 3.01E+05 | 2.07E−02 | 6.88E−08 |
| AbR | 1.70E+05 | 9.61E−05 | 5.67E−10 | 7.65E+04 | 4.93E−03 | 6.45E−08 |
| AbS | 1.44E+05 | 2.91E−04 | 2.02E−09 | 1.99E+05 | 3.32E−03 | 1.67E−08 |
| AbT | 1.79E+05 | 6.78E−05 | 3.79E−10 | 2.11E+05 | 3.31E−03 | 1.57E−08 |
| AbU | 1.86E+05 | 8.18E−05 | 4.40E−10 | 9.81E+04 | 4.34E−03 | 4.42E−08 |

TABLE 7B

Kinetic Parameters of Anti-IL-21R Antibody Binding Human IL-21R-His/FLAG

| | Human IL-21R | | |
|---|---|---|---|
| Antibody | ka (1/Ms) | kd (1/s) | KD (M) |
| 18A5 | 3.04E+05 | 1.34E−03 | 4.40E−09 |
| AbP | 2.33E+05 | 1.02E−04 | 4.36E−10 |
| AbQ | 4.39E+05 | 9.34E−05 | 2.13E−10 |
| AbR | 2.48E+05 | 9.76E−05 | 3.94E−10 |
| AbS | 2.02E+05 | 3.05E−04 | 1.51E−09 |
| AbT | 2.73E+05 | 7.42E−05 | 2.72E−10 |
| AbU | 2.38E+05 | 7.83E−05 | 3.29E−10 |

Example 9.7

BIACORE™ Epitope Competition Assay

Antibodies AbS and AbT and the parental antibody 18A5 were immobilized directly onto a CM5 BIACORE™ chip. Murine IL-21R-H/F (100 nM) was allowed to flow over the chip for 300 sec, followed by a wash (100 sec), and then a 5 μg/ml solution of either AbS, AbT, D5, or a nonneutralizing anti-mIL-21R antibody (7C2) was allowed to flow over the surface. No additional binding was observed with AbS, AbT, and D5, indicating that their binding site on mIL-21R-H/F was blocked by concurrent binding to AbS, AbT, or 18A5 antibody (FIG. 10a). In contrast, the nonneutralizing control anti-IL-21R antibody 7C2 was able to bind to mIL-21R-H/F captured on AbS, AbT, or 18A5 antibody, indicating that this control antibody bound at a different epitope from the one bound by the capture antibodies.

Figure 10B:
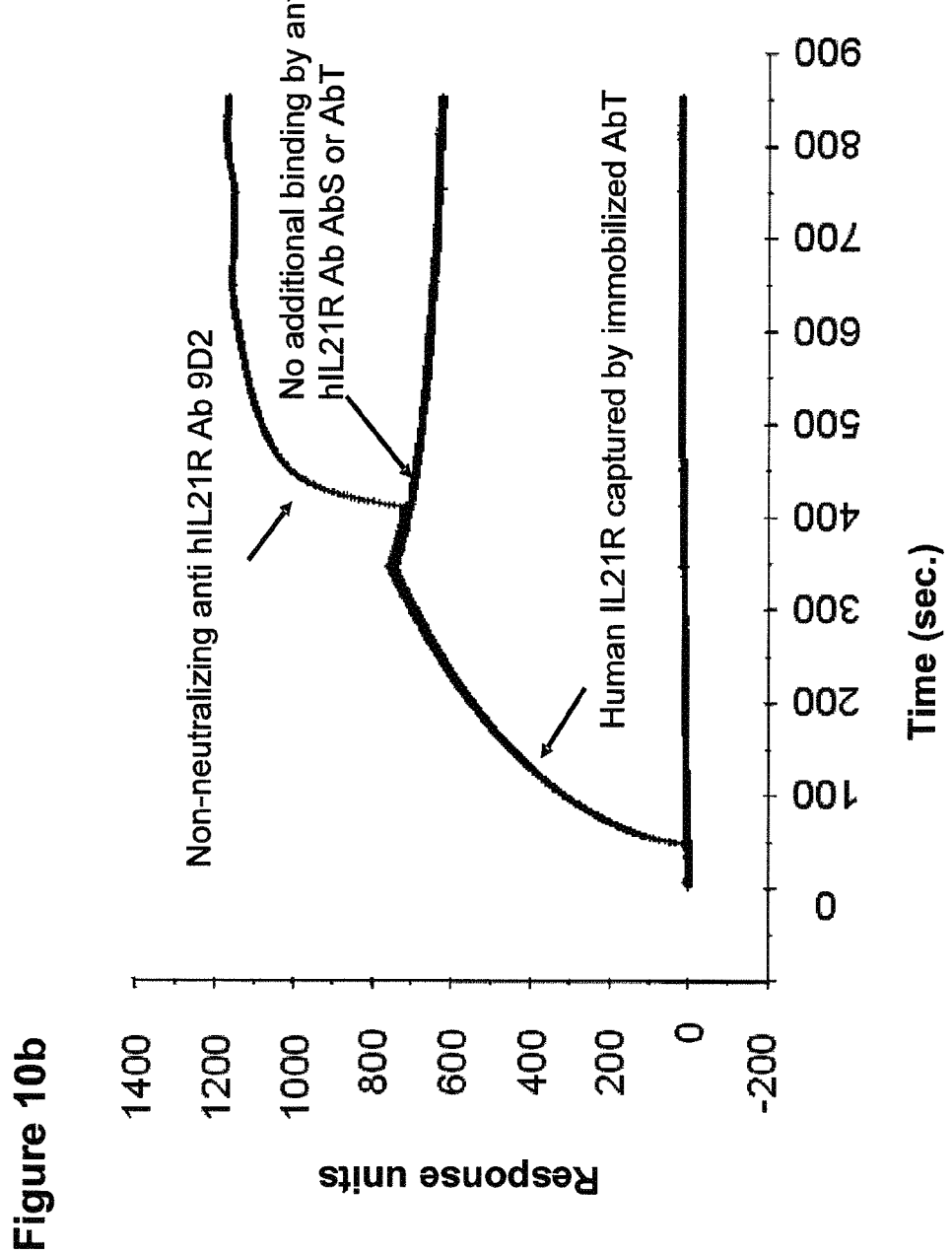
FIG. 10 depicts an epitope assessment of IL-21R antibodies. In the experiment depicted in FIG. 10a (see also illustration at left of Y-axis), murine IL-21R-H/F (His-Flag fusion protein) was captured by anti-IL-21R antibody AbS immobilized on a BIACORE™ chip. Additional anti-IL-21R antibodies (AbS, AbT, D5 (D5-20, a neutralizing anti-murine IL-21R antibody), and 7C2 (a nonneutralizing anti-murine IL-21R control antibody)) were flowed over the chip and their binding to the captured IL-21R-H/F was monitored. In the experiment depicted in FIG. 10b, human IL-21R-H/F was captured by anti-IL-21R antibody AbS immobilized on a BIACORE™ chip. Additional anti-IL-21R antibodies (AbS, AbT, and 9D2 (a nonneutralizing anti-human IL-21R control antibody)) were flowed over the chip and their binding to the captured IL-21R-H/F was monitored.

Similarly, AbS and AbT did not bind to human IL-21R-H/F captured by AbS or AbT immobilized on a CM5 BIACORE™ chip, while the control anti-human IL-21R antibody (9D2) was able to bind human IL-21R-H/F captured by AbS or AbT (FIG. 10b). This observation suggested that the binding site for AbS is blocked by concurrent binding by AbT, and vice versa.

Example 9.8

Cell-Based Proliferation Assays

Figure 11B:
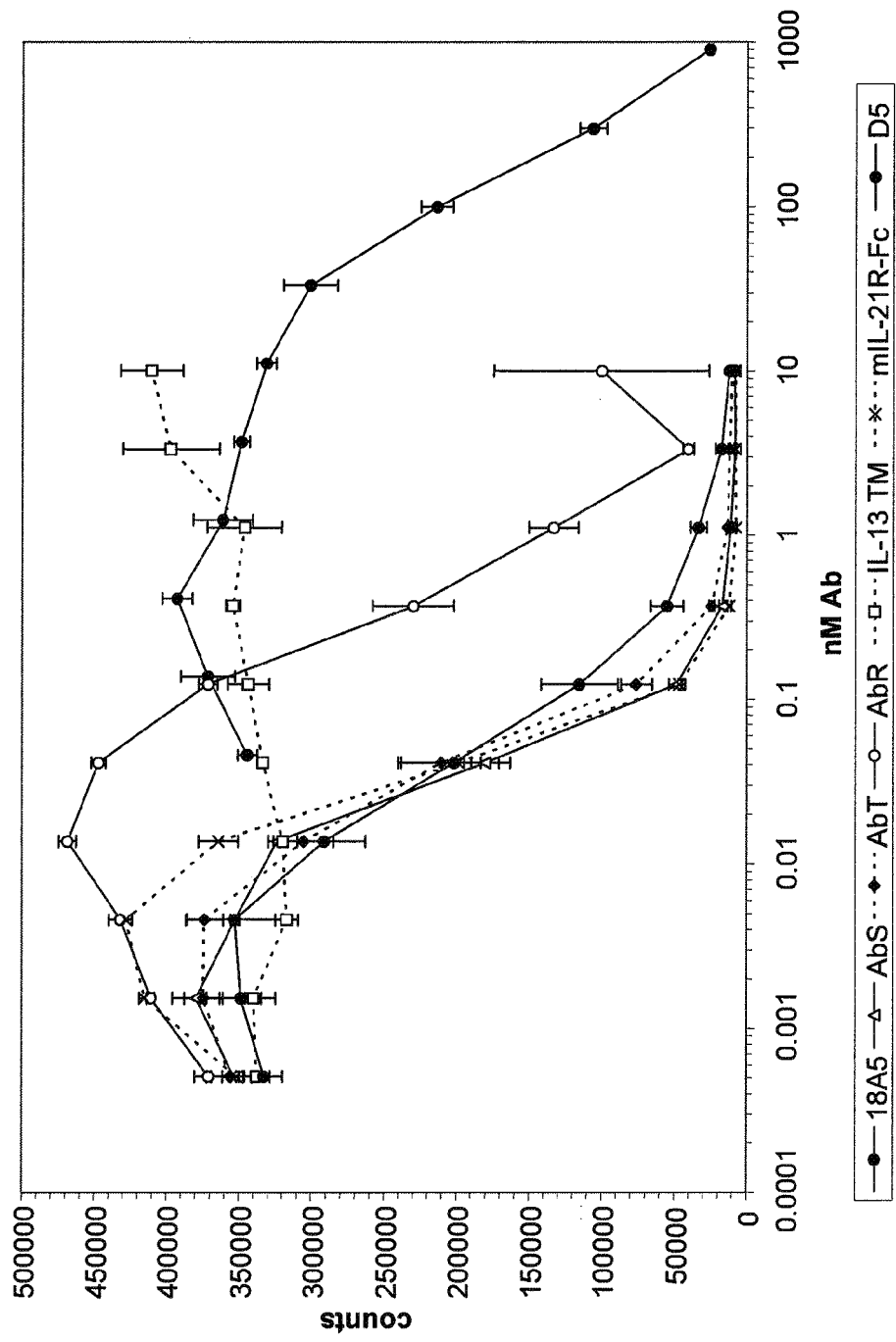
FIG. 11 depicts the neutralization of proliferation of human IL-21R-BaF3 cells and murine IL-21R-BaF3 cells by the indicated antibodies. Antibodies were added to cells. IL-21 was subsequently added and proliferation measured with CELLTITER-GLO® after 48 hr. Assays were conducted on human IL-21R-BaF3 cells with 100 pg/ml of human IL-21 (FIG. 11a), murine IL-21R-BaF3 cells with 200 pg/ml of murine IL-21 (FIG. 11b), and human IL-21R-TF1 cells with 100 pg/ml of human IL-21 (FIG. 11c).
Figure 11C:
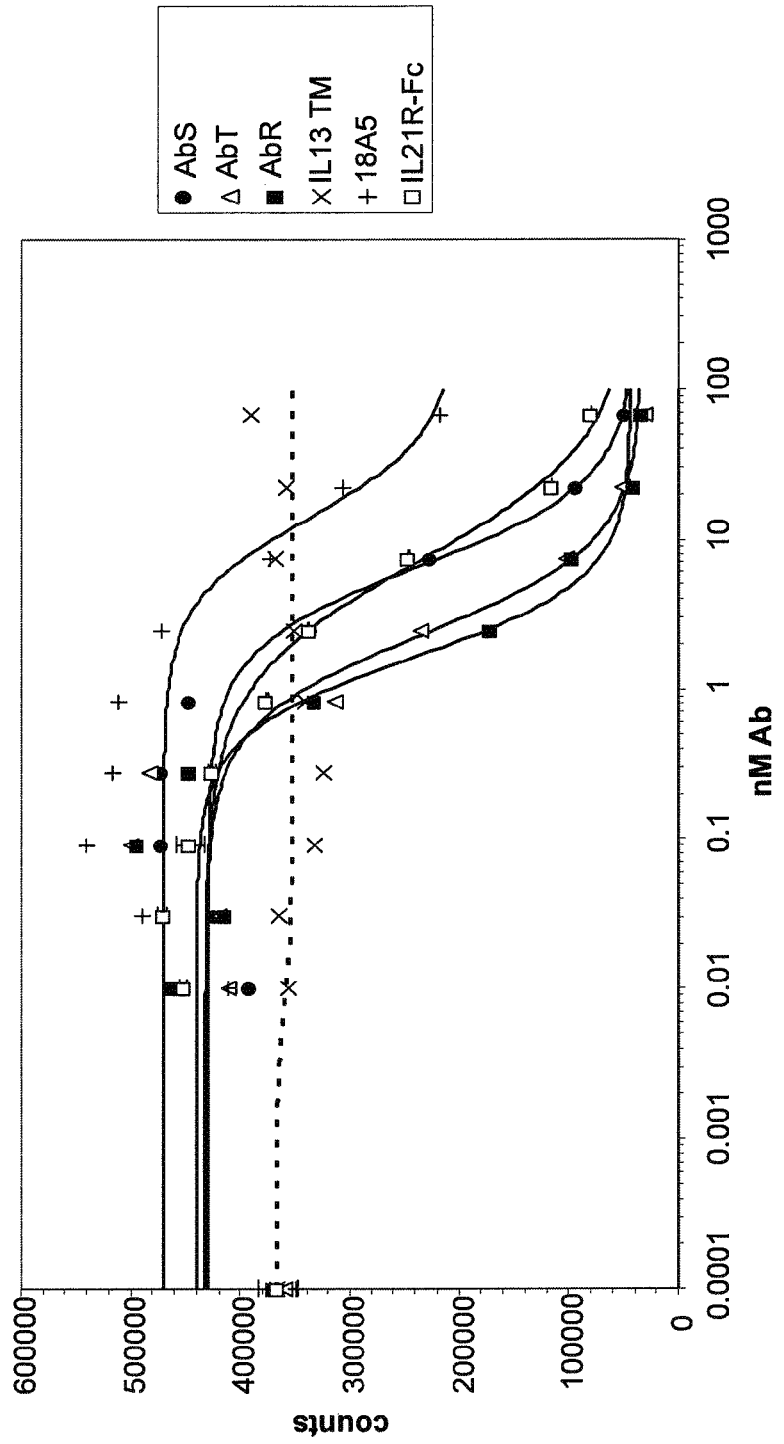
Figure 26D:
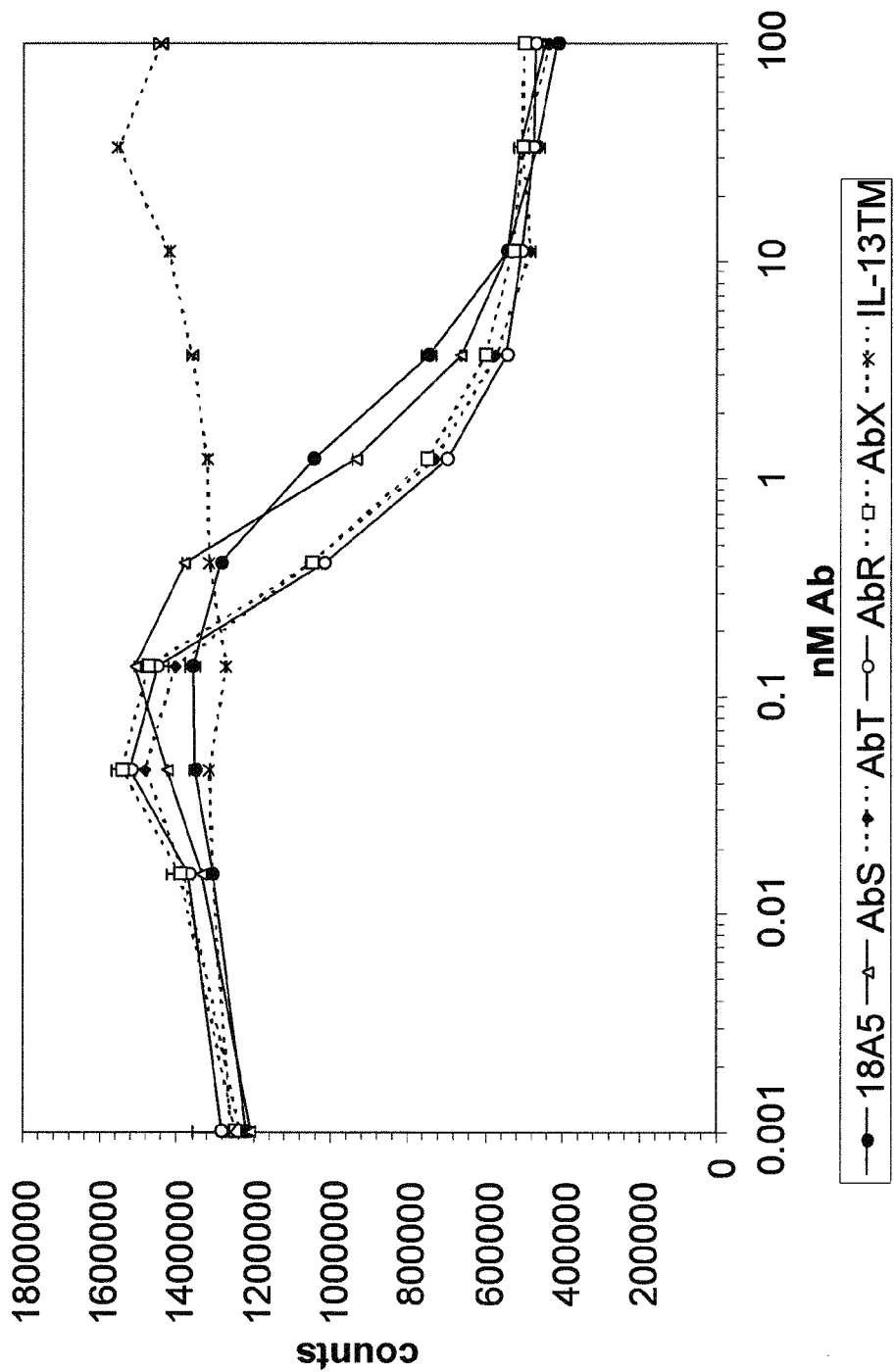

Purified IgGs were tested for activity in IL-21-dependent proliferation assays in three cell lines as described above:

human IL-21R-BaF3 cells, murine IL-21R-BaF3 cells, and human IL-21R-TF-1 cells. All showed strong inhibition of both human and murine IL-21R-dependent proliferation with greater potency than that of the parental 18A5 IgG (FIG. 11, Table 8). Assays were conducted on human IL-21R-BaF3 cells with 100 pg/ml of human IL-21 (FIG. 11*a*), murine IL-21R-BaF3 cells with 200 pg/ml of murine IL-21 (FIG. 11*b*), and human IL-21R-TF-1 cells with 100 pg/ml of human IL-21 (FIG. 11*c*). FIG. 26*d* depicts the results of an additional study of the effects of these antibodies on human IL-21R-BaF3 cells.

TABLE 8

Neutralization of Proliferation of Human IL-21R-BaF3 Cells, Murine IL-21R-BaF3 Cells, and Human IL-21R-TF-1 Cells

| Antibody | Human IL-21R-BaF3 Neutralization $IC_{50}$ (nM) | Murine IL-21R-BaF3 Neutralization $IC_{50}$ (nM) | Human IL-21R-TF1 Neutralization $IC_{50}$ (nM) |
|---|---|---|---|
| 18A5 antibody | 1.71 | 177.23 | 13.99 |
| AbR | 0.56 | 0.34 | 1.63 |
| AbS | 0.68 | 0.04 | 6.67 |
| AbT | 0.30 | 0.05 | 2.32 |
| AbX | 0.54 | nd | nd |
| IL21R-Fc | 0.20 (human IL-21R-Fc) | 0.04 (mouse IL-21R-Fc) | 7.22 (human IL-21R-Fc) |

Example 9.9

Primary Human B Cell Proliferation Assays

Figure 12A:
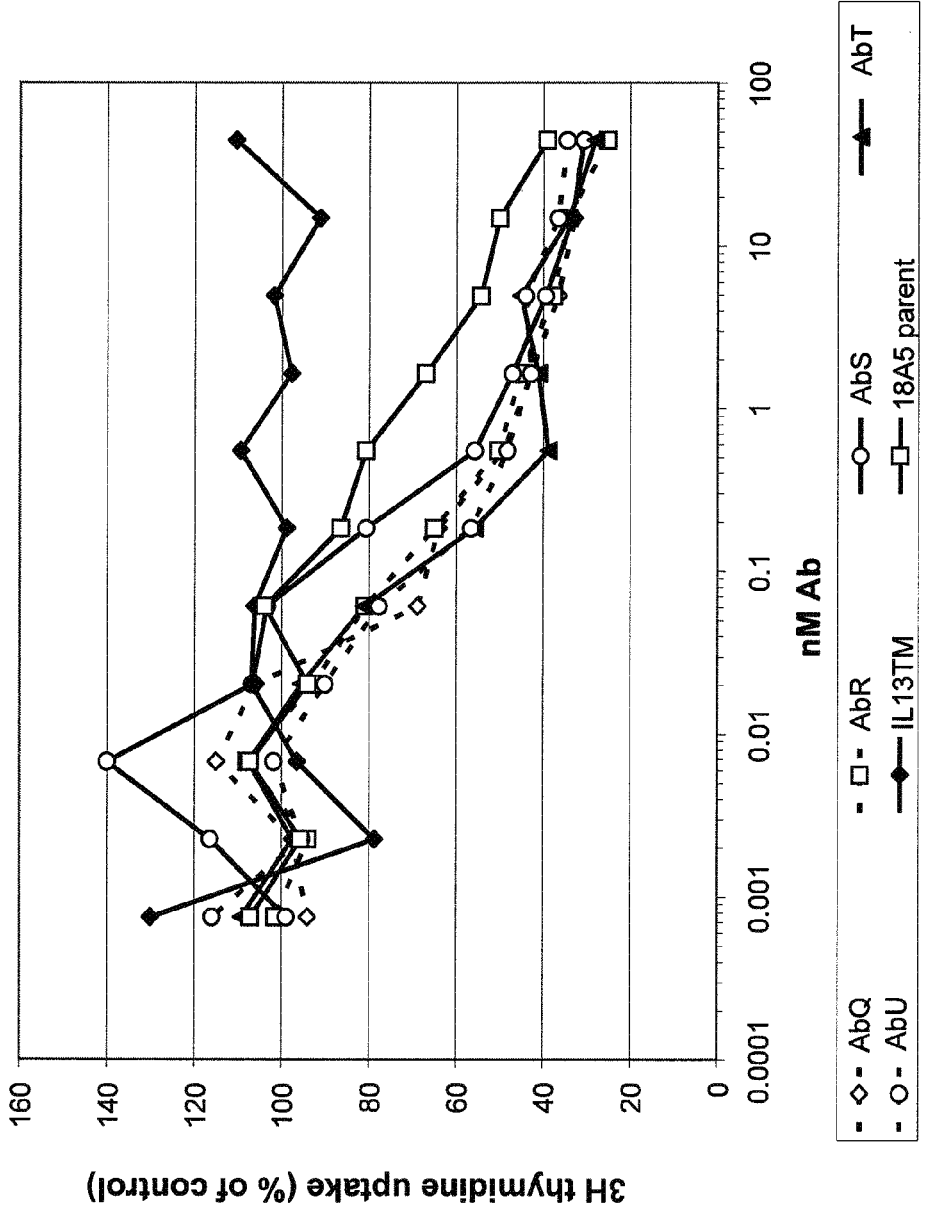
FIG. 12a depicts the comparison between AbQ, AbR, AbS, AbT, AbU, IL-13 triple-mutant, and 18A5 parental antibody.
Figure 12B:
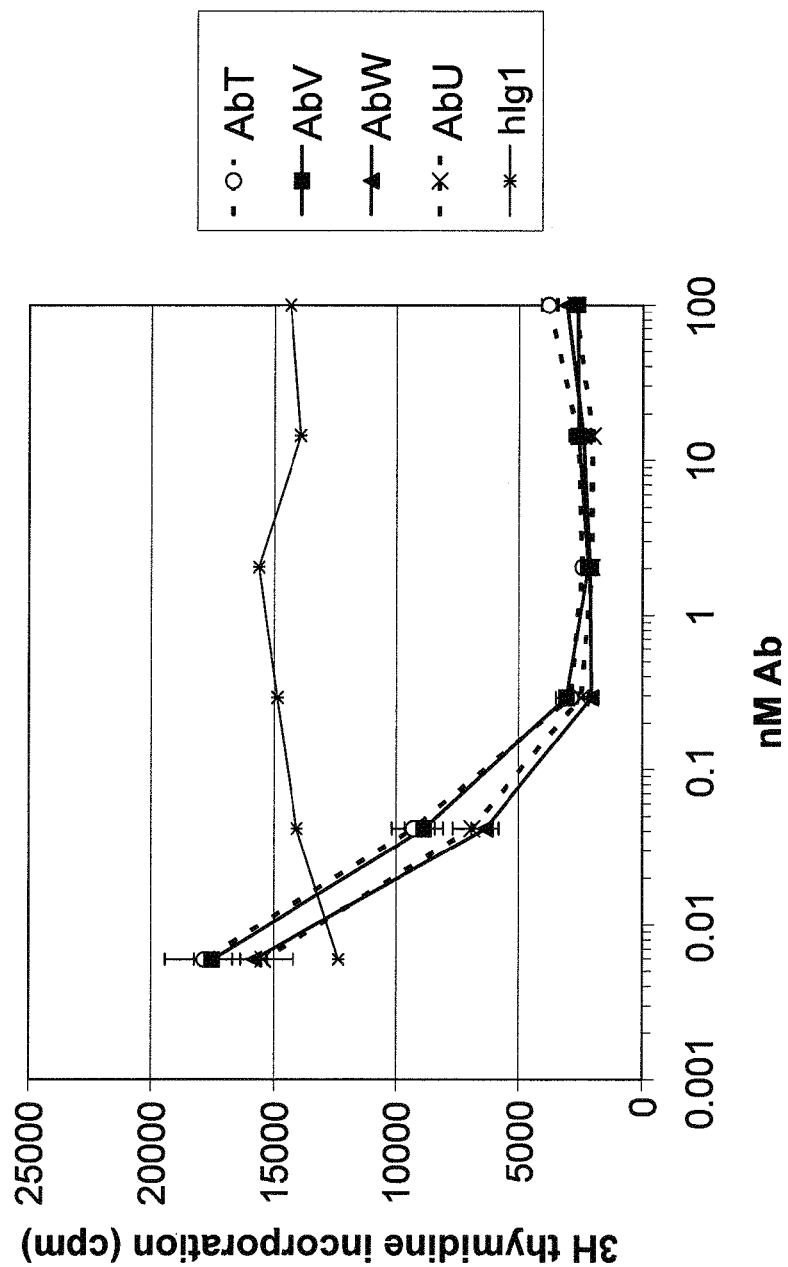
FIG. 12b depicts the comparison between AbT, AbV, AbW, AbU, and human IgG1 control (hIg1).
Figure 26E:
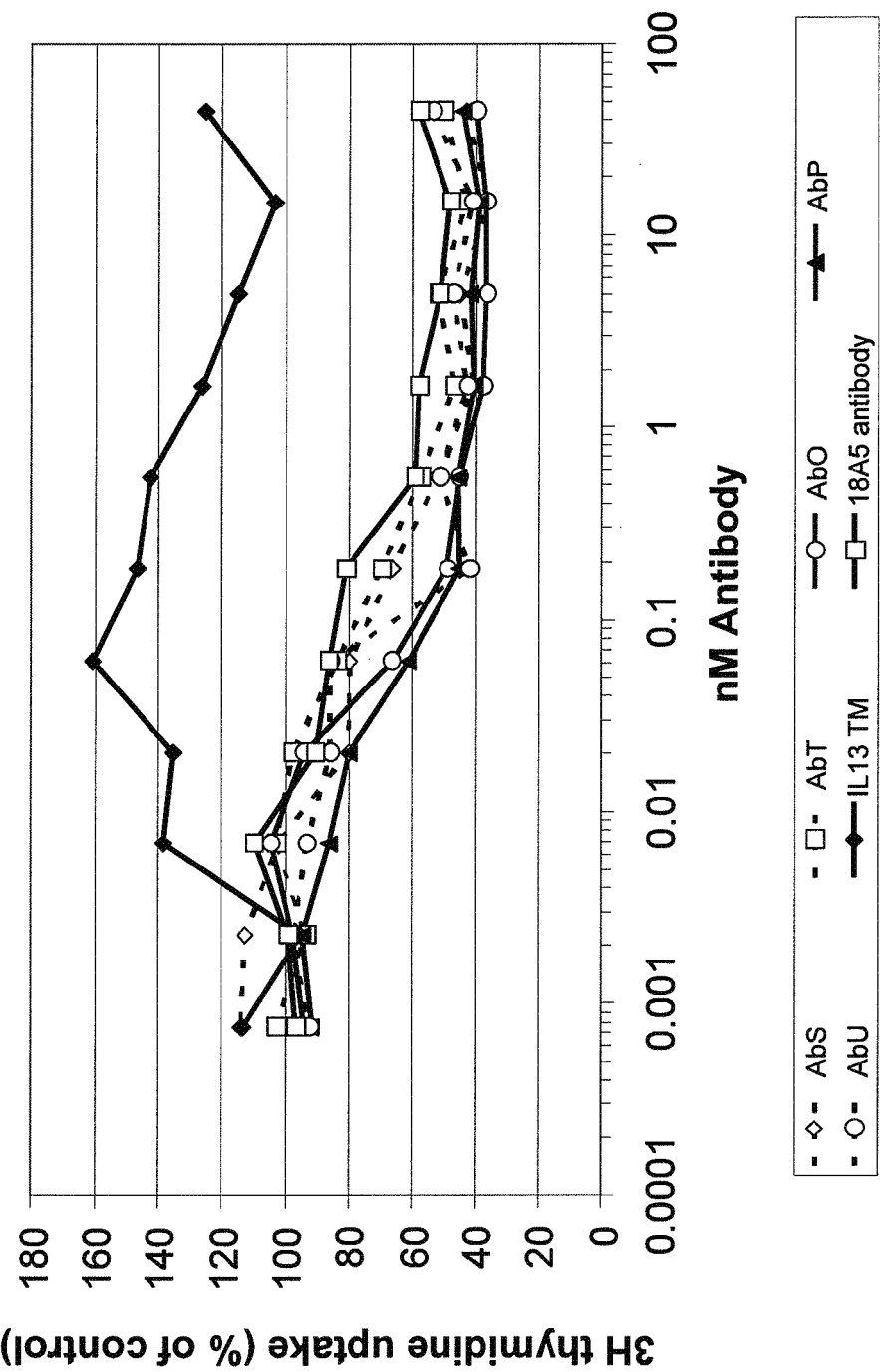

Anti-IL-21R antibodies were tested for their ability to inhibit IL-21-dependent proliferation of primary human B cells. Buffy coat cells from healthy human donors were obtained from Massachusetts General Hospital (Boston, Mass.). The cells were incubated with a ROSETTESEP™ B cell enrichment cocktail (StemCell Technologies, Vancouver, Canada), and B cells isolated according to the manufacturer's instructions. The resulting population (60-80% CD19$^+$ B cells) were cultured in RPMI containing 10% FBS, 50 U/ml penicillin, 50 μg/ml streptomycin, and 2 mM L-glutamine at 1×10$^5$/well in 96-well flat-bottom plates. B cells were pretreated with serially diluted anti-human IL-21R antibodies in a 37° C. incubator adjusted to 5% CO$_2$ for 30 min. The treated B cells were then stimulated with 0.5 μg/ml anti-CD40 mAb (BD Biosciences, San Jose, Calif.) and 10 ng/ml IL-21 cytokine for 3 days in a 37° C. incubator adjusted to 5% CO$_2$. On day 3, cultures were pulsed with 0.5 μCi/well $^3$H-thymidine (Perkin Elmer (NEN)) and harvested 5 hr later onto glass fiber filter mats. $^3$H-thymidine incorporation was determined by liquid scintillation counting. All of the improved antibodies neutralized IL-21-dependent proliferation with greater potency than the parental 18A5 antibody (FIGS. 12*a-b*, Table 9; also see FIG. 26*e*).

TABLE 9

Neutralization of Human Primary B cell Proliferation

| Antibody | Neutralization of B cell proliferation $IC_{50}$ (nM) |
|---|---|
| AbQ | 0.16 |
| AbR | 0.22 |
| AbS | 0.44 |
| AbT | 0.14 |
| AbU | 0.13 |
| 18A5 antibody | 1.86 |

Example 9.10

Primary Human T Cell Proliferation Assays

Figure 13:
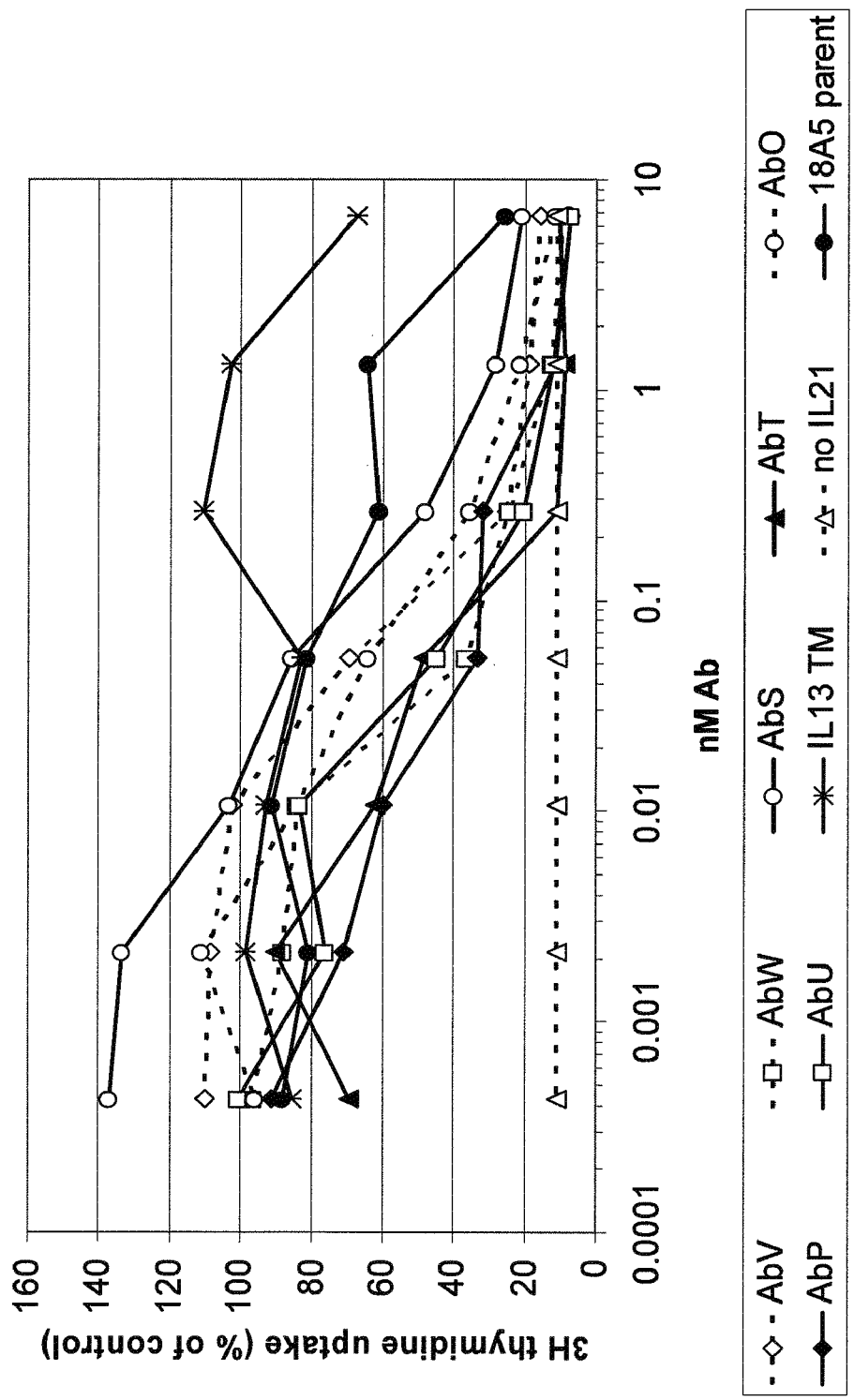
FIG. 13 depicts the neutralization of IL-21-dependent proliferation of human primary CD4$^+$ T cells. The indicated antibodies were added to activated primary human CD4$^+$ T cells along with human IL-21, and incorporation of $^3$H-thymidine was measured after three days.
Figure 26F:
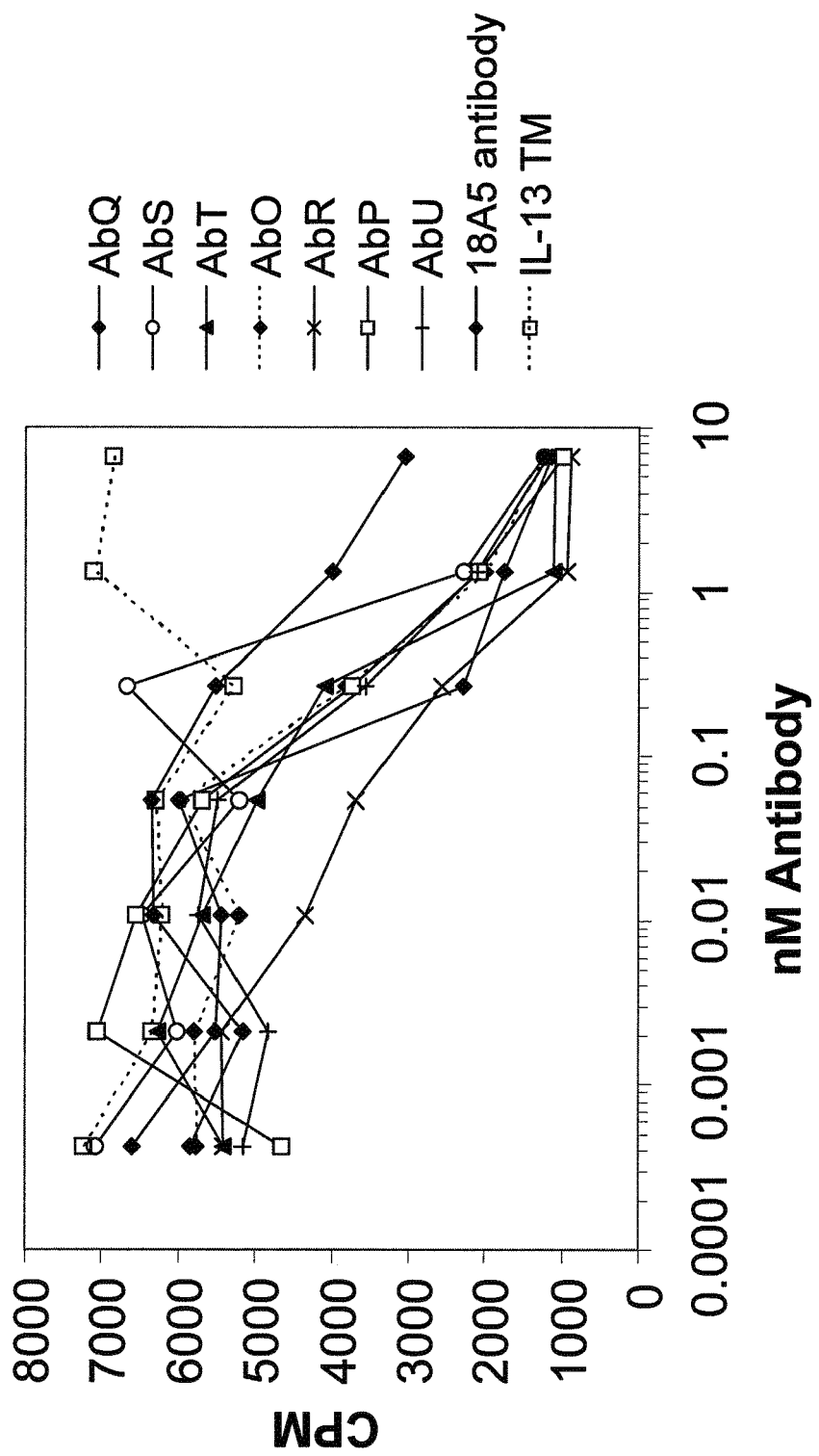

Anti-IL-21R antibodies were tested for their ability to inhibit IL-21-dependent proliferation of primary human CD4$^+$ T cells. Buffy coat cells from healthy human donors were obtained from Massachusetts General Hospital. CD4$^+$ T cells were isolated by negative selection using ROSETTE-SEP™ CD4$^+$ T cell enrichment cocktail (StemCell Technologies), according to the manufacturer's instructions. The resulting population was ~80-90% CD4$^+$/CD3$^+$ T cells. Enriched human CD4$^+$ T cells were activated for 3 days with anti-CD3/anti-CD28-coated microspheres in RPMI containing 10% FBS, 100 U/ml penicillin, 100 μg/ml streptomycin, 2 mM L-glutamine, and HEPES in a 37° C. incubator adjusted to 5% CO$_2$. After activation, the microspheres were removed and the cells were washed and rested overnight at approximately 1×10$^6$ cells/ml in culture medium. The rested cells were then washed again before addition to the assay plates. Serial dilutions of anti-human IL-21 receptor antibodies were made in culture medium in flat-bottomed 96-well plates, followed by the sequential addition of human IL-21 (20 ng/ml final concentration) and the activated and rested CD4$^+$ T cells (10$^5$ cells/well). The plates were then incubated for an additional 3 days and pulsed with 1 μCi/well 3H-thymidine (Perkin Elmer (NEN)) during the final 6 hr of the assay. Cells were harvested onto glass fiber filter mats and $^3$H-thymidine incorporation was determined by liquid scintillation counting. All of the improved antibodies neutralized IL-21-dependent proliferation with greater potency than the parental 18A5 antibody (FIG. 13, Table 10A; also see FIG. 26*f*).

TABLE 10A

Neutralization of Human Primary T cell Proliferation

| Antibody | Neutralization of T cell Proliferation $IC_{50}$ (nM) |
|---|---|
| AbO | 0.06 |
| AbP | 0.02 |
| AbQ | 0.08 |
| AbR | 0.04 |
| AbS | 0.06 |
| AbT | 0.03 |
| AbU | 0.03 |
| 18A5 antibody | 1.42 |

Example 9.11

Primary Murine T Cell Proliferation Assays

Figure 14:
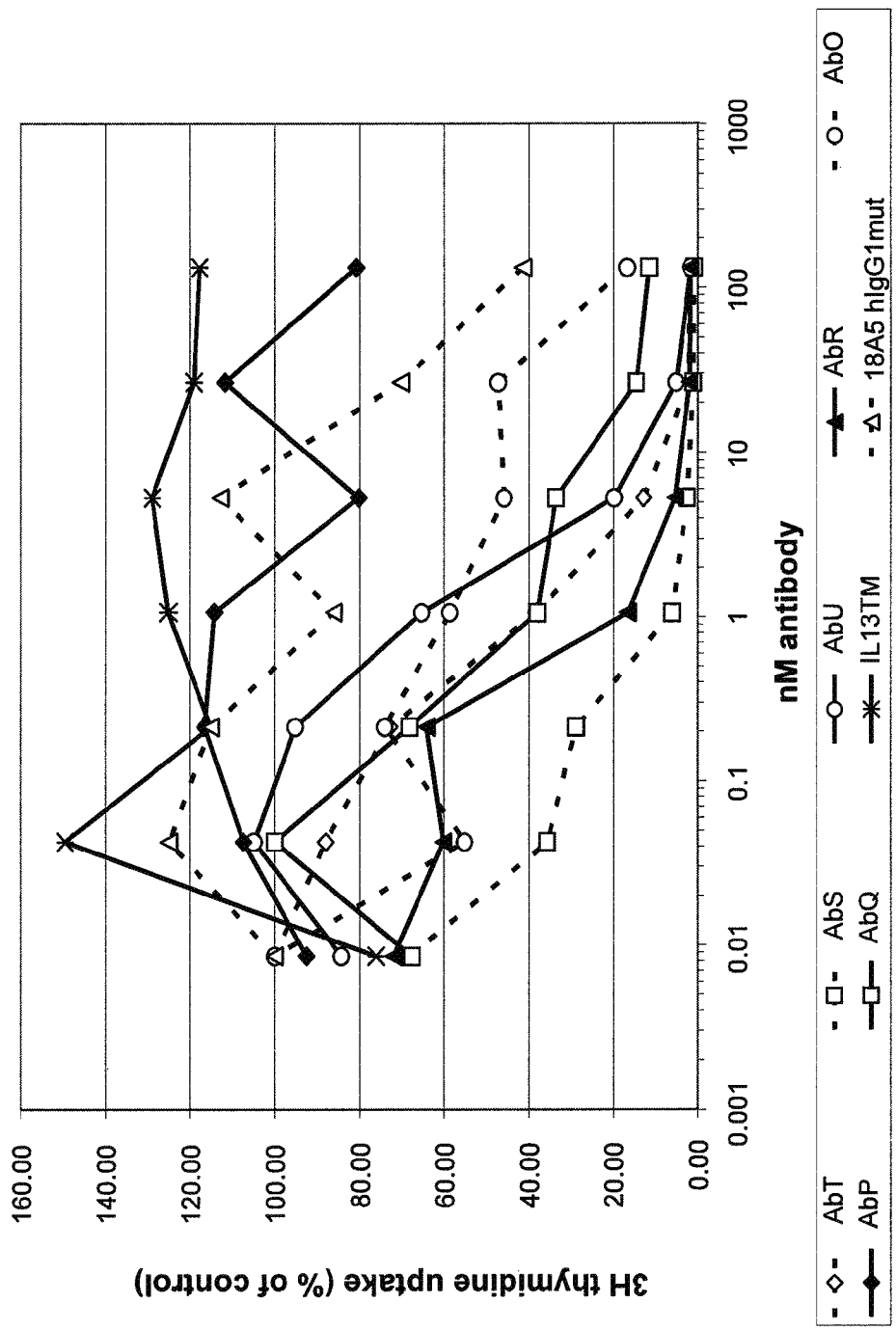
FIG. 14 depicts the neutralization of IL-21-dependent proliferation of murine primary CD8$^+$ T cells. The indicated antibodies were added to activated primary murine CD8$^+$ T cells along with human IL-21, and incorporation of $^3$H-thymidine was measured after three days.
Figure 26G:
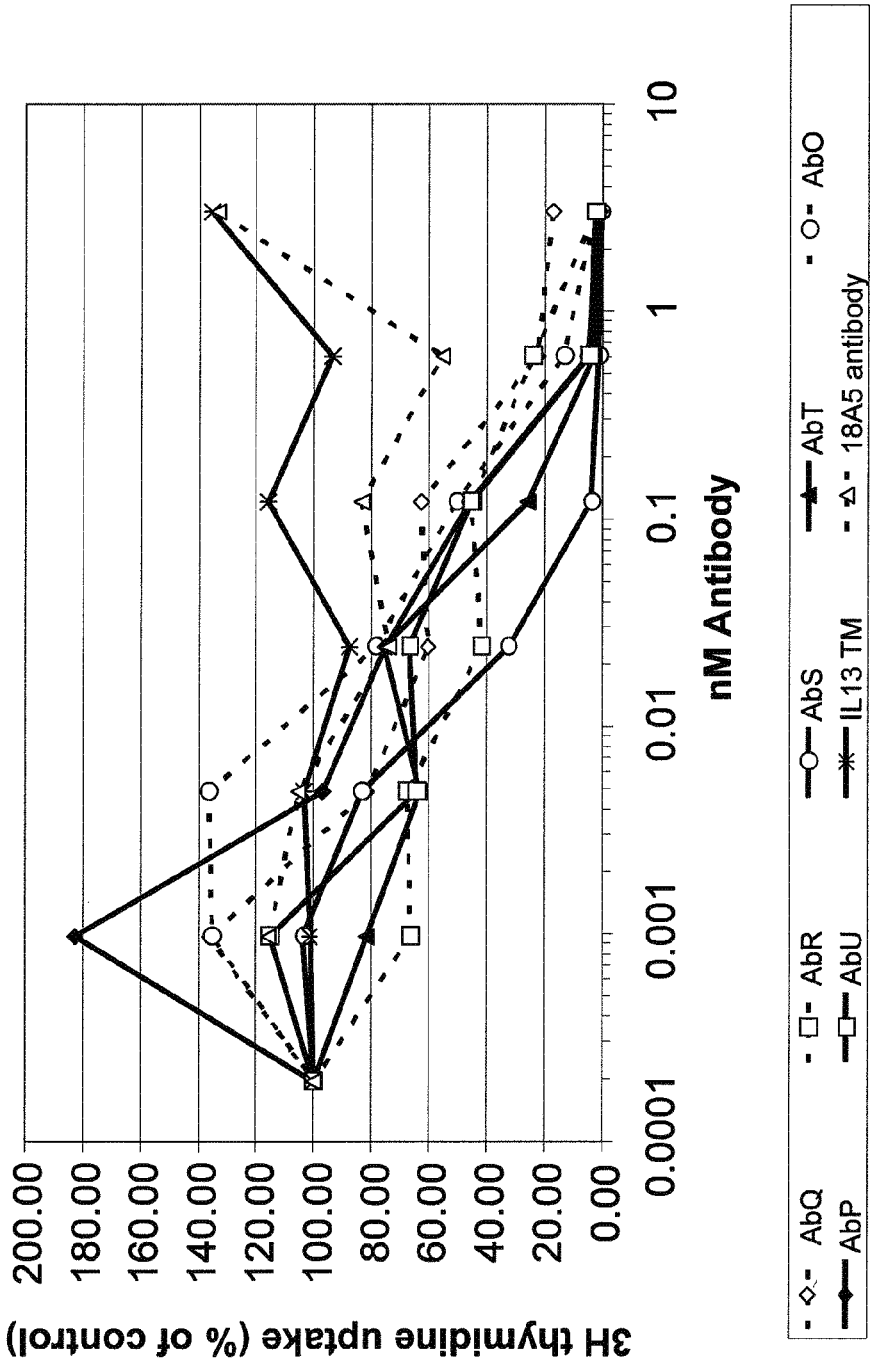

Anti-IL-21R antibodies were tested for their ability to inhibit IL-21-dependent proliferation of primary murine CD8$^+$ T cells. Popliteal, axillary, brachial, and inguinal lymph nodes and spleens from 12-week-old female BALB/C mice were collected. A single-cell suspension of the spleen cells was depleted of red blood cells using 0.16 M NH$_4$Cl in 0.017 M Tris (pH 7.4). The spleen and lymph node cells were pooled and enriched for CD8$^+$ cells using a murine T cell CD8 Subset Column Kit (R&D Systems). Murine CD8$^+$ cells (3×10$^4$; suspended in DMEM containing 10% fetal calf serum and supplemented with 0.05 mM β-mercaptoethanol, 2 mM L-glutamine, 0.1 mM nonessential amino acids, 1 mM sodium pyruvate, 100 U/ml penicillin, 100 μg/ml streptomycin and 50 μg/ml gentamicin) were plated in 96-well, anti-mCD3 activation plates (BD Biosciences); mIL-21 (50 ng/ml) was added to all the wells. The test antibodies were titered in triplicate beginning at 20 μg/ml. Cells were grown for 3 days in a 37° C./10% $CO_2$ incubator. During the last 5 hr of culture, cells were labeled with 0.5 µCi methyl-3H-thymidine/well (GE Healthcare). The cells were harvested using a Mach III cell harvester (TomTec, Hamden, Conn.) and counted using a Trilux microbeta counter (Perkin Elmer). Aside from AbP, all of the improved antibodies neutralized IL-21-dependent proliferation with greater potency than the parental 18A5 antibody (FIG. 14, Table 10B; also see FIG. 26*g*).

TABLE 10B

Neutralization of Murine Primary T cell Proliferation

| Antibody | Neutralization of T cell Proliferation $IC_{50}$ (nM) |
|---|---|
| AbO | 4.92 |
| AbP | no inhibition |
| AbQ | 0.85 |
| AbR | 0.13 |
| AbS | 0.02 |
| AbT | 0.61 |
| AbU | 1.79 |
| 18A5 antibody | >85 |

Example 9.12

ADCC Assay

Figure 15:
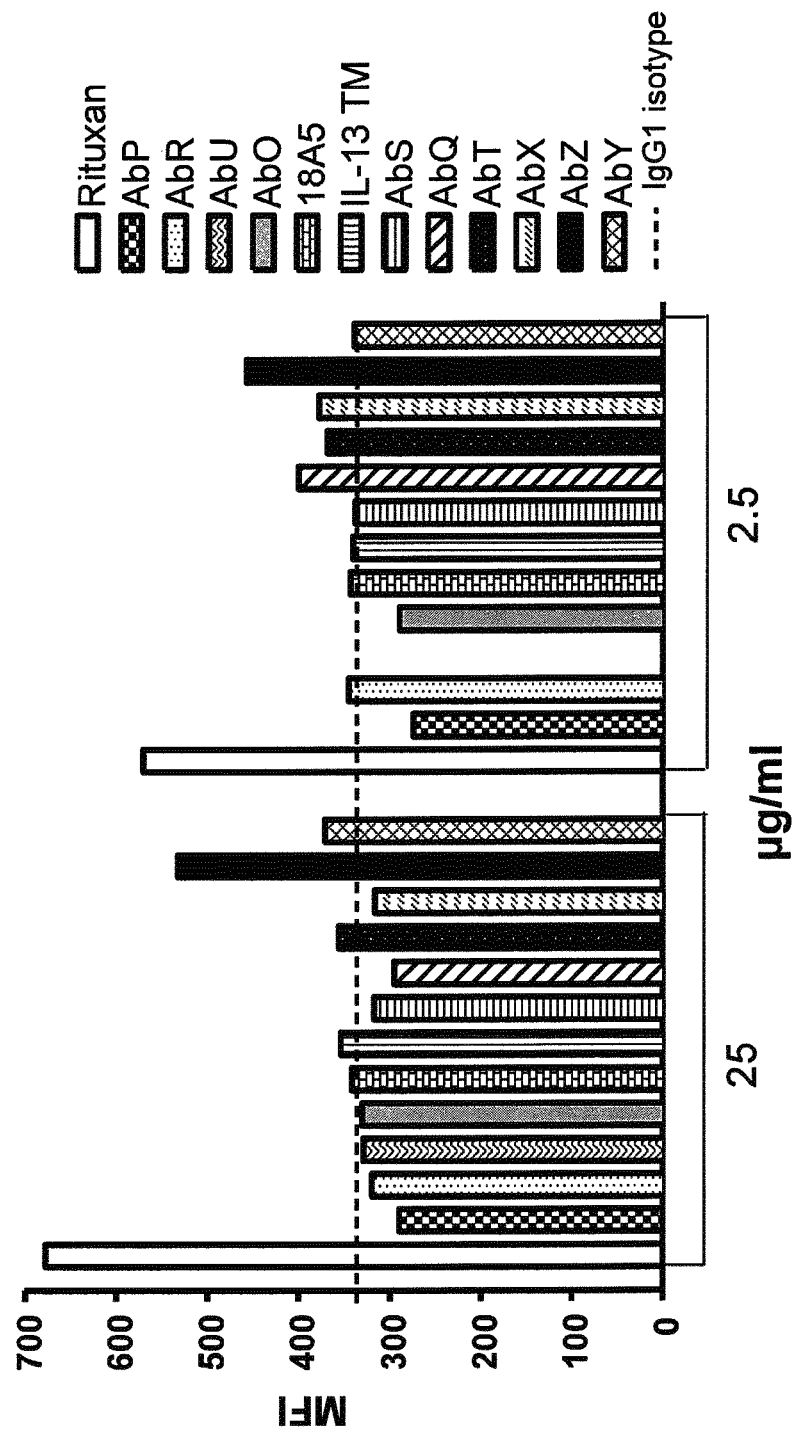
FIG. 15 depicts the measurement of antibody-dependent cellular cytotoxicity (ADCC) induced by anti-IL-21R antibodies. PBMC-dependent killing of CFSE-labeled BJAB cells coated with the indicated anti-IL-21R antibodies was measured by incorporation of propidium iodide. The anti-CD20 antibody rituximab (RITUXAN®, Genentech, Inc., South San Francisco, Calif.) was included as a positive control, and an anti-IL-13 antibody was included as a negative control.

Anti-IL-21R antibodies were tested for their ability to induce antibody-dependent cellular cytotoxicity (ADCC) when bound to target cells. The day before the experiment, PBMC were isolated from buffy coat by diluting the buffy coat 1:1 in PBS, layering it over FICOLL® (GE Healthcare) and centrifuging at 1200 g for 20 min. PBMCs were removed from the top of the FICOLL® layer, washed, and stimulated overnight with 10 ng/ml IL-2 and 10 ng/ml IL-12 (R&D Systems). The day of the experiment, stimulated PBMCs were collected by centrifugation and resuspended in media at $1\times10^8$ cells/ml. BJAB cells were labeled with 0.5 µM CFSE (MOLECULAR PROBES®, Invitrogen Corporation) for 10 min at 37° C., and then washed with fetal bovine serum once and PBS twice. Cells were then plated into a 96-well flat-bottom plate at $2\times10^5$ cells/well in 100 µl media. Fifty µl of the 4× antibodies were added to the BJAB cells, followed by $5\times10^6$ PBMC in 50 µl, giving a final 1:25 target:effector cell ratio. Cells were incubated at 37° C. for 6 hr and stained with propidium iodide (PI) to label dead and dying cells. Killing of target cells ($CFSE^+$) was assessed by measuring PI staining in a FACSCALIBUR™ flow cytometer (BD Biosciences). Only one anti-IL-21R antibody, AbZ, which has a wild-type human IgG1 constant region, showed ADCC above the background level displayed by a control anti-IL-13 antibody that did not bind to the target cells. All antibodies with the same variable domains as AbZ, including forms with human IgG4 (AbY), and those with double-mutant (AbX) and triple-mutant (AbT) forms of human IgG1, showed only background levels of ADCC (FIG. 15). All other anti-IL-21R antibodies tested contained the triple-mutant form of human IgG1 and showed background ADCC. A positive control antibody, rituximab (RITUXAN®), induced ADCC in all experiments.

Example 9.13

C1q ELISA

Figure 16:
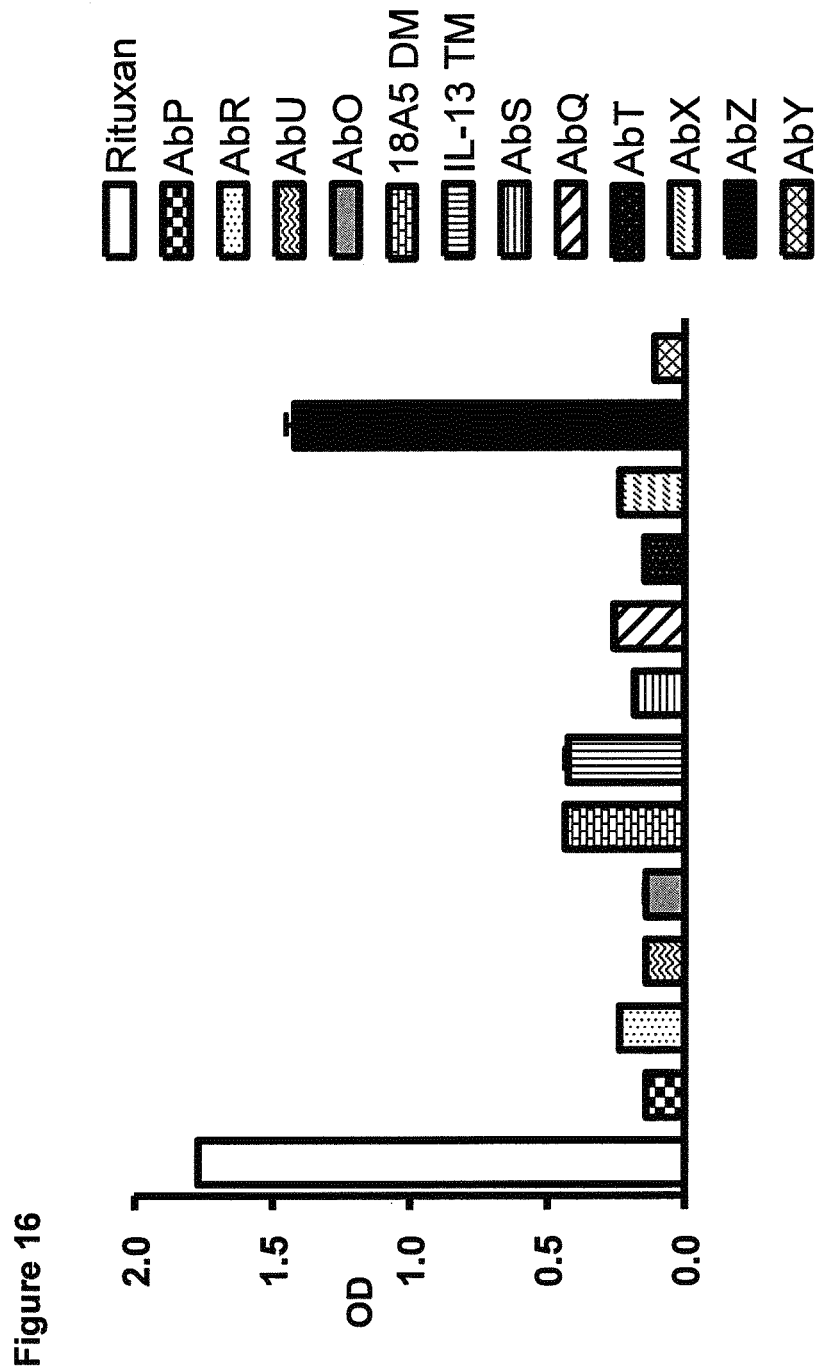
FIG. 16 depicts complement C1q binding by anti-IL-21R antibodies. The indicated anti-IL-21R antibodies were immobilized on an ELISA plate and, following incubation with human serum, C1q binding was measured with chicken anti-human C1q and an HRP-conjugated anti-chicken IgY antibody. The anti-CD20 antibody rituximab (RITUXAN®) was included as a positive control, and an anti-IL-13 antibody was included as a negative control.

In order to determine whether cell-surface binding by anti-IL-21R antibodies is likely to lead to complement-dependent cytotoxicity (CDC), the antibodies were tested for their ability to bind to the complement component C1q in an ELISA. IL-21R antibodies and rituximab (RITUXAN®) were diluted in PBS to 5 µg/ml. Diluted antibodies (100 µl) were coated onto a COSTAR® high-binding ELISA plate (Corning Life Sciences, Lowell, Mass.) overnight at 4° C. Plates were washed 3× with PBS/Tween-20 and blocked with 200 µl of blocking buffer (0.1 M $NaPO_4$, 0.1 M NaCl, 0.1% gelatin, 0.01% Tween) for 1 hr at RT. Human serum previously determined to contain C1q (Quidel, San Diego, Calif.) was diluted 1:50 in PBS. After 1 hr of blocking, plates were washed and 100 µl of diluted serum was added to each well and incubated for 2 hr at RT on a shaker. Following three washes, 100 µl of 0.1 µg/ml chicken polyclonal anti-human C1q antibody (AbCam, Cambridge, Mass.) was added to each well and incubated for 1 hr at RT. Plates were again washed and incubated with 100 µl of a rabbit polyclonal antibody to chicken Ig-Y-HRP diluted 1:4000 (AbCam) for 1 hr at RT. Plates were washed and developed with TMB for 5 min, followed by 50 µl of 1 M $H_2SO_4$ to stop the reaction, and then read at 450 nm. Only one anti-IL-21R antibody, AbZ, which has a wild-type human IgG1 constant region, showed C1q binding above the background level displayed by a control antibody with a triple-mutant human IgG1 constant region that had previously been shown to lack C1q binding. All antibodies with the same variable domains as AbZ, including forms with human IgG4 (AbY), and those with double-mutant (AbX) and triple-mutant (AbT) forms of human IgG1, showed only background levels of C1q binding (FIG. 16). All other anti-IL-21R antibodies tested contained the triple-mutant form of human IgG1 and showed background C1q binding.

Example 9.14

Cytokine Competition Assay

Figure 27A:
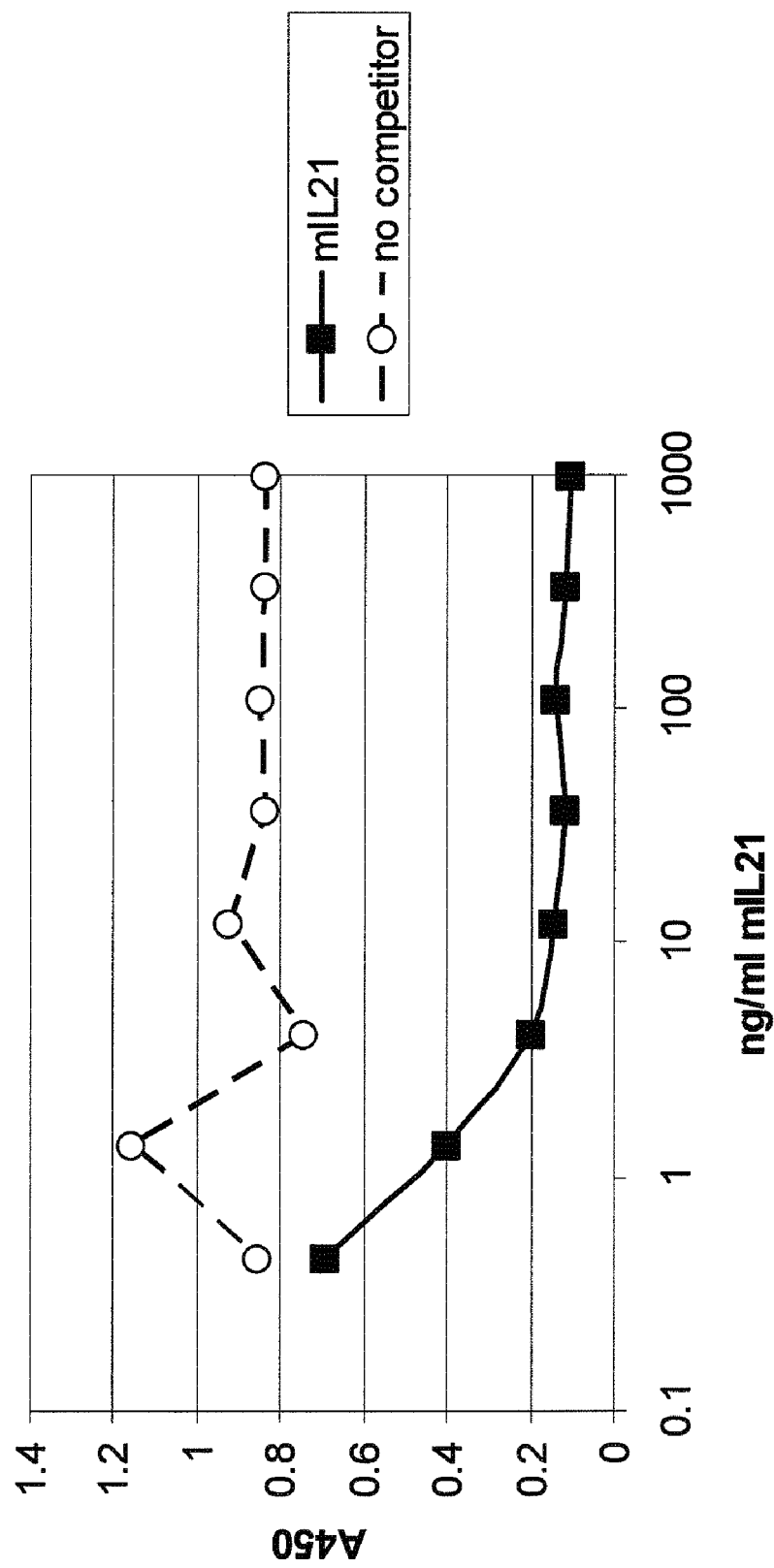
FIG. 27a depicts IL-21 cytokine competition with antibody AbT for binding to murine IL-21R. Vehicle, or increasing amounts of IL-21, was mixed with biotinylated murine IL-21R-His/FLAG, and the mixtures were added to AbT immobilized on an ELISA plate. Capture of mIL-21R was detected with HRP-streptavidin, and competition for binding to mIL-21R was indicated by a reduction in the A450 signal.

In order to demonstrate that antibody AbT binds to the murine IL-21R in a manner that competes with the IL-21 cytokine, a cytokine competition assay was performed. Antibody AbT was coated at 1 µg/ml onto ELISA plates, which were then blocked with 1% BSA in PBS/0.05% Tween. Biotinylated murine IL-21R-His/FLAG (1.5 ng/ml) was added to the wells, either alone or in the presence of increasing concentrations of murine IL-21, and the binding of the receptor to the immobilized antibody was detected with HRP-conjugated streptavidin and subsequent incubation with TMB detection reagent. Mouse IL-21 was able to block the binding of mIL-21R to AbT nearly completely above 4 ng/ml, indicating that the antibody and the cytokine compete for binding to murine IL-21R (FIG. 27*a*).

Figure 27B:
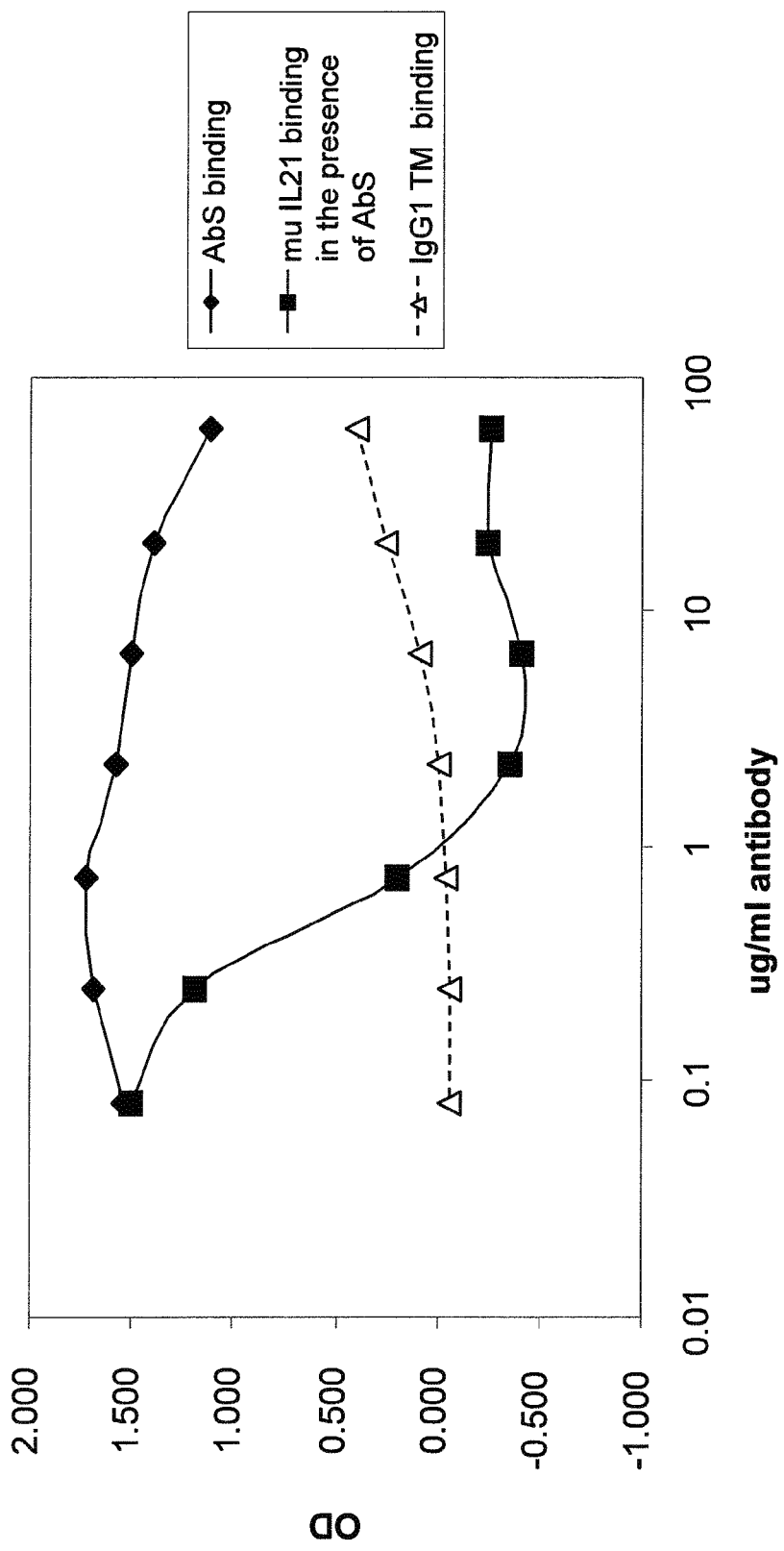
FIG. 27b depicts the competition of AbS and IL-21 for binding to murine IL-21R. AbS and mIL-21 were mixed and applied to immobilized mIL-21R-Fc in ELISA plates, and the binding of AbS (filled diamonds), isotype control antibody (open triangles), or mIL-21 (squares) was monitored.

A second assay was performed to demonstrate that antibody AbS binds to the murine IL-21R in a manner that competes with the IL-21 cytokine. Murine IL-21R-Fc was captured on ELISA plates coated with an anti-mouse IgG2a antibody. Plates were blocked with 1% BSA in PBS and washed, and varying concentrations of AbS were added to the plate in the presence of 10 µg/ml mIL-21. The binding of mIL-21 to the receptor was detected by an HRP-conjugated anti-$His_6$ antibody, and the binding of AbS to the receptor was detected by an anti-human Ig antibody. Concentrations of AbS above approximately 2 µg/ml completely prevented binding of mIL-21 to mIL-21R-Fc, indicating that the antibody and the cytokine compete for binding to murine IL-21R (FIG. 27*b*).

Example 9.15

Inhibition of Rat T Cell Proliferation by Anti-IL-21R Antibodies

Lewis female rat splenic T cells were purified to 95% $CD3^+$ using Rat T cell Enrichment Columns (RTCC-25; R&D Systems) according to the manufacturer's instructions. Serial dilutions of the anti-human IL-21R antibodies and isotype control protein were made in culture medium (Dulbecco's Modified Eagle Medium containing 10% FCS, L-glutamine, beta-mercaptoethanol, nonessential amino acids, sodium pyruvate, penicillin, streptomycin, and gentamycin) in flat-bottomed 96-well tissue culture plates which had been pre-coated with 1 µg of anti-rat CD3 antibody (BD Pharmingen Cat #554829), followed by the addition of 5 ng/ml rat IL-21 and 20,000 CD3 T cells per well. The cells were grown for 3 days in a 10% $CO_2$, 37° C., humidified incubator. For the last 5 hr of culture, cells were labeled with 0.5 µCi of $^3$H-thymidine (GE Amersham Cat# TRA-120). The plates were harvested onto glass fiber filter mats by a Tomtec Mach III plate harvester and were counted on a Perkin Elmer 1450 Microbeta Counter.

Figure 28:
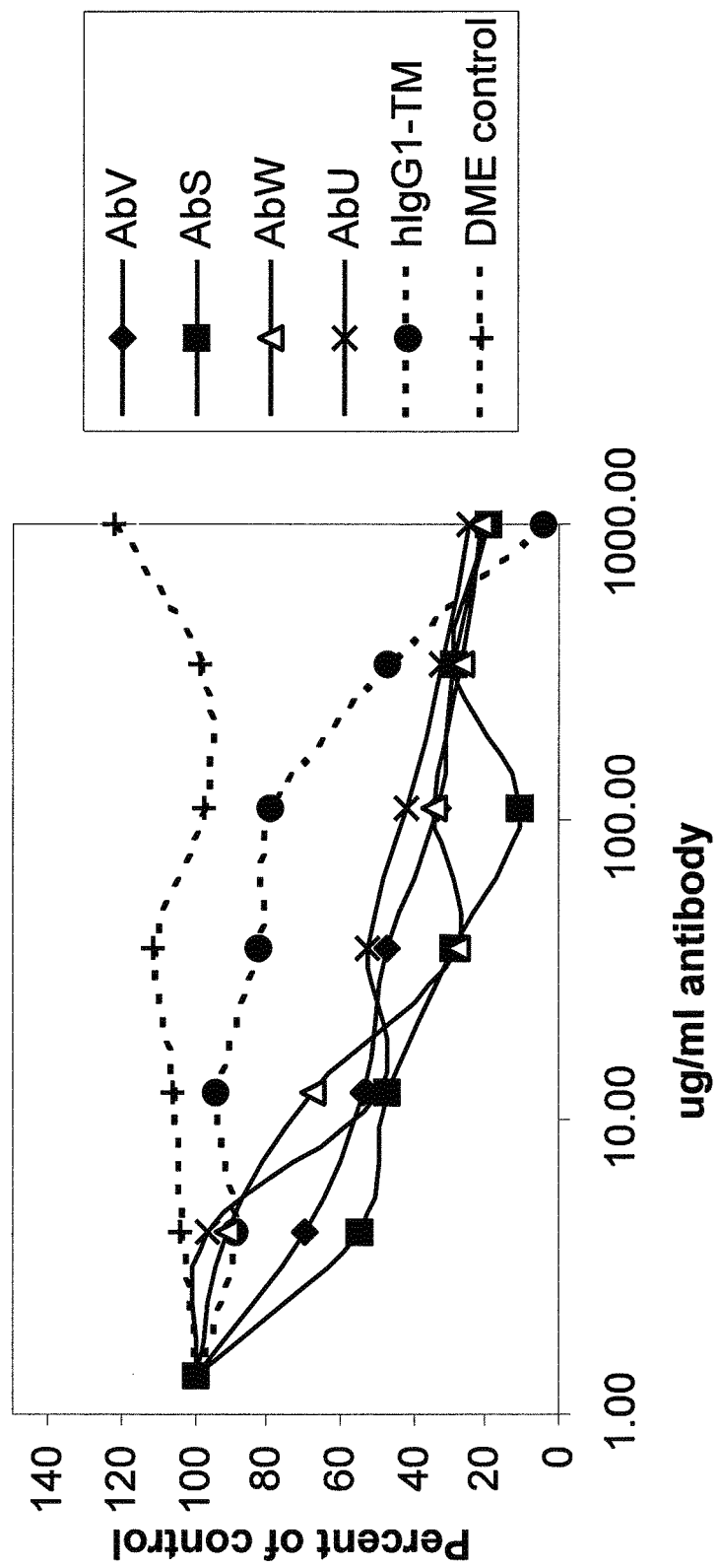
FIG. 28 depicts IL-21-dependent $^3$H thymidine incorporation into rat CD3 T cells in the presence of anti-IL-21R antibodies AbS, AbU, AbV, or AbW, or an isotype control antibody, hIgG1-TM.

The response of the rat T cells to 5 ng/ml rat IL-21 was 6-fold above the background response to 1 µg of anti-CD3 alone. Antibodies AbS, AbU, AbV, and AbW were able to inhibit the $^3$H thymidine incorporation stimulated by 5 ng/ml rat IL-21 (57,000 cpm in the absence of antibody treatment; FIG. 28). $IC_{50}$ values for neutralization in two independent experiments are shown in Table 11.

TABLE 11

Blockade of IL-21-dependent Rat T cell Proliferation by Anti-IL-21R Antibodies.

| Antibody | IC50 (nM) experiment 1 | IC50 (nM) experiment 2 |
|---|---|---|
| AbS | 35.98 | 27.07 |
| AbU | 172.79 | 105.46 |
| AbV | 70.55 | 59.23 |
| AbW | 159.06 | 94.74 |

Example 9.16

Binding of AbS to Rabbit IL-21R

Figure 29A:
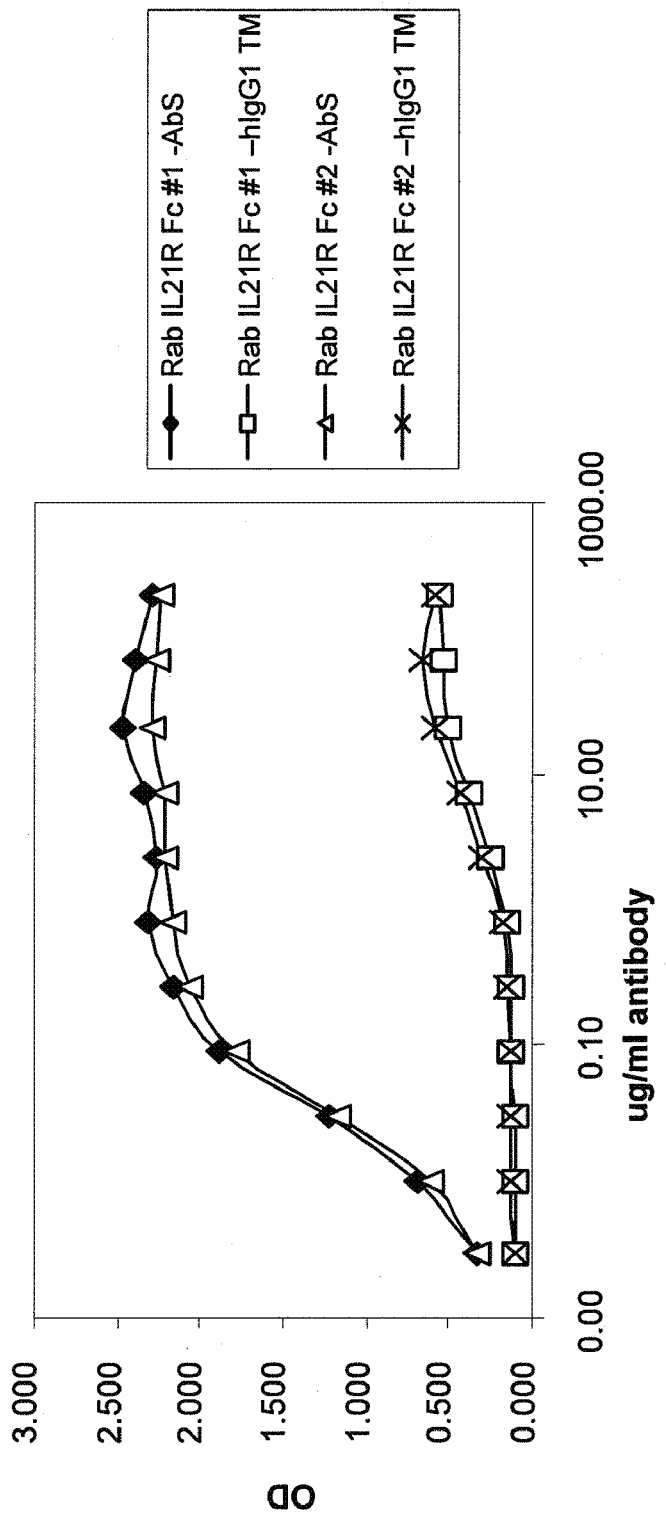
FIG. 29 depicts binding of AbS to either of two isoforms of rabbit IL-21R-Fc presented by immobilized anti-mouse IgG antibodies in the absence (FIG. 29a) or presence (FIG. 29b) of 10% conditioned medium containing rabbit IL-21.
Figure 29B:
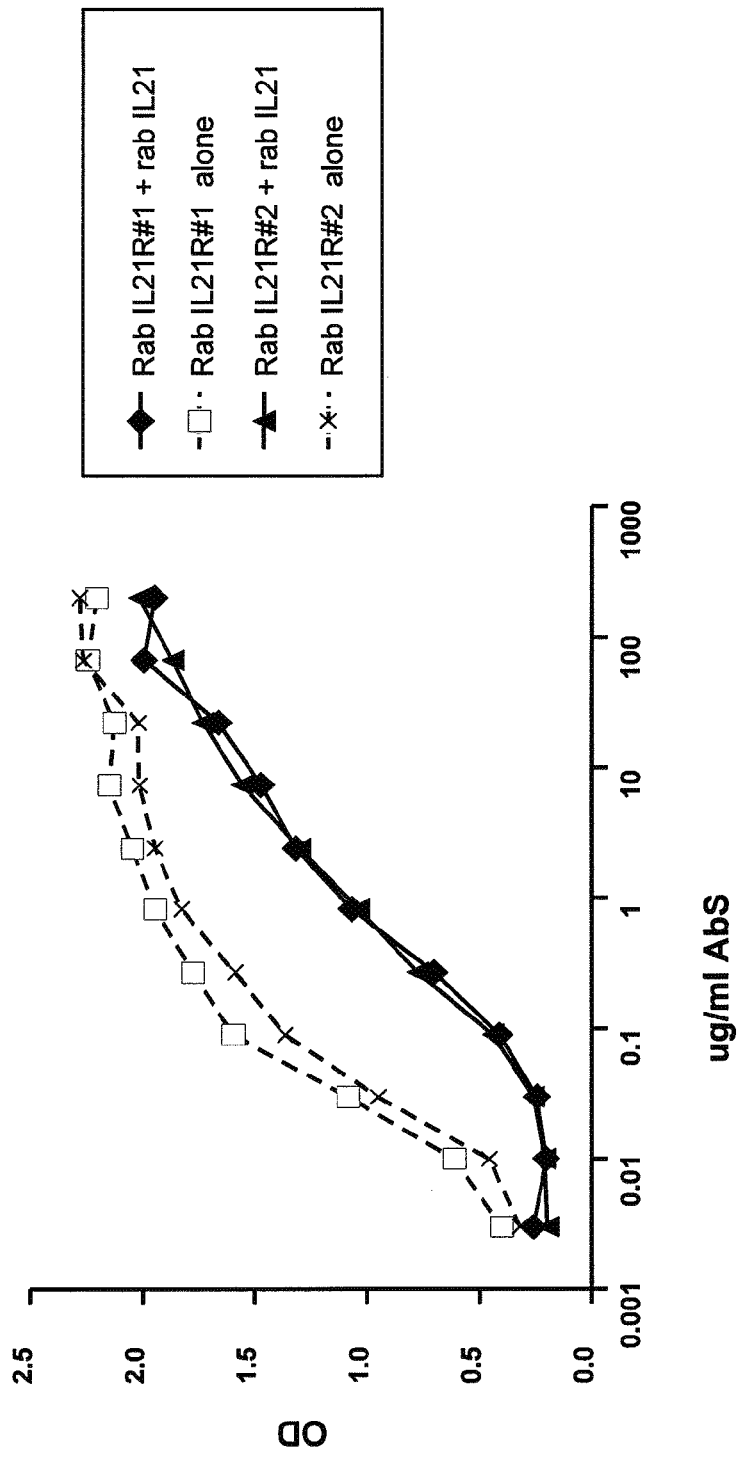

In order to demonstrate that antibody AbS binds to rabbit IL-21R, the extracellular domains of two isoforms of rabbit IL-21R were subcloned as Fc fusions and transiently expressed in HEK293 cells. Rabbit IL-21R-Fc (either isoform 1 or isoform 2) was captured from conditioned medium onto ELISA plates coated with anti-mouse IgG2a. Varying concentrations of AbS were added, the plates were washed, and antibody binding was detected with an HRP-conjugated anti-human IgG antibody. AbS showed clear binding to both isoforms of rabbit IL-21R Fc (FIG. 29a). When binding of AbS to rabbit IL-21R-Fc was carried out in the presence of 10% conditioned medium containing rabbit IL-21, binding of AbS to either receptor isoform was reduced by approximately 10-fold, indicating that AbS competes with rabbit IL-21 for binding to rabbit IL-21R (FIG. 29b).

Example 10

Characterization of Improved IgG In Vivo

Example 10.1

Figure 30A:
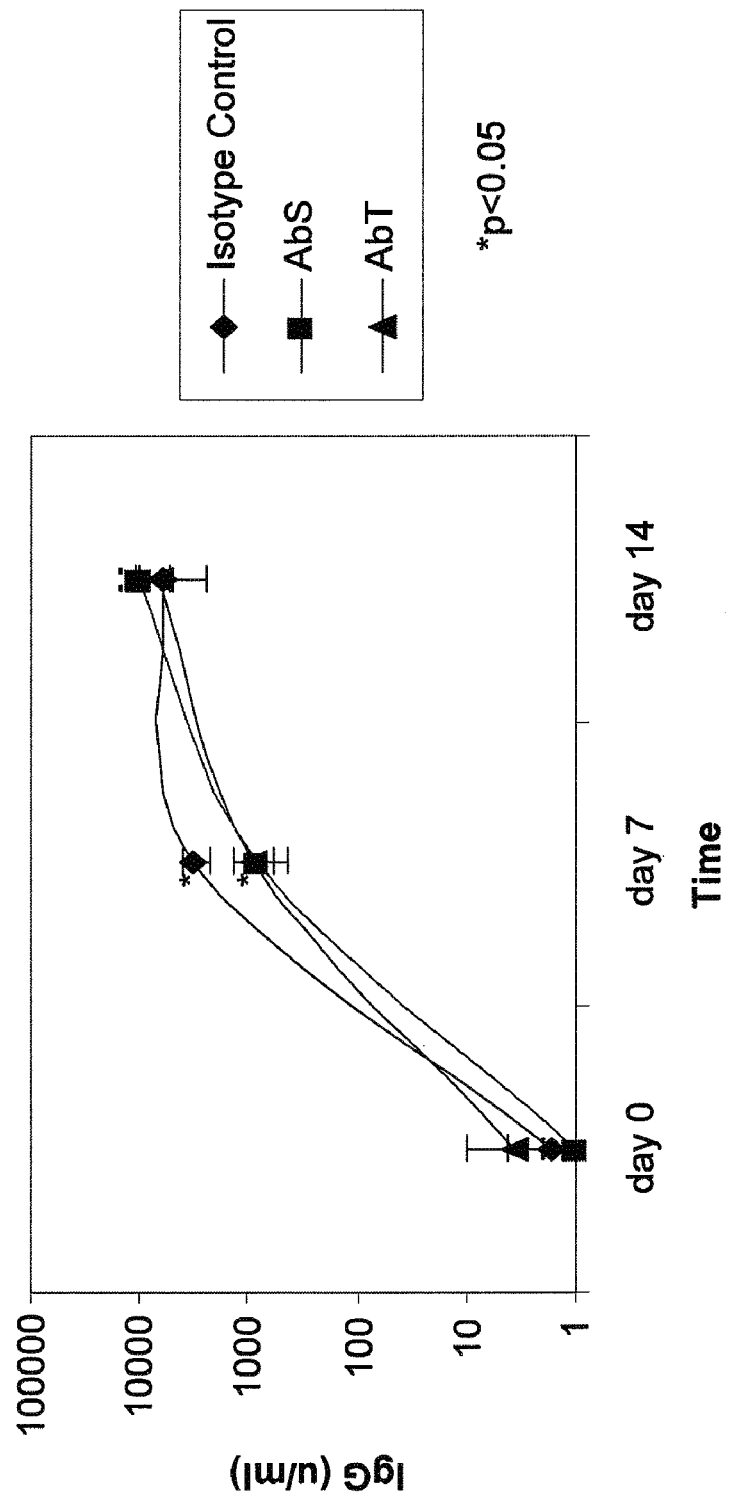
FIG. 30a depicts NP-specific IgG response and FIG. 30b depicts NP-specific IgM response.
Figure 30B:
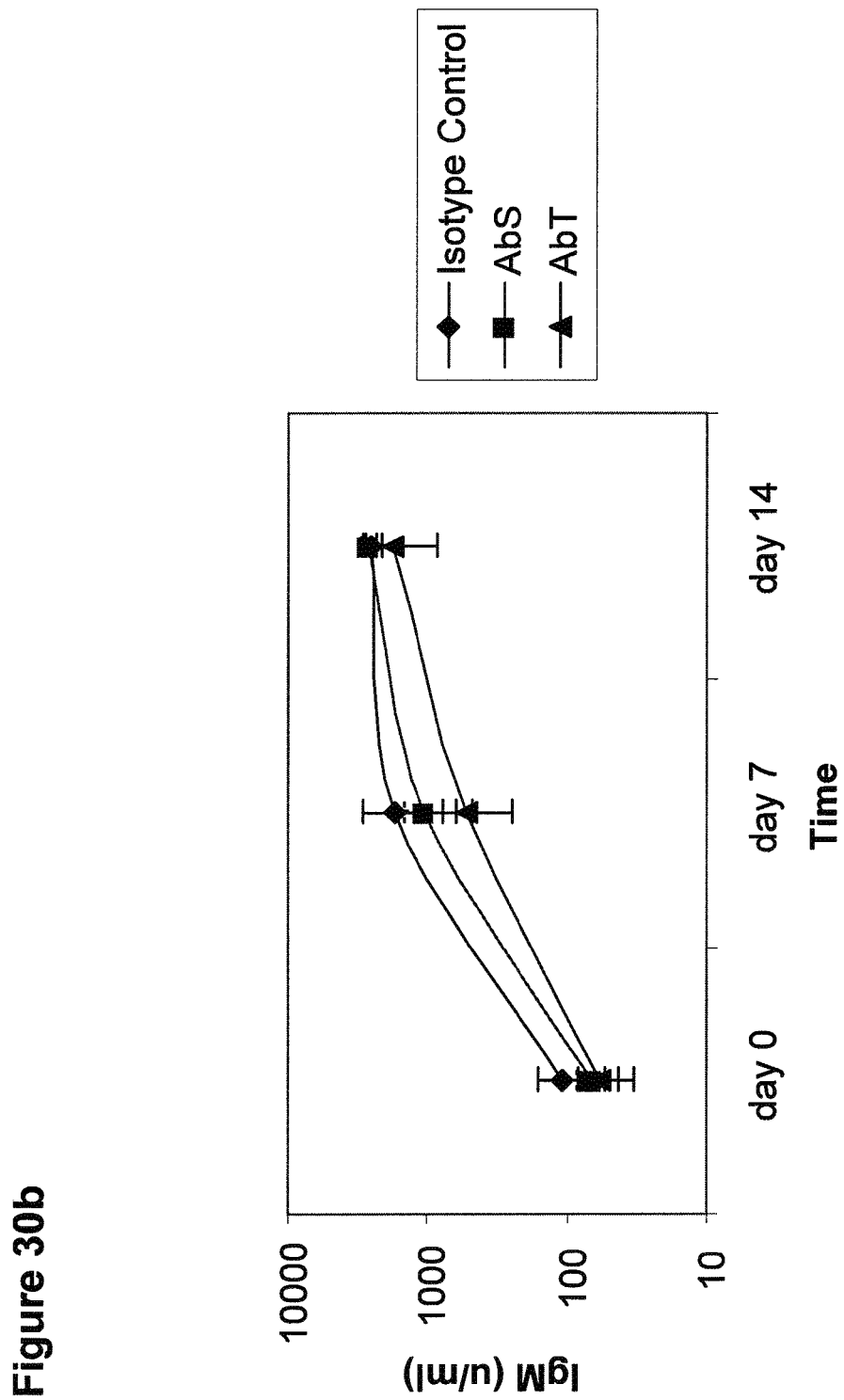
Figure 30C:
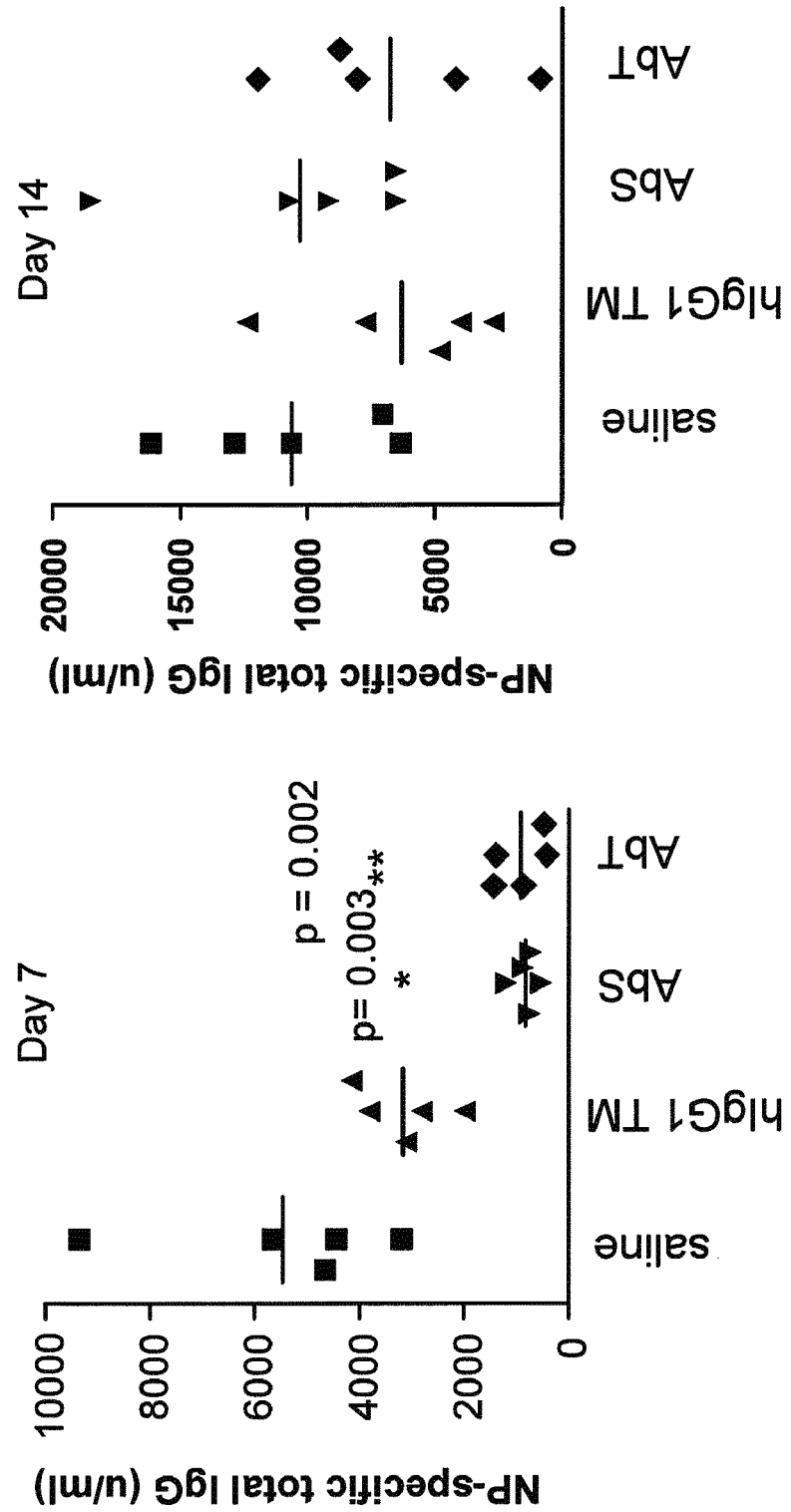
FIGS. 30c-f depict the NP-specific IgG subclass responses in repeats of the experiment shown in FIG. 30a, with ELISA data shown for individual animals: total IgG (FIG. 30c), IgG1 (FIG. 30d), IgG2a (FIG. 30e), and IgG2c (FIG. 30f).
Figure 30D:
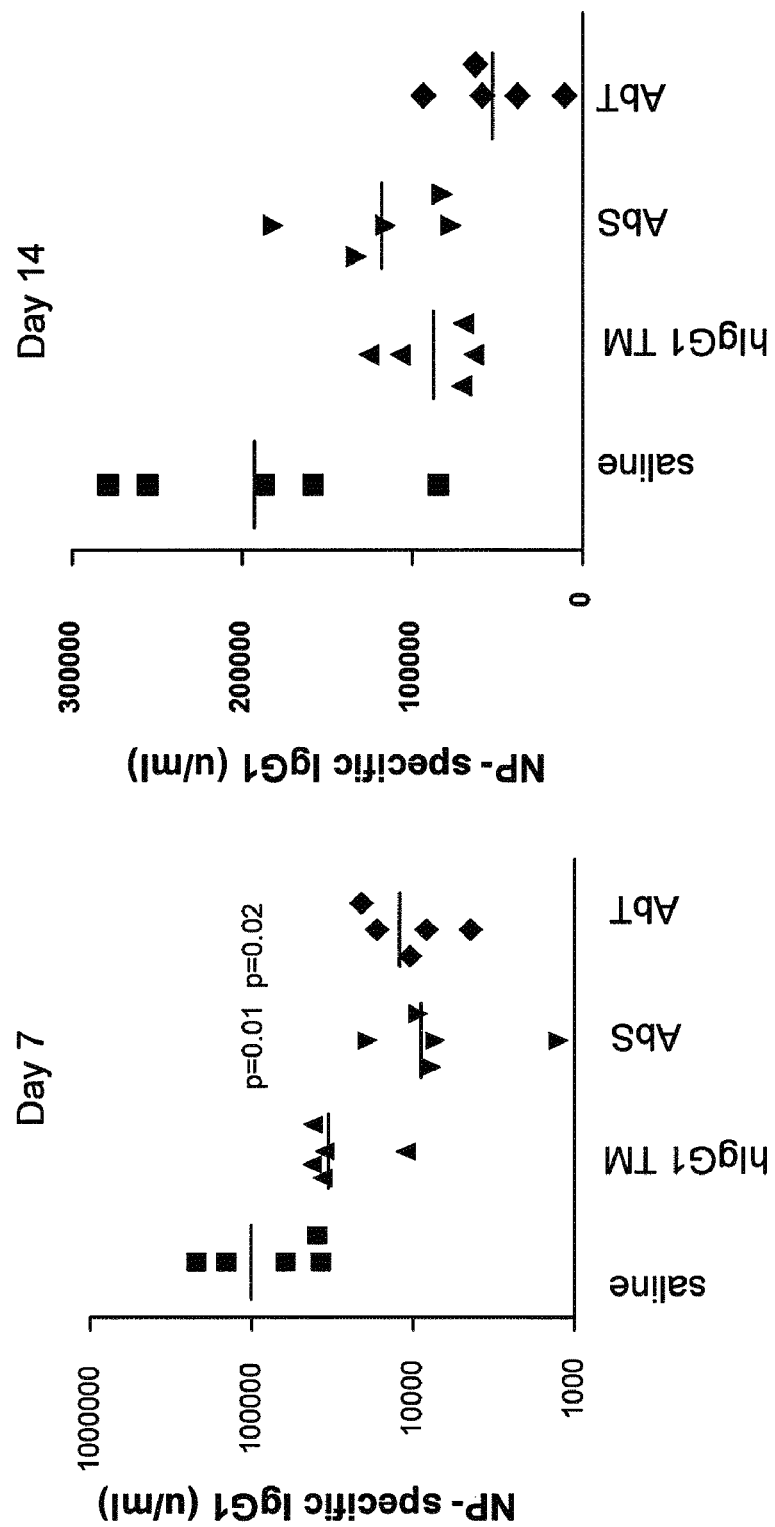

Neutralization of IL-21R with the Anti-IL-21R Antibodies, AbS and AbT, Inhibits the Generation of IgG Antibody Responses to a T Cell-Dependent Antigen In Vivo IL-21 is important for B cell isotype switching to certain subclasses of IgG and differentiation to plasma cells. Thus, to determine the efficacy of the anti-IL-21R antibodies, AbS and AbT, in vivo, the ability of these antibodies to inhibit IgM and IgG antibody responses to the T cell-dependent antigen, NP-chicken gamma globulin (NP-CGG) were tested in C57BL/6 mice. Mice were treated 3×/week with 10 mg/kg anti-IL-21R antibody or isotype control beginning one day prior to immunization with NP-CGG. NP-specific IgG and IgM were detected by ELISA. NP-specific IgM and IgG antibodies were readily detected in serum of isotype control-treated animals within 7 days following immunization, and these responses increased in magnitude to day 14 (FIG. 30b). Treatment with either AbS or AbT did not affect the magnitude of IgM responses in this study. NP-specific IgG antibody responses were delayed in AbS- or AbT-treated cells, as demonstrated by a decreased response compared to isotype control on day 7. NP-specific IgG antibody responses were similar in isotype control-, AbS- and AbT-treated mice at day 14 (FIG. 30a). These data show that neutralization of IL-21R in vivo using either AbS or AbT can transiently inhibit the induction of early IgG antibody responses to a T cell-dependent antigen.

Figure 30E:
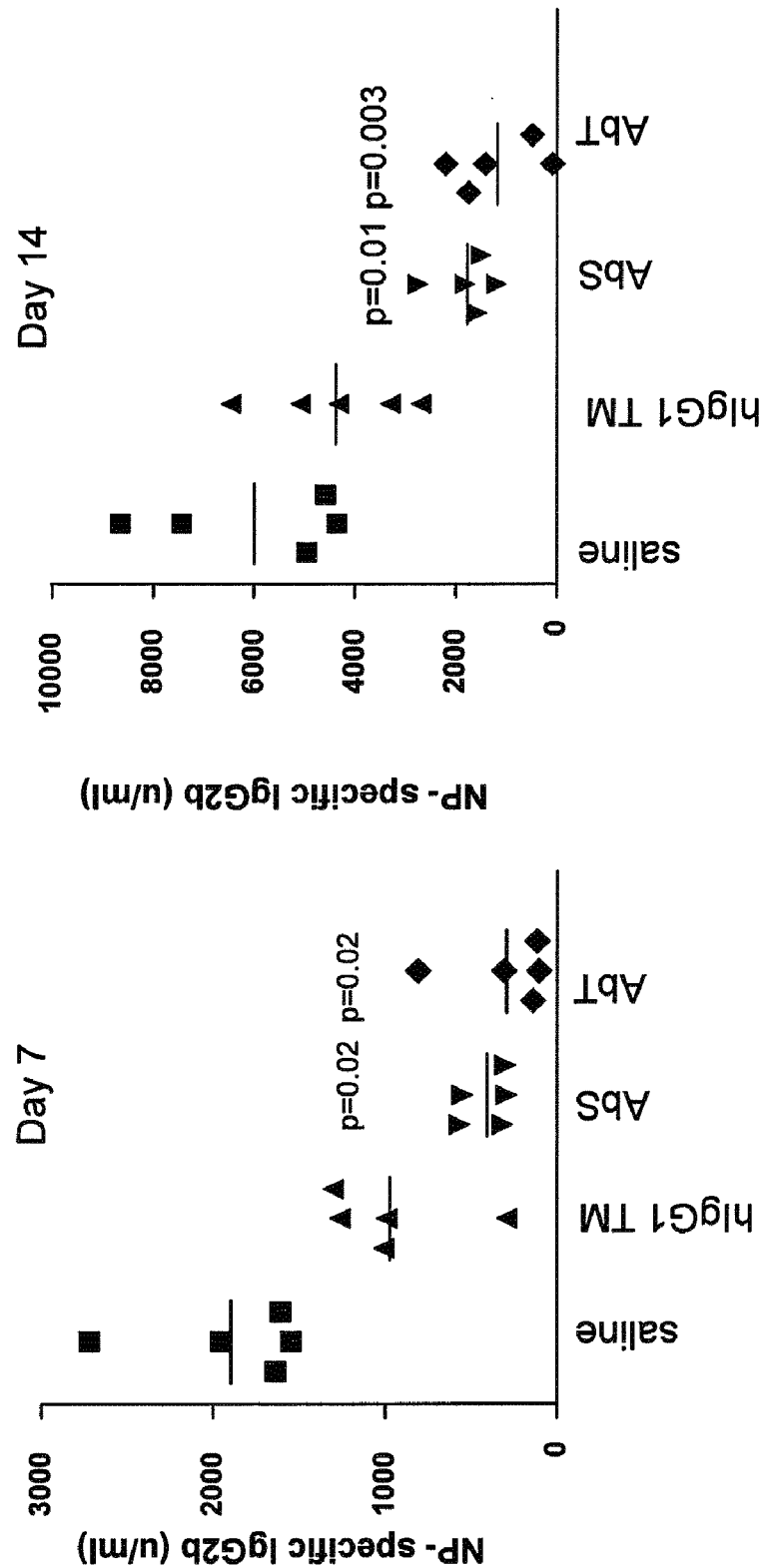
Figure 30F:
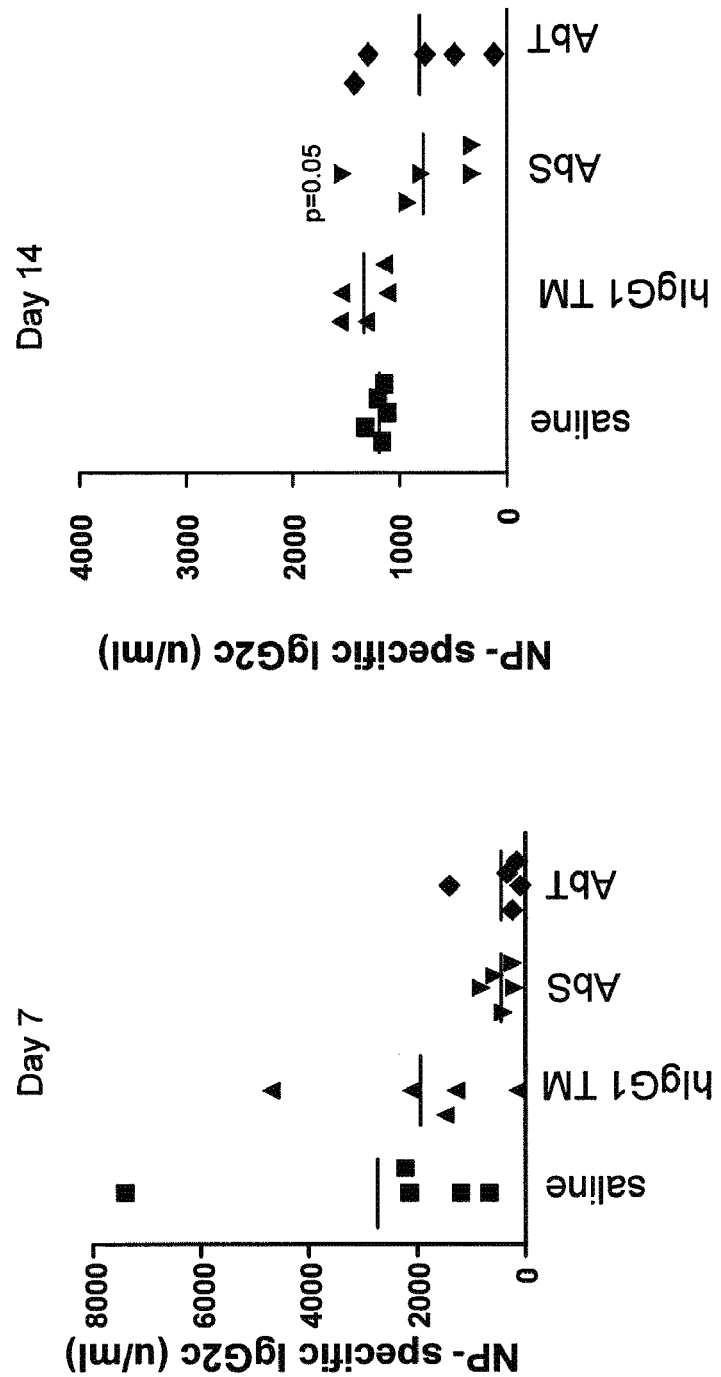

A second study testing AbS and AbT also yielded similar results (FIGS. 30c-f). NP-specific IgG responses were transiently reduced at day 7 of immunization in mice treated with either AbS or AbT, but were similar to isotype control-treated mice at later timepoints. Isotype-specific ELISAs indicated that IgG2b and IgG2c were significantly reduced by AbS and AbT compared to controls at day 7 (FIGS. 30e-f). These data show that neutralization of IL-21R in vivo using either AbS and AbT can transiently inhibit the induction of early IgG antibody responses to a T cell-dependent antigen.

Figure 30G:
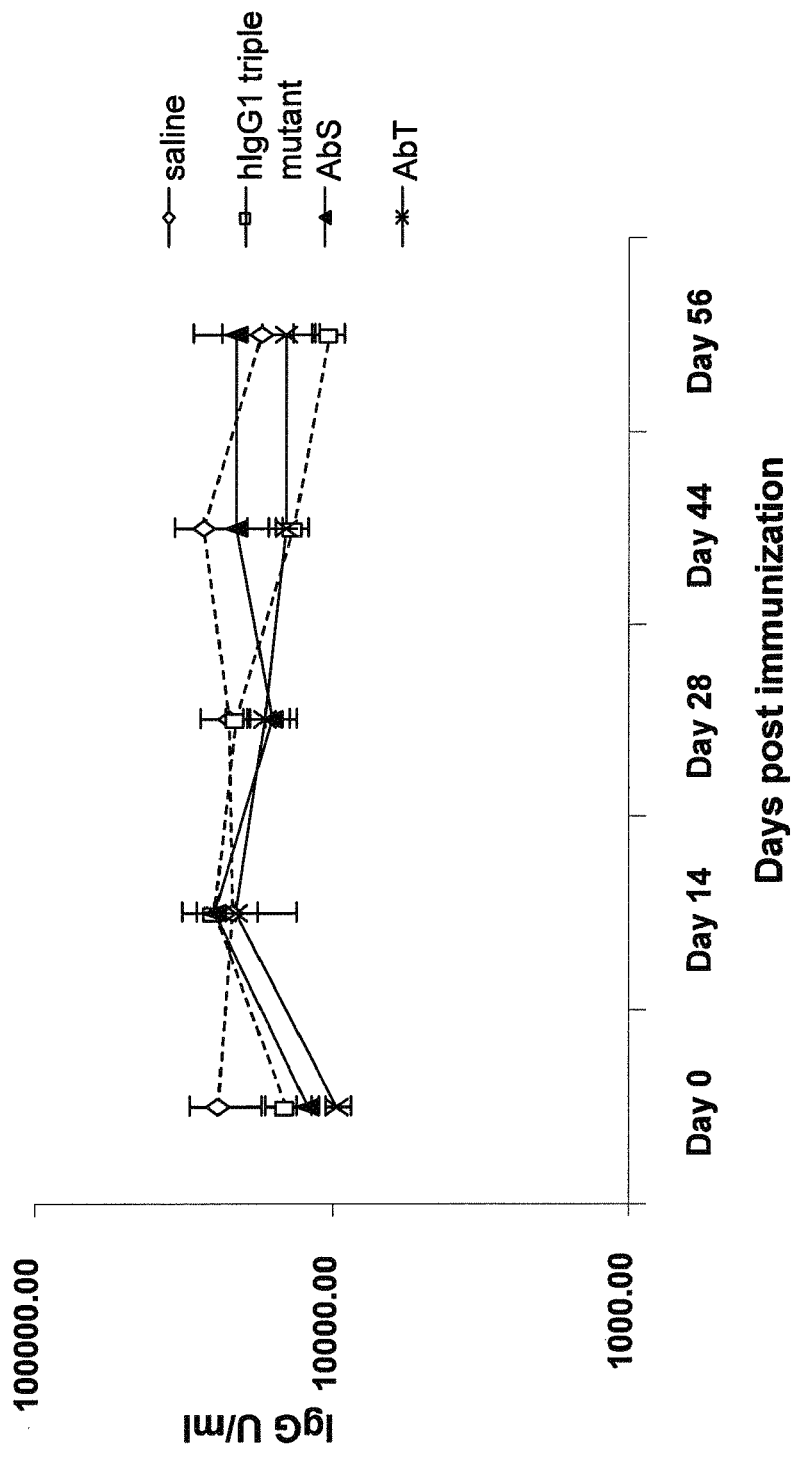
FIG. 30g depicts NP-specific IgG response over a two-month period.
Figure 30H:
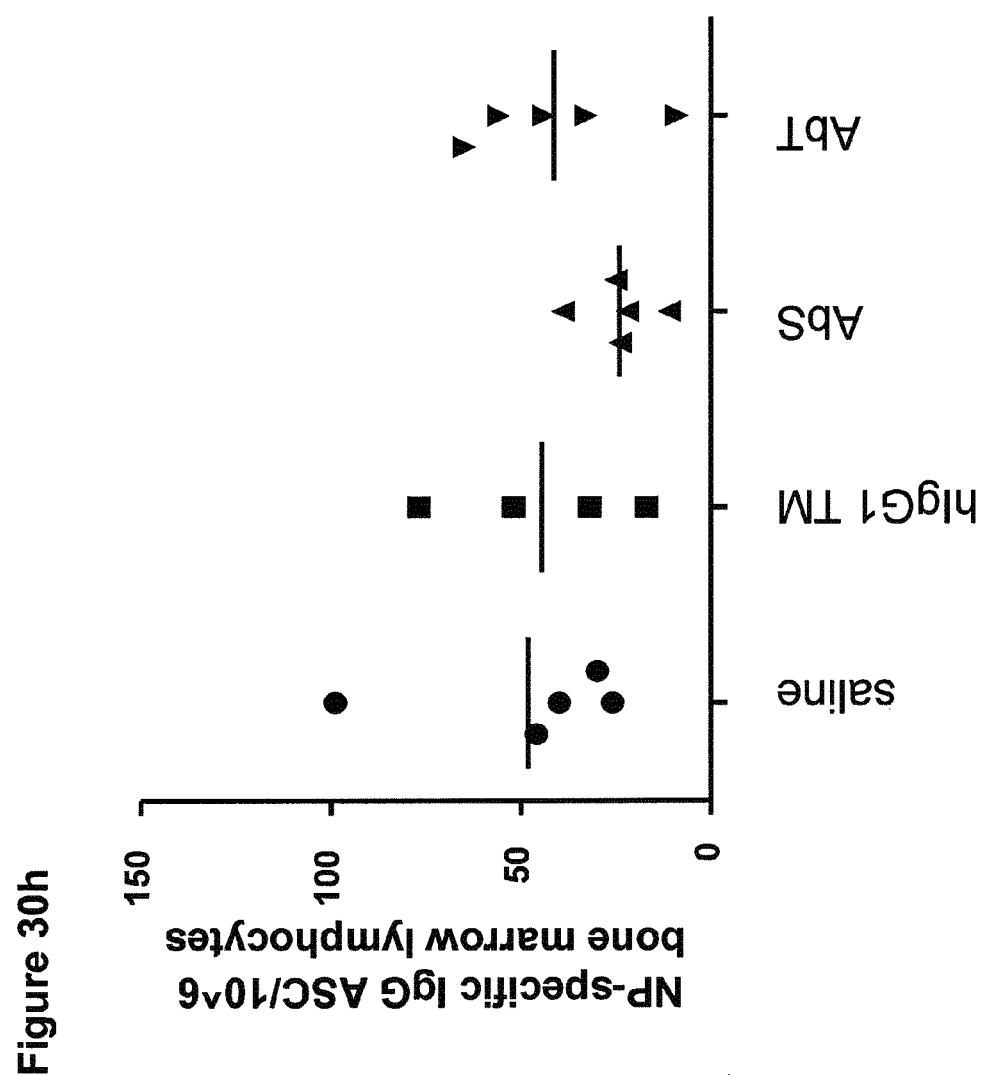
FIG. 30h depicts NP-specific IgG antibody-secreting cells (ASC) found in bone marrow at the end of the two-month study period.

To test the effects of IL-21R neutralization on the maintenance of established long-term humoral immunity, C57BL/6 mice were immunized with NP-CGG and rested for at least one month to allow them to generate memory B cells and long-lived plasma cells, which give rise to long-term IgG serum antibody titers. Approximately one month after immunization, mice were treated 3×/week i.p. with saline, or 10 mg/kg of either AbS or AbT, or isotype control antibody for two months. NP-specific IgG serum antibody titers were monitored every two weeks by ELISA. C57BL/6 mice had high titers of NP-specific IgG serum antibodies one month after immunization when compared to naïve C57BL/6 mice, consistent with the formation of long-term humoral immunity to NP. NP-specific IgG serum antibody titers remained stable over the course of the study in both mice treated with the isotype control antibody, and treatment with either AbS or AbT did not affect these antibody titers (FIG. 30g). Following immunization, B cells generate plasma cells (in bone marrow), which give rise to long-term serum antibody titers. At the end of the study, the number of NP-specific IgG plasma cells in the bone marrow of the mice was measured, and the cell numbers were unaffected by treatment with AbS or AbT (FIG. 30h). These data indicate that neutralization of IL-21R with AbS and AbT in this treatment regimen does not affect the maintenance of established long-term serum antibody titers.

Example 10.2

Anti-IL-21R Antibody Function in a Model of SLE

The anti-IL-21R antibodies AbS and AbT were tested for their ability to ameliorate disease in the MRL-Fas$^{lpr}$ murine model of systemic lupus erythematosus (SLE). MRL-Fas$^{lpr}$ mice spontaneously develop symptoms resembling those observed in human lupus, including high titers of anti-double-stranded DNA (anti-dsDNA) autoantibodies in circulation, immunoglobulin and complement C3 deposits in the glomeruli, presence of lymphocytic infiltrates in the kidney and lung, and, in severe disease, proteinuria, lymphadenopathy, and skin lesions. Male MRL-Fas$^{lpr}$ mice were obtained from Jackson Laboratory (Bar Harbor, Me.) and, starting at 12 weeks of age, were given AbS, AbT, saline, or a control anti-human IL-13 antibody with the same triple-mutant human IgG1 constant region at a dosage of 400 µg/mouse (10 mg/kg) 3×/week over 10 weeks via i.p. injection. Serum samples were taken biweekly and examined for anti-dsDNA antibodies by ELISA. Urine was collected biweekly and tested for protein (using protein test strips); neither control animals nor treated animals developed significant proteinuria. Animals were also monitored for enlarged lymph nodes and skin lesions; neither control animals nor treated animals showed abnormalities. After 10 weeks of treatment, animals were sacrificed, and kidney and brain sections were examined for Ig and C3 deposits by immunohistochemistry. Cellular infiltrations into kidney and lungs were measured by examination of H/E-stained tissue sections.

Treatment of MRL-Fas$^{lpr}$ mice with the IL-21R blocking antibody AbS significantly reduced anti-dsDNA IgG serum antibody levels as compared to animals treated with saline or a control anti-human IL-13 antibody, beginning at 2 weeks post-treatment and continuing until 10 weeks post-treatment (FIG. 31). Anti-dsDNA antibodies were reduced to undetectable levels by AbS treatment in 8/10 mice at week 4 (FIG. 31d), 5/10 at week 6 (FIG. 31e), and 7/10 at week 8 (FIG. 31f), as compared to saline and IL-13 control antibody-treated animals (all control mice had detectable anti-dsDNA antibody titers). Treatment with the IL-21R blocking antibody AbT did not significantly affect anti-dsDNA IgG serum antibody levels.

Figure 31A:
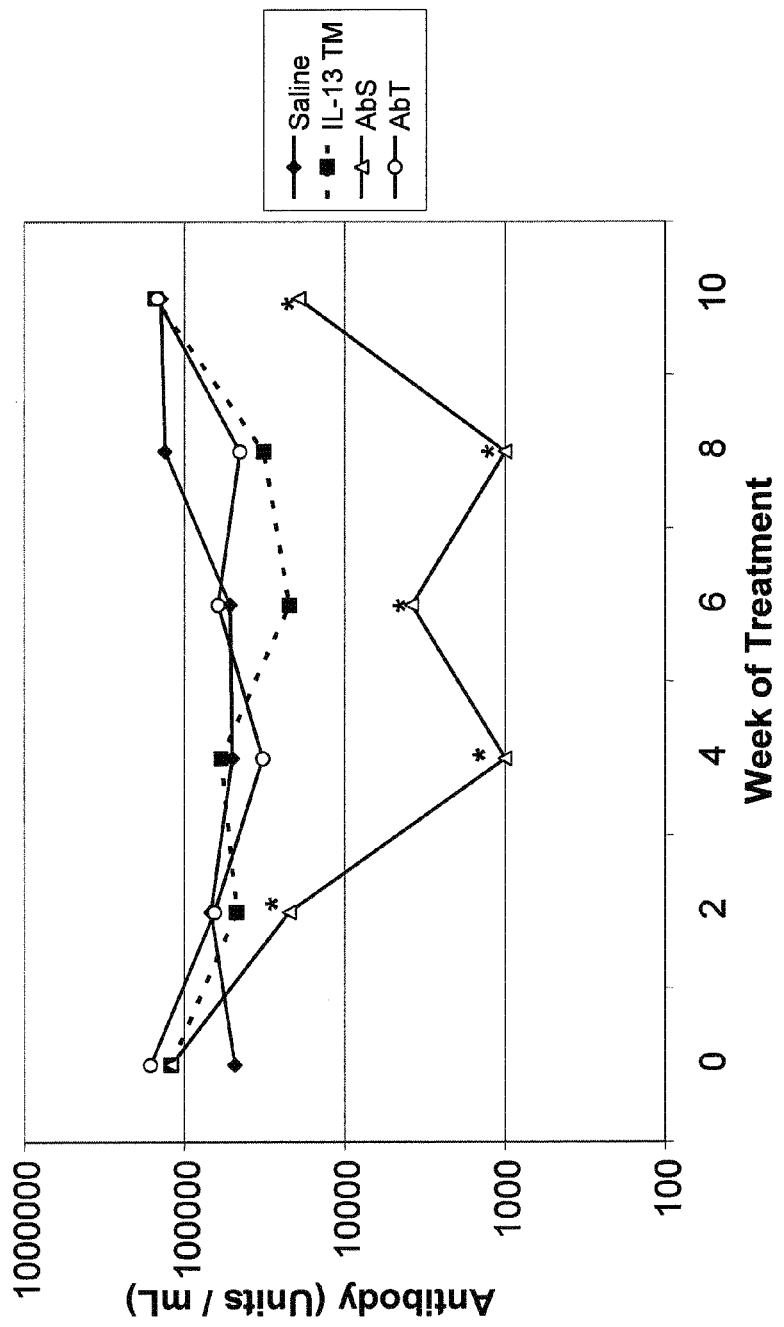
FIG. 31a shows anti-dsDNA antibody titers following treatment.
Figure 31B:
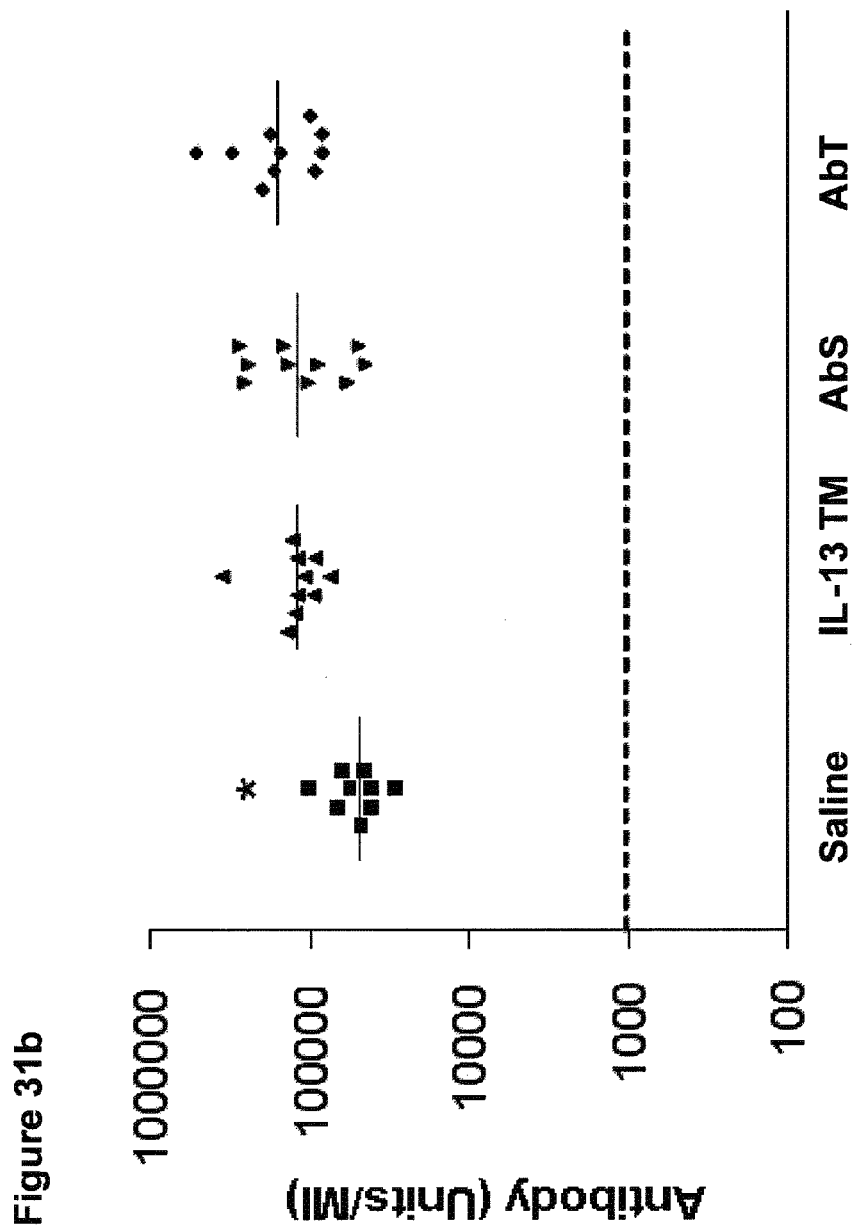
FIG. 31b shows prebleed anti-dsDNA antibody titers.
Figure 31C:
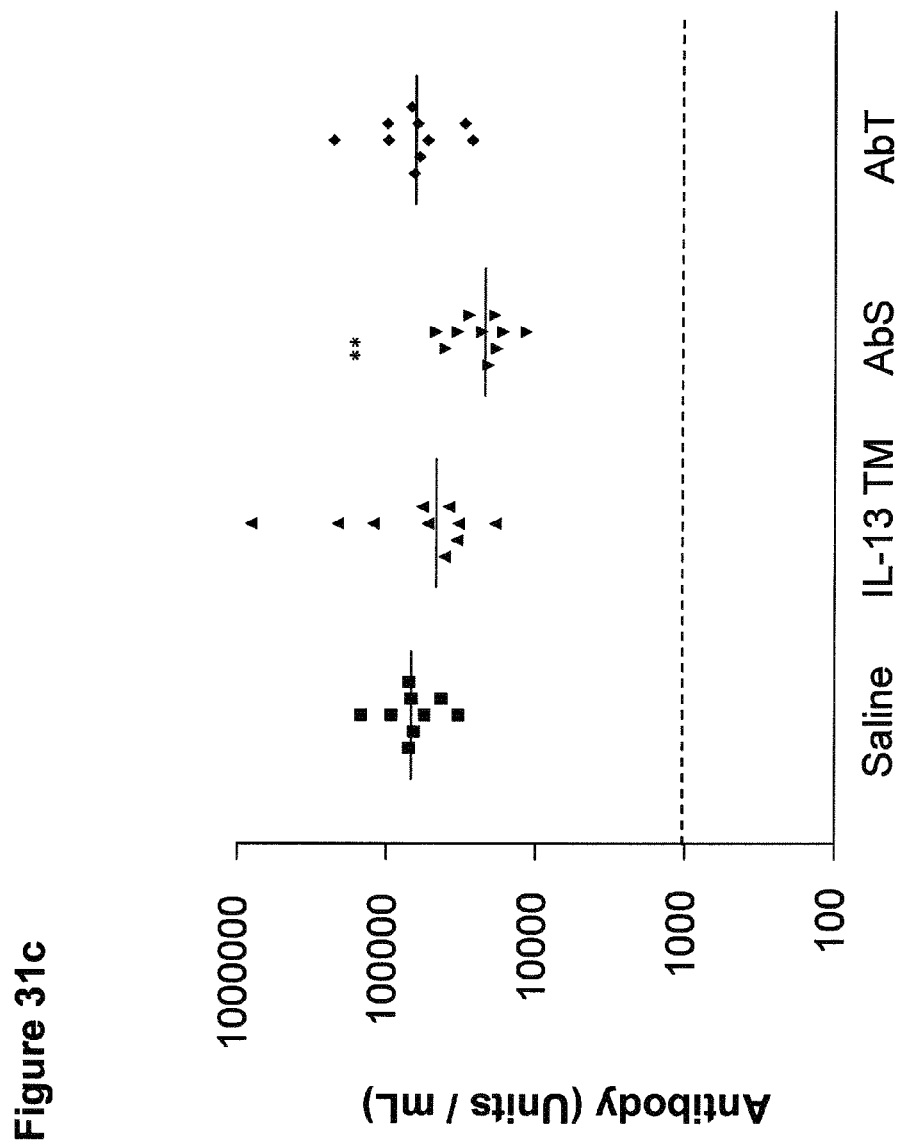
FIG. 31c shows anti-dsDNA antibody titers after two weeks of dosing.
Figure 31D:
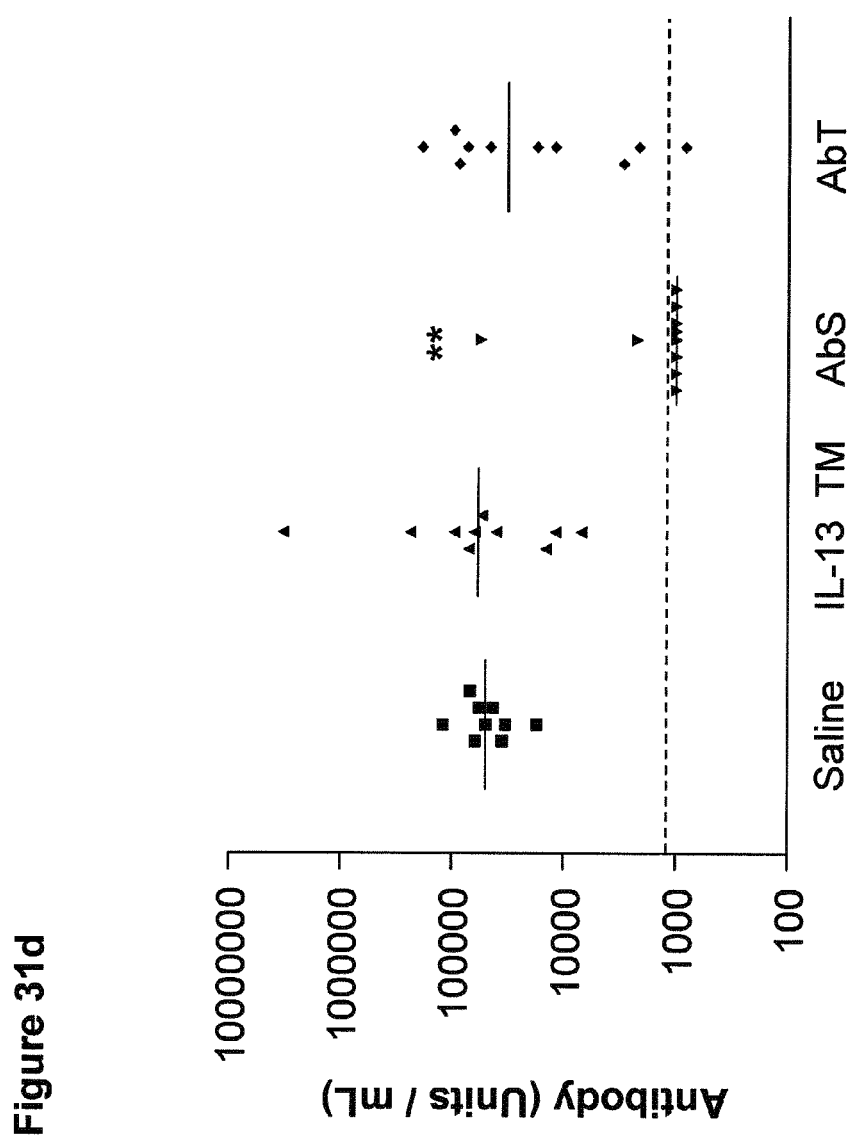
FIG. 31d shows anti-dsDNA antibody titers after four weeks of dosing.
Figure 31E:
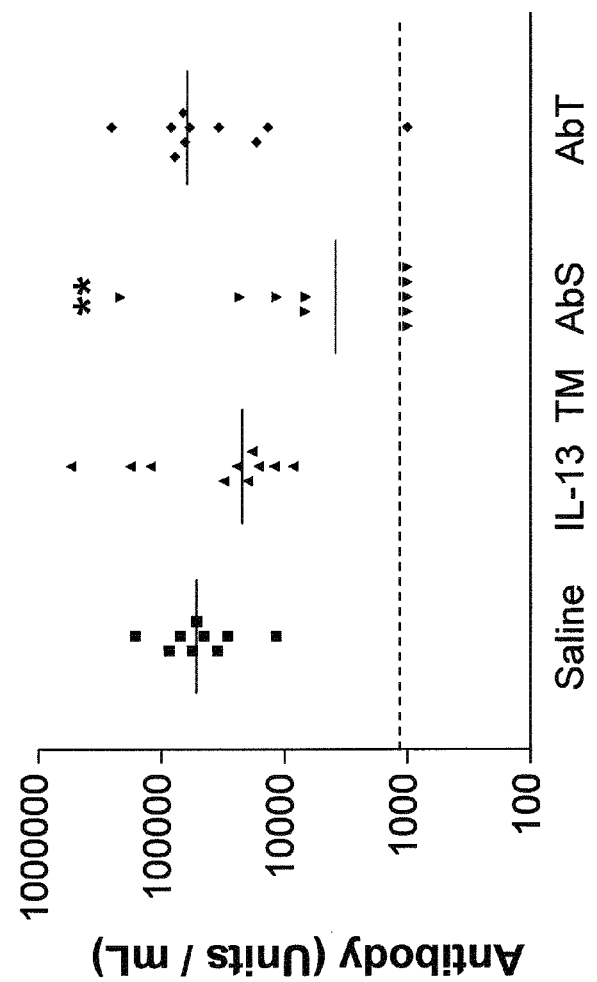
FIG. 31e shows anti-dsDNA antibody titers after six weeks of dosing.
Figure 31F:
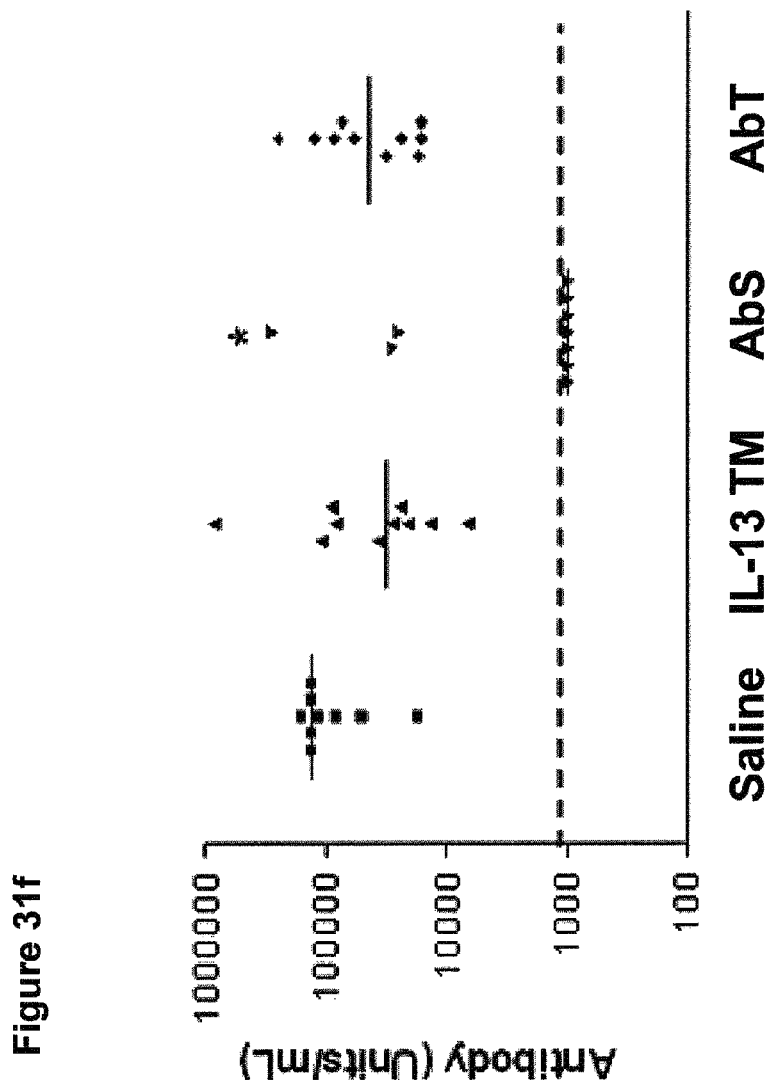
FIG. 31f shows anti-dsDNA antibody titers after eight weeks of dosing.
Figure 31G:
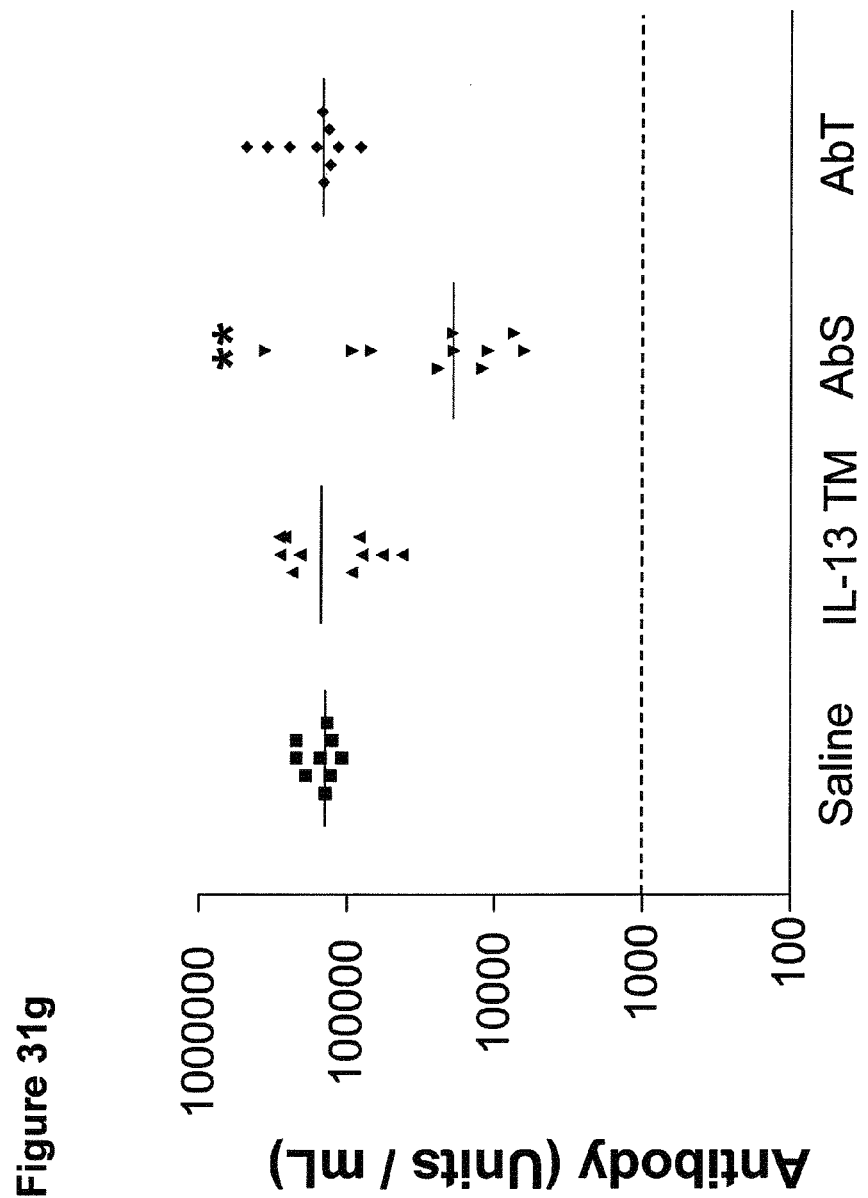
FIG. 31g shows anti-dsDNA antibody titers after ten weeks of dosing.

FIG. 31a shows anti-dsDNA antibody titers following treatment (AbS-treated group is significantly different from both saline- and anti-IL-13-treated groups (p<0.01)). FIG. 31b shows prebleed anti-dsDNA antibody titers (saline-treated group is significantly different from AbS-, AbT-, and anti-IL-13-treated groups (p<0.01)). The AbS-treated group is significantly different from both saline- and anti-IL-13-treated groups (p<0.01) after 2 weeks of dosing (FIG. 31c); 4 weeks (FIG. 31d); 6 weeks (FIG. 31e); 8 weeks (FIG. 31f); and 10 weeks (FIG. 31g).

Figure 32A:
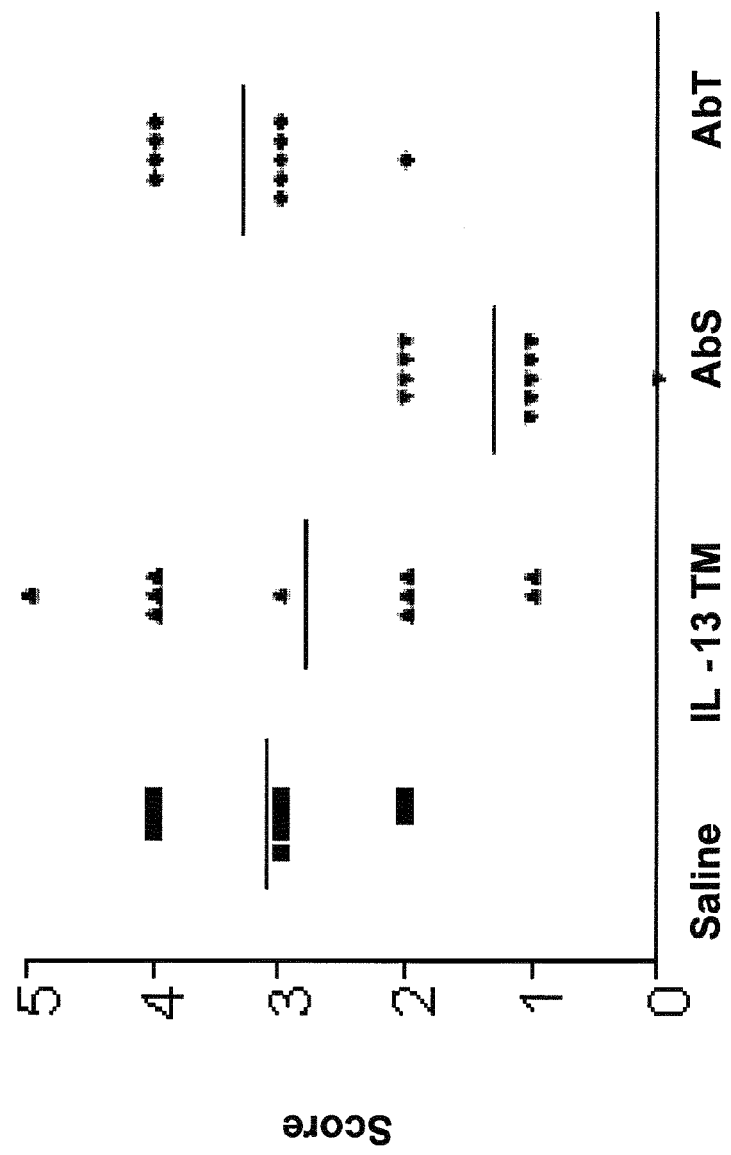
FIG. 32 depicts IgG deposits in kidneys of MRL-Fas$^{lpr}$ mice treated with anti-IL-21R antibodies. Twelve-week-old male MRL-Fas$^{lpr}$ mice were treated (10 mg/kg i.p., 3×/week) with either saline (control) or the indicated triple-mutant antibodies; anti-human IL-13 human IgG1 A234 A235 A237 triple-mutant antibody with no reactivity to murine IL-21 was used as an isotype control. Following 10 weeks of treatment, mice were sacrificed and IgG deposits in the kidneys were identified by immunocytochemistry (FIG. 32b; glomeruli are indicated by dashed circles; examples of IgG deposits are indicated by arrowheads). Staining intensity was scored on a scale of 1-5 (FIG. 32a).
Figure 32B:
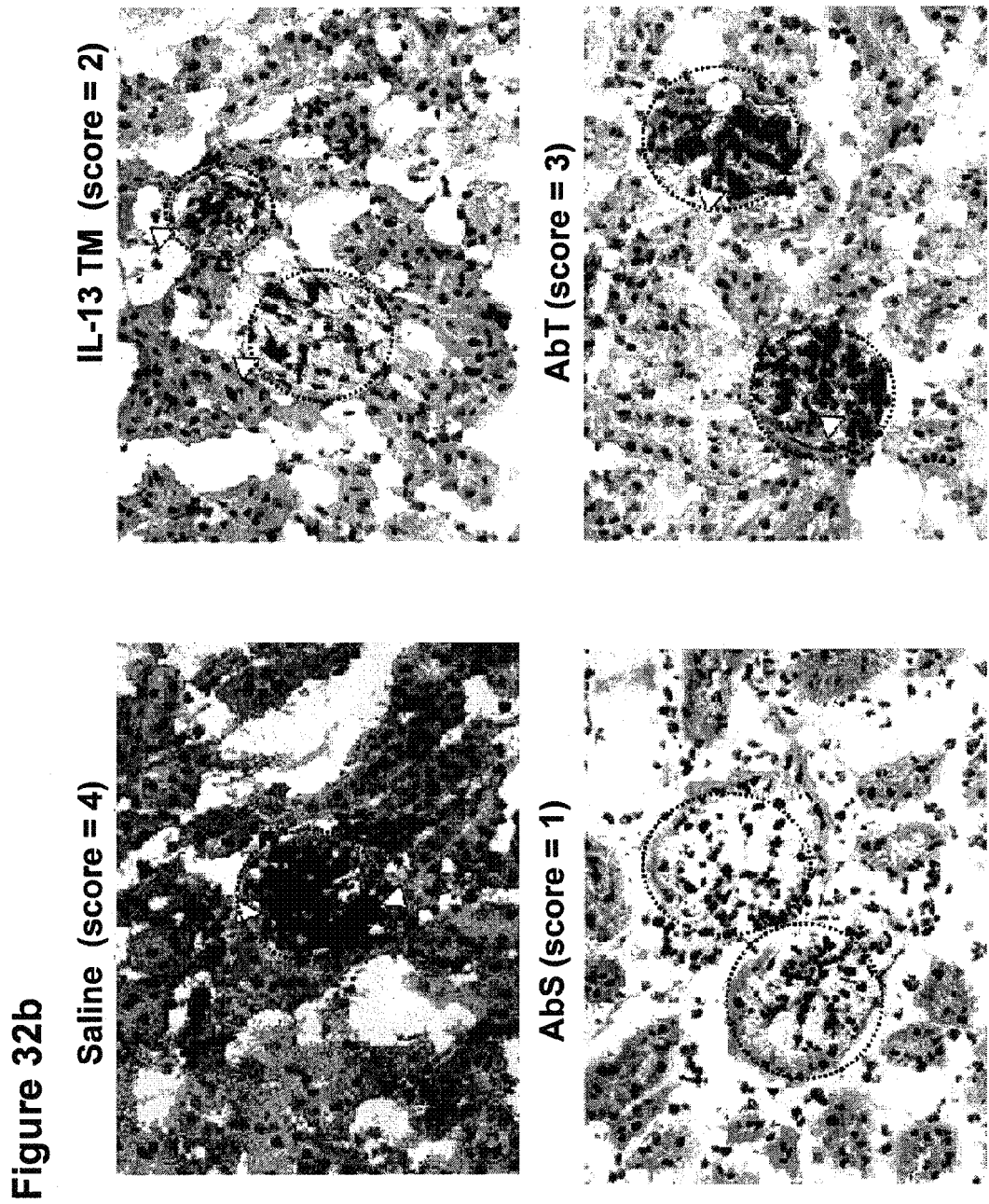
Figure 33A:
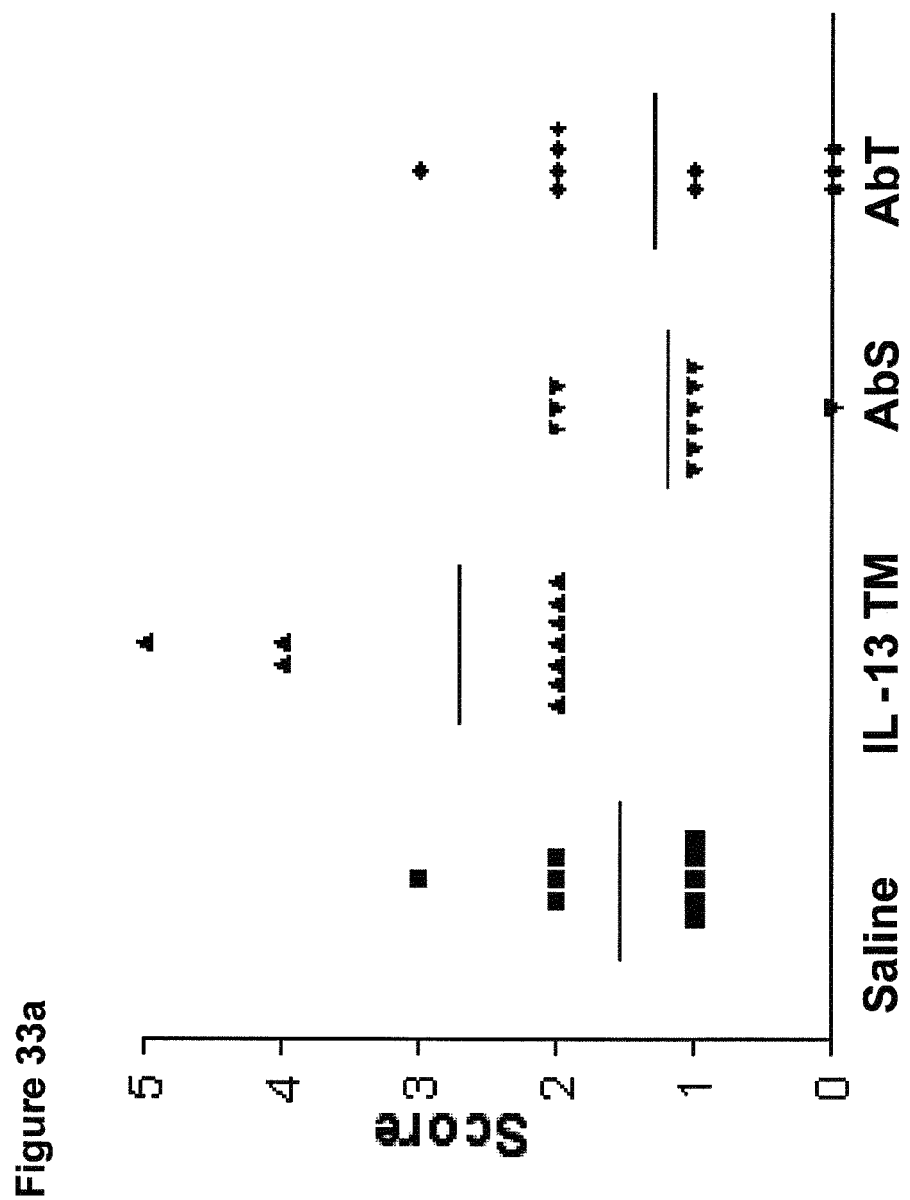
FIG. 33 depicts IgM and complement C3 deposits in kidneys of MRL-Fas$^{lpr}$ mice treated with anti-IL-21R antibodies. Twelve-week-old male MRL-Fas$^{lpr}$ mice were treated (10 mg/kg i.p., 3×/week) with either saline (control) or the indicated triple-mutant antibodies. Following ten weeks of treatment, mice were sacrificed and IgM (FIG. 33a) and complement C3 (FIG. 33b) deposits in the kidneys were identified by immunocytochemistry. Staining intensity was scored on a scale of 1-5.
Figure 33B:
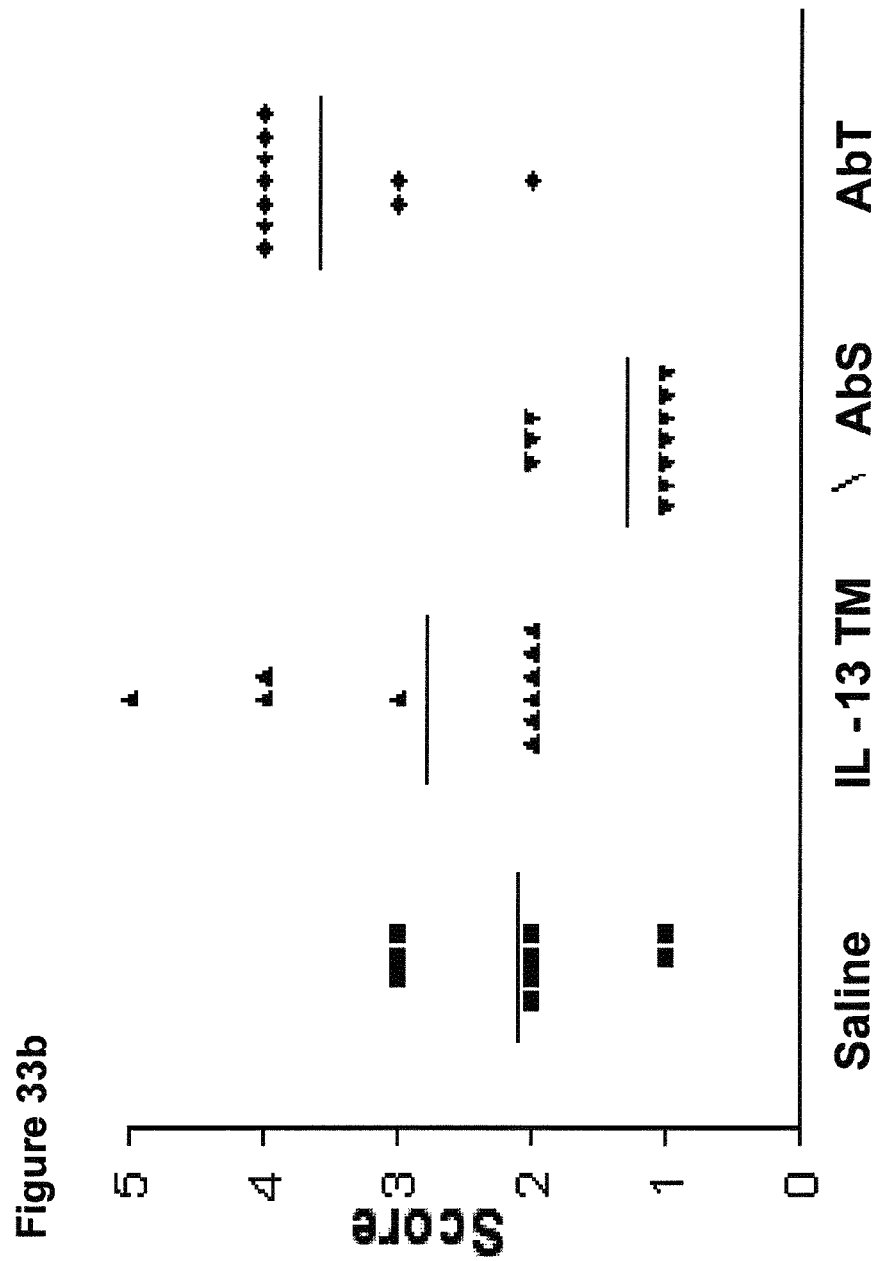
Figure 34A:
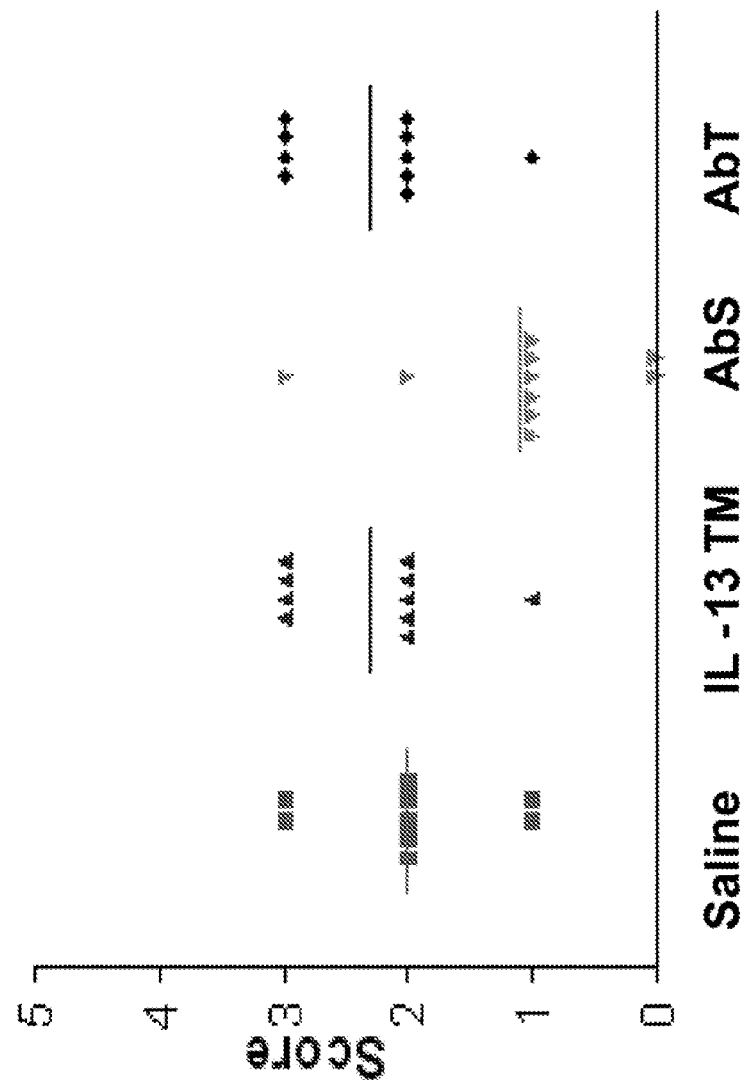
FIG. 34 depicts IgG, IgM and complement C3 deposits in brains of MRL-Fas$^{lpr}$ mice treated (10 mg/kg i.p., 3×/week) with anti-IL-21R antibodies. Twelve-week-old male MRL-Fas$^{lpr}$ mice were treated with either saline (control) or the indicated triple-mutant antibodies. Following ten weeks of treatment, mice were sacrificed and IgG (FIG. 34a), IgM (FIG. 34b), and complement C3 (FIG. 34c) deposits in the brain were identified by immunocytochemistry. Staining intensity was scored on a scale of 1-5.
Figure 34B:
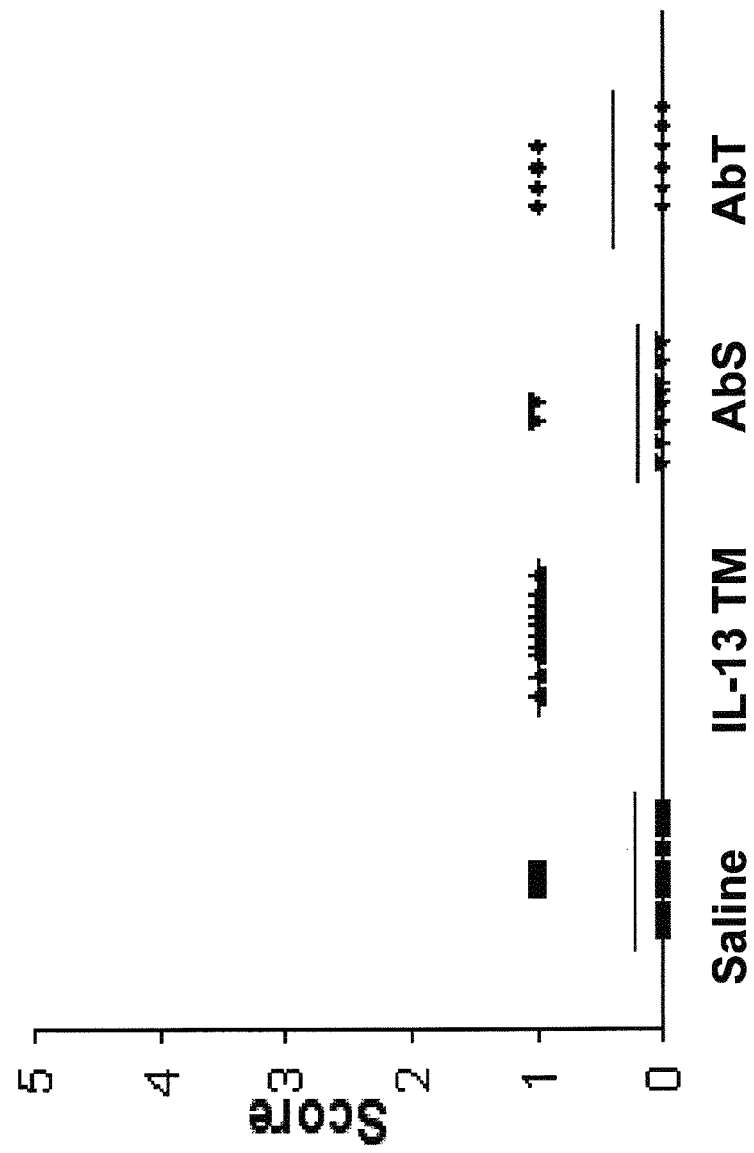
Figure 34C:
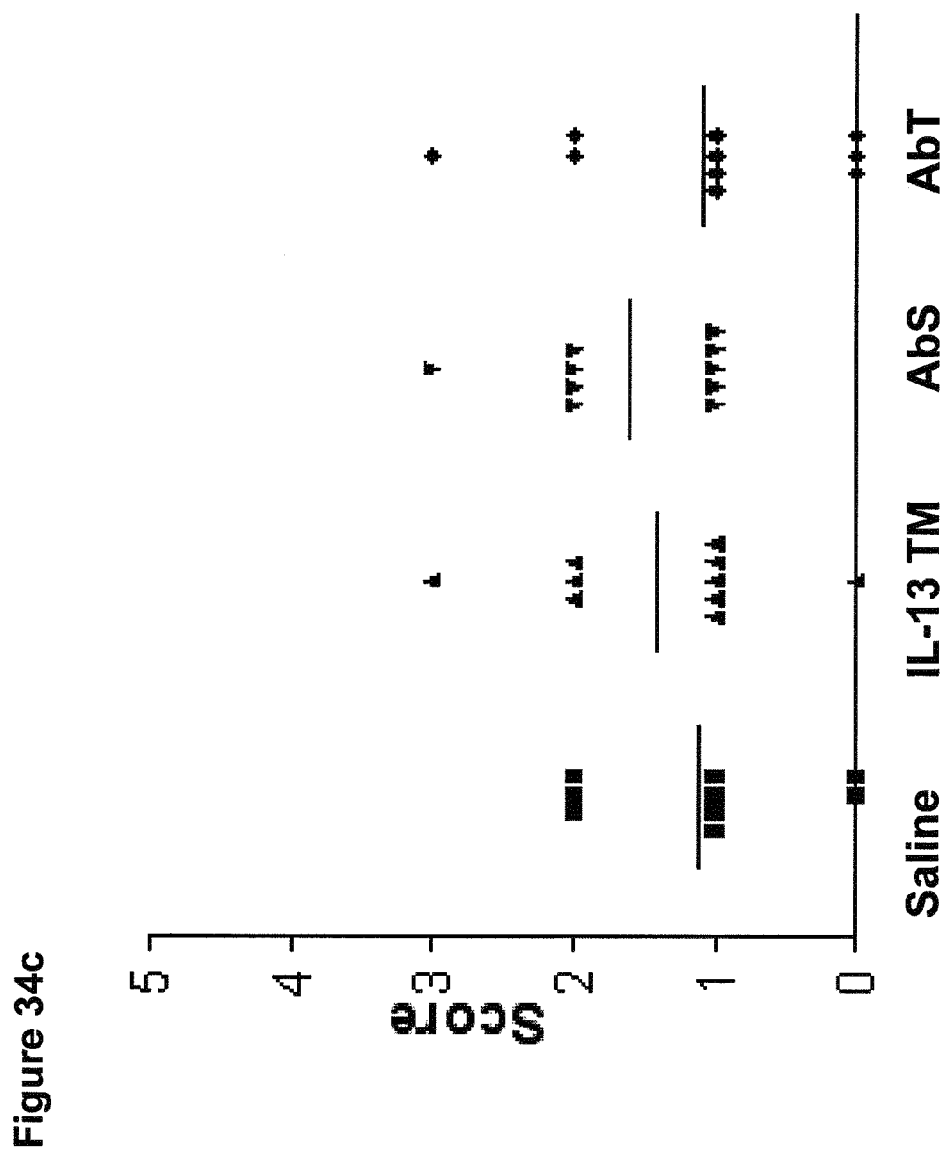

Treatment with AbS also significantly reduced Ig and C3 immune complex deposition and kidney pathology as compared to anti-IL-13 antibody-treated controls (p<0.01) (FIGS. 32, 33). Twelve-week-old male MRL-Fas$^{lpr}$ mice were treated (10 mg/kg i.p., 3×/week) with either saline (control) or the indicated triple-mutant antibodies (an anti-human IL-13 human IgG1 A234 A235 A237 mutant antibody with no reactivity to murine IL-21 was used as an isotype control). Following 10 weeks of treatment, mice were sacrificed and Ig and C3 deposits in the kidneys were identified by immunocytochemistry. FIG. 32 depicts IgG deposits in kidneys of MRL-Fas$^{lpr}$ mice treated as indicated (in FIG. 32b, glomeruli are indicated by dashed circles, and examples of diffuse stain, indicating IgG deposits, are indicated with white arrowheads). Staining intensity was scored on a scale of 1-5 (FIG. 32a). Kidney IgG deposits in animals treated with AbS were significantly lower (p<0.01) than those in IL-13 triple-mutant-treated controls. FIG. 33 depicts IgM (FIG. 33a) and complement C3 (FIG. 33b) deposits in kidneys of MRL-Fas$^{lpr}$ mice treated as indicated. Staining intensity was scored on a scale of 1-5. IgM and complement C3 deposition in the kidneys were significantly reduced (p<0.05) by AbS compared to the anti-IL-13 control antibody (FIG. 33). FIG. 34 depicts deposition of IgG (FIG. 34a), IgM (FIG. 34b), and C3 (FIG. 34c) in the brains of treated mice. IgG (p<0.05; FIG. 34a) but not IgM (FIG. 34b) or C3 (FIG. 34c) deposits were reduced in the brains of AbS-treated mice as compared to anti-IL-13 antibody-treated controls. Staining intensity was scored on a scale of 1-5. Treatment with AbT did not reduce immune complex deposition in the kidneys or brains of MRL-Fas$^{lpr}$ mice (FIGS. 32-34).

Figure 35A:
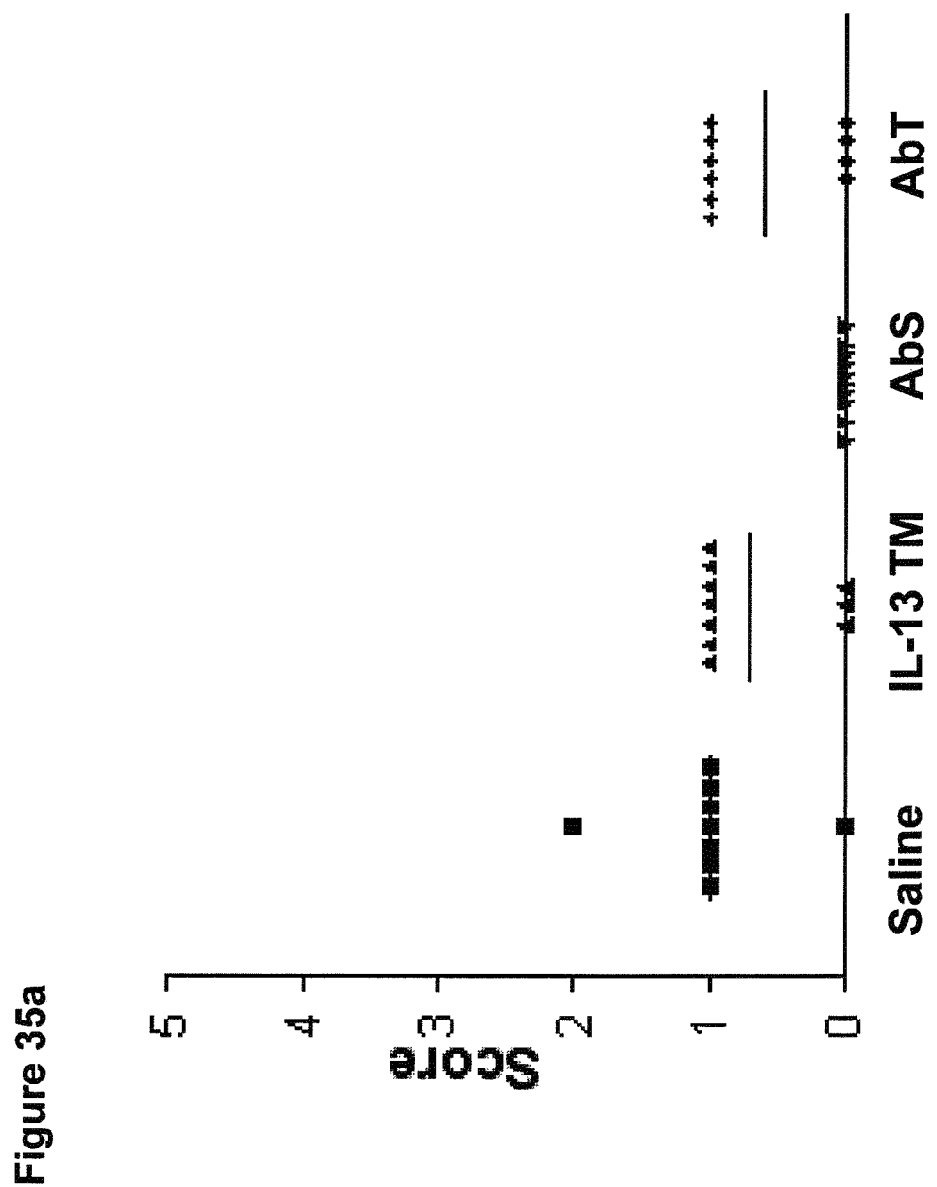
FIG. 35 depicts lymphocytic infiltrates in kidneys of MRL-Fas$^{lpr}$ mice treated with anti-IL-21R antibodies. Twelve-week-old male MRL-Fas$^{lpr}$ mice were treated (10 mg/kg i.p., 3×/week) with either saline (control) or the indicated triple-mutant antibodies. Following ten weeks of treatment, mice were sacrificed and hematoxylin/eosin (H/E)-stained kidney sections were examined for lymphocyte infiltration in three zones, cortex interstitium (a support structure for the glomeruli) (FIG. 35a), cortex perivascular (FIG. 35b), and peripelvic (near the origin of the ureter) (FIG. 35c). Lymphocyte numbers were scored on a scale of 1-5.
Figure 35B:
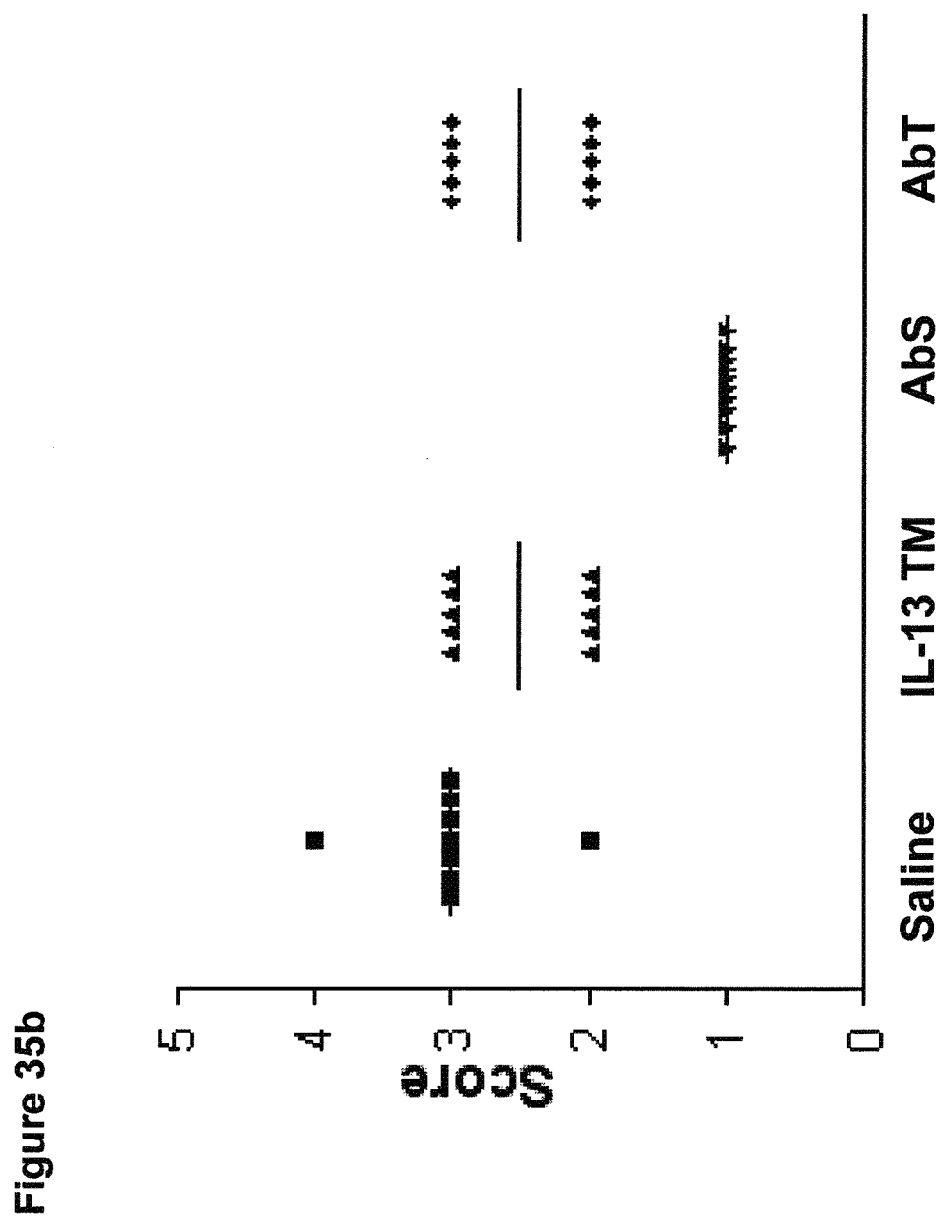
Figure 35C:
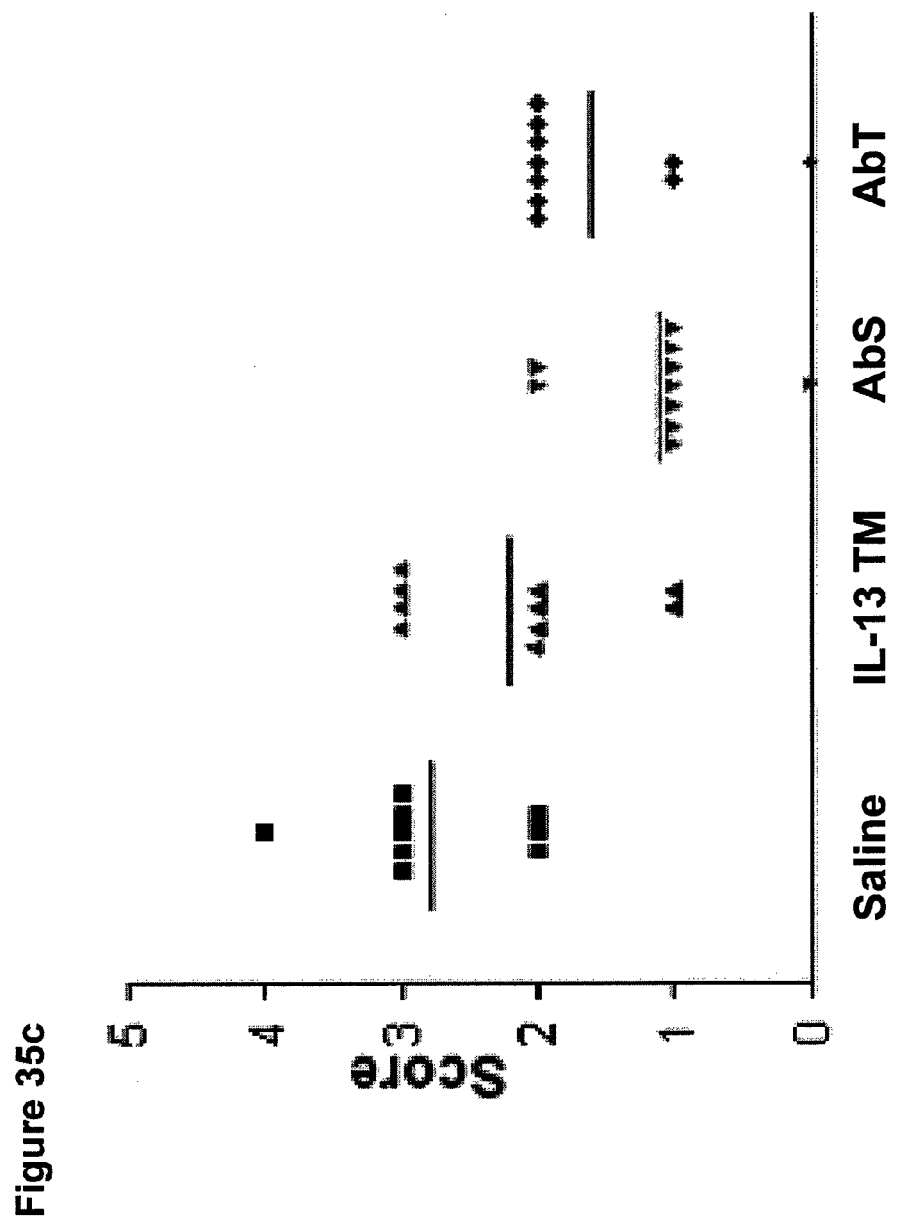
Figure 36:
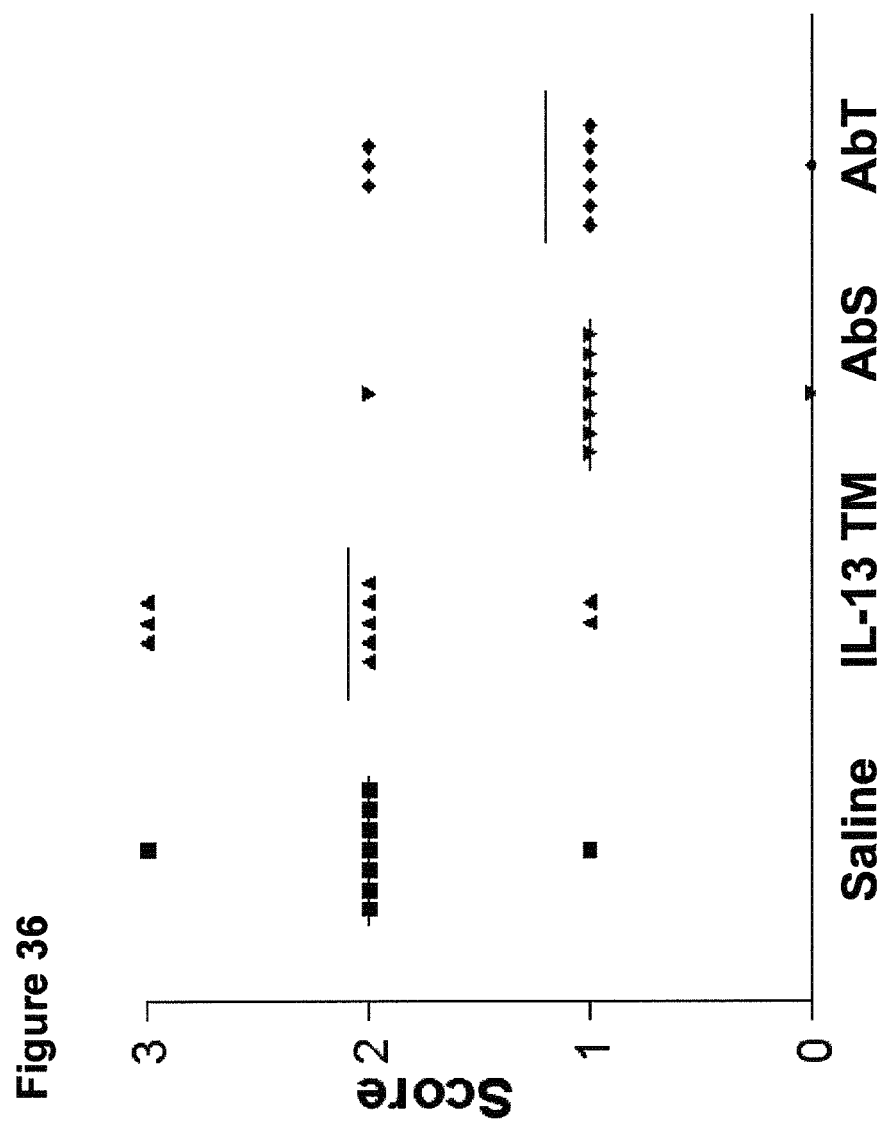
FIG. 36 depicts lymphocytic infiltrates in lungs of MRL-Fas$^{lpr}$ mice treated with anti-IL-21R antibodies. Twelve-week-old male MRL-Fas$^{lpr}$ mice were treated (10 mg/kg i.p., 3×/week) with either saline (control) or the indicated triple-mutant antibodies. Following ten weeks of treatment, mice were sacrificed and H/E-stained lung sections were examined for lymphocyte infiltration. Lymphocyte numbers were scored on a scale of 1-5.

Infiltration of lymphocytes into the kidneys and lungs of MRL-Fas$^{lpr}$ mice was also examined histologically. Twelve-week-old male MRL-Fas$^{lpr}$ mice were treated (10 mg/kg i.p., 3×/week) with either saline (control) or the indicated triple-mutant antibodies. Following 10 weeks of treatment, mice were sacrificed and H/E-stained kidney and lung sections were examined for lymphocyte infiltration. Lymphocyte numbers were scored on a scale of 1-5. In the kidney, AbS but not AbT significantly reduced lymphocyte infiltration in three zones: cortex-interstitium (a support structure for the glomeruli) (FIG. 35a), cortex-perivascular region (FIG. 35b), and peripelvic region (near the origin of the ureter) (FIG. 35c) (p<0.01). Both AbS and AbT treatment significantly reduced the number of lymphocytes measured in the lungs of MRL-Fas$^{lpr}$ mice as compared to saline-treated and anti-IL-13 antibody-treated controls (p<0.01 and p<0.05, respectively; FIG. 36).

Figure 37A:
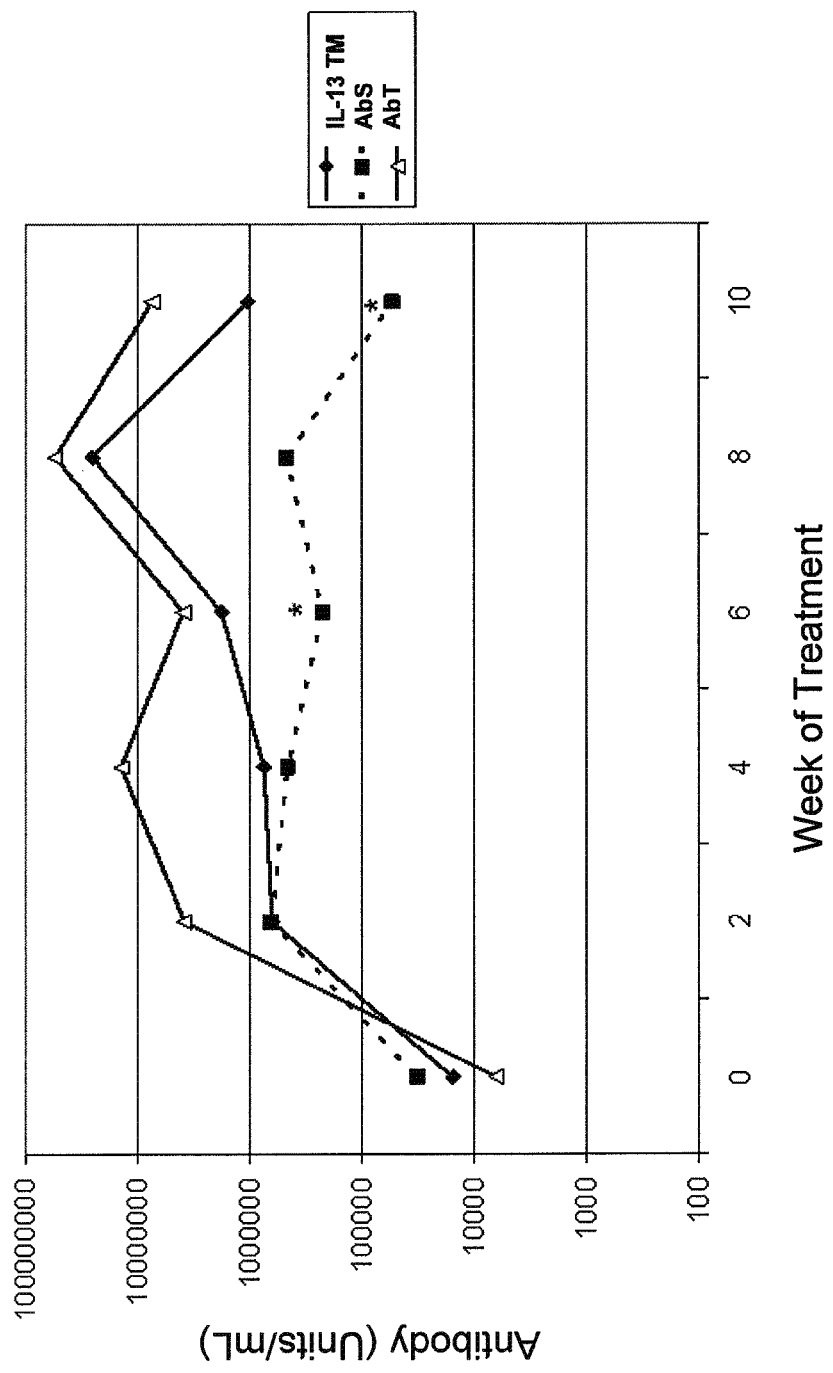
FIGS. 37a-b depict the mouse anti-human antibody (MAHA) response in MRL-Fas$^{lpr}$ mice treated with anti-IL-21R antibodies. Twelve-week-old male MRL-Fas$^{lpr}$ mice were treated (10 mg/kg i.p., 3×/week) with the indicated triple-mutant antibodies. Serum, collected biweekly, was tested by ELISA for the presence of murine antibodies capable of binding to the same human antibodies with which the mice were treated (FIG. 37a), or for the presence of murine antibodies capable of binding to the other anti-IL-21 human antibodies (FIG. 37b). Asterisks in FIG. 37a indicate a significant difference as compared to the anti-IL-13-treated group (p<0.05).
Figure 37B:
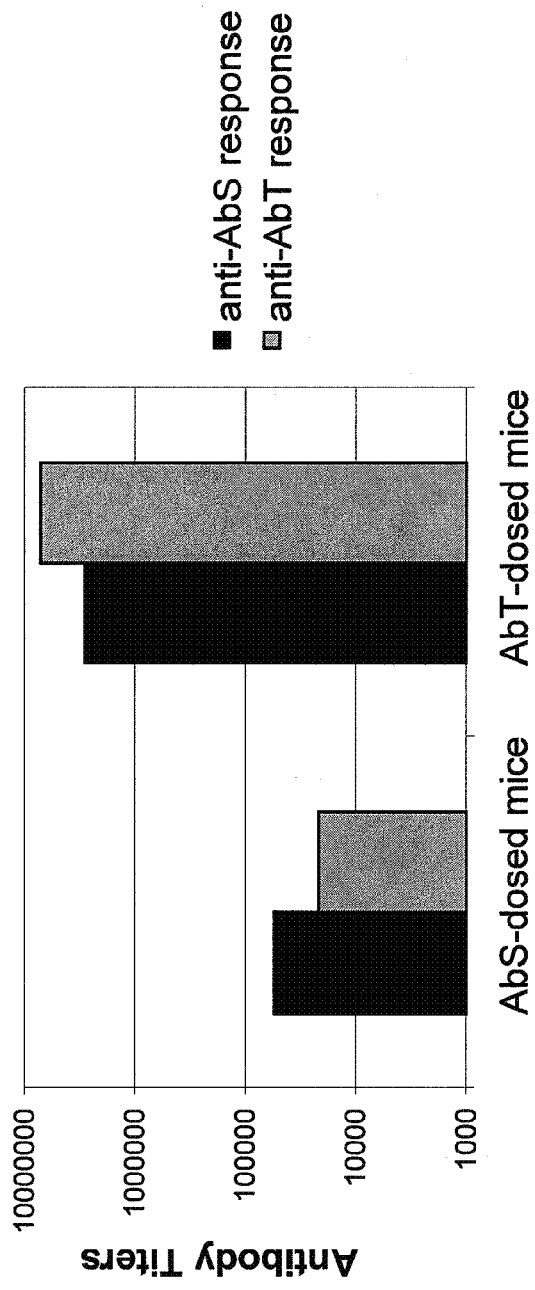

Taken together, these data show that treatment with AbS ameliorates lupus-like disease in MRL-Fas$^{lpr}$ mice, whereas treatment with AbT seemed to be less efficacious in this model of SLE. To examine the discrepancy in efficacy of AbS and AbT treatment of MRL-Fas$^{lpr}$ mice, sera from these mice were examined for anti-product antibody responses by ELISA. Twelve-week-old male MRL-Fas$^{lpr}$ mice were treated (10 mg/kg i.p.; 3×/week) with the indicated triple-mutant antibodies. Serum collected biweekly was tested by ELISA for the presence of murine antibodies capable of binding to the same human antibodies with which the mice were treated. MRL-Fas$^{lpr}$ mice generated anti-human antibody (MAHA) responses to all three tested antibodies as early as 2 weeks after treatment (FIG. 37a). However, anti-product IgG antibody responses were more than 10-fold greater against AbT or the control antibody than against AbS (p<0.05 for AbS vs. IL-13 control). It is unlikely that the AbS CDR sequence is more immunogenic than that of AbT, as for both AbS and AbT the majority of anti-product antibodies recognized epitopes common to both molecules (FIG. 37b)

To examine the dose-dependency of IL-21R neutralization on disease development in the MRL-Fas$^{lpr}$ model, eight-week-old female mice were administered either AbS (10, 5 or 2.5 mg/kg doses), AbT (20 mg/kg doses) or isotype control antibody (20, 10, 5, or 2.5 mg/kg doses) i.p. 3×/week for 10 weeks. Mice were tested for anti-dsDNA serum antibodies, and examined for proteinuria, lymphadenopathy, and skin lesions every two weeks. After 10 weeks of dosing, animals were sacrificed and kidney sections were examined for immunoglobulin deposits by immunohistochemistry, and immune cell infiltrates were measured by examination of H&E-stained kidney sections.

Figure 38A:
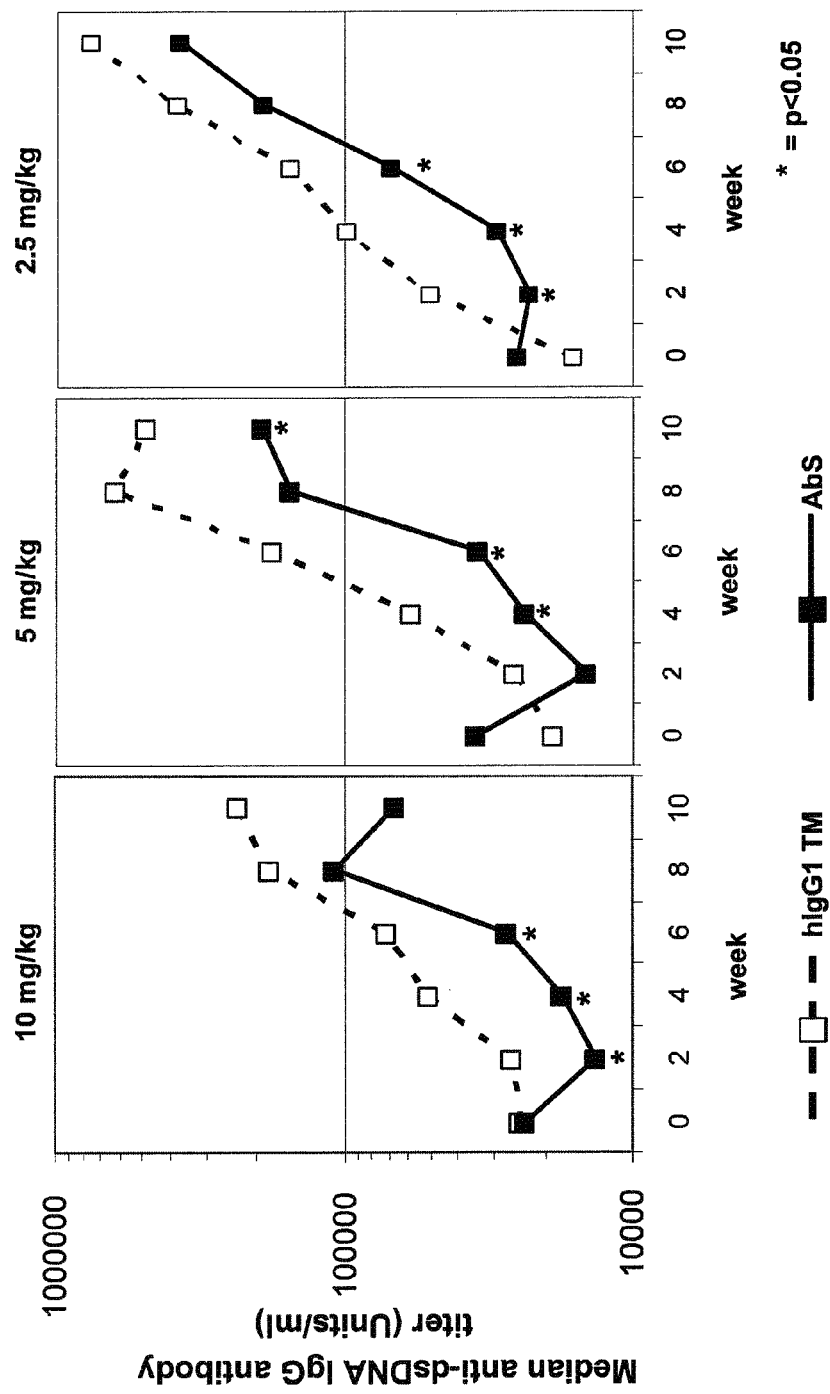
FIG. 38a depicts anti-dsDNA antibody titer for mice treated with AbS.
Figure 38B:
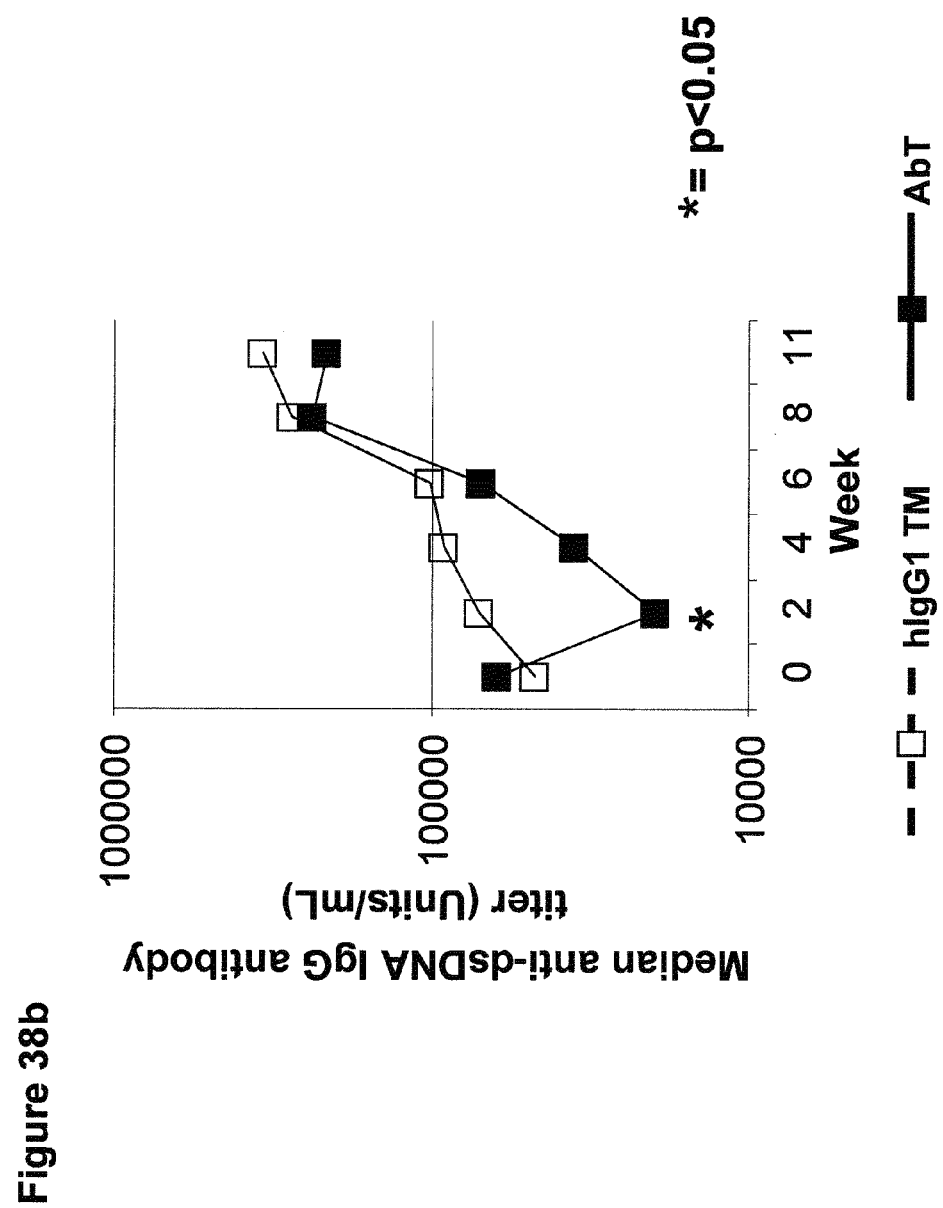
FIG. 38b depicts anti-dsDNA antibody titer for mice treated with AbT.

MRL-Fas$^{lpr}$ mice had detectable levels of anti-dsDNA IgG antibodies at the onset of the study, and these antibodies increased in titer over the course of the study in all treatment groups. However, treatment with AbS at all doses tested (10, 5 and 2.5 mg/kg) significantly reduced antibody titers in MRL-Fas$^{lpr}$ mice in a dose-dependant fashion when compared to isotype control-treated mouse serum (FIG. 38a). AbT (20 mg/kg) also reduced anti-dsDNA antibody titers in these mice, but only at one time point (week 2 of dosing) (FIG. 38b).

Figure 38C:
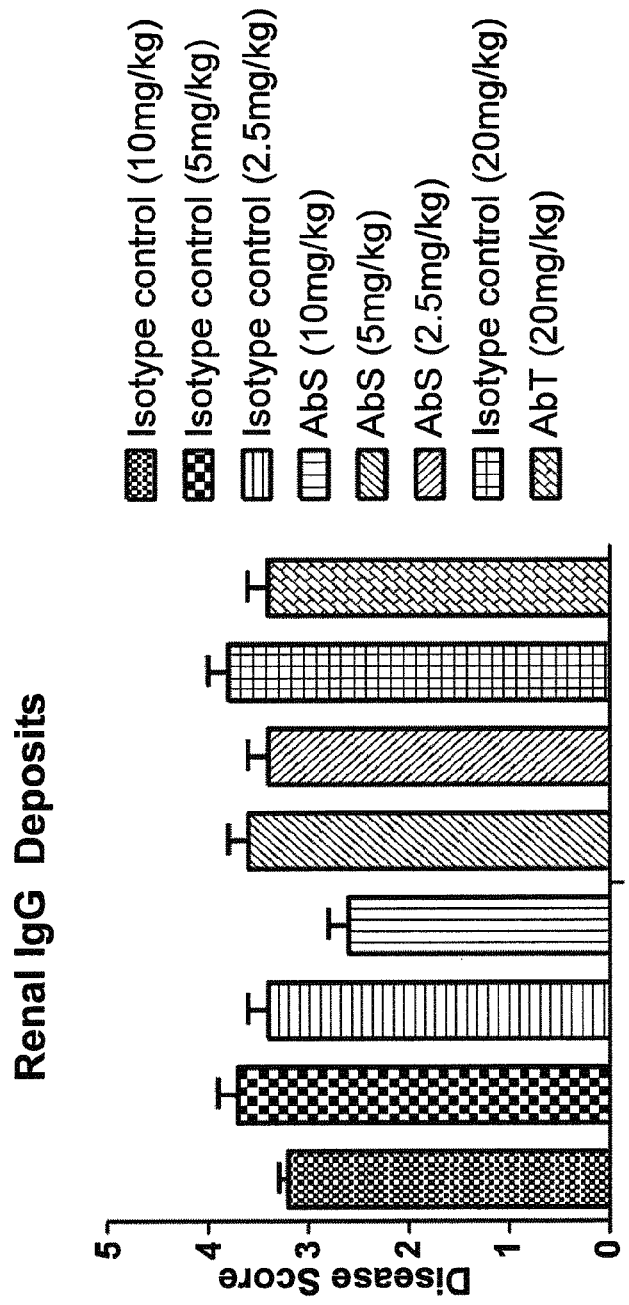
FIGS. 38c-d represent kidney pathology and renal inflammatory foci in MRL-Fas$^{lpr}$ mice treated with AbS and AbT.
Figure 38D:
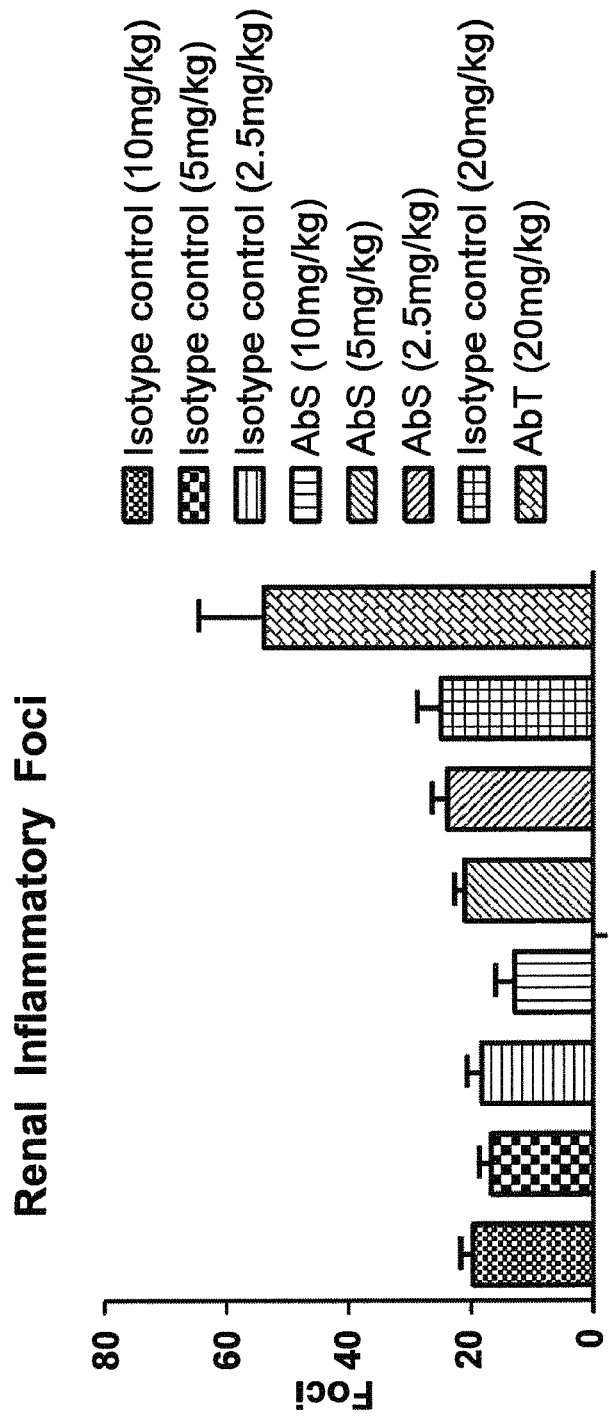

To further assess the impact of IL-21R neutralization on disease progression in MRL-Fas$^{lpr}$ mice, the mice were examined for clinical signs of disease. Very few of the MRL-Fas$^{lpr}$ mice used in this study developed skin lesions or clinically significant proteinuria, so the effects of AbS and AbT treatment on these aspects of disease could not be assessed. Treatment with AbS and AbT at all of the doses tested did not affect the development of lymphadenopathy in the study. However, IgG deposits and immune cell infiltrates were readily observed in kidneys from isotype control-treated mice, consistent with the development of lupus nephritis in these mice. Treatment with 10 mg/kg AbS significantly reduced the mean number of immune cell infiltrates and IgG deposits in the kidney, whereas treatment with 5 and 2.5 mg/kg AbS had no effect on these parameters in this study (FIG. 38c-d). Treatment with AbT at the 20 mg/kg dose increased mean number of immune cell infiltrates and did not affect IgG deposits in the kidney of MRL-Fas$^{lpr}$ mice in this study (FIG. 38c-d).

Example 10.3

IL-21R Antibodies Block Cellular Infiltration in a Murine Air Pouch Assay

The ability of AbS and AbT to neutralize IL-21R function in vivo was tested in a short-term murine air pouch assay. Air pouches were created by injecting 8-10 week old BALB/C mice with 3 ml of air under the dorsal skin. Three days later, pouches were reinflated. Two days after reinflation, either saline (control) or the indicated antibodies were injected i.p. at the indicated dose. Murine IL-21 (100 ng) was injected into the air pouch 24 hr after antibody injection. Six hr later, the pouches were washed out with 3 ml PBS, and total cell counts (FIG. 39a), monocytes (FIG. 39b), lymphocytes (FIG. 39c), and neutrophils (FIG. 39d) were determined with a CELL-DYN® (Abbott, Abbott Park, Ill.).

Figure 39A:
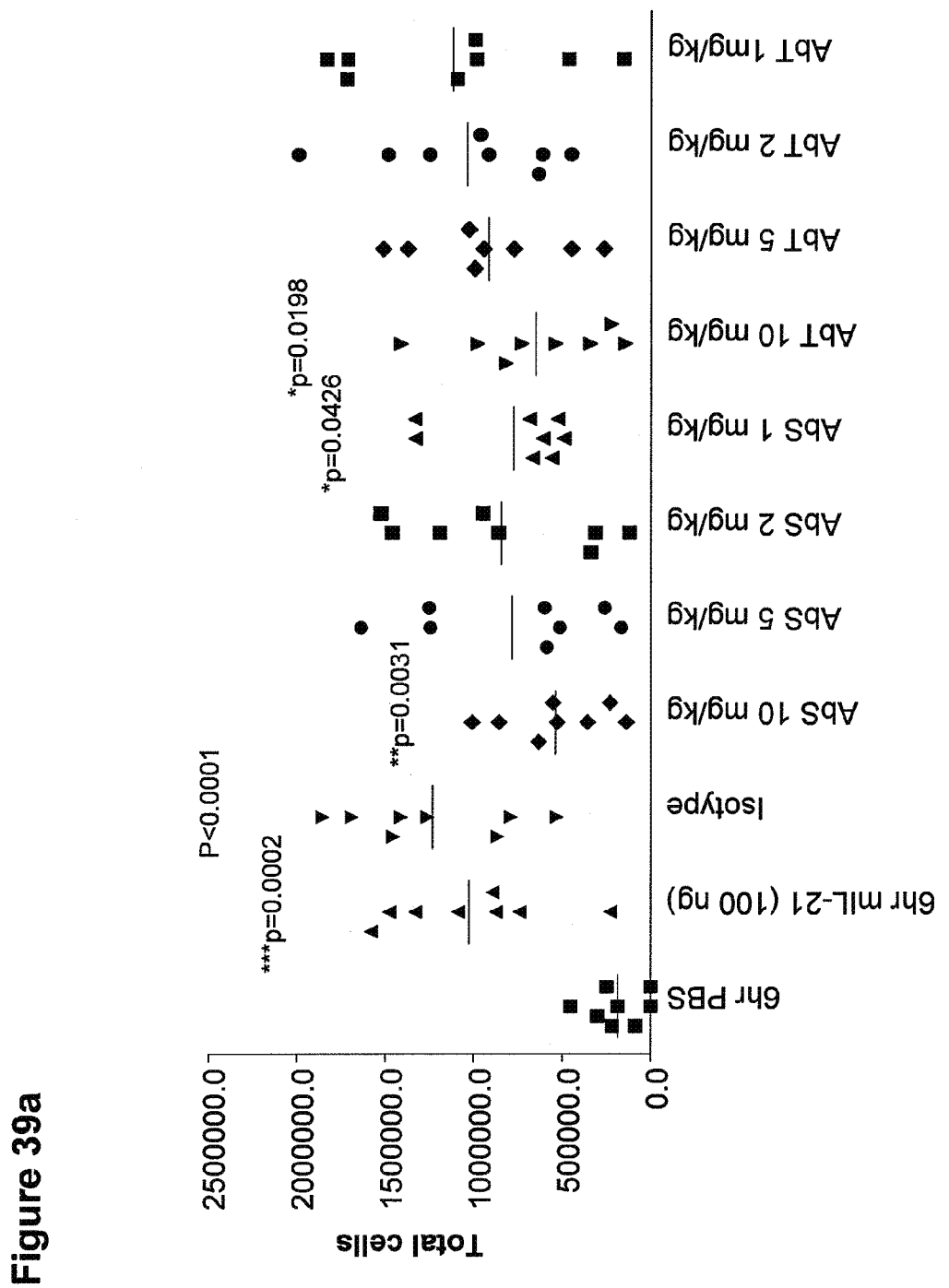
Figure 39B:
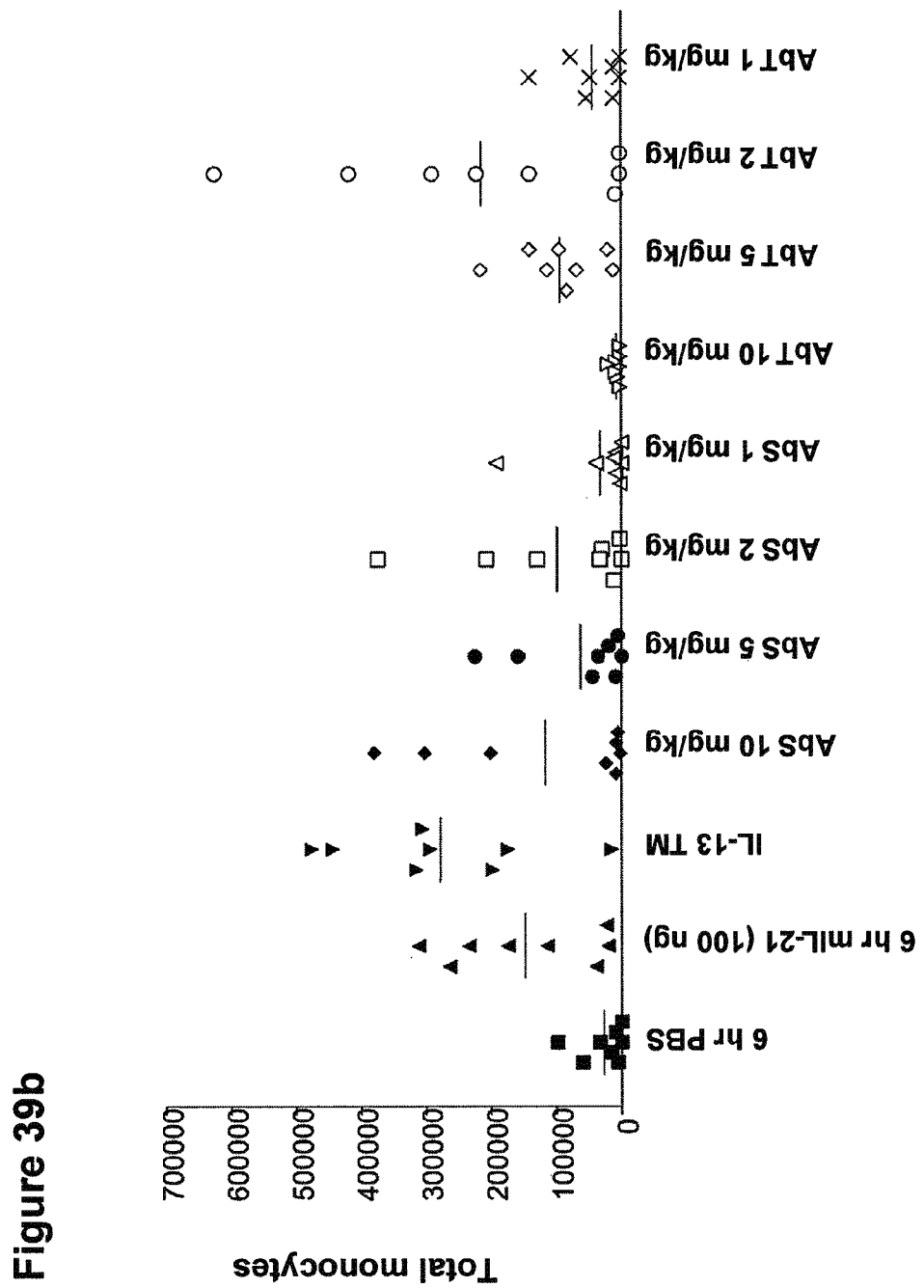
Figure 39D:
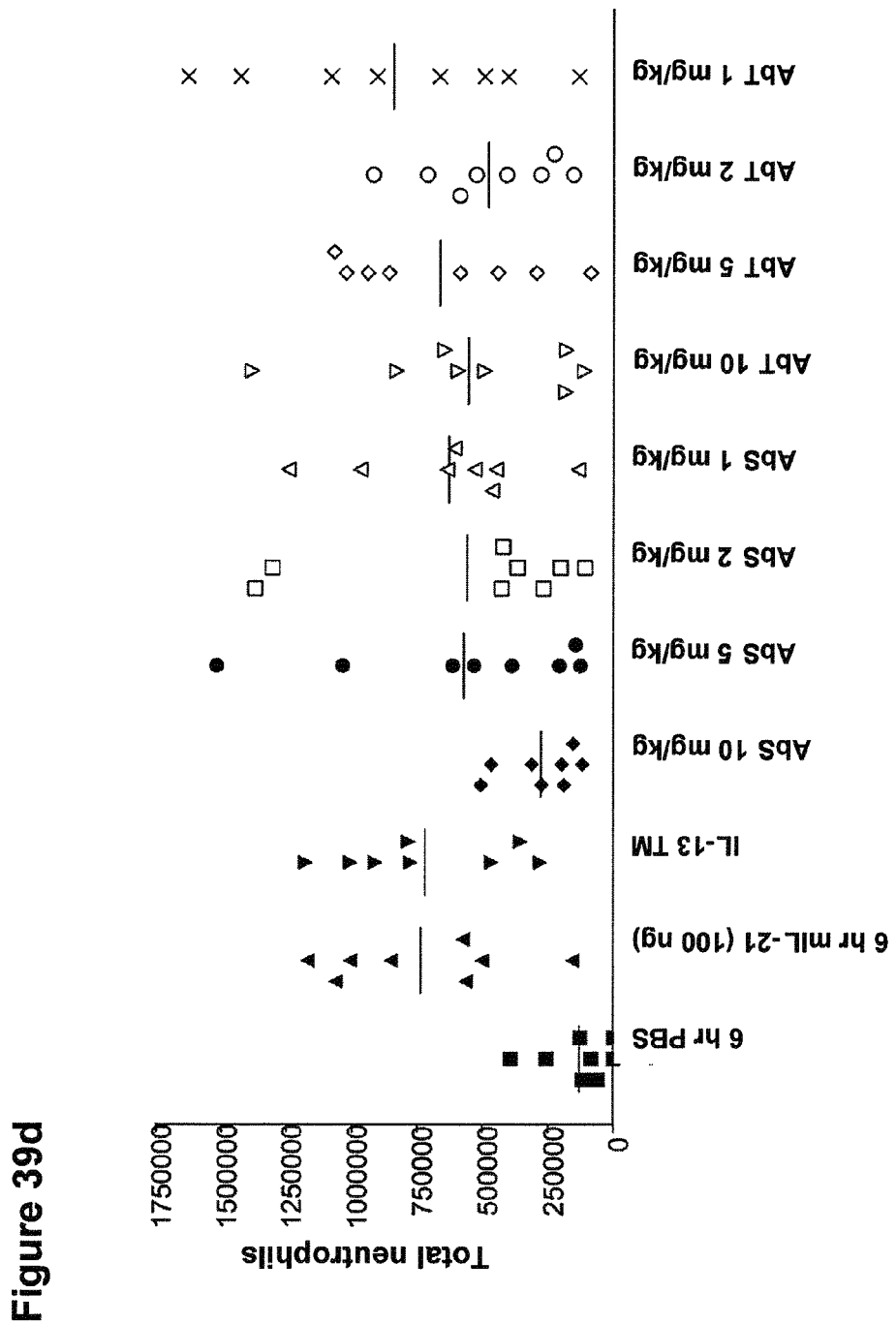

Injection of murine IL-21 into the air pouch led to a significant increase in total cells (p=0.0002), monocytes (p=0.0137), lymphocytes (p=0.0035), and neutrophils (p=0.0004) in the air pouch 6 hr later as compared to saline (FIG. 39a). Treatment with either AbS or AbT led to significant reductions in cellular infiltration into the air pouch as compared to treatment with the control IgG1 (anti-IL-13). Total cellular infiltration was reduced significantly compared to the control IgG by both AbS (10 mg/kg, p=0.0031; 1 mg/kg, p=0.00426) and AbT (10 mg/kg, p=0.0198) (FIG. 39a). Monocyte infiltration was significantly decreased: AbS (5 mg/kg, p=0.0031; 2 mg/kg p=0.0239; 1 mg/kg, p=0.0008) and AbT (10 mg/kg, p=0.0002; 5 mg/kg p=0.0066; 1 mg/kg, p=0.0009) (FIG. 39b). Lymphocyte infiltration was also significantly decreased: AbS (1 mg/kg, p=0.0049) and AbT (10 mg/kg, p=0.0222) (FIG. 39c). Neutrophil infiltration was significantly reduced by AbS (10 mg/kg, p=0.0032), but not AbT.

Figure 39E:
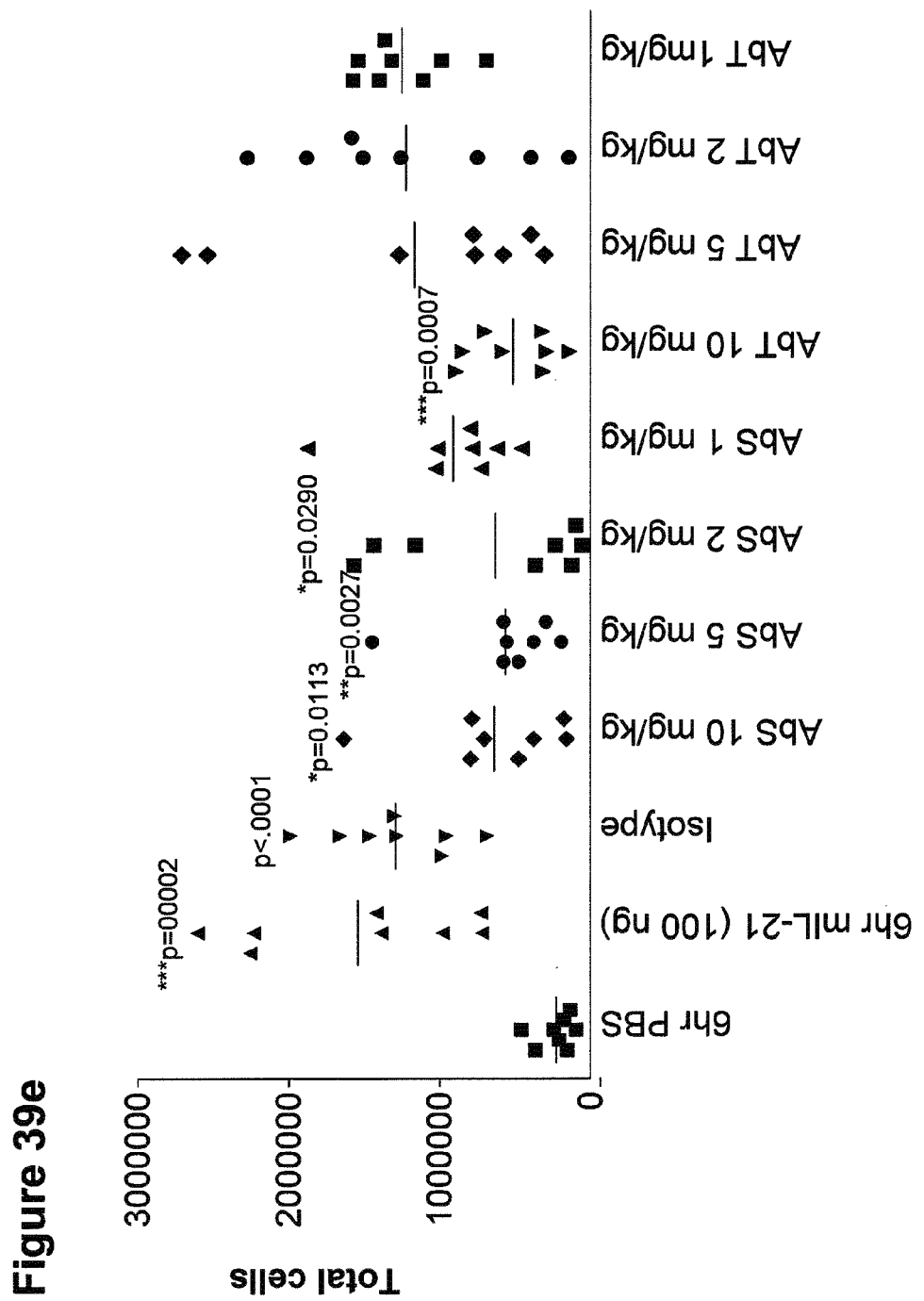

Similar results were obtained in a second study conducted to examine the ability of AbS and AbT in the murine air pouch model. Total cell infiltration into the air pouch was significantly reduced by AbS when administered at 10 (p=0.0113), (p=0.0027), and 2 mg/kg (p=0.029), and by AbT at 10 mg/kg (p=0.0007) (FIG. 39e).

The effect of AbS on cell infiltration in response to IL-21 in the rat air pouch model was also examined to determine if these antibodies could neutralize IL-21R in the rat. Pouches were created by injecting 8-week-old female S-D rats with 20 ml of air into the subcutaneous tissue of the back. Three days later, pouches were reinflated by injecting an additional 10 mL of air into the pouch. Two days later, the rats were injected with the designated amount of isotype control or AbS antibody. The next day, either saline or 1-20 μg of murine IL-21 was injected into the pouch, and six hr later the pouch contents were washed out and total cells counted using a Cell Dyne machine.

Figure 39F:
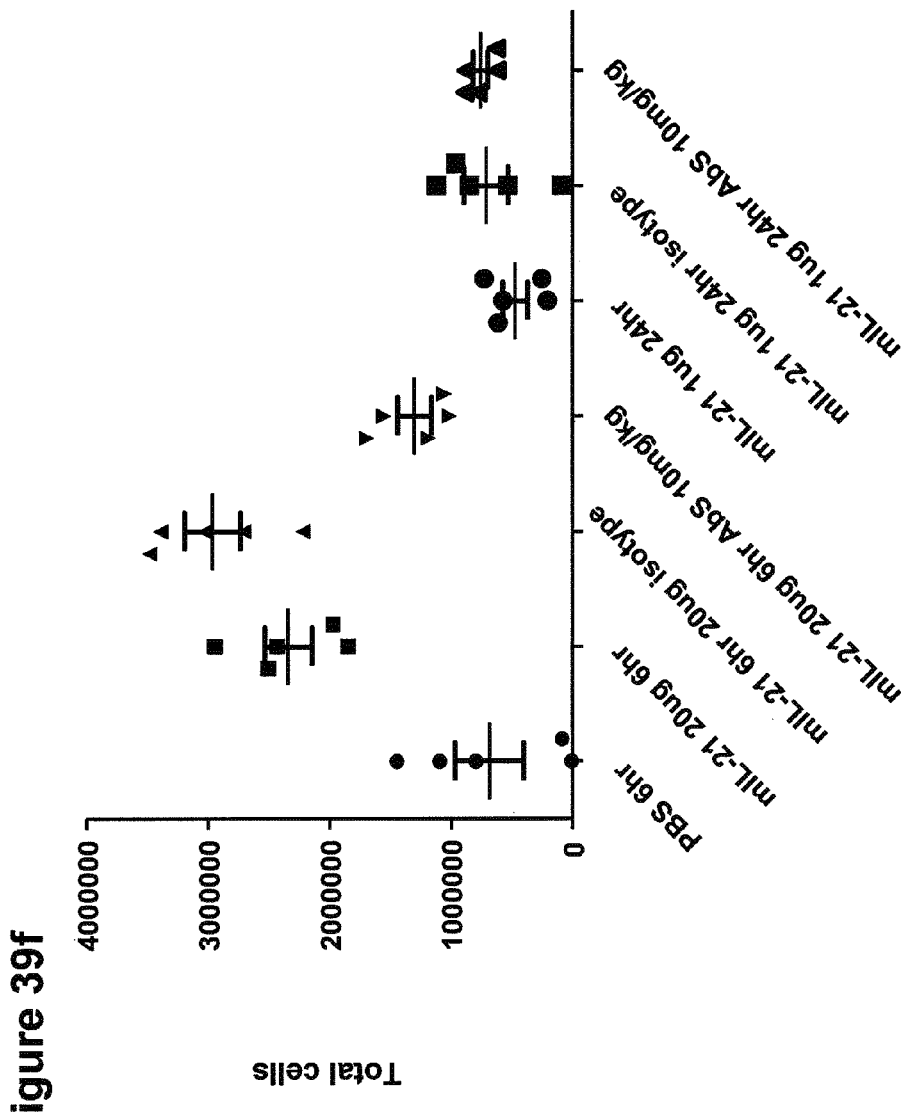
FIGS. 39f-j depict total cell infiltration into air pouches in rats following treatment with mouse IL-21 and anti-IL-21R antibodies.
Figure 39G:
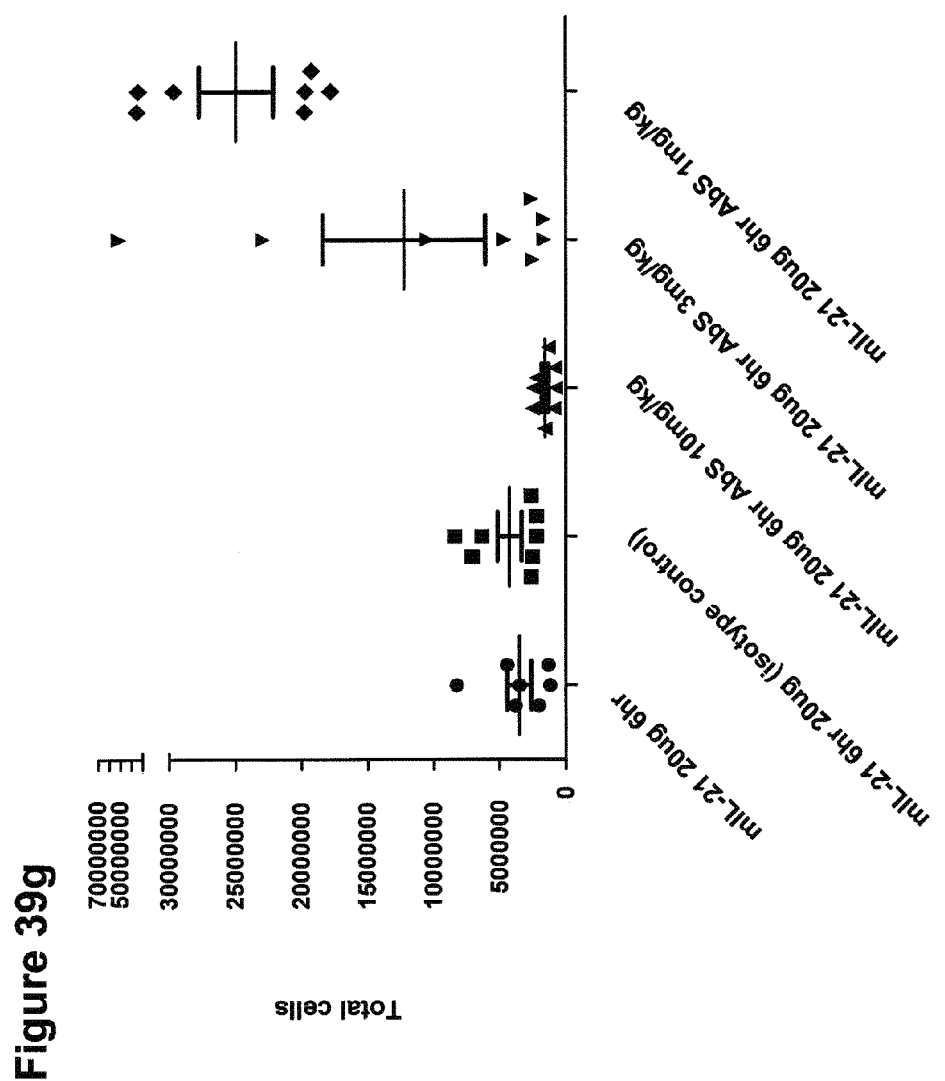
Figure 39H:
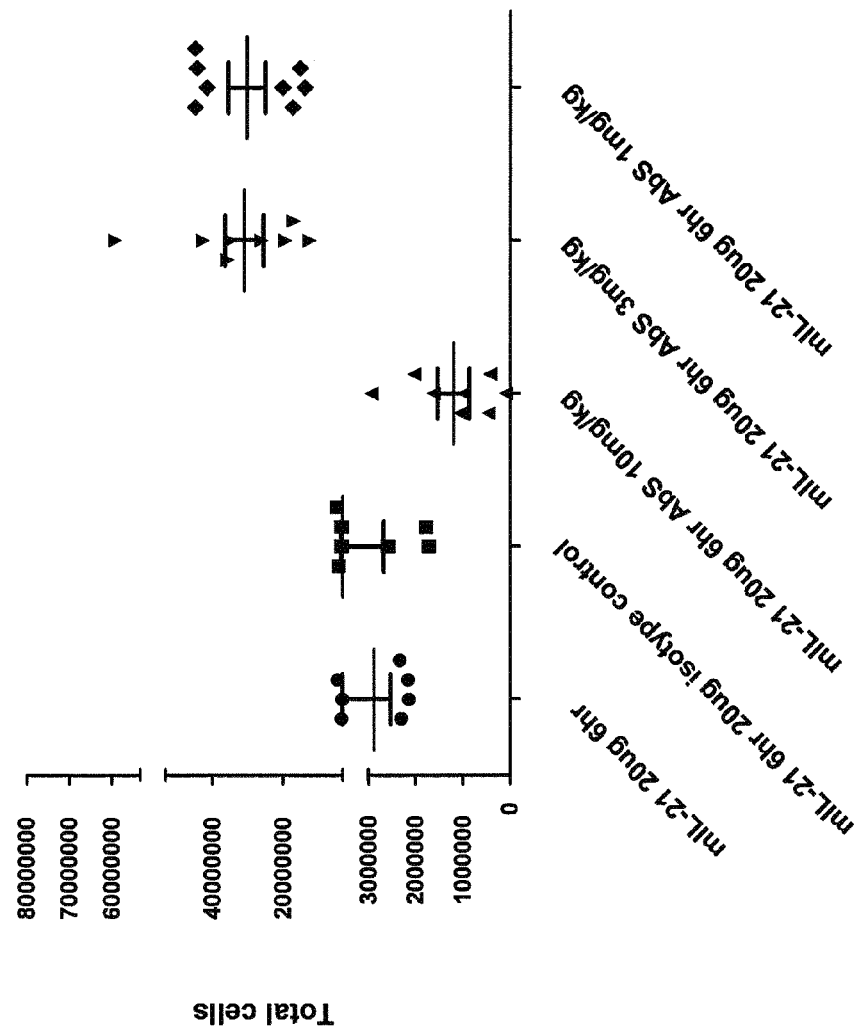

Injection of 1 μg of murine IL-21 into the air pouch did not result in significant cell infiltration into the pouch. However, administration of 20 μg of murine IL-21 led to an increase in total cells in the air pouch 6 hr later as compared to saline, and treatment with 10 mg/kg AbS significantly reduced IL-21 mediated cell infiltration into the pouch under these conditions (p<0.05) (FIG. 39f). To determine the minimal dose of AbS that could inhibit cell infiltration into the air pouch in this rat model, additional studies were performed in which rats were administered 20 μg of murine IL-21 and either 10 mg/kg isotype control or 10, 3 or 1 mg/kg of AbS. Administration of 10 mg/kg AbS significantly reduced cell infiltration into the rat air pouch (p<0.05). A nonsignificant increase in cell infiltration into the air pouch was observed in rats treated with 3 mg/kg of AbS. Treatment with 1 mg/kg AbS significantly increased cell infiltration into the pouch compared to isotype control treated rats (p<0.05) (FIG. 39g). These observations were repeated in a second study, in which treatment with 10 mg/kg significantly reduced cell infiltration into the rat air pouch induced by 20 μg murine IL-21 (p<0.05); in this study, treatment with both 3 and 1 mg/kg AbS significantly increased cell infiltration into the pouch (p<0.05) (FIG. 39h).

Figure 39I:
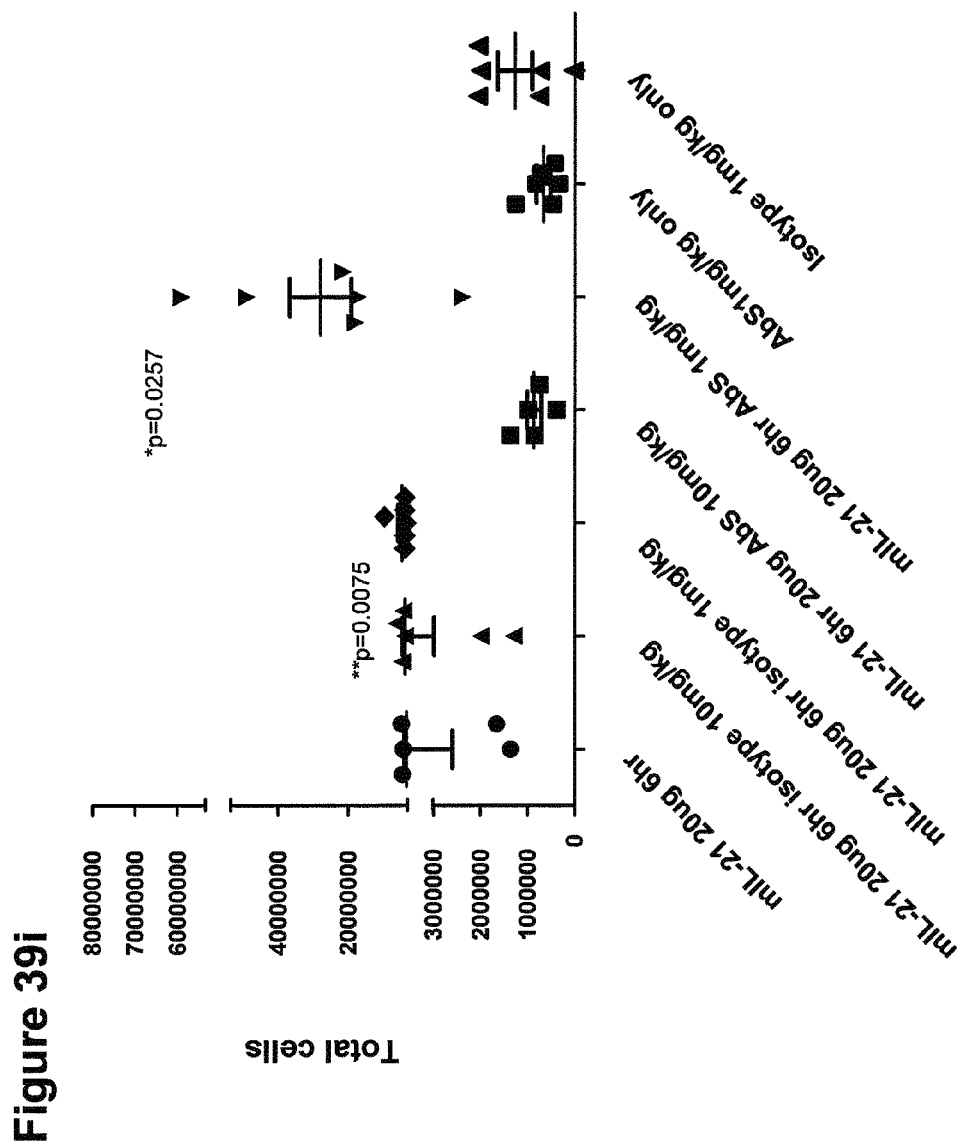

Treatment with AbS significantly increased cell infiltration into the pouch in response to IL-21 when AbS was administered at low doses (e.g., 1 mg/kg). To determine if administration of antibody alone into the pouch at low concentrations (1 mg/kg) elicited cell migration into the pouch, an additional study was performed in which rats were treated with 1 mg/kg AbS or isotype control antibody in the absence of IL-21 treatment. As observed in previous studies, administration of AbS at 10 mg/kg significantly reduced IL-21-driven cell infiltration into the pouch (p=0.0075), whereas administration of AbS at 1 mg/kg significantly increased IL-21-induced cell infiltration into the pouch (p=0.0257). Treatment with either AbS or isotype control antibody at 1 mg/kg in the absence of IL-21 treatment did not increase cell infiltration into the pouch, indicating that the increased cell infiltration into the pouch elicited by treatment with AbS at 1 mg/kg was dependent on administration of both murine IL-21 and anti-IL-21R antibody in this model (FIG. 39i).

Figure 39J:
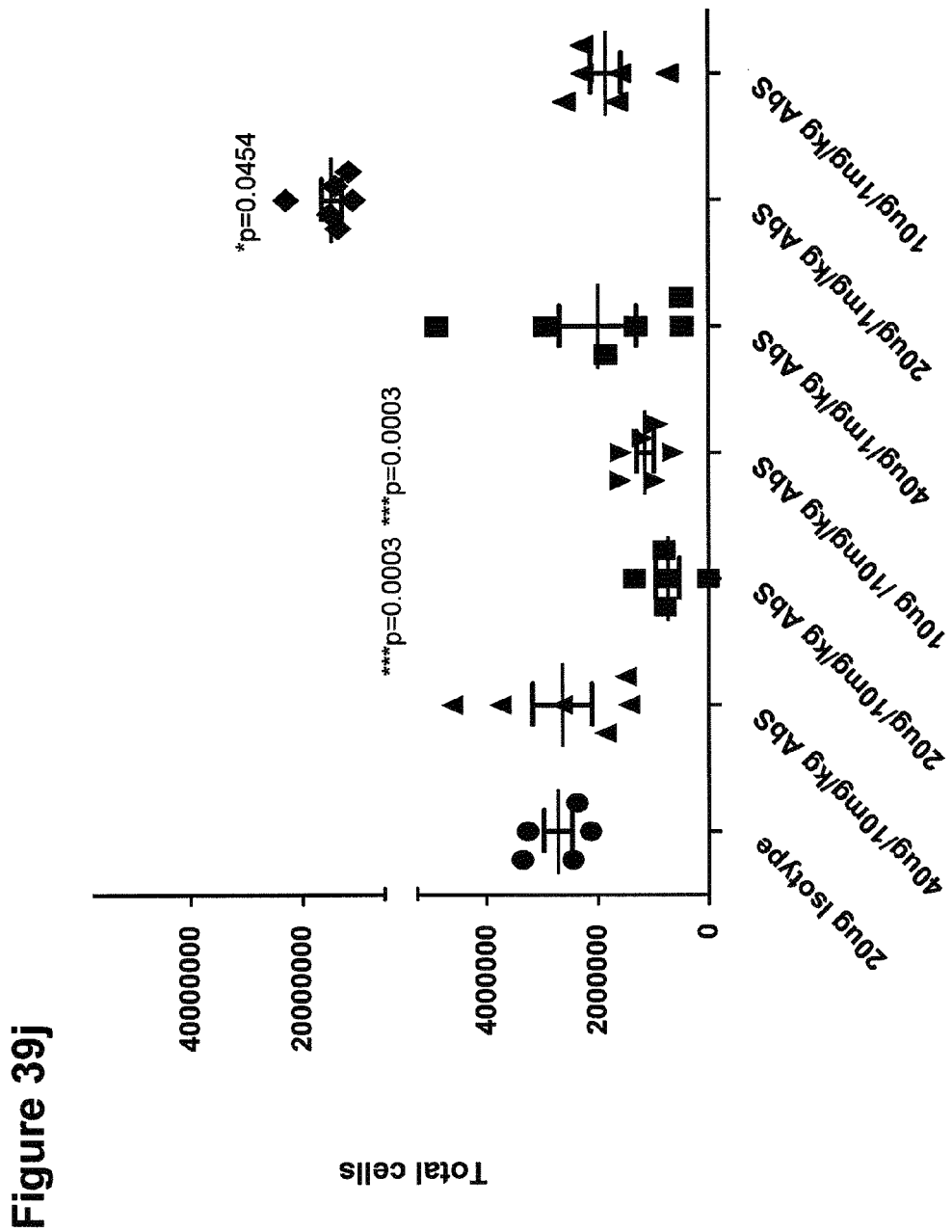

To determine whether the increase in cells in the rat air pouch model was dependent on administration of the dose of murine IL-21 (20 μg), an experiment was done in which rats were treated with either 10, 20 or 40 μg murine IL-21 and either 1 or 10 mg/kg AbS. A significant inhibition of cell infiltration into the pouch was observed with 10 mg/kg AbS in response to both 10 (p=0.003) and 20 µg (p=0.003) murine IL-21. Treatment with 10 mg/kg AbS did not affect cell infiltration in response to 40 µg murine IL-21 in this study. Treatment with 1 mg/kg AbS significantly increased cell infiltration into the air pouch in response to 20 µg murine IL-21 (p=0.0454), as previously observed. However, treatment with 1 mg/kg AbS did not affect cell infiltration into rat air pouch in response to either 10 or 40 µg murine IL-21, indicating that increased cell infiltration into the rat air pouch is very specific to the dose of 1 mg/kg Abs and 20 µg murine IL-21 in this model (FIG. 39j). These data indicate that AbS can affect cell infiltration into the rat air pouch in response to murine IL-21, with inhibition of this response achieved with a dose of 10 mg/kg of AbS.

Example 10.4

Pharmacokinetics in CD-1 Mice After Intravenous or Subcutaneous Administration of AbS The serum concentrations of human anti-IL-21R antibodies were determined by qualified ELISAs as described in Table 13. The anti-IL-21R ELISA used a monomeric His-tagged IL-21R as a capture reagent and an anti-human-Fc (conjugated to horseradish peroxidase (HRP)) as a detector reagent. The enzyme substrate, 3,3',5,5'-tetramethylbenzidine (TMB), was used to produce a colored endproduct to visualize the bound test article. Optical density (OD) was measured calorimetrically at a wavelength of 405 or 450 nm. Sample concentrations were determined by interpolation from a standard curve that was fit using a four-parameter equation.

Pharmacokinetic parameters were calculated based on mean concentrations. Individual concentration values below the LOQ were treated as zero for calculation of the mean and SD. The PK parameters were determined using a noncompartmental analysis module (Model 200 for i.p. and s.c. dosing and Module 201 for i.v. dosing) of the PK software package WinNonlin (version 4.1; Pharsight, Mountain View, Calif.). The program applies a model-independent approach and the standard methods described by Gibaldi and Perrier (Pharmacokinetics (2nd ed. 1982) Marcel-Dekker, Inc., New York). The area under the serum concentration vs. time curve (AUC) was calculated using the linear trapezoidal method. The slope of the apparent terminal phase was estimated by log-linear regression using at least three data points and the terminal rate constant ($\lambda$) was derived from the slope. $AUC_{0-\infty}$ was estimated as the sum of the $AUC_{0-\infty}$ (where t is the time of the last measurable concentration) and $C_t/\lambda$. The apparent elimination half-life ($t_{1/2}$) was calculated as $0.693/\lambda$. Predictions of concentrations after a multiple dose regimens, were conducted by nonparametric superposition using WinNonlin software.

Figure 40:
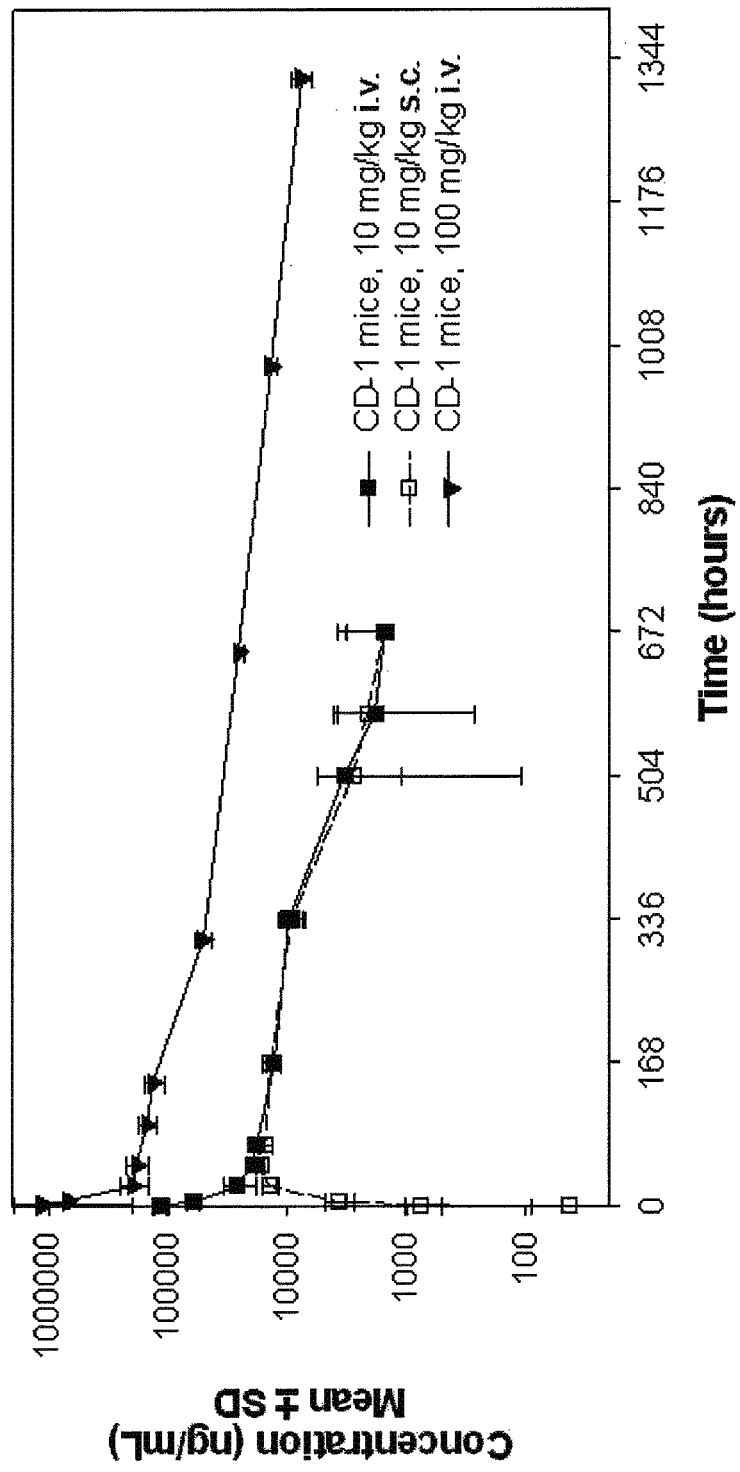

After intravenous administration of 10 mg/kg of AbS to male CD-1 mice, the exposure ($AUC_{0-\infty}$) of AbS was 7272 µg*hr/ml. The mean concentration at the first sampling time point after intravenous administration ($C_{5min}$) was 113 µg/ml. The elimination of AbS in CD-1 mice was relatively slow, as evidenced by the low total body clearance (CL) of ~1.4 ml/hr/kg and long elimination half-life ($t_{1/2}$) of 162 hr (~6.8 days). The steady-state volume of distribution ($Vd_{SS}$) was 306 ml/kg, suggesting that AbS was mainly confined to the vascular system (FIG. 40; Table 14).

Pharmacokinetics of AbS in CD-1 mice appeared linear in the 10-100 mg/kg dose range. After intravenous administration of 100 mg/kg of AbS to male CD-1 mice, $AUC_{0-\infty}$ was 75792 µg*hr/ml, $C_{5min}$ was 1160 µg/ml, CL was ~1.3 ml/hr/ kg, $Vd_{SS}$ was 473 ml/kg, and elimination half-life was ~391 hr (~16.2 days) (FIG. 40; Table 14).

After 10 mg/kg s.c. administration of AbS to CD-1 mice the absorption of AbS was slow ($T_{max}$ of 48 hr) and the subcutaneous bioavailability was 81%. The mean $t_{1/2}$ value after subcutaneous administration was ~195 hr (~8.1 days) and similar to that observed after 10 mg/kg intravenous administration.

The presence of anti-AbS antibodies was evaluated using a qualified immunoassay at 576 hr (24 days) and 672 hr (28 days) following 10 mg/kg i.v. or s.c. administration of AbS to CD-1 mice (n=8 per time point per group). An electrochemiluminescent, paramagnetic bead assay was used to detect anti-AbS antibodies. In this assay, samples were coincubated with biotinylated AbS overnight. Streptavidin-coated paramagnetic beads were incubated with the mixture. After incubation with the beads, the plate was placed in the BioVeris M-Series 384 Analyzer. A magnet was applied to capture the paramagnetic beads onto a surface electrode, and unbound reactants were washed away. The ruthenylated AbS captured on the beads was electrically excited by a voltage application, resulting in the production of light. The light was measured by photodetectors with the read-out in response units (RU).

Positive and negative controls were also used to determine the cutpoint RU, which was defined as twice the mean RU of the negative control. Samples were initially tested in a screening format at dilutions of 1:25 and 1:75. Samples generating an RU greater than or equal to the cutpoint RU were considered positive and reanalyzed in a full-dilution series to confirm the positive result and determine the titer (the reciprocal dilution that would generate an RU equal to the cutpoint RU). For positive samples, the log of titer is reported. The minimum required dilution was 1:25, and the limit of detection was 1.40 (the log of 25). Therefore, negative samples were designated as <1.40.

In both i.v. and s.c. treatment groups, 5 or 6 (of 8) mice per time point per group tested positive for anti-AbS antibodies (Table 15). The majority of the mice with detectable anti-AbS antibodies had lower AbS concentrations than those observed in animals without anti-AbS antibodies; of some note, the high levels of AbS in some samples could have interfered with the detection of anti-AbS antibodies. The summary of the onset of anti-AbS antibody response across various times, and across animal species and strains/models, is shown in Table 23.

The presence of anti-AbS antibodies was also tested at 648 hr (27 days), 984 hr (41 days), and 1320 hr (55 days) following 100 mg/kg i.v. of AbS to CD-1 mice (n=3 per time point). None of the mice tested were positive for anti-AbS antibodies at these time points.

Example 10.5

Pharmacokinetics in DBA and MRL-Fas$^{lpr}$ Mice After Intraperitoneal Administration of AbS The serum concentrations of human anti-IL-21R antibodies were determined by qualified ELISAs as described in Table 13. The anti-IL-21R ELISA used anti-human-Fc as a capture reagent and biotinylated anti-human-Fc as a detector reagent. Avidin-HRP, and the enzyme substrate TMB or 2,2'-azino di (3-ethyl-benzthiazoline-6-sulfonate) (ABTS), were used to produce a colored endproduct. OD was measured calorimetrically at a wavelength of 405 or 450 nm. Sample concentrations were determined by interpolation from a standard curve that was fit using a four-parameter equation. PK parameters were calculated as noted in Example 10.4. Predictions of concentrations after a multiple dose regimens, were conducted by nonparametric superposition using Win-Nonlin software and assuming linear kinetics in MRL-Fas$^{lpr}$ and DBA mice in the 2.5-10 mg/kg dose range (single dose).

Figure 41:
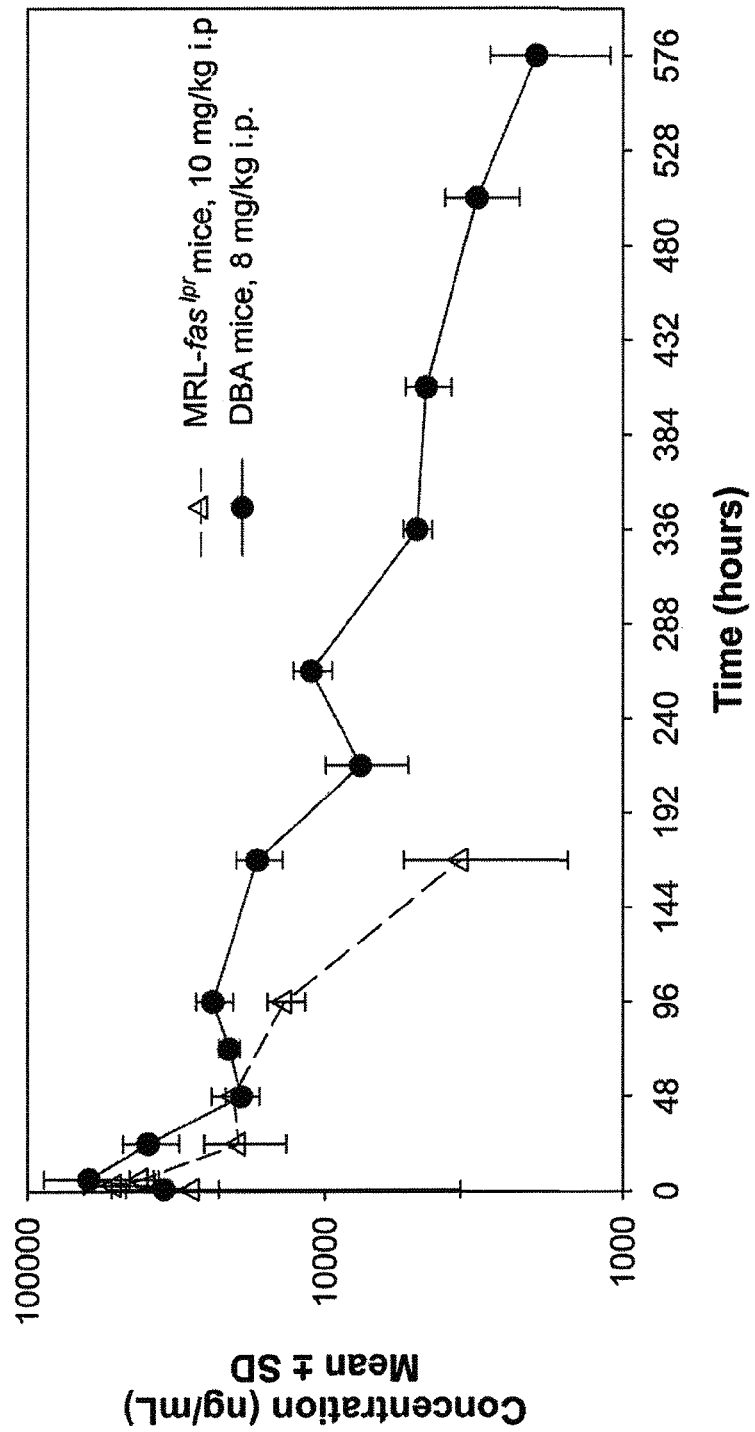
FIG. 41 depicts the concentration-time profiles of AbS in DBA and MRL-Fas$^{lpr}$ mice after a single intraperitoneal administration. Concentrations below the limit of quantitation were treated as zero for the calculation of mean and standard deviation. N=4-8 for each data point.

Following a single i.p. dose of 8 mg/kg of AbS to male DBA mice, the maximum serum concentration ($C_{max}$) and exposure (AUC$_{0-\infty}$) of AbS were 62 µg/ml and 7229 µg*hr/ml, respectively. The $T_{max}$ and the elimination half-life ($t_{1/2}$) of AbS were 6 hr and 140 hr (~5.8 days), respectively (FIG. 41). Out of eight animals tested, three developed anti-AbS antibody response at 672 hr, determined using the paramagnetic bead assay described in Example 10.4 (Table 12). The summary of the onset of anti-AbS antibody across various times and species/strains is shown in Table 23.

TABLE 12

Formation of Anti-AbS Antibodies After a Single 8 mg/kg i.p. Dose to DBA Mice

| | Onset (hr) | | | |
|---|---|---|---|---|
| | 408 hr | 504 hr | 576 hr | 672 hr |
| Positive | 0 of 8 | 0 of 8 | 0 of 8 | 3 of 8 |

Following a single intraperitoneal dose of 10 mg/kg to female, 12-week-old MRL-Fas$^{lpr}$ mice, the maximum serum concentration ($C_{max}$) and exposure (AUC$_{0-\infty}$) of AbS were 51 µg/ml and 2798 µg*hr/ml, respectively. The $T_{max}$ and the elimination half-life ($t_{1/2}$) of AbS were 3 hr and 46 hr (~1.9 days), respectively (FIG. 41).

Compared to DBA and CD-1 mice, dose-normalized exposure of AbS appeared to be lower in MRL-Fas$^{lpr}$ mice (Table 14). This was not entirely unexpected, as fast elimination of normal IgG in MRL-Fas$^{lpr}$ mice (especially with disease symptoms) and in SLE patients has been reported (see Zhou et al. (2005) *Lupus* 4(6):458-66; Newkirk et al. (1996) *Clin. Exp. Immunol.* 106(2):259-64; Wochner (1970) *J. Clin. Invest.* 49(3):454-64). The hypercatabolism of mouse IgG in MRL-Fas$^{lpr}$ mice has been proposed to be due to the disease-induced impairment of the function of the receptor FcRn, which regulates the homeostasis of IgG (Zhou et al. (2005) supra). As AbS is a human IgG, differences in elimination of AbS at the terminal phase among the different strains of mice also may be explained, at least in part, by a differential MAHA response.

Figure 42A:
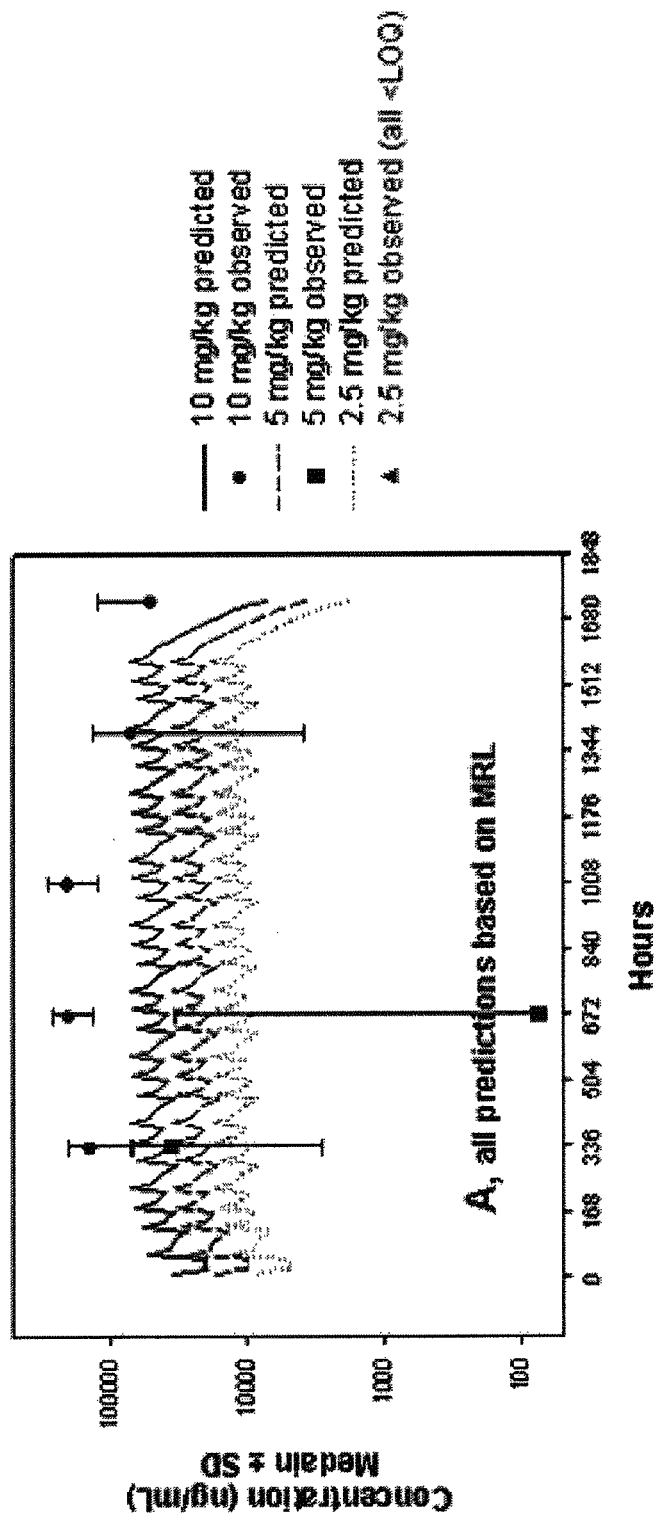
FIGS. 42a and b depict the observed and predicted AbS concentrations in MRL-Fas$^{lpr}$ mice after multiple i.p. administrations at 10, 5, and 2.5 mg/kg doses, 3×/week, for ten weeks. Concentrations below the limit of quantitation were treated as zero for the calculation of mean and SD. N=7-8 per time point.
Figure 42B:
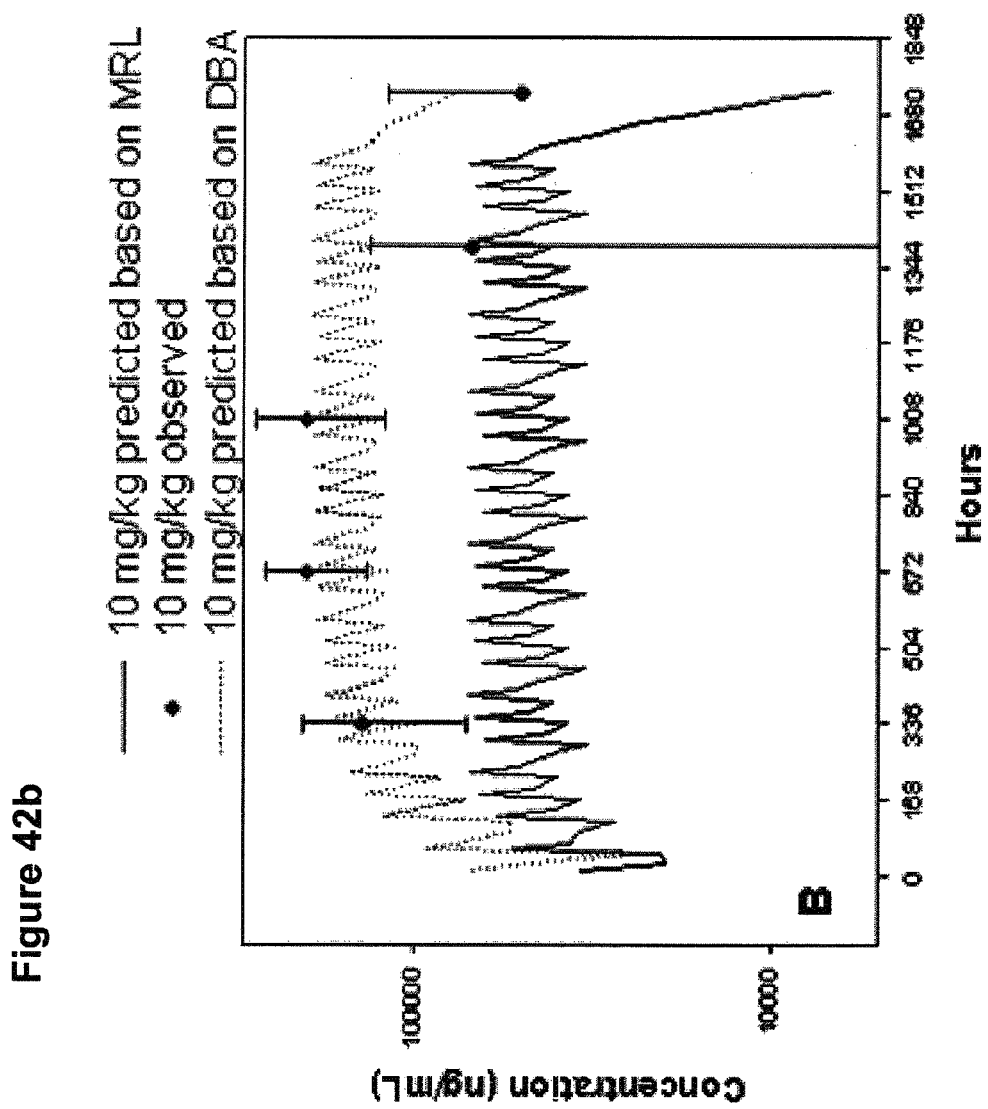

When AbS was administered to MRL-Fas$^{lpr}$ mice i.p. at 2.5, 5, or 10 mg/kg per dose 3×/week for 10 weeks (Example 10.2), all dose groups had significant reduction in titers of anti-dsDNA antibodies compared to the isotype control (anti-human IL-13 human IgG1 triple-mutant). For the 2.5 and 10 mg/kg dose groups, steady-state trough levels of AbS were assayed by ELISA. At 2- and 4-week time points, almost all samples tested from the 2.5 mg/kg group had undetectable levels (<34 ng/ml) of AbS in the serum; one sample had very low levels (57 ng/ml). For the 10 mg/kg group, there was high interanimal variability in the AbS serum concentrations; however, median steady-state trough levels were ~3-10 fold higher, compared to those predicted by simulations using PK data from the single dose study in MRL-Fas$^{lpr}$ mice (FIG. 42). When single-dose i.p. data obtained in the DBA mouse strain were used for predictions, there appeared to be an improved correlation between the observed and predicted AbS concentrations in the 10 mg/kg/dose group (FIG. 42). Without intending to be bound by theory, a possible explanation for the undetectable levels of AbS in the low-dose group is marked MAHA production triggered by multiple administration of AbS at relatively low dose levels, as week-2 serum samples from the 2.5 mg/kg/dose group were assayed for anti-AbS antibodies and all samples had very high titers above the upper limit of quantitation of 4.74 log titer units. However, in lieu of expected pharmacological action of AbS to delay and/or reduce IgG responses, it is possible that higher dosage of AbS under the multiple dose regimens would reduce MAHA response against itself, resulting in higher observed serum AbS concentrations, compared to those expected based solely on the single-dose PK data. In fact, in MRL-Fas$^{lpr}$ mice, MAHA response to AbS was ~10-fold lower, compared to that to an isotype control human IgG administered via the same multiple dose regimen of 10 mg/kg 3×/week for 10 weeks (FIG. 37a).

Example 10.6

PK of AbS in Female Cynomolgus Monkeys

Figure 43A:
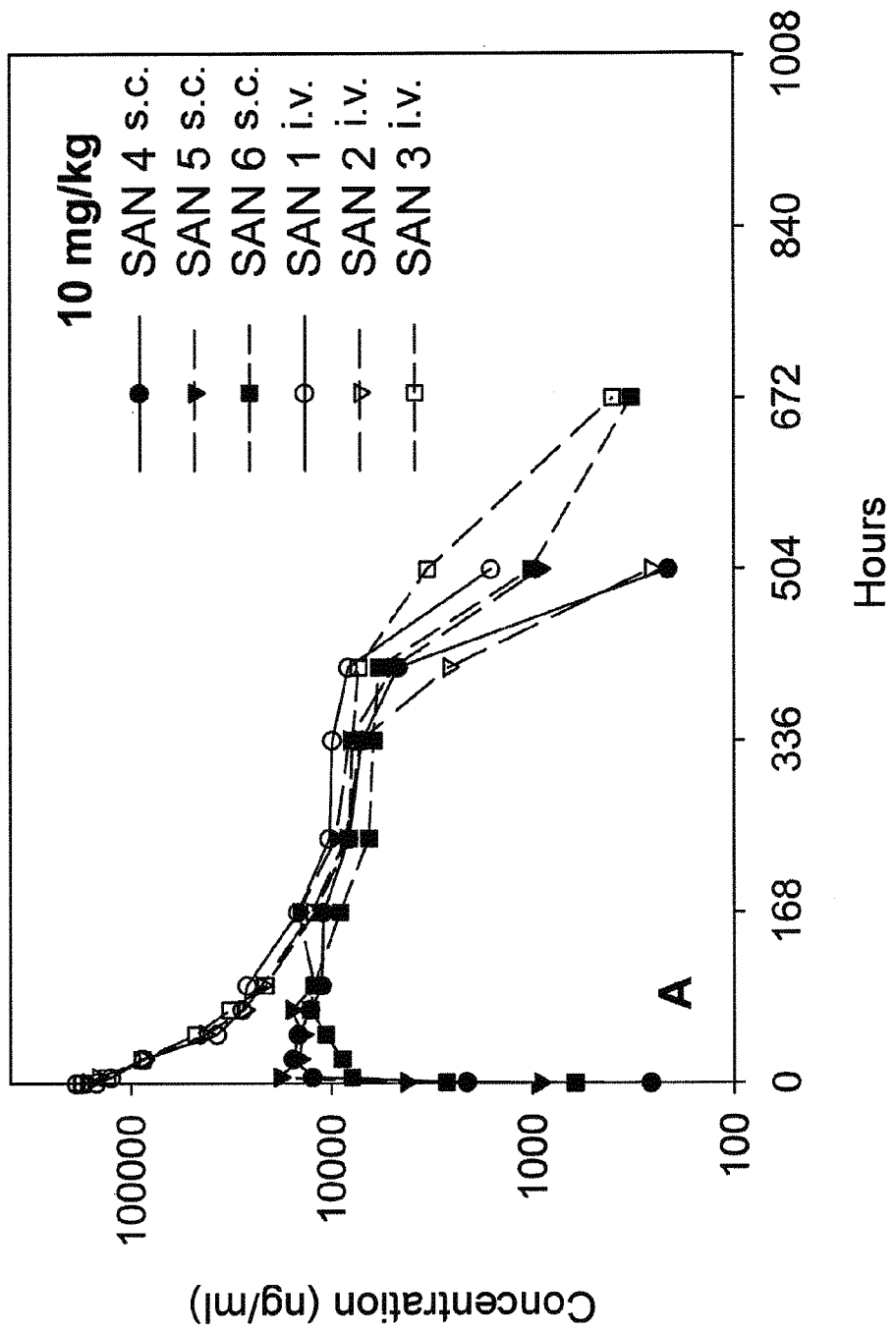
FIGS. 43a and b depict the concentration-time profiles of AbS in cynomolgus monkeys after administrations as shown. Concentrations below the limit of quantitation (<30 ng/ml) were treated as zero for the calculation of mean and standard deviation. N=3 for each group. SAN in FIG. 43a is the study animal number.
Figure 43B:
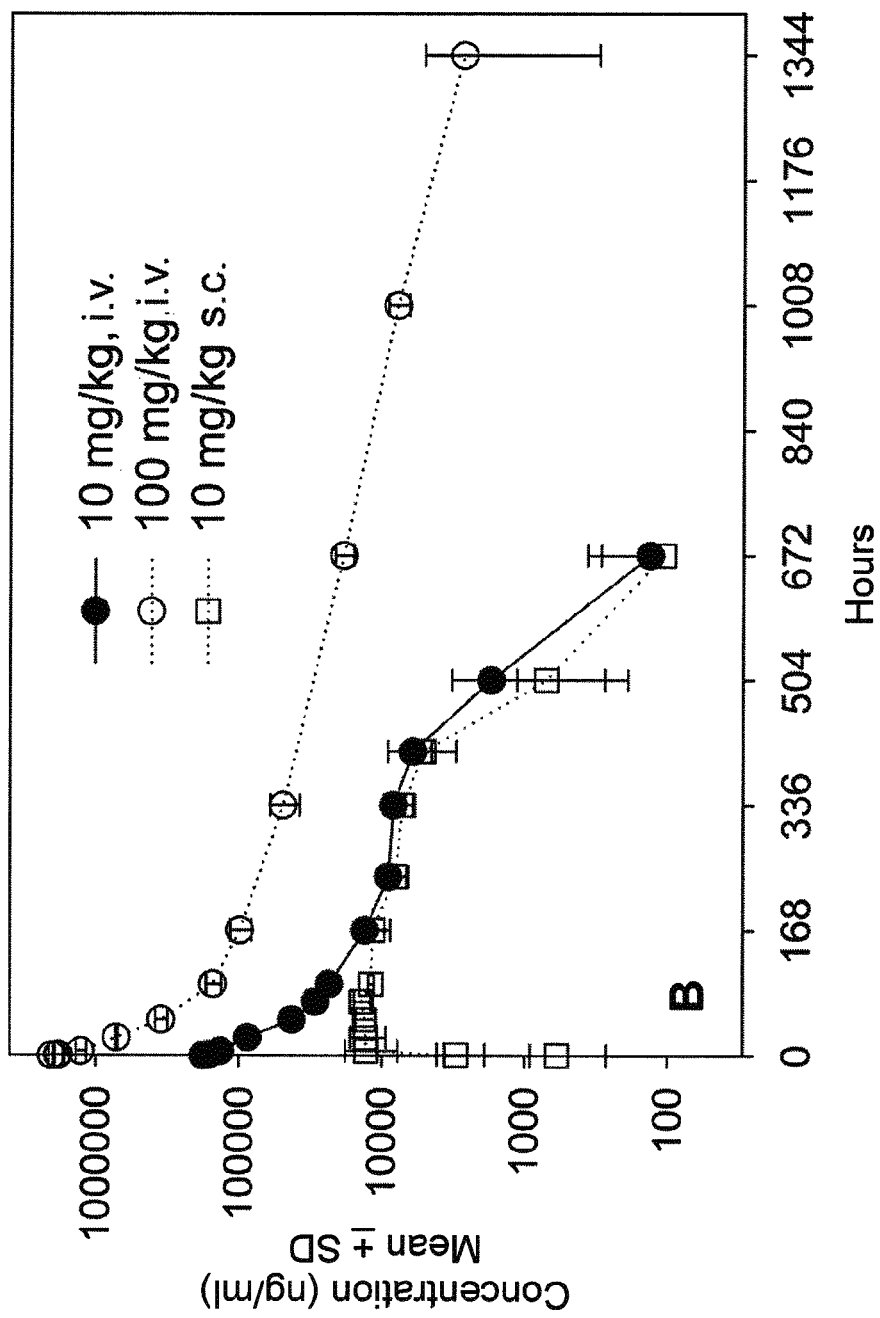

PK of AbS in female monkeys were determined following a single 10 mg/kg i.v. or s.c. administration. Individual animal and mean concentration-time profiles from this study are shown in FIGS. 43a and 43b, respectively, and mean PK parameters are summarized in Table 14.

The serum concentrations of human anti-IL-21R antibodies were determined by qualified ELISAs as described in Table 12. The anti-IL-21R ELISA used a monomeric His-tagged IL-21R as a capture reagent and an anti-human-Fc conjugated to HRP as a detector reagent, as described for CD-1 mice in Example 10.4. The serum concentration of the isotype control antibody in monkeys (anti-IL-13 antibody) was also measured by ELISA. In this assay, the recombinant human IL-13 ligand, which contains a FLAG octapeptide fusion tag, was captured by an anti-FLAG monoclonal antibody. The serum samples containing anti-IL-13 antibody were detected with an anti-human-Fc-HRP. The enzyme substrate ABTS was used to produce a colored endproduct to visualize the bound test article. PK parameters were calculated for each individual animal using noncompartmental methods.

All six female monkeys that were administered AbS at 10 mg/kg (n=3 for both i.v. and s.c. routes of administration) had a sharp drop in AbS levels in the terminal phase (at ~408 hr post-dose), suggesting the possible formation of anti-product antibodies. The elimination half-life values in the 10 mg/kg groups were calculated with and without the time points at which a sharp concentration drop was observed.

After a single 10 mg/kg i.v. administration of AbS to female cynomolgus monkeys, the mean serum clearance (CL) was 1.03 ml/hr/kg and the mean elimination half-life ($t_{1/2}$) was 74 hr (~3 days). When time points at which a sharp concentration drop was observed were excluded from calculations, the mean $t_{1/2}$ estimate was ~7.9 days. The mean steady-state volume of distribution (Vd$_{SS}$) was low (~125 ml/kg), suggesting that AbS was mainly confined to the vascular system. The mean exposure ($AUC_{0-\infty}$) of AbS was 9728 µg*hr/ml.

After a single 100 mg/kg i.v. administration of AbS to cynomolgus monkeys, CL was ~1.08 ml/hr/kg, $t_{1/2}$ was 279 hr (~11.6 days), $AUC_{0-\infty}$ was ~92867 µg*hr/ml, and $Vd_{SS}$ was ~211 ml/kg. Thus, in general, the PK of AbS were approximately linear in the 10-100 mg/kg dose range.

After 10 mg/kg s.c. administration of AbS to female monkeys, the absorption of AbS was slow (mean $T_{max}$ of ~34 hr) and the mean s.c. bioavailability was ~43%. The mean $t_{1/2}$ value after 10 mg/kg s.c. administration to monkeys was 52 hr (~2.2 days), and similar to that observed after 10 mg/kg i.v. administration. When time points at which a sharp concentration drop was observed were excluded from calculations, the mean $t_{1/2}$ was 258 hr (~10.8 days).

All six female monkeys that were administered AbS at 10 mg/kg had detectable anti-AbS antibodies starting at 504 hr (3 weeks) post-dose (Table 16), determined using the paramagnetic bead assay described in Example 10.4. These data are consistent with the observed sharp drop in AbS serum levels. The anti-AbS response persisted at all subsequent time points (up to 27 weeks). Thus, the anti-AbS antibody response appears to affect the PK of AbS in monkeys after a single 10 mg/kg i.v. or s.c. administration. For the 100 mg/kg i.v. dose group, 1 of 3 monkeys was positive for anti-AbS antibodies at weeks 6 and 8, with log titers of 1.8 and 4.6, respectively.

TABLE 13

ELISA Summary for AbS in Mouse and Female Monkey Serum

| Species strain | Assay Capture | Assay Detector | Range of quantitation (ng/mL in 100% serum) | Minimum Required Dilution | Standard curve (ng/ml in 5% serum | Serum used for assay diluent |
|---|---|---|---|---|---|---|
| Mouse DBA | anti-human IgG | anti-human IgG-biotin | 32-500 | 20 | 0.78-100 | Sprague-Dawley rat |
| Mouse MRL$^{lpr}$ | anti-human IgG | anti-human IgG-biotin | 33.4-630 | 20 | 0.514-102 | C57BL/6 mouse |
| Mouse CD-1 | Monomeric His-tagged Il-21R | anti-human IgG-HRP | 45-768 | 20 | 1-38.4 | CD-1 mouse |
| Monkey (cyno) | Monomeric His-tagged Il-21R | anti-human IgG-HRP | 30-512 | 20 | 0.44-38.4 | Pooled monkey |

TABLE 14

Mean PK Parameters of AbS in Mice and Female Monkeys

| Species strain | Dose (mg/kg), Route, Protocol | $C_{5\,min}$ or $C_{max}{}^{a}$ (µg/ml) | $T_{max}$ (hr) | $AUC_{0-\infty}$ (µg * hr/ml) | CL (ml/hr/kg) | $Vd_{ss}$ (ml/kg) | $t_{1/2}$ (hr) | F (%) |
|---|---|---|---|---|---|---|---|---|
| Mouse DBA | 8, ip | 62 | 6 | 7229 | NA | NA | 140 | ND |
| Mouse MRL$^{lpr}$ | 10, ip | 51 | 3 | 2798 | NA | NA | 46 | ND |
|  | 2.5, ip | 12 | 3 | 823 | NA | NA | 12 (54)$^{b}$ | ND |
| Mouse CD-1 | 10, iv | 113 | NA | 7272 | 1.38 | 306 | 162 | NA |
|  | 10, sc | 17 | 48 | 5913 | NA | NA | 195 | 81 |
|  | 100, iv | 1160 | NA | 75792 | 1.32 | 473 | 391 | NA |
| Mouse C57BL/6 | 2.5, iv | 29 | NA | 1927 | 1.30 | 208 | 120 | NA |
| Mouse IL-21R knockout | 2.5, iv | 32 | NA | 3415 | 0.73 | 273 | 256 | NA |
| Monkey (cyno) | 10, iv | 177 ± 10 | NA | 9728 ± 621 | 1.03 ± 0.07 | 125 ± 16 | 74 ± 46 (190 ± 38)$^{b}$ | NA |
|  | 10, sc | 15 ± 3 | 34 ± 34 | 4188 ± 542 | NA | NA | 52 ± 20 (258 ± 35)$^{b}$ | 43 ± 6 |
|  | 100, iv | 2030 ± 95 | NA | 92867 ± 9768 | 1.08 ± 0.11 | 211 ± 11 | 279 ± 28 | NA |

$^{a}C_{5\,min}$ was determined for i.v. route, or $C_{max}$ was determined for i.p. and s.c. routes.
$^{b}$Terminal half-life was calculated excluding the data points with the sharp concentration drop.
NA = not applicable
ND = not determined

TABLE 15

Formation of Anti-AbS Antibodies (Log Titer) in Male CD-1 Mice After a Single IV or SC Dose of 10 mg/kg

| SAN | Time (hr) 576 | 672 |
|---|---|---|
| Intravenous Group | | |
| 26 | 2.65 | |
| 27 | 2.54 | |
| 28 | <1.40[a] | |
| 29 | 2.16 | |
| 30 | <1.40[a] | |
| 40 | 2.81 | |
| 41 | 2.34 | |
| 42 | 2.32 | |
| 43 | | 2.79 |
| 44 | | <1.40[a] |
| 45 | | 3.25 |
| 46 | | 1.79 |
| 47 | | 3.28 |
| 48 | | <1.40[a] |
| 49 | | 3.21 |
| 50 | | 3.18 |
| Subcutaneous Group | | |
| 76 | 2.30 | |
| 77 | 2.55 | |
| 78 | <1.40[a] | |
| 79 | 2.71 | |
| 80 | 1.87 | |
| 90 | <1.40[a] | |
| 91 | 3.75 | |
| 92 | 2.35 | |
| 93 | | <1.40[a] |
| 94 | | 2.75 |
| 95 | | <1.40[a] |
| 96 | | 3.27 |
| 97 | | 3.53 |
| 98 | | 3.73 |
| 99 | | <1.40[a] |
| 100 | | 3.65 |

[a]<1.40 signifies a negative result.
SAN = study animal number

TABLE 16

Formation of Anti-AbS Antibodies (Log Titer) in Female Cynomolgus Monkeys After a Single IV or SC Dose of 10 mg/kg Intravenous Group

| Time (hr) | SAN 1 | SAN 2 | SAN 3 |
|---|---|---|---|
| 336 | <1.40[a] | <1.40 | <1.40 |
| 504 | 2.35 | 2.33 | 2.26 |
| 672 | 3.61 | 3.22 | 2.47 |
| 804 | 3.78 | 3.61 | 3.31 |
| 1008 | 3.80 | 3.72 | 4.18 |
| 1176 | 3.72 | 3.76 | 4.09 |
| 2016 | 3.70 | 4.44 | 4.14 |
| 2856 | 3.60 | 4.67 | 4.44 |
| 3696 | 3.60 | 4.71 | 4.24 |
| 4536 | 3.53 | 4.64 | 4.31 |

Subcutaneous Group

| Time (hr) | SAN 4 | SAN 5 | SAN 6 |
|---|---|---|---|
| 336 | <1.40[a] | <1.40 | <1.40 |
| 504 | 3.00 | 2.68 | 2.39 |
| 672 | 3.52 | 3.64 | 2.59 |
| 804 | 4.10 | 3.71 | 2.47 |
| 1008 | 3.91 | 3.73 | 2.89 |
| 1176 | 4.11 | 3.59 | 3.27 |
| 2016 | 4.29 | 3.77 | 3.65 |
| 2856 | 4.25 | 3.61 | 3.50 |
| 3696 | 4.26 | 3.49 | 3.45 |
| 4536 | 4.39 | 3.56 | 3.58 |

[a]<1.40 signifies a negative result.
SAN = study animal number

Example 10.7

PK of AbT in Mice

The serum concentrations of human anti-IL-21R antibodies were determined by qualified ELISAs as described in Table 17. The anti-IL-21R ELISA used a monomeric His-tagged IL-21R as a capture reagent and an anti-human-Fc (conjugated to horseradish peroxidase (HRP)) as a detector reagent for CD-1 mice, and anti-human Fc as a capture reagent and biotinylated anti-human Fc as a detector reagent for DBA and MRL-Fas$^{lpr}$ mice. PK parameters were calculated as noted in Example 10.4. Predictions of concentrations after a multiple dose regimens were conducted by nonparametric superposition using WinNonlin software and assuming linear kinetics in MRL-Fas$^{lpr}$ and DBA mice in the 2.5-10 mg/kg dose range (single dose) for AbS and in the 8-20 mg/kg dose range (single dose) for AbT.

Figure 44A:
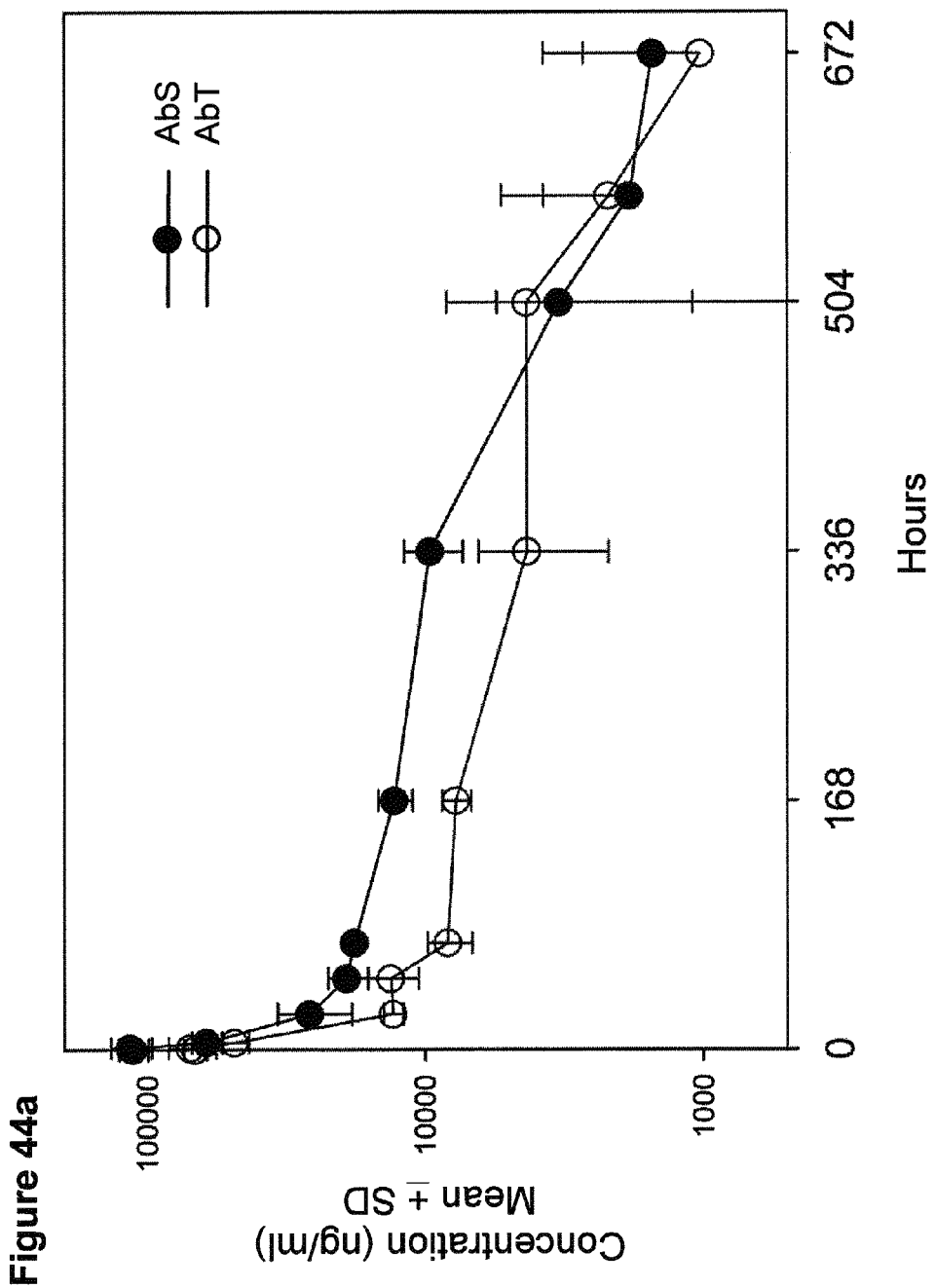
FIG. 44a shows a profile after a 10 mg/kg i.v. administration in CD-1 mice.

After i.v. administration of 10 mg/kg of AbT to male CD-1 mice, the exposure ($AUC_{0-\infty}$) of AbT was 4551 µg*hr/ml (FIG. 44a; Table 18). The mean concentration at the first sampling time point after i.v. administration (C5 min) was ~70 µg/ml. The elimination of AbT in CD-1 mice was relatively slow, as evidenced by the low total body clearance (CL) of ~2.2 ml/hr/kg and long elimination half-life ($t_{1/2}$) of 210 hr (~8.8 days). The steady-state volume of distribution ($Vd_{SS}$) was 572 ml/kg. Following 10 mg/kg i.v. administration to mice, AbT appeared to have higher CL (~60% increase), lower $AUC_{0-\infty}$ (~37% decrease) and larger $Vd_{SS}$ (~87% increase), compared to the corresponding values for AbS.

Figure 44B:
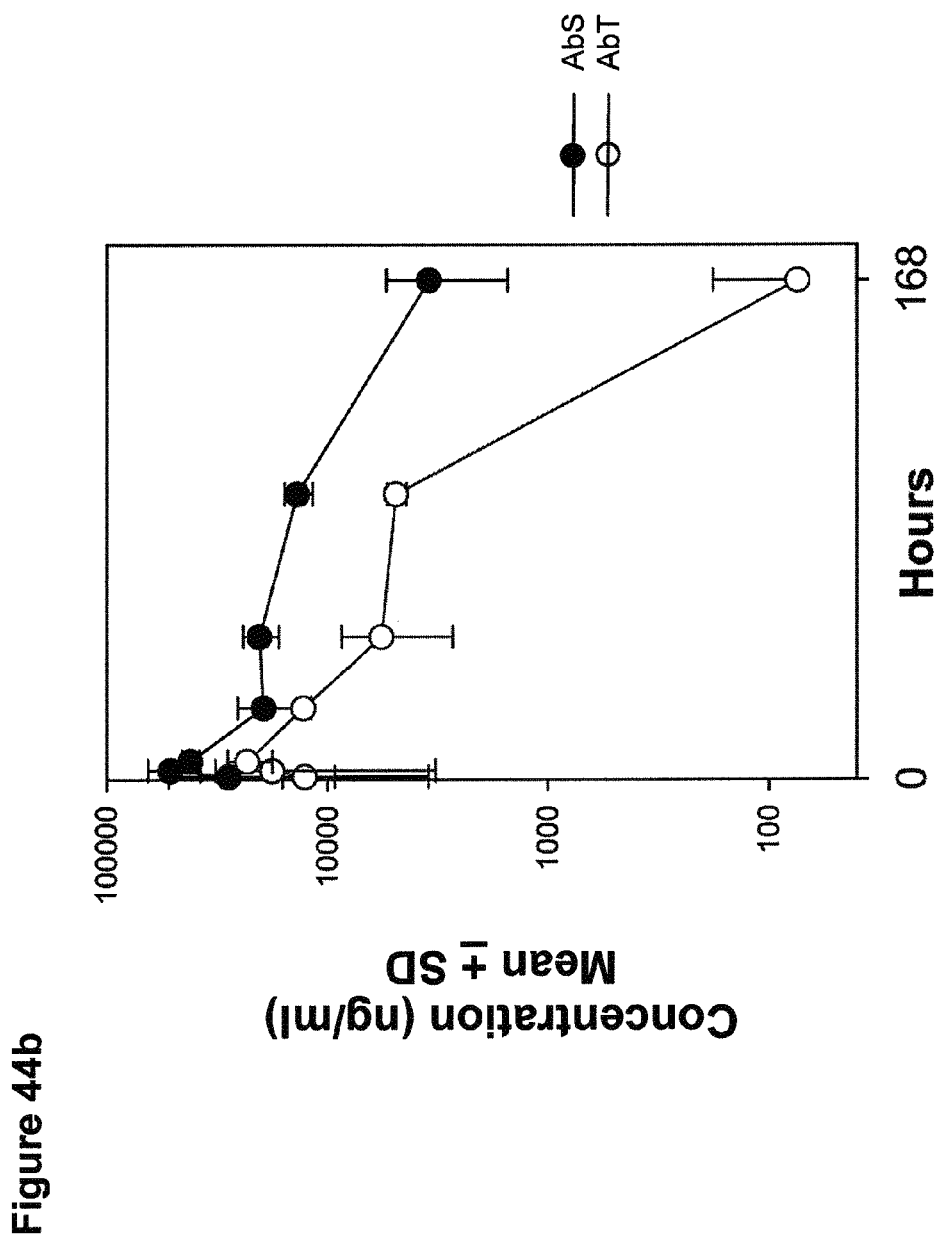
FIG. 44b shows a profile after a 10 mg/kg i.p. administration in MRL-Fas$^{lpr}$ mice.
Figure 44C:
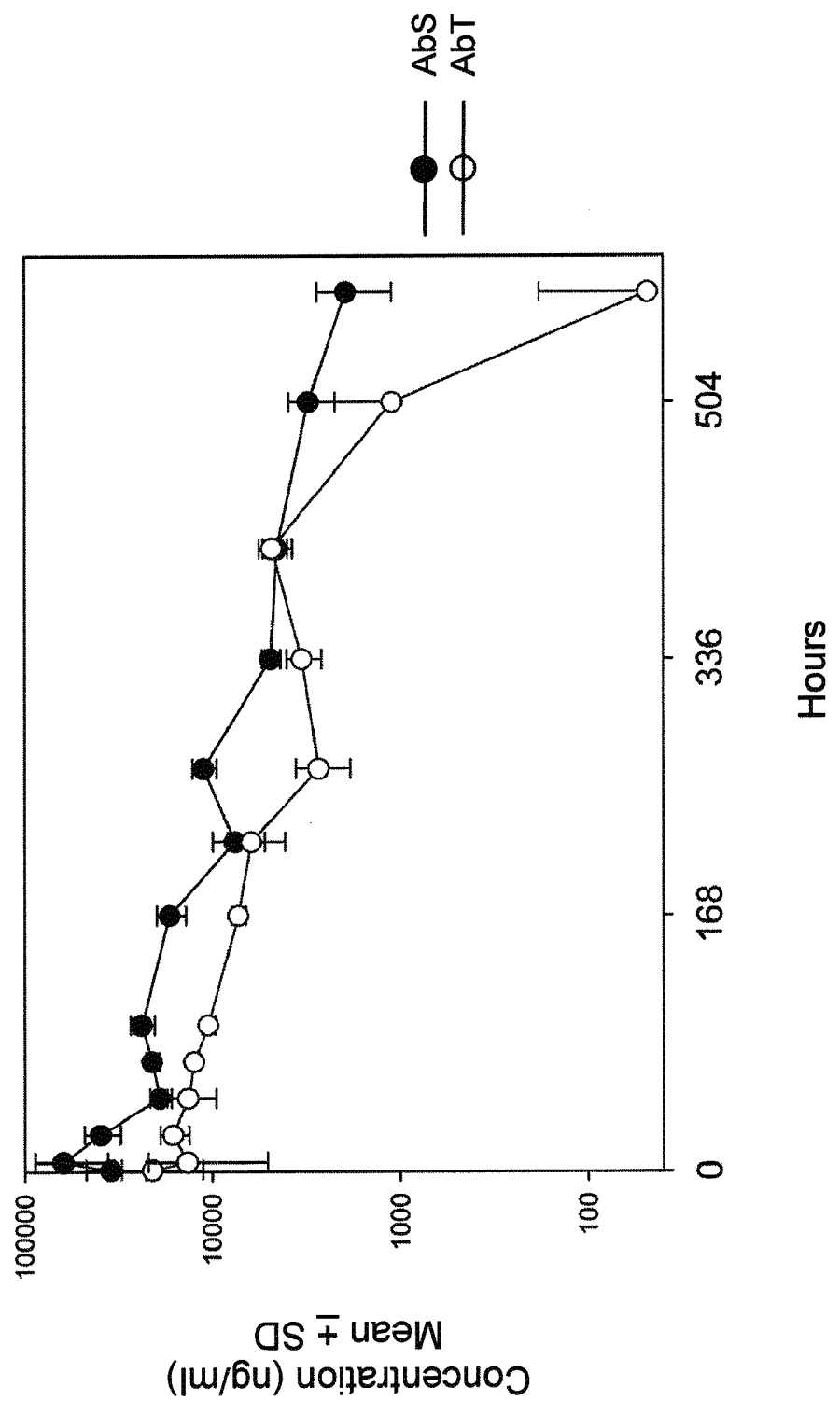
FIG. 44c shows a profile after an 8 mg/kg i.p. administration in DBA mice. Concentrations below the limit of quantitation were treated as zero for the calculation of mean and standard deviation. N=4-8 for each data point.

Following a single i.p. dose of 8 mg/kg to male DBA mice, the maximum serum concentration ($C_{max}$) and exposure ($AUC_{0-\infty}$) of AbT were 21 µg/ml and 3320 µg*hr/ml, respectively (FIG. 44c; Table 18). The $T_{max}$ and the elimination half-life ($t_{1/2}$) of AbT were 1 hr and 80 hr (~3.3 days), respectively. After i.p. administration to DBA mice, AbT exposure and half-life were reduced ~54% and ~43%, respectively, compared to the corresponding PK parameters of AbS.

Figure 45:
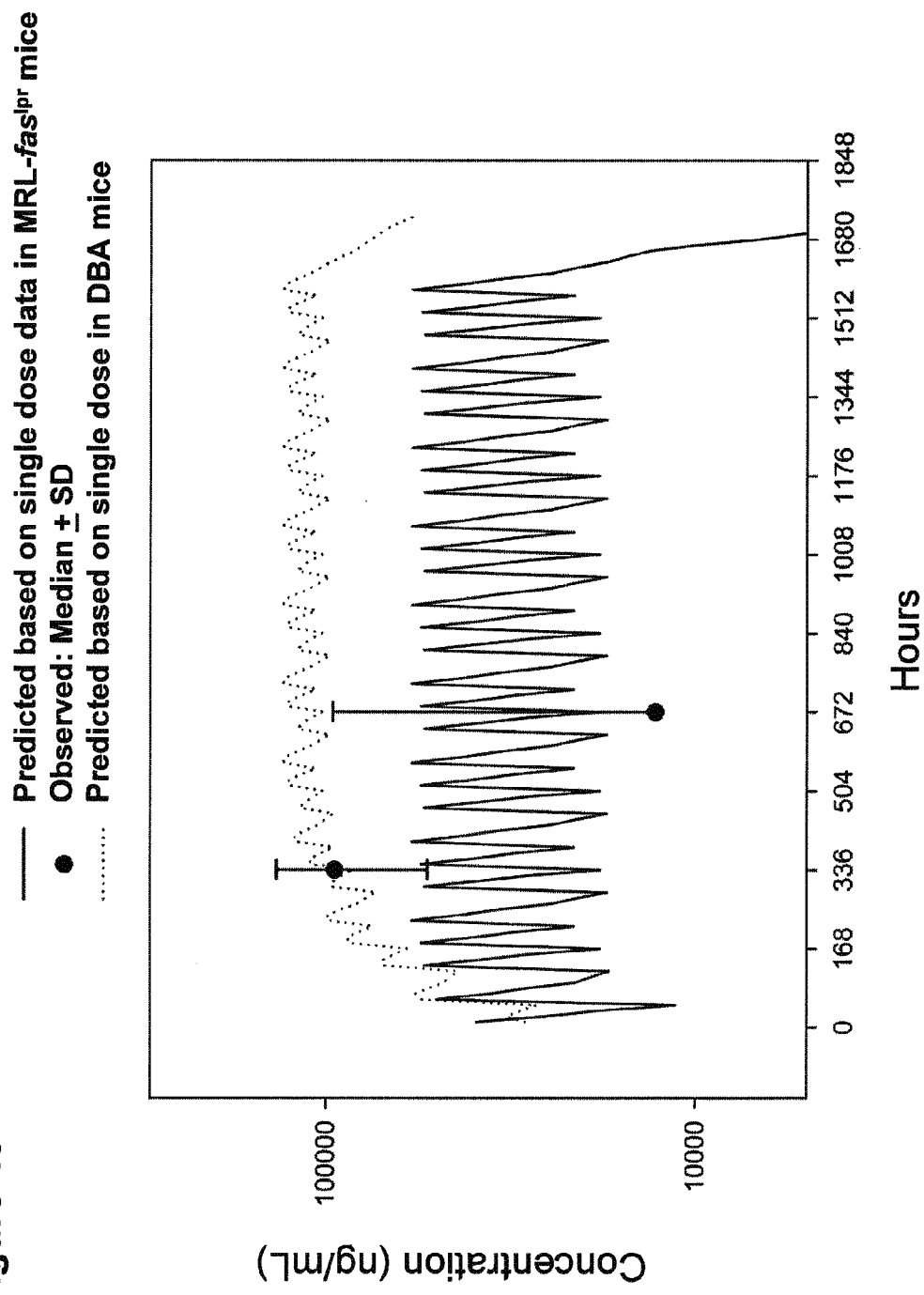
FIG. 45 depicts the observed and predicted AbT concentrations in MRL-Fas$^{lpr}$ mice after multiple i.p. administrations at 20 mg/kg doses, 3×/week, for ten weeks. Concentrations below the limit of quantitation were treated as zero for the calculation of mean and standard deviation. N=6-8 per time point.

Following a single i.p. dose of 10 mg/kg to female 12-week-old MRL-Fas$^{lpr}$ mice, the maximum serum concentration ($C_{max}$) and exposure ($AUC_{0-\infty}$) of AbT were 23 µg/ml and 957 µg*hr/ml, respectively (FIG. 44b; Table 18). The $T_{max}$ and the elimination half-life ($t_{1/2}$) of AbT were 6 hr and 21 hr, respectively. After i.p. administration to MRL-Fas$^{lpr}$ mice, AbT exposure and half-life was reduced ~66% and ~54%, respectively, compared to the corresponding PK parameters of AbS. At 2 weeks, the only time point for AbT at which a reduction in anti-ds DNA titers was observed, median AbT levels were 4-5-fold higher compared to those predicted by simulations using PK data from the single-dose study in MRL-Fas$^{lpr}$ mice and similar compared to those predicted by simulation with single-dose data obtained from DBA mice (FIG. 45). This observation is in line with that for the AbS 10 mg/kg group. Without intending to be bound by theory, a possible explanation for relatively lower levels of AbT at the 2-week time point (compared to those of AbS) and undetectable levels of AbT at later time points is marked MAHA production triggered by multiple administrations of AbT and the inability of AbT to suppress the MAHA response against itself.

In line with results described for AbT, dose-normalized exposure of AbT appeared to be lower in MRL-Fas$^{lpr}$ mice, compared to those in DBA and CD-1 mice (Table 18).

Unlike AbS, when AbT was administered to MRL-Fas$^{lpr}$ mice i.p. at 10 mg/kg or 20 mg/kg per dose 3×/week for 10 weeks, only limited effects on the development of disease in MRL-Fas$^{lpr}$ mice were observed (Example 10.2). Administration of AbT (10 mg/kg) did not result in significant reduction of titers of anti-dsDNA at all time points evaluated. Twenty mg/kg administration of AbT resulted in transient reduction in titers of anti-dsDNA at 2 weeks; however anti-dsDNA titers were not different from control at later time points (4, 6, 8, and 10 weeks) (Table 19). For the 20 mg/kg AbT group, steady-state trough levels of AbT were assayed by ELISA. There was high interanimal variability in the AbT serum concentrations; however, in general, median steady-state trough levels of AbT appeared to have an inverse correlation with the effect on median anti-dsDNA titers (Table 19). At 2 weeks, median AbT levels were ~8-fold higher than those at 4 weeks (but still lower than median AbS levels at 2 weeks in the 10 mg/kg group). At later time points (4, 6, 8, and 10 weeks), median AbT trough levels were less than the limit of detection (~66 ng/ml). At 2 weeks, the only time point for AbT at which a reduction in anti-dsDNA titers was observed, median AbT levels were 4-5-fold higher compared to those predicted by simulations using PK data from the single-dose study in MRL-Fas$^{lpr}$ mice and similar compared to those predicted by simulation with single-dose data obtained from DBA mice (FIG. 45). This observation is in line with that for the AbS 10 mg/kg group. Without intending to be bound by theory, a possible explanation for relatively lower levels of AbT at the 2-week time point (compared to those of AbS) and undetectable levels of AbT at later time points, is marked MAHA production triggered by multiple administrations of AbT and the inability of AbT to suppress the MAHA response against itself.

Example 10.8

PK of AbT in Cynomolgus Monkeys

Figure 46A:
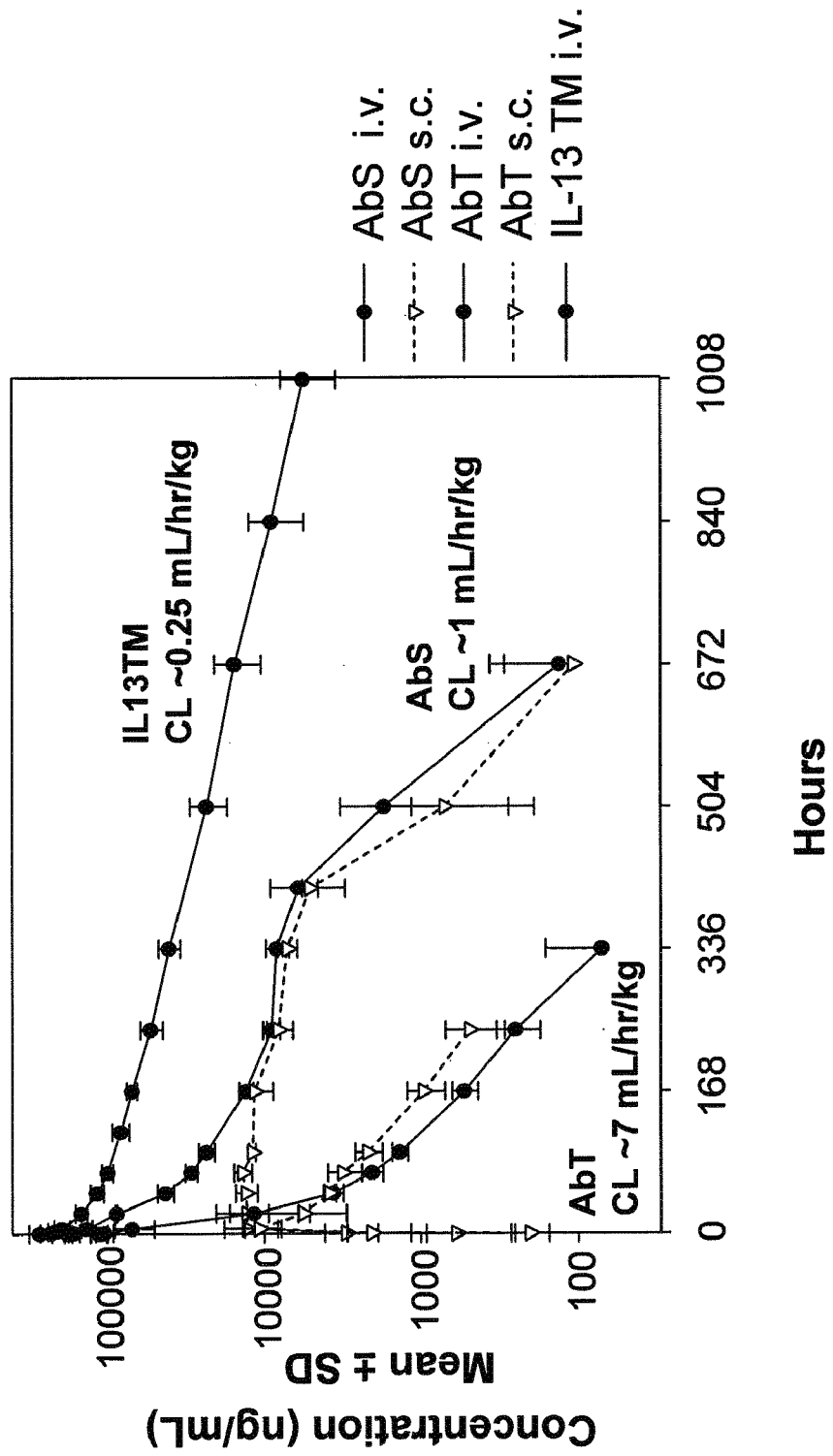
FIGS. 46a and b depict the concentration-time profiles of AbT and AbS in cynomolgus monkeys after administrations as shown. Concentrations below the limit of quantitation (<30 ng/ml) were treated as zero for the calculation of mean and standard deviation. N=3 for each group.
Figure 46B:
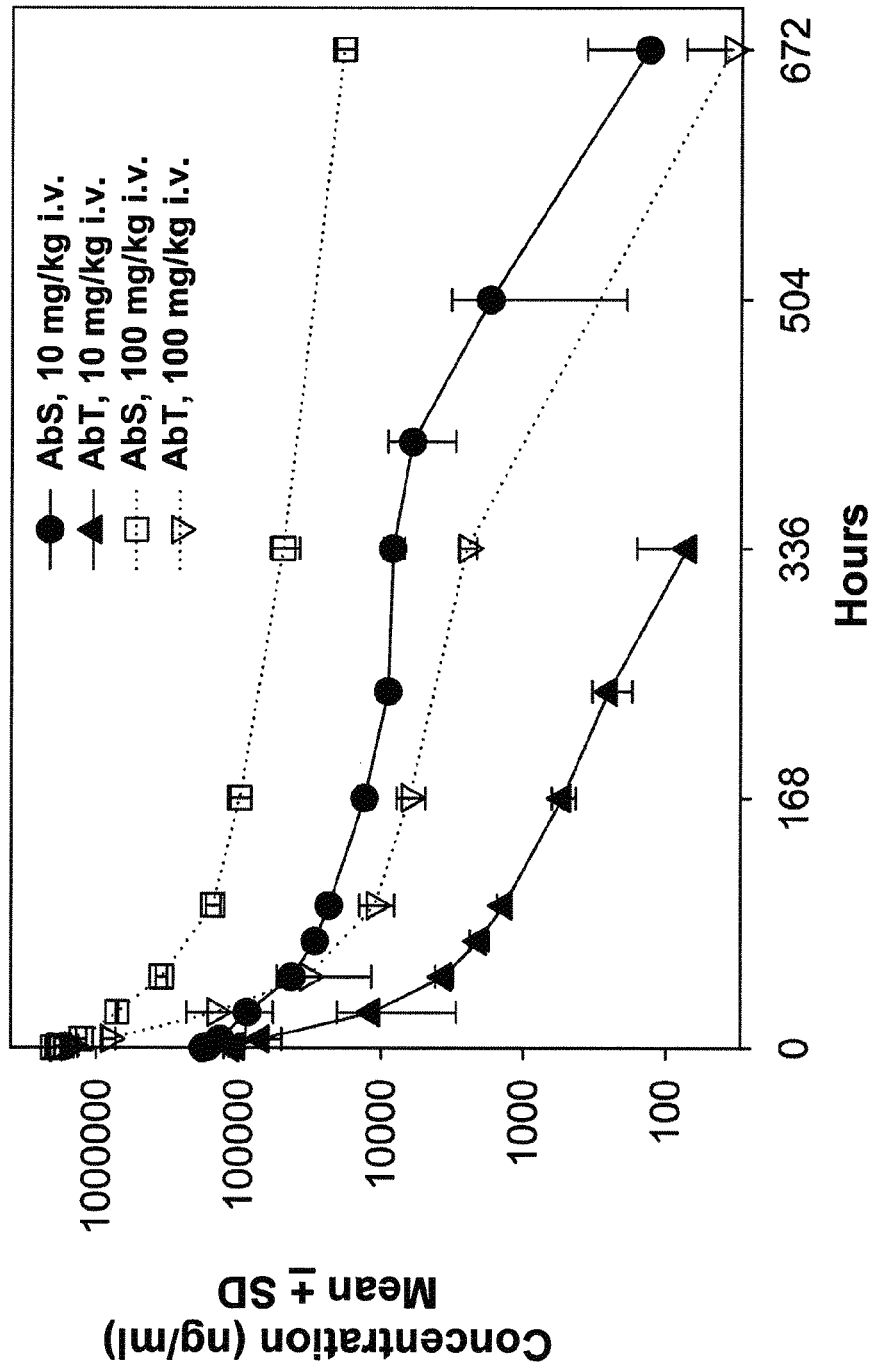

PK of AbT in female monkeys were determined following a single i.v. (10 mg/kg or 100 mg/kg) or s.c. (10 mg/kg) administration. Mean concentration-time profiles from this study were compared to those for AbS (FIGS. 46a-b) and mean PK parameters are summarized in Table 18.

The serum concentrations of human anti-IL-21R antibodies were determined by qualified ELISAs as described in Table 17. The anti-IL-21R ELISA used a monomeric His-tagged IL-21R as a capture reagent and an anti-human-Fc conjugated to HRP as a detector reagent, as described in Example 10.6. TMB was used to produce a colored endproduct to visualize the bound test article. The serum concentration of the isotype control antibody in monkeys (anti-IL-13 antibody) was also measured by ELISA, as described in Example 10.6. PK parameters were calculated as noted in Example 10.6.

After a single 10 mg/kg intravenous administration of AbT to female cynomolgus monkeys, the mean serum clearance (CL) was 7.01 ml/hr/kg and the mean elimination half-life ($t_{1/2}$) was ~2.6 days. The mean steady-state volume of distribution ($Vd_{SS}$) was ~202 ml/kg and the mean exposure ($AUC_{0-\infty}$) of AbT was 1476 µg*hr/ml (Table 18).

After a single 100 mg/kg i.v. administration of AbT to cynomolgus monkeys, CL was ~4.87 ml/hr/kg, $t_{1/2}$ was ~3.7 days, $AUC_{0-\infty}$ was ~20955 µg*hr/ml, and $Vd_{SS}$ was ~146 ml/kg (Table 18). There was no significant difference between the mean PK parameters of AbT in monkeys after a 10 vs. 100 mg/kg single i.v. dose; thus the PK of AbT were approximately linear in the 10-100 mg/kg dose range.

After a 10 mg/kg s.c. administration of AbT to monkeys, the mean $T_{max}$ was ~6 hr and the mean subcutaneous bioavailability was ~43%. The mean $t_{1/2}$ value after a 10 mg/kg s.c. administration to monkeys was 63 hr (~2.6 days), and similar to that observed after a 10 or 100 mg/kg i.v. administration (Table 18).

TABLE 17

ELISA Summary for AbT in Mouse and Female Monkey Serum

| Species strain | Assay Capture | Assay Detector | Range of quantitation (ng/ml in 100% serum) | Minimum Required Dilution | Standard curve (ng/ml) | Serum used for assay diluent |
| --- | --- | --- | --- | --- | --- | --- |
| Mouse DBA | anti-human IgG | anti-human IgG-biotin | 32-500 | 20 | 0.78-100 (in 5% serum) | S-D rat |
| Mouse MRL$^{lpr}$ | anti-human IgG | anti-human IgG-biotin | 66.8-1260 | 40 | 0.514-102 (in 2.5% serum) | C57BL/6 mouse |
| Mouse CD-1 | Monomeric His-tagged Il-21R | anti-human IgG-HRP | 45-768 | 20 | 1-38.4 (in 5% serum) | CD-1 mouse |
| Monkey (cyno) | Monomeric His-tagged Il-21R | anti-human IgG-HRP | 30-512 | 20 | 0.44-38.4 (in 5% serum) | Pooled cyno |

TABLE 18

Mean PK Parameters of AbT in Mice and Female Monkeys

| Species strain | Dose (mg/kg), Route | $C_{5\,min}$ or $C_{max}{}^a$ (μg/ml) | $T_{max}$ (hr) | $AUC_{0-\infty}$ (μ * hr/ml) | CL (ml/hr/kg) | $Vd_{ss}$ (ml/kg) | $t_{1/2}$ (hr) | F (%) |
|---|---|---|---|---|---|---|---|---|
| Mouse DBA | 8, i.p. | 21 | 1 | 3320 | NA | NA | 80 | ND |
| Mouse $MRL^{lpr}$ | 10, i.p. | 23 | 6 | 957 | NA | NA | 21 | ND |
| Mouse CD-1 | 10, i.v. | 70 | NA | 4551 | 2.194 | 572 | 210 | NA |
| Monkey cyno | 10, i.v. | 113 ± 14 | NA | 1476 ± 312 | 7.01 ± 1.68 | 202 ± 44 | 63 ± 24 | NA |
| | 10, s.c. | 11 ± 3 | 6 ± 0 | 638 ± 56 | NA | NA | 63 ± 10 | 43 ± 4 |
| | 100, i.v. | 1850 ± 415 | NA | 20955 ± 3702 | 4.87 ± 0.79 | 146 ± 24 | 88 ± 34 | NA |

TABLE 19

Median AbS and AbT Concentrations After Multiple Dosing to $MRL^{lpr}$ Mice

| Antibody (Dose) | 2 wk | 4 wk | 6 wk | 8 wk | 10 wk |
|---|---|---|---|---|---|
| AbS (2.5 mg/kg) | 0* | 0* | ND* | ND | ND |
| AbS (10 mg/kg) | 137940* | 196887* | 198707* | 68363 | 49563 |
| AbT (20 mg/kg) | 94456* | 12765 | 0 | 0 | 0 |

Example 10.9

Pharmacokinetics of $^{125}$I-D5 in DBA Mice

Figure 47:
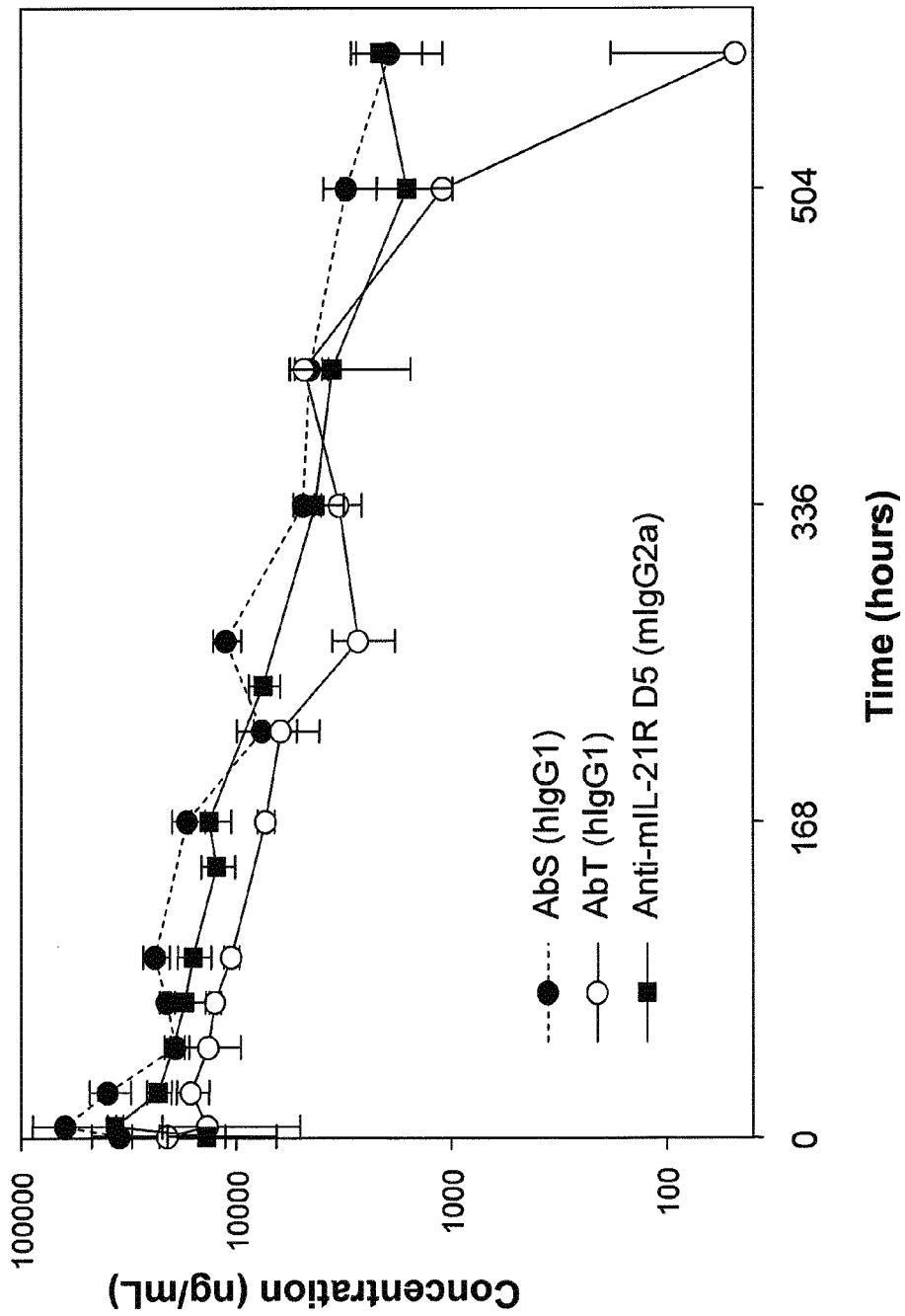
FIG. 47 depicts the concentration-time profiles of the anti-IL-21R antibodies AbS, AbT, and $^{125}$I-D5 (8 mg/kg, i.p.) in male DBA mice. Human antibodies AbS and AbT were quantitated by anti-human IgG ELISA, and the $^{125}$I-labeled murine antibody D5 was quantitated by monitoring the radiolabel.

The $^{125}$I-anti-murine IL-21R antibody D5-20 ("D5") was injected intraperitoneally into nonfasted male DBA mice in a single 8 mg/kg dose. Serum samples were taken at time points from 1-576 hr, and D5 levels were quantified by measuring trichloroacetic acid (TCA)-precipitable radioactivity. The PK profile of D5 antibody after i.p. dosage to DBA mice was, in general, similar to that of the human anti-IL-21R antibodies (Table 20, FIG. 47; see also Tables 14 and 18).

TABLE 20

Pharmacokinetic Parameters of $^{125}$I-D5 in Male DBA Mice

| | $t_{1/2}$ (hr) | $T_{max}$ (hr) | $C_{max}$ (μg/mL) | $AUC_{0-\infty}$ (μg * hr/ml) |
|---|---|---|---|---|
| $^{125}$I-D5 | 143.9 | 6 | 36 | 5422 |

Example 10.10

Pharmacokinetics in Sprague-Dawley Rats After Intravenous, Subcutaneous, or Intraperitoneal Administration of Anti-IL-21R Antibodies PK of AbS, AbT, AbV, AbU, and AbW, as well as an isotype control antibody, were examined after a single 10 mg/kg i.v. dose to S-D rats. Bioanalytical assay for quantitation of test article serum concentrations, an assay for detection of anti-AbS antibodies in rat serum, and pharmacokinetic calculations were performed as described for AbS and AbT for monkeys (Examples 10.6 and 10.8), with the following modifications: S-D serum was used as an assay diluent and LOQ for test article serum concentration assay was 45 ng/mL. For the ELISA method employed for an isotype control, an anti-human Fc antibody was used as both the capture and detector.

Figure 48A:
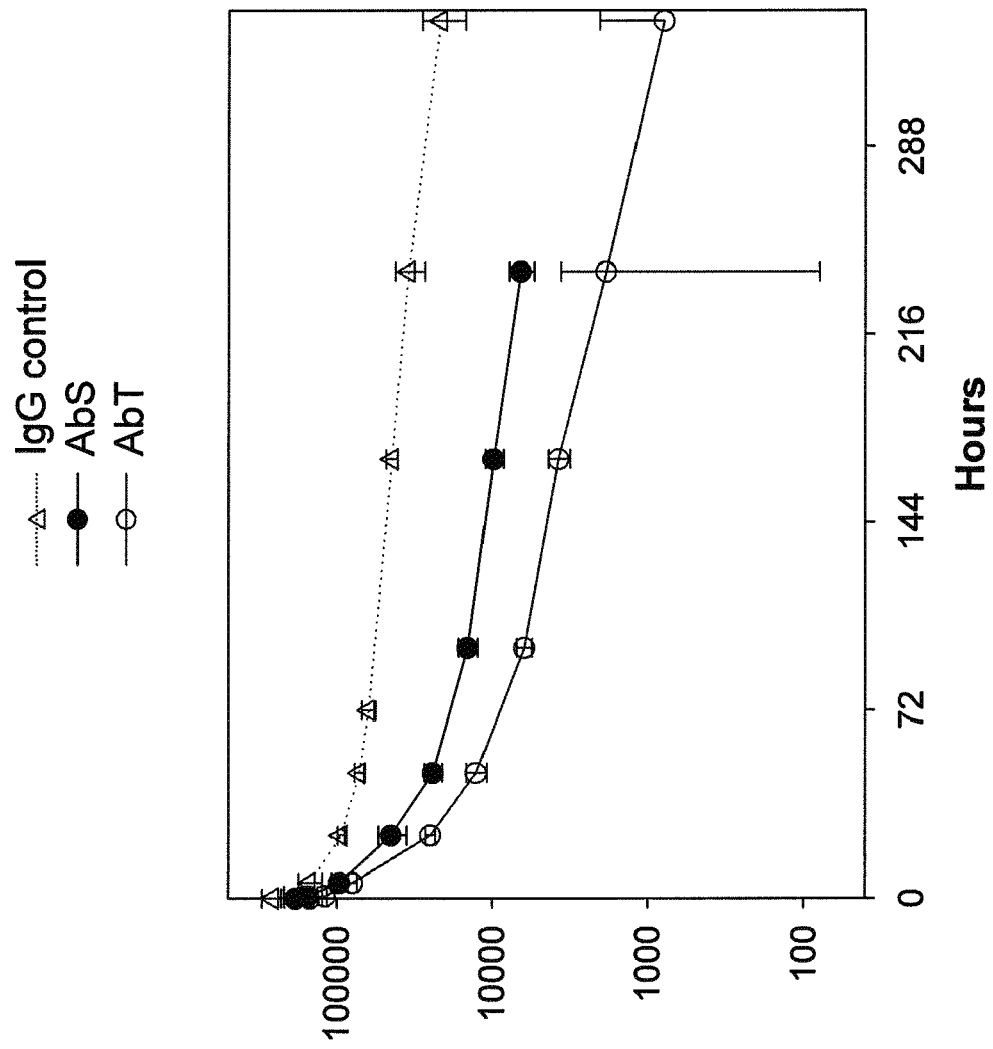
FIG. 48a depicts mean serum concentrations (Y-axis; ng/ml) of AbS, AbT, and an isotype control in Sprague-Dawley (S-D) rats after a single 10 mg/kg i.v. dose.

Following a single 10 mg/kg i.v. dose to S-D rats, antibody AbS was eliminated slowly (CL ~1.6 mL/hr/kg); albeit significantly faster (p<0.05) than that for an isotype control IgG (~0.4 mL/hr/kg). (Table 21 and FIG. 48a). All rats (n=6) had a sharp decline in AbS serum concentration, such that there was no detectable AbS at and after day 15 post-dose. This decline in AbS serum concentration was likely related to the presence of anti-AbS antibodies detected at day 15 and all subsequent time points in all six animals. It should be noted that differences in concentration-time profiles in rats between the AbS and the control IgG are not likely to be explained entirely by anti-product responses, as mean serum concentrations started to diverge as early as 24 hr post-dose and differed by more than 4-fold at the one-week time point. The concentration-time profile and PK parameters of AbV closely resembled those of AbS in rats.

Figure 48B:
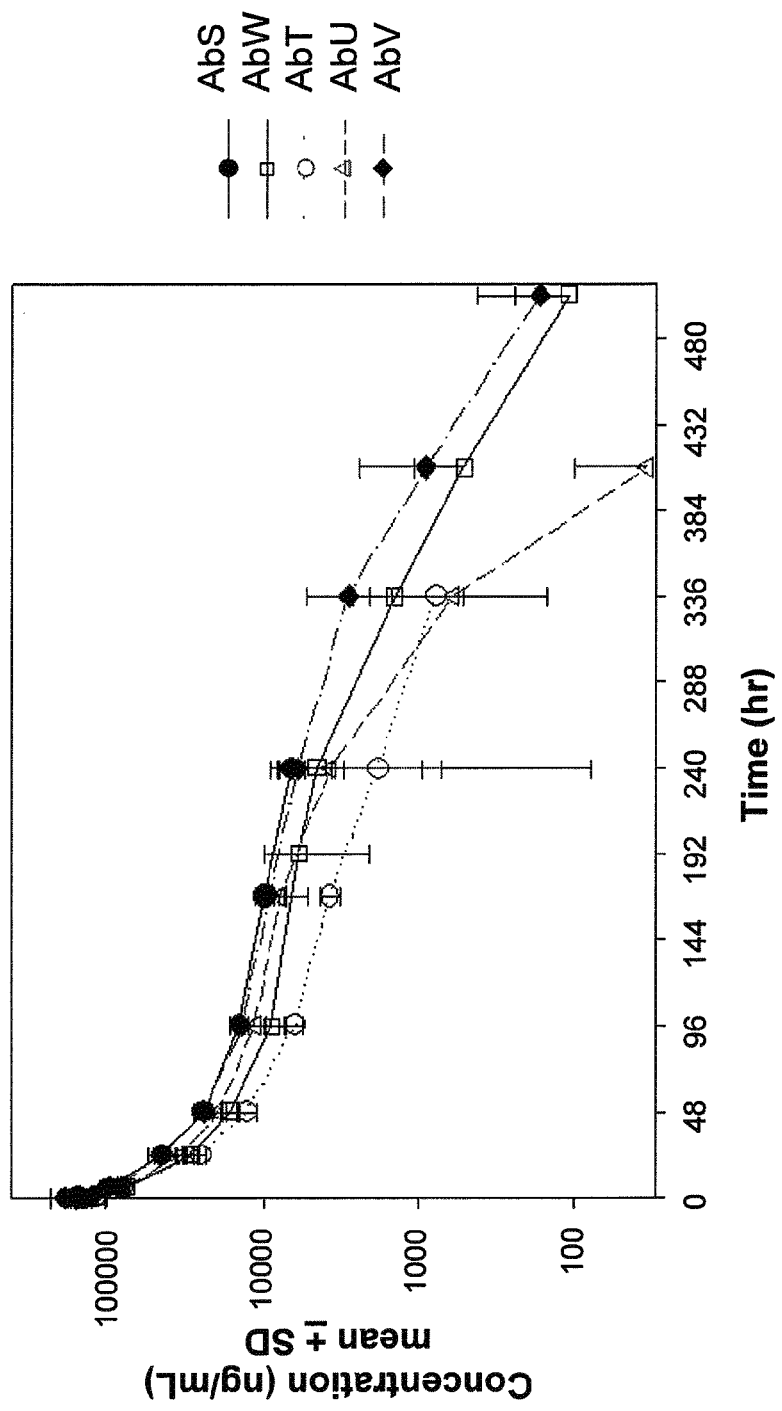
FIG. 48b depicts anti-IL-21R antibodies AbS-AbW after a single 10 mg/kg i.v. dose in S-D rats. Individual data points <LOQ (45 ng/mL) were treated as zero for calculations of mean and SD. If mean value was below LOQ (e.g., when all animals had value <LOQ), data points are not shown.

After a single 10 mg/kg i.v. dose to rats, AbT elimination was faster (CL ~2.1 mL/hr/kg) and the resulting $AUC_{0-\infty}$ was ~2-fold lower, compared to AbS. All of six AbT-dosed rats also had a sharp decline in the serum concentrations in the terminal phase. The concentration-time profiles of AbU and AbW and PK parameters (such as $AUC_{0-\infty}$, $AUC_{0-240hr}$, and CL) in rats were intermediate between those of AbS and AbT (FIG. 48b).

TABLE 21

Pharmacokinetic Properties of Anti-IL-21R Antibodies in S-D Rats After 10 mg/kg i.v. Administration

| Compound (n) | $C_{5\,min a}$ (μg/ml) | $AUC_{0-\infty}$ (μg * hr/ml) | $AUC_{0-240\,h}{}^b$ (μg * hr/ml) | CL (ml/hr/kg) | $Vd_{ss}$ (ml/kg) |
|---|---|---|---|---|---|
| AbS (n = 6) | 191 ± 38.5 | 6361 ± 184 | 5266 ± 625 | 1.60 ± 0.210 | 191 ± 33.0 |
| AbT (n = 5) | 149 ± 51.1 | 3233 ± 356 | 3036 ± 167 | 3.12 ± 0.312 | 182 ± 46.0 |
| AbU (n = 7) | 161 ± 15.0 | 4371 ± 552 | 4116 ± 392 | 2.32 ± 0.328 | 160 ± 24.2 |

TABLE 21-continued

Pharmacokinetic Properties of Anti-IL-21R Antibodies in S-D Rats After 10 mg/kg i.v. Administration

| Compound (n) | $C_{5\,min\,a}$ (μg/ml) | $AUC_{0-\infty}$ (μg * hr/ml) | $AUC_{0-240\,h}{}^b$ (μg * hr/ml) | CL (ml/hr/kg) | $Vd_{ss}$ (ml/kg) |
|---|---|---|---|---|---|
| AbV (n = 7) | 153 ± 14.4 | 5541 ± 691 | 4907 ± 374 | 1.83 ± 0.211 | 161 ± 20.3 |
| AbW (n = 5) | 144 ± 7.78 | 4002 ± 737 | 3613 ± 591 | 2.58 ± 0.522 | 200 ± 36.7 |

CL = serum clearance.
$Vd_{ss}$ = Volume of distribution at steady-state.
AUC = Area under the curve.
$^a$Concentration at 5 min, the first sampling time point after IV administration.
$^b$AbS levels were <LOQ after 240 hr time point in all rats.
$^c$All animals in all dose groups had sharp drop in test article levels during the 168-504 hr period.
Thus, the terminal phase was not well defined and the resulting apparent $t_{1/2}$ values were driven by the differences in the onset of this concentration drop. Therefore, $t_{1/2}$ values were not used for comparison of PK across constructs and are not shown.

For AbS, PK in rats was also examined after 10 mg/kg s.c. and i.p. administrations, as well as at two dose levels (1 and 10 mg/mg) after i.v. administration.

Figure 49:
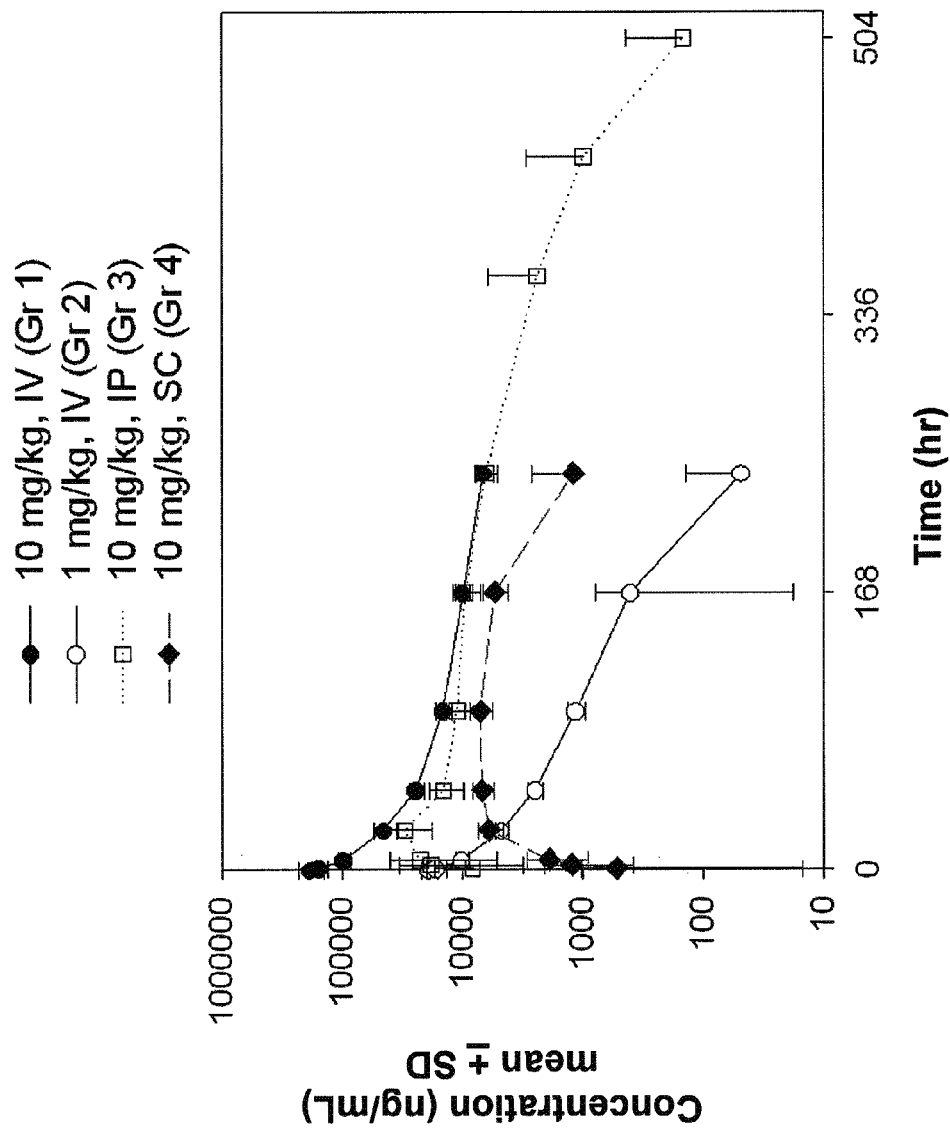
FIG. 49 depicts means serum concentrations (Y-axis; ng/ml) of AbS in S-D rats after a single i.v., i.p., or s.c. dose.

At 168-504 hr after a single i.v., s.c., or i.p. administration to rats, there was a sharp decline in AbS levels in all animals (FIG. 49). In the i.v. and s.c. groups, AbS levels were below LOQ for the assay (45.0 ng/mL) at 360 hr through the end of the study (840 hr). In the i.p. group, there was no detectable AbS starting at 576 hr through the end of the study. Using the paramagnetic bead assay described in Examples 10.4 and 11, anti-AbS antibodies were detected in all animals for all dose groups as early as 360 hr post-dose (the first sampling timepoint taken for anti-AbS antibody evaluation) and persisted through the end of the study (840 hr). Log titers for the anti-AbS response reached 4.01 to >4.74 units by the end of the study for all samples tested. Thus, the sharp decline in AbS was likely related to the formation of anti-AbS antibodies.

After a single 1 or 10 mg/kg i.v. dose of AbS in rats, the average exposures ($AUC_{0-\infty}$) were 470±45 or 6361±845 μg·hr/mL, respectively (Table 22). The average steady-state volume of distribution ($Vd_{ss}$) after a single 1 or 10 mg/kg i.v. dose of AbS was low (101±24 or 191±33 mL/kg, respectively), suggesting that AbS was mainly distributed throughout the vascular space and into limited extracellular fluids after i.v. administration. The average clearance (CL) of AbS was 2.14±0.21 and 1.60±0.21 mL/hr/kg for the 1 mg/kg and 10 mg/kg i.v. doses, respectively. The average elimination half-life ($t_{1/2}$) was 40±10 and 113±24 hr for the 1 mg/kg and 10 mg/kg i.v. doses, respectively. AbS PK parameters were not dose-proportional in the 1-10 mg/kg dose range after i.v. administration to rats, as the average dose-normalized exposures ($AUC_{0-\infty}$/dose), CL, and $t_{1/2}$ were significantly different (p<0.01, unpaired t-test) between the 1 and 10 mg/kg dose groups.

After a single 10 mg/kg i.p. dose of AbS to rats, the average serum $AUC_{0-\infty}$ was 3929±979 μg·hr/mL and the average estimated bioavailability (BA) was 62±15% (with the $AUC_{0-\infty}$ data from the 10 mg/kg, i.v. group used for the BA calculation) (Table 22). The average serum $C_{max}$ was 31±14 μg/mL and was reached at $T_{max}$ of 20±9 hr. After a 10 mg/kg i.p. dose to rats, there was significant interanimal variability in the apparent terminal $t_{1/2}$ with the average value of 78±70 hr.

After a single 10 mg/kg s.c. dose of AbS to rats, the average serum $AUC_{0-\infty}$ was 1595±456 μg·hr/mL and the average estimated BA was relatively low, 25±7% (with the $AUC_{0-\infty}$ data from the 10 mg/kg i.v. group used for the BA calculation) (Table 22). The average serum $C_{max}$ was 8±1 μg/mL and was reached at $T_{max}$ of 77±26 hr. After 10 mg/kg s.c. dose to rats, there was also significant interanimal variability in the apparent terminal $t_{1/2}$ with the average value of 88±78 hr.

TABLE 22

Mean (±SD) Pharmacokinetic Parameters of AbS in S-D Rats After a Single i.v., i.p., or s.c. Dosage

| Group | N | Route, Dose (mg/kg) | $C_{5\,min\,or}$ $C_{max}{}^a$ (μg/mL) | $T_{max}$ (hr) | $AUC_{0-\infty}$ (μg · hr/mL) | $AUC_{0-\infty}$/Dose (μg · hr/mL)/(mg/kg) | CL (mL/hr/kg) | $t_{1/2}$ (hr) | $Vd_{ss}$ (mL/kg) | $BA^b$ (%) |
|---|---|---|---|---|---|---|---|---|---|---|
| 1 | 6 | IV, 10 | 191 ± 38 | NA | 6361 ± 845 | 636 ± 85 | 1.60 ± 0.21 | 113 ± 24 | 191 ± 33 | NA |
| 2 | $6^e$ | IV, 1 | 19 ± 3 | NA | 470 ± 45 | 470 ± 45$^e$ | 2.14 ± 0.2$^e$ | 40 ± 10$^e$ | 101 ± 24 | NA |
| 3 | 4 | IP, 10 | 31 ± 14 | 20 ± 9 | 3929 ± 979 | 393 ± 98 | NA | 78 ± 70 | NA | 62 ± 15 |
| 4 | $4^c$ | SC, 10 | 8 ± 1 | 77 ± 26 | 1595 ± 456 | 160 ± 46 | NA | 88 ± 78 | NA | 25 ± 7 |

NA = Not applicable.
Note:
PK parameters were calculated for each individual animal.
$^a$$C_{5\,min}$ concentration at the first sampling time point after i.v. administration is shown for Groups 1 and 2. $C_{max}$ is shown for Groups 3 and 4.
$^b$BA, bioavailability after i.p. or s.c. administration, was calculated using AUC data for Group 1 (10 mg/kg, IV).
$^c$Statistically significant difference from Group 1 (p < 0.01).

The summary of the onset anti-AbS antibody response in all animals, including S-D rats, is summarized in Table 23.

TABLE 23

Onset of Anti-AbS Antibody Response Following a Single Dose of AbS to Mice, Rats, and Monkeys

| Species, strain | Dose (mg/kg) Route | Onset (hr)$^a$ | % positive at onset |
|---|---|---|---|
| Mouse, DBA | 8, ip | 672 | 37% |
| Mouse, MRL-fas$^{lpr}$ | 10, ip | 336 | 100% |
| | 2.5 ip | 312 | 100% |
| Mouse, CD-1 | 10, iv | 576 | 75% |
| Rat, Sprague-Dawley | 10, iv | 360 | 100% |
| Monkey, Cynomolgus | 10, iv | 504 | 100% |
| | 10, sc | 504 | 100% |

Example 11

Pharmacokinetics and Biodistribution of $^{125}$I-AbS in Wild-Type Control (C57BL/6), IL-21R Knockout, and MRL-Fas$^{lpr}$ Mice

Example 11.1

$^{125}$I Labeling

Iodination was performed using the IODO-BEADS method (Pierce, Rockford, Ill.) according to the manufacturer's instructions, and purified by filtration. Briefly, ~100-200 µg of test article were incubated for 25 min with 1-2 mCi of $^{125}$I (PerkinElmer), three IODO-BEADS, and ~100-200 µl of PBS. The reaction mixture was separated from the IODO-BEADS and transferred to a Centricon filtration device (10 kD cut-off, Millipore). The purification was performed by adding ~5-10 ml of PBS (in aliquots of 1-2 mL) and spinning at 2,000×g until the volume in the upper chamber of the filtration device was down to ~200-500 µl.

The dosing solution was prepared by combining the stock solution of unlabeled test article, the formulation buffer, and the $^{125}$I tracer. The purity of the dosing solution was analyzed using reducing and nonreducing SDS-PAGE. The dosing solution was prepared once, one day prior to dosing of the first cohort of animals.

Example 11.2

Determination of Radioactive Equivalent Concentrations in Serum

Total radioactivity (in counts per min (cpm)) in 50-100 µl of serum samples (in duplicate) was determined by gamma-counting (1480 WIZARD™, Wallac Inc., Gaithersburg, Md.). An equal volume of 20% TCA (trichloroacetic acid) was added to each aliquot, and samples were spun at ~12,000 rpm for 10 min. TCA-soluble radioactivity in the supernatant (with the volume equal to the sample volume used for total radioactivity count) was determined by gamma-counting. TCA-precipitable radioactivity in a given sample [total cpm−2×TCA−soluble cpm], the specific activity of the dosing solution (cpm/ng), as well as the dates of the sample ($t_S$ (day)) and the dosing solution ($t_D$ (day)) measurements, were used to calculate the radioactive equivalent concentration (ng eq/ml) in a given sample using the formula: [average TCA−precipitable cpm/EXP(−0.693/60.2×($t_S$−$t_D$)]/[specific activity× sample volume].

Example 11.3

Determination of the Cumulative Total Count (as Percentage of Dose Count) and Free $^{125}$Iodine Fraction in Urine Total counts were used to calculate urinary excretion (excreted cpm as % dose) for each collection period, using the formula: [100%×urine cpm/EXP(−0.693/60.2×($t_S$−$t_D$))]/ [specific activity×dose]. Cumulative radioactivity in the urine (cumulative excreted cpm as % dose) was defined as the sum of urinary excretions (cpm, as % dose) from time 0 up to an indicated time point.

To determine the fraction of TCA-soluble radioactivity, 50 µl urine aliquots were mixed with 50 µl of normal mouse serum (resulting in 100 µl samples) and analyzed by gamma-counting. A 100 µl aliquot of 20% TCA was added to each 100 µl sample, and the 200 µl samples were spun at ~12,000 rpm for 10 min. TCA-soluble radioactivity in the 100 µl of supernatant was determined by gamma-counting. The fraction of free iodine was obtained using the formula: [2×100%×TCA-soluble cpm in 100 µl of supernatant/total cpm in 50 µl of urine].

Example 11.4

Biodistribution Analysis

Tissue samples were placed into preweighed tubes, weighed to determine tissue weights in grams, and counted for total radioactivity (cpm). The quantitation of radioactive equivalent tissue concentration (ng eq/g) was based on the total radioactivity in tissues and the specific activity of the dosing solution (cpm/ng) after a correction for half-life of $^{125}$I using the formula: [sample cpm/EXP(−0.693/60.2×($t_S$−$t_D$)]/ [specific activity×sample weight].

Tissue to serum concentration ratios (T/S) for a given tissue at a given time point were calculated using the ratio of radioactive equivalent concentration in tissue (µg eq/g) to that in serum (µg eq/ml). Total tissue counts as % dose were calculated using the formula: [100%×sample cpm/EXP(−0.693/ 60.2×($t_S$−$t_D$)]/[specific activity×dose].

Example 11.5

Figure 50A:
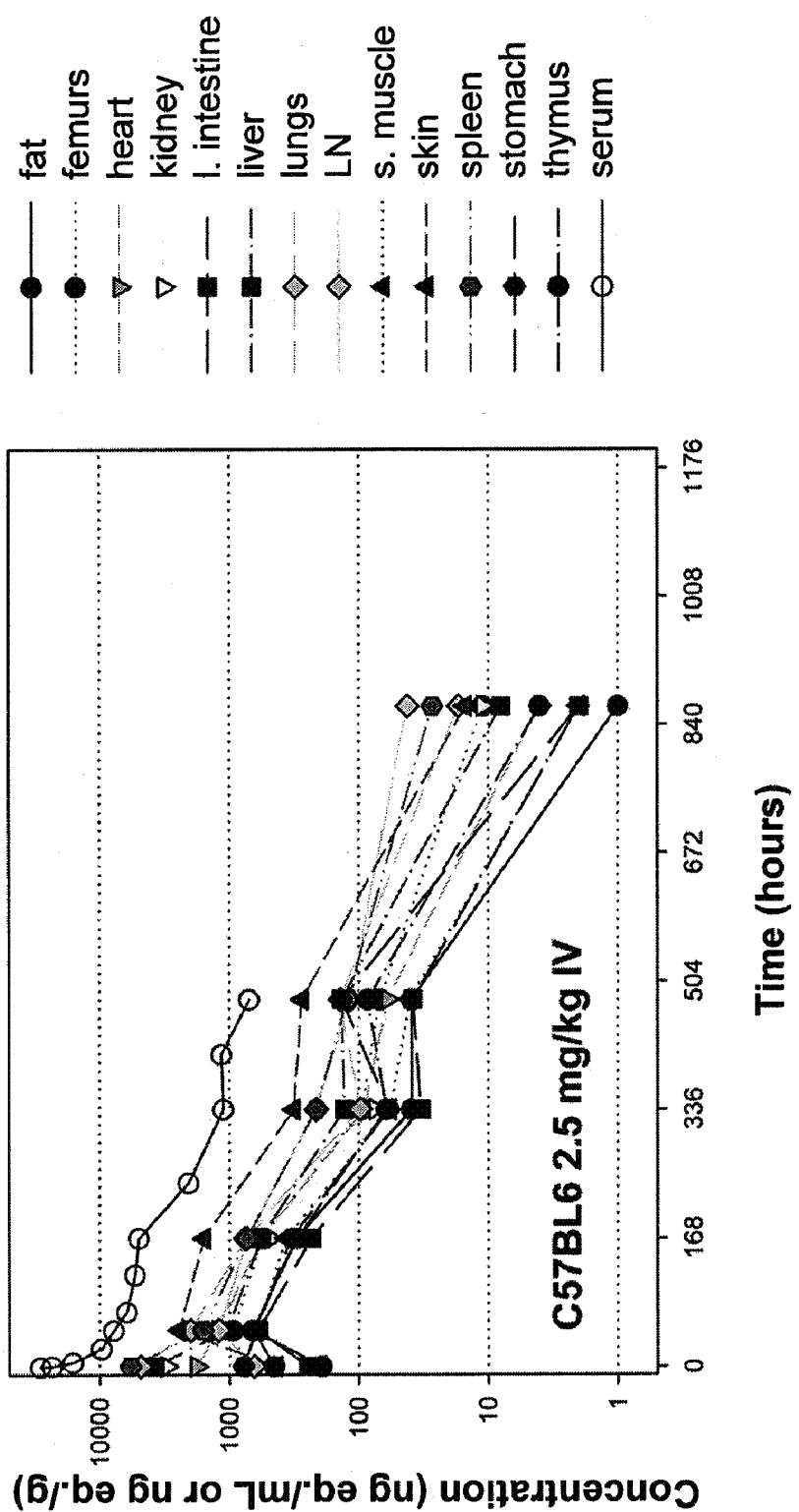
FIG. 50a shows the concentration of $^{125}$I-AbS in tissues in control C57BL/6 mice.
Figure 50B:
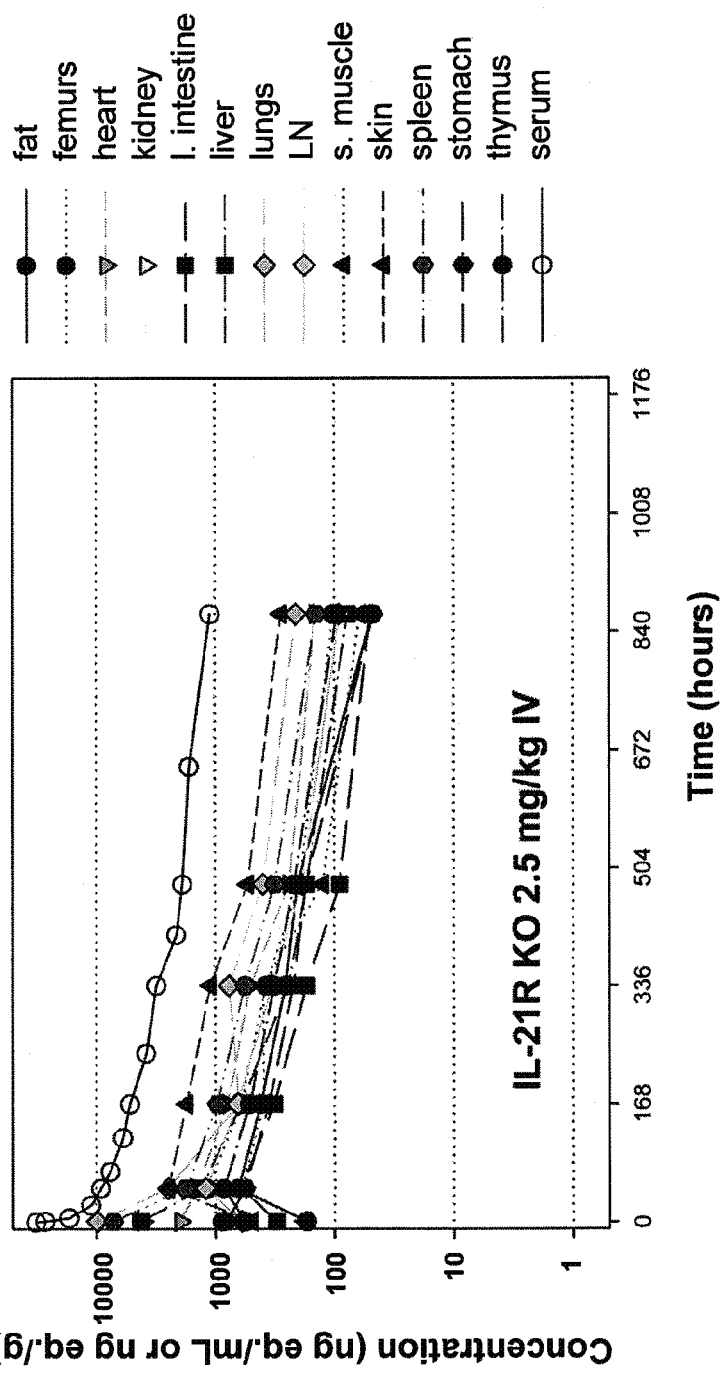
FIG. 50b shows the concentration of $^{125}$I-AbS in IL-21R knockout mice.
Figure 50C:
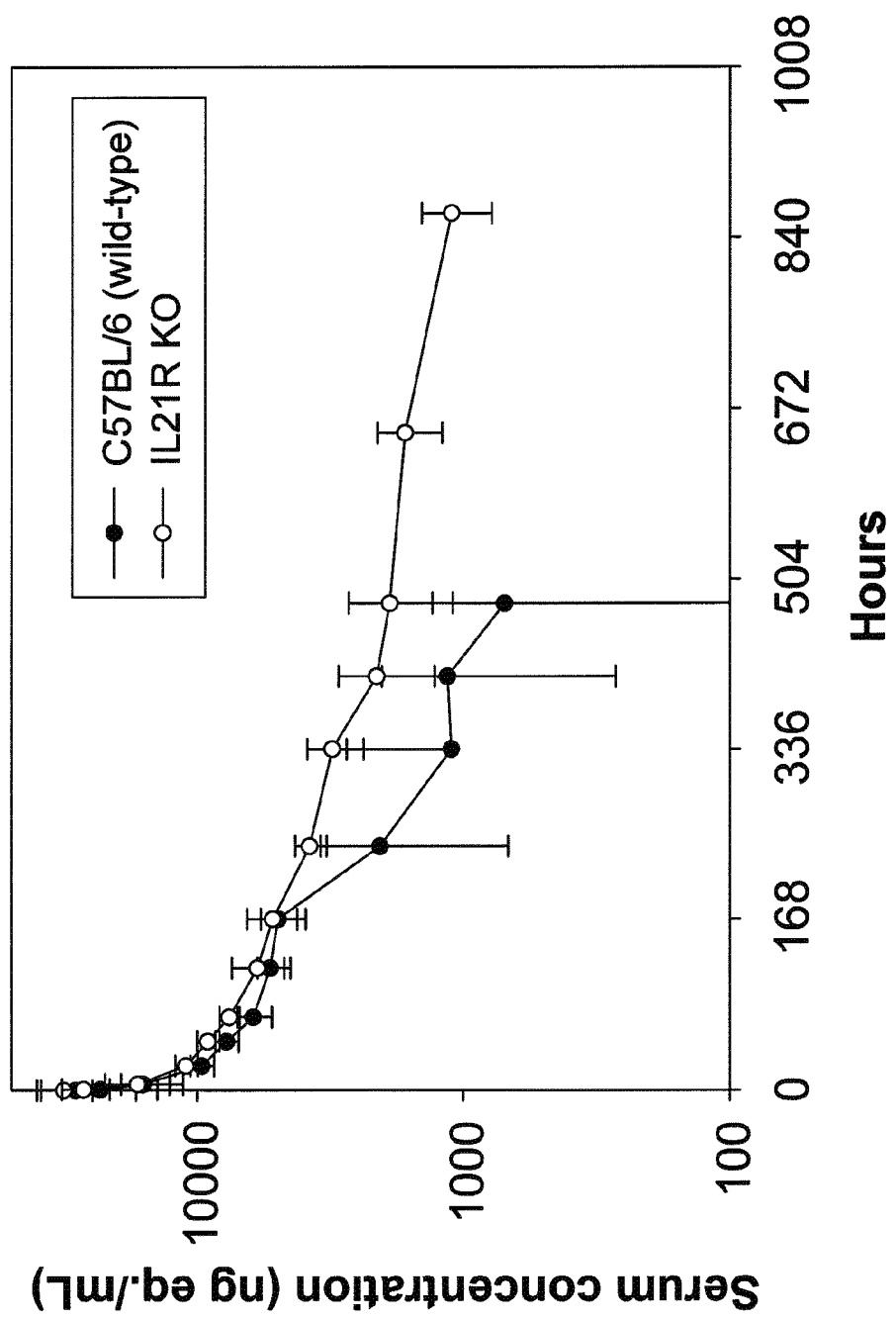
FIG. 50c shows the serum concentration of $^{125}$I-AbS in control C57BL/6 and IL-21R knockout mice.
Figure 50D:
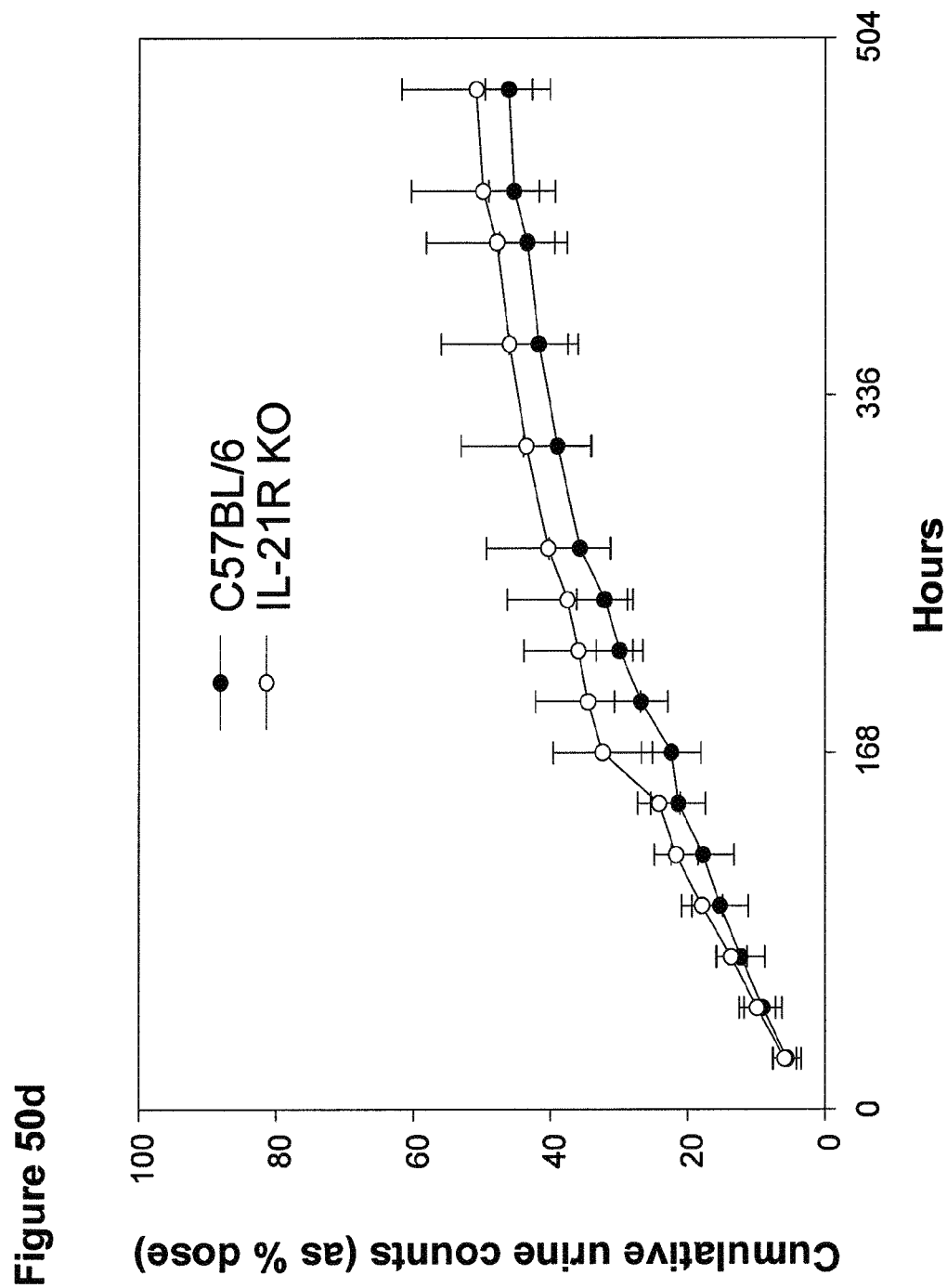
FIG. 50d shows cumulative urine counts of $^{125}$I-AbS in control C57BL/6 and IL-21R knockout mice. Concentrations below LOQ were treated as zero for the calculation of mean and SD. N=9-10 for each serum or tissue data point; N=5-10 for each urine data point.

Pharmacokinetics and Biodistribution in Control and IL-21R Knockout Mice After a 2.5 mg/kg Intravenous Dose In wild-type C57BL/6 (control) mice, there was a decline in mean AbS serum levels relative to those in IL-21R knockout mice, starting at 10-14 days after a single 2.5 mg/kg i.v. dose of $^{125}$I-AbS (FIG. 50c). At day 14 (336 hr), 60% of controls (n=10) and 0% of IL-21R knockout mice (n=10) had undetectable or very low levels of AbS. After day 20 (480 hr), there were no detectable AbS levels in the serum of all control mice. In IL-21R knockout mice, AbS was detected in serum as late as day 36 (864 hr) post-dose, the last sampling time point. The differences in concentration-time profile of $^{125}$I-AbS in control vs. IL-21R knockout appears to be due to possible differences in anti-AbS responses in these two mouse strains. At the five-week time point, about 55% (five out of nine) wild-type serum samples and none of IL-21R knock out serum samples tested positive in the anti-AbS antibody assay.

In control mice, the total body clearance (CL) was ~1.3 ml/hr/kg, and the elimination half-life ($t_{1/2}$) was 120 hr (~5.0 days). In IL-21R knockout mice, CL was ~0.7 ml/hr/kg, and $t_{1/2}$ was 256 hr (10.7 days) (Table 14). Accordingly, after a 2.5 mg/kg i.v. dose, IL-21R knockout mice had a higher serum exposure ($AUC_{0-\infty}$) as compared to controls (Table 14).

In general, for both controls and IL-21R knockout mice, the highest concentrations of $^{125}$I-AbS were found in serum as compared to other tissues examined (FIGS. 50a and 50b; Tables 24 and 25). However, at the last tissue sampling time point (864 hr), detectable $^{125}$I-AbS levels were found in tissues, but not in serum, of control mice.

In accordance with differences in serum levels of AbS between control and IL-21R knockout mice, radioactive equivalent concentrations of AbS in tissues were lower in controls as compared to IL-21R knockouts, starting at ~2 weeks post-dose (FIG. 50). Likewise, tissue elimination half-lives ($t_{1/2}$) were shorter in control mice (~90-165 hr) as compared to those in tissues of IL-21R knockout mice (~230-270 hr). Accordingly, the tissue exposures ($AUC_{0-\infty}$) were lower in control mice compared to IL-21R knockout mice (Table 26). Thus, after a 2.5 mg/kg i.v. dose of $^{125}$I to IL-21R knockout mice, exposure in both serum and tissues was higher as compared to controls.

TABLE 24

Mean (±SD) Tissue to Serum (T/S) Radioactive Equivalent Concentration Ratio After a Single Intravenous Dose of 2.5 mg/kg of $^{125}$I-AbS to C57BL/6 Mice

|  | 1 hr | 48 hr | 168 hr | 336 hr |
| --- | --- | --- | --- | --- |
| fat | 0.0099 ± 0.0062 | 0.0849 ± 0.0289 | 0.0619 ± 0.0144 | 0.2316 ± 0.2619 |
| femurs | 0.0360 ± 0.0126 | 0.1203 ± 0.0124 | 0.1108 ± 0.0140 | 0.6979 ± 1.0550 |
| heart | 0.0776 ± 0.0109 | 0.1588 ± 0.0143 | 0.1122 ± 0.0123 | 0.3837 ± 0.4993 |
| kidney | 0.1293 ± 0.0311 | 0.2497 ± 0.2105 | 0.0957 ± 0.0215 | 0.6350 ± 0.8669 |
| large intestine | 0.0122 ± 0.0056 | 0.0760 ± 0.0127 | 0.0466 ± 0.0078 | 0.2102 ± 0.2544 |
| liver | 0.1600 ± 0.0770 | 0.1342 ± 0.0679 | 0.1206 ± 0.0717 | 1.1834 ± 1.4455 |
| lungs | 0.1968 ± 0.0863 | 0.2522 ± 0.0714 | 0.1462 ± 0.0776 | 1.3408 ± 2.4852 |
| lymph node | 0.0314 ± 0.0163 | 0.1554 ± 0.0333 | 0.1504 ± 0.0542 | 3.7491 ± 5.7164 |
| skeletal muscle | 0.0099 ± 0.0048 | 0.0789 ± 0.0108 | 0.0724 ± 0.0064 | 0.2461 ± 0.3171 |
| skin | 0.0243 ± 0.0195 | 0.3125 ± 0.0327 | 0.3145 ± 0.1155 | 1.4147 ± 1.6123 |
| spleen | 0.2450 ± 0.0289 | 0.2043 ± 0.0403 | 0.1470 ± 0.0232 | 2.2414 ± 3.4892 |
| stomach | 0.0471 ± 0.0530 | 0.0791 ± 0.0249 | 0.0674 ± 0.014 | 0.4292 ± 0.5801 |
| thymus | 0.0215 ± 0.0117 | 0.0842 ± 0.0174 | 0.0590 ± 0.0125 | 0.2794 ± 0.3901 |

Individual values below the limit of quantitation (LOQ, defined as 3X the background cpm) were treated as "0" for calculations of the mean and the standard deviation (SD).
T/S were not calculated for time points after 336 hr (480 and 864 hr), as serum concentrations were below the limit of detection

TABLE 25

Mean (±SD) Tissue to Serum (T/S) Radioactive Equivalent Concentration Ratio After a Single Intravenous Dose of 2.5 mg/kg of $^{125}$I-AbS to IL-21R Knockout Mice

|  | 1 hr | 48 hr | 168 hr | 336 hr |
| --- | --- | --- | --- | --- |
| fat | 0.0063 ± 0.0022 | 0.0718 ± 0.0353 | 0.0856 ± 0.0475 | 0.0885 ± 0.0381 |
| femurs | 0.0327 ± 0.0069 | 0.1283 ± 0.0555 | 0.1169 ± 0.0104 | 0.1238 ± 0.0217 |
| heart | 0.0733 ± 0.0152 | 0.1569 ± 0.0172 | 0.1526 ± 0.0213 | 0.1681 ± 0.0315 |
| kidney | 0.1491 ± 0.0417 | 0.1570 ± 0.0218 | 0.1588 ± 0.0347 | 0.1687 ± 0.0417 |
| large intestine | 0.0112 ± 0.0034 | 0.0666 ± 0.0133 | 0.0612 ± 0.0111 | 0.0568 ± 0.0122 |
| liver | 0.1550 ± 0.0466 | 0.1434 ± 0.0706 | 0.1190 ± 0.0549 | 0.0784 ± 0.0282 |
| lungs | 0.3495 ± 0.1671 | 0.2722 ± 0.0529 | 0.1178 ± 0.0707 | 0.2510 ± 0.1016 |
| lymph node | 0.0224 ± 0.0096 | 0.1337 ± 0.0369 | 0.1215 ± 0.0345 | 0.1118 ± 0.0384 |
| skeletal muscle | 0.0068 ± 0.0016 | 0.0663 ± 0.0077 | 0.0761 ± 0.0115 | 0.1227 ± 0.1479 |
| skin | 0.0185 ± 0.0029 | 0.2716 ± 0.0315 | 0.3244 ± 0.0607 | 0.3593 ± 0.1247 |
| spleen | 0.2682 ± 0.0425 | 0.1943 ± 0.0304 | 0.1809 ± 0.0322 | 0.1846 ± 0.0483 |
| stomach | 0.0318 ± 0.0151 | 0.0617 ± 0.0165 | 0.0689 ± 0.0237 | 0.0724 ± 0.0174 |
| thymus | 0.0206 ± 0.0099 | 0.0929 ± 0.0178 | 0.0979 ± 0.0127 | 0.1049 ± 0.0233 |

Individual values below the limit of quantitation (LOQ, defined as 3X the background cpm) were treated as "0" for calculations of the mean and the standard deviation (SD).
T/S were not calculated for time points after 336 hr (480 and 864 hr), as serum concentrations were below the limit of detection.

TABLE 26

Exposure of $^{125}$I-AbS in Tissue of C57BL/6 and IL-21R Knockout Mice Following a Single 2.5 mg/kg Intravenous Dose

|  | C57BL/6 | | | IL-21R KO | | |
| --- | --- | --- | --- | --- | --- | --- |
|  | Cmax$^a$ µg eq/ml | Tmax hr | AUC$_{0-\infty}$ hr * µg eq/ml | Cmax$^a$ µg eq/ml | Tmax hr | AUC$_{0-\infty}$ hr * µg eq/ml |
| fat | 0.66 | 48 | 120 | 0.64 | 48 | 236 |
| femurs | 0.93 | 48 | 213 | 1.17 | 48 | 370 |
| heart | 1.79 | 1 | 258 | 1.97 | 1 | 501 |
| kidnely | 3.06 | 1 | 352 | 4.07 | 1 | 573 |
| large intestine | 0.59 | 48 | 105 | 0.61 | 48 | 181 |
| liver | 3.77 | 1 | 317 | 4.24 | 1 | 419 |
| lymph node | 1.21 | 48 | 303 | 9.88 | 1 | 882 |
| lung | 4.84 | 1 | 447 | 1.21 | 48 | 357 |
| skeletal muscle | 0.61 | 48 | 128 | 0.60 | 48 | 238 |
| skin | 2.44 | 48 | 567 | 2.48 | 48 | 939 |
| spleen | 5.77 | 1 | 454 | 7.20 | 1 | 706 |
| stomach | 0.78 | 1 | 163 | 0.81 | 1 | 222 |
| thymus | 0.65 | 48 | 141 | 0.85 | 48 | 320 |
| serum | 29 | NA | 1927 | 32 | NA | 3415 |

$^a$C$_{5\ min}$ concentration at the first sampling time point is shown for serum. Tissue sampling time points were: 1, 48, 168, 336, 480, and 864 hr.

Example 11.6

Figure 51A:
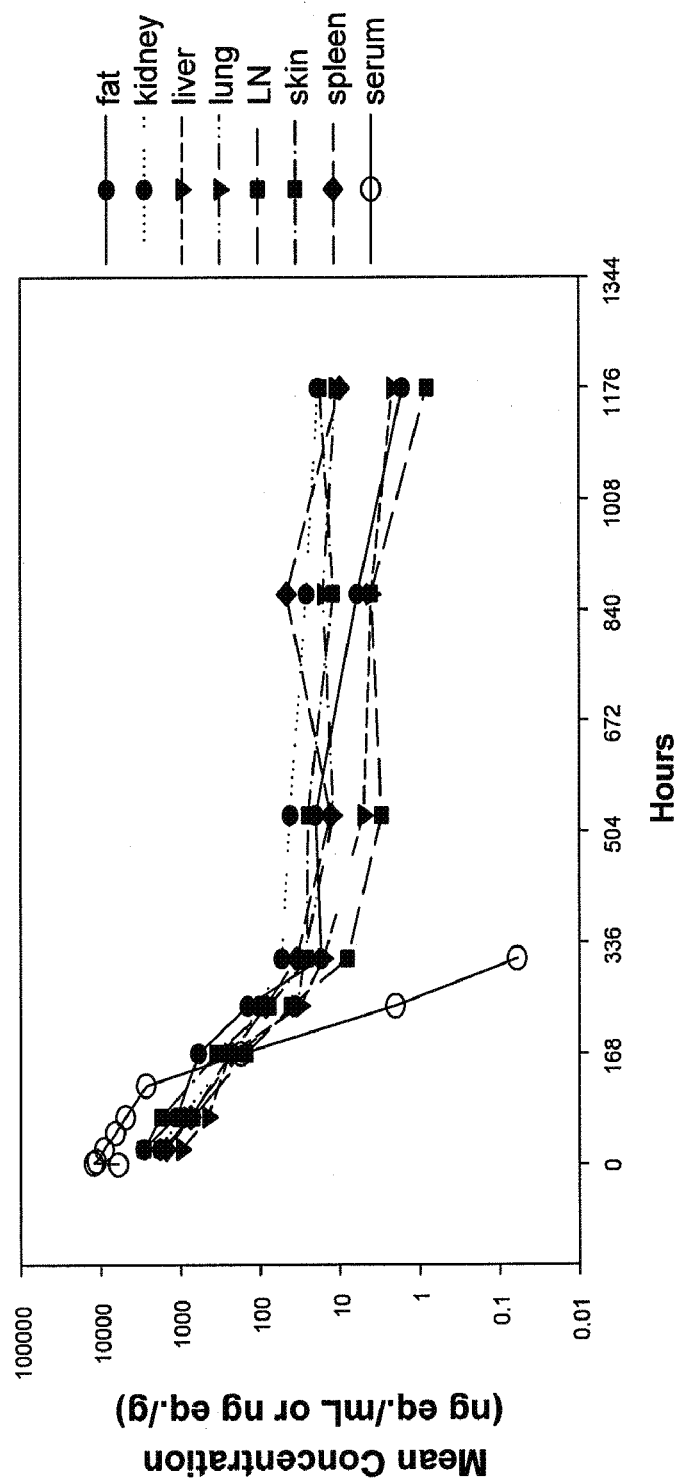
FIG. 51a shows the concentration of $^{125}$I-AbS in tissues in MRL-Fas$^{lpr}$ mice.
Figure 51B:
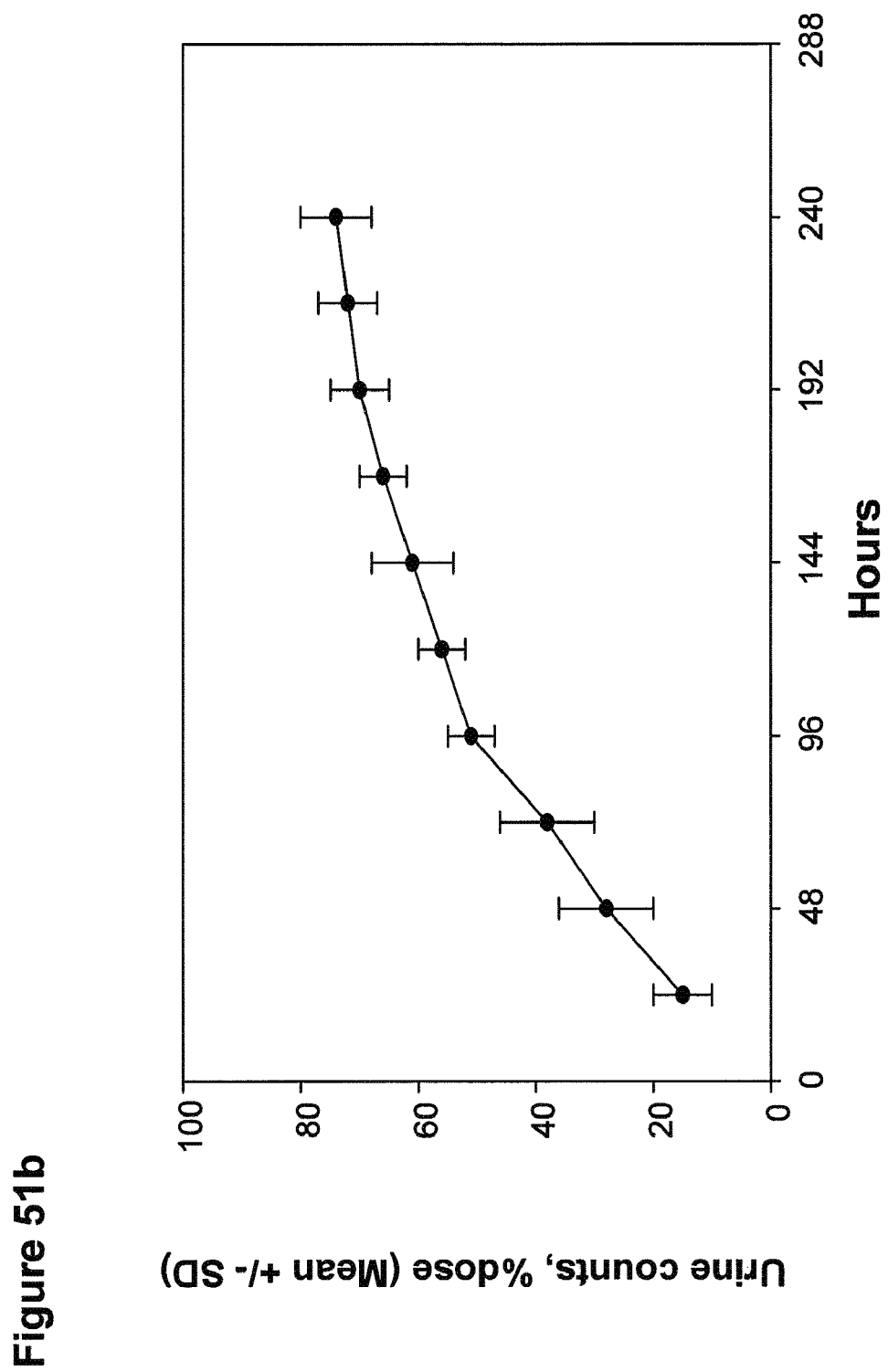
FIG. 51b shows urine counts of $^{125}$I-AbS in MRL-Fas$^{lpr}$ mice.
Figure 52:
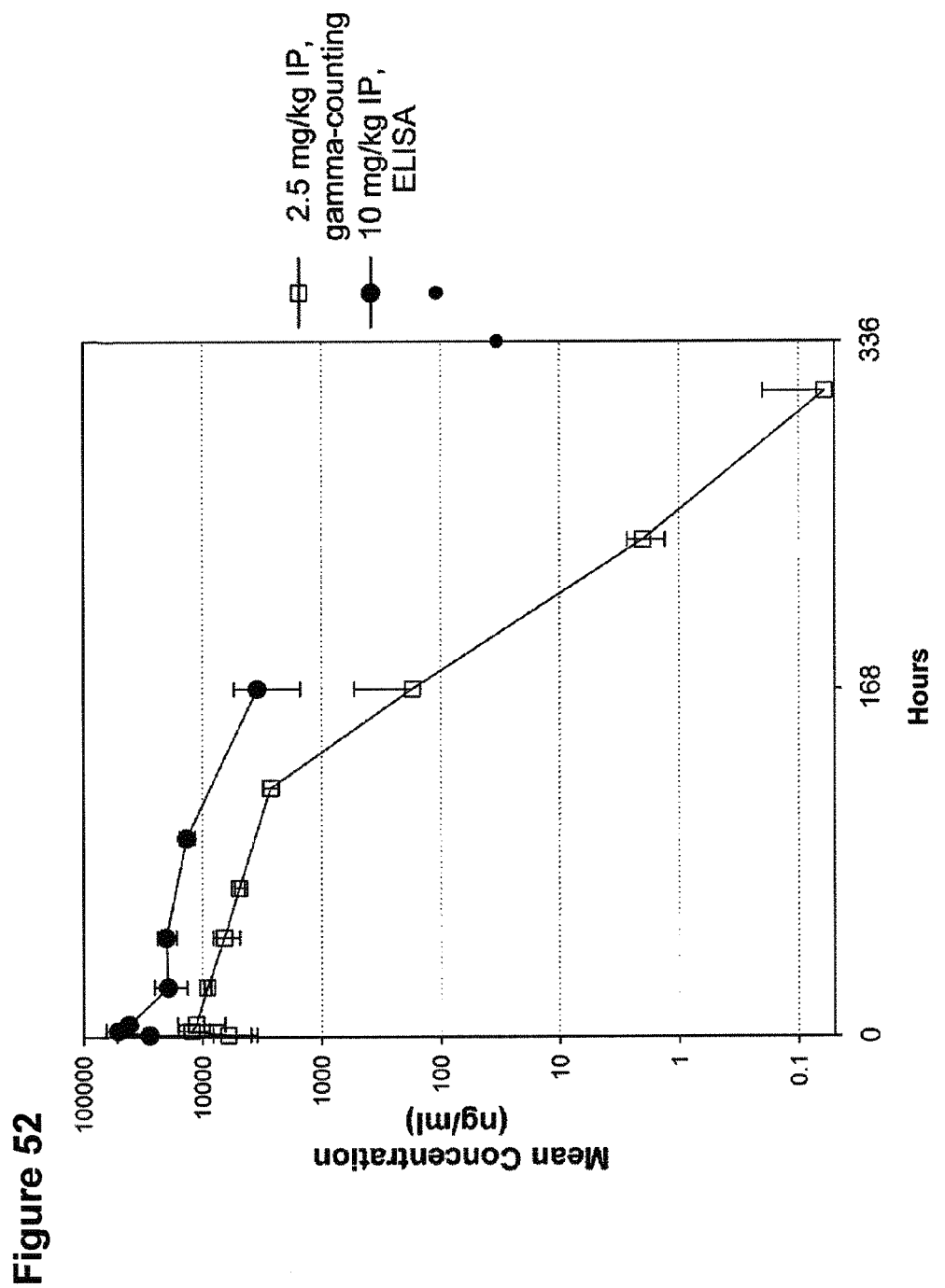
FIG. 52 depicts the serum concentration of $^{125}$I-AbS in MRL-Fas$^{lpr}$ mice after single 2.5 and 10 mg/kg i.p doses. Concentrations below LOQ were treated as zero for the calculation of mean and SD. N=4-8 for each data point.

Pharmacokinetics and Biodistribution in MRL-Fas$^{lpr}$ Mice After a 2.5 mg/kg Intraperitoneal Dose Following a single i.p. dose of 2.5 mg/kg of $^{125}$I, to female MRL-Fas$^{lpr}$ mice (~10-12 weeks old), the serum concentration-time profile was biphasic, showing a relatively slower decline in AbS levels during the first week post-dose ($t_{1/2}$~54 hr) and a faster decline after 5 days post-dose ($t_{1/2}$~12 hr), suggesting the formation of anti-AbS antibodies (FIGS. 51a and 52). In fact, 4 of 4 mice at the 312 hr time point, and 4 of 4 mice at the 408 hr time point, tested positive for anti-product antibodies (with relative media titers of ~4.01 and ~4.43 log titer units, respectively). After a 2.5 mg/kg i.p. dose of $^{125}$I, the maximum serum concentration (C$_{max}$) and exposure (AUC$_{0-\infty}$) of AbS were 12 µg eq/ml and 823 µg eq·hr/ml, respectively. Thus, after a single i.p. dose to MRL-Fas$^{lpr}$ mice, PK were approximately linear in the 2.5-10 mg/kg dose range (FIG. 52; Table 14) (see also Example 10.4). Urine counts of $^{125}$I-AbS in MRL-Fas$^{lpr}$ mice were elevated as of the 10 day time point (FIG. 51b).

During the first week following a single 2.5 mg/kg i.p. dose (likely prior to formation of anti-product antibodies), the highest concentrations of AbS were found in serum for all tissues examined. After the first week, serum concentration declined more rapidly as compared to the decline of AbS in tissue, so that T/S concentration ratios were significantly higher than 1 (Table 27), and AUC$_{0-\infty}$ in tissues was ~90-300 µg eq·hr/ml (Table 28). In tissue, the apparent elimination half-life (calculated based on the 24-312 hr data set) was ~40-55 hr. Relatively low (but still detectable) levels of radioactivity persisted in tissues until the end of the study (seven weeks post-dose) (FIG. 51a).

TABLE 27

Mean (±SD) Tissue to Serum (T/S) Radioactive Equivalent Concentration Ratio After a Single IP Dose of 2.5 mg/kg of $^{125}$I-AbS to MRL-Fas$^{lpr}$ Mice

|  | 24 hr | 72 hr | 168 hr | 240 hr |
| --- | --- | --- | --- | --- |
| fat | 0.321 ± 0.073 | 0.233 ± 0.070 | 41.125 ± 69.735 | 71.500 ± 131.496 |
| kidney | 0.195 ± 0.026 | 0.202 ± 0.036 | 9.831 ± 6.787 | 56.205 ± 25.079 |
| liver | 0.104 ± 0.028 | 0.091 ± 0.032 | 8.067 ± 5.587 | 16.820 ± 6.892 |
| lungs | 0.177 ± 0.074 | 0.159 ± 0.070 | 7.621 ± 6.512 | 20.127 ± 12.783 |
| lymph node | 0.197 ± 0.055 | 0.141 ± 0.020 | 5.490 ± 3.707 | 22.497 ± 16.812 |
| skin | 0.318 ± 0.023 | 0.305 ± 0.056 | 12.237 ± 8.734 | 50.869 ± 59.413 |
| spleen | 0.166 ± 0.022 | 0.105 ± 0.020 | 9.648 ± 6.834 | 50.418 ± 33.424 |

Individual values below the limit of quantitation (LOQ, defined as 3X the background cpm) were treated as "0" for calculations of the mean and the standard deviation (SD).
T/S were not calculated for time points after 240 hr, as serum concentrations were below the limit of detection in most of the mice.

TABLE 28

Exposure of $^{125}$I-AbS in Tissue of MRL-Fas$^{lpr}$ Mice Following a Single 2.5 mg/kg IP Dose

|  | Cmax µg eq/ml | Tmax hr | AUC$_{0-\infty}$ hr * µg eq/ml |
| --- | --- | --- | --- |
| fat | 2.9 | 24 | 255 |
| kidney | 1.8 | 24 | 197 |
| liver | 1.0 | 24 | 95 |
| lymph node | 1.8 | 24 | 133 |
| lung | 1.6 | 24 | 150 |
| skin | 2.9 | 24 | 285 |
| spleen | 1.5 | 24 | 161 |
| serum | 12 | 3 | 823 |

Tissue sampling time points were: 24, 72, 168, 240, 312, 528, 864, and 1176 hr.

Example 12

Inhibitory Properties of Anti-IL-21R Antibodies in Human Blood

Example 12.1

Agonistic Response of Human Whole Blood to IL-21 is Neutralized by Ex Vivo Treatment of Anti-IL-21R Antibody Human whole blood was drawn by the Human Blood Donor Program in Cambridge, Mass. All human blood samples were collected in BD Vacutainer™ CPT™ cell preparation tubes. Collection tubes contained sodium heparin. Samples were maintained at ambient temperature and processed immediately. Blood was divided into 1 to 2 mL aliquots in cryovials, treated with IL-21, AbS, or control proteins. When samples were treated with both antibody and IL-21, the antibody was added immediately prior to IL-21. Samples were then incubated at 37° C. in a Form a Scientific Reach-In Incubator Model #3956 for four hr while mixed continuously at 15 RPM using the Appropriate Technical Resources Inc (ATR) Rotamix (Cat. # RKVS) rotating mixer (serial #0995-52 and #0695-36), or using the Labquake® Tube Shaker/Rotator (Cat. #400110) during the incubation. Aliquots (0.5 mL) were removed using a Gilson P1000 pipette with ART 1000E tips (Cat. #72830-042) and added to 2.0 mL microtubes (Axygen Scientific, Cat. #10011-744) containing 1.3 mL of RNAlater® supplied with the Human RiboPure™-Blood Kit (Ambion, Austin, Tex.; Cat. # AM1928) and mixed thoroughly by five complete inversions. Samples were stored at ambient temperature overnight and then frozen at −80° C. pending RNA purification.

RNA was isolated using the Human RiboPure™-Blood Protocol (Ambion, Cat. # AM1928). The Human RiboPure™ RNA isolation procedure consists of cell lysis in a guanidinium-based solution and initial purification of the RNA by phenol/chloroform extraction, and final RNA purification by solid-phase extraction on a glass-fiber filter. The residual genomic DNA was removed according to the manufacturer's instructions for DNAse treatment using the DNA-Free™ reagents provided in the kit. For all samples, RNA quantity was determined by absorbance at 260 nm with a NanoDrop 1000 (NanoDrop, Wilmington, Del.). RNA quality was spot-checked using a 2100 Bioanalyzer (Agilent, Palo Alto, Calif.). Samples were stored at −80° C. until cDNA synthesis was performed.

According to the manufacturer's instructions, cDNA was reverse transcribed from total RNA using a High Capacity cDNA Reverse Transcription Kit (ABI, Cat. #4368814) with additional RNase inhibitor at 50 U/sample (ABI, Cat. # N808-0119). cDNA samples were stored at −20° C. until RT-PCR (real-time PCR) was performed. The amount of cDNA loaded on a Taqman® Low Density Array card was determined using the lowest RNA yield obtained within an experiment. cDNA samples were assayed on an ABI PRISM 7900 Sequence detector (Sequence Detector Software v2.2.2, Applied Biosystems) using universal thermal cycling conditions of 50° C. for 2 min, 95° C. for 10 min, then 40 cycles of 95° C. for 15 sec and 60° C. for 1 min.

To check for ex vivo effects of IL-21, experiments were conducted to test whether human whole blood responded to IL-21 with detectable changes in gene expression levels. Whole blood from human donors was incubated in the presence and absence of IL-21, and RNA levels were determined using TLDA cards. Two different TLDAs were used to measure RNA expression levels. The first, Human Immune TLDA (ABI, Catalog #4370573), tested 96 genes, of which 91 were detectable in stimulated human blood. PBMCs stimulated with LPS or PHA from human donor whole blood was used as a positive control. To test the upregulation of IL-21R in response to IL-21 stimulation, results were obtained using a custom designed TLDA that contained the IL-21R gene.

Data for the seven most consistent IL-21-dependent gene expression changes observed in whole blood samples of the four humans tested under the selected assay conditions are shown in Table 29. Significant responses to IL-21 were observed for IL6, IFNγ, CD19, PRF1, IL10, IL2Rα, and GNLY. Interestingly, IL-21 treatment at concentrations of 30 ng/mL, 100 ng/mL and 500 ng/mL produced similar results (Table 29).

TABLE 29

IL-21-dependent gene expression changes in human whole blood samples

| Gene | IL21 (30 ng/mL) Average Fold Change (2 Humans) | IL21 (100 ng/mL) Average Fold Change (4 Humans) | IL21 (500 ng/mL) Average Fold Change (2 Humans) | Composite Average Fold Change | Composite Standard Deviation | Paired T-test (P-Value) |
|---|---|---|---|---|---|---|
| IL6 | 20.17 | 13.24 | 32.14 | 19.70 | 22.51 | 1.35E−01 |
| IFNG | 7.65 | 6.51 | 7.23 | 6.97 | 2.34 | 5.86E−02 |
| CD19 | 2.72 | 2.78 | 2.78 | 2.76 | 0.94 | 6.09E−02 |
| PRF1 | 2.43 | 2.87 | 2.72 | 2.72 | 1.08 | 5.21E−02 |
| IL10 | 3.17 | 2.49 | 2.66 | 2.70 | 1.26 | 3.78E−02 |
| IL2RA | 2.82 | 2.07 | 2.15 | 2.28 | 0.86 | 5.35E−02 |
| GNLY | 2.12 | 2.07 | 2.66 | 2.23 | 0.38 | 1.76E−03 |

Fold change was calculated by dividing RQ of treated group by RQ of control group. Paired T-test values were calculated using the RQ values and pairing control and treated values from each human donor.

Figure 53A:
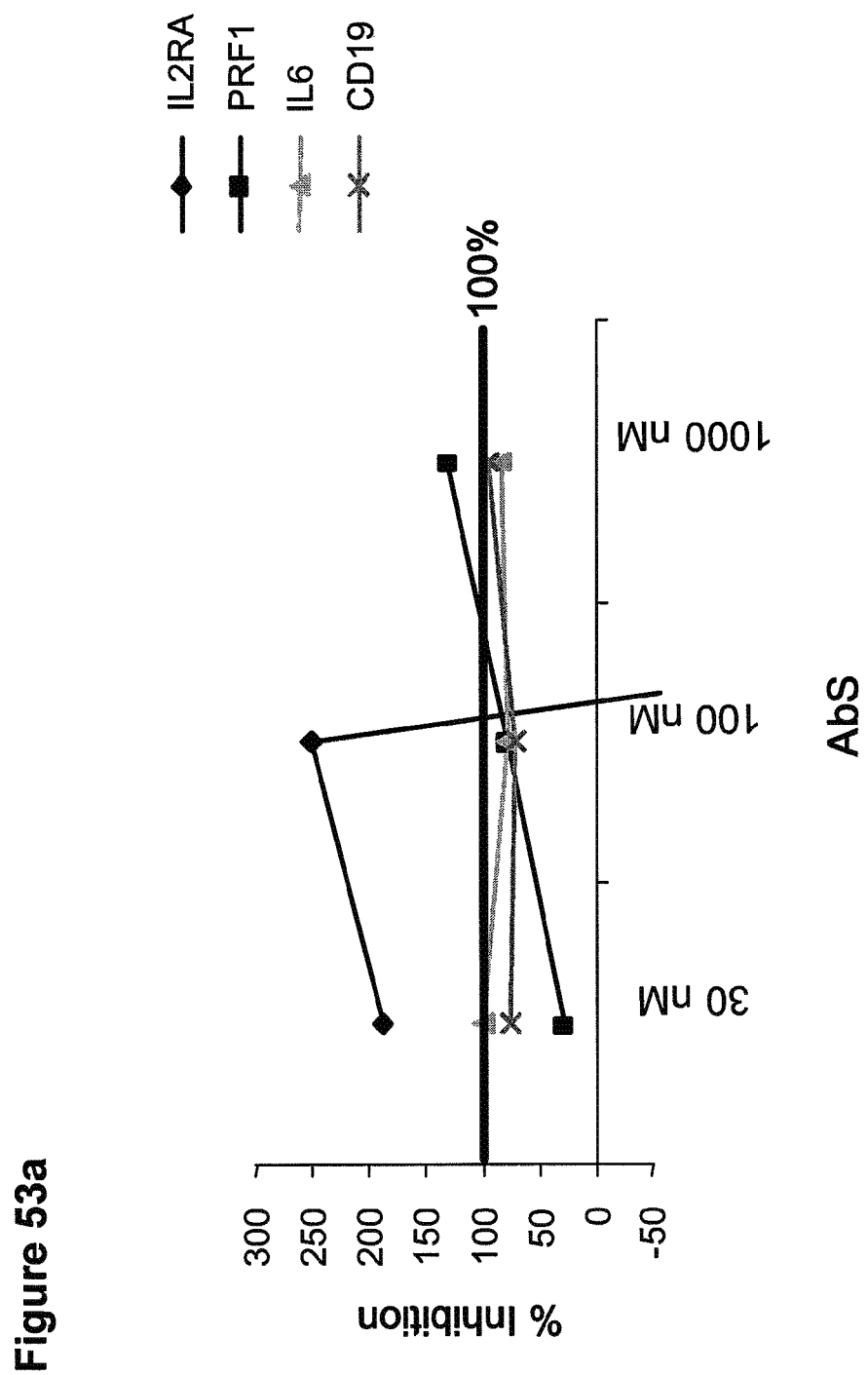
FIG. 53a depicts percent inhibition (Y-axis) of IL-21-induced IL-2Rα (IL2RA), PRF1, IL-6, and CD19 expression upon increasing concentrations of AbS (X-axis) in human whole blood samples, calculated from fold-change.
Figure 53B:
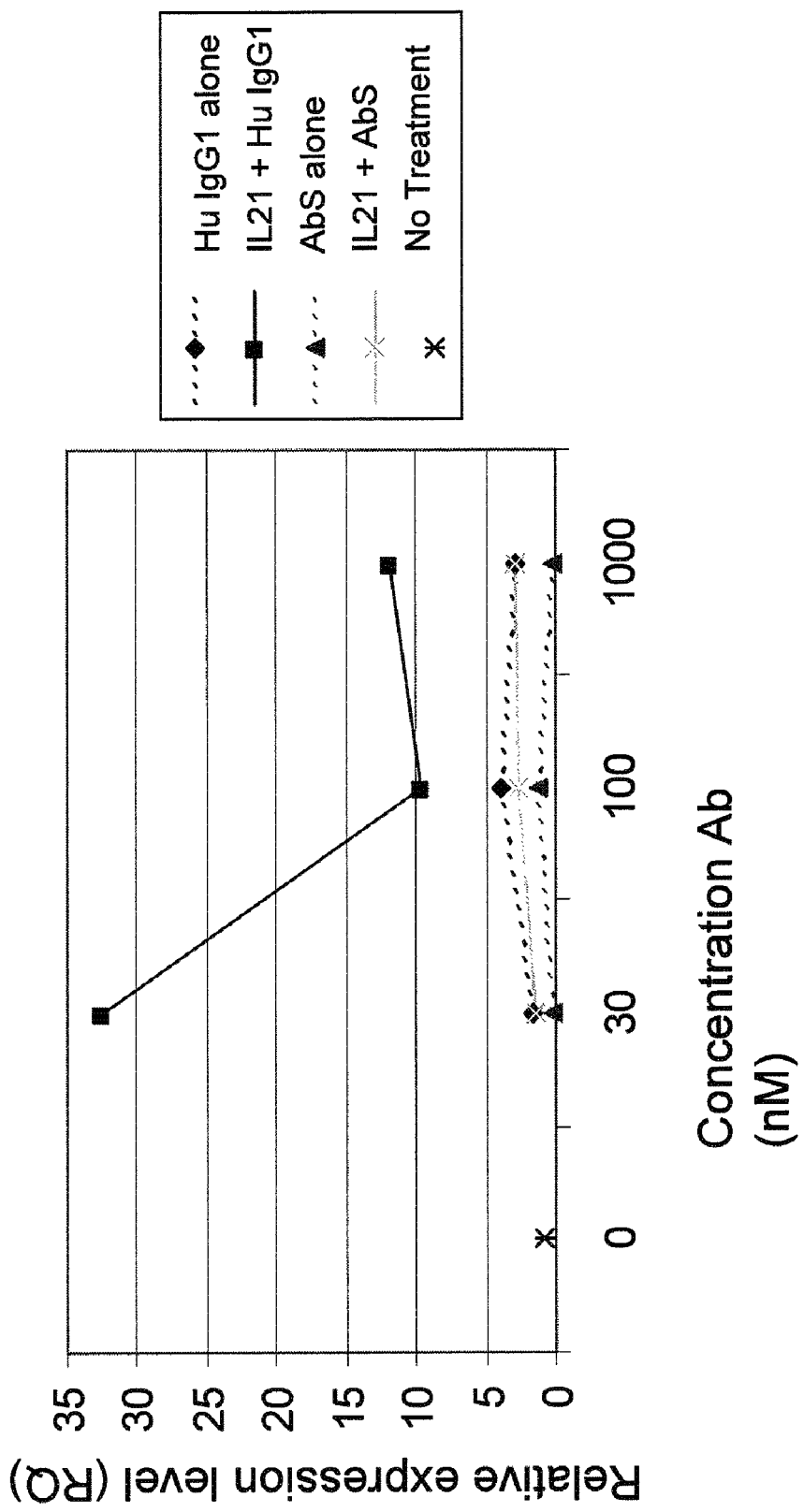
FIG. 53b depicts inhibition of IL-21-induced relative expression level (RQ; Y-axis) of IL-6 in response to increasing AbS concentrations (X-axis; concentration Ab (nM)) in human whole blood samples.

To determine if AbS had the desired blocking activity of IL-21/IL-21R-dependent activation of human cells, the ability of this antibody to block IL-21-dependent activation in whole blood was tested on one of the human donors. FIGS. 53a-b show the effective inhibition (compared to the Hu IgG1 control) of IL-21-dependent activation of IL-21-responsive genes by the antibodies.

These results define methods for measuring the response to IL-21 in human whole blood samples; thus, this assay can be used to detect the inhibition of IL-21-dependent activation by anti-IL-21R antibodies in experimental or clinical settings, because the assay does not require more blood than can be routinely collected and involves minimal ex vivo manipulation.

Example 12.2

An Assay Measuring PD Activity of AbS in Whole Human Blood

A total of five healthy human donors were used in these studies. All human whole blood samples were collected in BD Vacutainer™ CPT™ cell preparation tubes containing sodium heparin (Catalog #362753). Human whole blood was drawn by the Human Blood Donor Program in Cambridge, Mass. Samples were maintained at ambient temperature and, except where otherwise stated, were processed within an hour of collection. When samples were treated with immunoglobulin reagents and IL-21, the immunoglobulin reagent was added prior to addition of IL-21. Samples were incubated at 37° C. in a Form a Scientific Reach-In Incubator Model #3956 for the duration noted while mixed continuously at about 7 RPM using the Appropriate Technical Resources Inc (ATR) Rotamix (Catalog #RKVS) rotating mixer (serial #0995-52 and #0695-36), or using the Labquake® Tube Shaker/Rotator (Catalog #400110) during the incubation. Subsequently, 0.5 mL of each sample was removed and added to 2.0 mL microtubes (Axygen Scientific, Catalog #10011-744,) containing 1.3 mLs of RNAlater® which is provided with the Human RiboPure™-Blood Kit (Ambion, Catalog #AM1928), and mixed thoroughly by five complete inversions. Following procedure described in Example 12.1, samples were processed to isolate and quantify RNA yield, and synthesize cDNA; and 200 ng of cDNA was loaded onto a custom TLDA plate, comprising 24 genes (19 test genes whose RNA expression levels had been observed to change in whole human blood upon stimulation with IL-21, and 5 endogenous control genes), shown in FIG. 54.

For quantification of RNA expression levels, average Real-Time PCR threshold cycle (Ct) values from several endogenous controls (GAPDH, GUSB, ZNF592, and PGK1 in FIG. 54) were used as "normalizers" because the expression of these genes did not change with treatment and the genes yielded the most consistent Ct values across all samples. Average Ct values of experimental controls (no AbS and no IL-21 added) were used as "calibrators." Expression of a gene in a given sample was calculated as Ct of gene–Ct of average of endogenous controls for that sample (ΔCt of sample). The gene expression value (ΔΔCt) was calculated as ΔCt of sample–ΔCt of "calibrator." Relative quantification (RQ) or fold change was calculated as $2^{-\Delta\Delta Ct}$.

Figure 55:
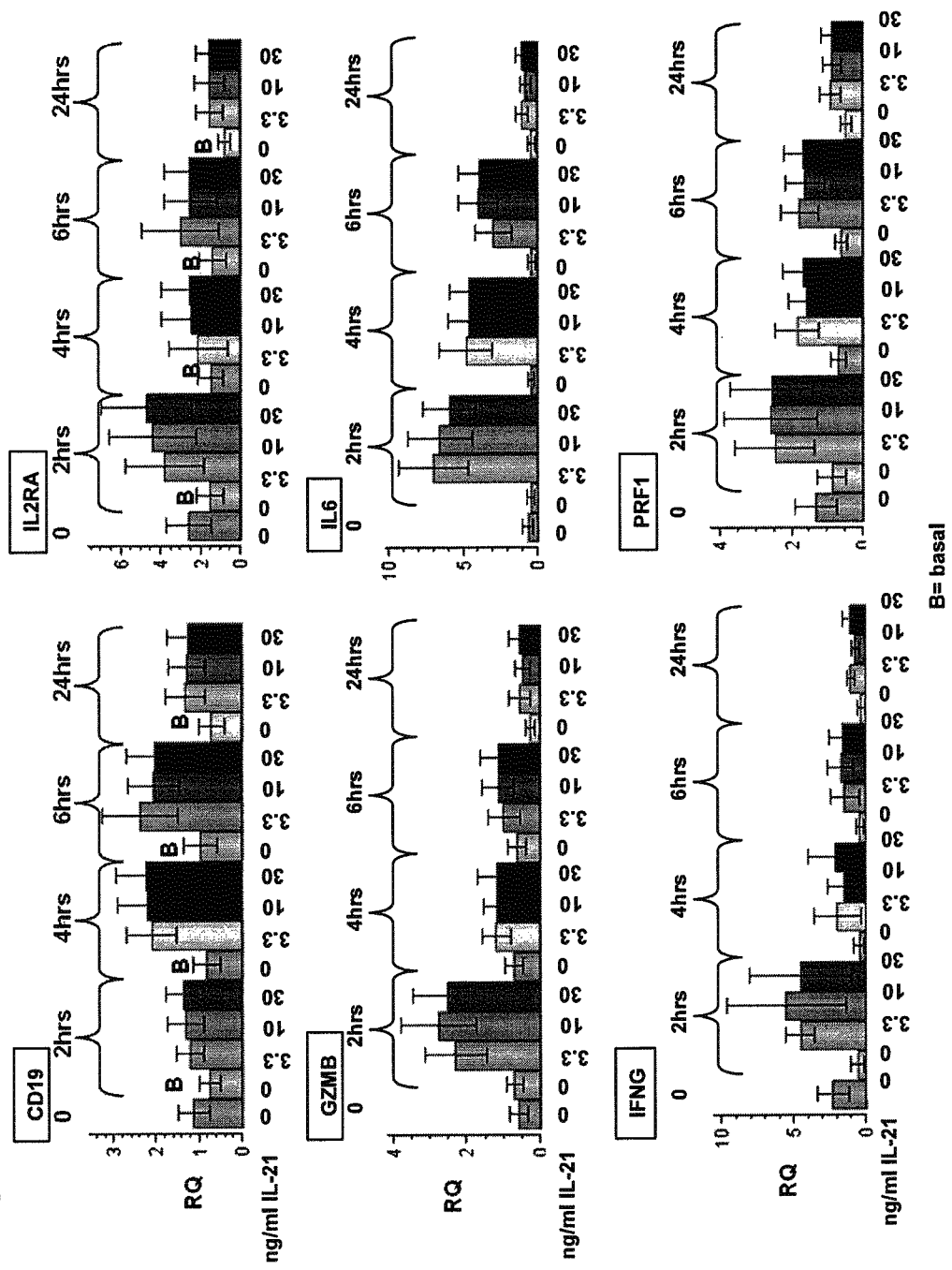
FIG. 55 demonstrates relative quantification (RQ; Y-axis) of gene expression of six examined genes (CD19, GZMB, IFNγ (IFNG), IL-2Rα (IL2RA), IL-6, and PRF1) at different concentrations of IL-21 at either 2, 4, 6, or 24 hr time points (X-axis).

In order to determine optimal time and dose of IL-21 treatment for generation of maximal signal, whole blood samples from five healthy donors were incubated in the presence of 3.3, 10 or 30 ng/ml of IL-21 for 2, 4, 6 or 24 hr. RNA was isolated and gene expression levels measured. Significant and robust IL-21 dependent signals were obtained for six genes: IL6, IFNγ, IL2Rα, GZMB, PRF1, CD19. The optimal signal for all but CD19 was obtained at 2 hr (FIG. 55). There was little difference in the response obtained at 3.3, 10 or 30 ng/ml IL-21. Response to ex vivo IL-21 treatment was consistent between all five donors (data not shown). Based on the results obtained with these five donors, the assay conditions chosen to titrate the inhibitory effect of AbS on the ex vivo response to IL-21 were: two hr stimulation with 10 ng/ml of IL-21. The most reliable IL-21-responsive genes were GZMB, IFNγ, IL-21RA, IL-6, and PRF1.

To determine the dose of AbS to optimally block the effect of IL-21, samples from four individual donors were preincubated for 2 hr at the indicated concentrations of AbS and IgG₁TM, both diluted in PBS, before the addition of 10 ng/ml of IL-21. Following the addition of IL-21, samples were incubated for an additional two hr.

Figure 56A:
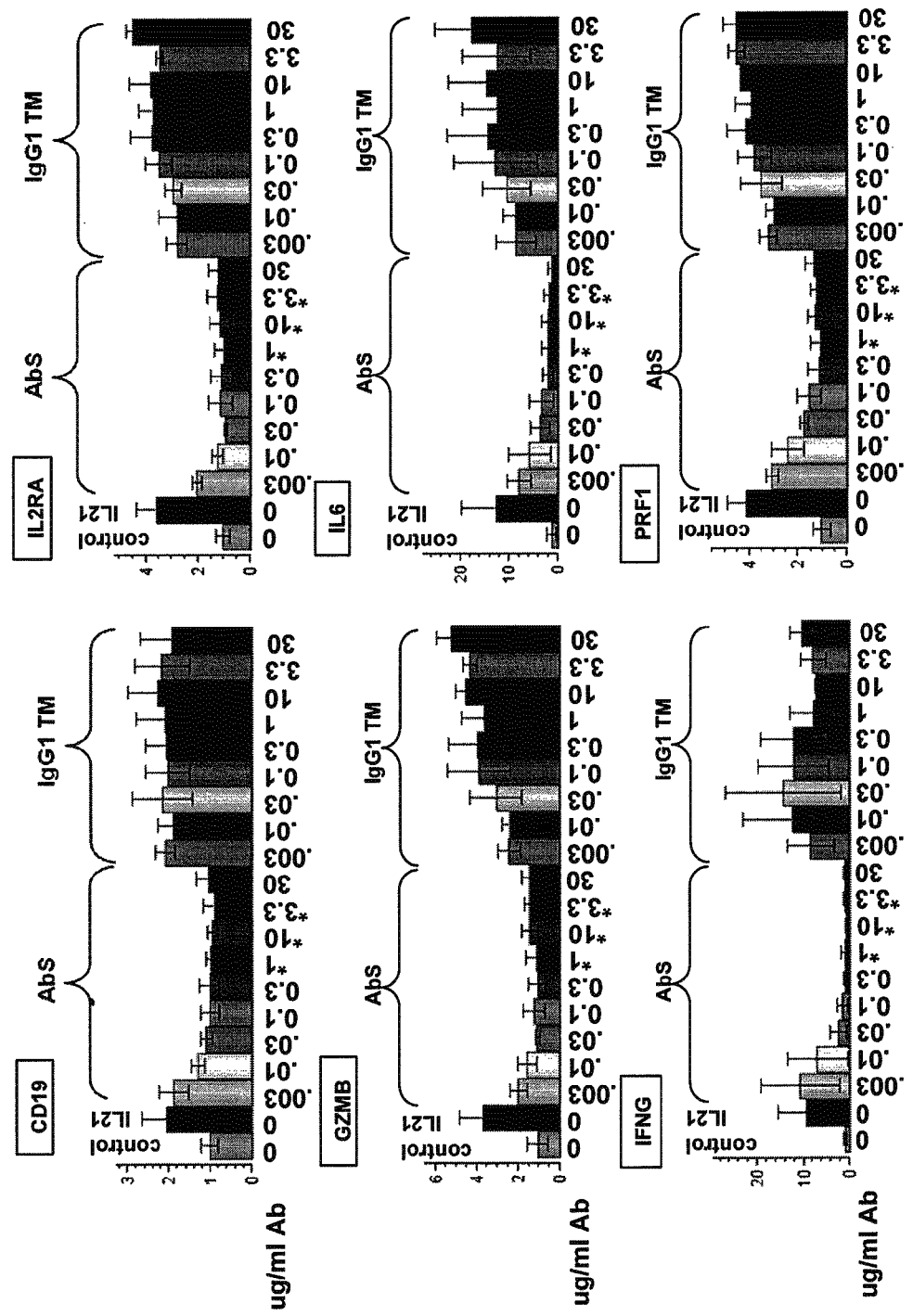
FIG. 56a demonstrates relative quantification (RQ; Y-axis) of gene expression of six examined genes (CD19, GZMB, IFNγ, IL-2Rα, IL-6, and PRF1) after incubation with IL-21 and different concentrations of either AbS or IgG1 TM control (X-axis).
Figure 56C:
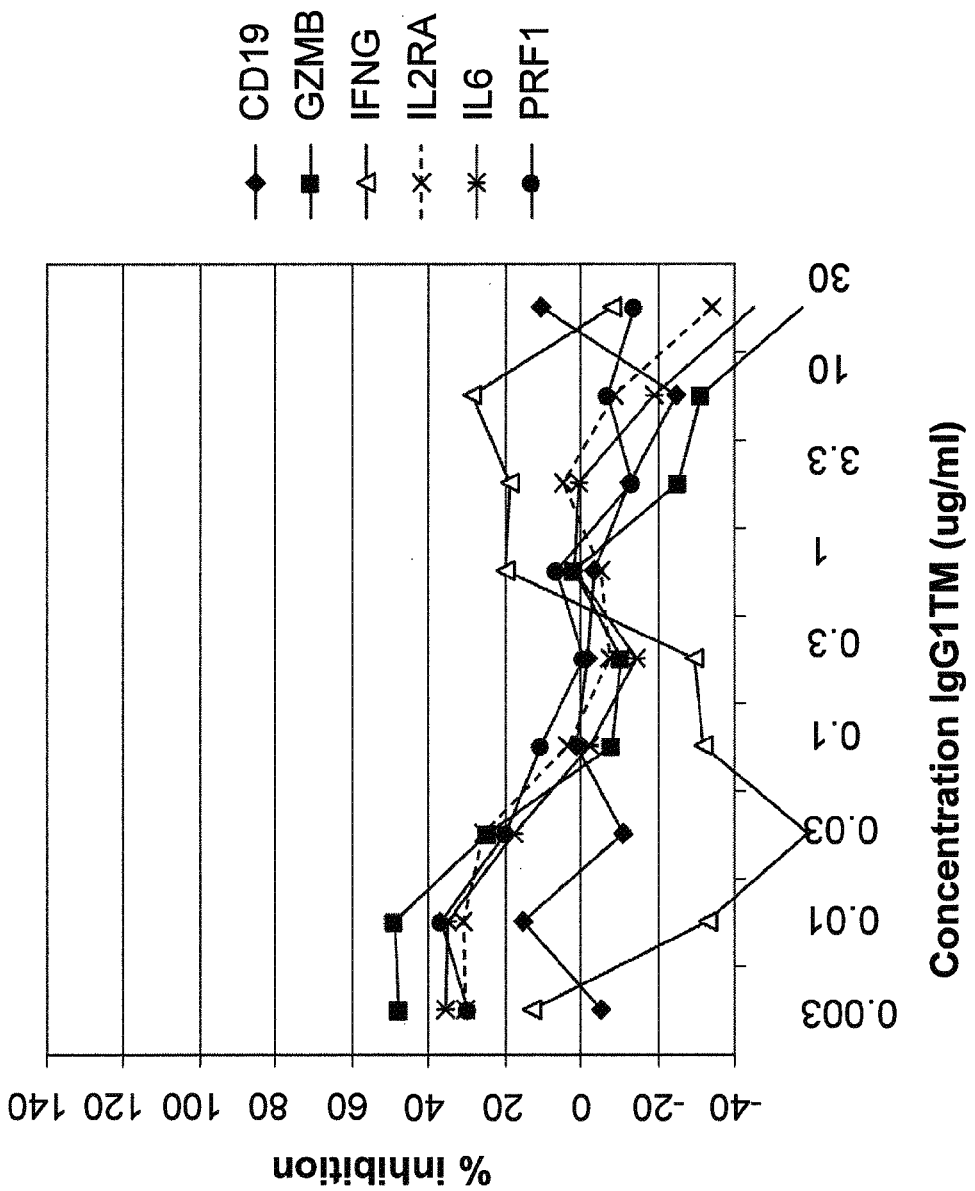

Addition of 0.1 μg/mL AbS resulted in full inhibition, so 0.003 μg/mL of AbS was used for subsequent experiments. AbS, but not IgG₁TM, inhibited the response of all six genes tested in all four donors, as demonstrated in FIGS. 56a-c. The $IC_{50}$ for all six genes is presented in Table 30.

TABLE 30

Inhibitory Activity of AbS on IL-21 Response Signal in Whole Blood

|  | CD19 | GZMB | IFNG | IL2Rα | IL6 | PRF1 |
|---|---|---|---|---|---|---|
| IC₅₀ (ug/mL) | 0.007 | <0.003 | 0.015 | 0.002 | 0.005 | 0.007 |

As demonstrated in FIG. 56, AbS at concentration as low as 0.03 μg/mL (200 pM or $6\times10^4$ molecules/cell) successfully blocked the effects of 10 ng/mL of IL-21 on gene expression. This inhibition was reduced when the concentration of AbS was lowered to ≦0.003 μg/mL (20 pM). GZMB, IFNγ, IL-2Rα, IL-6, and PRF1 were reliable blood biomarkers of IL-21R/IL-21 and antibody activity at 2 hr; however all six genes (GZMB, IFNγ, IL-2Rα, IL-6, PRF1, and CD19) were identified as useful human blood biomarkers for IL-21R/IL-21 activity. Moreover, 10 ng/mL of IL-21 was shown to decrease gene expression of TBX-21 gene in the same assay, and this decrease was completely reversed by AbS at 0.03 μg/mL (data not shown).

Example 13

PK and PD of AbS and AbT in Male Cynomolgus Monkeys

Example 13.1

Animal Selection for AbS and AbT Study

Animals used in the study were protein-naïve and selected for inclusion based on results obtained with recombinant human IL-21 stimulation in the whole blood ex vivo assay prior to dosing.

Specifically, for male monkeys, whole blood samples (0.5-1.5 mL) were placed in sterile, nuclease-free, 2 mL microcentrifuge tubes (Axygen, cat. #1011-744) and treated with vehicle (10 mM L-histidine, 5% sucrose), 50 ng/mL recombinant human IL-21 (rhuIL-21), 50 ng/mL rhuIL-21 with 30 nM IgG control antibody, or 50 ng/mL rhuIL-21 with 30 nM anti-IL-21R antibody for 4 hrs at 37° C. on a platform shaker. For female monkeys, whole blood samples (0.5 mL) were treated with either vehicle or 20 ng/mL rhuIL-21. Peripheral blood mononuclear cells in the blood samples were isolated by Ficoll method according to manufacturer's instructions (GE Healthcare, Ficoll-Paque™ plus) and washed once in PBS.

RNA isolation was performed using the RiboPure™-Blood Kit (Ambion, Cat#AM1928; males) or RNeasy kit (Qiagen, females) according to manufacturer's instructions. RNA yield was determined using a NanoDrop 1000A spectrophotometer (NanoDrop, Wilmington, Del.) and RNA quality was assessed using a 2100 Bioanalyzer (Agilent, Santa Clara, Calif.). RNA concentration was adjusted to 28 ng/mL (males) or 20 ng/μL (females).

For male monkeys, synthesis of cDNA was performed using a High Capacity cDNA Reverse Transcription Kit (Applied Biosystems, Foster City, Calif., cat. #4368814) according to manufacturer's instructions with 700 ng of RNA and gene expression analysis was performed using a Wyeth custom TLDA card (Applied Biosystems, part #4342249) designed for detection of cynomolgus monkey genes. Each cDNA synthesis reaction was mixed with TaqMan® 2×PCR Master Mix (Applied Biosystems, cat. #430-4437), and 100 µL was loaded onto a TLDA card. TLDA cards were processed according to manufacturer instructions and amplification was performed using an ABI Prism 7900HT Sequence Detection System. Cycling parameters used for each run were as follows: 50° C. for 2 min, 95° C. for 10 min, and 40 cycles of 95° C. for 15 sec followed by 60° C. for 1 min. Cycle thresholds (CT) were calculated using Sequence Detection Software (version 2.3, Applied Biosystems).

For female monkeys, TaqMan quantitative RT-PCR for IL-2Rα only was performed using prequalified primers and probes to IL-2Rα (Applied Biosystems; the same IL-2Rα primers and probes as those in custom TLDA for male monkeys).

For both males and females, the relative quantification (RQ) of gene expression was then calculated using the delta delta Ct (ΔΔCt) method where $RQ=2^{-\Delta\Delta Ct}$. Zinc finger protein 592 (ZNF592, males) or protein kinase G-1 (PKG1, females) was used as the endogenous control and the vehicle control sample was used as the calibrator for RQ calculations. Samples with RQ values greater or equal to 1.5 were considered to have gene expression higher than the corresponding vehicle control sample.

Male monkeys whose blood showed higher expression of several immune function-related genes when stimulated ex vivo with IL-21 compared with vehicle (RQ≧1.5) were selected for inclusion in this study. The RQ values of five genes (IL-2Rα, IL-21R, PRF1, GZMB, and IL-6) for nine monkeys selected for further studies described below, represented by animal number (Animal #), are shown in Table 31. The group number (A-C) represents whether the animals selected were treated with AbS (Group A), AbT (Group B), or IgG control (Group C) in subsequent experiments. Animals 10-13 were not selected for further studies.

TABLE 31

Relative Quantification (RQ) of Gene Expression Induced by Ex Vivo Addition of IL-21 to Whole Blood Obtained from Male Cynomolgus Monkeys

| Group; Animal # | IL-2Rα | IL-21R | PRF1 | GZMB | IL-6 |
|---|---|---|---|---|---|
| A; 1 | 2.8 | 2.5 | 2.8 | 2.0 | 4.2 |
| A; 2 | 3.4 | 2.3 | 1.2 | 1.1 | 1.7 |
| A; 3 | 5.5 | 2.9 | 2.5 | 1.4 | 3.6 |
| B; 4 | 4.1 | 2.1 | 2.5 | 1.1 | 4.9 |
| B; 5 | 5.3 | 3.2 | 2.1 | 2.1 | 4.1 |
| B; 6 | 2.8 | 1.8 | 1.8 | 2.0 | 0.5 |
| C; 7 | 6.3 | 1.9 | 2.4 | 1.9 | 2.6 |
| C; 8 | 2.2 | 1.8 | 1.6 | 1.6 | 6.7 |
| C; 9 | 3.8 | 2.0 | 1.9 | 2.2 | 1.2 |
| 10 | 2.9 | 1.8 | 0.7 | 1.0 | 0.9 |
| 11 | 7.7 | 3.4 | 2.6 | 2.2 | 2.8 |
| 12 | 4.5 | 3.6 | 1.4 | 1.5 | 1.1 |
| 13 | 2.1 | 1.5 | 1.1 | 1.2 | 1.4 |

IL-2Rα was determined to have the largest magnitude (highest RQ) and most consistent change (highest percentage of animals that had RQ>1.5) in IL-21-induced gene expression of the genes evaluated, and was therefore considered the best single gene for assessing pharmacodynamic (PD) activity of the anti-IL-21R antibodies. Whole blood samples from all monkeys included in the in vivo study had IL-2Rα RQ values greater than 1.5 following ex vivo stimulation with IL-21. However, significant interanimal variability in IL-2Rα RQ values was observed, with values ranging from 2.8 to 6.3.

To obtain a larger number of samples for characterization of the distribution of the IL-2Rα response to rhuIL-21 in the ex vivo assay, blood samples were obtained from 24 additional female cynomolgus monkeys, stimulated ex vivo with rhuIL-21, and analyzed for IL-2Rα gene expression by using a quantitative RT-PCR method (IL-21R, PRF1, GZMB, and IL-6 expression was not analyzed for these monkeys). There were no noticeable differences in IL-2Rα RQ distribution between male and female monkeys (with the median±SD RQ values of 3.8±1.7 and 3.0±1.9, respectively) and subsequent analysis of IL-2Rα RQ distribution was performed using a combined data set with n=37. All cynomolgus monkeys tested had IL-2Rα RQ values greater or equal to 1.5 following ex vivo stimulation with rhuIL-21. The median IL-2Rα RQ value (n=37) was 3.2 and the range was 1.5-8.1.

Figure 57A:
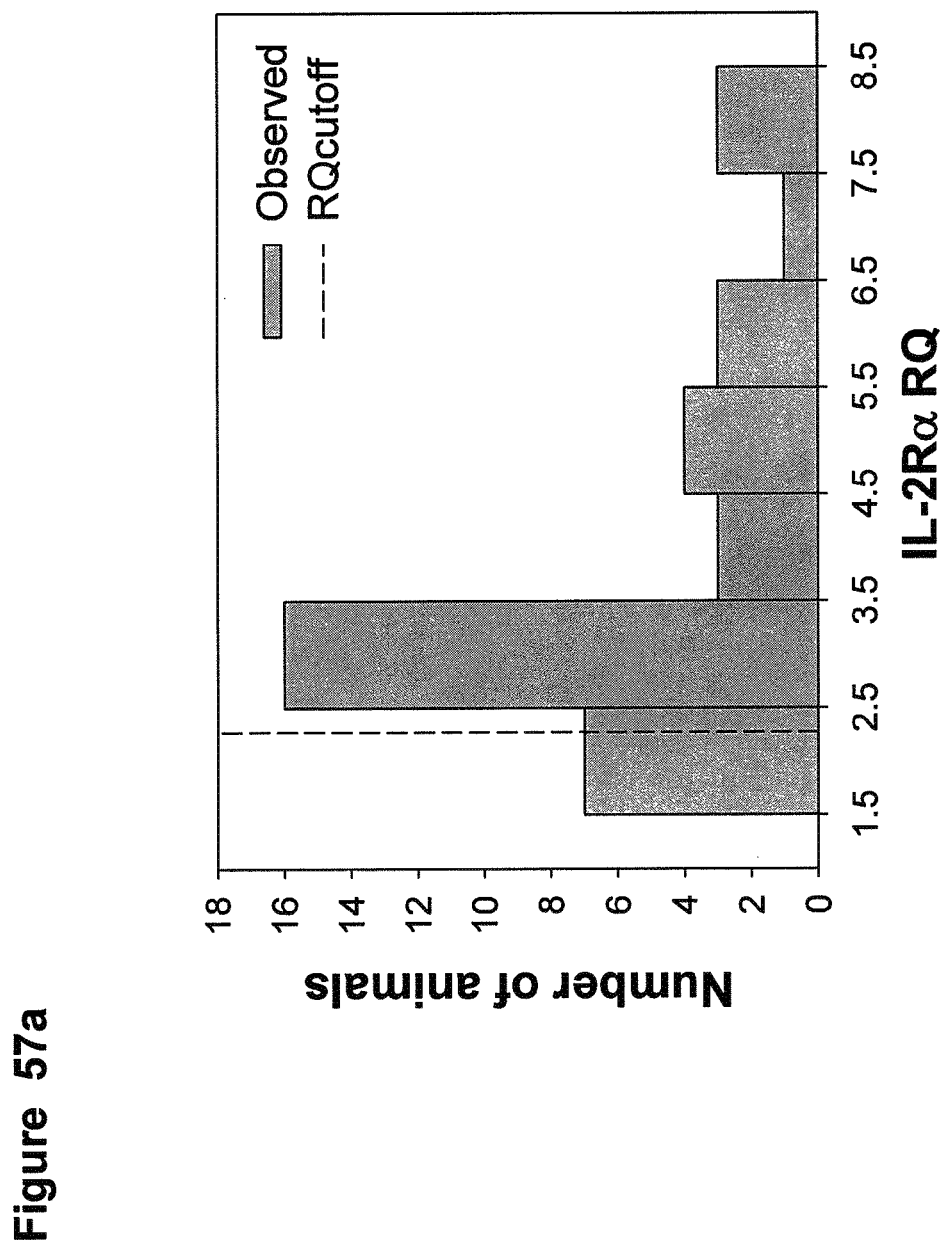
FIG. 57a demonstrates the histogram analysis (Y-axis) for the RQ values (X-axis), and FIG. 57b demonstrates histogram analysis (Y-axis) for the log$_2$-transformed RQ values (X-axis), which were obtained using a statistical software package. The solid line represents Gaussian distribution. The dotted line represents cutoff RQ for the enrollment into the in vivo study, defined using the formula: log $\{RQ_{cutoff}\}$=mean of the log-transformed RQ values–SD of the log-transformed RQ values.
Figure 57B:
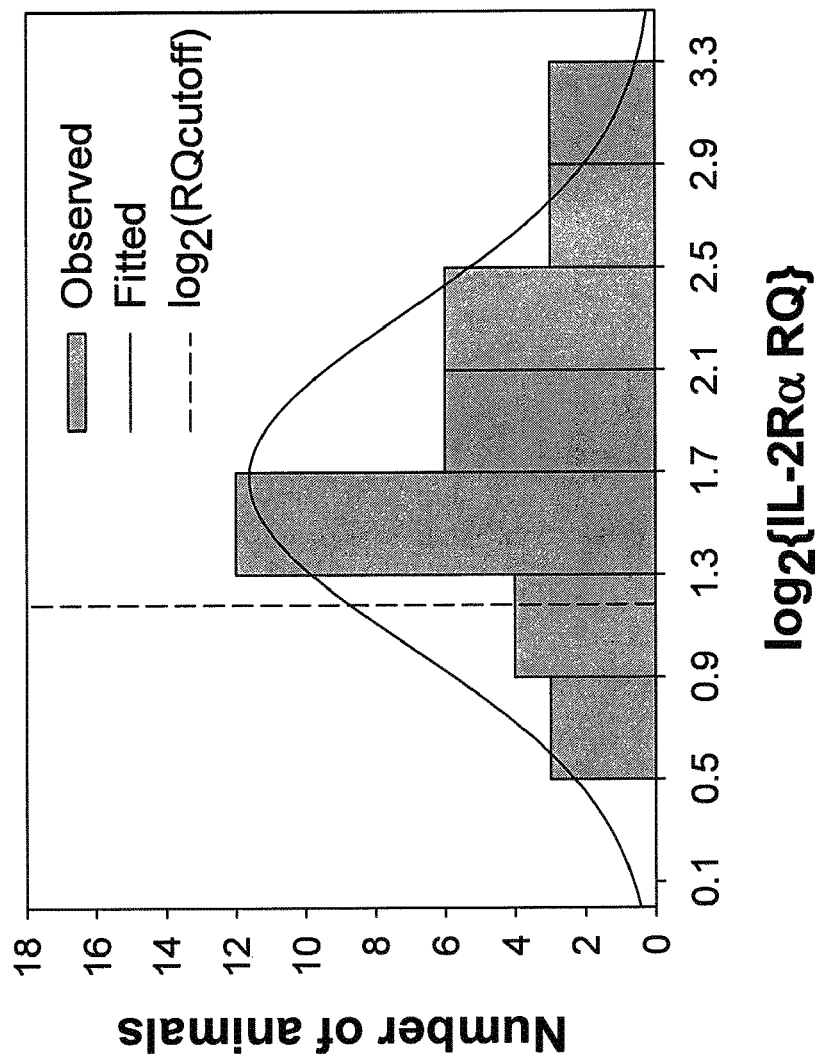
FIG. 57 depicts distribution of Relative Quantification (RQ) values for IL-2Rα gene expression in whole blood of male cynomolgus monkeys following ex vivo stimulation with recombinant human IL-21.
FIG. 57c compares individual animal and median (solid lines) RQ values (Y-axis) of whole blood aliquots stimulated with IL-21 and AbT (triangles) or IL-21 and control IgG (squares) as compared to those with IL-21 stimulation alone (circles).

RQ values for IL-2Rα expression obtained at baseline from 37 monkeys were log-transformed and the distribution of the RQ and log {RQ} values was tested in the Shapiro-Wilk and D'Agostino & Pearson normality tests (GraphPad Prizm 5, GraphPad Software Inc). The normality hypothesis was rejected for the RQ distribution (p<0.05) but not for log {RQ} distribution (p=0.16 for the Shapiro-Wilk test; and p=0.48 for the D'Agostino & Pearson test). The log-transformed RQ values were fitted into normal distribution ($R^2=0.69$) using GraphPad Prizm 5 software. The distribution of the IL-2Rα RQ values and log transformation (log 2) of the RQ values obtained in the ex vivo assay for all 37 monkeys (n=13 males; n=24 females) are shown in FIGS. 57a and 57b, respectively. The distribution of IL-2Rα RQ values appeared approximately log-normal and passed normality tests. The inclusion criterion for future pharmacodynamic (PD) studies with anti-IL-21R antibodies in cynomolgus monkeys was defined as 2.3, based on the formula: log {$RQ_{cutpoint}$}=mean of the log-transformed RQ values−standard deviation of the log-transformed RQ values. Thus, animals with distribution of the IL-2Rα RQ values greater than 2.3 were considered to be good responders to IL-21 stimulation. Animals with RQ values of greater than 2.3 (~81%; 30 of 37) were defined as good responders and were considered to satisfy the inclusion criterion for the PD study of anti-IL-21R antibodies.

Figure 57C:
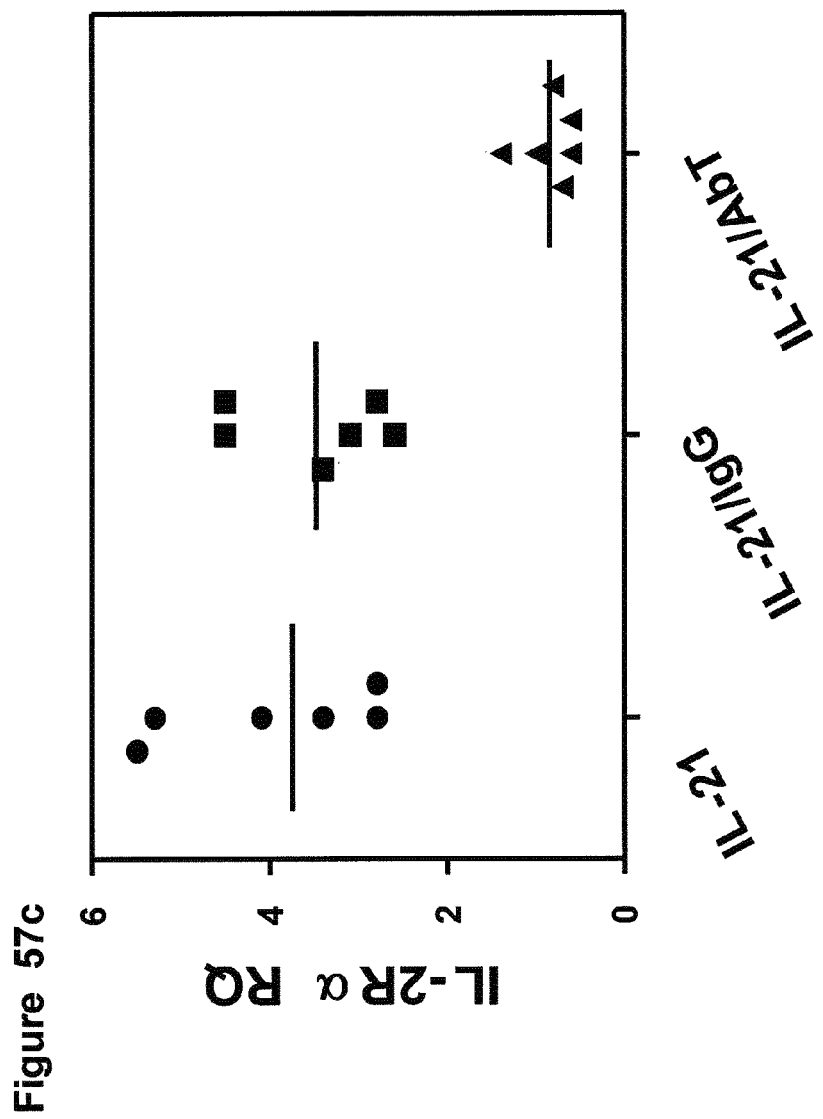

To confirm that IL-21-induced gene expression was dependent on engagement of cynomolgus monkey IL-21R, monkey whole blood samples were incubated simultaneously with IL-21 and an anti-IL-21R antibody (AbT; 30 nM) prior to RNA isolation and gene expression analysis. As expected, ex vivo addition of AbT simultaneously with IL-21 strongly inhibited IL-21-induced gene expression changes in the whole blood assay (i.e., RQ value <1.5; FIG. 57c).

Example 13.2

Study Design for In Vivo Experiments

Nine male protein-naive cynomolgus monkeys that were identified as responders to IL-21 stimulation in the ex vivo pharmacodynamic (PD) whole blood assay (described in Example 12.1), were dosed with 10 mg/kg of AbS (Group A), AbT (Group B), or IgG control antibody (Group C), with three animals per group. The dose was administered i.v. (infusion rate of ~4 mL/min) into the saphenous vein with a dose volume of 2.5 mL/kg.

Blood samples (~7.0 mL) for the determination of PD activity (all three groups) were collected into tubes containing sodium citrate as the anticoagulant. Blood samples (~3.0 mL)

for the determination of serum AbS or AbT concentrations and for the evaluation of anti-product antibodies were collected into tubes without anticoagulant, allowed to clot at room temperature for approximately 15 min, and processed for serum collection by centrifugation. The sample collection schedule is shown in Table 32. After day 50, additional sampling time points were added for animals 1 and 3 in the AbS group (Group A) to demonstrate reversibility of PD activity. Day 1, also referred to as "dose administration," is the day on which antibodies were administered to the monkeys. "Pre-dose" refers to sample collection time prior to dose administration, and "post-dose" refers to sample collection time after dose administration.

TABLE 32

In Vivo Study Design and Sample Collection in Male Cynomolgus Monkeys

| Group (Dose) Animal # | Time (days) | Sample collection[a] |
|---|---|---|
| A; AbS (10 mg/kg, IV) Animals 1-3 | −13, 1 (pre-[b] and 5 min post-dose), 2, 8, 15, 22, 36, 50 71, 92[c] 92, 106, 113, 134, 148[c] | Animals 1-3 Animal 3 Animal 1 |
| B; AbT (10 mg/kg, IV) Animals 4-6 | −13, 1 (pre- and 5 min post-dose), 2, 8, 15, 22, 36 | Animals 4-6 |
| C; IgG control (10 mg/kg, IV) Animals 7-9 | −13, 1 (pre- and 5 min post-dose), 2, 8, 15, 22, 36 | Animals 7-9 |

[a] For Groups A and B, serum was collected to assay for test article concentrations and anti-product antibodies, and whole blood was collected for ex vivo PD assay. For Group C, only whole blood samples were collected.
[b] For animal 1, pre-dose day 1 samples were not collected.
[c] Following PD analysis at day 50, additional sampling time points were included to demonstrate reversibility of PD activity.

Example 13.3

AbS and AbT Serum Concentrations

To determine AbS and AbT serum concentrations, ELISAs described in Example 10 were used. PK studies in cynomolgus monkeys described in Example 10 indicated that following single i.v. administration, AbS was cleared markedly faster compared to AbT. In this study, extensive serum sampling required for determination of a complete set of PK parameters were not performed because of the relatively large sample volume required for the PD assay and limitations on blood volumes that could be collected from each individual cynomolgus monkey. Samples for determination of anti-IL-21R serum concentrations were taken only at those time points at which PD activity was assessed to enable correlation between the serum concentrations and PD activity for each individual animal. Thus, only elimination half-life ($t_{1/2}$) was estimated based on the terminal phases of serum concentration-time profiles. The apparent $t_{1/2}$ was determined as described in Example 10.

Figure 58:
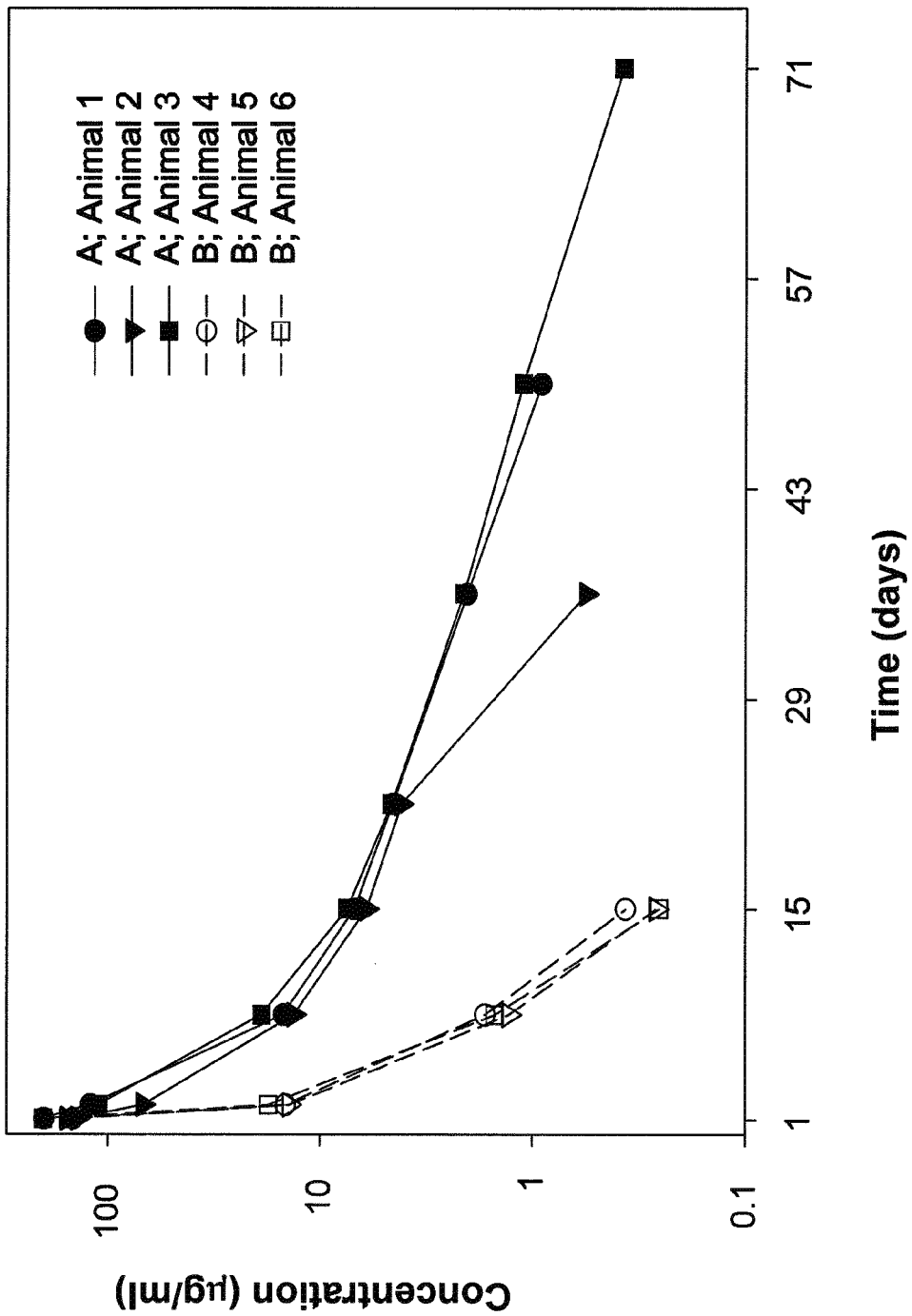
FIG. 58 depicts serum concentrations (Y-axis) following single 10 mg/kg i.v. administration of anti-IL-21R antibody AbS ("A") or AbT ("B") to male cynomolgus monkeys, collected up to day 148 for AbS and up to day 36 for AbT (X-axis). Data points with serum concentrations below the lower LOQ (30 ng/mL) are not shown.

Following a single 10 mg/kg i.v. dose, AbS was eliminated slowly from male cynomolgus monkeys, with a mean apparent terminal half-life ($t_{1/2}$) of ~10.6±3.92 days (Table 33). Up until day 22, AbS serum concentrations were very similar between all three AbS-dosed animals (FIG. 58). However, at day 36 and later time points, AbS serum concentrations in animal 2 declined rapidly (to ~0.6 µg/mL) compared to those for animals 1 and 3 (to ~2 µg/mL). At day 50, animal 2 had no detectable AbS in the serum (less than LOQ of 30 ng/mL), while animals 1 and 3 had AbS serum concentrations of ~0.9-1 µg/mL. Thus, the estimated $t_{1/2}$ of AbS was shorter for animal 2 (~6.2 days), compared to that for animals 1 and 3 (~12 and 14 days, respectively).

As expected based on the initial PK studies, after a single 10 mg/kg i.v. dose administration, the serum concentration of AbT declined markedly faster, compared to that of AbS (FIG. 58). All three AbS-dosed monkeys had similar concentration time-profiles and apparent $t_{1/2}$ values (Table 33), with serum concentrations declining to relatively low levels at day 15 (<0.4 µg/mL) and to less than the LOQ at day 22. The estimated mean $t_{1/2}$ of AbT was 2.3±0.16 days. AbS and AbT concentrations started to diverge as early as 24 hrs post-dose and differed by more than ten-fold at the one-week time point. These data confirmed observations from the earlier PK studies in which AbT had ~5-7 fold faster total body clearance (CL), compared to AbS (see, e.g., Example 10).

TABLE 33

Peak and Last Detectable Concentrations and Elimination Half-Life After 10 mg/kg IV Administration of AbS and AbT to Male Cynomolgus Monkeys

| Group | Animal | $C_{peak}$ (µg/mL) | $t_{1/2}$ (days) | $C_{last}$ (µg/mL) | $T_{last}$ (days) |
|---|---|---|---|---|---|
| A (AbS) | 1 | 200 | 12 | 0.91 | 50 |
| | 2 | 139 | 6.2 | 0.56 | 36 |
| | 3 | 153 | 14 | 0.37 | 71 |
| | Mean | 164 | 11 | 0.61 | 52 |
| | SD | 32 | 3.9 | 0.27 | 18 |
| B (AbT) | 4 | 145 | 2.5 | 0.36 | 15 |
| | 5 | 155 | 2.3 | 0.26 | 15 |
| | 6 | 201 | 2.1 | 0.25 | 15 |
| | Mean | 167 | 2.3 | 0.29 | 15 |
| | SD | 30 | 0.16 | 0.06 | 0 |

$C_{peak}$ Concentration at 5 min (also referred to as $C_{5min}$), the first sampling time point after i.v. administration
$t_{1/2}$ Elimination half-life
$T_{last}$ Last time point at which the test article concentration was above the lower limit of quantitation (LOQ = 30.0 ng/mL)
$C_{last}$ Concentration at $T_{last}$ Example 13.4

AbS and AbT PD Response in Male Cynomolgus Monkeys

Ex vivo whole blood assay for detection of inhibition of IL-21-induced expression by anti-IL-21R antibodies was described in Example 12.1. For all nine monkeys enrolled into this study, each pre-dose and post-dose whole blood sample was divided into four 1.5 mL aliquots. First and second aliquots were treated with either recombinant human IL-21 or vehicle (a calibrator for RQ calculations), and were used to assess whether the circulating test article affected ex vivo IL-21-induced IL-2Rα gene expression (i.e., PD activity). The third aliquot was treated with IL-21 and an anti-IL-21R antibody (30 nM), and the fourth aliquot was treated with IL-21 and an IgG control antibody (negative control for the anti-IL-21R antibody). The third and fourth aliquots were used to assess whether inhibition of IL-21-induced IL-2Rα gene expression by the circulating test article in a given post-dose sample was complete (for time points at which PD activity was observed), whether the return of IL-21-induced gene expression was mediated through the IL-21R (for time points at which PD activity was later lost), and to monitor for the presence of neutralizing anti-product antibodies.

Figure 59A:
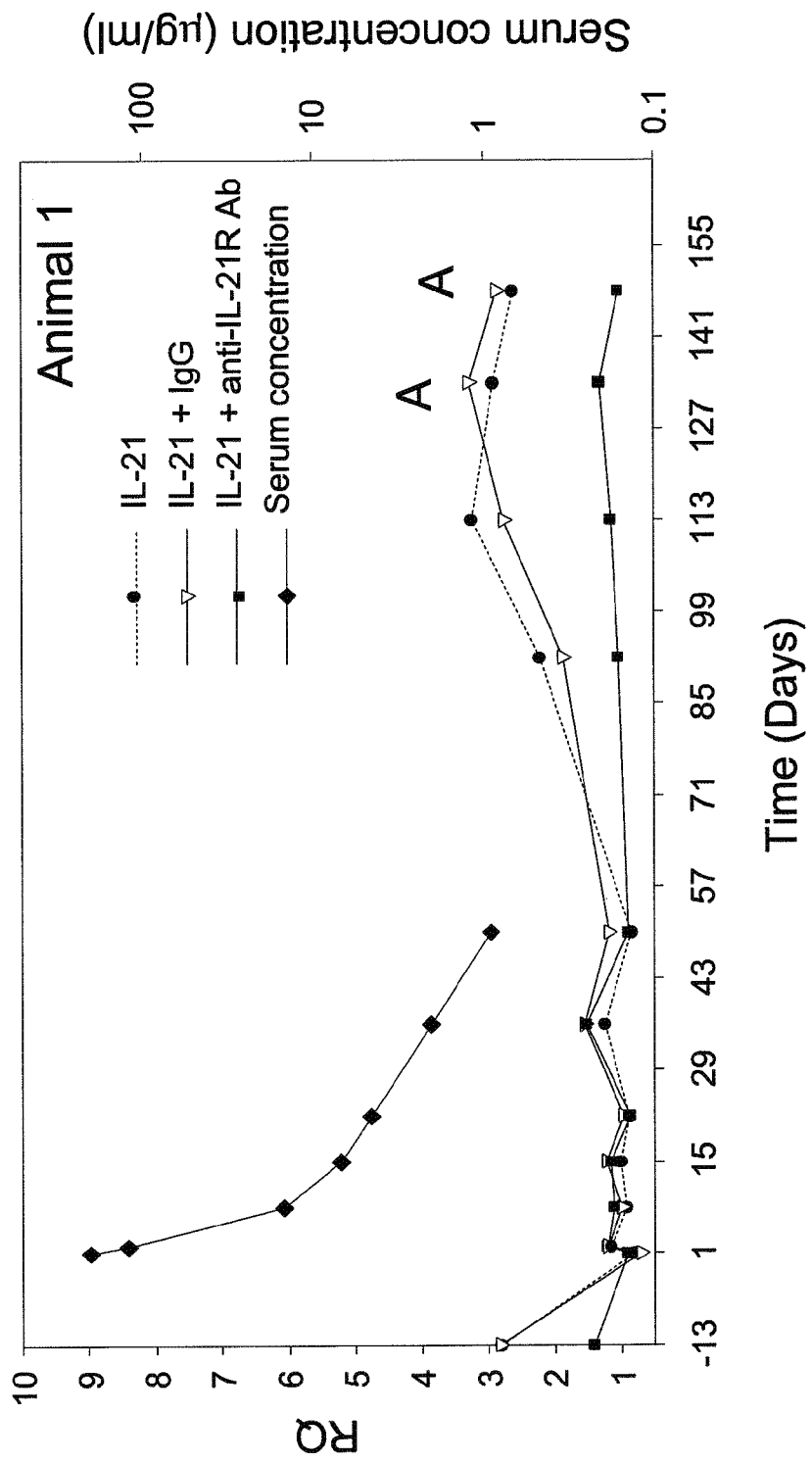
FIGS. 59a-c depict results for Animals 1-3, respectively.
Figure 59B:
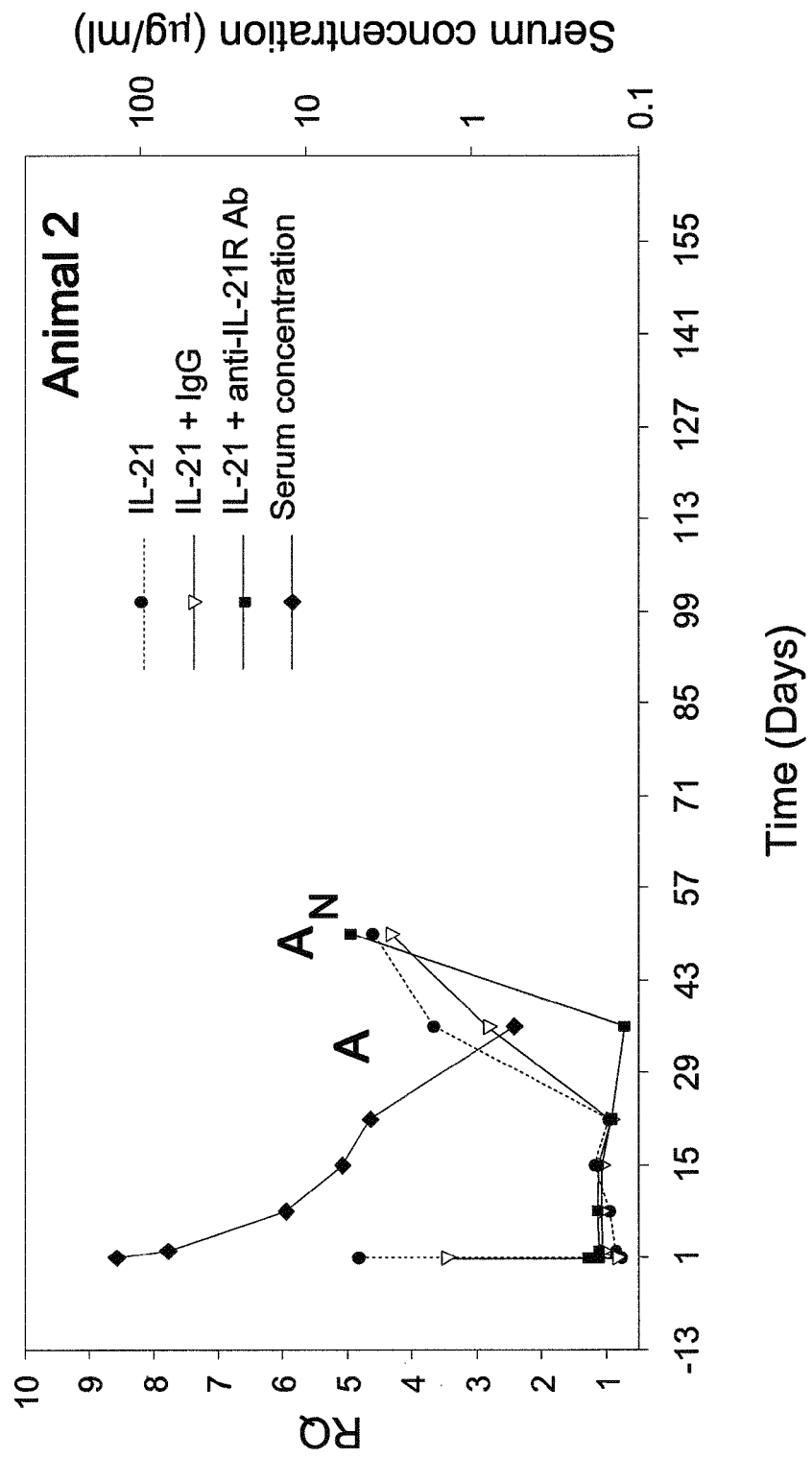
Figure 59C:
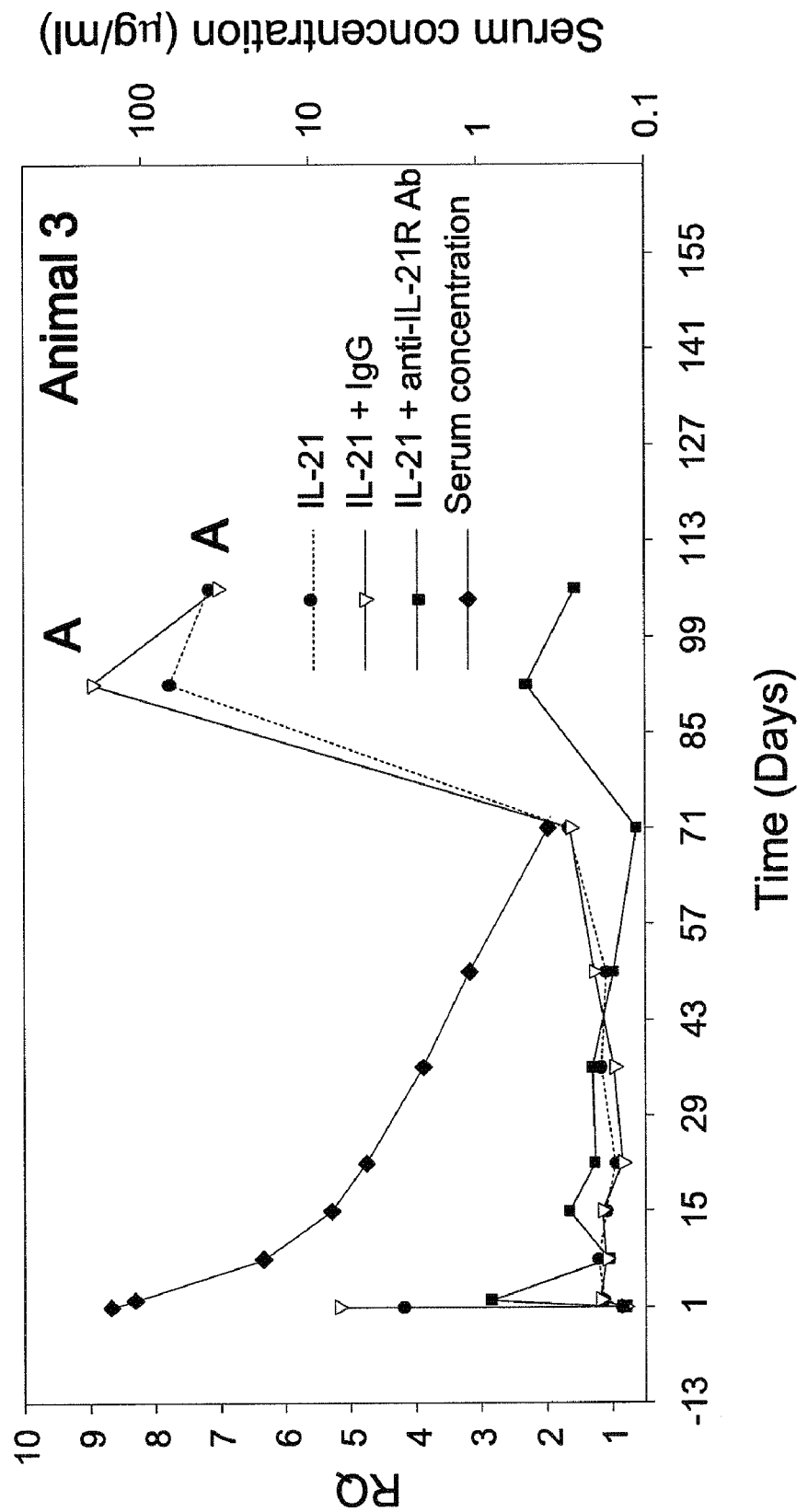

For AbS, full inhibition of IL-21-induced IL-2Rα gene expression (IL-2Rα RQ<1.5) was observed immediately after dose administration and persisted until at least day 22 for animal 2 and at least day 50 for animals 1 and 3, when serum AbS concentrations were at or above 6 nM (0.9 µg/mL) for all three monkeys (FIGS. 59a-c and Table 33). Ex vivo IL-21-induced IL-2Rα expression returned to pre-dose values (i.e., PD activity was lost) at day 92 for animals 1 and 3, coincident with the time points at which serum concentrations were <LOQ (FIGS. 59a and c). For animal 2, PD activity was lost at day 36, when serum AbS concentration declined to a relatively low level of ~4 nM (0.6 µg/mL). For all time points examined in this study, PD activity of AbS appeared all or none, such that there was typically either complete inhibition of IL-21-induced IL-2Rα gene expression (RQ<1.5), or a lack of inhibition (RQ similar to that in the corresponding pre-dose sample). A partial PD response was difficult to differentiate because of the intra-animal variability observed in IL-2Rα RQ values. It is possible that data points with partial PD responses for AbS would have been observed if additional sampling time points were collected at the terminal phase. The minimum concentration that was needed to maintain minimum PD activity of AbS ($C_{min}$) could not be precisely estimated, but is likely to be ~4-6 nM.

Figure 60A:
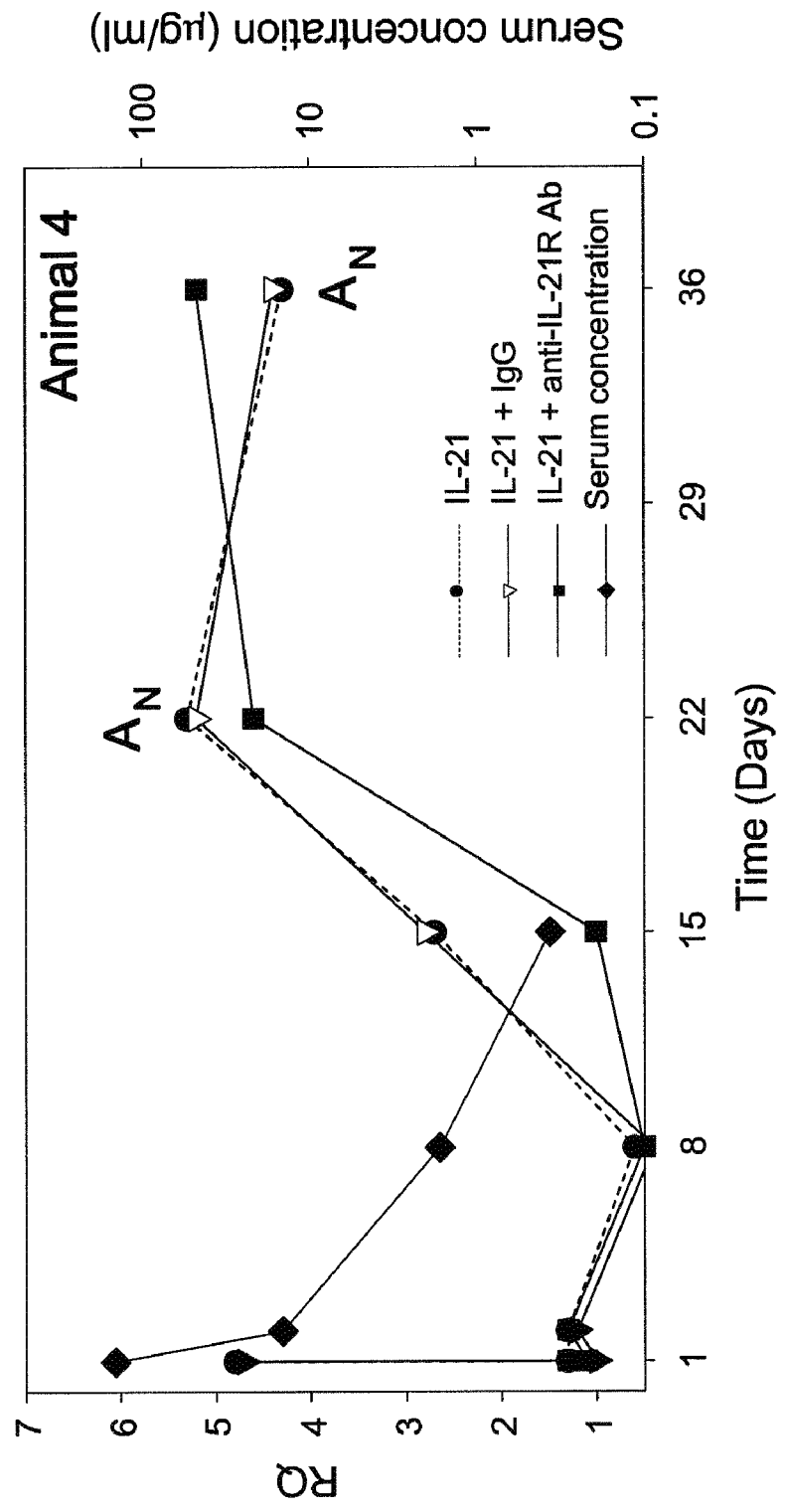
FIGS. 60a-c depict results for Animals 4-6, respectively.
Figure 60B:
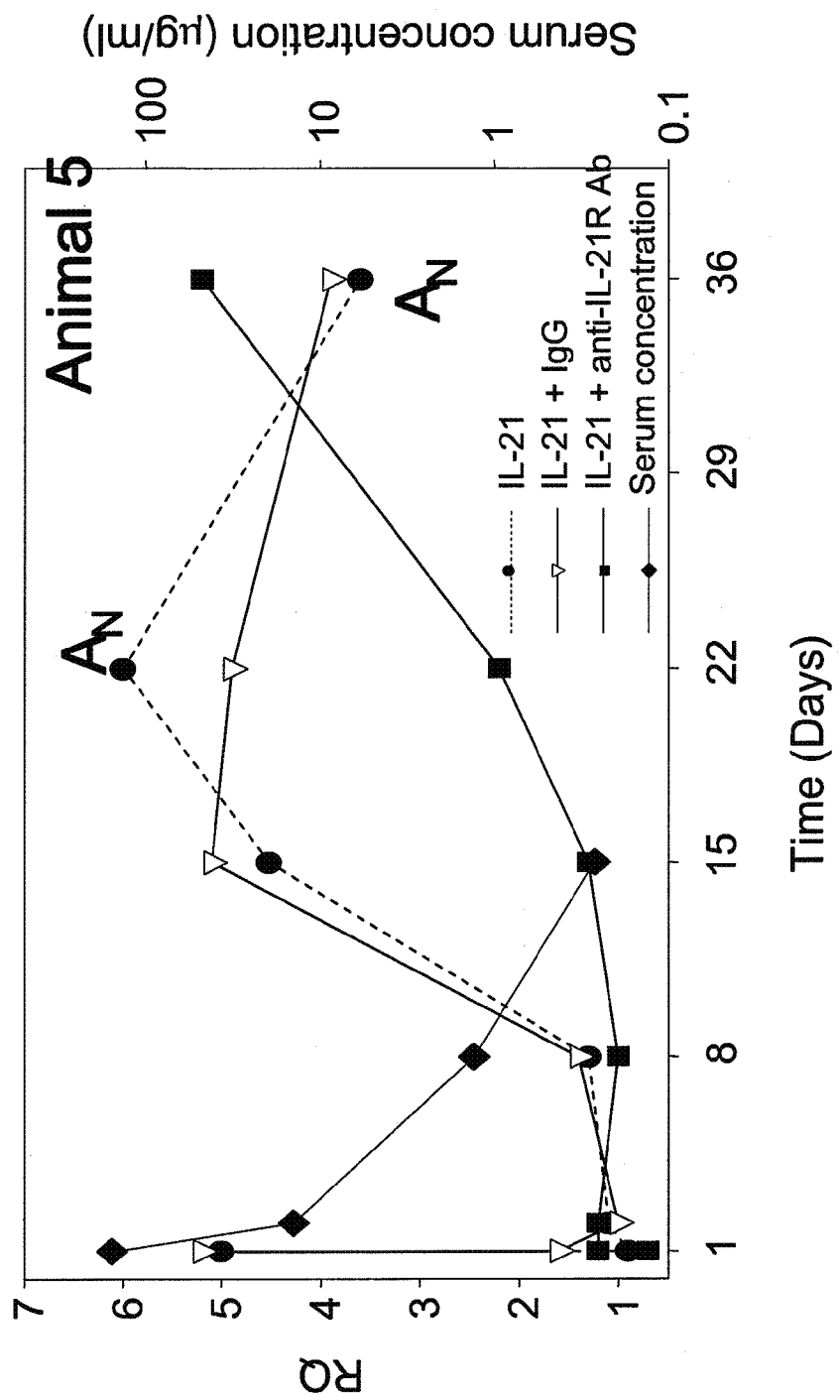
Figure 60C:
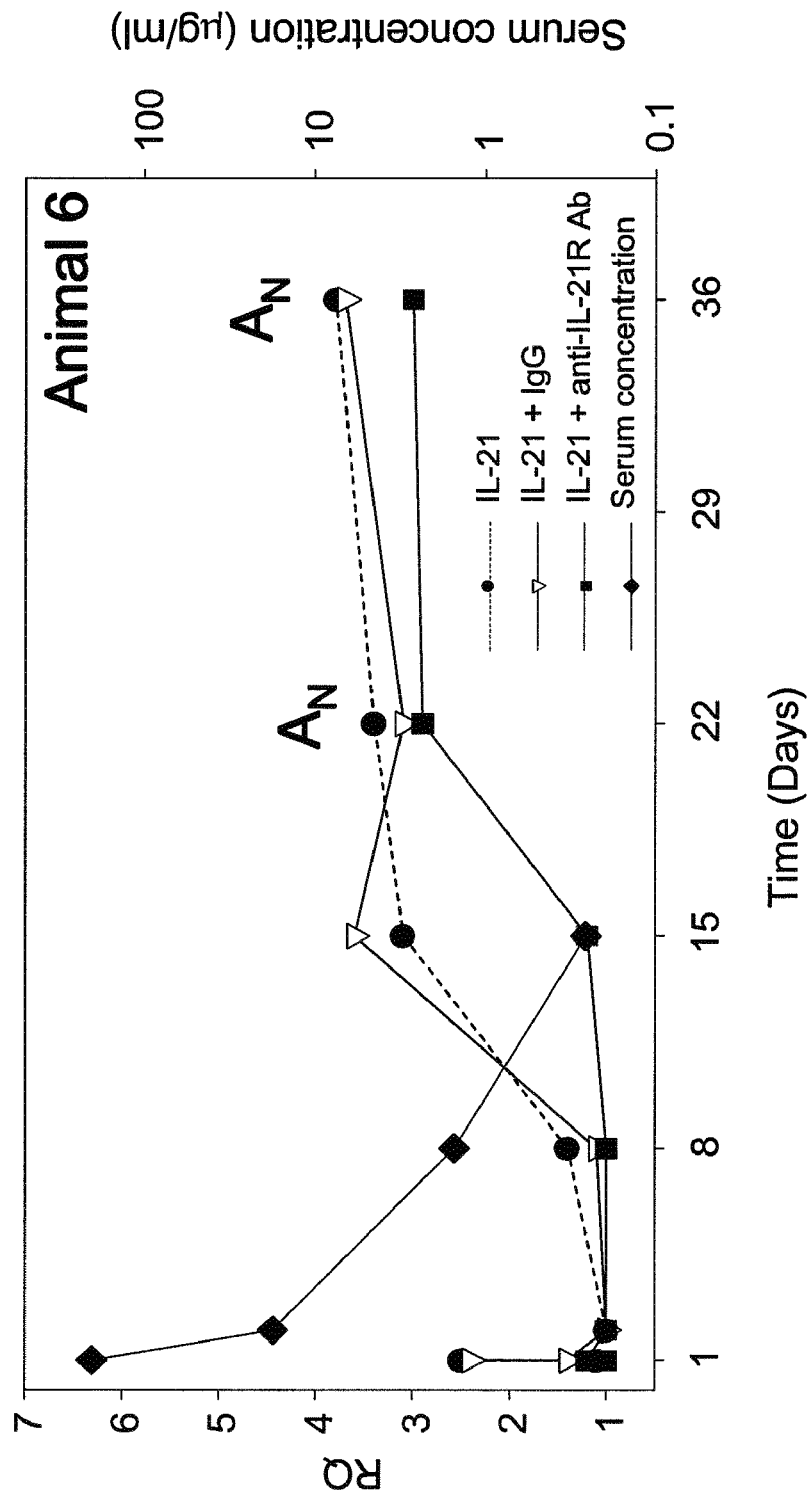

For AbT, PD activity was also observed immediately after dose administration and persisted until at least day 8 (RQ<1.5), when serum AbT concentrations were at or above 1.3 µg/mL (FIGS. 60a-c and Table 33). PD activity was lost (RQ>1.5) at day 15 for all three monkeys. In blood samples obtained at day 15 from animals 5 and 6, IL-2Rα RQ values appeared similar to the corresponding pre-dose values (i.e., complete loss of PD activity) and serum AbT concentrations were less than 1.8 nM. There was a partial PD response in blood samples obtained at day 15 from animal 4, as the observed IL-2Rα RQ value of 2.7 was less than that at pre-dose (RQ=4.8) and at the subsequent day 22 time-point (RQ=5.3; FIG. 60a). Animal 4 also had a slightly longer estimated $t_{1/2}$ and a somewhat higher AbT serum concentration at day 15 (~2.5 nM), compared to animals 5 and 6 (FIGS. 60a-c). These data suggest that the $C_{min}$ of AbT needed to maintain PD activity was approximately 2.5 nM.

For the isotype control group, ex vivo-added recombinant human IL-21 induced IL-2Rα gene expression in whole blood samples from all three monkeys at all time points, with noticeable intra-animal variability in the IL-2Rα RQ values (data not shown).

In agreement with the earlier PK studies (see Example 10), AbT had faster elimination in monkeys compared with AbS, with a mean apparent $t_{1/2}$ of 10.6 and 2.3 days for AbS and AbT, respectively. At the day 15 time point, PD activity was completely or partially lost in all three AbT-dosed monkeys, while all three monkeys in the AbS dose group had relatively high serum AbS concentrations (~6.0-7.4 µg/mL) and full PD activity. Thus, AbS had a longer duration of PD activity and a longer $t_{1/2}$ in cynomolgus monkeys.

Example 13.5

Anti-Product Antibody Response

At the first time point where loss of PD activity was observed, ex vivo addition of an anti-IL-21R antibody simultaneous with rhuIL-21 inhibited the induction of IL-2Rα gene expression (RQ<1.5) in all AbS- and AbT-dosed monkeys, indicating that the return of rhuIL-21-induced gene expression was mediated through the IL-21R and that neutralizing anti-IL-21R antibodies were not present (FIGS. 59 and 60). Ex vivo addition of AbS continued to demonstrate inhibitory activity at subsequent time points collected from animals 1 and 3. However, AbS had no ex vivo inhibitory activity at the day 50 time point from animal 2 (FIG. 59). Similarly, AbT had no ex vivo inhibitory activity at days 22 and/or 36 collected from all animals in AbT-dosed groups (FIG. 60). These data suggested that animal 2 in the AbS group, and all three animals (4-6) in the AbT group, had developed neutralizing anti-product antibodies.

The presence of neutralizing anti-AbT antibodies in AbT-dosed animals was confirmed using an orthogonal flow cytometric (FACS)-based assay. TF-1 and TF-1/rhuIL-21R (TF-1 cells transfected with rhuIL-21R) were grown in RPMI media containing 25 ng/ml huGMCSF (R&D Systems). Confluent cell cultures were centrifuged at 300 g for 10 min, resuspended in OptiMEM serum-free medium (Invitrogen Corporation) at $10^6$ cells/mL, and incubated at 37° C. for 2 hr. The cells were then washed in cold PBS/0.5% BSA, resuspended in ice-cold PBS buffer, and kept on ice until staining. To determine the $EC_{50}$ for AbS-biotin and AbT-biotin binding to TF-1/rhuIL-21R cells, both the parental TF-1 and the TF-1/rhuIL-21R cells ($10^5$ cells per test) were incubated with either AbT-biotin, or IgG-biotin control using serial 3-fold dilutions (range=16-0.0002 µg/mL) on ice for 30 min, washed in PBS/0.5% BSA, and then incubated with streptavidin-allophycocyanin (APC; Invitrogen Corporation). Geometric mean fluorescent intensities ("GMFI") of the APC channel peaks was collected on an LSRII flow cytometer (BD Biosciences) and analyzed using Flowjo 8.3.3 software (Treestar). Linear regression analysis of the plots was performed using Prism 4 for Macintosh v4.0b (GraphPad Software, Inc.).

The minimum required dilution (MRD) for testing serum samples in this assay was determined to be 1:6 in PBS/0.5% BSA. To test for inhibition of AbT-biotin to TF-1/rhuIL-21R cells (i.e. for the presence of neutralizing activity), TF-1/rhuIL-21R cells were preincubated with sera from anti-IL-21R-dosed monkeys (using a 3-fold dilution series starting at the MRD), stained with an anti-IL-21R-biotin (at the estimated $EC_{50}$ concentration), washed in PBS/0.5% BSA, stained with streptavidin-APC, and analyzed for GMFI as described above. Each serum sample was run in duplicate in two individual experiments, and the average GMFI value for the four replicates was obtained for each dilution point. The relative GMFI value for each serum sample for each dilution point was calculated using the formula [100%*average GMFI/average GMFI pre-dose]. A sample was considered positive if the relative GMFI value was less than or equal to 80% at the MRD. For positive samples, the log titer was calculated as the log [reciprocal dilution that would generate relative GMFI >80%]. Based on the MRD, log titers for negative samples were reported as <0.78 (log 6).

All three AbT-dosed animals tested positive in the FACS-based neutralizing antibody assay at days 22 and 36, with log titers ranging from 2.2 to 4.1 (Table 34).

TABLE 34

Formation of Neutralizing anti-AbT Antibodies (log Titer) After 10 mg/kg i.v. Administration of AbT to Male Cynomolgus Monkeys

| TIME (DAYS) | ANIMAL 4 | ANIMAL 5 | ANIMAL 6 |
|---|---|---|---|
| Pre-dose | Negative | Negative | Negative |
| 15 | Negative | Negative | Negative |
| 22 | 4.12 | 2.7 | 2.2 |
| 36 | 2.2 | 2.7 | 2.7 |

As only one of the AbS-dosed animals showed evidence of neutralizing anti-AbS antibodies in the ex vivo IL-2Rα gene expression assay, serum samples from AbS-dosed monkeys were tested in an electrochemiluminescent paramagnetic bead-based assay described in Example 11.5 that detected both neutralizing and nonneutralizing anti-AbS antibodies. In this assay, serum samples were coincubated with biotinylated-AbS and ruthenylated-AbS, streptavidin-coated paramagnetic beads were added to the mixture, and the emitted light was detected using BioVeris technology. All three AbS-dosed monkeys were positive for anti-AbS antibodies in this assay, with log titers ranging from 1.86 to 3.43 (Table 35). There was significant interanimal variability in the apparent onset of anti-AbS generation. The first serum sample that was positive for anti-AbS antibodies in the BioVeris-based assay was obtained at days 134, 36, and 92 for animals 1, 2, and 3, respectively. Thus, among the three AbS-dosed animals, animal 2 had the shortest $t_{1/2}$ and the fastest onset and highest titer of anti-AbS antibody response. Animal 2 was also the only AbS-dosed monkey that showed evidence of neutralizing anti-AbS antibody response in the ex vivo IL-2Rα gene expression assay, similar to all three AbS-dosed monkeys.

TABLE 35

Formation of Anti AbS Antibodies (log Titer) After 10 mg/kg i.v. Administration of AbS to Male Cynomolgus Monkeys

| TIME (DAYS) | ANIMAL 1 | ANIMAL 2 | ANIMAL 3 |
|---|---|---|---|
| Pre-dose | Negative | Negative | Negative |
| 15 | Negative | Negative | Negative |
| 22 | Negative | Negative | Negative |
| 36 | Negative | 2.13 | Negative |
| 50 | Negative | 3.43 | Negative |
| 71 | ND | ND | Negative |
| 92 | Negative | ND | 2.27 |
| 106 | ND | ND | 2.79 |
| 113 | Negative | ND | ND |
| 134 | 1.86 | ND | ND |
| 148 | 2.4 | ND | ND |

"ND" = Not determined

Example 14

PK and PD of Additional Anti-IL-21R Antibodies in Cynomolgus Monkeys

Figure 61:
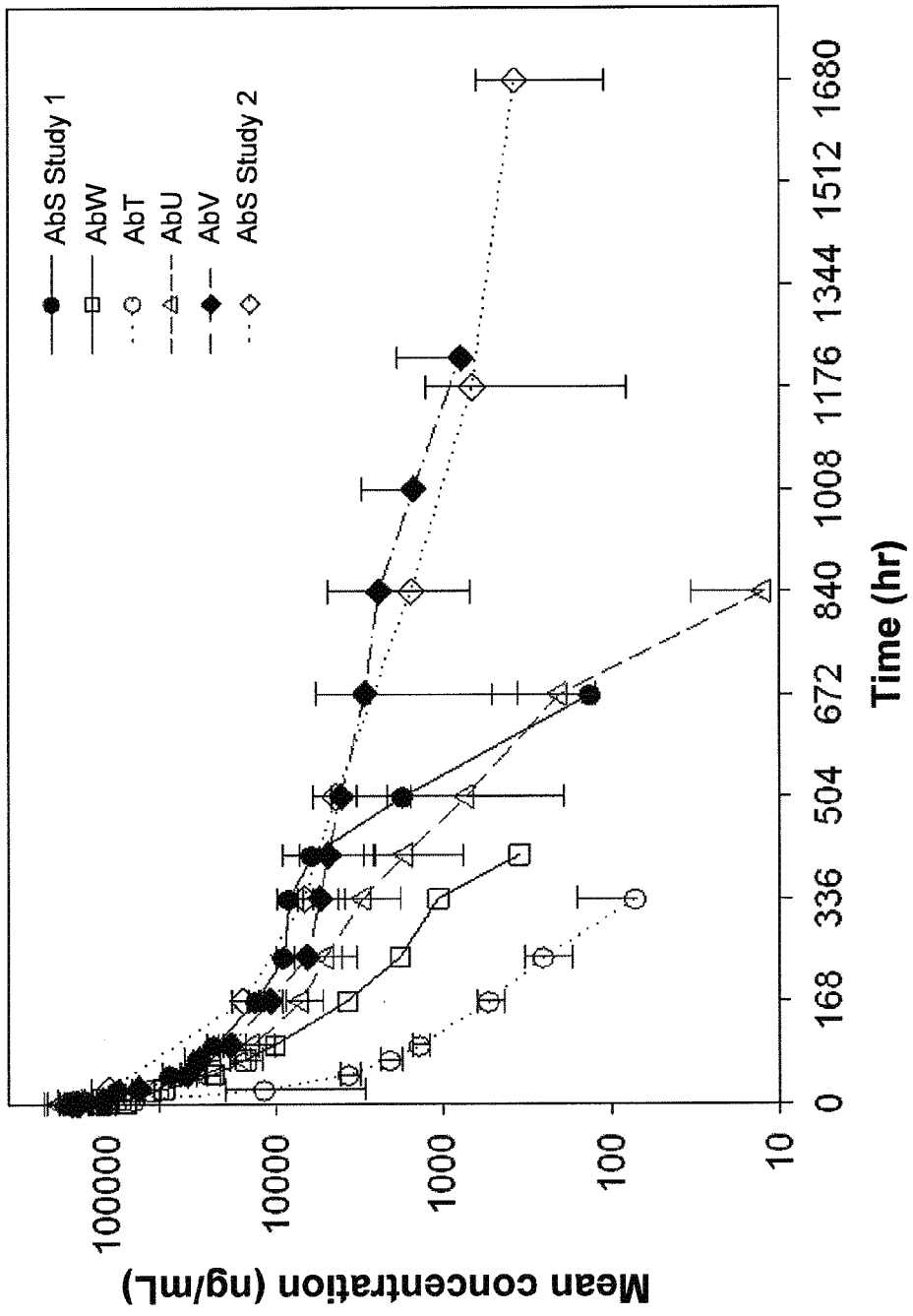
FIG. 61 depicts the concentration-time profiles of AbS-AbW in cynomolgus monkeys after a single i.v. administration. Concentrations below the limit of quantitation (<30 ng/ml) were treated as zero for calculations. For AbS (filled circles, Study 1; open diamonds, Study 2), AbT (open circles), AbV (filled diamonds), and AbU (open triangles), n=3; 10 mg/kg dose. For AbW (open squares), n=2; 1 mg/kg dose.

Pharmacokinetics of AbV, AbU, and AbW were examined after a single i.v. dose (10, 10, and 1 mg/kg, respectively) to protein-naïve cynomolgus monkeys, and PK parameters were compared to earlier PK data obtained with AbS and AbT (Table 36 and FIG. 61). Bioanalytical assays and PK calculations were performed as described for AbS and AbT in Example 13.

For all compounds, there was significant interanimal variability in the terminal phase, likely related to different onset of formation of anti-product antibodies. Following a single 10 mg/kg i.v. dose to monkeys, AbV and AbS appeared to have similar mean serum concentrations and PK parameters. After a single i.v. dose to monkeys, AbV and AbS appeared to have the slowest mean CL, longest mean $t_{1/2}$, and highest (dose-normalized) mean serum concentrations among all human anti-IL-21R antibodies tested. AbT had the fastest mean CL, shortest mean $t_{1/2}$ and lowest (dose-normalized) mean serum concentrations among all human anti-IL-21R antibodies tested. Comparison of mean concentration profiles and PK parameters after a single i.v. dose to cynomolgus monkeys suggested that ranking of human anti-IL-21R Ab antibodies based on PK profiles was similar between the S-D rats and cynomolgus monkeys (see also Example 10.10).

TABLE 36

PK Parameters After a Single i.v. Administration of Human Anti-IL-21R Antibodies to Cynomolgus Monkeys

| Compound | Sex | | Dose (mg/kg) | $C_{5\,min}{}^{a}$ (µg * hr/ml) | $AUC_{0-\infty}$ (µg * hr/ml) | $AUC_{0-\infty}$/Dose (µg * hr/ml)/(mg/kg) | CL (ml/hr/kg) | $Vd_{ss}$ (ml/kg) | $t_{1/2}$ (hr) |
|---|---|---|---|---|---|---|---|---|---|
| AbS | F | MEAN | 2 | 33.3 | 1575 | 788 | 1.28 | 122 | 78.5 |
|  |  | SD |  | 3.84 | 184 | 91.9 | 0.150 | 25.0 | 16.4 |
|  | F | MEAN | 10 | 177 | 9728 | 973 | 1.03 | 125 | 74 |
|  |  | SD |  | 10 | 621 | 62.1 | 0.07 | 16 | 46 |
|  | M | MEAN | $10^{b}$ | 164 | ND | ND | ND | ND | 255 |
|  |  | SD |  | 32 | ND | ND | ND | ND | 94 |
|  | M | MEAN | 100 | 2030 | 92867 | 929 | 1.08 | 211 | 279 |
|  |  | SD |  | 95 | 9768 | 97.7 | 0.108 | 8.00 | 27.6 |
| AbT | F | MEAN | 10 | 113 | 1476 | 148 | 7.01 | 202 | 63 |
|  |  | SD |  | 14 | 312 | 31.2 | 1.68 | 44 | 24 |
|  | M | MEAN | $10^{b}$ | 167 | ND | ND | ND | 55 |  |
|  |  | SD |  | 30 | ND | ND | ND | 4 |  |
|  | M | MEAN | 100 | 1850 | 20955 | 210 | 4.87 | 146 | 87.8 |
|  |  | SD |  | 415 | 3702 | 37.0 | 0.790 | 24.4 | 34.0 |
| AbW | F | MEAN | 1 | 10.0 | 430 | 430 | 2.33 | 165 | 73.2 |
|  |  | SD |  | NA | NA | NA | NA | NA | NA |
| AbV | F | MEAN | 10 | 152 | 9895 | 989 | 1.00 | 228 | 201 |
|  |  | SD |  | 46.0 | 3181 | 318 | 0.367 | 70.4 | 113 |
| AbU | F | MEAN | 10 | 197 | 6807 | 1947 | 1.55 | 140 | 89.6 |
|  |  | SD |  | 35.5 | 681 | 195 | 0.447 | 25.6 | 35.2 |

All studies were run in protein-naïve monkeys, n = 3 per dose group, unless otherwise noted
$^{a}C_{5\,min}$ = concentration at 5 min, the first time point after IV administration
$^{b}$PK data from a separate PK-PD study
NA = Not applicable (n = 2)
ND = Not determined; insufficient sampling time points In the same study, PD activity of AbU-AbW (AbU, AbV, and AbW) in monkeys was examined using ex vivo rhuIL-21-induced gene expression assay (described in Example 13).

At five min, the first sampling time point, AbU-AbW had PD activity in all monkeys, i.e., displayed complete inhibition of rhuIL-21-induced gene expression in the ex vivo whole blood assay, similar to data obtained for AbS and AbT. PD activity was lost with the washout of AbU-AbW from serum.

Example 15

Pharmacokinetics of AbS After Intravenous Administration to Tetanus-Toxoid-Challenged Male and Female Cynomolgus Monkeys PK of AbS was examined after a single three weekly i.v. administration of 2 or 10 mg/kg of AbS to tetanus-toxoid-challenged cynomolgus monkeys. AbS serum concentrations and anti-AbS antibodies were monitored by specific ELISA, and PK parameters were calculated by noncompartmental analysis, as described, e.g., in Example 13.

Following three weekly i.v. administrations of 2 or 10 mg/kg to monkeys, AbS concentration-time profiles and PK parameters were generally similar between the male and female monkeys in the same dose group (n=3 per sex per group). The mean concentration at 5 min after the $1^{st}$ dose (C5 min) and the $3^{rd}$ dose ($C_{day14,\ 5min}$), as well as the mean exposure after the $3^{rd}$ dose ($AUC_{day14-day21}$) increased with the dose level. In the 2 mg/kg group, the mean $C_5$ min was 28.4±2.50 µg/mL, the mean $C_{day14,\ 5min}$ was 35.7±11.0 µg/mL, and the mean $AUC_{day14-day21}$ was 1279±592 µg·hr/mL. In the 10 mg/kg group, the mean $C_5$ min was 120±59.9, the mean $C_{day14,\ 5min}$ was 152±21.9 µg/mL, and the mean $AUC_{day14-day21}$ was 7700±782 µg·hr/mL. Elimination half-life ($t_{1/2}$) after the third IV administration of AbS was 25.6±22.7 and 168±56.5 hr in the 2 and 10 mg/kg groups, respectively (p=0.0002) (FIG. 62).

Figure 62A:
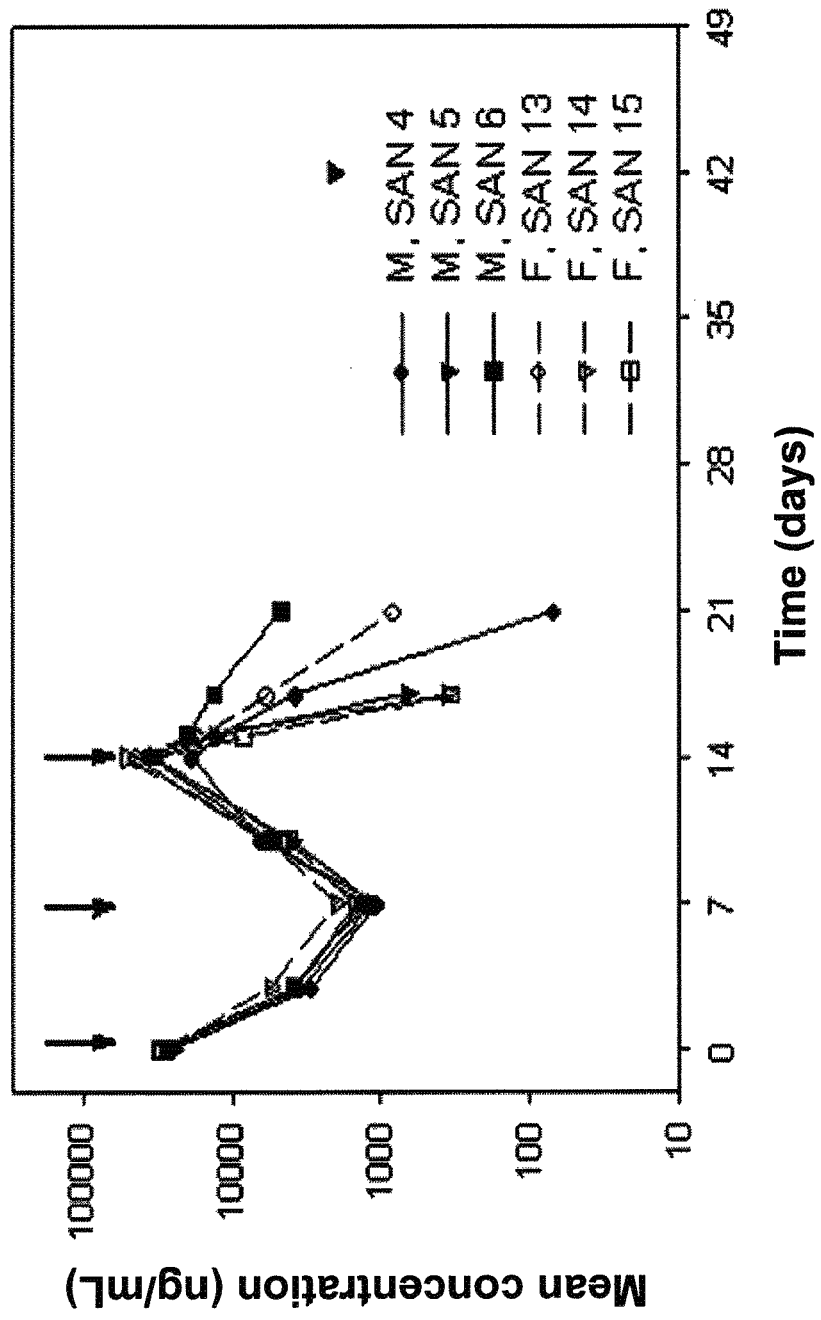
FIG. 62 depicts individual concentrations (ng/ml) of AbS after three weekly i.v. administrations (arrows) of 2 (FIG.
Figure 62B:
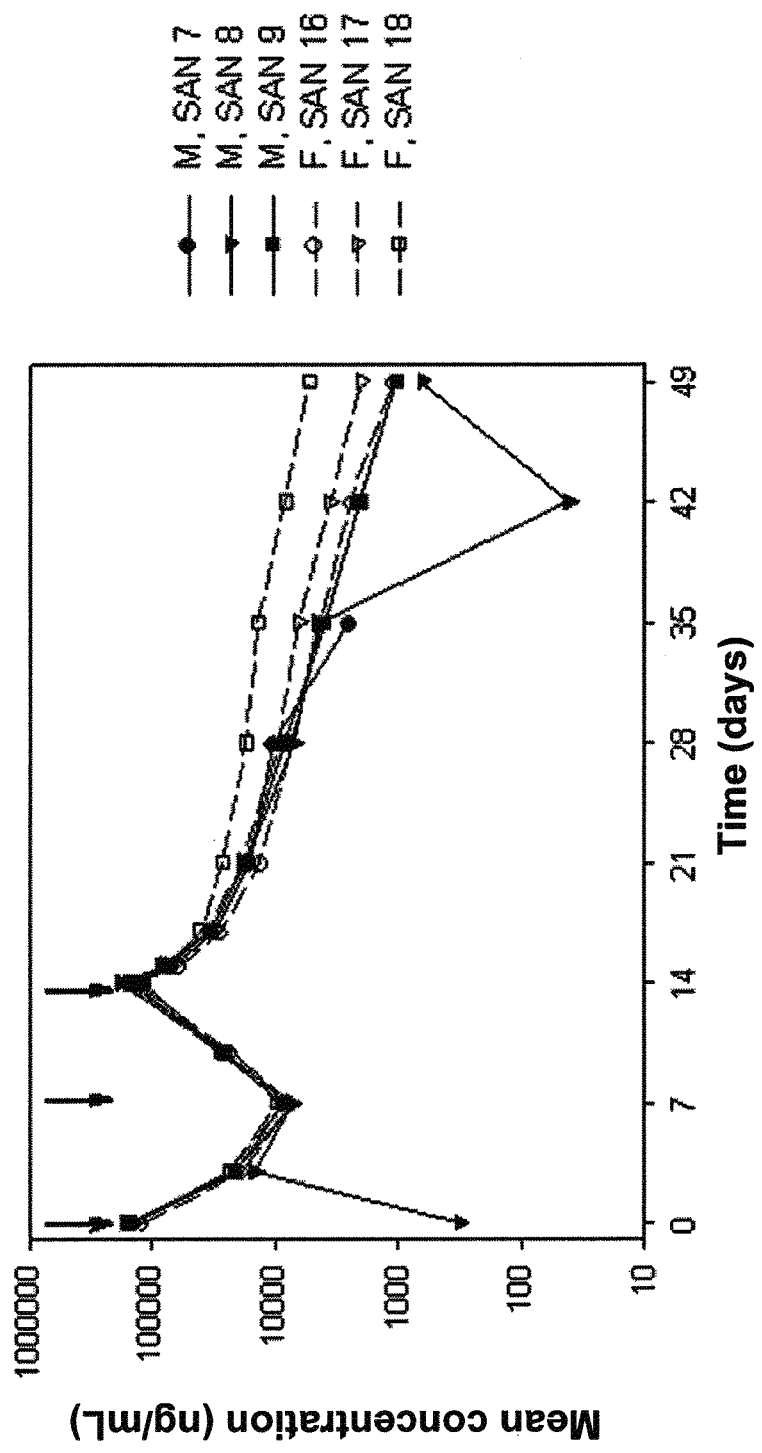

In the 2 mg/kg group, AbS concentrations declined rapidly after the third i.v. administration, and all six monkeys tested positive for anti-AbS antibodies at day 28 (two weeks after the third dose) through the end of the study, in line with the relatively short $t_{1/2}$ (FIG. 62a). In the 10 mg/kg group, two of the six monkeys (SAN 7 and SAN 8) tested positive for anti-AbS antibodies (at day 42 or 49), and these monkeys had the shortest $t_{1/2}$ values in the dose group, suggesting that formation of anti-AbS antibodies correlated with the $t_{1/2}$ of AbS (FIG. 62b).

Example 16

Prediction of Pharmacokinetics of AbS and AbT in Humans after Single Administration To predict the PK of AbS and AbT in humans, two approaches were used. For the first approach, it was assumed that the PK parameters (such as CL and volume of distribution) of an anti-IL-21R Ab in humans would be similar to those in cynomolgus monkeys. For the second approach, allometric scaling was used to estimate human PK parameters based on the animal data obtained from mice, rats, and cynomolgus monkeys following single i.v. administration of an anti-IL-21R antibody. Allometric scaling of CL was performed using adjustment for maximal life-span potential (MLP) for AbS and brain weight adjustments for AbT, according to the methods previously described in Mahmood (1996) *Eur. J. Drug Metab. Pharmacokinet.* 21:275-78; Mahmood and Balian (1996) *Xenobiotica* 26:887-95; Sacher, "Relation of lifespan to brain weight and body weight in mammals" in CIBA Foundation Symposium—The Lifespan of Animals (Colloquia on Aging), 115-33 (Wolstenholme G E W, O'Connor M, eds, 1959); and Hahn M E, Haber S B. (1978) *Behav Genet.,* 8:251-260. The allometric scaling data for AbS and AbT is demonstrated in FIGS. 63a-b and 64a-b, respectively.

Collectively, these two approaches suggested a low clearance (CL) and a small steady-state volume of distribution ($Vd_{SS}$) of AbS in humans. The predicted CL of AbS would be ~0.72-1.3 mL/hr/kg and the estimated $Vd_{SS}$ would be ~92.4-125 mL/kg. Following an i.v. dose of 1 mg/kg of AbS to a 60 kg human subject, the estimate of exposure ($AUC_{0-\infty}$) is 1393 µg·hr/mL, based on the CL value obtained by the allometric scaling method. For AbT, these two approaches suggested a higher CL of ~5-8.5 mL/hr/kg and $Vd_{ss}$ of ~115-202 mL/hr/kg.

Example 17

Treatment with AbS Does Not Affect Disease in the NZBWF1/J Murine Lupus Nephritis Model The anti-IL-21R antibody AbS was tested for its ability to reduce disease in a murine model of lupus, using NZBWF/1J mice. Female NZBWF1/J mice spontaneously develop symptoms resembling those observed in human lupus nephritis, including high titers of circulating IgG anti-nuclear and anti-double-stranded DNA autoantibodies, IgG deposits in the glomeruli, and proteinuria. The onset of kidney disease, as measured by the presence of protein in the urine, occurs at approximately 26 weeks of age in female NZBWF1/J mice. To examine the effects of IL-21R blockade with AbS, 26 week old female NZBWF1/J mice were administered either saline (vehicle control), CTLA-4Ig (murine IgG2a, positive control), anti-*E. tenalla* antibody (murine IgG2a isotype control), AbS, or a human antibody isotype control (human IgG1 antibody with triple mutation) at a dosage of 400 µg/mouse 3×/week over 10 weeks via i.p. injection. Serum samples were taken every two weeks and assayed for IgG anti-dsDNA antibodies by ELISA. Urine was collected and examined every two weeks for protein levels using Albustix (Bayer HealthCare, Tarrytown, N.Y.). All groups of animals had similar levels of proteinuria at the onset of the study, and the degree of proteinuria escalated in the saline, anti-*E. tenella*, and hIgG1TM control over the course of the study (FIG. 65a). Treatment with CTLA-4Ig protein, which has previously been shown to ameliorate disease in this model, prevented the development of increased proteinuria in these mice. In contrast, treatment with AbS did not affect the development of proteinuria in NZBWF1/J mice when compared to control mice (FIG. 65a). Similarly, treatment with CTLA-41 g significantly reduced anti-dsDNA IgG serum antibody titers in NZBWF1/J mice, where treatment with AbS did not affect the development of anti-dsDNA antibodies in these mice (FIG. 65b).

Example 18

Effects of Treatment with Anti-IL-21R Antibodies in a Semi-Therapeutic Collagen-Induced Arthritis (CIA) Mouse Model Antibodies AbS and AbT were tested for their ability to reduce disease in a murine collagen-induced arthritis model of rheumatoid arthritis. Female DBA/1 mice were immunized intradermally in the tail with 100 mg bovine collagen type II emulsified in complete Freund's adjuvant, and then boosted with 100 mg bovine collagen type II emulsified in incomplete Freund's adjuvant 21 days later at the same site. After the second immunization with bovine collagen type II, paws were examined for swelling and scored for severity on a scale of 0-16, with 0 representing no swelling and 16 indicating severe disease. Once 10% of animals in the study showed signs of disease, animals were either left untreated, or dosed 3x/week for 30 days with 8 mg/kg either murine IgG2a isotype control antibody, anti-mouse IL-21R antibody D5 (murine IgG2a antibody), mTNFRII-Fc (positive control, murine IgG2a isotype), anti-IL-13TM antibody (human IgG1 isotype control antibody), AbT, or AbS. Overall disease severity in this study was not observed to be as severe as normally observed in this model. Mean disease severity in the untreated and isotype control treated mice on the final day of the study was less than 4, on a scale of 0-16 (FIG. 66c). Additionally, although treatment with the mTNFRII-Fc positive control reduced disease in this study, statistically significant differences in disease severity were only observed between this treatment group and isotype control treated group disease on day 22 after dosing. Treatment with anti-mouse IL-21R antibody (D5) or anti-human IL-21R antibodies (AbS and AbT) also did not affect disease severity in this study (FIGS. 66a-b).

Example 19

Testing Antibody Effects on the Formation of Amnestic Antibody Response to Tetanus Immunization in Cynomolgus Monkeys The anti-IL-21R antibody AbS was examined for its effects on the development of amnestic antibody responses to tetanus immunization in cynomolgus monkeys. Nine female and nine male cynomolgus monkeys were tested for serum antibody titers to tetanus toxoid to identify tetanus-naïve animals. These animals were then administered 0.5 ml of tetanus toxoid in two equally divided (0.25 ml) doses intramuscularly, and blood was collected every 7 days for 35 days and examined for anti-tetanus IgM and IgG serum antibodies by ELISA. Forty-three days after primary immunization, groups of 3 male and 3 female cynomolgus monkeys were randomly assigned and administered either saline (vehicle), 2 mg/kg AbS, or mg/kg AbS as an i.v slow bolus into the brachial/ cephalic or saphenous vein at a dose volume of 1 ml/kg (flushed with 2 ml vehicle) 1x/week for 3 weeks. Twenty-four hr after administering the first dose of AbS or vehicle, monkeys were immunized a second time with 0.5 ml of tetanus toxoid in two equally divided (0.25 ml) doses intramuscularly, and blood was collected routinely and examined for anti-tetanus IgM and IgG antibody titers by ELISA. IgM and IgG tetanus serum antibodies were detectable in both male and female cynomolgus monkeys within 14 days after the first immunization with tetanus toxoid (FIG. 67a). Tetanus specific serum IgM titers did not change following secondary immunization with tetanus toxoid in any of the treatment groups. Tetanus-specific IgG serum titers were approximately 10-20 fold greater, and generated more rapidly in saline treated animals following secondary immunization, consistent with the kinetics of amnestic antibody responses (FIG. 67b). Treatment with 2 mg/kg or 10 mg/kg AbS did not affect the development of tetanus-specific IgG serum antibody responses in cymolgus monkeys following secondary immunization, indicating that treatment with AbS does not affect the formation of amnestic antibody responses to tetanus toxoid using this treatment protocol (FIG. 67b).

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method of treating lupus in a subject in need thereof, comprising administering to the subject a binding protein or antigen-binding fragment thereof that specifically binds to human interleukin-21 receptor ("IL-21R") in an amount sufficient to inhibit or reduce immune cell activity in the subject thereby treating the lupus, wherein the binding protein or antigen-binding fragment thereof comprises the CDR sequences set forth in SEQ ID NOs:163, 164, 169, 194, 195, and 176.

2. The method of claim 1, wherein the binding protein or antigen-binding fragment is an antibody.

3. The method of claim 1, wherein the binding protein or antigen-binding fragment is an scFv.

4. A method of treating lupus in a subject in need thereof, comprising administering to the subject a binding protein or antigen-binding fragment thereof that specifically binds to human IL-21R in an amount sufficient to inhibit or reduce immune cell activity in the subject thereby treating the lupus, wherein the binding protein or antigen-binding fragment thereof comprises the CDR sequences encoded by the nucleotide sequences of:
   (a) nucleotide 148 to 165 of SEQ ID NO:239;
   (b) nucleotide 208 to 255 of SEQ ID NO:239;
   (c) nucleotide 352 to 378 of SEQ ID NO:239;
   (d) nucleotide 124 to 156 of SEQ ID NO:97;
   (e) nucleotide 202 to 222 of SEQ ID NO:97; and
   (f) nucleotide 319 to 354 of SEQ ID NO:97.

5. The method of claim 4, wherein the binding protein or antigen-binding fragment is an antibody.

6. The method of claim 4, wherein the binding protein or antigen-binding fragment is an scFv.

7. A method of treating lupus in a subject in need thereof, comprising administering to the subject a binding protein or antigen-binding fragment thereof that specifically binds to human IL-21R in an amount sufficient to inhibit or reduce immune cell activity in the subject thereby treating the lupus, wherein the binding protein or antigen-binding fragment thereof comprises a $V_L$ domain and a $V_H$ domain, and wherein the $V_L$ domain comprises
   SEQ ID NO:221 and the $V_H$ domain comprises amino acid 1 to 118 of SEQ ID NO:219.

8. The method of claim 7, wherein the binding protein or antigen-binding fragment is an antibody.

9. The method of claim 7, wherein the binding protein or antigen-binding fragment is an scFv.

10. A method of treating lupus in a subject in need thereof, comprising administering to the subject a binding protein or antigen-binding fragment thereof that specifically binds to human IL-21R in an amount sufficient to inhibit or reduce immune cell activity in the subject thereby treating the lupus, wherein the binding protein or antigen-binding fragment thereof comprises a $V_L$ domain and a $V_H$ domain, and wherein the $V_L$ domain comprises an amino acid sequence encoded by nucleotide 58 to 384 of SEQ ID NO:97, and the $V_H$ domain comprises an amino acid sequence encoded by nucleotide 58 to 411 of SEQ ID NO:239.

11. The method of claim 10, wherein the binding protein or antigen-binding fragment is an antibody.

12. The method of claim 10, wherein the binding protein or antigen-binding fragment is an scFv.

13. The method of any one of claims 1, 4, 7, and 10, wherein the lupus is systemic lupus erythematosus.

14. The method of any one of claims 1, 4, 7, and 10, wherein the lupus is cutaneous lupus erythematosus.

15. The method of any one of claims 1, 4, 7, and 10, wherein the binding protein or antigen-binding fragment thereof has an association constant for human IL-21R of at least $10^5$ $M^{-1}s^{-1}$.

16. The method of any one of claims 1, 4, 7, and 10, wherein the binding protein or antigen-binding fragment thereof inhibits interleukin-21 ("IL-21")-mediated BAF3 cell proliferation with an $IC_{50}$ of about 1.75 nM or less, and wherein the BAF3 cells comprise a human IL-21 receptor.

17. The method of any one of claims 1, 4, 7, and 10, wherein the binding protein or antigen-binding fragment thereof inhibits IL-21-mediated proliferation of TF1 cells with an $IC_{50}$ of about 14 nM or less, and wherein the TF1 cells comprise a human IL-21 receptor.

18. The method of any one of claims 1, 4, 7, and 10, wherein the binding protein or antigen-binding fragment thereof inhibits IL-21-mediated proliferation of primary human B cells with an $IC_{50}$ of about 1.9 nM or less, and wherein the B cells comprise a human IL-21R.

19. The method of any one of claims 1, 4, 7, and 10, wherein the binding protein or antigen-binding fragment thereof inhibits IL-21-mediated proliferation of primary human $CD4^+$ cells with an $IC_{50}$ of about 1.5 nM or less, and wherein the $CD4^+$ cells comprise a human IL-21R.

20. The method of any one of claims 1, 4, 7, and 10, wherein the binding protein or antigen-binding fragment specifically binds to an amino acid sequence that is at least about 95% identical to any sequence of at least 100 contiguous amino acids of SEQ ID NO:2.

21. The method of any one of claims 1, 4, 7, and 10, wherein the binding protein or antigen-binding fragment inhibits the binding of IL-21 to IL-21R.

22. The method of any one of claims 1, 4, 7, and 10, wherein the binding protein or antigen-binding fragment is IgG1.

23. The method of any one of claims 1, 4, 7, and 10, wherein the binding protein or antigen-binding fragment is human.

\* \* \* \* \*